(12) United States Patent
Schlapbach et al.

(10) Patent No.: US 7,838,674 B2
(45) Date of Patent: Nov. 23, 2010

(54) TETRACYCLIC LACTAME DERIVATIVES

(75) Inventors: Achim Schlapbach, Lorrach (DE); Laszlo Revesz, Therwil (CH); Guido Koch, Bettingen (CH)

(73) Assignee: Novartis AG, Basel (CH)

( * ) Notice: Subject to any disclaimer, the term of this patent is extended or adjusted under 35 U.S.C. 154(b) by 211 days.

(21) Appl. No.: 12/174,324

(22) Filed: Jul. 16, 2008

(65) Prior Publication Data

US 2009/0098218 A1 Apr. 16, 2009

(30) Foreign Application Priority Data

Jul. 16, 2007 (EP) ................... 07112549

(51) Int. Cl.
C07D 239/00 (2006.01)
C07D 471/00 (2006.01)
C07D 487/00 (2006.01)
C07D 491/00 (2006.01)

(52) U.S. Cl. .................................... 544/247
(58) Field of Classification Search .......... 544/247
See application file for complete search history.

(56) References Cited

U.S. PATENT DOCUMENTS

2004/0127492 A1* 7/2004 Vazquez et al. .......... 514/224.2

FOREIGN PATENT DOCUMENTS

WO WO2004/058176 A2 7/2004
WO WO2004/058762 A1 7/2004

* cited by examiner

*Primary Examiner*—James O Wilson
*Assistant Examiner*—Erich A Leeser

(74) *Attorney, Agent, or Firm*—Sophie Binet Cross

(57) ABSTRACT

The present invention describes tetracyclic compounds of formula (IA) or (IB),

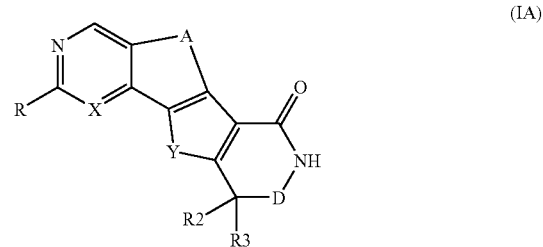

(IA)

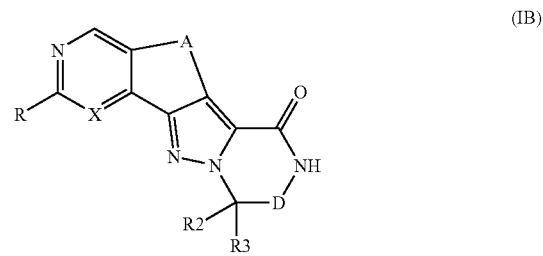

(IB)

wherein the symbols R, X, A, Y, R2, R3 and D are as defined in the specification, their use in the treatment of certain diseases, e.g. depending on MK-2 or TNF activity, and ways of manufacturing them.

12 Claims, No Drawings

TETRACYCLIC LACTAME DERIVATIVES

This application claims benefit under 35 U.S.C. §119(a)-(d) or (f) or 365(b) of EP Application No. 07112549.6, filed Jul. 16. 2007, the contents of which are incorporated herein by reference in their entirety.

This US utility application claims priority under 35 U.S.C. §119(a) to EP application no. 07112549.6 filed 16 Jul. 2007, the contents of which are incorporated herein by reference in their entirety.

The present invention relates to novel aromatic compounds useful especially as inhibitors of mitogen-activated protein kinase-activated protein kinase-2 (MK2 or MAPKAP kinase-2 ), methods of use for them, their uses, ways of manufacture thereof and other aspects related thereto given below in detail.

Accordingly the present invention, in a first aspect, provides a compound of formula (IA) or (IB),

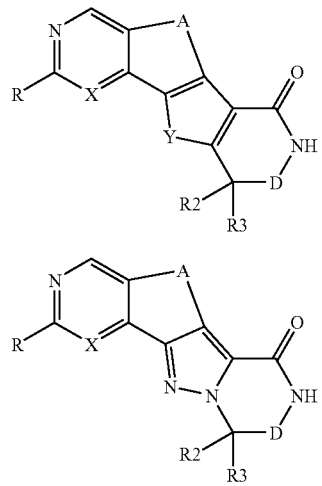

wherein

R is hydrogen, halogen, —Y—$C_3$-$C_7$cycloalkyl, unsubstituted or substituted aryl, unsubstituted or substituted heterocyclyl, unsubstituted or substituted aryl-$C_2$-$C_7$-alkenyl, mono- or di-(unsubstituted or substituted $C_1$-$C_7$-alkyl)-amino or unsubstituted or substituted-arylamino;

A is —$CH_2$—, —$CH_2$—$CH_2$—, —$CH_2$—$CH_2$—$CH_2$— or —CH=CH—;

D is a bond between the carbon and the nitrogen atom to which it is bound or is C(R4R5);

R2 and R3 are hydrogen or together form an ethylene or trimethylene bridge in each of which one of the carbon atoms can be replaced with O, S or NR6;

R3 and R4 are hydrogen or $C_1$-$C_4$-alkyl or together form an ethylene or trimethylene bridge in each of which one of the carbon atoms can be replaced with O, S or NR6;

or one of R2 and R3 is hydrogen and one of R4 and R5 is hydrogen, while the other of R2 and R3 together with the other of R4 and R5 forms an ethylene wherein one of the carbon atoms can be replaced with O, S or NR6, or a methylene bridge, with the proviso that at least one of the mentioned bridges must be present in a compound of formula (IA) or (IB) and is formed by R2 and R3, by R4 and R5, or by R2 or R3 and R4 or R5, so that not more than two of R2, R3, R4 and R5 are hydrogen or $C_1$-$C_4$-alkyl;

R6 is hydrogen, alkyl, $C_1$-$C_7$-alkyl, halo-$C_1$-$C_7$-alkyl, hydroxy-$C_1$-$C_7$-alkyl, unsubstituted or substituted aryl-$C_1$-$C_7$-alkyl or acyl, X is CH or N; and Y is O, S or NR7 wherein R7 is hydrogen, unsubstituted or substituted alkyl, unsubstituted or substituted cycloalkyl, unsubstituted or substituted aryl-$C_1$-$C_7$-alkyl, unsubstituted or substituted saturated heterocyclyl or unsubstituted or substituted heterocyclyl-$C_1$-$C_7$-alkyl; a pharmaceutically acceptable cleavable ester or amide thereof, and/or a pharmaceutically acceptable salt thereof.

In another aspect the invention pertains to a compound of formula (IA) or (IB),

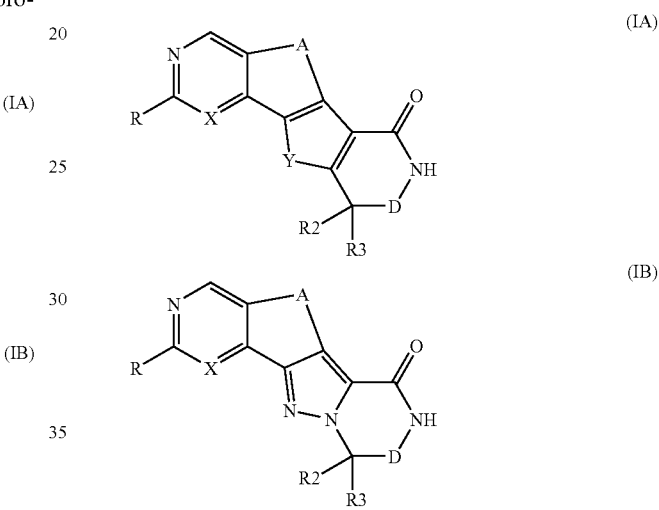

wherein

R is hydrogen, unsubstituted or substituted aryl, unsubstituted or substituted heterocyclyl, unsubstituted or substituted aryl-$C_2$-$C_7$-alkenyl, mono- or di-(unsubstituted or substituted $C_1$-$C_7$-alkyl)-amino or unsubstituted or substituted-arylamino;

A is —$CH_2$—, —$CH_2$—$CH_2$—, —$CH_2$—$CH_2$—$CH_2$— or —CH=CH—;

D is a bond between the carbon and the nitrogen atom to which it is bound or is C(R4R5);

R2 and R3 are hydrogen or together form an ethylene or trimethylene bridge in each of which one of the carbon atoms can be replaced with O, S or NR6;

R3 and R4 are hydrogen or $C_1$-$C_4$-alkyl or together form an ethylene or trimethylene bridge in each of which one of the carbon atoms can be replaced with O, S or NR6;

or one of R2 and R3 is hydrogen and one of R4 and R5 is hydrogen, while the other of R2 and R3 together with the other of R4 and R5 forms an ethylene wherein one of the carbon atoms can be replaced with O, S or NR6, or a methylene bridge, with the proviso that at least one of the mentioned bridges must be present in a compound of formula (IA) or (IB) and is formed by R2 and R3, by R4 and R5, or by R2 or R3 and R4 or R5, so that not more than two of R2, R3, R4 and R5 are hydrogen or $C_1$-$C_4$-alkyl;

R6 is hydrogen, alkyl, unsubstituted or substituted aryl-$C_1$-$C_7$-alkyl or acyl, X is CH or N; and Y is O, S or especially NR7 wherein R7 is hydrogen, unsubstituted or substituted alkyl, unsubstituted or substituted cycloalkyl, unsubstituted or substituted aryl-$C_1$-$C_7$-alkyl, unsubstituted or substituted saturated heterocyclyl or unsubstituted or substituted heterocyclyl-$C_1$-$C_7$-alkyl;

a pharmaceutically acceptable cleavable ester or amide thereof, and/or a pharmaceutically acceptable salt thereof.

For the avoidance of doubt, the terms listed below are to be understood to have the following meaning throughout the present description and claims:

In the present application, oxygen containing substituents, e.g. alkoxy, alkenyloxy, alkynyloxy, carbonyl, or the like, are meant to encompass as alternative their sulphur containing homologues, e.g. thioalkyl, alkyl-thioalkyl, thioalkenyl, alkenyl-thioalkyl, thioalkynyl, thiocarbonyl, sulfonyl, sulfonyloxy, or the like.

Halo or halogen represents chloro, fluoro, bromo or iodo.

The term "lower" (or $C_1$-$C_7$), when referring to organic radicals or compounds means a compound or radical with may be branched or unbranched with up to and including 7 carbon atoms, preferably up to and including 4 carbon atoms.

Unsubstituted or substituted aryl is generally aryl with 6 to 28, typically with 6 to 18 ring carbon atoms, and may be mono-, bi-, tri- or tetracyclic, e.g. phenyl, indenyl, naphthyl or fluorenyl, and is unsubstituted or substituted by one or more, especially up to three, substituents independently selected from the group consisting of unsubstituted or substituted phenyl, such as 4-fluorophenyl, unsubstituted or substituted phenyloxy, such as 2,4-difluorophenoxy, unsubstituted or substituted saturated heterocyclyl, such as 1-morpholinyl, 4-alkyl-piperazin-1-yl or 1-piperidinyl, $C_1$-$C_7$-alkyl, such as methyl, halo-$C_1$-$C_7$-alkyl, such as trifluoromethyl or bromomethyl, hydroxyl-$C_1$-$C_7$-alkyl, especially 3-hydroxy-3-methyl-butyl, amino-$C_1$-$C_7$-alkyl, especially 3-amino-3-methyl-butyl, mono- or di-$C_1$-$C_7$-alkyl-amino-$C_1$-$C_7$-alkyl, saturated heterocyclyl-$C_1$-$C_7$-alkyl, such as pyrrolidinyl-$C_1$-$C_7$-alkyl, especially pyrrolidino-methyl, imidazolidinyl-$C_1$-$C_7$-alkyl, especially imidazolidino-$C_1$-$C_7$-alkyl, pyrazolidinyl-$C_1$-$C_7$-alkyl, especially pyrazolidin-1-yl-$C_1$-$C_7$-alkyl, piperidinyl-$C_1$-$C_7$-alkyl, especially piperidino-methyl or 2-piperidino-ethyl, (unsubstituted or $C_1$-$C_7$-alkyl-substituted piperazino)-$C_1$-$C_7$-alkyl, especially 4-methylpiperazin-1-yl-methyl or -ethyl, morpholinyl-$C_1$-$C_7$-alkyl, especially morpholino-methyl or 2-morpholino-ethyl, thiomorpholinyl-$C_1$-$C_7$-alkyl, especially thiomorpholino-methyl or 2-thiomorpholino-ethyl, S-oxo-thiomorpholinyl-$C_1$-$C_7$-alkyl, especially S-oxo-thiomorpholino-methyl or 2-S-oxo-thiomorpholino-ethyl, or S,S-dioxo-thiomorpholinyl-$C_1$-$C_7$-alkyl, especially S,S-di-thiomorpholino-methyl or 2-S,S-di-thiomorpholino-ethyl, $C_2$-$C_7$-alkenyl, $C_6$-$C_{10}$-aryl-$C_2$-$C_7$-alkenyl, such as (E,Z)- or preferably (E)- or (Z)-styryl, $C_2$-$C_7$-alkynyl, amino-$C_3$-$C_7$-alkynyl, especially 3-amino-3-methyl-but-1-ynyl, hydroxyl-$C_3$-$C_7$-alkynyl, especially 3-hydroxy-3-methylbut-1-ynyl, halo, especially fluoro, chloro or bromo, hydroxyl, $C_1$-$C_7$-alkoxy, especially methoxy or isopropoxy, $C_1$-$C_7$-alkoxy-$C_1$-$C_7$-alkoxy, especially 2-methoxy-ethoxy, halo-$C_1$-$C_7$-alkoxy, especially trifluoromethoxy, saturated heterocyclyl-$C_1$-$C_7$-alkoxy, preferably pyrrolidinyl-$C_1$-$C_7$-alkoxy, especially pyrrolidino-methoxy, imidazolidinyl-$C_1$-$C_7$-alkoxy, especially imidazolidino-$C_1$-$C_7$-alkoxy, pyrazolidinyl-$C_1$-$C_7$-alkoxy, especially pyrazilidin-1-yl-$C_1$-$C_7$-alkoxy, piperidinyl-$C_1$-$C_7$-alkoxy, especially piperidino-methoxy or 2-piperidino-ethoxy, (unsubstituted or $C_1$-$C_7$-alkyl-substituted piperazino)-$C_1$-$C_7$-alkoxy, especially 4-methylpiperazin-1-yl-methoxy or 2-(4-methylpiperazin-1-yl)-ethoxy, morpholinyl-$C_1$-$C_7$-alkoxy, especially morpholino-methoxy or 2-morpholino-ethoxy, thiomorpholinyl-$C_1$-$C_7$-alkoxy, especially thiomorpholino-methoxy or 2-thiomorpholino-ethoxy, S-oxo-thiomorpholinyl-$C_1$-$C_7$-alkoxy, especially S-oxo-thiomorpholino-methoxy or 2-S-oxo-thiomorpholino-ethoxy, or S,S-dioxo-thiomorpholinyl-$C_1$-$C_7$-alkoxy, especially S,S-di-thiomorpholino-methoxy or 2-S,S-di-thiomorpholino-ethoxy, mono- or di-($C_1$-$C_7$-alkyl)-amino-$C_1$-$C_7$-alkoxy, especially dimethylamino-ethoxy, $C_1$-$C_7$-alkylenedioxy, especially ethlyendioxy, especially with the two oxygen atoms bound to vicinal aryl ring atoms, amino, mono- or di-($C_1$-$C_7$-alkyl and/or phenyl-$C_1$-$C_7$-alkyl)-amino, formyl, carboxy, $C_1$-$C_7$-alkoxycarbonyl, aryl-$C_1$-$C_7$-alkoxycarbonyl, especially phenyl-$C_1$-$C_7$-alkoxycarbonyl, carbamoyl, mono- or di-($C_1$-$C_7$-alkyl, unsaturated heterocyclyl-$C_1$-$C_7$-alkyl and/or aryl-$C_1$-$C_7$-alkyl, especially phenyl-$C_1$-$C_7$-alkyl)-carbamoyl, sulfonyl (—S(O)$_2$—OH), sulfamoyl, mono- or di-($C_1$-$C_7$-alkyl and/or phenyl-$C_1$-$C_7$-alkyl)-sulfamoyl, nitro, acyl and cyano.

In particular, unsubstituted or substituted aryl is preferably aryl with 6 to 18, more preferably with 6 to 14 ring carbon atoms, which can be mono-, bi-, tri- or tetracyclic, especially e.g. phenyl, indenyl, naphthyl or fluorenyl, and is unsubstituted or substituted by one or more, especially up to three, substituents independently selected from the group consisting of $C_1$-$C_7$-alkyl, halo-$C_1$-$C_7$-alkyl, such as trifluoromethyl or bromomethyl, hydroxyl-$C_1$-$C_7$-alkyl, especially 3-hydroxy-3-methyl-butyl, amino-$C_1$-$C_7$-alkyl, especially 3-amino-3-methyl-butyl, or saturated heterocyclyl-$C_1$-$C_7$-alkyl, such as pyrrolidinyl-$C_1$-$C_7$-alkyl, especially pyrrolidino-methyl, imidazolidinyl-$C_1$-$C_7$-alkyl, especially imidazolidino-$C_1$-$C_7$-alkyl, pyrazolidinyl-$C_1$-$C_7$-alkyl, especially pyrazilidin-1-yl-$C_1$-$C_7$-alkyl, piperidinyl-$C_1$-$C_7$-alkyl, especially piperidino-methyl or 2-piperidino-ethyl, (unsubstituted or $C_1$-$C_7$-alkyl-substituted piperazino)-$C_1$-$C_7$-alkyl, especially 4-methylpiperazin-1-yl-methyl or -ethyl, morpholinyl-$C_1$-$C_7$-alkyl, especially morpholino-methyl or 2-morpholino-ethyl, thiomorpholinyl-$C_1$-$C_7$-alkyl, especially thiomorpholino-methyl or 2-thiomorpholino-ethyl, S-oxo-thiomorpholinyl-$C_1$-$C_7$-alkyl, especially S-oxo-thiomorpholino-methyl or 2-S-oxo-thiomorpholino-ethyl, or S,S-dioxo-thiomorpholinyl-$C_1$-$C_7$-alkyl, especially S,S-di-thiomorpholino-methyl or 2-S,S-di-thiomorpholino-ethyl, $C_2$-$C_7$-alkenyl, $C_6$-$C_{10}$-aryl-$C_2$-$C_7$-alkenyl, such as (E,Z)- or preferably (E)- or (Z)-styryl, $C_2$-$C_7$-alkynyl, amino-$C_3$-$C_7$-alkynyl, especially 3-amino-3-methyl-but-1-ynyl, hydroxyl-$C_3$-$C_7$-alkynyl, especially 3-hydroxy-3-methylbut-1-ynyl, halo, especially fluoro, chloro or bromo, hydroxyl, $C_1$-$C_7$-alkoxy, especially methoxy or isopropoxy, $C_1$-$C_7$-alkoxy-$C_1$-$C_7$-alkoxy, especially 2-methoxy-ethoxy, halo-$C_1$-$C_7$-alkoxy, especially trifluoromethoxy, saturated heterocyclyl-$C_1$-$C_7$-alkoxy, preferably pyrrolidinyl-$C_1$-$C_7$-alkoxy, especially pyrrolidino-methoxy, imidazolidinyl-$C_1$-$C_7$-alkoxy, especially imidazolidino-$C_1$-$C_7$-alkoxy, pyrazolidinyl-$C_1$-$C_7$-alkoxy, especially pyrazilidin-1-yl-$C_1$-$C_7$-alkoxy, piperidinyl-$C_1$-$C_7$-alkoxy, especially piperidino-methoxy or 2-piperidino-ethoxy, (unsubstituted or $C_1$-$C_7$-alkyl-substituted piperazino)-$C_1$-$C_7$-alkoxy, especially 4-methylpiperazin-1-yl-methoxy or 2-(4-methylpiperazin-1-yl)-ethoxy, morpholinyl-$C_1$-$C_7$-alkoxy, especially morpholino-methoxy or 2-morpholino-ethoxy, thiomorpholinyl-$C_1$-$C_7$-alkoxy, especially thiomorpholino-methoxy or 2-thiomorpholino-ethoxy, S-oxo-thiomorpholinyl-$C_1$-$C_7$-alkoxy, especially S-oxo-thiomorpholino-methoxy or 2-S-oxo-thiomorpholino-ethoxy, or S,S-dioxo-thiomorpholinyl-$C_1$-$C_7$-alkoxy, especially S,S-di-thiomorpholino-methoxy or 2-S,S- di-thiomorpholino-ethoxy, $C_1$-$C_7$-alkylenedioxy, especially with the two oxygen atoms bound to vicinal aryl ring atoms, amino, mono- or di-($C_1$-$C_7$-alkyl and/or phenyl-$C_1$-$C_7$-alkyl)-amino, carboxy, $C_1$-$C_7$-alkoxycarbonyl, especially phenyl-$C_1$-$C_7$-alkoxycarbonyl, carbamoyl, mono- or di-($C_1$-$C_7$-alkyl, and/or, especially phenyl-$C_1$-$C_7$-alkyl)-carbamoyl, sulfonyl (—S(O)$_2$—OH), sulfamoyl, mono- or di-($C_1$-$C_7$-alkyl and/or phenyl-$C_1$-$C_7$-alkyl)-sulfamoyl, nitro and cyano.

In a more preferred embodiment, the optional substituents on R (aryl or heterocyclyl) are one or more, especially up to three, groups independently selected from halo-$C_1$-$C_7$-alkyl, such as trifluoromethyl or bromomethyl, hydroxyl-$C_1$-$C_7$-alkyl, especially 3-hydroxy-3-methyl-butyl, amino-$C_1$-$C_7$-alkyl, especially 3-amino-3-methyl-butyl, pyrrolidinyl-$C_1$-$C_7$-alkyl, especially pyrrolidino-methyl, imidazolidinyl-$C_1$-$C_7$-alkyl, especially imidazolidino-$C_1$-$C_7$-alkyl, piperidinyl-$C_1$-$C_7$-alkyl, especially piperidino-methyl or 2-piperidino-ethyl, (unsubstituted or $C_1$-$C_7$-alkyl-substituted piperazino)-$C_1$-$C_7$-alkyl, especially 4-methylpiperazin-1-yl-methyl or -ethyl, $C_6$-$C_{10}$-aryl-$C_2$-$C_7$-alkenyl, such as (E,Z)- or preferably (E)- or (Z)-styryl, amino-$C_3$-$C_7$-alkynyl, especially 3-amino-3-methyl-but-1-ynyl, hydroxyl-$C_3$-$C_7$-alkynyl, especially 3-hydroxy-3-methylbut-1-ynyl, halo, especially fluoro, chloro or bromo, $C_1$-$C_7$-alkoxy, especially methoxy or isopropoxy, $C_1$-$C_7$-alkoxy-$C_1$-$C_7$-alkoxy, especially 2-methoxy-ethoxy, halo-$C_1$-$C_7$-alkoxy, especially trifluoromethoxy, pyrrolidinyl-$C_1$-$C_7$-alkoxy, especially pyrrolidino-methoxy, imidazolidinyl-$C_1$-$C_7$-alkoxy, especially imidazolidino-$C_1$-$C_7$-alkoxy, piperidinyl-$C_1$-$C_7$-alkoxy, especially piperidino-methoxy or 2-piperidino-ethoxy, (unsubstituted or $C_1$-$C_7$-alkyl-substituted piperazino)-$C_1$-$C_7$-alkoxy, especially 4-methylpiperazin-1-yl-methoxy or 2-(4-methylpiperazin-1-yl)-ethoxy, $C_1$-$C_7$-alkylenedioxy, especially with the two oxygen atoms bound to vicinal aryl ring atoms, amino, carbamoyl, nitro and cyano.

Unsubstituted or substituted heterocyclyl is preferably a mono- or poly-, especially mono-, di- or tricyclic ring with 3 to 24, more preferably 3 to 20, ring atoms, of which one or more, especially one, two, three or four, independently of each other, are heteroatoms selected from N, O and S, and is saturated, e.g. selected from the group consisting of azetidinyl, pyrrolidinyl, imidazolidinyl, pyrazolidinyl, piperidinyl, piperazinyl, indolinyl, isoindolinyl, quinuclidinyl, morpholinyl, thiomorpholinyl, S-oxo-thiomorpholinyl and S,S-di-oxothiomorpholinyl; or partially unsaturated or unsaturated (=carrying the highest possible number of conjugated double bonds in the ring), e.g. selected from the group consisting of pyrrolyl, imidazolyl, pyrazolyl, indazolyl, purinyl, pyridinyl, pyrazinyl, pyrimidinyl, pyridazinyl, indolyll, isoindolyl, quinolyl, isoquinolyl, quinolizinyl, phthalazinyl, napthyridinyl, quinoxalinyl, quinazolinyl, cinnolinyl, pteridinyl, indolizinyl, carbazolyl, beta-carbolinyl, acridinyl, phenanthridinyl, phenazinyl, phenanthrolinyl, perimidinyl, furyl, thiophenyl (=thienyl), 2H— or 4H-pyranyl or -thiopyranyl, oxazolyl, thiazolyl, isochromanyl, chromanyl, benzofuranyl, 2H-benzo[1,4]oxazinyl, isobenzofuranyl, 2H-chromenyl, 2H-thiochromenyl, thianthrenyl, xanthenyl, phenoxathiinyl, phenoxazinyl and phenothiazinyl; where heterocyclyl is unsubstituted or substituted by one or more, preferably one to three, substituents independently selected from those mentioned as substituents for substituted aryl, especially from $C_1$-$C_7$-alkoxy, such as methoxy or isopropoxy, $C_1$-$C_7$-alkyl, such as methyl, hydroxy-$C_1$-$C_7$-alkyl, such as hydroxy-ethyl, acyl, such as acetyl, $C_1$-$C_7$-alkoxy-$C_1$-$C_7$-alkoxy, such as 2-methoxyethoxy, halo, such as fluoro or chloro, amino, mono- or di-$C_1$-$C_7$-alkyl-amino, and hydroxyl; more especially from $C_1$-$C_7$-alkoxy, such as methoxy or isopropoxy, and $C_1$-$C_7$-alkoxy-$C_1$-$C_7$-alkoxy, such as 2-methoxyethoxy.

Mono- or di-(unsubstituted or substituted $C_1$-$C_7$-alkyl)-amino is preferably amino substituted by one or two moieties selected from $C_1$-$C_7$-alkyl, $C_1$-$C_7$-alkoxy-$C_1$-$C_7$-alkyl, amino- or mono- or di-($C_1$-$C_7$-alkyl and/or $C_6$-$C_{10}$-aryl-$C_1$-$C_7$-alkyl), or $C_1$-$C_7$-alkyl substituted by one or more, e.g. up to three, of the further substituents mentioned as substituents for substituted aryl.

In unsubstituted or substituted-arylamino, unsubstituted or substituted aryl is preferably as defined above.

A is —CH$_2$—, —CH$_2$—CH$_2$—CH$_2$— or —CH=CH—, or more preferably —CH$_2$—CH$_2$—.

If D is a bond between the carbon and nitrogen atom to which it is bound, then the ring including D has five ring atoms.

If R2 and R3 together form an ethylene or trimethylene bridge in each of which one of the carbon atoms can be replaced with O, S or NR6, then R2 and R3 together with the binding carbon atoms form a 3- to 4-membered ring.

If R3 and R4 together form an ethylene or trimethylene bridge in each of which one of the carbon atoms can be replaced with O, S or NR6, then R3 and R4 together with the binding carbons atoms form a 3- to 4-membered ring.

If one of R2 and R3 is hydrogen and one of R4 and R5 is hydrogen, while the other of R2 and R3 together with the other of R4 and R5 forms an ethylene wherein one of the carbon atoms can be replaced with O, S or NR6, or a methylene bridge, R2 or R3 and R4 or R5 together with the two carbon atoms to which they are bound form a three- to four-membered ring.

The proviso that at least one ring is formed by R2 and R3, by R4 and R5, or by R2 or R3 and R4 or R5, so that not more than two of R2, R3, R4 and R5 are hydrogen or $C_1$-$C_4$-alkyl, means that at least one annelated or spiro ring must be formed by these substituents and the carbon atoms to which they are bound.

Alkyl may be branched, unbranched or cyclic, and preferably is $C_1$-$C_{20}$-alkyl, more preferably $C_1$-$C_7$-alkyl (lower alkyl). $C_1$-$C_7$ alkyl represents, for example: methyl, ethyl, propyl, butyl, isopropyl, isobutyl, tertiary butyl or 2,2-dimethylpropyl. In substituted alkyl, it may be substituted by one or more, e.g. up to three, substituents as mentioned as substituents mentioned for aryl, especially hydroxyl.

Unsubstituted or substituted aryl-$C_1$-$C_7$-alkyl is $C_1$-$C_7$-alkyl that is substituted by unsubstituted or substituted aryl as defined above, preferably benzyl.

Cycloalkyl represents a cyclic hydrocarbon containing from 3 to 12 ring atoms, preferably from 3 to 8 ring atoms (then called $C_3$-$C_8$-cycloalkyl). Cycloalkyl represents, for example: cyclopropyl, cyclobutyl, cyclopentyl, or cyclohexyl. The cycloalkyl may optionally be substituted by one or more substituents independently selected from those mentioned as substituents for substituted aryl, especially from hydroxyl, e.g. in the (R,S)— or preferably in the (R)— or (S)— form. In the case of R7, cycloalkyl is preferably cyclohexyl or cyclopentyl, each unsubstituted or preferably substituted with hydroxyl.

Acyl preferably is the radical of an organic acid, especially an carboxylic acid or a sulfonic acid, and is especially $C_1$-$C_7$-alkanoyl, preferably acetyl, $C_1$-$C_7$-alkanesulfonyl, benzoyl, naphthoyl, $C_1$-$C_7$-alkoxycarbonyl, preferably tert-butoxycarbonyl, or $C_6$-$C_{10}$-aryl-$C_1$-$C_7$-alkoxycarbonyl, such as benzyloxycarbonyl.

Unsubstituted or substituted saturated heterocyclyl is preferably unsubstituted or substituted heterocyclyl as defined above and is unsubstituted or substituted by one or more, especially up to three, of the substituents independently selected from the substituents mentioned for substituted aryl above.

In unsubstituted or substituted heterocyclyl-$C_1$-$C_7$-alkyl, unsubstituted or substituted heterocyclyl is preferably as defined above and is unsubstituted or substituted by one or more, especially up to three, of the substituents independently selected from the substituents mentioned for substituted aryl above, while —$C_1$-$C_7$-alkyl is preferably -methyl.

A pharmaceutically acceptable cleavable ester or amide thereof, and/or a pharmaceutically acceptable salt thereof means that the compound can be present in free form, as a salt, as a mixture of the free form and a salt, or in the form of a physiologically cleavable ester (with an esterified hydroxyl substituent if present) or amide (with an acylated amino or imino if present), which may also be in free and/or in salt form.

Pharmaceutically acceptable salts refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids, e.g., acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable.

The present invention includes all pharmaceutically acceptable isotopically-labeled compounds of the invention, i.e. compounds of formula (IA) or (IB), wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Isotopically-labeled compounds of the invention, i.e. compounds of formula (IA) or (IB), can generally be prepared by conventional techniques known to those skilled in the art or by processes analogous to those described in the accompanying Examples and Preparations Sections using an appropriate isotopically-labeled reagent in place of the non-labeled reagent previously.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

Wherever a compound of the formula IA or IB, or a compound of or according to the invention, is mentioned, this is intended to include any one or more of these forms.

Pharmaceutically acceptable esters are preferably prodrug ester derivatives, such being convertible by solvolysis or cleavage under physiological conditions to the corresponding agents of the invention which comprise free hydroxyl groups. Suitable pharmaceutically acceptable prodrug esters are those derived from a carboxylic acid, a carbonic acid monoester or a carbamic acid, advantageously esters derived from an optionally substituted lower alkanoic acid or an arylcarboxylic acid.

In particular, the invention relates to a compound described in the working examples and may be selected from the following compounds of formula (IA) or (IB):

2-(1-aminomethyl-cyclopropyl)-8-[5-(2-methoxy-ethoxy)-pyridin-3-yl]-4,5-dihydro-1H-pyrrolo[2,3-f]isoquinoline-3-carboxylic acid lactame, 2-(1-aminomethyl-cyclopropyl)-8-((E)-styryl)-4,5-dihydro-1H-pyrrolo[2,3-f]isoquinoline-3-carboxylic acid lactame, 2-(1-amino-cyclobutylmethyl)-8-[5-(2-methoxy-ethoxy)-pyridin-3-yl]-4,5-dihydro-1H-pyrrolo[2,3-f]isoquinoline-3-carboxylic acid lactame, 2-(1-amino-cyclopropylmethyl)-8-[4-(3-amino-3-methyl-but-1-ynyl)-phenyl]-4,5-dihydro-2H-1,2,7-triaza-cyclopenta[a]naphthalene-3-carboxylic acid lactame, 2-(1-amino-cyclopropylmethyl)-8-[4-(3-amino-3-methyl-butyl)-phenyl]-4,5-dihydro-2H-1,2,7-triaza-cyclopenta[a]naphthalene-3-carboxylic acid lactame, 2-(1-amino-cyclobutylmethyl)-8-((E)-styryl)-4,5-dihydro-1H-pyrrolo[2,3-f]isoquinoline-3-carboxylic acid lactame, 2-(1-amino-cyclopropylmethyl)-8-[4-(3-hydroxy-3-methyl-but-1-ynyl)-phenyl]-4,5-dihydro-2H-1,2,7-triaza-cyclopenta[a]naphthalene-3-carboxylic acid lactame, 2-(1-amino-cyclopropylmethyl)-8-[4-(3-hydroxy-3-methyl-butyl)-phenyl]-4,5-dihydro-2H-1,2,7-triaza-cyclopenta[a]naphthalene-3-carboxylic acid lactame, 2-(1-amino-cyclopropylmethyl)-8-[5-(2-methoxy-ethoxy)-pyridin-3-yl]-4,5-dihydro-2H-1,2,7-triaza-cyclopenta[a]naphthalene-3-carboxylic acid lactame, 2-(1-amino-cyclopropylmethyl)-8-((E)-styryl)-4,5-dihydro-2H-1,2,7-triaza-cyclopenta[a]naphthalene-3-carboxylic acid lactame, 2-(3-amino-azetidin-3-ylmethyl)-8-(4-methoxy-phenyl)-4,5-dihydro-2H-1,2,7-triaza-cyclopenta[a]naphthalene-3-carboxylic acid lactame, 2-(1-acetyl-3-amino-azetidin-3-ylmethyl)-8-(4-methoxy-phenyl)-4,5-dihydro-2H-1,2,7-triaza-cyclopenta[a]naphthalene-3-carboxylic acid lactame, 2-(3-amino-azetidin-3-ylmethyl)-8-[5-(2-methoxy-ethoxy)-pyridin-3-yl]-4,5-dihydro-2H-1,2,7-triaza-cyclopenta[a]naphthalene-3-carboxylic acid lactame, 2-(1-amino-cyclobutylmethyl)-8-(4-methoxy-phenyl)-4,5-dihydro-1H-1,7,9-triazacyclopenta[a]naph-thalene-3-carboxylic acid lactame, 2-(1-amino-cyclobutylmethyl)-8-[4-(3-amino-3-methyl-but-1-ynyl)-phenyl]-4,5-dihydro-1H-1,7,9-triaza-cyclopenta[a]naphthalene-3-carboxylic acid lactame, 2-(1-amino-cyclobutylmethyl)-8-[4-(3-amino-3-methyl-butyl)-phenyl]-4,5-dihydro-1H-1,7,9-triaza-cyclopenta[a]naphthalene-3-carboxylic acid lactame, 2-(1-aminomethyl-cyclopropyl)-8-(4-methoxy-phenyl)-4,5-dihydro-1H-1,7,9-triaza-cyclopenta[a]naphthalene-3-carboxylic acid lactame, 2-(3-amino-azetidin-3-ylmethyl)-8-(4-methoxy-phenyl)-4,5-dihydro-1H-1,7,9-triaza-cyclopenta[a]naphthalene-3-carboxylic acid lactame, 2-(1-amino-cyclobutylmethyl)-8-(3-fluoro-phenyl)-4,5-dihydro-1H-1,7,9-triaza-cyclopenta[a]naphthalene-3-carboxylic acid lactame, 2-(3-amino-oxetan-3-ylmethyl)-8-(4-methoxy-phenyl)-4,5-dihydro-1H-pyrrolo[2,3-f]isoquinoline-3-carboxylic acid lactame, 2-(3-amino-oxetan-3-ylmethyl)-8-(4-methoxy-phenyl)-4,5-dihydro-1H-1,7,9-triaza-cyclopenta[a]naphthalene-3-carboxylic acid lactame, 2-(3-amino-oxetan-3-ylmethyl)-8-(3-fluoro-phenyl)-4,5-dihydro-1H-1,7,9-triaza-cyclopenta[a]naphthalene-3-carboxylic acid lactame, and 2-(3-amino-azetidin-3-ylmethyl)-8-(4-methoxy-phenyl)-4,5-dihydro-1H-pyrrolo[2,3-f]isoquinoline-3-carboxylic acid lactame, or any other compound mentioned in the Examples and falling under formula IA or IB, or also 9-chloromethyl-9-hydroxymethyl-2-(4-methoxy-phenyl)-5,6,8,9,10,11-hexahydro-1,3,8,11-tetraaza-benzo[a]fluoren-7-one or 9-chloromethyl-2-(3-fluoro-phenyl)-9-hydroxymethyl-5,6,8,9,10,11-hexahydro-1,3,8,11-tetraaza-benzo[a]fluoren-7-one, or 2-(3-Amino-azetidin-3-ylmethyl)-8-(3-fluoro-phenyl)-4,5-dihydro-1H-pyrrolo[2,3-f]isoquinoline-3-carboxylic acid lactam;

a pharmaceutically acceptable ester or amide thereof, and/or a pharmaceutically acceptable salt thereof.

The invention in another aspect provides a compound of formula (IA) or (IB), a pharmaceutically acceptable cleavable ester or amide thereof, and/or a pharmaceutically acceptable salt thereof, respectively, for use in the diagnostic or therapeutic or prophylactic treatment of the animal, especially the human body, more especially a disease or condition as mentioned below.

The invention in another aspect provides the use of a compound of formula (IA) or (IB), a pharmaceutically acceptable cleavable ester or amide thereof, and/or a pharmaceutically acceptable salt thereof, respectively, in the manufacture of a medicament for the treatment of an autoimmune disease or condition.

The invention in another aspect provides the use of a compound of formula (IA) or (IB), a pharmaceutically acceptable cleavable ester or amide thereof, and/or a pharmaceutically acceptable salt thereof, respectively, for the treatment of cytokine mediated, e.g. TNF alpha mediated and/or MK2 related conditions.

The invention in another aspect provides a method of treatment of cytokine mediated, e.g. TNF alpha mediated and/or MK2 related conditions comprising administering an effective amount of a compound of formula (IA) or (IB), a pharmaceutically acceptable cleavable ester or amide thereof, and/or a pharmaceutically acceptable salt thereof, respectively, to a patient in need of such treatment.

The invention in another aspect provides a pharmaceutical composition comprising a compound of formula (IA) or (IB), a pharmaceutically acceptable cleavable ester or amide thereof, and/or a pharmaceutically acceptable salt thereof, respectively, together with one or more pharmaceutically acceptable excipients, diluents or carriers, collectively also referred to as carrier materials herein.

In the following description of the processes for manufacture, both in the starting materials as well as in the intermediates R, R2, R3, D, R4, R5, X, R6, R7, Y and A, where present, have the meanings given above, especially as preferred, for compounds of the formula IA or IB, if not mentioned otherwise.

In another aspect the invention provides a process for preparing a compound of formula (IA) or (IB), a pharmaceutically acceptable cleavable ester or amide thereof, and/or a pharmaceutically acceptable salt thereof, respectively, comprising a) reacting, for the manufacture of a compound of the formula IA wherein X is CH and the other moieties are as defined for a compound of the formula IA, a compound of the formula IIA,

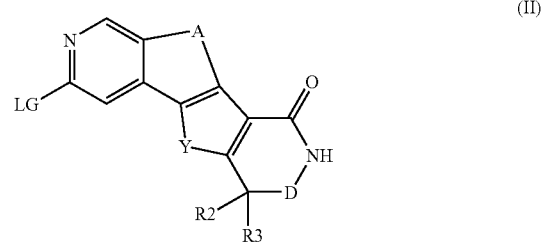

(II)

wherein LG is a leaving group and A, Y, R2, R3 and D are as defined for a compound of the formula IA, with a compound of the formula III, R—B(R$^a$)$_2$ (III)

wherein R is as defined for a compound of the formula IA and $R^a$ is hydroxyl or $C_1$-$C_7$-alkoxy or both moieties $R^a$ together form a $C_2$-$C_4$-alkylene bridge that is unsubstituted or substituted by up to 4 $C_1$-$C_4$-alkyl moieties, under coupling conditions in the presence of a catalyst; or b) for the manufacture of a compound of the formula IB wherein A is —$CH_2$— or —$CH_2$—$CH_2$— and X is N, reacting a compound of the formula IV,

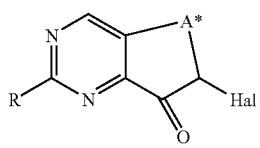

(IV)

wherein R is as defined for a compound of the formula IB, Hal is halo and A* is —$CH_2$— or is —$CH_2$—$CH_2$—, with a compound of the formula V,

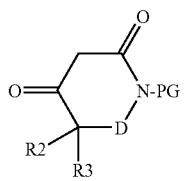

(V)

wherein PG is a protecting group, e.g. tert-butoxycarbonyl, and R2, R3 and D are as defined for a compound of the formula IB, in the presence of an amine of the formula VI,

R7-NH₂ (VI)

wherein R7 is as defined for a compound of the formula I, or a salt thereof, and removing the protecting group PG, or c) for the manufacture of a compound of the formula IB, deprotecting a compound of the formula VII,

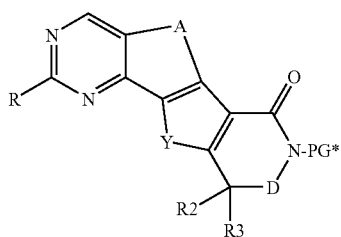

(VII)

wherein R, A, Y, R2, R3 and D are as defined for a compound of the formula IB, and PG* is an amino protecting group, e.g. tert-butoxycarbonyl, wherein in any of the starting materials mentioned in process variants a), b) or c) protecting groups may be present that can be removed at appropriate stages;

and, if desired, converting an obtainable free compound of the formula (IA) or (IB) into a pharmaceutically acceptable cleavable ester or amide thereof, and/or a pharmaceutically acceptable salt thereof, respectively, an obtainable salt into the free compound or into a different salt, and/or into a different compound of the formula IA or IB, if desired separating the isomers of a compound of the formula (IA) or (IB) into the isomers thereof.

Referring to the reaction under a), the leaving group LG is preferably lower alkanesulfonyloxy or more preferably halo, especially chloro or bromo, and the coupling reaction is conducted under Suzuki or Suzuki-Miyaura or analogous reaction conditions, e.g. using an appropriate solvent, such as an alcohol, e.g. 1-propanol, an ether, e.g. tetrahydrofurane, dimethylformamide or diethylformamide, dimethyl- or diethylacetamide, dimethoxyethyne, a cyclic hydrocarbon, such as toluene, a haloalkane, such as dichloromethyne, or a mixture of two or more such solvents and optionally water, on the presence of a noble metal catalyst for cross-coupling, such as a palladium(II)complex, for example bis(triphenylphosphine)palladium(II)dichloride or [1,1'-bis(diphenylphosphino)ferrocene]-dichloropalladium(II) (e.g. as dichloromethane complex), in the presence of a base, such as potassium carbonate, an alkalimetal-$C_1$-$C_7$-alkanoate, such as sodium or potassium acetate, sodium hydroxide or sodium carbonate, at a preferred temperature in the range from 70 to 160° C. or the like; or according to another preferred method in a cyclic ether solvent, e.g. tetrahydrofurane, with or without the presence of water, in the presence of a catalyst for cross-coupling, e.g. a noble metal catalyst, such as a palladium(0)complex, for example tris(dibenzylideneacetone)-dipalladium(0), or of palladium dibenzoylideneacetone as precursor, wherein useful in the presence of an appropriate ligand, such as 2-dicyclohexylphosphino-2',6'-dimethoxybiphenyl (SPhos) or 2-dicyclohexylphosphino-2'-(N,N-dimethylamino)biphenyl (P1), and in the presence of a base, e.g. as mentioned above or potassium or sodium phosphate, and at preferred temperatures in the range from 80 to 160° C.; if required, another or additional catalysts can be added, e.g. Pd(dppf)Cl₂.CH₂Cl₂, or mixtures of catalysts can be used.

The reaction under variant b) can preferably be conducted in the presence of an appropriate solvent, e.g. an alcohol, such as methanol or ethanol, at preferred temperatures e.g. in the range from 0 to 50° C.

The deprotection under c) can take place according to standard methods. For example, tert-butoxycarbonyl as amino protecting group can be removed under conditions as described in Examples 11, 13 and 14.

Generally, protecting groups, their introduction and their removal are as known in the art, e.g. as described in T. W. Greene, "Protective Groups in Organic Synthesis", $3^{rd}$ edition, Wiley, New York 1999, or comparable textbooks or publications.

Reaction, where appropriate, may be lead under pressure in closed vessels, heating may, inter alia, be done by microwaves.

The compounds of formula (IA) or (IB) (also referred herein to as "compounds of the invention) in free form may be converted into salt forms in conventional manner and viceversa.

The compounds of the invention can be recovered from the reaction mixture and purified in conventional manner. Isomers, such as enantiomers, may be obtained in conventional manner, e.g. by fractional crystallization or asymmetric synthesis from corresponding asymmetrically substituted, e.g. optically active starting materials.

Among the possible conversions of compounds of the formula IA or IB obtainable according to any one of variants a), b) or c), an amino- or hydroxyl-$C_3$-$C_7$-alkynyl group can be converted into the corresponding amino- or hydroxyl-$C_3$-$C_7$-alkyl group by reduction with an appropriate reductant, preferably hydrogen in the presence of a catalyst or by transfer hydrogenation e.g. using ammonium formate, booth variants in the presence of a noble metal catalyst, especially palladium, preferably on carbon, in an appropriate solvent, such as an alcohol, e.g. methanol or ethanol, preferably at temperatures between room temperature and the reflux temperature of the reaction mixture, e.g. under reflux.

$C_1$-$C_7$-alkoxy substituents e.g. as part of R in formula IA or IB can be converted into hydroxyl, e.g. by using pyridine in salt form, e.g. pyridine.HCl, in a melt, e.g. at 100 to 210° C.

Hydrogen R6 can be converted to acyl R6 e.g. by reaction with an acid halogenide or anhydride or activated ester capable of introducing R6, e.g. R6-Cl, in an appropriate solvent, e.g. an ether, such as tetrahydrofurane, e.g. in the presence of a base, such as sodium carbonate, e.g. at temperatures as given in the Examples.

Y=O or S in a compound of the formula IA or IB can be converted into Y=NR7, e.g. by reaction with a compound of the formula VI mentioned above in the absence or presence of a solvent, such as the compound of the formula VI itself and/or an alcohol, such as propanol, in the absence or presence of a base, e.g. sodium hydroxide, at elevated temperatures, e.g. in the range from 100 to 160° C.

Y=NR7 in a compound of the formula IA or IB can be converted into Y=O or S, e.g. by reaction with a compound of the formula VI mentioned above in the absence or presence of a solvent, such as the compound of the formula VI itself, at elevated temperatures, e.g. in the range from 100 to 160° C.

In another aspect the invention provides a combination comprising a compound according to any one of claims 1 to 6 in combination with one or more active agents selected from the following: Anti IL-1 agents, anti cytokine and anti-cytokine receptor agents, B-cell and T-cell modulating drugs, disease-modifying anti-rheumatic agents (DMARDs), gold salts, penicillamine, hydroxychloroquine and chloroquine, azathioprine, glucocorticoids, non-steroidal anti-inflammatories (NSAIDs), selective COX-2 inhibitors, agents which modulate migration of immune cells, chemokine receptor antagonists, modulators of adhesion molecules, for simultaneous, separate or sequential administration, e.g. in the form of a fixed combination and/or as a kit of parts.

The invention further relates either to a compound of the formula IA or to a compound of the formula IB, as described hereinabove- or especially hereinbelow, or a pharmaceutically acceptable salt thereof.

The invention also relates to any one of the compounds of the formula IA or IB given in the Examples, or a pharmaceutically acceptable salt thereof.

The invention also relates to the embodiments in the claims which are therefore included into the description by reference.

Starting materials can be synthesized as shown below in Schemes 1 to 6, or as or in analogy to methods specifically described in the Examples. For example, a compound of the formula II can be obtained as shown for a compound 5 in Scheme 2 below, a compound of the formula IV as a compound of the formula 15 in Scheme 4 below.

Other starting materials can be obtained commercially, by methods described in the examples or in analogy thereto, by methods known in the art and/or in analogy to such methods.

Novel starting materials and intermediates, in free, in salt form, in unprotected form and/or in protected form, also form part of the invention.

Agents of the invention may be prepared by processes described below, which serve to illustrate the invention without limiting its scope:

If no reaction temperatures are given, the reaction takes place at about room temperature. Relative shares of solvents, e.g. in eluents or the like, are given as part per volume (v/v).

Experimental Procedures

| Abbreviations: | |
|---|---|
| Ac | acetyl |
| AcOH | acetic acid |
| Boc | tert-butoxycarbonyl |
| brine | sodium chloride solution in water saturated at room temperature |
| tBu | tert-butyl |
| $CH_2Cl_2$ | methylene chloride |
| conc. | concentrated |
| DMAP | 4-dimethylaminopyridine |
| DMF | N,N-dimethylformamide |
| DMSO | dimethyl sulfoxide |
| dppf | (diphenylphosphino)ferrocene |
| EDC | N-(3-dimethylaminopropyl)-N'-ethyl-carbodiimide |
| Et | ethyl |
| EtOAc | ethyl acetate |
| EtOH | ethanol |
| $HCl_{conc}$ | concentrated hydrochloric acid (37 % in water) |
| Me | methyl |
| MeOH | methanol |
| Meldrum's acid | 2,2-dimethyl-1,3-dioxane-4,6-dione |
| min, min. | minute(s) |
| MS | mass spectrometry |
| $Na_2SO_4$ | sodium sulfate |
| NBS | N-bromosuccinimide |
| $NEt_3$ | triethylamine |
| $NH_3$ | ammonia |
| $NH_{3conc}$ | concentrated ammonia (25 % in water) |
| NMR | Nuclear Magnetic Resonance |
| OAc | acetate |
| $PPh_3$ | triphenylphosphine |
| $SiO_2$ | silica |
| TBME | tert-butyl methyl ether |
| THF | tetrahydrofuran |

Note: Compounds mentioned as "by-product" in the Examples are also active in the test systems and thus form part of the present invention.

The synthesis of intermediates 2 and 3 is described in Scheme 1. 3-Chloro-5,6,7,8-tetrahydro-isoquinoline 1 is first converted into its oxime derivative, which after hydrolysis delivers the desired ketone 2. Bromination renders bromoketone 3.

In the following reaction schemes, A, X, D, Y, R, R2, R3, R4, R5 and R7 (also represented as $R_7$ in some formulae) are as defined for a compound of the formula I Scheme 1

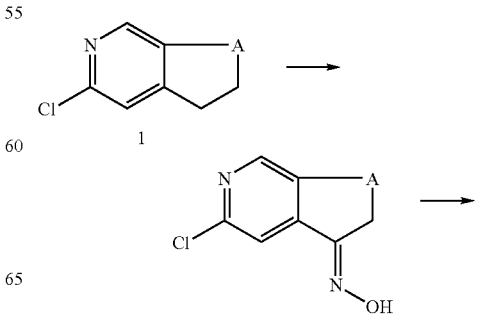

-continued

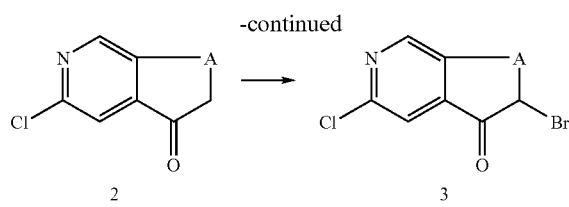

Bromoketone 3 is reacted with piperidine-2,4-dione derivatives and ammonium acetate or an amine R7-NH₂ (preferably as acetate) in MeOH to yield the desired products 4 and 6 (Scheme 2). Suzuki coupling delivers products 5 and 7.

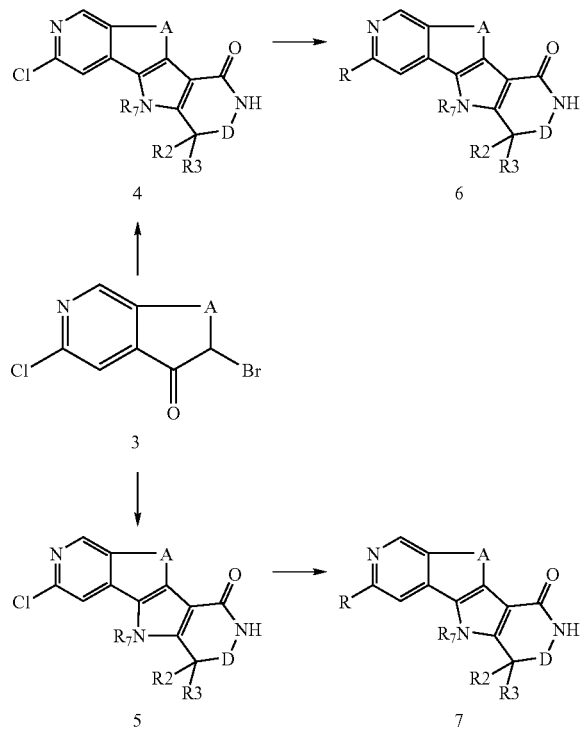

Scheme 2

Treatment of 3 with piperidine-2,4-dione in NaOAc followed by dehydration with H₂SO₄ renders 5,8,9,10-tetrahydro-6H-11-oxa-3,8-diaza-benzo[a]fluoren-7-one or analogues 8 (Scheme 3). Treatment of 8 or 10 at elevated temperature with primary amines R7-NH₂ generates 11. Suzuki couplings are performed with 8 and 10 yielding 10 and 11.

Scheme 3

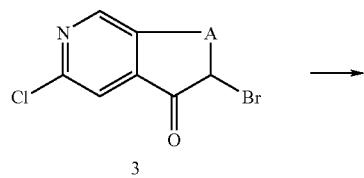

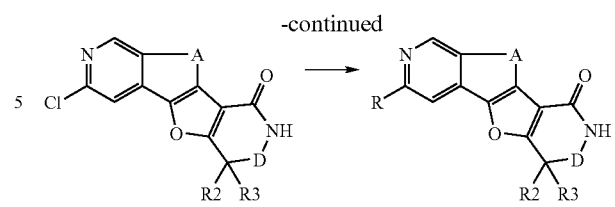

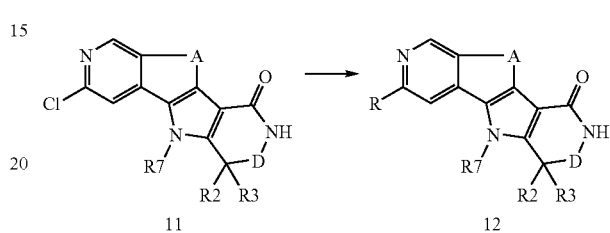

Alternatively, for compounds of the formula I wherein X is N, amidines 12 and 6-[1-dimethyl-amino-meth-(E)-ylidene]-2-ethoxy-cyclohex-2-enone analogues 13 are reacted to enolether 14 which after hydrolysis gives ketone 15 (Scheme 4).

Scheme 4

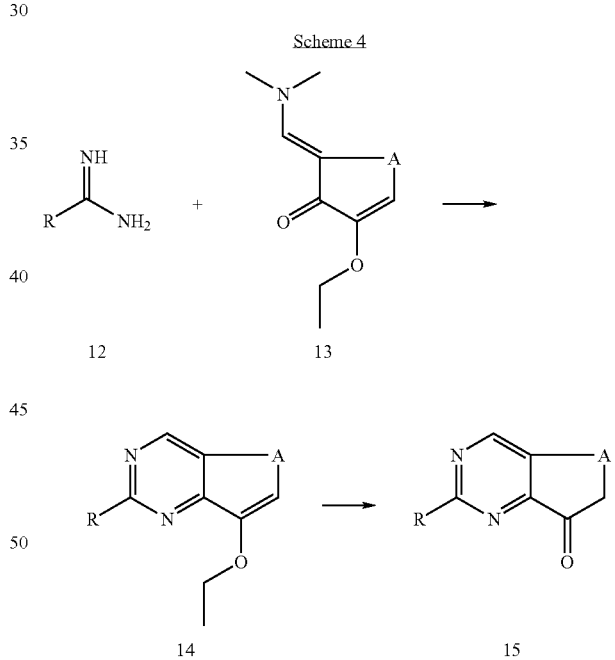

Bromination yields bromoketone 16. The latter is reacted with a piperidine-2,4-dione or pyrrolidin-2,4-dione compound and R7-NH2 (preferably in acetate salt form) in MeOH to yield the tetracyclic products 17. Alternatively, deprotonation of ketone 15 and reacting the anion with diethyl oxalate generates diketone 18. Condensation of the latter with hydrazine delivers the tricyclic 4,5-dihydro-2H-1,2,7,9-tetraazacyclopenta[a]naphthalene-3-carboxylic acid ethyl ester or analogues 19. N-alkylation e.g. with amines of the formula Boc-NH-D-C(R2)(R3)-Br yields 20, which after deprotection and lactamization delivers 21 (Scheme 5)

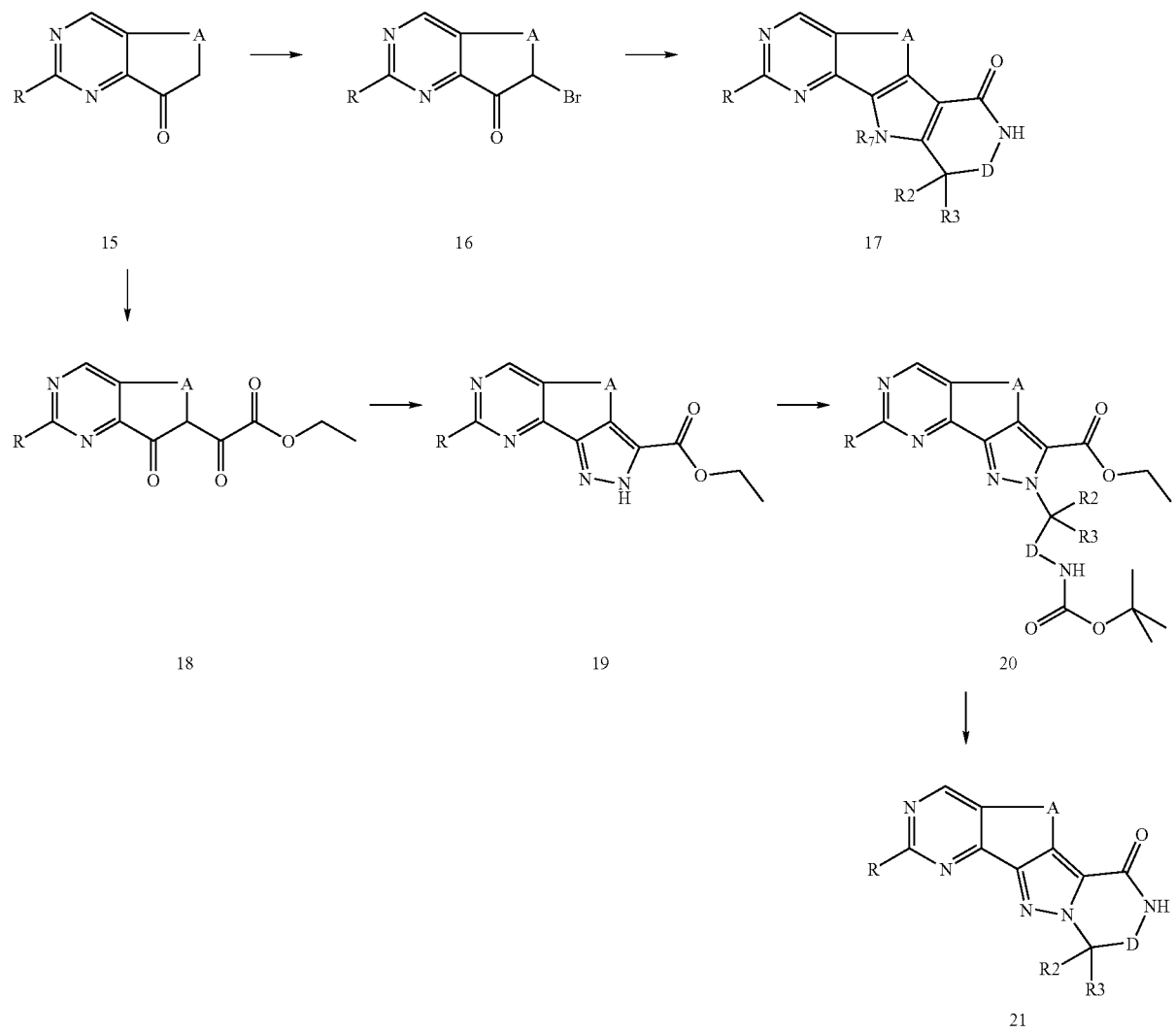

Alternatively, deprotonation of ketone 2 and reacting the anion with diethyl oxalate generates diketone 22 (Scheme 6). Condensation of the latter with hydrazine delivers the tricyclic 8-chloro-4,5-dihydro-2H-1,2,7-triaza-cyclopenta[a]naphthalene-3-carboxylic acid ethyl ester or analogue 23. N-alkylation e.g. with Boc-NH-C(R2)(R3)-D-Br, deprotection and lactamization delivers 26. Suzuki coupling reactions yield 5,6,9,10-tetrahydro-8H-3,8,10a,11-tetraaza-benzo[a]fluoren-7-ones or analogues 25.

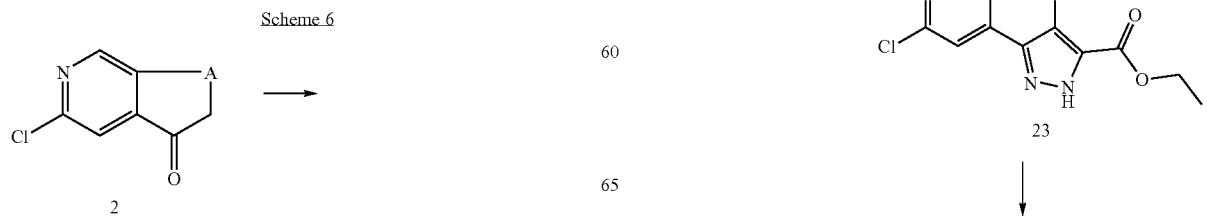

-continued

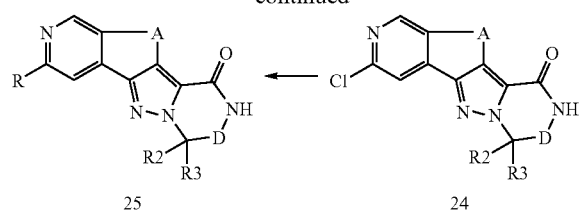

Experimental

EXAMPLE 1

2-(1-Aminomethyl-cyclopropyl)-8-[5-(2-methoxy-ethoxy)-pyridin-3-yl]-4,5-dihydro-1H-pyrrolo[2,3-f]isoquinoline-3-carboxylic acid lactame

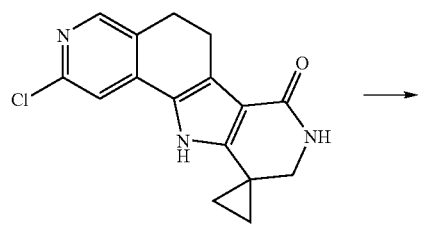

2-(1-Aminomethyl-cyclopropyl)-8-chloro-4,5-dihydro-1H-pyrrolo[2,3-f]isoquinoline-3-carboxylic acid lactame (80 mg; 0.26 mmol), 3-(2-methoxy-ethoxy)-5-(4,4,5,5-tetramethyl-[1,3,2]dioxaborolan-2-yl)-pridine (149 mg; 0.53 mmol), Pd(PPh$_3$)$_2$Cl$_2$ (56 mg; 0.08 mmol), Pd(dppf)Cl$_2$.CH$_2$Cl$_2$ (8.7 mg; 0.001 mmol), PPh$_3$ (70 mg; 0.26 mmol) and 2N Na$_2$CO$_3$ (0.8 ml; 1.6 mmol) in 1-propanol (4 ml) are microwaved at 150° C. for 20 minutes. The reaction mixture is filtered and purified via chromatography (SiO$_2$; TBME/MeOH/NH3$_{conc}$ 95:5:1) to yield a brown resin, which after trituration with MeOH delivers the title compound as yellow crystals.

1H-NMR (400 MHz; DMSO-d6: 11.20 (s, 1H); 8.83 (d, 1H); 8.42 (s, 1H); 8.37 (d, 1H); 8.03 (s, 1H); 7.93 (dd, 1H); 7.13 (s, 1H); 4.29 (dd, 2H); 3.73 (dd, 2H); 3.35 (s, 3H); 3.28 (d, 2H); 2.95 (m, 2H); 2.89 (m, 2H); 1.21 (dd, 2H); 1.07 (dd, 2H). MS (m/z) ES+: 417 (MH+).

The starting materials are prepared as follows:

1.a: 3-Chloro-7,8-dihydro-6H-isoquinolin-5-one oxime

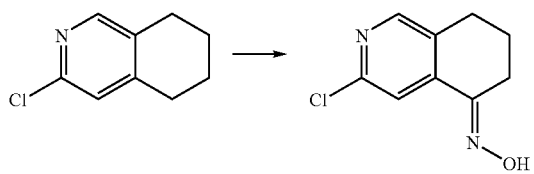

3-Chloro-5,6,7,8-tetrahydro-isoquinoline (Chemische Berichte 1948, 81, 279) (8.82 g; 52.6 mmol) dissolved in THF (65 ml) is added under stirring at room temperature to a solution of KOtBu (11.78 g; 105.2 mmol) in THF (100 ml). The red turbid solution is stirred for 12 hours and then cooled to 0° C. tert-Butyl nitrite (18.7 ml; 157.8 mmol) is added dropwise, the reaction mixture is stirred at room temperature for 4 hours and poured on brine. The reaction mixture is extracted with ethyl acetate three times, the organic phases are combined, dried over Na$_2$SO$_4$ and evaporated to dryness, yielding the desired product as brownish crystals. 1H-NMR (400 MHz; DMSO-d6): 11.83 (s, 1H); 8.28 (s, 1H); 7.66 (s, 1H); 2.72 (m, 2H); 2.66 (m, 2H); 1.77 (m, 2H). MS (m/z) ES+: (197, MH+).

1.b: 3-Chloro-7,8-dihydro-6H-isoquinolin-5-one

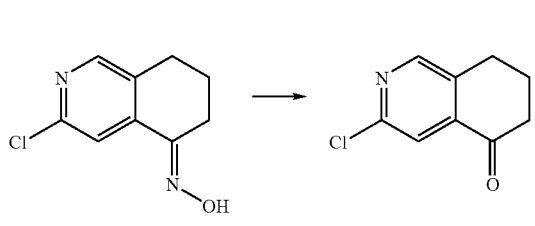

3-Chloro-7,8-dihydro-6H-isoquinolin-5-one oxime (9.10 g; 46.3 mmol) dissolved in acetone (105 ml) and HCl$_{conc}$ (105 ml) is heated at 60° C. for 1 hour. The reaction mixture is poured on 2N Na$_2$CO$_3$ and extracted with ethyl acetate three times, the organic phases are combined, dried over Na$_2$SO$_4$ and evaporated to dryness. Chromatography (SiO$_2$; Hexanes/acetone 85:15) yields the desired ketone as yellowish crystals. 1H-NMR (400 MHz; DMSO-d6): 8.57 (s, 1H); 7.66 (s, 1H); 2.96 (m, 2H); 2.71 (m, 2H); 2.10 (m, 2H). MS (m/z) ES+: 182 (MH+).

1.c: 6-Bromo-3-chloro-7,8-dihydro-6H-isoquinolin-5-one

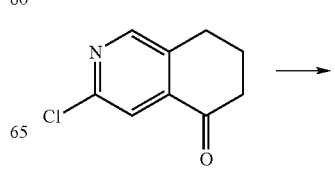

-continued

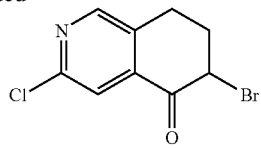

3-Chloro-7,8-dihydro-6H-isoquinolin-5-one (4.5 g; 24.78 mmol) is dissolved in 48% HBr and combined under stirring with Br$_2$ (3.96 g; 24.78 mmol) in AcOH (27 ml). After 30 min. at room temperature, the reaction mixture is poured on 2N Na$_2$CO$_3$ and extracted with TBME three times. The organic phases are combined, dried over Na$_2$SO$_4$ and evaporated to dryness to yield the bromoketone as brownish crystals, which are used without further purification in the next step.

1.d: 2-(1-Aminomethyl-cyclopropyl)-8-chloro-4,5-dihydro-1H-pyrrolo[2,3-f]isoquinoline-3-carboxylic acid lactame

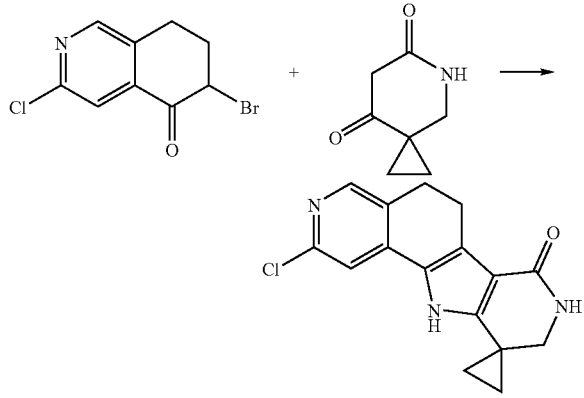

6-Bromo-3-chloro-7,8-dihydro-6H-isoquinolin-5-one (200 mg; 0.77 mmol) and 5-aza-spiro[2.5]octane-6,8-dione (230 mg; 1.1 mmol) (WO 2005014572, WO 2005013986), together with ammonium acetate (178 mg; 2.3 mmol), in MeOH (5 ml) are refluxed for 1 hour and kept at room temperature for 12 hours. After another 2 hours of refluxing, the reaction mixture is evaporated, taken up in CH$_2$Cl$_2$, filtered and purified via chromatography chromatography (SiO$_2$; TBME/MeOH/NH$_{3conc}$ 96:4:0.5>93:7:1) to yield the title compound as yellowish crystals. 1H-NMR (400 MHz; DMSO-d6): 11.29 (s, 1H); 8.11 (s, 1H); 7.45 (s, 1H); 7.15 (s, 1H); 3.26 (d, 2H); 2.92 (bt, 2H); 2.82 (bt, 2H); 1.19 (m, 2H); 1.04 (m, 2H).

MS (m/z) ES+: (300, MH+).

1.e: 5-Bromo-3-(2-methoxy-ethoxy)-pyridine

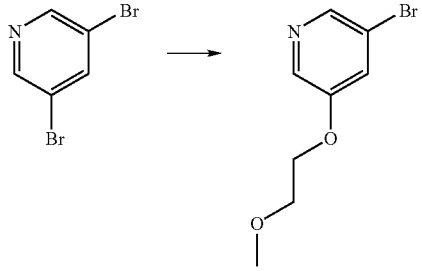

2-Methoxyethanol (2.7 ml; 33.8 mmol) is added dropwise to a suspension of NaH (55% suspension; 1.62 g; 37.14 mmol) in DMF (60 ml). After stirring for 30 minutes, 3,5-dibromopyridine (4.0 g; 16.88 mmol) is introduced and the mixture heated to 50° C. for 1 hour. The reaction mixture is poured on water and extracted with ethyl acetate three times, the organic phases are combined, dried over Na$_2$SO$_4$ and evaporated to dryness. Chromatography (SiO$_2$; Hexanes/acetone 85:15) yields the title compound as yellow solid.

1H-NMR (400 MHz; DMSO-d6): 8.31 (d, 1H); 8.28 (d, 1H); 7.73 (t, 1H); 4.23 (dd, 2H); 3.67 (dd, 2H); 3.32 (s, 3H). MS (m/z) ES+: 232, 234 (MH+).

1.f: 3-(2-Methoxy-ethoxy)-5-(4,4,5,5-tetramethyl-[1,3,2]dioxaborolan-2-yl)-pyridine

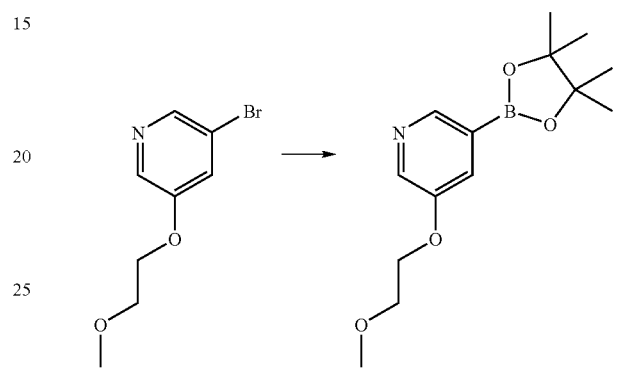

5-Bromo-3-(2-methoxy-ethoxy)-pyridine (6.7 g; 28.9 mmol), bis(pinacolato)diboron (8.8 g; 34.7 mmol), Pd(dppf)Cl$_2$.CH$_2$Cl$_2$ (660 mg; 0.81 mmol) and KOAc (8.5 g; 86.7 mmol) in DMF (240 ml) are heated to 160° C. for 20 minutes. The reaction mixture is evaporated, dissolved in TBME, filtered and evaporated again to deliver the target compound as a semi-crystalline red-brown solid, which is used in the next step without further purification.

EXAMPLE 2

2-(1-Aminomethyl-cyclopropyl)-8-((E)-styryl)-4,5-dihydro-1H-pyrrolo[2,3-f]isoquinoline-3-carboxylic acid lactame

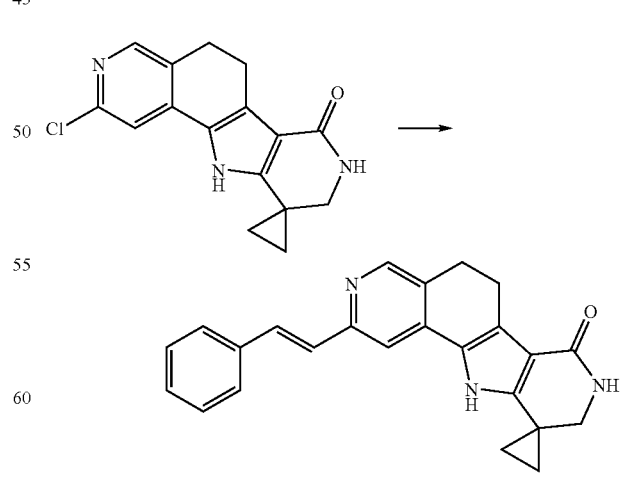

2-(1-Aminomethyl-cyclopropyl)-8-chloro-4,5-dihydro-1H-pyrrolo[2,3-f]isoquinoline-3-carboxylic acid lactame (74 mg; 0.25 mmol), trans-2-phenylvinyl boronic acid (73 mg;

0.5 mmol), Pd(PPh$_3$)$_2$Cl$_2$ (52 mg; 0.074 mmol), Pd(dppf) Cl$_2$.CH$_2$Cl$_2$ (8 mg; 0.01 mmol), PPh$_3$ (65 mg; 0.24 mmol) and 2N Na$_2$CO$_3$ (0.74 ml; 1.4 mmol) in 1-propanol (3 ml) are microwaved at 150° C. for 20 minutes. The reaction mixture is filtered and purified via chromatography (SiO$_2$; TBME/MeOH/NH$_{3conc}$ 95:5:1>92:8:1) to yield a brown resin, which after trituration with MeOH delivers the title compound as yellow crystals.

1H-NMR (400 MHz; DMSO-d6: 11.28 (s, 1H); 8.32 (s, 1H); 7.66 (d, 2H); 7.57 (s, 1H); 7.54 (d, 1H); 7.43 (dd, 2H); 7.34 (m, 1H); 7.22 (d, 1H); 7.10 (s, 1H); 3.28 (s, 2H); 2.93 (m, 2H); 2.86 (m, 2H); 1.23 (m, 2H); 1.03 (m, 2H). MS (m/z) ES+: 368 (MH+).

EXAMPLE 3

2-(1-Amino-cyclobutylmethyl)-8-[5-(2-methoxy-ethoxy)-pyridin-3-yl]-4,5-dihydro-1H-pyrrolo[2,3-f]isoquinoline-3-carboxylic acid lactame

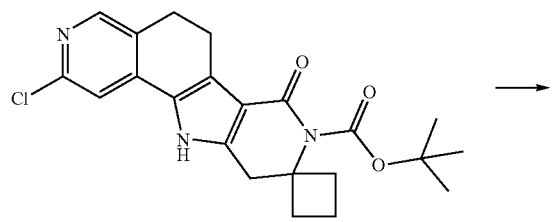

The title compound is prepared in analogy to Example 1. The reaction mixture is evaporated and purified via chromatography (SiO$_2$; TBME/MeOH/NH3$_{conc}$ 95:5:1) to yield a brown foam, which after trituration with MeOH delivers the title compound as greenish crystals.

1H-NMR (400 MHz; DMSO-d6): 11.89 (s, 1H); 8.85 (s, 1H); 8.43 (s, 1H); 8.39 (d, 1H); 8.05 (s, 1H); 7.95 (s, 1H); 7.50 (s, 1H); 4.30 (m, 2H); 3.74 (m, 2H); 3.35 (s, 3H); 3.04 (s, 2H); 2.92 (m, 4H); 2.14 (m, 2H); 2.07 (m, 2H); 1.77 (m, 2H). MS (m/z) ES+: 431 (MH+).

The starting materials are prepared as follows:

3.a: 6,8-Dioxo-5-aza-spiro[3.5]nonane-5-carboxylic acid tert-butyl ester

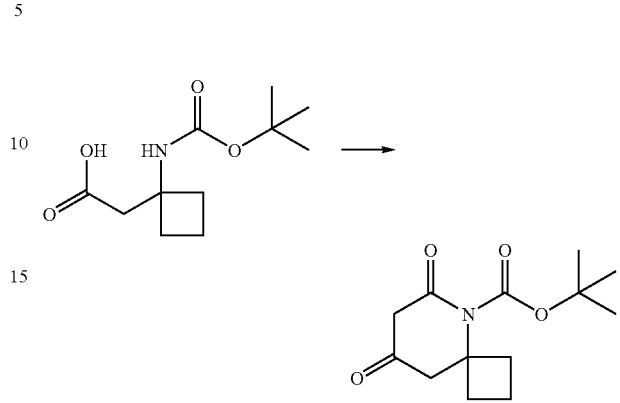

(1-tert-Butoxycarbonylamino-cyclobutyl)-acetic acid (6 g; 26 mmol) (Eur.J.Med.Chem. 34 (1999) 363), EDC (7.5 g; 39 mmol) DMAP (4.8 g; 39 mmol) and Meldrum's acid (3.77 g; 26 mmol) in CH2Cl2 (120 ml) are stirred at room temperature over night and poured on 2N HCl/water (40 ml/400 ml). The aqueous phase is extracted with CH$_2$Cl$_2$ twice, the organic phases are combined and dried over Na$_2$SO$_4$ and evaporated to dryness. The orange-colored residue is taken up in ethyl acetate (200 ml) and refluxed for 2.5 hours, diluted with hexanes (600 ml) and purified via chromatography (SiO$_2$; Hexanes/acetone 92:8) yielding the title compound as yellowish crystals in a modest purity, which is sufficient to perform the next steps.

3.b: 2-(1-tert-Butoxycarbonylamino-cyclobutylmethyl-8-chloro-4,5-dihydro-1H-pyrrolo[2,3-f]isoquinoline-3-carboxylic acid imide

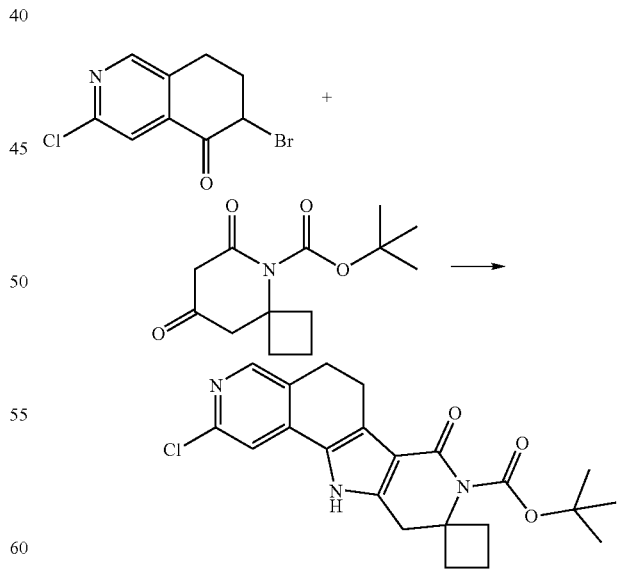

6-Bromo-3-chloro-7,8-dihydro-6H-isoquinolin-5-one (200 mg; 0.77 mmol), 6,8-dioxo-5-aza-spiro[3.5]nonane-5-carboxylic acid tert-butyl ester (200 mg; 0.93 mmol) and ammonium acetate (120 mg; 1.5 mmol) in MeOH (4 ml) are refluxed for 1 hour and left at room temperature over night.

The reaction mixture is evaporated, taken up in TBME and washed with 0.5 N NaOH. The organic phase is dried over Na$_2$SO$_4$, evaporated to dryness and purified via chromatography (SiO$_2$; acetone/hexanes 2:8) to yield the title compound as slightly grey crystals.

EXAMPLE 4

2-(1-Amino-cyclobutylmethyl)-8-((E)-styryl)-4,5-dihydro-1H-pyrrolo[2,3-f]isoquinoline-3-carboxylic acid lactame

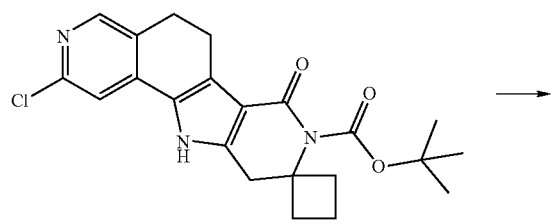

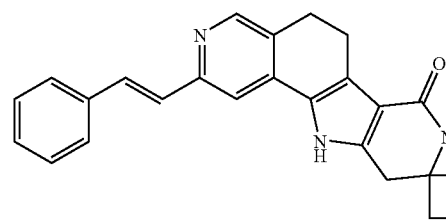

The title compound is prepared in analogy Example 2. The reaction mixture is evaporated and purified via chromatography (SiO$_2$; TBME/MeOH/NH$_{3conc}$ 95:5:1>92:8:1) to yield a brown resin, which after trituration with MeOH delivers the title compound as yellow crystals. 1H-NMR (400 MHz; DMSO-d6): 11.94 (s, 1H); 8.32 (s, 1H); 7.66 (d, 2H); 7.59 (d, 1H); 7.55 (s, 1H); 7.47 (s, 1H); 7.43 (dd, 2H); 7.34 (dd, 1H); 7.22 (d, 1H); 3.02 (s, 2H); 2.89 (m, 4H); 2.14 (m, 2H); 2.07 (m, 2H); 1.77 (m, 2H). MS (m/z) ES+: 382 (MH+).

EXAMPLE 5

2-(1-Amino-cyclopropylmethyl)-8-[4-(3-amino-3-methyl-but-1-ynyl)-phenyl]-4,5-dihydro-2H-1,2,7-triaza-cyclopenta[a]naphthalene-3-carboxylic acid lactame

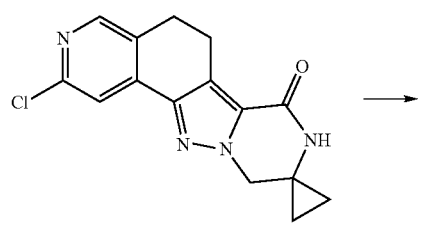

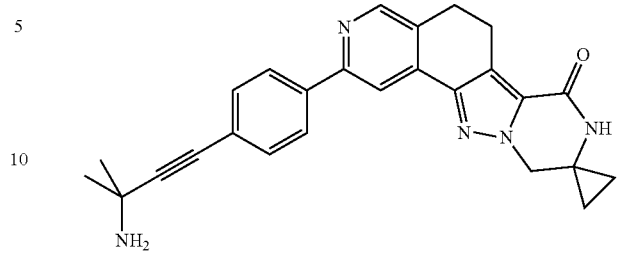

2-(1-Aminomethyl-cyclopropyl)-8-chloro-4,5-dihydro-1H-pyrrolo[2,3-f]isoquinoline-3-carboxylic acid lactame and 1,1-dimethyl-3-[4-(4,4,5,5-tetramethyl-[1,3,2]dioxaborolan-2-yl)-phenyl]-prop-2-ynylamine are reacted in analogy to Example 1 and purified via chromatography (SiO$_2$; CH$_2$Cl$_2$/MeOH/NH$_{3conc}$ 96:4:0.4) to yield the title compound as yellowish crystals, recrystallized from CH$_2$Cl$_2$/MeOH. 1H-NMR (400 MHz; DMSO-d6): 8.62 (s, 1H); 8.50 (s, 1H); 8.10 (m, 3H); 7.49 (d, 2H); 4.37 (s, 2H); 3.03 (m, 4H); 2.11 (s, 2H); 1.41 (s, 6H); 0.97 (bs, 2H); 0.93 (bs, 2H). MS (m/z) ES+: 424 (MH+).

The starting materials are prepared as follows:

5.a: (3-Chloro-5-oxo-5,6,7,8-tetrahydro-isoquinolin-6-yl)-oxo-acetic acid ethyl ester

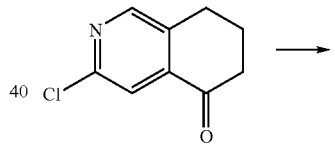

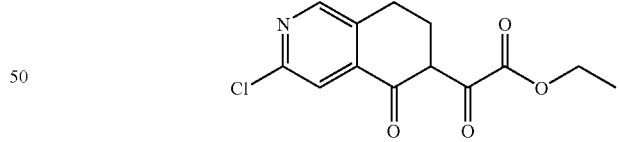

Sodium (253 mg; 11 mmol) is added portion-wise to EtOH (6 ml). After complete dissolution, diethyl oxalate (800 mg; 5.5 mmol) is introduced at room temperature, followed by 3-chloro-7,8-dihydro-6H-isoquinolin-5-one (1 g; 5.5 mmol) in EtOH (30 ml). The reaction mixture is stirred for 3 h at room temperature, poured on 1 N HCl and extracted with TBME three times. The organic phases are combined, dried over Na$_2$SO$_4$ and evaporated to dryness, yielding the desired product as orange oil. 1H-NMR (400 MHz; DMSO-d6): 8.47 (s, 1H); 7.68 (s, 1H); 4.29 (q, 2H); 3.42 (bs, 1H); 2.86 (bt, 2H); 2.63 (bt, 2H); 1.29 (t, 3H).

MS (m/z) ES+: 282 (MH+).

5.b: 8-Chloro-4,5-dihydro-2H-1,2,7-triaza-cyclopenta[a]naphthalene-3-carboxylic acid ethyl ester

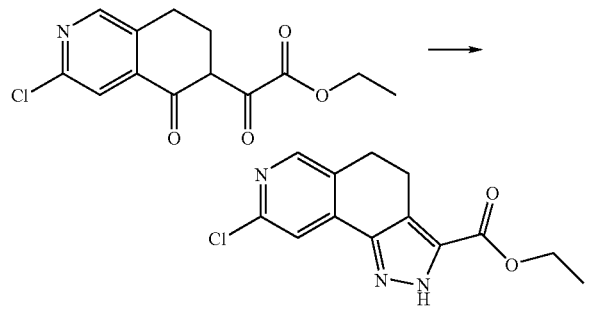

(3-Chloro-5-oxo-5,6,7,8-tetrahydro-isoquinolin-6-yl)-oxo-acetic acid ethyl ester (1.4 g; 4.8 mmol) in EtOH (15 ml) is combined with H₂NNH₂.H₂O (242 mg; 4.8 mmol) and refluxed for 1 hour. The mixture is left over night at room temperature and delivers the title compound as yellowish crystals. 1H-NMR (400 MHz; DMSO-d6): 8.37 (s, 1H); 7.68 (s, 1H); 4.36 (q, 2H); 3.5 (bs, 1H); 2.99 (m, 2H); 2.97 (m, 2H); 1.35 (t, 3H). MS (m/z) ES+: 278 (MH+).

5.c: 2-(1-tert-Butoxycarbonylamino-cyclopropylmethyl)-8-chloro-4,5-dihydro-2H-1,2,7-triaza-cyclopenta[a]naphthalene-3-carboxylic acid ethyl ester

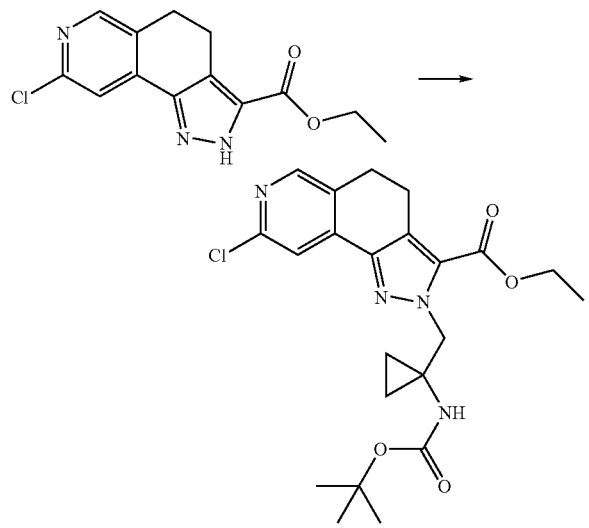

8-Chloro-4,5-dihydro-2H-1,2,7-triaza-cyclopenta[a]naphthalene-3-carboxylic acid ethyl ester (239 mg; 0.9 mmol) in DMF (4 ml) is treated at 50 C with LiOtBu (1N in THF; 0.9 ml; 0.9 mmol) for 10 minutes. (1-tert.-Butoxycarbonylamino-1-methanesulfonyloxymethyl)-cyclo-propane (U.S. Pat. No. 4,622,418) (250 mg; 0.9 mmol) in DMF (1 ml) is added and the mixture heated to 100° C. for 30 minutes. The reaction mixture is evaporated to dryness, taken up in TBME and washed several times with 0.5 N NaOH. The organic phase is dried over Na₂SO₄ and evaporated to dryness to yield the title compound as yellow crystals. 1H-NMR (400 MHz; DMSO-d6): 8.37 (s, 1H); 7.62 (s, 1H); 7.04 (s, 1H); 4.69 (s, 2H); 4.33 (q, 2H); 3.02 (m, 2H); 2.95 (m, 2H); 1.37 (t, 3H); 1.35 (s, 9H); 0.93 (m, 2H); 0.65 (m, 2H). MS (m/z) ES+: 447 (MH+).

5.d: 2-(1-Amino-cyclopropylmethyl)-8-chloro-4,5-dihydro-2H-1,2,7-triaza-cyclopenta[a]naphthalene-3-carboxylic acid ethyl ester hydrochloride

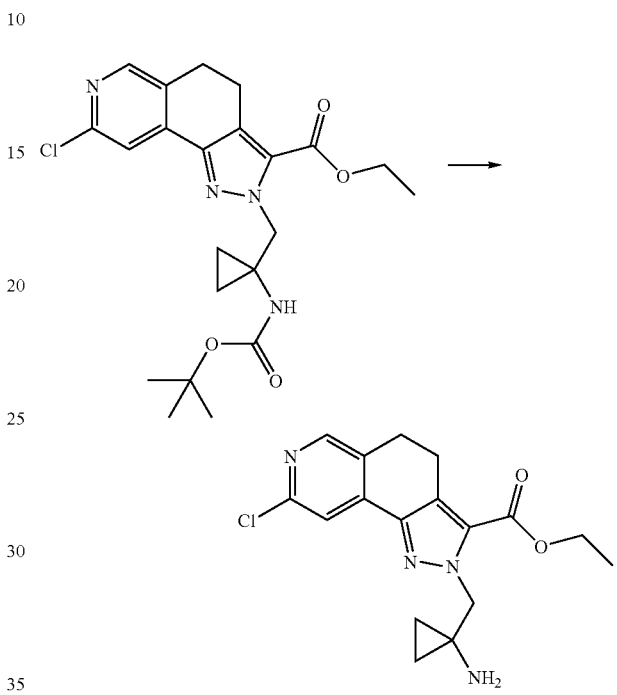

2-(1-tert-Butoxycarbonylamino-cyclopropylmethyl)-8-chloro-4,5-dihydro-2H-1,2,7-triaza-cyclopenta[a]naphthalene-3-carboxylic acid ethyl ester (236 mg; 0.53 mmol) is dissolved in HCl_conc (2 ml), kept at room temperature for 2 minutes, evaporated to dryness and triturated with diethyl ether to deliver the target compound as off-white solid. 1H-NMR (400 MHz; DMSO-d6): 8.25 (bs, 2H); 8.39 (s, 1H); 7.86 (s, 1H); 4.82 (s, 2H); 4.35 (q, 2H); 3.04 (m, 2H); 2.97 (m, 2H); 1.36 (t, 3H); 1.12 (m, 2H); 1.05 (m, 2H). MS (m/z) ES+: 347 (MH+).

5.e: 2-(1-Amino-cyclopropylmethyl)-8-chloro-4,5-dihydro-2H-1,2,7-triaza-cyclopenta[a]naphthalene-3-carboxylic acid lactame

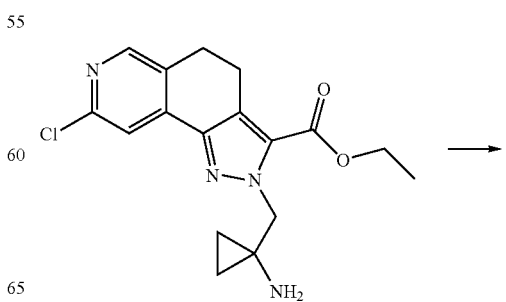

-continued

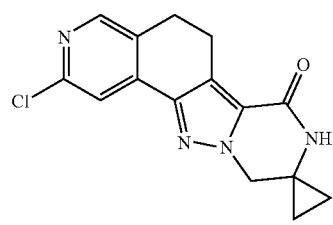

2-(1-Amino-cyclopropylmethyl)-8-chloro-4,5-dihydro-2H-1,2,7-triaza-cyclopenta[a]naphthalene-3-carboxylic acid ethyl ester hydrochloride (220 mg; 0.57 mmol) and $Cs_2CO_3$ (750 mg; 2.28 mmol) are dissolved in MeOH (12 ml) and stirred for 45 minutes. The precipitate formed is filtered, washed with water and dried in vacuum to deliver the title compound as light yellow crystals. 1H-NMR (400 MHz; DMSO-d6): 8.52 (bs, 1H); 8.37 (s, 1H); 7.59 (s, 1H); 4.37 (s, 2H); 3.00 (m, 2H); 2.96 (m, 2H); 0.95 (d, 2H); 0.93 (d, 2H). MS (m/z) ES+: 301 (MH+).

EXAMPLE 6

2-(1-Amino-cyclopropylmethyl)-8-[4-(3-amino-3-methyl-butyl)-phenyl]-4,5-dihydro-2H-1,2,7-triaza-cyclopenta[a]naphthalene-3-carboxylic acid lactame

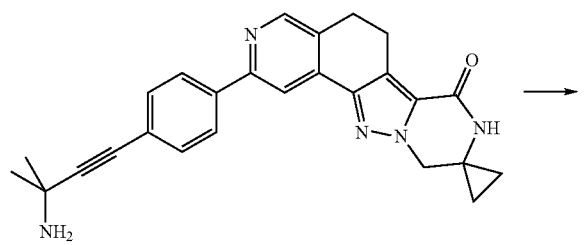

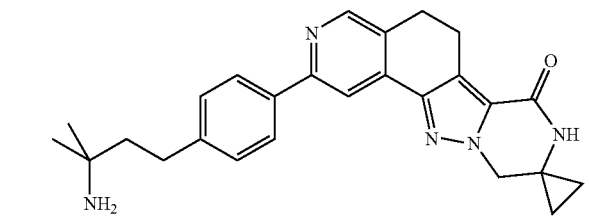

2-(1-Amino-cyclopropylmethyl)-8-[4-(3-amino-3-methyl-but-1-ynyl)-phenyl]-4,5-dihydro-2H-1,2,7-triaza-cyclopenta[a]naphthalene-3-carboxylic acid lactame (45 mg; 0.10 mmol) and ammonium formate (40 mg; 0.52 mmol) dissolved in MeOH (10 ml) are refluxed with 10% Pd/C (20 mg) for 30 minutes. The reaction mixture is diluted with $CH_2Cl_2$, filtered, evaporated, taken up in water and the title compound precipitated by adjusting the pH to 10 by adding 2 N NaOH. The precipitate is filtered, washed with water and dried to deliver the title compound as colorless crystals. 1H-NMR (400 MHz; DMSO-d6): 8.59 (s, 1H); 8.50 (bs, 1H); 8.05 (s, 1H); 8.00 (d, 2H); 7.34 (d, 2H); 4.37 (s, 2H); 3.03 (dd, 4H); 2.68 (m, 2H); 1.61 (m, 2H); 1.48 (bs, 2H); 1.09 (s, 6H); 0.99 (bs, 2H); 0.94 (bs, 2H). MS (m/z) ES+: 428 (MH+).

EXAMPLE 7

2-(1-Amino-cyclopropylmethyl)-8-[4-(3-hydroxy-3-methyl-but-1-ynyl)-phenyl]-4,5-dihydro-2H-1,2,7-triaza-cyclopenta[a]naphthalene-3-carboxylic acid lactame

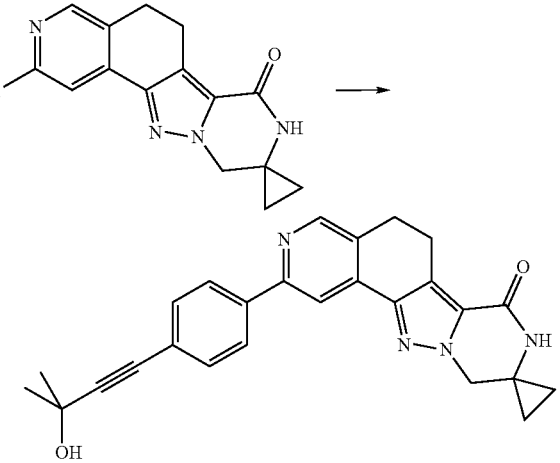

2-(1-Aminomethyl-cyclopropyl)-8-chloro-4,5-dihydro-1H-pyrrolo[2,3-f]isoquinoline-3-carboxylic acid lactame and 2-methyl-4-[4-(4,4,5,5-tetramethyl-[1,3,2]dioxaborolan-2-yl)-phenyl]-but-3-yn-2-ol are reacted in analogy to example 1. The reaction mixture is evaporated, taken up in $CH_2Cl_2/MeOH/NH_{3\ conc}$ (90:10:1) and purified via chromatography ($SiO_2$; $CH_2Cl_2/MeOH/NH_{3\ conc}$ (95:5:0.7>90:10:1) to yield—after trituration with MeOH—the title compound as yellowish crystals. 1H-NMR (400 MHz; DMSO-d6: 8.63 (s, 1H); 8.50 (s, 1H); 8.13 (d, 3H); 7.52 (d, 2H); 5.51 (s, 1H); 4.37 (s, 2H); 3.03 (m, 4H); 1.50 (s, 6H); 0.97 (dd, 4H). MS (m/z) ES+: 425 (MH+).

EXAMPLE 8

2-(1-Amino-cyclopropylmethyl)-8-[4-(3-hydroxy-3-methyl-butyl)-phenyl]-4,5-dihydro-2H-1,2,7-triaza-cyclopenta[a]naphthalene-3-carboxylic acid lactame

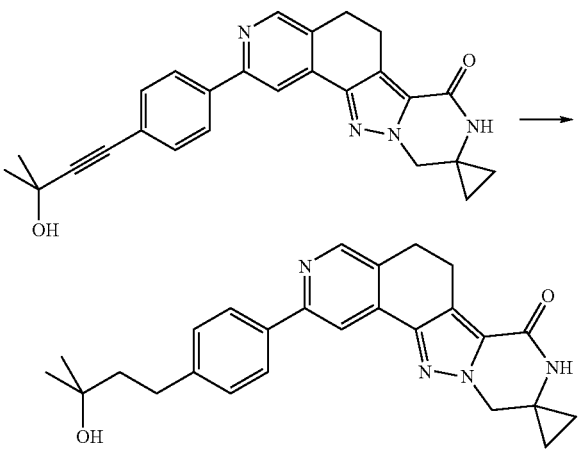

The hydrogenation is performed in analogy to example 6. The mixture is diluted with $CH_2Cl_2$, filtered, evaporated and washed with water to yield the title compound as colorless crystals. 1H-NMR (400 MHz; DMSO-d6: 8.59 (s, 1H); 8.49

(s, 1H); 8.05 (s, 1H); 8.00 (d, 2H); 7.34 (d, 2H); 4.37 (s, 2H); 4.28 (s, 1H); 3.03 (dd, 4H); 2.69 (m, 2H); 1.69 (m, 2H); 1.18 (s, 6H); 0.99 (bs, 2H); 0.94 (bs, 2H). MS (m/z) ES+: 429 (MH+).

EXAMPLE 9

2-(1-Amino-cyclopropylmethyl)-8-[5-(2-methoxy-ethoxy)-pyridin-3-yl]-4,5-dihydro-2H-1,2,7-triaza-cyclopenta[a]naphthalene-3-carboxylic acid lactame

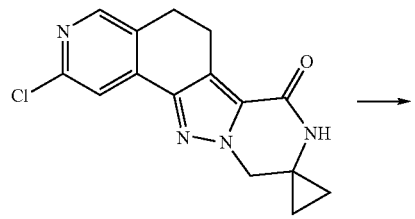

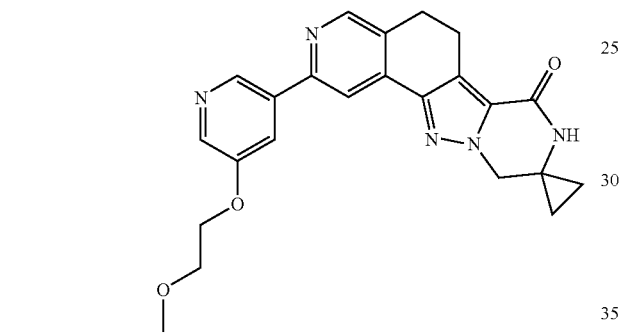

The compound is prepared in analogy to Example 1 and purified via chromatography (SiO$_2$; TBME/MeOH/NH$_{3conc}$ 95:5:0.7>90:10:1) to yield the title compound as yellowish crystals, washed with MeOH. 1H-NMR (400 MHz; DMSO-d6: 8.88 (d, 1H); 8.66 (s, 1H); 8.51 (s, 1H); 8.12 (d, 1H); 8.19 (s, 1H); 8.03 (dd, 1H); 4.38 (s, 2H); 4.32 (m, 2H); 3.73 (m, 2H); 3.03 (m, 4H); 2.52 (s, 3H); 0.97 (bs, 2H); 0.92 (bs, 2H). MS (m/z) ES+: 418 (MH+).

EXAMPLE 10

2-(1-Amino-cyclopropylmethyl)-8-((E)-styryl)-4,5-dihydro-2H-1,2,7-triaza-cyclopenta[a]naphthalene-3-carboxylic acid lactame

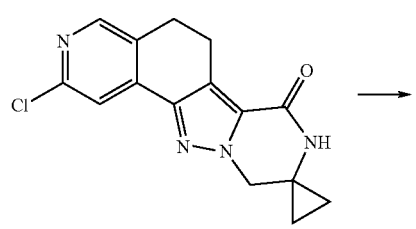

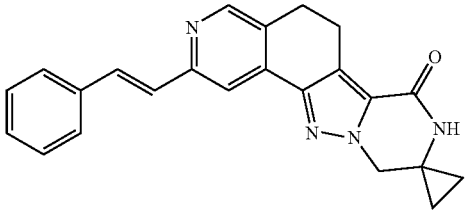

The reaction is performed as described for Example 4. (microwave; 150° C. for 20 minutes) and delivers after chromatography (acetone/hexanes 2:8>6:4) and trituration with MeOH the title compound as yellow crystals. 1H-NMR (400 MHz; DMSO-d6: 8.53 (s, 1H); 8.49 (s, 1H); 7.79 (s, 1H); 7.69 (m, 3H); 7.41 (m, 2H); 7.33 (m, 2H); 4.37 (s, 2H); 3.03 (m, 2H); 2.97 (m, 2H); 0.97 (bs, 2H); 0.93 (bs, 2H). MS (m/z) ES+: 369 (MH+).

EXAMPLE 11

2-(3-Amino-azetidin-3-ylmethyl)-8-(4-methoxy-phenyl)-4,5-dihydro-2H-1,2,7-triaza-cyclopenta[a] naphthalene-3-carboxylic acid lactame hydrochloride 2-(1-tert.-Butyloxycarbonyl-3-amino-azetidin-3-ylmethyl)-8-(4-methoxy-phenyl)-4,5-dihydro-2H-1,2,7-triaza-cyclopenta[a]naphthalene-3-carboxylic acid lactame (84 mg; 0.17 mmol) is dissolved in HCl$_{conc}$ (4 ml) and kept at room temperature for 2 minutes. Evaporation to dryness and recrystallization from MeOH/TBME yields the title compound as yellow crystals. 1H-NMR (400 MHz; DMSO-d6: 10.05 (bs, 1H); 9.29 (s, 1H); 9.21 (bs, 1H); 8.70 (s, 1H); 8.27 (s, 1H); 8.12 (d, 2H); 7.16 (d, 2H); 4.96 (s, 2H); 4.25 (m, 2H); 4.07 (m, 2H); 3.88 (s, 3H); 3.07 (s, 4H). MS (m/z) ES+: 387 (MH+).

The starting materials are prepared as follows:

11.a: Azetidine-1,3,3-tricarboxylic acid 1-tert-butyl ester 3,3-diethyl ester

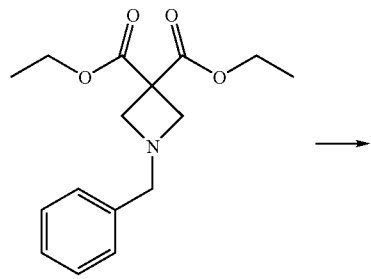

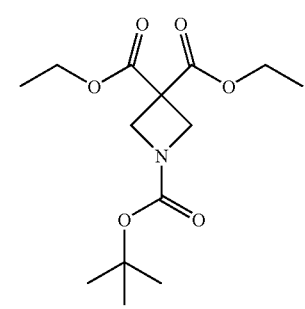

1-Benzyl-azetidine-3,3-dicarboxylic acid diethyl ester (1.9 g; 0.05 mmol) (Synth. Commun. 2003, 33(19), 3347), ammonium formate (2.0 g) and Pd/C (10%, 200 mg) in EtOH are refluxed for 50 minutes, filtered, evaporated, taken up in $CH_2Cl_2$ and extracted with water/10% acetic acid. The aqueous phase is adjusted to pH 10 by adding 2N $Na_2CO_3$, combined with $(Boc)_2O$ (2.8 g) in $CH_2Cl_2$, and stirred for 30 minutes at room temperature. The organic phase is dried over $Na_2SO_4$, evaporated to dryness and purified via chromatography ($SiO_2$; TBME/hexanes 5:95>15:85) to yield the title compound as colorless oil. 1H-NMR (400 MHz; DMSO-d6: 4.17 (q, 4H); 3.33 (bs, 4H); 1.39 (s, 9H); 1.21 (t, 6H). MS (m/z) ES+: 302 (30, MH+); 202 (100).

11.b: Azetidine-1,3,3-tricarboxylic acid 1-tert-butyl ester 3-ethyl ester

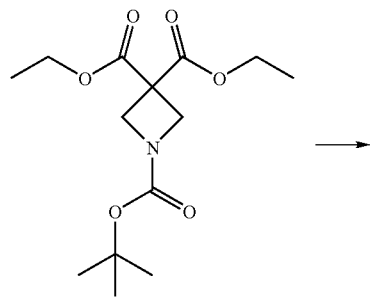

-continued

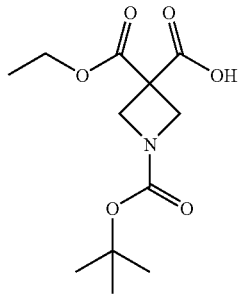

Azetidine-1,3,3-tricarboxylic acid 1-tert-butyl ester 3,3-diethyl ester (1.2 g; 0.4 mmol) in EtOH (12 ml) is cooled to 5° C. under stirring and combined with NaOH (60 mg; 0.04 mmol) in water (4 ml). The reaction mixture is left at room temperature for 1 hour, heated to 50° C. for 5 minutes, poured on brine, acidified with 2N HCl and extracted with TBME three times. The reaction mixture is extracted with TBME three times, the organic phases are combined, dried over $Na_2SO_4$ and evaporated to dryness, yielding the desired product as colorless crystals. 1H-NMR (400 MHz; DMSO-d6: 13.58 (bs, 1H); 4.20 (q, 2H); 4.12 (bs, 4H); 1.39 (s, 9H); 1.21 (t, 3H). MS (m/z) ES+: 274 (30; MH+); 174 (100).

11.c: 3-tert-Butoxycarbonylamino-azetidine-1,3-dicarboxylic acid 1-tert-butyl ester 3-ethyl ester

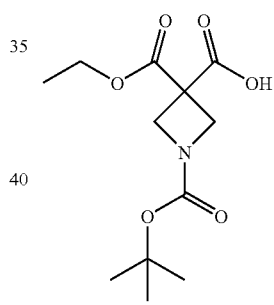

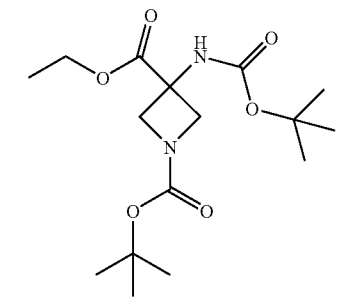

Azetidine-1,3,3-tricarboxylic acid 1-tert-butyl ester 3-ethyl ester (1 g; 3.67 mmol), triethyl-amine (0.52 ml; 3.7 mmol) and diphenylphosphoryl azide (0.8 ml; 3.67 mmol) in toluene (6 ml) are heated to 80° C. for 4 hours. tert-Butanol (6 ml) is added and heating continued for 4 hours. The reaction mixture is poured on 2N $Na_2CO_3$, extracted with TBME three times, the organic phases are combined, dried over $Na_2SO_4$ and evaporated to dryness. Purification via chromatography ($SiO_2$; TBME/hexanes 2:8>1:0) yields the desired compound as colorless crystals. 1H-NMR (400 MHz; DMSO-d6: 8.04

(s, 1H); 4.14 (q, 2H); 4.09 (bd, 2H); 3.81 (bd, 2H); 1.39 (s, 18H); 1.19 (t, 3H). MS (m/z) ES+: 345 (MH+).

11.d: 3-tert-Butoxycarbonylamino-3-hydroxymethyl-azetidine-1-carboxylic acid tert-butyl ester

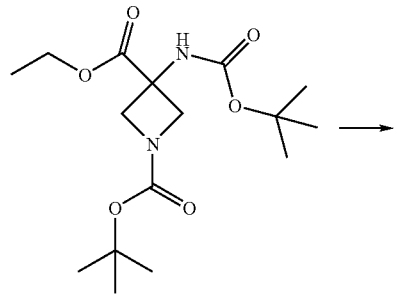

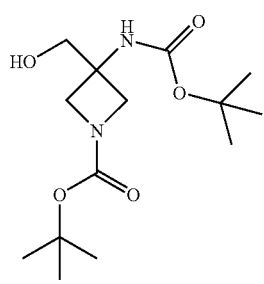

3-tert-Butoxycarbonylamino-azetidine-1,3-dicarboxylic acid 1-tert-butyl ester 3-ethyl ester (520 mg; 1.5 mmol) in THF (15 ml) is refluxed with LiBH₄ (67 mg; 3 mmol) for 20 minutes. The reaction mixture is diluted with water, acidified with 2N HCl to destroy excess of LiBH₄, neutralized again with 2N Na₂CO₃ and extracted with TBME three times. The organic phases are combined, dried over Na₂SO₄ and evaporated to dryness, yielding the desired product as colorless crystals. 1H-NMR (400 MHz; DMSO-d6: 7.27 (bs, 1H); 5.07 (bt, 1H); 3.78 (bs, 4H); 3.46 (d, 2H); 1.40 (s, 9H); 1.38 (s, 9H). MS (m/z) ES+: 303 (MH+).

11.e: 3-tert-Butoxycarbonylamino-3-methanesulfonyloxymethyl-azetidine-1-carboxylic acid tert-butyl ester

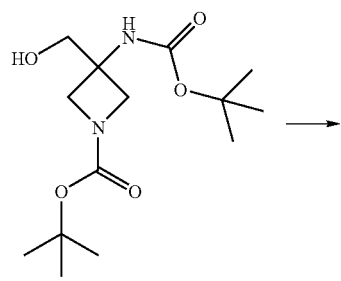

-continued

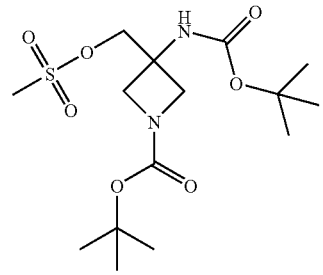

3-tert-Butoxycarbonylamino-3-hydroxymethyl-azetidine-1-carboxylic acid tert-butyl ester (490 mg; 1.6 mmol) and triethylamine (1.7 ml; 19 mmol), dissolved in CH₂Cl₂ (3 ml), are cooled to −5° C. and treated with methanesulfonyl chloride (280 mg; 2.43 mmol). The reaction mixture is kept at 0° C. for 35 minutes, poured on 10% acetic acid in water and extracted with TBME. The combined organic phases are washed with 2N Na₂CO₃, dried over Na₂SO₄, filtered and evaporated to dryness, yielding the desired product as colorless crystals. 1H-NMR (400 MHz; DMSO-d6: 7.75 (bs, 1H); 4.40 (s, 2H); 3.81 (bs, 4H); 3.23 (s, 3H); 1.40 (s, 9H); 1.38 (s, 9H). MS (m/z) ES+: 381 (MH+).

11.f: 2-(1-tert.-butyloxycarbonyl-3-tert.-butyloxycarbonylamino-azetidin-3-ylmethyl)-8-chloro-4,5-dihydro-2H-1,2,7-triaza-cyclopenta[a]naphthalene-3-carboxylic acid ethyl ester

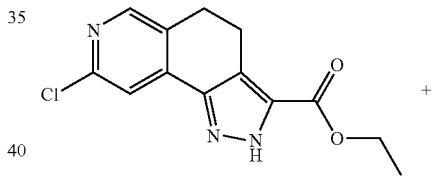

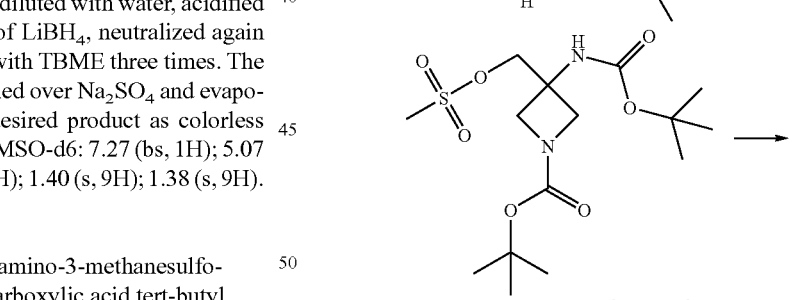

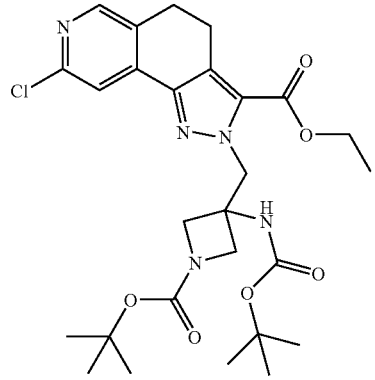

8-Chloro-4,5-dihydro-2H-1,2,7-triaza-cyclopenta[a]naphthalene-3-carboxylic acid ethyl ester (320 mg; 1.15 mmol) in DMF (4 ml) is treated at 5° C. with LiOtBu (1N in THF; 1.16 ml; 1.16 m mol) for 5 minutes. 3-tert-butoxycarbonylamino-3-methanesulfonyloxymethyl-azetidine-1-carboxylic acid tert-butyl ester (0.32 mg; 1.15 mmol) is added and the mixture heated to 90° C. for 30 minutes. The reaction mixture is poured on brine and extracted with TBME three times. The combined organic phases are dried over Na$_2$SO$_4$, evaporated to dryness and yield the title compound as colorless crystals. 1H-NMR (400 MHz; DMSO-d6: 8.38 (s, 1H); 7.65 (s, 1H); 7.42 (bs, 1H); 5.00 (bs, 2H); 4.34 (q, 2H); 4.03 (bd, 2H); 3.79 (m, 2H); 3.00 (m, 2H); 2.95 (m, 2H); 1.40 (s, 18H); 1.36 (t, 3H). MS (m/z) ES+: 562 (MH+).

11.g: 2-(3-amino-azetidin-3-ylmethyl)-8-chloro-4,5-dihydro-2H-1,2,7-triaza-cyclopenta[a]naphthalene-3-carboxylic acid ethyl ester dihydrochloride

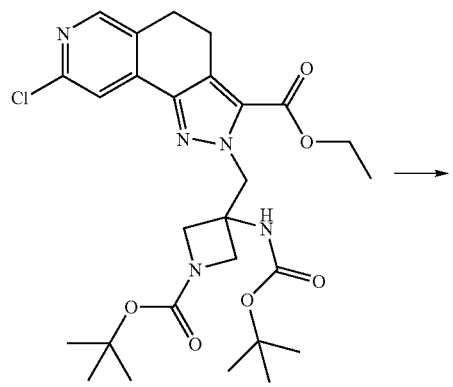

2-(1-tert.-Butyloxycarbonyl-3-tert.-butyloxycarbonylamino-azetidin-3-ylmethyl)-8-chloro-4,5-dihydro-2H-1,2,7-triaza-cyclopenta[a]naphthalene-3-carboxylic acid ethyl ester (440 mg; 0.78 mmol) in HCl$_{conc}$ (7 ml) is kept at room temperature for 1 minute and then evaporated to dryness and washed with EtOH to deliver the title compound as colorless crystals. 1H-NMR (400 MHz; DMSO-d6: 9.75 (bs, 1H); 9.35 (bs, 1H); 9.19 (bs, 2H); 8.40 (s, 1H); 7.90 (s, 1H); 5.17 (s, 2H); 4.46 (m, 2H); 4.39 (q, 2H); 4.29 (m, 2H); 3.04 (m, 2H); 2.98 (m, 2H); 1.39 (t, 3H). MS (m/z) ES+: 362 (MH+).

11.h: 2-(1-tert.-Butyloxycarbonyl-3-amino-azetidin-3-ylmethyl)-8-chloro-4,5-dihydro-2H-1,2,7-triaza-cyclopenta[a]naphthalene-3-carboxylic acid lactame

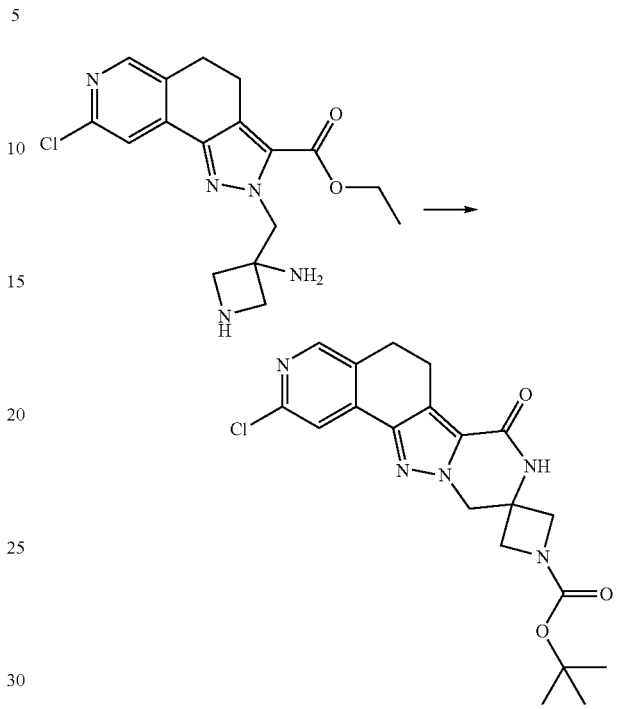

2-(3-Amino-azetidin-3-ylmethyl)-8-chloro-4,5-dihydro-2H-1,2,7-triaza-cyclopenta[a]naphthalene-3-carboxylic acid ethyl ester dihydrochloride (39 mg; 0.08 mmol) in MeOH (3 ml) are treated with Cs$_2$CO$_3$ (214 mg; 0.66 mmol) for 1 hour. (Boc)$_2$O (200 mg; 0.9 mmol) in THF/water (4 ml/1 ml) is added and stirring continued for 1 hour. The reaction mixture is diluted with TBME/water and extracted with TBME three times, the organic phases are combined, dried over Na$_2$SO$_4$ and evaporated to dryness, yielding the desired product as colorless crystals. 1H-NMR (400 MHz; DMSO-d6: 9.10 (s, 1H); 8.37 (s, 1H); 7.62 (s, 1H); 4.68 (s, 2H); 3.99 (bq, 4H); 2.98 (m, 4H); 1.40 (s, 9H). MS (m/z) ES+: 416 (MH+).

11.i: 2-(1-tert.-Butyloxycarbonyl-3-amino-azetidin-3-ylmethyl)-8-(4-methoxy-phenyl)-4,5-dihydro-2H-1,2,7-triaza-cyclopenta[a]naphthalene-3-carboxylic acid lactame

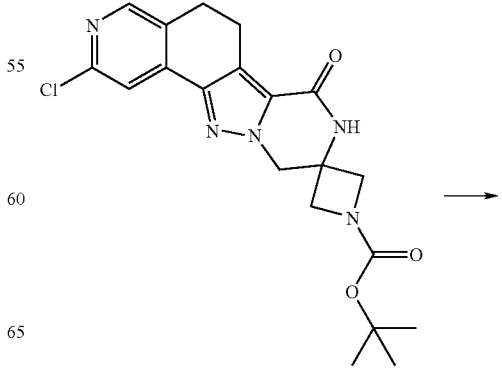

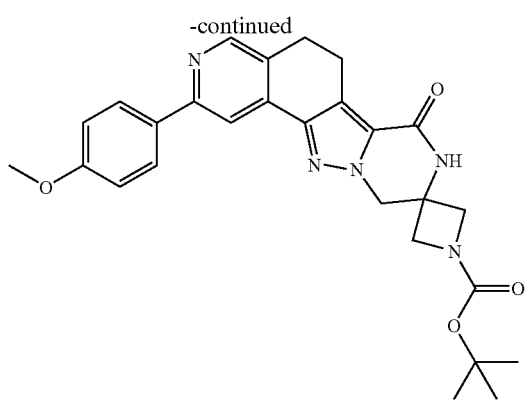

2-(1-tert.-Butyloxycarbonyl-3-amino-azetidin-3-ylmethyl)-8-chloro-4,5-dihydro-2H-1,2,7-triaza-cyclopenta[a]naphthalene-3-carboxylic acid lactame (100 mg; 0.24 mmol), 4-methoxyphenylboronic acid (73 mg; 0.48 mmol), Pd(PPh$_3$)$_2$Cl$_2$ (50 mg; 0.07 mmol), Pd(dppf)Cl$_2$.CH$_2$Cl$_2$ (8 mg; 0.01 mmol), PPh$_3$ (63 mg; 0.24 mmol), 2N Na$_2$CO$_3$ (0.72 ml; 1.4 mmol) in 1-propanol (4 ml) were microwaved at 150° C. for 20 minutes. The reaction mixture was filtered, evaporated, taken up in CH$_2$Cl$_2$ and treated with (BOC)$_2$O (300 mg; 1.4 mmol) for 10 minutes at room temperature. The reaction mixture purified via chromatography (SiO$_2$; acetone/hexanes 2:8>3:7) to yield the title compound as colorless crystals. 1H-NMR (400 MHz; DMSO-d6: 9.07 (s, 1H); 8.57 (s, 1H); 8.08 (d, 2H); 8.03 (s, 1H); 7.08 (d, 2H); 4.68 (s, 2H); 3.84 (s, 3H); 3.98 (bq, 4H); 3.00 (m, 2H); 2.98 (m, 2H); 1.40 (s, 9H). MS (m/z) ES+: 487 (MH+).

EXAMPLE 12

2-(1-Acetyl-3-amino-azetidin-3-ylmethyl)-8-(4-methoxy-phenyl)-4,5-dihydro-2H-1,2,7-triaza-cyclopenta[a]naphthalene-3-carboxylic acid lactame

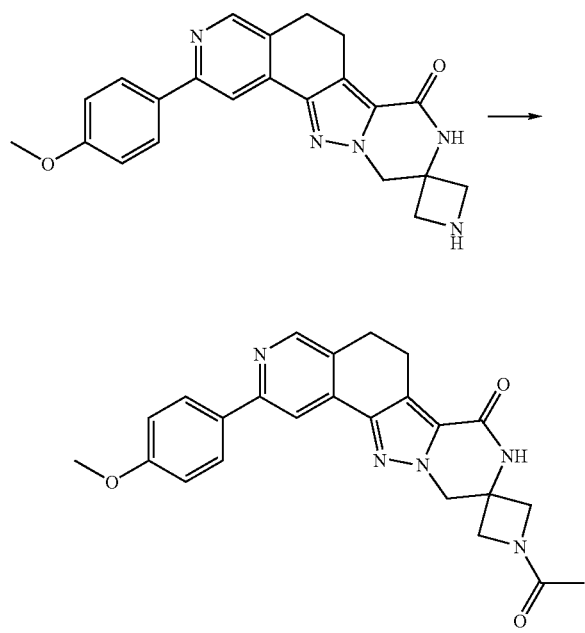

2-(3-Amino-azetidin-3-ylmethyl)-8-(4-methoxy-phenyl)-4,5-dihydro-2H-1,2,7-triaza-cyclo-penta[a]naphthalene-3-carboxylic acid lactame hydrochloride (10 mg; 0.023 mmol) is suspended in THF (1 ml) and treated with 2N Na$_2$CO$_3$ (0.5 ml) followed by acetyl chloride (1 drop). The reaction mixture is left at room temperature for 5 minutes, diluted with TBME/water and extracted with TBME. The organic phase is dried over Na$_2$SO$_4$ and evaporated to dryness, yielding the desired product as colorless crystals. 1H-NMR (400 MHz; DMSO-d6: 9.12 (s, 1H); 8.57 (s, 1H); 8.08 (d, 2H); 8.04 (s, 1H); 7.08 (d, 2H); 4.74 (d, 1H); 4.66 (d, 1H); 4.30 (d, 1H); 4.18 (d, 1H); 4.02 (dd, 2H); 3.84 (s, 3H); 2.98 (m, 4H); 1.81 (s, 3H).

MS (m/z) ES+: 430 (MH+).

EXAMPLE 13

2-(3-Amino-azetidin-3-ylmethyl)-8-[5-(2-methoxy-ethoxy)-pyridin-3-yl]-4,5-dihydro-2H-1,2,7-triaza-cyclopenta[a]naphthalene-3-carboxylic acid lactame hydrochloride

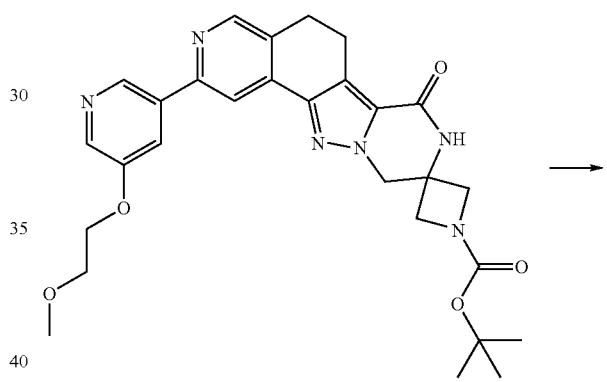

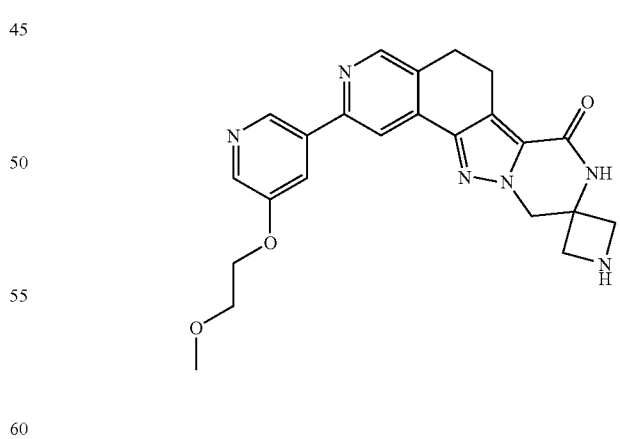

The reaction is performed in analogy to Example 11 to yield the title compound as colorless crystals: 1H-NMR (400 MHz; DMSO-d6: 10.28 (bs, 1H); 9.25 (s, 1H); 9.08 (s, 1H); 8.73 (s, 1H); 8.60 (d, 1H); 8.46 (s, 1H); 4.96 (s, 2H); 4.44 (m, 2H); 4.24 (m, 2H); 4.04 (m, 2H); 4.02 (bs, 2H); 3.76 (m, 2H); 3.36 (s, 3H); 3.04 (s, 4H). MS (m/z) ES+: 433 (MH+).

The starting materials can be prepared as follows:

13.a: 2-(1-tert.-butyloxycarbonyl 3-amino-azetidin-3-ylmethyl)-8-[5-(2-methoxy-ethoxy)-pyridin-3-yl]-4,5-dihydro-2H-1,2,7-triaza-cyclopenta[a]naphthalene-3-carboxylic acid lactame

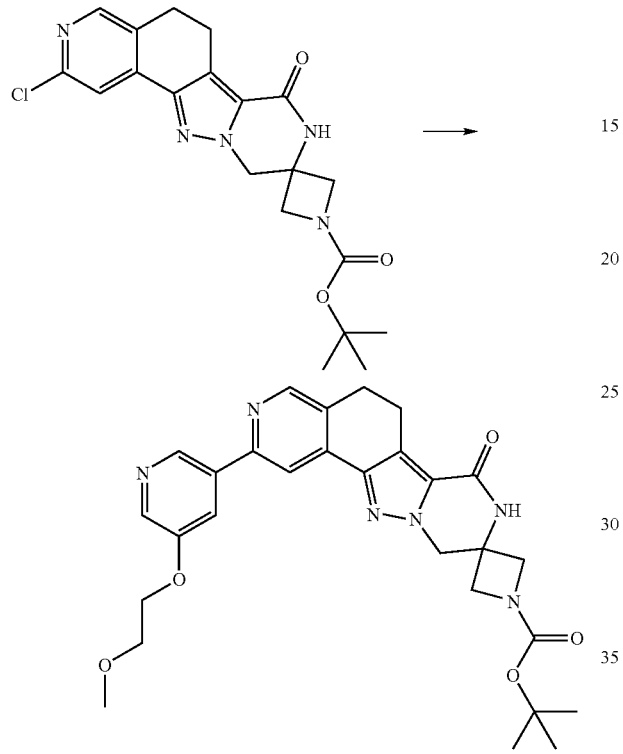

The reaction is performed in analogy to Example 1 and the product purified via chromatography (SiO$_2$; TBME/MeOH/NH$_{3conc}$ 98:2:0.2>95:5:1) to yield the title compound as colorless crystals. 1H-NMR (400 MHz; DMSO-d6: 9.08 (s, 1H); 8.88 (d, 1H); 8.66 (s, 1H); 8.37 (d, 1H); 8.21 (s, 1H); 8.02 (m, 1H); 4.68 (s, 2H); 4.32 (m, 2H); 4.00 (m, 4H); 3.73 (m, 2H); 3.35 (s, 3H); 3.02 (m, 4H); 1.41 (s, 9H). MS (m/z) ES+: 533 (MH+).

EXAMPLE 14

2-(1-Amino-cyclobutylmethyl)-8-(4-methoxy-phenyl)-4,5-dihydro-1H-1,7,9-triazacyclopenta[a]naphthalene-3-carboxylic acid lactame

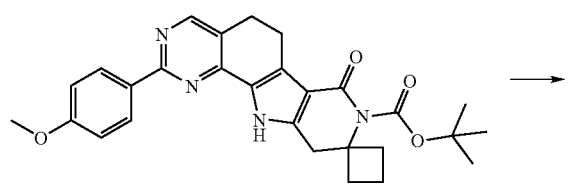

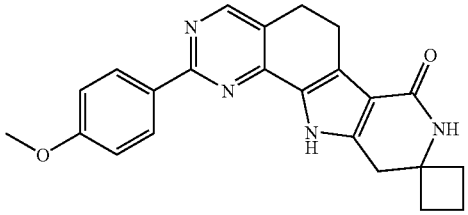

2-(1-tert-Butoxycarbonylamino-cyclobutylmethyl)-8-(4-methoxy-phenyl)-4,5-dihydro-1H-1,7,9-triaza-cyclopenta[a]naphthalene-3-carboxylic acid imide (76 mg; 0.16 mmol) is suspended in HCl$_{conc}$ (2 ml) and kept at room temperature for 5 minutes. HCl$_{conc}$ is evaporated and the residue washed with 0.5 N NH4OH several times. The solid is dried and recrystallized from MeOH to yield the title compound as slightly yellow crystals. 1H-NMR (400 MHz; DMSO-d6): 12.10 (s, 1H); 8.47 (s, 1H); 8.43 (d, 2H); 7.55 (s, 1H); 7.08 (d, 2H); 3.85 (s, 3H); 3.07 (s, 2H); 2.97 (m, 2H); 2.90 (m, 2H); 2.18 (m, 2H); 2.08 (m, 2H); 1.78 (m, 2H). MS (m/z) ES+: 387 (MH+).

The starting materials can be prepared as follows:

14.a: 8-Ethoxy-2-(4-methoxy-phenyl)-5,6-dihydro-quinazoline

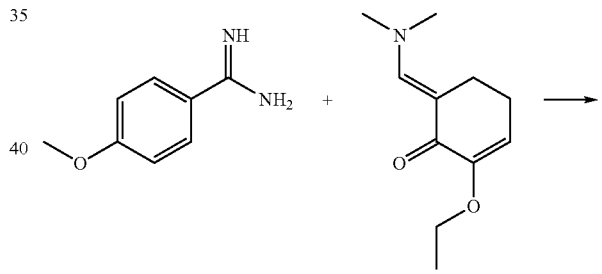

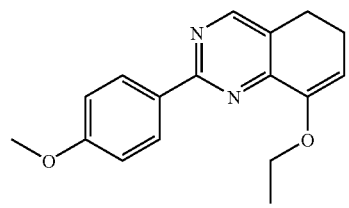

6-[1-Dimethylamino-meth-(E)-ylidene]-2-ethoxy-cyclohex-2-enone (WO 2004/104007) (1 g; 5 mmol) and 4-methoxybenzamidine (0.92 g; 6.1 mmol) are refluxed in EtOH (20 ml) for 14 hours. The reaction mixture is evaporated to dryness, taken up in CH$_2$Cl$_2$ and purified via chromatography (SiO$_2$; acetone/hexanes 5:95) to yield the title compound as yellow resin. 1H-NMR (400 MHz; DMSO-d6): 8.58 (s, 1H); 8.31 (d, 2H); 7.07 (d, 2H); 5.64 (t, 1H); 3.93 (q, 2H); 3.84 (s, 3H); 2.78 (t, 2H); 2.40 (m, 2H); 1.40 (t, 3H). MS (m/z) ES+: 283 (MH+).

14.b: 2-(4-Methoxy-phenyl)-6,7-dihydro-5H-quinazolin-8-one

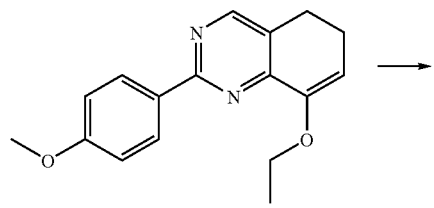

8-Ethoxy-2-(4-methoxy-phenyl)-5,6-dihydro-quinazoline (860 mg; 3.05 mmol) is dissolved in acetic acid/water (16 ml/1.6 ml) and refluxed for 15 minutes. Evaporation to dryness delivers the title compound as yellow crystals. 1H-NMR (400 MHz; DMSO-d6): 9.04 (s, 1H); 8.34 (d, 2H); 7.10 (d, 2H); 3.86 (s, 3H); 2.99 (t, 2H); 2.79 (t, 2H); 2.15 (m, 2H). MS (m/z) ES+: 255 (MH+).

14.c: 7-Bromo-2-(4-methoxy-phenyl)-6,7-dihydro-5H-quinazolin-8-one

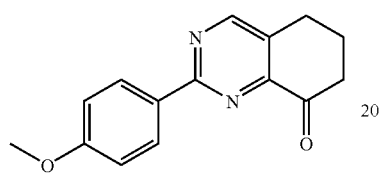

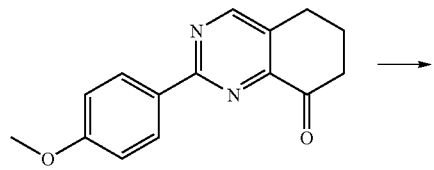

2-(4-Methoxy-phenyl)-6,7-dihydro-5H-quinazolin-8-one (300 mg; 1.2 mmol) in 48% HBr (30 ml) is treated drop-wise with Br$_2$ (189 mg; 1.2 mmol) dissolved in 48% HBr (0.8 ml). The reaction mixture is heated to 350 C for 10 minutes, poured on NaHCO$_3$/water (20 g/100 ml) and extracted with TBME three times. The organic phases are combined, dried over Na$_2$SO$_4$ and evaporated to dryness, yielding the desired product as brown-yellow crystals. 1H-NMR (400 MHz; DMSO-d6): 9.08 (s, 1H); 8.33 (d, 2H); 7.10 (d, 2H); 5.22 (m, 1H); 3.84 (s, 3H); 3.07 (m, 2H); 2.73 (m, 1H); 2.45 (m, 1H). MS (m/z) ES+: 335, 333 (MH+); 255 (80).

14.d: 2-(1-tert-Butoxycarbonylamino-cyclobutylmethyl)-8-(4-methoxy-phenyl)-4,5-dihydro-1H-1,7,9-triaza-cyclopenta[a]naphthalene-3-carboxylic acid imide

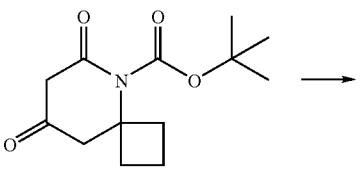

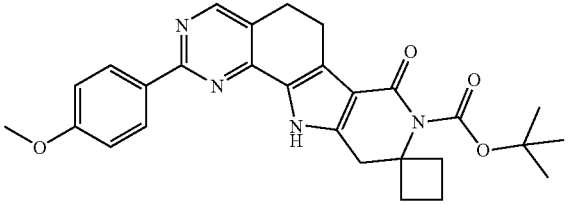

7-Bromo-2-(4-methoxy-phenyl)-6,7-dihydro-5H-quinazolin-8-one (150 mg; 0.45 mmol) and 6,8-dioxo-5-aza-spiro[3.5]nonane-5-carboxylic acid tert-butyl ester (200 mg; 0.8 mmol) and ammonium acetate (100 mg; 1.3 mmol) in MeOH (3 ml) are left at room temperature over night. The reaction mixture is evaporated, taken up in TBME and washed with 0.5 N NaOH. The organic phase is dried over Na$_2$SO$_4$, evaporated to dryness and purified via chromatography (SiO$_2$; acetone/hexanes 2:8) to yield the title compound as slightly green crystals. 1H-NMR (400 MHz; DMSO-d6): 12.38 (bs, 1H); 8.49 (s, 1H); 8.44 (d, 2H); 7.10 (d, 2H); 3.87 (s, 3H); 3.23 (s, 2H); 2.95 (m, 4H); 2.56 (m, 2H); 2.06 (m, 2H); 1.85 (m, 2H); 1.53 (s, 9H). MS (m/z) ES+: 487 (MH+).

EXAMPLE 15

2-(1-Amino-cyclobutylmethyl)-8-[4-(3-amino-3-methyl-but-1-ynyl)-phenyl]-4,5-dihydro-1H-1,7,9-triaza-cyclopenta[a]naphthalene-3-carboxylic acid lactame

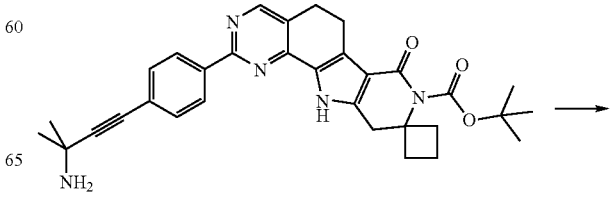

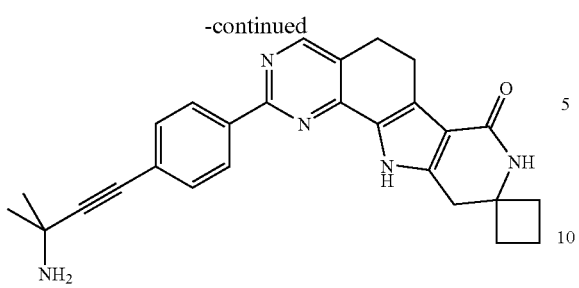

2-(1-tert-Butoxycarbonylamino-cyclobutylmethyl)-8-[4-(3-amino-3-methyl-but-1-ynyl)-phenyl]-4,5-dihydro-1H-1,7,9-triaza-cyclopenta[a]naphthalene-3-carboxylic acid imide (48 mg; 0.09 mmol) is dissolved in HCl$_{conc}$. and left at room temperature for 5 minutes. The suspension is evaporated and purified via chromatography (SiO$_2$; TBME/MeOH/NH$_{3conc}$ 95:5:0.5>80:20:2) to yield the title compound as colorless crystals. 1H-NMR (400 MHz; DMSO-d6: 12.16 (s, 1H); 8.51 (s, 1H); 8.46 (d, 2H); 7.62 (bs, 2H); 7.57 (s, 1H); 7.52 (d, 2H); 3.05 (s, 2H); 2.94 (m, 4H); 2.18 (m, 2H); 2.07 (m, 2H); 1.75 (m, 2H); 1.41 (s, 6H); MS (m/z) ES+: 438 (MH+; 80); 421 (100).

The starting materials can be prepared as follows:

15.a: 2-(1-Amino-cyclobutylmethyl)-8-(4-bromo-phenyl)-4,5-dihydro-1H-1,7,9-triazacyclopenta[a]naph-thalene-3-carboxylic acid imide

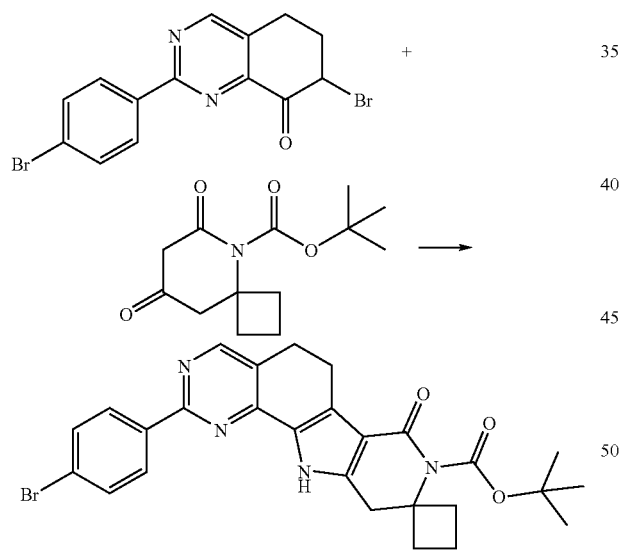

7-Bromo-2-(4-bromo-phenyl)-6,7-dihydro-5H-quinazolin-8-one (100 mg; 0.26 mmol) (prepared from 4-bromobenzeneamidine in analogy to 7-bromo-2-(4-methoxy-phenyl)-6,7-dihydro-5H-quinazolin-8-one) and 6,8-dioxo-5-aza-spiro[3.5]nonane-5-carboxylic acid tert-butyl ester (170 mg; 0.36 mmol) and ammonium acetate (61 mg; 0.79 mmol) in MeOH (2 ml) are left at room temperature over night. The reaction mixture is evaporated, taken up in TBME and washed with 1 N NaOH. The organic phase is dried over Na$_2$SO$_4$, evaporated to dryness and purified via chromatography (SiO$_2$; TBME/hexanes 4:6) to yield the title compound as colorless crystals. 1H-NMR (400 MHz; DMSO-d6): 12.43 (bs, 1H); 8.55 (s, 1H); 8.55 (d, 2H); 7.77 (d, 2H); 3.23 (s, 2H); 2.98 (m, 4H); 2.56 (s, 2H); 2.06 (m, 2H); 1.86 (m, 2H); 1.55 (s, 9H). MS (m/z) ES+: 537 (MH+).

15.b: 2-(1-tert-Butoxycarbonylamino-cyclobutylmethyl)-8-[4-(3-amino-3-methyl-but-1-ynyl)-phenyl]-4,5-dihydro-1H-1,7,9-triaza-cyclopenta[a]naphthalene-3-carboxylic acid imide

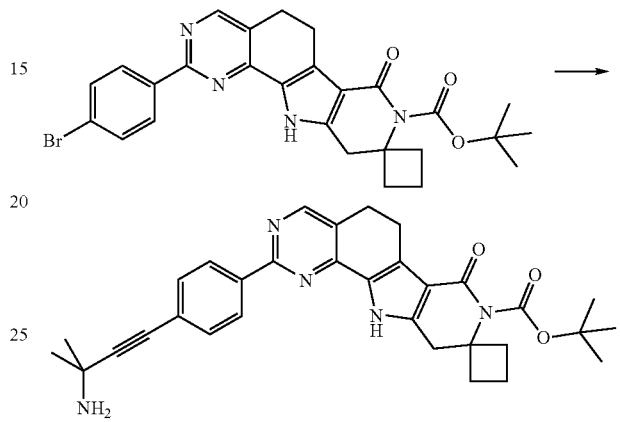

2-(1-Amino-cyclobutylmethyl)-8-(4-bromo-phenyl)-4,5-dihydro-1H-1,7,9-triazacyclopenta[a]naph-thalene-3-carboxylic acid lactame (105 mg; 0.19 mmol)), 1,1-dimethyl-prop-2-ynylamine (98 mg; 1.12 mmol), Pd(PPh$_3$)2Cl2 (28 mg; 0.04 mmol) and CuI (7.5 mg; 0.04 mmol) are dissolved in DMF/NEt$_3$ (3.5 ml/1.5 ml) and microwaved at 100° C. for 80 minutes. The reaction mixture is evaporated and purified via chromatography (SiO2; TBME/MeOH/NH$_{3conc}$ 98:2:0.4) to yield the title compound—after trituration with TBME—as colorless crystals. 1H-NMR (400 MHz; DMSO-d6): 12.42 (bs, 1H); 8.55 (s, 1H); 8.47 (d, 2H); 7.53 (d, 2H); 3.23 (s, 2H); 2.98 (m, 4H); 2.56 (m, 2H); 2.14 (bs, 2H); 2.05 (m, 2H); 1.86 (m, 2H); 1.55 (s, 9H); 1.49 (s, 6H). MS (m/z) ES+: 538 (MH+).

EXAMPLE 16

2-(1-Amino-cyclobutylmethyl)-8-[4-(3-amino-3-methyl-butyl)-phenyl]-4,5-dihydro-1H-1,7,9-triaza-cyclopenta[a]naphthalene-3-carboxylic acid lactame

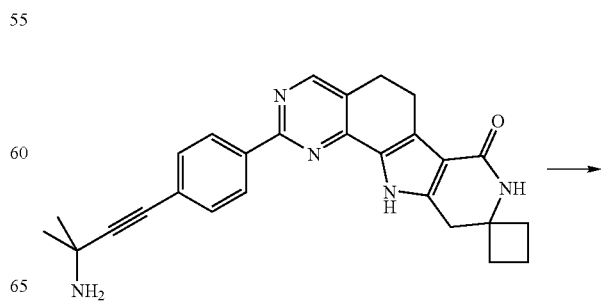

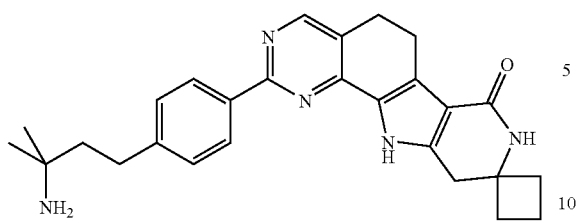

The reaction is performed in analogy to Example 7. Purification via chromatography (SiO$_2$; TBME/MeOH/NH$_{3conc}$ 95:5:0.5>80:20:2) yields the title compound as colorless crystals. 1H-NMR (400 MHz; DMSO-d6: 12.13 (bs, 1H); 8.49 (s, 1H); 8.44 (d, 2H); 7.67 (bs, 2H); 7.58 (s, 1H); 7.39 (d, 2H); 3.06 (d, 2H); 2.97 (m, 2H); 2.93 (m, 2H); 2.74 (m, 2H); 2.16 (m, 2H); 2.06 (m, 2H); 1.86 (m, 2H); 1.76 (m, 2H); 1.31 (s, 6H). MS (m/z) ES+: 442 (MH+).

EXAMPLE 17

2-(1-Aminomethyl-cyclopropyl)-8-(4-methoxy-phenyl)-4,5-dihydro-1H-1,7,9-triaza-cyclopenta[a]naphthalene-3-carboxylic acid lactame

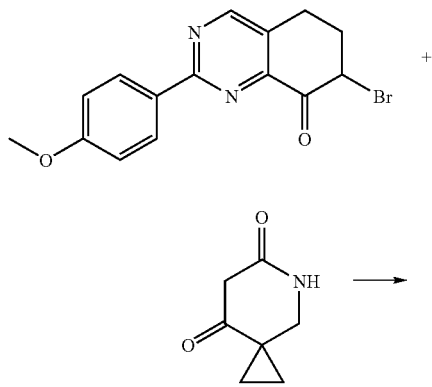

6-Bromo-3-chloro-7,8-dihydro-6H-isoquinolin-5-one (150 mg; 0.45 mmol) and 5-aza-spiro[2.5]octane-6,8-dione (134 mg; 0.67 mmol) (WO 2005014572, WO 2005013986), ammonium acetate (104 mg; 1.3 mmol) in MeOH (3 ml) are kept at room temperature over night. The precipitated product is filtered and washed with MeOH to yield the title compound as yellowish crystals. 1H-NMR (400 MHz; DMSO-d6: 11.51 (bs, 1H); 8.49 (s, 1H); 8.44 (d, 2H); 7.20 (s, 1H); 7.08 (d, 2H); 3.86 (s, 3H); 3.27 (d, 2H); 3.00 (dd, 2H); 2.89 (dd, 2H); 1.40 (dd, 2H); 1.02 (dd, 2H). MS (m/z) ES+: 373 (MH+).

EXAMPLE 18

2-(3-Amino-azetidin-3-ylmethyl)-8-(4-methoxy-phenyl)-4,5-dihydro-1H-1,7,9-triaza-cyclopenta[a]naphthalene-3-carboxylic acid lactame hydrochloride

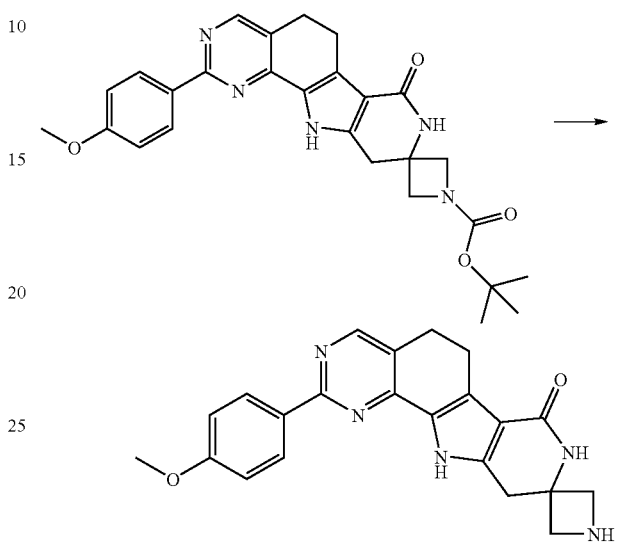

2-(3-Amino-1-tert-butoxycarbonyl-azetidin-3-ylmethyl)-8-(4-methoxy-phenyl)-4,5-dihydro-1H-1,7,9-triaza-cyclopenta[a]naphthalene-3-carboxylic acid lactame (83 mg; 0.17 mmol) is suspended in HCl$_{conc}$ (4 ml) and stirred at room temperature for 3 minutes. The mixture is evaporated and dried under reduced pressure to deliver the title compound as colorless crystal. 1H-NMR (400 MHz; DMSO-d6): 12.56 (bs, 1H); 9.70 (bs, 1H); 9.00 (bs, 1H); 8.50 s, 1H); 8.47 (d, 2H); 8.08 (s, 1H); 7.13 (d, 2H); 4.10 (m, 2H); 3.97 (m, 2H); 3.88 (s, 3H); 3.47 (s, 2H); 2.99 (m, 4H). MS (m/z) ES+: 388 (MH+)

The starting materials are prepared as follows:

18.a:
3-Methoxycarbonylmethylene-azetidine-1-carboxylic acid tert-butyl ester

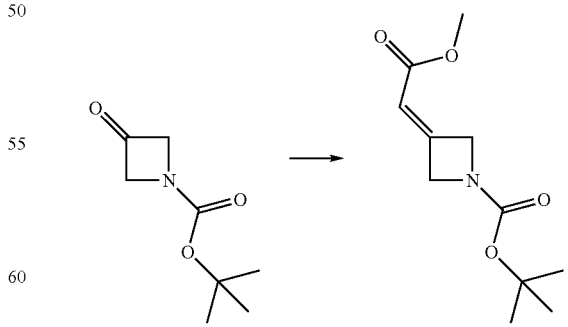

3-Oxo-azetidine-1-carboxylic acid tert-butyl ester (1.67 g; 9.7 mmol) and methoxycarbonyl-methylene-triphenylphosphorane (3.42 g; 10.25 mmol) are dissolved in toluene (5 ml), refluxed for 2.5 hours and left over night at room temperature.

The precipitate is filtered off, washed with TBME, and the filtrate purified via chromatography (TBME/hexane 2:8>3:7) to yield the title compound as colorless crystals. 1H-NMR (400 MHz; DMSO-d6): 5.90 (m, 1H); 4.71 (bs, 2H); 4.58 (bs, 2H); 3.67 (s, 3H); 1.42 (s, 9H). MS (m/z) ES+: 171 (10; MH+ minus tert-butyl); 57 (100).

18.b: 3-Amino-3-methoxycarbonylmethyl-azetidine-1-carboxylic acid tert-butyl ester

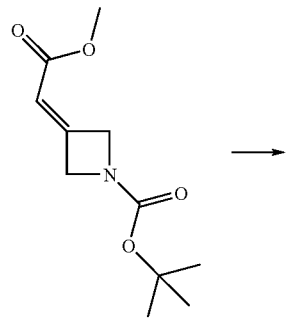

3-Methoxycarbonylmethylene-azetidine-1-carboxylic acid tert-butyl ester (1.97 g; 8.7 mmol) in EtOH (20 ml) and liquid NH3 (11 g) are heated in a steel cylinder at 800 C for 6 hours. Evaporation of the solvent delivers the title compound as yellow resin. 1H-NMR (400 MHz; DMSO-d6): 3.81 (d, 2H); 3.65 (s, 2H); 3.60 (d, 2H); 2.86 (s, 3H); 2.07 (bs, 2H); 1.43 (s, 9H). MS (m/z) ES+: 245 (100, MH+); 189 (90).

18.c: 3-Ethoxycarbonylmethyl-3-(2-methoxycarbonyl-acetylamino)-azetidine-1-carboxylic acid tert-butyl ester

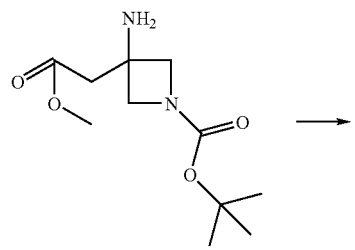

3-Amino-3-methoxycarbonylmethyl-azetidine-1-carboxylic acid tert-butyl ester (2 g; 8.2 mmol) dissolved in $CH_2Cl_2$ (100 ml) and triethylamine (3.4 ml; 24.5 mmol) is cooled to −5° C. Chlorocarbonyl-acetic acid ethyl ester (1.23 ml; 9.8 mmol) is slowly added under stirring. The reaction mixture is warmed to room temperature, stirred for 20 minutes, poured on 2N HCl (15 ml) and extracted with TBME three times. The organic phases are combined, washed with a saturated solution of $NaHCO_3$, dried over $Na_2SO_4$ and evaporated to dryness. Chromatography ($SiO_2$; Hexanes/acetone 7:3) yields the title compound as colorless crystals. 1H-NMR (400 MHz; DMSO-d6): 8.62 (s, 1H); 4.08 (q, 2H); 3.88 (m, 4H); 3.60 (s, 3H); 3.21 (s, 2H); 3.02 (s, 2H); 1.38 (s, 9H); 1.18 (t, 3H). MS (m/z) ES+: 359 (80; MH+); 303 (100);

18.d: 6,8-Dioxo-2,5-diaza-spiro[3.5]nonane-2,7-dicarboxylic acid 2-tert-butyl ester 7-methyl ester

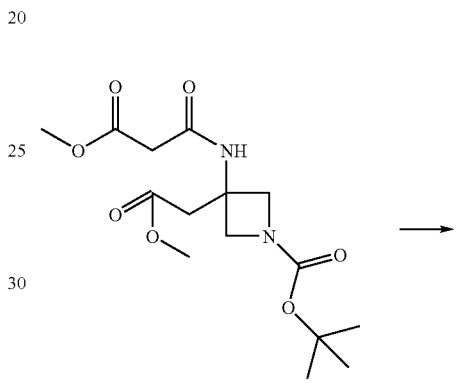

Sodium (84 mg; 3.6 mmol) is dissolved in MeOH (3 ml) and combined with 3-methoxy-carbonylmethyl-3-(2-methoxycarbonyl-acetylamino)-azetidine-1-carboxylic acid tert-butyl ester (1.3 g; 3.6 mmol) in toluene (15 ml). The mixture is refluxed for 90 minutes, cooled to room temperature, poured on TBME and extracted with water three times. The aqueous phase is combined with 2N HCl (1.85 ml) and evaporated to dryness to deliver the title compound as pink foam. 1H-NMR (400 MHz; DMSO-d6): 8.75 (s, 1H); 3.82 (m, 4H); 7.71 (s, 3H); 3.59 (s, 1H); 2.84 (bs, 2H); 1.39 (s, 9H). MS (m/z) ES+: 313 (100, MH+); 257 (50).

18.e:
6,8-Dioxo-2,5-diaza-spiro[3.5]nonane-2-carboxylic acid tert-butyl ester

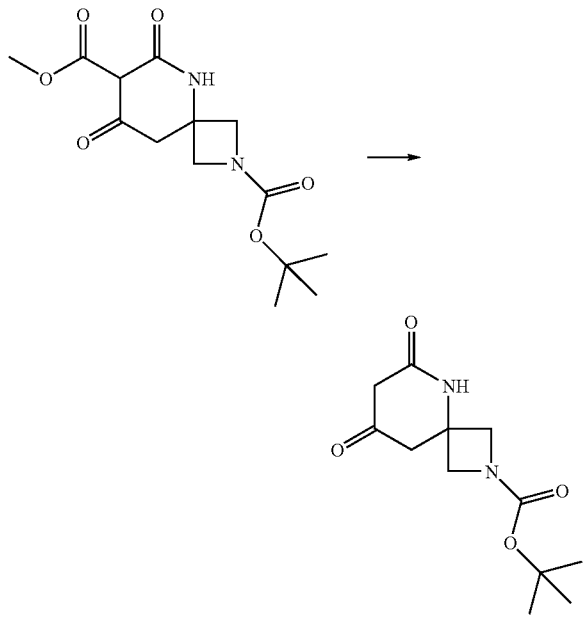

6,8-Dioxo-2,5-diaza-spiro[3.5]nonane-2,7-dicarboxylic acid 2-tert-butyl ester 7-methyl ester (1.1 g; 3.5 mmol) is refluxed in acetonitrile/water (18 ml/2 ml) for 50 minutes and evaporated to dryness. The residue is triturated with $CH_2Cl_2$ to deliver the title compound as colorless crystals. 1H-NMR (400 MHz; DMSO-d6): Keto-enol tautomerism. 10.70 (s, 1H); 8.75 (s, 0.5H); 7.55 (s, 0.5H); 4.85 (s, 1H); 3.94 (bd, 2H); 3.86 (bd, 2H); 3.78 (bs, 2H); 1.40 (s, 9H); MS (m/z) ES+: 255 (25; MH+); 199 (100).

18.f: 2-(3-Amino-1-tert-butoxycarbonyl-azetidin-3-ylmethyl)-8-(4-methoxy-phenyl)-4,5-dihydro-1H-1,7,9-triaza-cyclopenta[a]naphthalene-3-carboxylic acid lactame

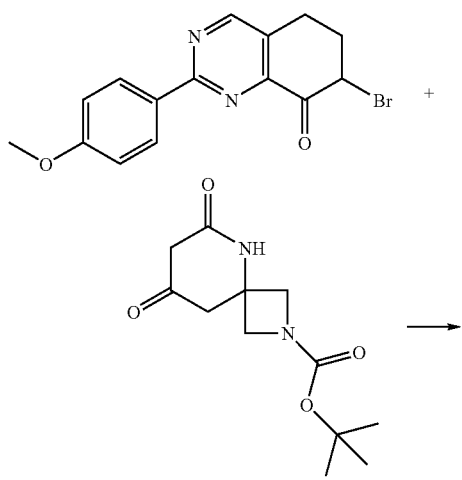

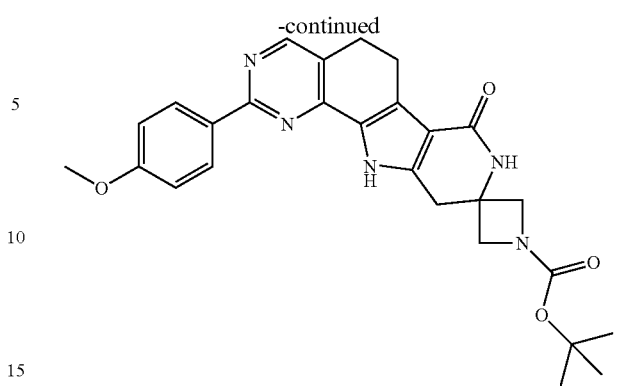

7-Bromo-2-(4-methoxy-phenyl)-6,7-dihydro-5H-quinazolin-8-one (100 mg; 0.3 mmol), 6,8-dioxo-2,5-diaza-spiro[3.5]nonane-2-carboxylic acid tert-butyl ester (100 mg; 0.39 mmol) and ammonium acetate (69 mg; 0.9 mmol) are dissolved in MeOH (2 ml) and stirred over night at room temperature. The precipitate is filtered, washed with TBME/MeOH and delivers the title compound as colorless crystals. 1H-NMR (400 MHz; DMSO-d6): 12.21 (bs, 1H); 8.47 (s, 1H); 8.43 (d, 2H); 7.87 (s, 1H); 7.06 (d, 2H); 3.89 (bs, 4H); 3.86 (s, 3H); 3.20 (s, 2H); 2.98 (m, 2H); 2.91 (m, 2H); 1.41 (s, 9H). MS (m/z) ES+: 488 (MH+)

EXAMPLE 19

2-(1-Amino-cyclobutylmethyl)-8-(3-fluoro-phenyl)-4,5-dihydro-1H-1,7,9-triaza-cyclopenta[a]naphthalene-3-carboxylic acid lactame

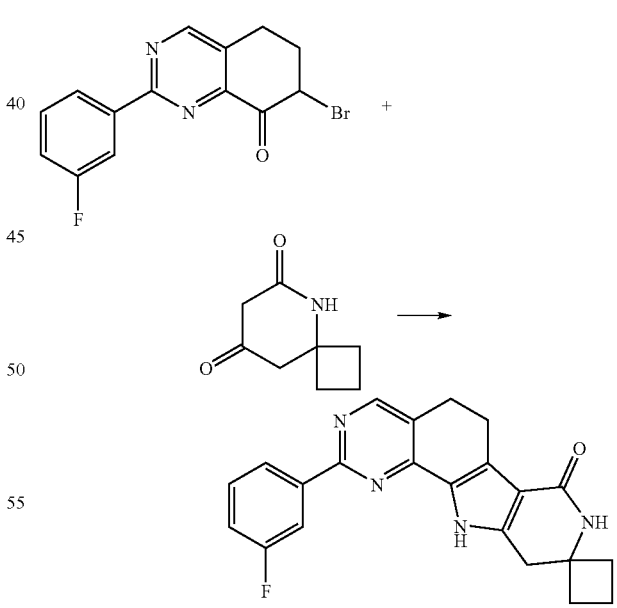

7-Bromo-2-(3-fluoro-phenyl)-6,7-dihydro-5H-quinazolin-8-one (110 mg; 0.34 mmol) (prepared from 3-fluorobenzamidine in analogy to 7-bromo-2-(4-methoxy-phenyl)-6,7-dihydro-5H-quinazolin-8-one described above) and 5-aza-spiro[3.5]nonane-6,8-dione (68 mg; 0.44 mmol) (obtained in analogy to 6,8-dioxo-2,5-diaza-spiro[3.5]nonane-2-carboxylic acid tert-butyl ester described above) and ammonium acetate (80 mg; 1.03 mmol) are suspended in MeOH (3 ml) and stirred over night at room temperature. The mixture is heated to 500 C for 30 minutes and gives a clear solution. Upon cooling to 100 C the title compound precipitates as colorless crystals. 1H-NMR (400 MHz; DMSO-d6): 12.18 (bs, 1H); 8.52 (s, 1H); 8.32 (m, 1H); 8.28 (m, 1H); 7.58 (m, 1H); 7.57 (s, 1H); 7.36 (dt, 1H); 3.06 (s, 2H); 2.98 (m, 4H); 2.15 (m, 2H); 2.05 (m, 2H); 1.75 (m, 2H).

MS (m/z) ES+: 375 (MH+)

EXAMPLE 20

2-(3-Amino-oxetan-3-ylmethyl)-8-(4-methoxy-phenyl)-4,5-dihydro-1H-pyrrolo[2,3-f]isoquinoline-3-carboxylic acid lactame

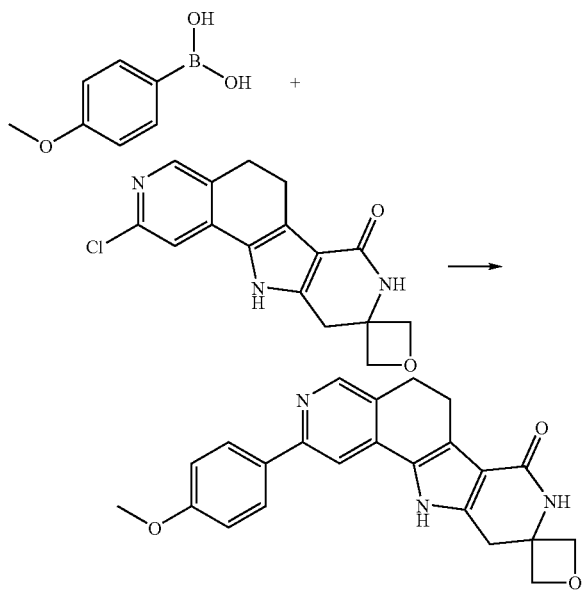

2-(3-Amino-oxetan-3-ylmethyl)-8-chloro-4,5-dihydro-1H-pyrrolo[2,3-f]isoquinoline-3-carboxylic acid lactame is coupled with 4-methoxyphenylboronic acid in analogy to example 23. Purification via chromatography (SiO$_2$; CH$_2$Cl$_2$/MeOH/NH$_{3conc}$ 95:5:0.5) yields the title compound as off-white crystals. 1H-NMR (400 MHz; DMSO-d6): 12.06 (s, 1H); 8.35 (s, 1H); 8.01 (d, 2H); 7.97 (s, 1H); 7.93 (s, 1H); 7.08 (d, 2H); 4.60 (d, 2H); 4.49 (d, 2H); 3.84 (s, 3H); 2.89 (m, 4H); 0.85 (m, 2H). MS (m/z) ES+: 388 (MH+)

The starting materials can be prepared as follows:

20.a: (3-Amino-oxetan-3-yl)-acetic acid methyl ester

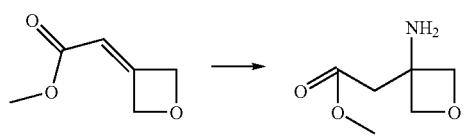

Oxetan-3-ylidene-acetic acid methyl ester (Angewandte Chemie, International Edition (2006), 45(46), 7736-7739) ester (1.5 g; 11.72 mmol) in EtOH (20 ml) and liquid NH$_3$ (11 g) are heated in a steel cylinder at 800 C for 5 hours. Evaporation of the solvent delivers the title compound as yellow resin. 1H-NMR (400 MHz; DMSO-d6): 4.42 (d, 2H); 4.34 (d, 2H); 3.61 (s, 3H); 2.77 (s, 2H); 2.33 (bs, 2H). MS (m/z) ES+: 145 (MH+; 15); 96 (100).

20.b: N-(3-Methoxycarbonylmethyl-oxetan-3-yl)-malonamic acid ethyl ester

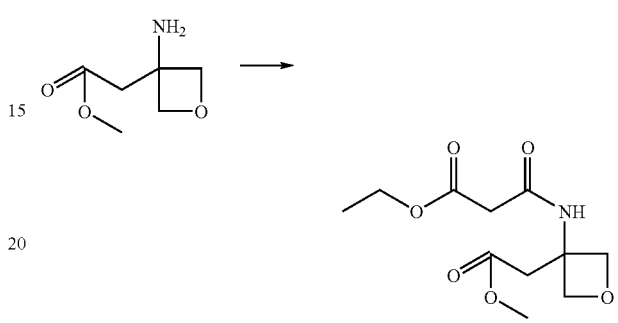

(3-Amino-oxetan-3-yl)-acetic acid methyl ester (95 mg; 0.655 mmol) dissolved in CH$_2$Cl$_2$ (5 ml) and triethylamine (0.22 ml; 1.6 mmol) are cooled to −5° C. Chlorocarbonyl-acetic acid ethyl ester (0.1 ml; 0.79 mmol) is slowly added under stirring. The reaction mixture is warmed to room temperature, stirred for 20 minutes, poured on a saturated solution of NaHCO$_3$ and extracted with CH$_2$Cl$_2$ three times. The organic phases are combined, dried over Na$_2$SO$_4$, filtered and evaporated to dryness. Chromatography (SiO$_2$; Hexanes/acetone 4:1) yields the title compound as yellow resin. 1H-NMR (400 MHz; DMSO-d6): 8.93 (s, 1H); 4.54 (dd, 4H); 4.09 (q, 2H); 3.60 (s, 3H); 3.23 (s, 2H); 3.10 (s, 2H); 1.19 (t, 3H). MS (m/z) ES+: 260 (MH+)

20.c: 6,8-Dioxo-2-oxa-5-aza-spiro[3.5]nonane-7-carboxylic acid methyl ester and 6-chloromethyl-6-hydroxymethyl-2,4-dioxo-piperidine-3-carboxylic acid methyl ester

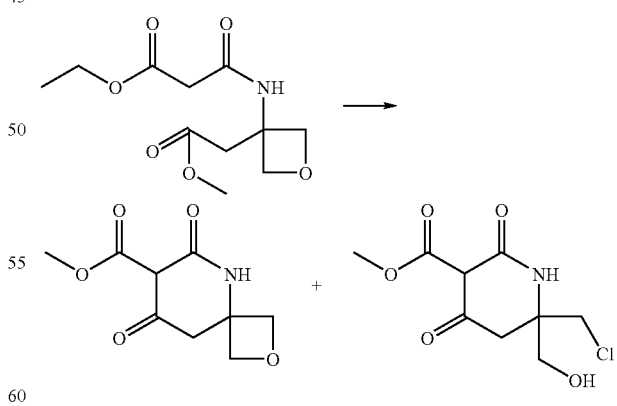

Sodium (93 mg; 4.05 mmol) is dissolved in MeOH (5 ml) and combined with N-(3-methoxycarbonylmethyl-oxetan-3-yl)-malonamic acid ethyl ester (1.05 g; 4.05 mmol) in toluene (15 ml). The mixture is refluxed for 45 minutes, cooled to room temperature, poured on TBME and extracted with water three times. The aqueous phase is acidified with 2N HCl (2.2 ml) and evaporated to dryness to deliver the title compound as orange foam. The mixture is used in the following step.

20.d: 2-Oxa-5-aza-spiro[3.5]nonane-6,8-dione and 6-chloromethyl-6-hydroxymethyl-piperidine-2,4-dione

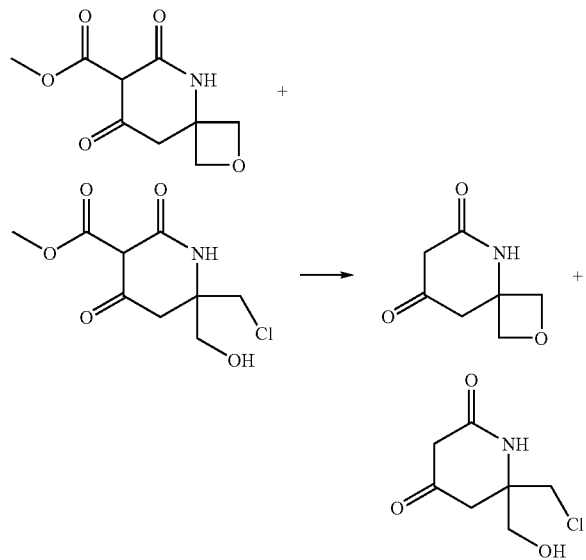

6,8-Dioxo-2-oxa-5-aza-spiro[3.5]nonane-7-carboxylic acid methyl ester and 6-chloromethyl-6-hydroxymethyl-2,4-dioxo-piperidine-3-carboxylic acid methyl ester (0.9 g) are refluxed in acetonitrile/water (1.35 ml/0.15ml) for 60 minutes. The reaction mixture is evaporated and the resulting residue washed several times with ethyl acetate. The combined ethyl acetate phases are evaporated and deliver the target compounds as an orange resin used in the following steps without further purification.

20.e: 2-(3-Amino-oxetan-3-ylmethyl)-8-chloro-4,5-dihydro-1H-pyrrolo[2,3-f]isoquinoline-3-carboxylic acid lactame (and 2-Chloro-9-chloromethyl-9-hydroxymethyl-5,6,8,9,10,11-hexahydro-3,8,11-triaza-benzo[a]fluoren-7-one)

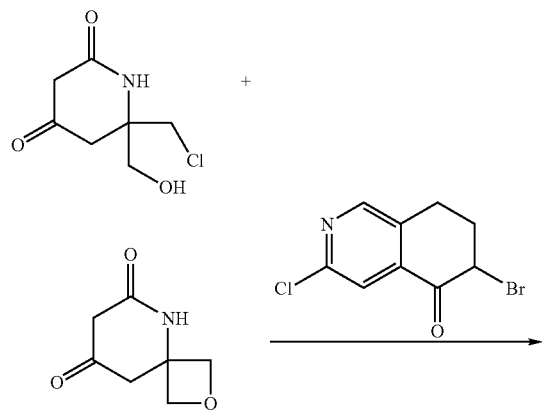

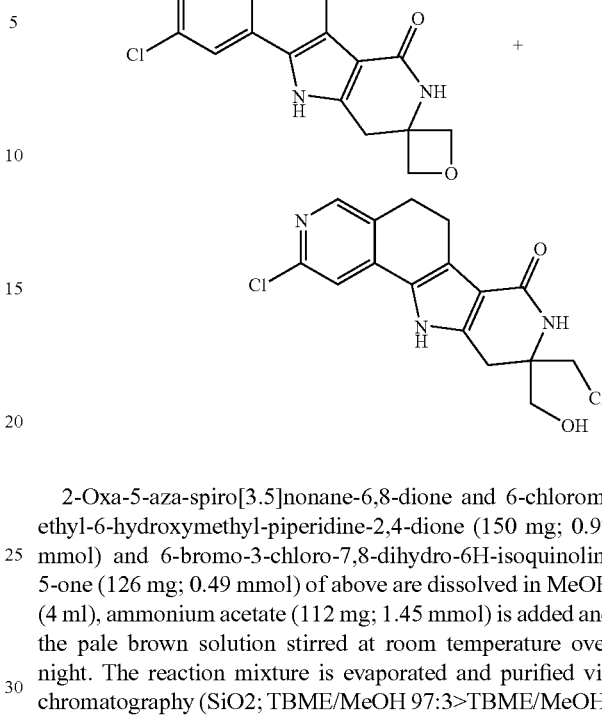

2-Oxa-5-aza-spiro[3.5]nonane-6,8-dione and 6-chloromethyl-6-hydroxymethyl-piperidine-2,4-dione (150 mg; 0.97 mmol) and 6-bromo-3-chloro-7,8-dihydro-6H-isoquinolin-5-one (126 mg; 0.49 mmol) of above are dissolved in MeOH (4 ml), ammonium acetate (112 mg; 1.45 mmol) is added and the pale brown solution stirred at room temperature over night. The reaction mixture is evaporated and purified via chromatography (SiO2; TBME/MeOH 97:3>TBME/MeOH/ $N_H3_{conc}$ 95:5:1) to yield 2-(3-amino-oxetan-3-ylmethyl)-8-chloro-4,5-dihydro-1H-pyrrolo[2,3-f]isoquinoline-3-carboxylic acid lactame (Example 20): 1H-NMR (400 MHz; DMSO-d6): 12.1 (s, 1H); 8.15 (s, 1H); 7.40 (s, 1H); 6.93 (s, 1H); 4.60 (d, 2H); 4.96 (d, 2H); 4.35 (d, 1H); 4.29 (d, 1H); 2.88 (m, 4H). MS (m/z) ES−: 314 (MH−), and by-product 2-chloro-9-chloromethyl-9-hydroxymethyl-5,6,8,9,10,11-hexahydro-3,8,11-triaza-benzo[a]fluoren-7-one: 1H-NMR (400 MHz; DMSO-d6): 1.99 (s, 1H); 8.13 (s, 1H); 7.40 (s, 1H); 6.87 (s, 1H); 5.24 (t, 1H); 3.72 (dd, 2H); 3.51 (m, 1H); 3.45 (m, 1H); 3.00 (s, 2H); 2.86 (m, 4H). MS (m/z) ES+: 352 (MH+)

EXAMPLE 21

2-(3-Amino-oxetan-3-ylmethyl)-8-(4-methoxy-phenyl)-4,5-dihydro-1H-1,7,9-triaza-cyclopenta[a]naphthalene-3-carboxylic acid lactame (and 9-chloromethyl-9-hydroxymethyl-2-(4-methoxy-phenyl)-5,6,8,9,10,11-hexahydro-1,3,8,11-tetraaza-benzo[a]fluoren-7-one)

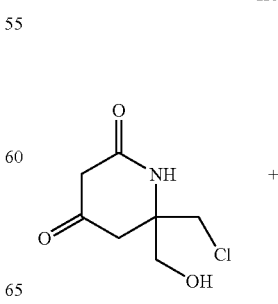

-continued

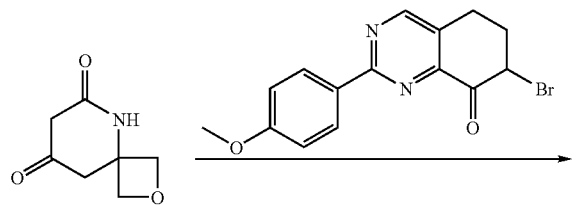

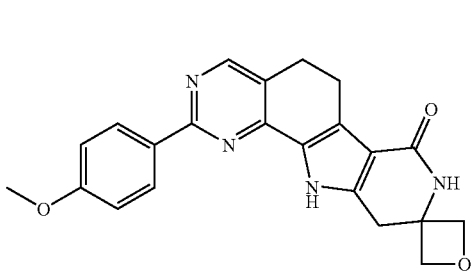

+

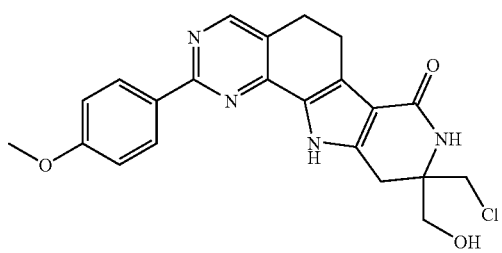

2-Oxa-5-aza-spiro[3.5]nonane-6,8-dione and 6-chloromethyl-6-hydroxymethyl-piperidine-2,4-dione (50 mg; 0.322 mmol) and 7-bromo-2-(4-methoxy-phenyl)-6,7-dihydro-5H-quinazolin-8-one (72 mg; 0.21 mmol) and ammonium acetate (132 mg; 1.72 mmol) are suspended in MeOH (2 ml) and stirred over night at room temperature. The reaction mixture is purified via chromatography (SiO$_2$; CH$_2$Cl$_2$/MeOH/ NH$_{3conc}$ 97:3:0.3 followed by TBME/MeOH/NH$_{3conc}$ 97:3: 0.6) to yield the title compound and the by-product as off-white crystals: 2-(3-amino-oxetan-3-ylmethyl)-8-(4-methoxy-phenyl)-4,5-dihydro-1H-1,7,9-triaza-cyclopenta [a]naphthalene-3-carboxylic acid lactame (Example 21) and 9-chloromethyl-9-hydroxymethyl-2-(4-methoxy-phenyl)-5, 6,8,9,10,11-hexahydro-1,3,8,11-tetraaza-benzo[a]fluoren-7-one (by-product).

Example 21: 1H-NMR (400 MHz; DMSO-d6): 12.23 (bs, 1H); 8.46 (s, 1H); 8.44 (d, 2H); 8.05 (s, 1H); 7.09 (d, 2H); 4.60 (d, 2H); 4.47 (d, 2H); 3.86 (s, 3H); 3.31 (bs, 2H); 2.95 (m, 4H). MS (m/z) ES+: 389 (MH+)

By-product: 1H-NMR (400 MHz; DMSO-d6): 12.11 (bs, 1H); 8.46 (s, 1H); 8.43 (d, 2H); 7.08 (d, 2H); 6.88 (s, 1H); 5.22 (t, 1H); 3.86 (s, 3H); 3.74 (dd, 2H); 3.46 (m, 2H); 3.10-2.85 (m, 6H). MS (m/z) ES+: 425 (MH+)

EXAMPLE 22

2-(3-Amino-oxetan-3-ylmethyl)-8-(3-fluoro-phenyl)-4,5-dihydro-1H-1,7,9-triaza-cyclopenta[a]naphthalene-3-carboxylic acid lactame (and 9-chloromethyl-2-(3-fluoro-phenyl)-9-hydroxymethyl-5,6,8,9,10,11-hexahydro-1,3,8,11-tetraaza-benzo[a]fluoren-7-one)

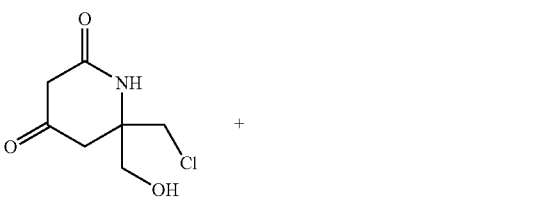

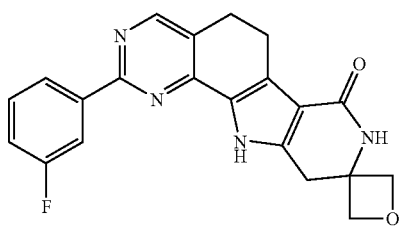

+

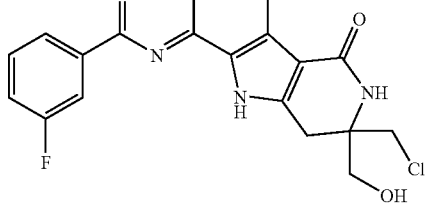

The compound is prepared in analogy to example 21. Purification via chromatography (SiO$_2$; CH$_2$Cl$_2$/MeOH 97.5:2.5) delivered the title compounds 2-(3-amino-oxetan-3-ylmethyl)-8-(3-fluoro-phenyl)-4,5-dihydro-1H-1,7,9-triaza-cyclopenta[a]naphthalene-3-carboxylic acid lactame (Example 23) and 9-chloromethyl-2-(3-fluoro-phenyl)-9-hydroxymethyl-5,6,8,9,10,11-hexahydro-1,3,8,11-tetraaza-benzo[a] fluoren-7-one (by-product) as colorless crystals. Example 22: 1H-NMR (400 MHz; DMSO-d6): 12.30 (bs, 1H); 8.54 (s, 1H); 8.32 (d, 1H); 8.27 (d, 1H); 8.07 (bs, 1H); 7.60 (dd, 1H); 7.36 (dt, 1H); 4.62 (d, 2H); 4.48 (d, 2H); 3.36 (s, 2H); 2.99 (m, 4H). MS (m/z) ES+: 377 (MH+)

By-product: 1H-NMR (400 MHz; DMSO-d6): 12.21 (s, 1H); 8.54 (s, 1H); 8.32 (d, 1H); 8.27 (d, 1H); 7.58 (dd, 1H); 7.37 (dt, 1H); 6.92 (s, 1H); 5.27 (t, 1H); 3.75 (dd, 2H); 3.53 (m, 1H); 3.47 (m, 1H); 3.07 (d, 2H); 2.99 (bd, 2H); 2.96 (bd, 2H); MS (m/z) ES+: 413 (MH+)

EXAMPLE 23

2-(3-Amino-azetidin-3-ylmethyl)-8-(4-methoxy-phenyl)-4,5-dihydro-1H-pyrrolo[2,3-f]isoquinoline-3-carboxylic acid lactame hydrochloride

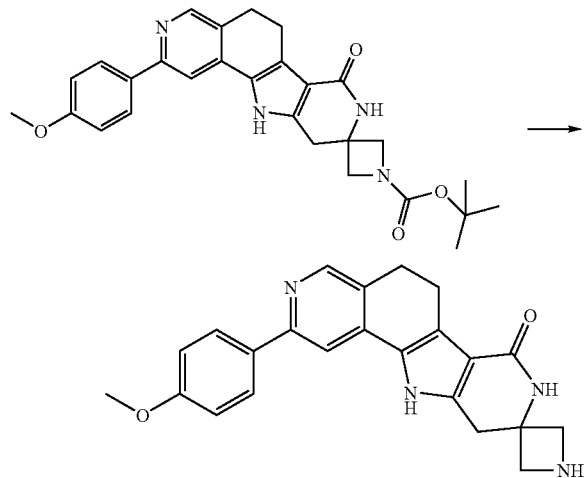

2-(3-Amino-1-tert-butoxycarbonyl-azetidin-3-ylmethyl)-8-(4-methoxy-phenyl)-4,5-dihydro-1H-pyrrolo[2,3-f]isoquinoline-3-carboxylic acid lactame (26 mg; 0.05 mmol) is dissolved in HCl$_{conc}$ (2 ml) and left at room temperature for 1 minute, when the product precipitates as colorless crystals. The mixture is evaporated an dried under reduced pressure to deliver the title compound as HCl-salt. 1H-NMR (400 MHz; DMSO-d6): 13.22 (bs, 1H); 9.80 (bs, 1H); 9.01 (bs, 1H); 8.44 (s, 1H); 8.17 (s, 1H); 8.04 (d, 2H); 7.26 (d, 2H); 4.10 (m, 2H); 3.96 (m, 2H); 3.90 (s, 3H); 3.55 (s, 2H); 3.03 (s, 4H). MS (m/z) ES+: 387 (MH+)

The starting materials are prepared as follows:

23.a: 2-(3-Amino-1-tert-butoxycarbonyl-azetidin-3-ylmethyl)-8-chloro-4,5-dihydro-1H-pyrrolo[2,3-f]isoquinoline-3-carboxylic acid lactame

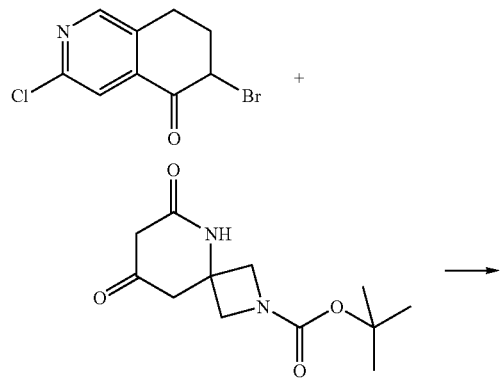

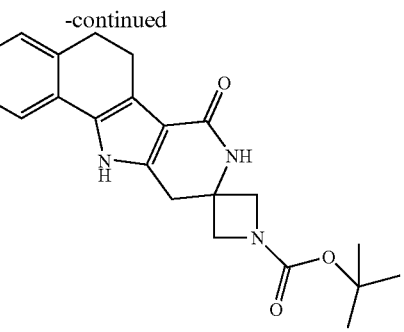

6-Bromo-3-chloro-7,8-dihydro-6H-isoquinolin-5-one (300 mg; 1.15 mmol) and 6,8-dioxo-2,5-diaza-spiro[3.5]nonane-2-carboxylic acid tert-butyl ester (324 mg; 1.27 mmol) and ammonium acetate (268 mg; 3.47 mmol) dissolved in MeOH (3.5 ml) are heated to 60° C. over night. The black-green solution is diluted with CH$_2$Cl$_2$, filtered, evaporated to dryness and purified via chromatography (SiO$_2$; acetone/hexane 2:8>4:6) to deliver the title compound as light-brown crystals. 1H-NMR (400 MHz; DMSO-d6): 12.07 (s, 1H); 8.13 (s, 1H); 7.84 (s, 1H); 7.45 (s, 1H); 3.86 (bs, 4H); 3.18 (s, 2H); 2.88 (m, 2H); 2.84 (m, 2H); 1.40 (s, 9H).
MS (m/z) ES+: 415 (MH+)

23.b: 2-(3-Amino-1-tert-butoxycarbonyl-azetidin-3-ylmethyl)-8-(4-methoxy-phenyl)-4,5-dihydro-1H-pyrrolo[2,3-f]isoquinoline-3-carboxylic acid lactame

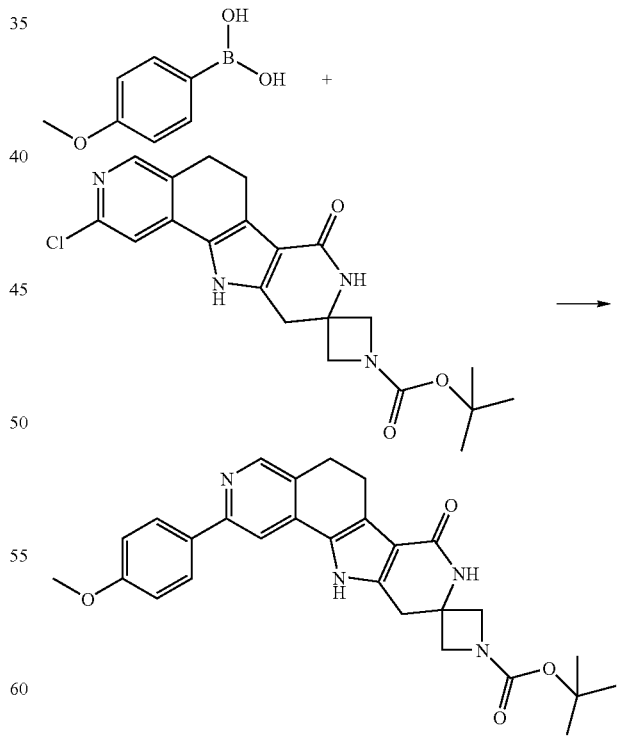

The reaction is performed in analogy to example 12.i. Purification via chromatography (SiO$_2$; acetone/hexane 3:7>6:4) and recrystallization from MeOH deliver the title compound as light-brown crystals. 1H-NMR (400 MHz;

DMSO-d6): 12.03 (s, 1H); 8.36 (s, 1H); 8.00 (d, 2H); 7.94 (s, 1H); 7.80 (s, 1H); 7.10 (d, 2H); 3.88 (bs, 4H); 3.85 (s, 3H); 3.20 (s, 2H); 2.91 (m, 2H); 2.86 (m, 2H); 1.41 (s, 9H). MS (m/z) ES+: 487 (MH+)

The following compounds are intermediates useful in the manufacture of further compounds of the formula I and serve to introduce the moiety R by reactions as described in Schemes 2, 3 or 6, or Scheme 4 as shown above, respectively:

Intermediate A: 1,1-Dimethyl-3-[4-(4,4,5,5-tetramethyl-[1,3,2]dioxaborolan-2-yl)-phenyl]-prop-2-ynyl-lamine

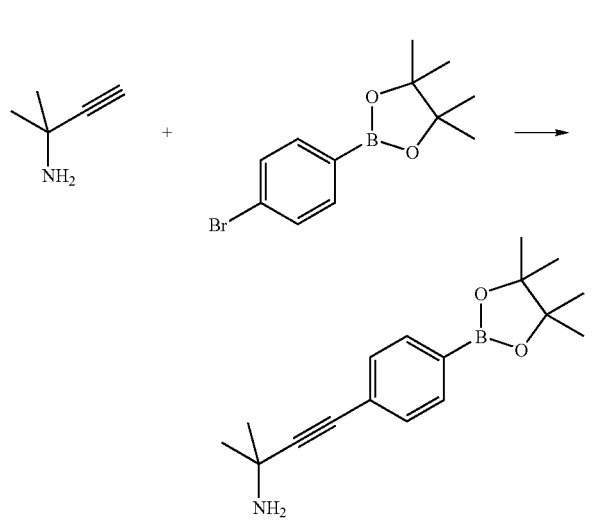

4-(4,4,5,5-Tetramethyl-1,3,2-dioxaborolan-2-yl)bromobenzene (J. Organomet. Chem. 2006, 691 (26), 5725) (200 mg; 0.71 mmol) 1,1-dimethyl-prop-2-ynylamine (350 mg; 4.25 mmol) Pd(PPh$_3$)$_2$Cl$_2$ (99 mg; 0.14 mmol) and CuI (27 mg; 0.14 mmol) are dissolved in DMF/NEt$_3$ (3.5 ml/1.5 ml) and microwaved at 100° C. for 20 minutes. The reaction mixture is evaporated and purified via chromatography (SiO$_2$; TBME/MeOH/M/NH$_{3conc}$ 95:5:0.8) to yield the title compound as yellowish crystals. H-NMR (400 Hz; DMSO-d6): 7.64 (d, 2H); 7.38 (d, 2H); 2.08 (bs, 2H); 1.39 (s, 6H); 1.31 (s, 12H). MS (m/z) ES+: 285 (MH+).

Intermediate B: trans-2-phenylvinylboronic acid (Sigma-Aldrich, order number 473790)

Intermediate C: 1,4-benzodioxan-6-boronic acid (Sigma-Aldrich, order number 635995)

Intermediate D: 5-methoxypyridine boronic acid pinacolester (Sigma-Aldrich, order number 676624)

Intermediate E: 2-methoxy-5-pyridine boronic acid (Sigma-Aldrich, order number 637610)

Intermediate F: 4-methoxyphenyl boronic acid (Sigma-Aldrich, order number 417599)

Intermediate G: 4-{2-[4-(4,4,5,5-tetramethyl[1,3,2]dioxaborolan-2-yl)-phenoxy]-ethyl}morpholine (TimTec Overseas Stock, Newark, Del., 19711, USA, order number OVS20111867)

Intermediate H: 4-(4-morpholinomethyl)-phenylboronic acid pinacol ester (Sigma-Aldrich, order number 680230)

Intermediate I: 2-(4-bromomethyl-phenyl)-4,4,5,5-tetramethyl-[1,3,2]dioxaborolane (ABCR Products, Karlsruhe, D-76187, Germany, order number AB150276)

Intermediate J: 1-Methyl-4-[4-(4,4,5,5-tetramethyl-[1,3,2]dioxaborolan-2-yl)-benzyl]-piperazine

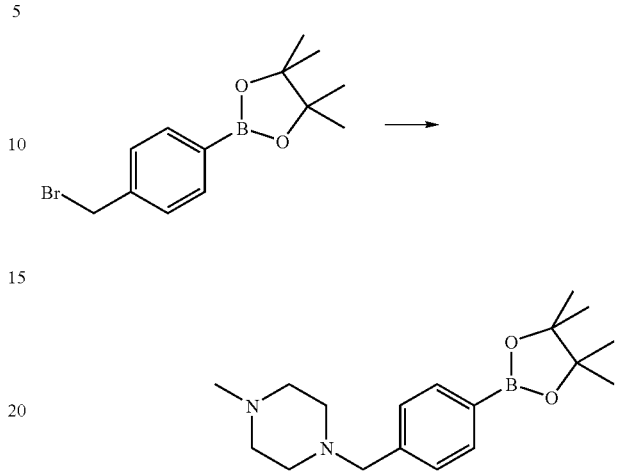

2-(4-Bromomethyl-phenyl)-4,4,5,5-tetramethyl-[1,3,2]dioxaborolane (300 mg; 1.01 mmol), N-methylpiperazine (132 mg; 1.32 mmol) and K$_2$CO$_3$ (168 mg; 1.22 mmol) in DMF (4 ml) are heated to 80° C. for 45 minutes. The reaction mixture was diluted with MeOH, filtered and purified via chromatography (SiO$_2$; CH$_2$Cl$_2$/MeOH/NH$_{3conc}$ 95:5:0.5) to yield the title compound as yellow resin. 1H-NMR (400 MHz; DMSO-d6): 7.63 (d, 2H); 7.33 (d, 2H); 3.47 (s, 1H); 2.34 (bs, 8H); 2.16 (s, 3H); 1.30 (s, 12H). MS (m/z) ES+: 317 (MH+).

Intermediate K: 1-[4-(4,4,5,5-Tetramethyl-[1,3,2]dioxaborolan-2-yl)-benzyl]-piperidine

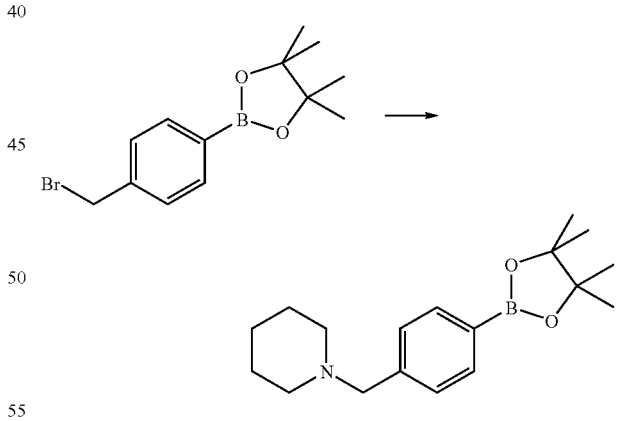

2-(4-Bromomethyl-phenyl)-4,4,5,5-tetramethyl-[1,3,2]dioxaborolane (250 mg; 0.84 mmol), piperidine (94 mg; 1.1 mmol) and K$_2$CO$_3$ (140 mg; 1.01 mmol) in DMF (4 ml) are heated to 80° C. for 45 minutes. The reaction mixture is cooled to room temperature, diluted with TBME, filtered and evaporated to dryness to deliver the title compound as orange crystals.

N 1H-NMR (400 MHz; DMSO-d6): 7.63 (d, 2H); 7.33 (d, 2H); 3.44 s, 2H); 2.31 (bs, 4H); 1.50 (m, 4H); 1.39 (m, 2H); 1.30 (s, 12H). MS (m/z) ES+: 302 (MH+).

Intermediate L: 2-Methyl-4-[4-(4,4,5,5-tetramethyl-[1,3,2]dioxaborolan-2-yl)-phenyl]-but-3-yn-2-ol

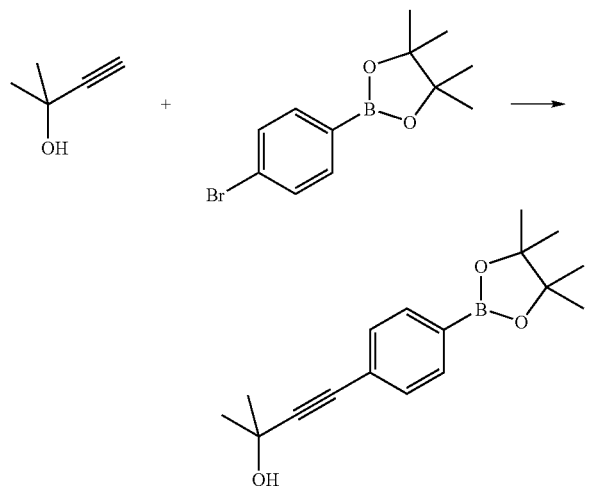

2-Methyl-but-3-yn-2-ol (24 ml; 247 mmol), 2-(4-bromophenyl)-4,4,5,5-tetramethyl-[1,3,2]dioxaborolane (8.7 g; 30.85 mmol) (J.Organomet. Chem. 2006, 691(26), 5725), Pd(PPh$_3$)$_2$Cl$_2$ (4.33 g; 6.17 mol) CuI (1.17 g; 6.17 mmol) in DMF (140 ml) and triethylamine (60 ml) are heated to 110° C. for 20 minutes. The reaction mixture is evaporated to dryness and the residue taken up in hexanes/acetone (85:15), filtered and the filtrate purified via chromatography ((SiO$_2$; hexaneslacetone 85:15) to deliver the target compound as light-brown crystals. 1H-NMR (400 MHz; DMSO-d6): 7.65 (d, 2H); 7.40 (d, 2H); 5.51 (s, 1H); 1.48 (s, 6H); 1.31 (s, 12H). MS (m/z) ES+: 269 (100).

Intermediate M (Scheme 4): 4-methoxybenzamidine (Sigma-Aldrich, order number 64785)

Intermediate N (Scheme 4): 4-trifluoromethoxy-benzamidine (Tyger Scientific Products, Ewing, N.J. 08638, USA, order number T32010)

Intermediate O (Scheme 4): 4-ethoxy-benzamidine (Tyger Scientific Products, Ewing, N.J. 08638, USA, order number E33005)

Intermediate P (Scheme 4): 4-((E)-styryl)-benzamidine (J. Chem. Coc. 1942, 103)

Intermediate Q (Scheme 4): 4-bromobenzamidine benzamidine (Tyger Scientific Products, Ewing, N.J. 08638, USA, order number B64081)

Intermediate R: 2,4-difluorophenylboronic acid (Sigma-Aldrich, order number 465070)

Intermediate S: 4-fluorophenylboronic acid (Sigma-Aldrich, order number 47330)

Intermediate T: 2-fluorophenylboronic acid (Sigma-Aldrich, order number 445223)

Intermediate U: 3-fluorophenylboronic acid (Sigma-Aldrich, order number 441643)

LC-MS Methods as Used Herein

LC-MS Method 1:
Waters Acquity UPLC method
Mass-spectrometer: Waters, model ZQ2000
Column: Acquity Column 1.0×50 mm HSS T3 1.8 m
Solvent A: Water+3 mM ammonium acetate+0.05% formic acid
Solvent B: Acetonitrile+0.04% formic acid
Gradient: linear from A/B 98:2 to A/B 2:98 within 5 minutes LC-MS Method 2:
Waters Acquity UPLC method
Mass-spectrometer: Waters, model ZQ2000
Column: Acquity Column 2.1×50 mm HSS T3 1.8 m
Solvent A: Water+3 mM ammonium acetate+0.05% formic acid
Solvent B: Acetonitrile+0.04% formic acid
Gradient: linear from A/B 98:2 to A/B 2:98 within 5 minutes LC-MS Method 3:
Waters Acquity UPLC method
Mass-spectrometer: Waters, model SQD
Column: Acquity Column 2.1×50 mm HSS T3 1.8 m
Solvent A: Water+3 mM ammonium acetate+0.05% formic acid
Solvent B: Acetonitrile+0.04% formic acid
Gradient: linear from A/B 98:2 to A/B 2:98 within 5 minutes LC-MS Method 4:
Waters Acquity CapLC-LTQ method
Mass-spectrometer: ThermoFinnigan, Model Linear Ion Trap, ESI, APCI
Column: Acquity Column 2.1×50 mm HSS T3 1.8 m
Solvent A: Water+3 mM ammonium acetate+0.05% formic acid
Solvent B: Acetonitrile+0.04% formic acid
Gradient: linear from A/B 98:2 to A/B 2:98 within 5 minutes LC-MS Method 5:
Agilent 1100 Bin
Mass-spectrometer: ZQ 2000
Column: Waters×Bridge 3×30 mm 2.5 um C18
Solvent A: Water/acetonitrile (5%)+0.2% formic acid
Solvent B: Acetonitrile+0.2% formic acid
Gradient: linear from A/B 9:1 to A/B 5:95 within 2.4 minutes LC-MS Method 6:
Agilent 1100 Bin
Mass-spectrometer: ZQ 2000
Column: Waters×Bridge 3×30 mm 2.5 um C18
Solvent A: Water/acetonitrile (5%)+0.2% formic acid
Solvent B: Acetonitrile+0.2% formic acid
Gradient: linear from A/B 99:1 to A/B 5:95 within 2.9 minutes LC-MS Method 7:
Agilent 1100 Bin
Mass-spectrometer: ZQ 2000
Column: Waters×Bridge 3×30 mm 2.5 um C18
Solvent A: Water/acetonitrile (5%)+0.5-1.0% formic acid
Solvent B: Acetonitrile+0.5-1.0% formic acid
Gradient: linear from A/B 90:10 to A/B 5:95 within 1.7 minutes, further elution with A/B 5:95 up to 2.40 minutes LC-MS Method 8:
Agilent 1100 Bin
Mass-spectrometer: ZQ 2000
Column: Waters×Terra 3×30 mm 2.5 um C18
Solvent A: Water/acetonitrile (5%)+0.2% formic acid
Solvent B: Acetonitrile+0.2% formic acid
Gradient: linear from A/B 90:10 to A/B 5:95 within 1.5 minutes, further elution with A/B 5:95 up to 2.50 minutes Commercial Reagents as Used Herein
1-Amino-cyclobutaneacetic acid (MicroChemistry Building Blocks, 15051)
(1-Amino-cyclopropyl)-acetic acid methyl ester (Chemstep Product List, 13926)

2-Aminopyridine-5-boronic acid, pinacol ester (ABCR Product List AB173868)
Benzofurane-2-boronic acid (Aldrich, 499943)
1,4-Benzodioxane-6-boronic acid (Aldrich, 635995)
Bis-(triphenylphosphin)-palladium(II)-dichlorid; $Pd(PPh_3)_2Cl_2$ (Fluka 15253)
Bis(pinacolato)diboron (Frontier Scientific Catalog D6878)
3-Bromo-5-(4-fluorophenyl)pyridine (Small Molecules Product List 12-1489)
4-Bromobenzimidamide, HCl (Combi-Blocks Catalog HC-6369)
Bromomethylcyclopropane (Fluka 17163)
3-Chlorophenylboronic acid (Aldrich, 417521)
4-Ccyanophenylboronic acid (ALDRICH, 521418)
3-Cyanophenylboronic acid (Aldrich 513016)
3-Cyano-4-fluorophenylboronic acid (ABCR, AB173953)
2-Cyanopyridine-5-boronic acid (SYNCHEM OHG Product List, un119)
(5-Cyanopyridin-3-yl)boronic acid (Anichem P20027)
3,5-Dibromopyridine (ABCR Product List AB115322)
3,3-Difluoroazetidine hydrochloride (ABCR, AB174329)
2,6-Difluoropyridine-3-boronic acid (SYNCHEM OHG Product List, un085)
2,3-Dihydro-benzo[1,4]dioxine-6-boronic acid (Aldrich 635995)
3,4-Dimethoxyphenylboronic acid (Aldrich, 480118)
3,5-Dimethoxyphenylboronic acid (Combi-Blocks Catalog BB-2622)
2-Dimethylaminopyridine-5-boronic acid (Frontier Scientific, D9115)
(1-diazo-2-oxo-propyl)-phosphonic acid dimethyl ester (Paragos, 40364, Bestmann-Ohira reagent)
4-Ethoxy-3-fluorophenyl-boronic acid (ABCR, AB150605)
4-Ethoxyphenyl-boronic acid (ABCR, AB175405)
6-Ethoxypyridine-3-boronic acid (ABCR, AB173053)
2-Fluoroaniline (Fluka 46470)
3-Fluoro-4-methoxyphenylboronic acid (Aldrich 564036)
3-Fluoro-2-methoxypyridine-5-boronic acid (Asymchem Product List 110641)
2-Fluoro-3-methylpyridine-5-boronic acid (Boron Molecular, BM616)
2-Fluoro-6-methylpyridine-3-trifluoroborate potassium salt (Frontier Scientific F10077)
3-Fluoro-4-(N-morpholinomethyl)phenylboronic acid pinacolester (Boron Molecular, BM632)
2-Fluorophenylboronic acid (Maybridge Building Blocks AC 35934)
3-Fluorophenylboronic acid (Sigma-Aldrich, order number 441643)
2-Fluoropyridine-3-boronic acid (ABCR, AB175551)
2-Fluoropyridine-4-boronic acid (SYNCHEM OHG Product List un100)
2-Fluoropyridine-5-boronic acid (ABCR, AB181129)
3-Fluoropyridine-5-boronic acid pinacol ester (Frontier Scientific, F2018)
3-Formyl-4-methoxyphenyl-boronic acid (ABCR, AB150374)
3-Hydroxyazetidine hydrochloride (Atlantic Scitech Group, 880012)
4-Hydroxy-3-methoxyphenylboronic acid pinacol ester (Aldrich, 518786)
6-(Hydroxymethyl)pyridine-3-boronic acid (Combi-Blocks BB-3541)
2-Isopropoxy-5-(4,4,5,5-tetramethyl-1,3,2-dioxaborolan-2-yl)pyridine (ABCR, AB173057)
Lithium hexamethyldisilazane 1M in hexane (Fluka 62445)
3-Methoxy-benzamidine HCl (Tyger Scientific Product List M33012)
4-Methoxyphenylboronic acid (ABCR Product List, AB169111)
5-Methoxy-3-pyridineboronic acid pinacol ester (Aldrich, 676624)
2-Methoxy-5-pyridineboronic acid (Aldrich, 637610)
5-Methoxy-3-pyridineboronic acid pinacol ester (Aldrich, 676624)
4-Methyl-7-(4,4,5,5-tetramethyl-1,3,2-dioxaborolan-2-yl)-3,4-dihydro-2H-1,4-benzoxazine (Maybridge Building Blocks CC 13539)
6-Methylpyridine-3-boronic acid (SYNCHEM OHG, un119)
5-Methylpyridine-3-boronic acid (ABCR Product List, AB175595)
4-(2-morpholin-4-ylethoxy)benzonitrile (Maybridge Building Blocks CC 42116)
6-Morpholinopyridine-3-boronic acid pinacolester (ABCR AB172701)
3-Morpholinophenylboronic acid pinacol ester (Frontier Scientific Catalog M1882)
4-Morpholinophenylboronic acid (Maybridge Building Blocks CC 17412)
2-(Piperidin-1-yl)pyridine-5-boronic acid pinacol ester (Frontier Scientific Catalog, P1758)
Pyridine-3-boronic acid (ABCR, AB152416)
Pyridine-3-carboxamidine hydrochloride (Maybridge Building Blocks MO 07766)
Pyridin-4-ylboronic acid (Maybridge Building Blocks, CC 04212)
5-Pyrimidinylboronic acid (Maybridge Building Blocks, CC 07412)
4-{2-[4-(4,4,5,5-Tetramethyl-[1,3,2]dioxaborolan-2-yl)-phenoxy]-ethyl}-morpholine (Focus Synthesis Products FS000534)
2-(Tetrahydropyran-4-yloxy)-5-(4,4,5,5-tetramethyl-1,3,2-dioxaborolan-2-yl)pyridine (Maybridge Building Blocks, CC 58339) for ex 96
2-Trifluoromethyl-pyridine-5-boronic acid (Focus Synthesis Product List, FS000599)
2-(Trifluoromethyl)phenylboronic acid (Frontier Scientific Catalog, T6300)

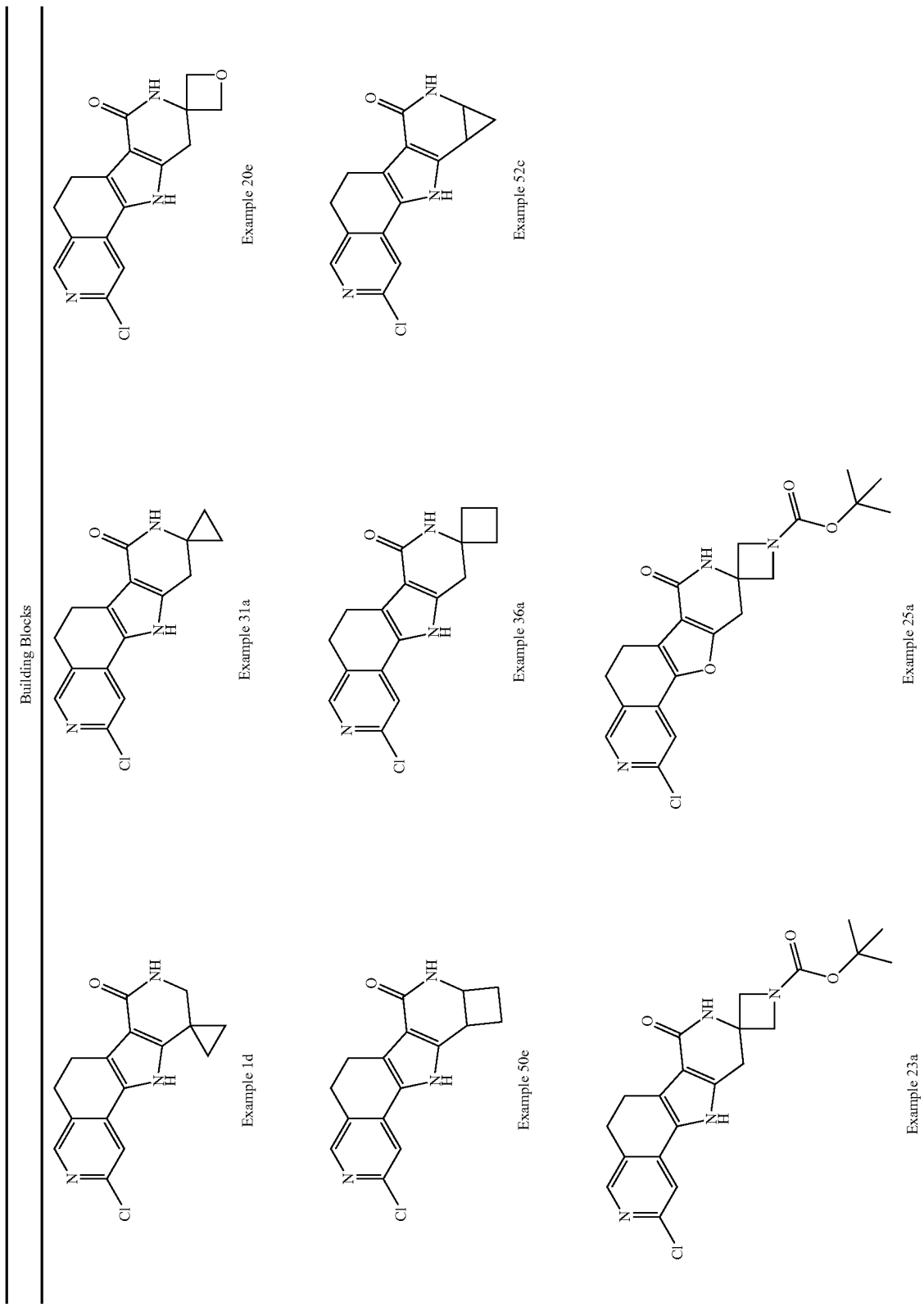

-continued
Building Blocks
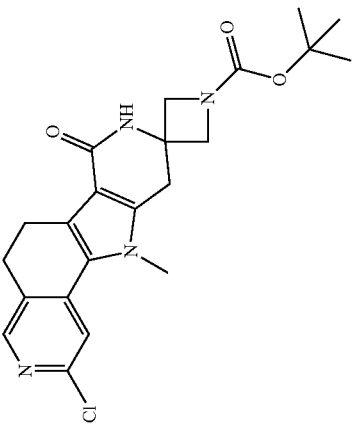
Example 132a
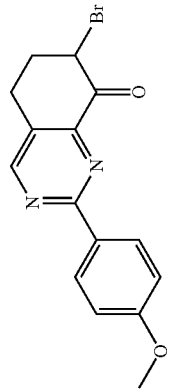
Example 14c
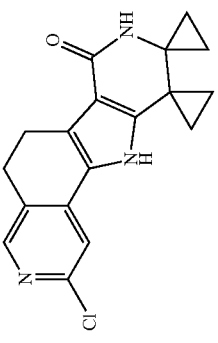
Example 179d
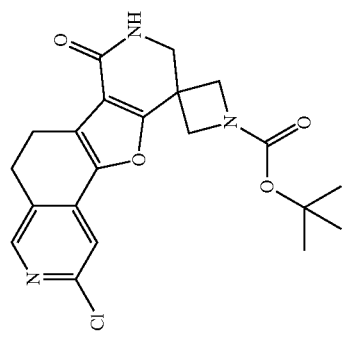
Example 178b
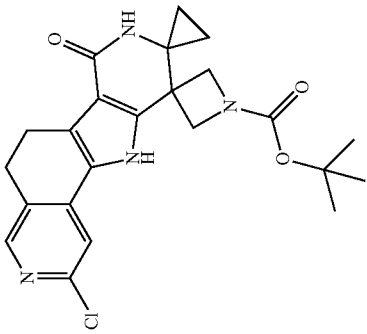
Example 180e
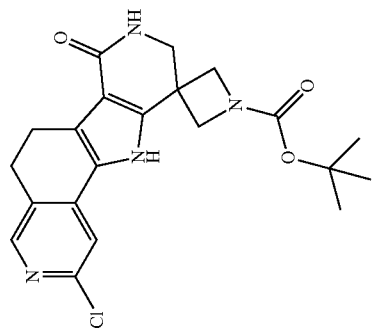
Example 156a -continued
Building Blocks
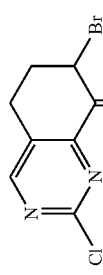
Example 257c
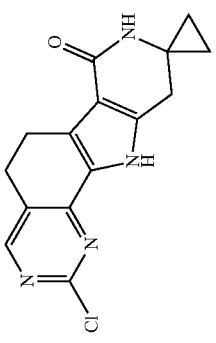
Example 257d
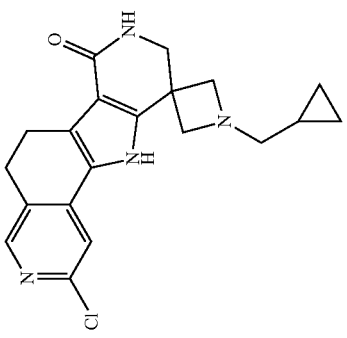
Example 261a
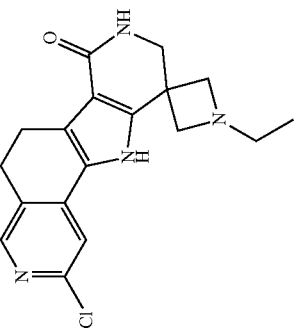
Example 263a
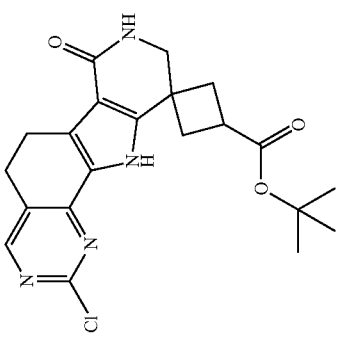
Example 268b
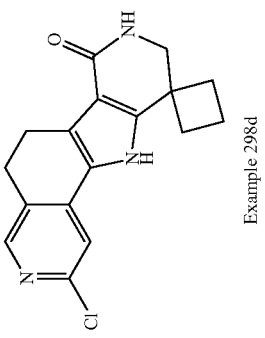
Example 298d

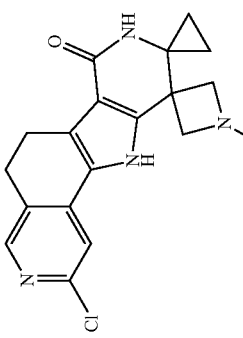

-continued
Building Blocks
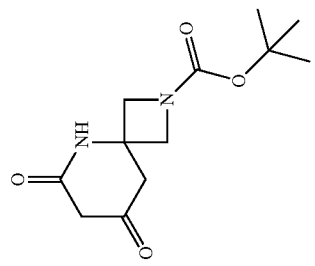
Example 34

Example 156
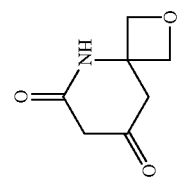
Example 298c
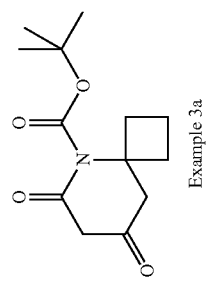
Example 3a
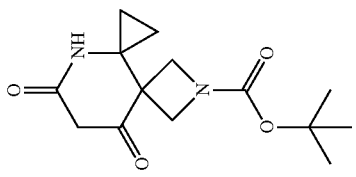
Example 180d
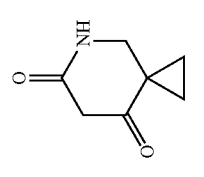
WO2005013986
WO2005014572
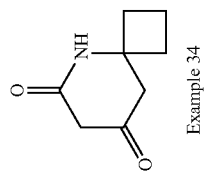
Example 18c
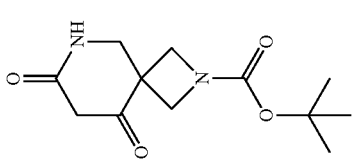
Example 179c
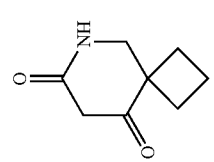
Example 20d -continued
Building Blocks
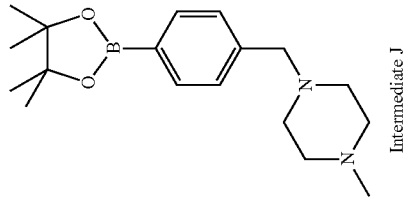
Example 11f
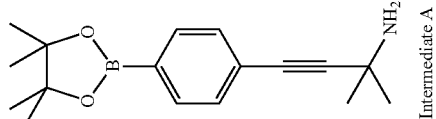
Intermediate A
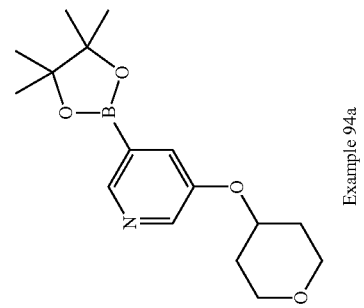
Intermediate J
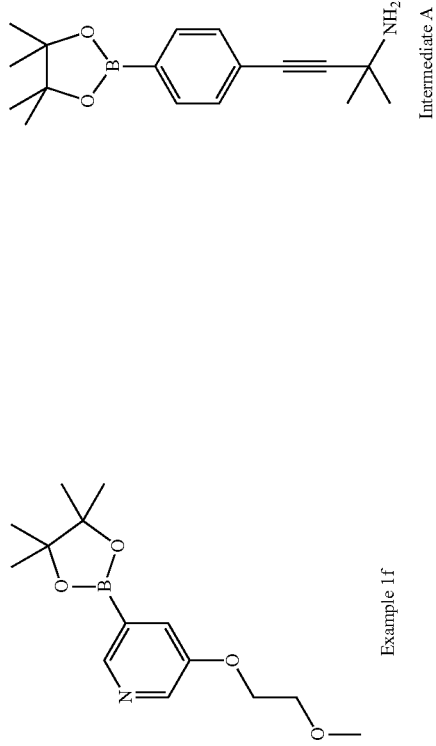
Intermediate K
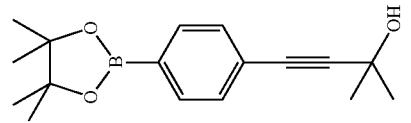
Intermediate L
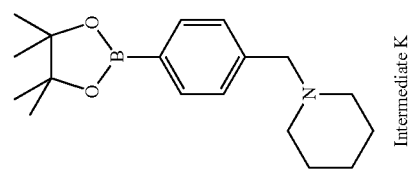
Example 94a -continued
Building Blocks
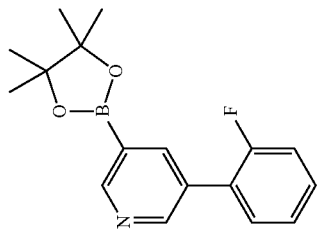
Example 135b
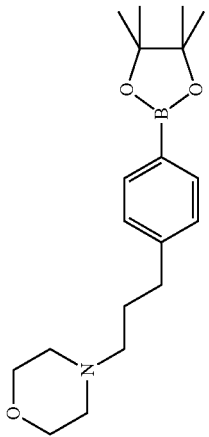
Example 246a
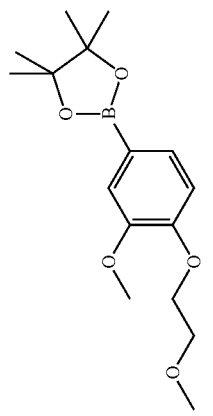
Example 79a
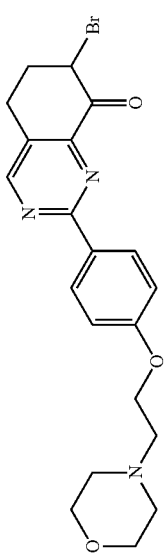
Example 48
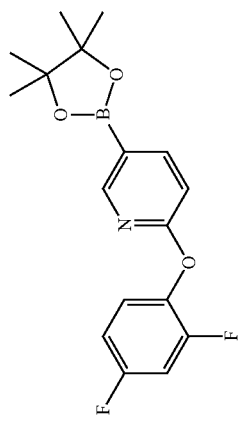
Example 95b
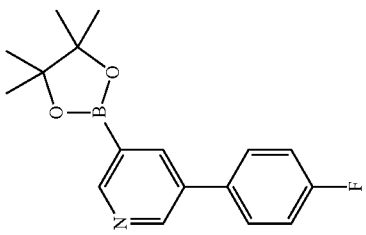
Example 136a
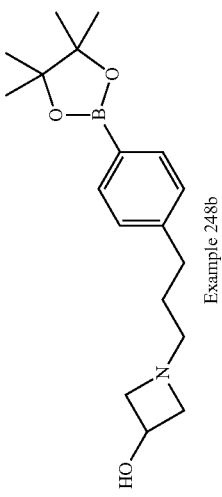
Example 248b

EXAMPLE 24

2-(3-Amino-azetidin-3-ylmethyl)-8-(3-fluoro-phenyl)-4,5-dihydro-1H-pyrrolo[2,3-f]isoquinoline-3-carboxylic acid lactam hydrochloride

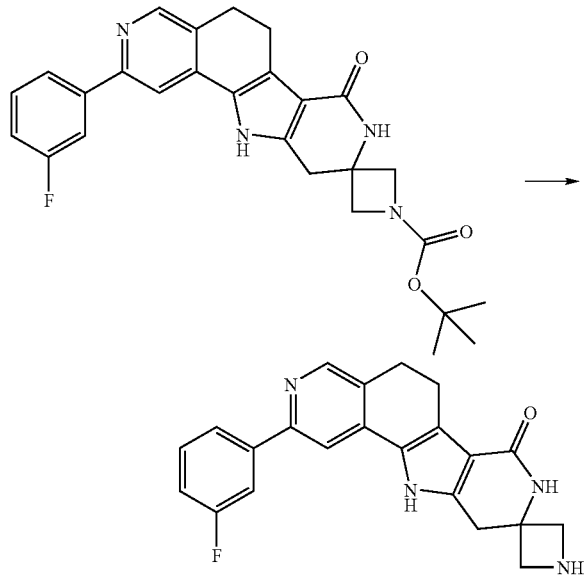

2-(3-Amino-1-tert-butoxycarbonyl-azetidin-3-ylmethyl)-8-(3-fluoro-phenyl)-4,5-dihydro-1H-pyrrolo[2,3-f]isoquinoline-3-carboxylic acid lactam (26.5 mg; 0.056 mmol) is dissolved in HCl$_{conc}$ (1 ml) and kept at room temperature for 2 minutes. Evaporation to dryness and recrystallization from MeOH/TBME yields the title compound as yellow crystals (26 mg; 100%) 1H-NMR (400 MHz; DMSO-d6): 13.10 (bs, 1H); 9.81 (bs, 1H); 9.00 (bs, 1H); 8.53 (s, 1H); 8.47 (s, 1H); 8.14 (s, 1H); 7.95 (d, 2H); 7.73 (m, 1H); 7.51 (bt, 1H); 4.10 (m, 2H); 3.96 (m, 2H); 3.56 (s, 2H); 3.03 (bs, 4H). MS (m/z) ES+: 375 (MH+).

Retention time: 1.46 minutes (LC-MS method 2)

The starting materials are prepared as follows:

24.a: 2-(3-Amino-1-tert-butoxycarbonyl-azetidin-3-ylmethyl)-8-(3-fluoro-phenyl)-4,5-dihydro-1H-pyrrolo[2,3-f]isoquinoline-3-carboxylic acid lactam

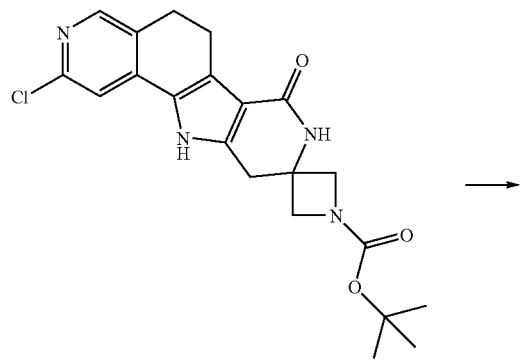

-continued

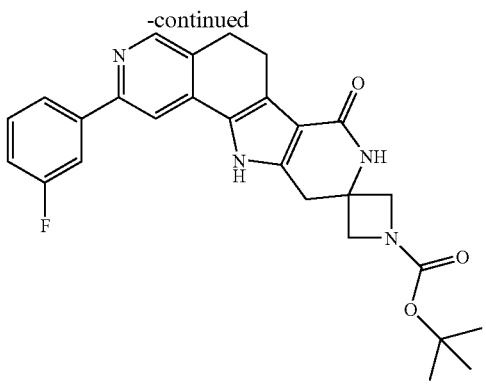

2-(3-Amino-1-tert-butoxycarbonyl-azetidin-3-ylmethyl)-8-chloro-4,5-dihydro-1H-pyrrolo[2,3-f]isoquinoline-3-carboxylic acid lactam (Example 23.a) (58 mg; 0.14 mmol) and 3-fluorobenzenboronic acid (39 mg; 0.28 mmol) are coupled in analogy to Example 1. Purification via chromatography (SiO$_2$; TBME/MeOH/NH$_{3conc}$ 100:0:0 to 98:2:0.2) followed by recrystallization from EtOAc yields the title compound as colorless crystals (28 mg; 43%). 1H-NMR (400 MHz; DMSO-d6): 12.04 (s, 1H); 8.43 (s, 1H); 8.06 (s, 1H); 7.92 (d, 1H); 7.85 (bs, 1H); 7.82 (s, 1H); 7.58 (bs, 1H); 7.30 (bt, 1H); 3.88 (bs, 4H); 3.22 (s, 2H); 2.93 (m, 4H); 1.41 (s, 9H). MS (m/z) ES+: 475 (MH+).

EXAMPLE 25

2-(3-Amino-azetidin-3-ylmethyl)-8-(3-fluoro-phenyl)-4,5-dihydro-furo[2,3-f]isoquinoline-3-carboxylic acid lactam dihydrochloride

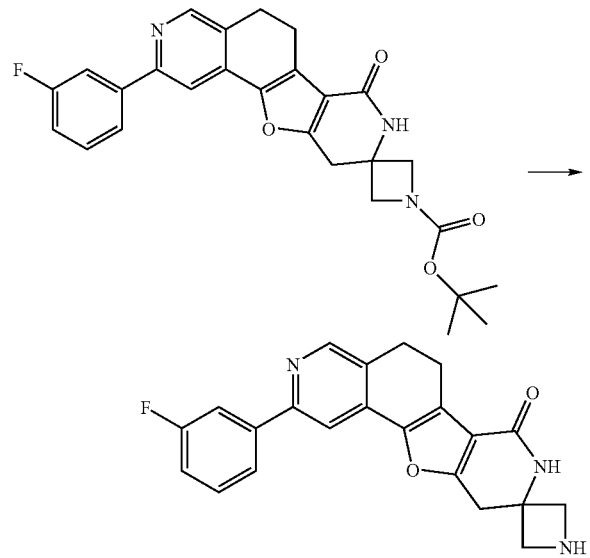

2-(3-Amino-1-tert-butoxycarbonyl-azetidin-3-ylmethyl)-8-(3-fluoro-phenyl)-4,5-dihydro-furo[2,3-f]isoquinoline-3-carboxylic acid lactam (40 mg; 0.08 mmol) is dissolved in HCl$_{conc}$ (1 ml) and kept at room temperature for 1 minute. Evaporation to dryness and washing with ether delivers the title compound as yellow crystals (39 mg; 100%). 1H-NMR (400 MHz; DMSO-d6): 10.04 (m, 1H); 9.12 (m, 1H); 8.64 (s, 1H); 8.55 (s, 1H); 8.11 (s, 1H); 8.05 (s, 1H); 8.01 (s, 1H); 7.63 (dd, 1H); 7.42 (bt, 1H); 4.15 (m, 2H); 4.03 (m, 2H); 3.74 (s, 2H); 3.11 (m, 2H); 3.02 (m, 2H). MS (m/z) ES+: 376 (MH+).

Retention time: 1.71 minutes (LC-MS method 2)

The starting materials are prepared as follows:

EXAMPLE 25.A 2-(3-Amino-1-tert-butoxycarbonyl-azetidin-3-ylm-ethyl)-8-chloro-4,5-dihydro-furo[2,3-f]isoquinoline-3-carboxylic acid lactam

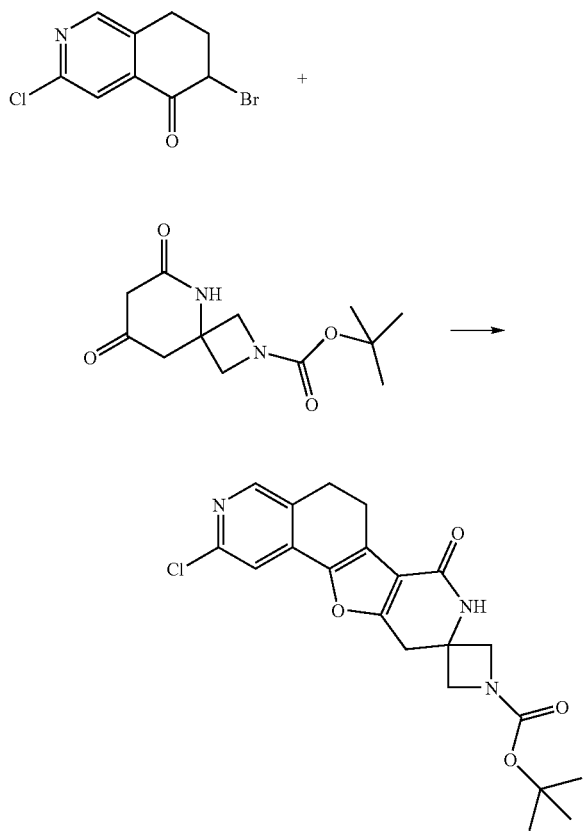

6-Bromo-3-chloro-7,8-dihydro-6H-isoquinolin-5-one (Example 1.c) (500 mg; 1.93 mmol) and 6,8-dioxo-2,5-diaza-spiro[3.5]nonane-2-carboxylic acid tert-butyl ester (Example 18.e) (588 mg; 2.3 mmol) and NaOAc (158 mg; 1.9 mmol) are dissolved in MeOH (5 ml) and stirred over night at room temperature. The reaction mixture is evaporated to dryness, dissolved in $H_2SO_{4conc}$ (10 ml) and stirred (~10 minutes) until the initial foaming has ceased. The reaction mixture is poured on 2N NaOH/ice and combined with TBME (100 ml) and BOC2O (2 g; 9 mmol) under stirring for 20 minutes. The reaction mixture is extracted with TBME three times. The combined organic phases are dried over $Na_2SO_4$ filtered and evaporated to dryness to deliver the target compound as slightly colored crystals (181 mg; 23%). 1H-NMR (400 MHz; DMSO-d6): 8.34 (s, 1H); 8.27 (s, 1H); 7.35 (s, 1H); 3.93 (bs, 4H); 3.42 (s, 2H); 2.95 (m, 4H); 1.41 (s, 9H). MS (m/z) ES+: 416 (MH+).

EXAMPLE 25.B 2-(3-Amino-1-tert-butoxycarbonyl-azetidin-3-ylm-ethyl)-8-(3-fluoro-phenyl)-4,5-dihydro-furo[2,3-f]isoquinoline-3-carboxylic acid lactam

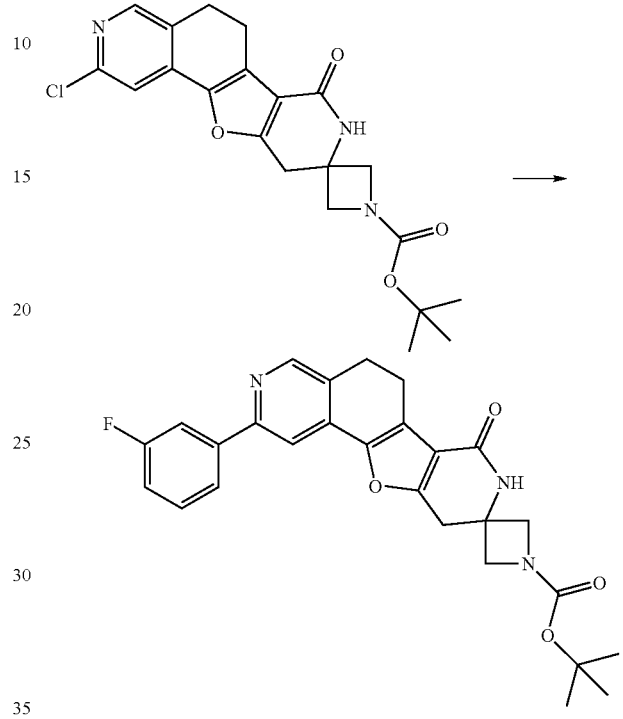

The coupling with 3-fluorophenylboronic acid is performed in analogy to Example 1 Purification via chromatography ($SiO_2$; TBME/MeOH/$NH_{3conc}$ 100:0:0 to 98:2:0.2) and trituration with TBME delivers the title compound as colorless crystals (81 mg; 71%). 1H-NMR (400 MHz; DMSO-d6): 8.55 (s, 1H); 8.33 (s, 1H); 7.98 (d, 1H); 7.93 (bd, 1H); 7.89 (s, 1H); 7.56 (dd, 1H); 7.29 (dd, 1H); 3.94 (bs, 4H); 3.44 (s, 2H); 3.02 (m, 2H); 2.97 (m, 2H); 1.35 (s, 9H). MS (m/z) ES+: 476 (MH+).

EXAMPLE 26

2-(3-Amino-azetidin-3-ylmethyl)-8-(3-fluoro-phenyl)-4,5-dihydro-1H-1,7,9-triaza-cyclopenta[a]naphthalene-3-carboxylic acid lactam hydrochloride

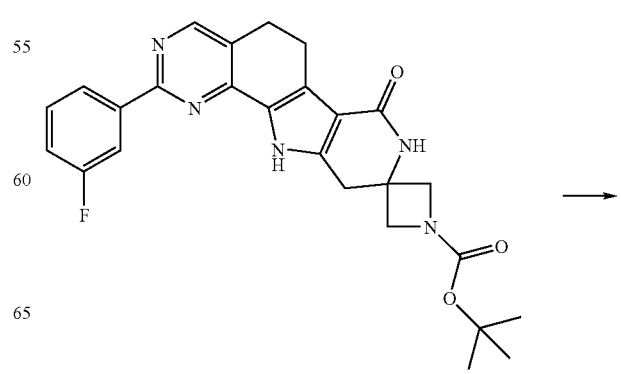

-continued

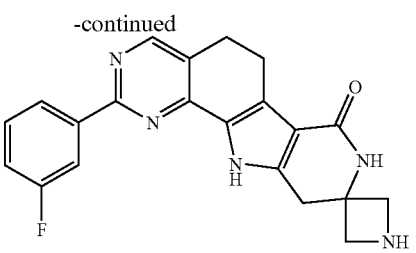

2-(3-Amino-1-tert-butoxycarbonyl-azetidin-3-ylmethyl)-8-(3-fluoro-phenyl)-4,5-dihydro-1H-1,7,9-triaza-cyclopenta[a]naphthalene-3-carboxylic acid lactam (65 mg; 0.137 mmol) is dissolved in $HCl_{conc}$ (1 ml). After 1 minute at room temperature a precipitate is formed, which is filtered and dried to yield the title compound as yellow crystals (64 mg; 100%). 1H-NMR (400 MHz; DMSO-d6): 12.54 (s, 1H); 9.80 (bs, 1H); 9.09 (bs, 1H); 8.57 (s, 1H); 8.34 (d, 1H); 8.30 (bd, 1H); 8.08 (s, 1H); 7.61 (m, 1H); 7.40 (bt, 1H); 4.12 (m, 2H); 3.97 (m, 2H); 3.49 (s, 2H); 2.99 (m, 4H). MS (m/z) ES+: 376 (MH+). Retention time: 1.88 minutes (LC-MS method 2)

The starting materials are prepared as follows:

EXAMPLE 26.A 2-(3-Amino-1-tert-butoxycarbonyl-azetidin-3-ylmethyl)-8-(3-fluoro-phenyl)-4,5-dihydro-1H-1,7,9-triaza-cyclopenta[a]naphthalene-3-carboxylic acid lactam

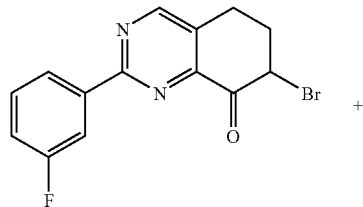

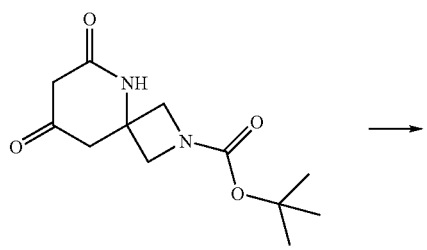

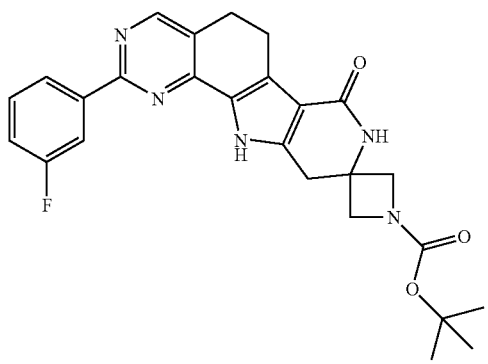

7-Bromo-2-(3-fluoro-phenyl)-6,7-dihydro-5H-quinazolin-8-one (prepared in analogy to Example 19 from 3-fluorobenzamidine) (120 mg; 0.37 mmol), 6,8-dioxo-2,5-diaza-spiro[3.5]nonane-2-carboxylic acid tert-butyl ester (Example 18.e) (105 mg; 0.41 mmol) and ammonium acetate (72 mg; 0.94 mmol) is suspended in MeOH (2.5 ml) and stirred over night at room temperature. The reaction mixture is diluted with $CH_2Cl_2$ and purified via chromatography ($SiO_2$; acetone/hexane 3:7>4:6) to yield the title compound as light yellow solid (93 mg; 52%). 1H-NMR (400 MHz; DMSO-d6): 12.29 (s, 1H); 8.55 (s, 1H); 8.34 (d, 1H); 8.28 (dd, 1H); 7.90 (s, 1H); 7.58 (m, 1H); 7.37 (bt, 1H); 3.88 (bs, 4H); 3.22 (s, 2H); 2.99 (m, 4H); 1.41 (s, 9H). MS (m/z) ES+: 476 (MH+).

EXAMPLE 27

2-(3-Amino-azetidin-3-ylmethyl)-8-(3-fluoro-phenyl)-1-methyl-4,5-dihydro-1H-1,7,9-triaza-cyclopenta[a]naphthalene-3-carboxylic acid lactam hydrochloride

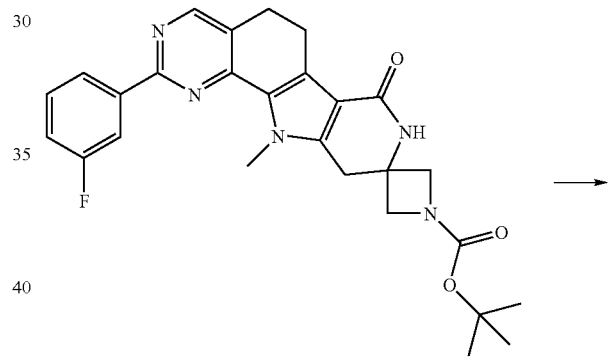

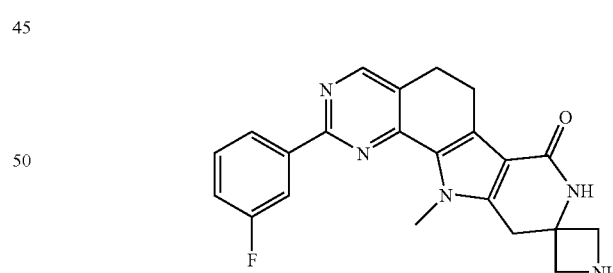

2-(3-Amino-1-tert-butoxycarbonyl-azetidin-3-ylmethyl)-8-(3-fluoro-phenyl)-1-methyl-4,5-dihydro-1H-1,7,9-triaza-cyclopenta[a]naphthalene-3-carboxylic acid lactam 31 mg; 0.064 mol) is dissolved in $HCl_{conc}$ (1 ml). After 2 minutes at room temperature a precipitate is formed, which is filtered and dried to yield the title compound as yellow crystals (28 mg; 100%). 1H-NMR (400 MHz; DMSO-d6): MS (m/z) ES+: 390 (MH+). Retention time: 1.90 minutes (LC-MS method 2).

The starting materials are prepared as follows:

27.a: 2-(3-Amino-1-tert-butoxycarbonyl-azetidin-3-ylmethyl)-8-(3-fluoro-phenyl)-1-methyl-4,5-dihydro-1H-1,7,9-triaza-cyclopenta[a]naphthalene-3-carboxylic acid lactam

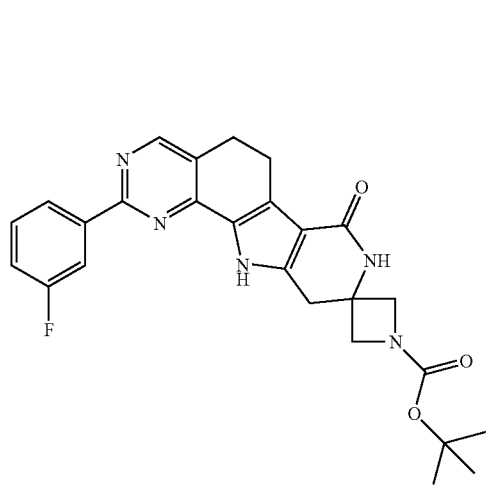

2-(3-Amino-1-tert-butoxycarbonyl-azetidin-3-ylmethyl)-8-(3-fluoro-phenyl)-4,5-dihydro-1H-1,7,9-triaza-cyclopenta[a]naphthalene-3-carboxylic acid lactam (25 mg; 0.053 mmol) in DMF (1 ml) is cooled to 5° C. and treated with KN(TMS)$_2$ (0.053 mmol; 0.066 ml of a 0.8 molar solution in toluene) under stirring. After 5 minutes at 5° C., MeI (0.05 ml; 0.8 mmol) in DMF (0.1 ml) is added and stirring continued for 5 minutes. The reaction mixture is evaporated and purified via chromatography (SiO$_2$; acetone/hexane 3:7>6:4) to yield the title compound as colorless crystals (18 mg; 69%).

1H-NMR (400 MHz; DMSO-d6): 8.59 (s, 1H); 8.23 (d, 1H); 8.08 (bd, 1H); 7.93 (s, 1H); 7.61 (m, 1H); 7.38 (dt, 1H); 4.19 (s, 3H); 3.91 (bs, 4H); 3.29 (bs, 2H); 3.00 (m, 2H); 2.91 (m, 2H); 1.41 (s, 9H). MS (m/z) ES+: 490 (MH+).

EXAMPLE 28

2-(3-Amino-1-methyl-azetidin-3-ylmethyl)-8-(3-fluoro-phenyl)-4,5-dihydro-1H-1,7,9-triaza-cyclopenta[a]naphthalene-3-carboxylic acid lactam

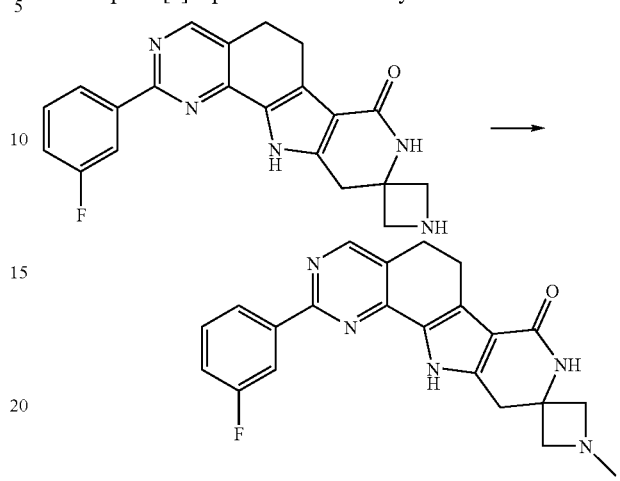

2-(3-Amino-azetidin-3-ylmethyl)-8-(3-fluoro-phenyl)-4,5-dihydro-1H-1,7,9-triaza-cyclopenta[a]naphthalene-3-carboxylic acid lactam (free base, Example 26) (39 mg; 0.1 mmol), paraformaldehyde (100 mg) and NaCNBH$_3$ (100 mg; 1.65 mmol) in MeOH (8 ml) are stirred as a suspension at room temperature. The reaction mixture is stirred for 10 minutes, 2N HCl (2 ml) is added, stirred for 2 minutes and poured on a saturated solution of K$_2$CO$_3$. The reaction mixture is extracted with TBME three times, the combined organic phases are dried over K$_2$CO$_3$, filtered and evaporated to dryness to yield the title compound after crystallization from MeOH as yellowish crystals (27 mg; 67%). 1H-NMR (400 MHz; DMSO-d6): 12.23 (s, 1H); 8.53 (s, 1H); 8.34 (d, 1H); 8.27 (dd, 1H); 7.63 (s, 1H); 7.58 (m, 1H); 7.37 (bt, 1H); 3.38 (m, 2H); 3.24 (s 2H); 3.19 (d, 2H); 2.98 (m, 4H); 2.27 (s, 3H). MS (m/z) ES+: 390 (MH+). Retention time: 1.91 minutes (LC-MS method 2).

EXAMPLE 29

2-(3-Amino-1-methyl-azetidin-3-ylmethyl)-8-(3-fluoro-phenyl)-1-methyl-4,5-dihydro-1H-1,7,9-triaza-cyclopenta[a]naphthalene-3-carboxylic acid lactam

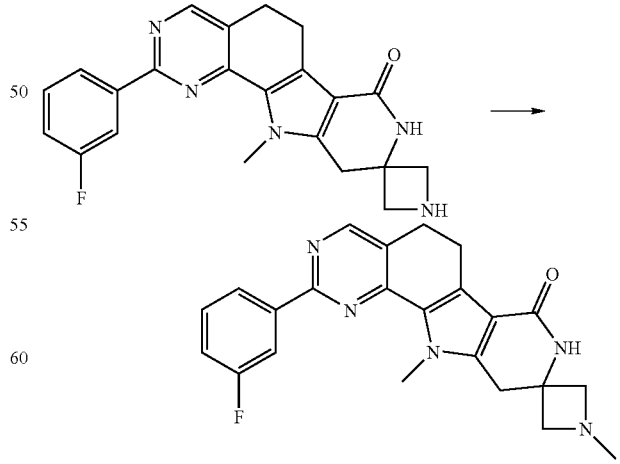

2-(3-Amino-azetidin-3-ylmethyl)-8-(3-fluoro-phenyl)-1-methyl-4,5-dihydro-1H-1,7,9-triaza-cyclopenta[a]naphthalene-3-carboxylic acid lactam (39 mg; 0.1 mmol)(free base, Example 27) paraformaldehyde (50 mg) and NaCNBH₃ (50 mg; 0.8 mmol) in MeOH (8 ml) are stirred as a suspension at room temperature. The reaction mixture is stirred for 10 minutes, 2N HCl (2 ml) is added, stirred for 2 minutes and poured on a saturated solution of K₂CO₃. The reaction mixture is extracted with TBME three times, the combined organic phases are dried over K₂CO₃, filtered and evaporated to dryness. Purification via chromatography (SiO₂; TBME/MeOH/ NH₃$_{conc}$ 95:5:1 to 90:10:2) delivers the title compound as light-yellow crystals (28 mg; 70%). 1H-NMR (400 MHz; DMSO-d6): 8.58 (s, 1H); 8.23 (d, 1H); 8.08 (bd, 1H); 7.69 (s, 1H); 7.59 (m, 1H); 7.38 (bt, 1H); 4.18 (s, 3H); 3.39 (d, 2H); 3.27 (s, 2H); 3.00 (m, 4H); 2.90 M, 2H); 2.28 (s, 3H). MS (m/z) ES+: 404 (MH+).

Retention time: 2.12 minutes (LC-MS method 2).

EXAMPLE 30

2-(1-Amino-cyclopropylmethyl)-8-(3-fluoro-phenyl)-4,5-dihydro-1H-1,7,9-triaza-cyclopenta[a]naphthalene-3-carboxylic acid lactam

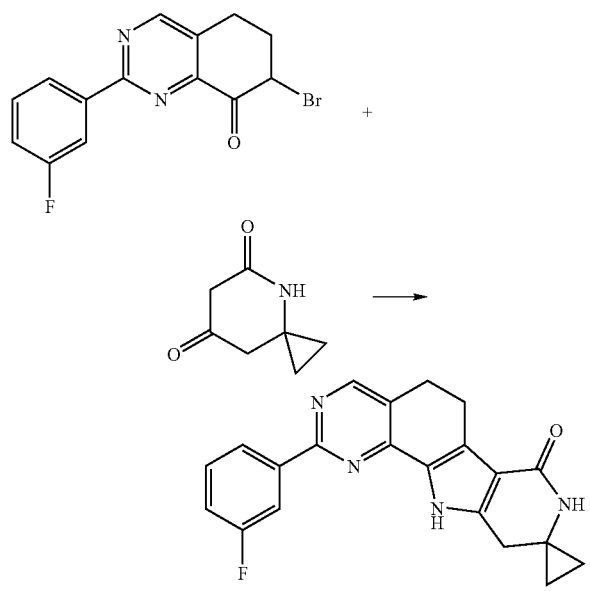

7-Bromo-2-(3-fluoro-phenyl)-6,7-dihydro-5H-quinazolin-8-one (prepared in analogy to Example 19 from 3-fluorobenzamidine) (50 mg; 0.156 mmol), 4-aza-spiro[2.5]octane-5,7-dione (43 mg; 0.313 mmol) ammonium acetate (36 mg; 0.468 mmol) dissolved in MeOH (3 ml) are stirred at room temperature over night. The reaction mixture is evaporated and purified via chromatography (SiO₂, hexane/acetone 1:f followed by TBME/MeOH 97:3) to yield the title compound as off-white crystals (33 mg; 59%).

1H-NMR (400 MHz; DMSO-d6): 12.16 (s, 1H); 8.53 (s, 1H); 8.32 (d, 1H); 8.27 (dd, 1H); 7.58 (m, 1H); 7.36 (dt, 1H); 7.27 (s, 1H); 3.03 (m, 2H); 2.93 (m, 2H); 2.89 (s, 2H); 0.79 (m, 2H); 0.72 (m, 2H).

MS (m/z) ES+: 361 (MH+). Retention time: 2.73 minutes (LC-MS method 2).

The starting materials are prepared as follows:

EXAMPLE 30.A

N-[1-(2-Oxo-ethyl)-cyclopropyl]-malonamic acid ethyl ester

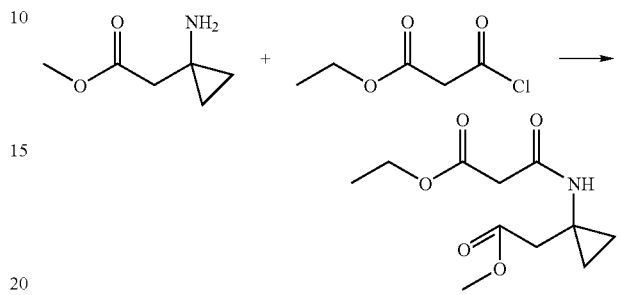

Chlorocarbonyl-acetic acid ethyl ester (2.75 ml; 22.1 mmol) is added dropwise under stirring and cooling to a solution of (1-amino-cyclopropyl)-acetic acid methyl ester (Chemstep Product List, 13926) (3.00 g; 23.2 mmol) in triethylamine (6.4 ml; 46.2 mmol) and CH₂Cl₂ (150 ml). After stirring at room temperature for 30 minutes, the reaction mixture is poured on a saturated solution of NaHCO3 and extracted with CH₂Cl₂ three times. The combined organic phases are dried over Na₂SO₄, filtered and evaporated to dryness. Purification via chromatography (SiO₂; hexane/acetone 6:4) yield the title compound as crystalline light-yellow solid (1.9 g; 34%) 1H-NMR (400 MHz; DMSO-d6): 8.40 (s, 1H); 4.07 (q, 2H); 3.60 (s, 3H); 3.12 (s, 2H); 2.58 (s, 2H); 1.17 (t, 3H); 0.71 (m, 2H); 0.66 (m, 2H). MS (m/z) ES+: 244 (MH+)

EXAMPLE 30.B 5,7-Dioxo-4-aza-spiro[2.5]octane-6-carboxylic acid methyl ester

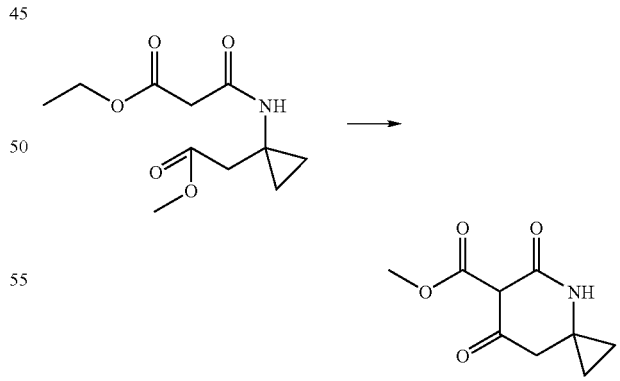

N-[1-(2-Oxo-ethyl)-cyclopropyl]-malonamic acid ethyl ester (200 mg; 0.823 mmol) in toluene (3 ml) is added to a solution of sodium (18.9 mg; 0.823 mmol) in MeOH (1 ml). The reaction mixture is refluxed for 45 minutes, poured on water and washed with TBME. The aqueous phase is acidified with 2N HCl (0.2 ml) and evaporated to dryness to yield the title compound as yellow resin (162 mg; 100%). 1H-NMR (400 MHz; DMSO-d6): 8.39 (s, 1H); 3.73 (s, 3H); 3.18 (s, 1H); 2.48 (s, 2H); 0.76 (m, 2H); 0.64 (m, 2H). MS (m/z) ES+: 198 (MH+).

EXAMPLE 30.C

4-Aza-spiro[2.5]octane-5,7-dione

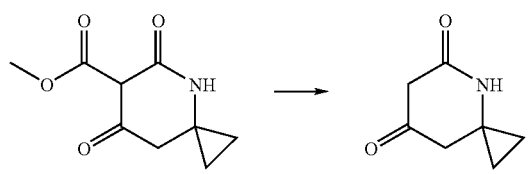

5,7-Dioxo-4-aza-spiro[2.5]octane-6-carboxylic acid methyl ester (162 mg; 0.852 mmol) is refluxed in acetonitrile/water (3 ml; 9:1) for 1 hour. The reaction mixture is evaporated to dryness and taken up in EtOAc/MeOH, filtered from undissolved material and evaporated to yield the title compound as light-brown solid (102 mg; 85%). 1H-NMR (400 MHz; DMSO-d6): 8.28 (s, 1H); 3.59 (s, 2H); 2.48 (s, 2H); 0.83 (m. 2H); 0.70 (m, 2H). MS (m/z) ES+: 140 (MH+).

EXAMPLE 31

2-(1-Amino-cyclopropylmethyl)-8-(3-fluoro-phenyl)-4,5-dihydro-1H-pyrrolo[2,3-f]isoquinoline-3-carboxylic acid lactam

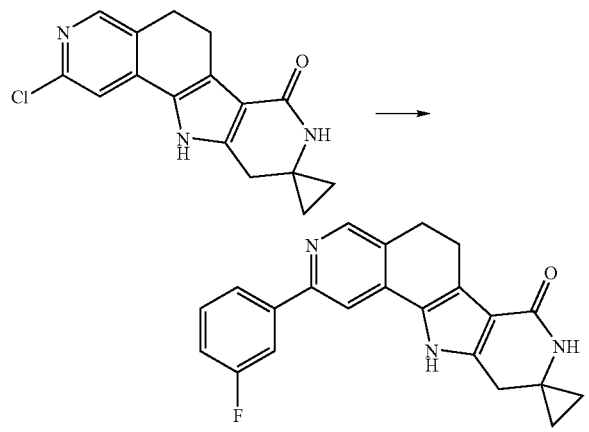

The coupling with 3-fluorophenylboronic acid is performed in analogy to Example 1. Purification via chromatography (SiO$_2$; TBME/MeOH 97:3>95:5) and trituration with diethyl ether/MeOH (10:1) delivers the title compound as light-yellow solid (31 mg; 46%). 1H-NMR (400 MHz; DMSO-d6): 11.89 (s, 1H); 8.42 (s, 1H); 8.03 (s, 1H); 7.90 (d, 1H); 7.84 (d, 1H); 7.59 (m, 1H); 7.29 (m, 1H); 7.19 (s, 1H); 2.95 (m, 4H); 2.86 (s, 2H); 0.78 (m, 2H); 0.72 (m, 2H). MS (m/z) ES+: 360 (MH+). Retention time: 2.07 minutes (LC-MS method 2).

The starting materials are prepared as follows:

EXAMPLE 31.A 2-(1-Amino-cyclopropylmethyl)-8-chloro-4,5-dihydro-1H-pyrrolo[2,3-f]isoquinoline-3-carboxylic acid lactam

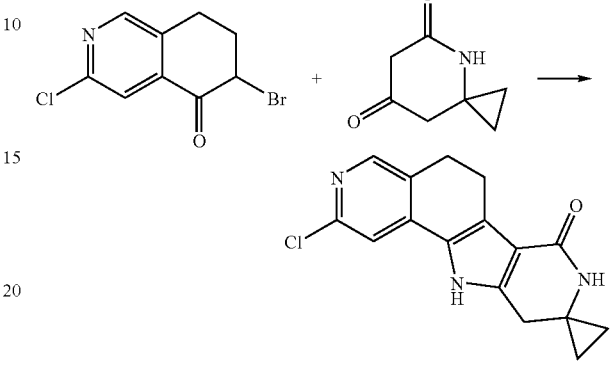

6-Bromo-3-chloro-7,8-dihydro-6H-isoquinolin-5-one (Example 1.c) (360 mg; 1.383 mmol), 4-aza-spiro[2.5]octane-5,7-dione (250 mg; 1.8 mmol) and ammonium acetate (851 mg; 11.06 mmol) dissolved in MeOH (8 ml) are stirred over night at room temperature. The light brown solution is evaporated and purified via chromatography (SiO$_2$; TBME/MeOH 97:3) and delivers the title compound as light-brown crystals (104 mg; 25%)

1H-NMR (400 MHz; DMSO-d6): 11.93 (bs, 1H); 8.13 (s, 1H); 7.42 (s, 1H); 7.22 (s, 1H); 2.91 (m, 2H); 2.86 (m, 2H); 2.84 (s, 2H); 0.77 (m, 2H); 0.71 (m, 2H). MS (m/z) ES+: 300 (MH+).

EXAMPLE 32

2-(3-Amino-oxetan-3-ylmethyl)-8-(3-fluoro-phenyl)-4,5-dihydro-1H-pyrrolo[2,3-f]isoquinoline-3-carboxylic acid lactam

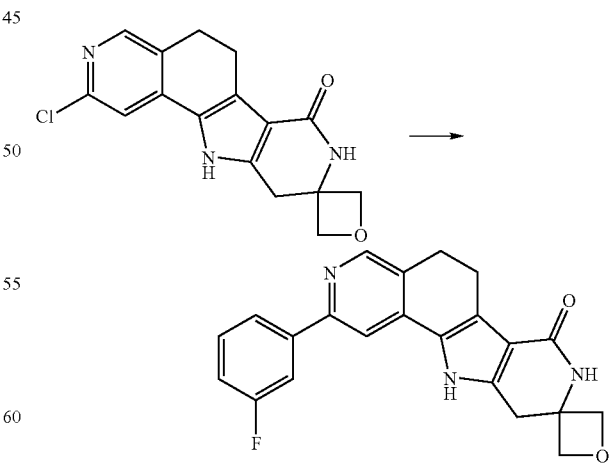

2-(3-Amino-oxetan-3-ylmethyl)-8-chloro-4,5-dihydro-1H-pyrrolo[2,3-f]isoquinoline-3-carboxylic acid lactam (Example 20.e) (40 mg; 0.127 mmol) and 3-fluorobenzeneboronic acid (36 mg; 0.254 mmol) are coupled in analogy to Example 1. Purification via chromatography (SiO$_2$; CH$_2$Cl$_2$/MeOH/NH$_{3conc}$ 97:3:0.3) yields the title compound as light-yellow solid (30 mg; 62%). 1H-NMR (400 MHz; DMSO-d6): 12.07 (bs, 1H); 8.42 (s, 1H); 8.04 (s, 1H); 7.99 (s, 1H); 7.90 (d, 1H); 7.75 (bd, 1H); 7.70 (m, 1H); 7.60 (m, 1H); 4.60 (d, 2H); 4.49 (d, 2H); 3.31 (s, 2H); 2.92 (m, 4H). MS (m/z) ES+: 376 (MH+). Retention time: 1.78 minutes (LC-MS method 2).

EXAMPLE 33

2-(3-Amino-oxetan-3-ylmethyl)-8-(3-fluoro-4-methoxy-phenyl)-4,5-dihydro-1H-pyrrolo[2,3-f]isoquinoline-3-carboxylic acid lactam

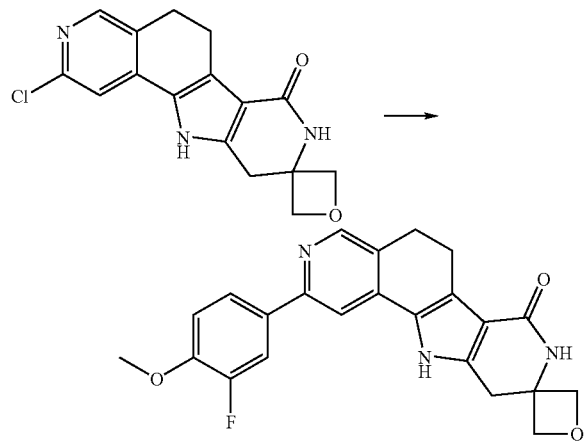

2-(3-Amino-oxetan-3-ylmethyl)-8-chloro-4,5-dihydro-1H-pyrrolo[2,3-f]isoquinoline-3-carboxylic acid lactam (Example 20.e) (40 mg; 0.127 mmol) and 3-fluoro-4-methoxy-benzeneboronic acid (43 mg; 0.254 mmol) are coupled in analogy to Example 1. Purification via chromatography (SiO$_2$; CH$_2$Cl$_2$/MeOH 95:5) yields the title compound as light-yellow solid (36 mg; 71%) 1H-NMR (400 MHz; DMSO-d6): 12.03 (s, 1H); 8.37 (s, 1H); 8.05 (s, 1H); 8.00 (s, 1H); 7.88 (s, 1H); 7.85 (s, 1H); 7.34 (t, 1H); 4.60 (d, 2H); 4.50 (d, 2H); 3.93 (s, 3H); 3.86 (s, 2H); 2.90 (m, 4H). MS (m/z) ES+: 406 (MH+). Retention time: 1.75 minutes (LC-MS method 2).

EXAMPLE 34

2-(1-Amino-cyclobutylmethyl)-8-(3-fluoro-4-methoxy-phenyl)-4,5-dihydro-1H-1,7,9-triaza-cyclopenta[a]naphthalene-3-carboxylic acid lactam

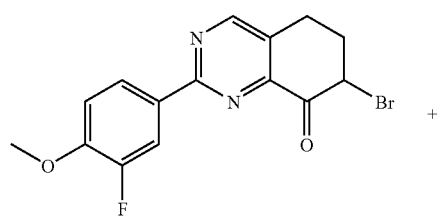

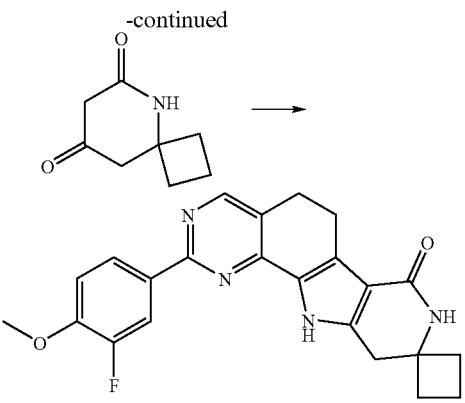

7-Bromo-2-(3-fluoro-4-methoxy-phenyl)-6,7-dihydro-5H-quinazolin-8-one (prepared from 3-fluoro-4-methoxy-benzamidine (EP339252) in analogy to Example 14.c) (100 mg; 0.285 mmol), 5-aza-spiro[3.5]nonane-6,8-dione (165 mg; 1.08 mmol) (prepared from 1-amino-cyclobutaneacetic acid (MicroChemistry Building Blocks, 15051) in analogy to Example 30.c) and ammonium acetate (66 mg; 0.85 mmol) are suspended in MeOH (2 ml) and stirred at room temperature over night. The reaction mixture is diluted with CH$_2$Cl$_2$ and purified via chromatography (SiO$_2$; TBME/MeOH/NH$_{3conc}$ 100:0:0>96:4:0.6) and triturated with acetone to yield the title compound as yellow crystals (35 mg; 31%). 1H-NMR (400 MHz; DMSO-d6): 12.14 (s, 1H); 8.46 (s, 1H); 8.31 s, 1H); 8.29 (d, 1H); 7.56 (s, 1H); 7.31 (t, 1H); 3.94 (s, 3H); 3.05 (s, 2H); 2.98 (m, 2H); 2.91 (m, 2H); 2.15 (m, 2H); 2.05 (m, 2H); 1.76 (m, 2H). MS (m/z) ES+: 405 (MH+). Retention time: 2.84 minutes (LC-MS method 2).

EXAMPLE 35

2-(1-Amino-cyclopropylmethyl)-8-(4-methoxy-phenyl)-4,5-dihydro-1H-1,7,9-triaza-cyclopenta[a]naphthalene-3-carboxylic acid lactam

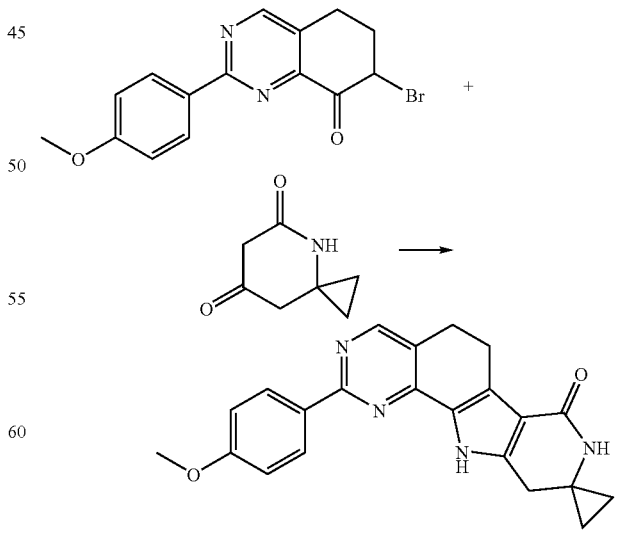

:4-Aza-spiro[2.5]octane-5,7-dione (Example 30.c) (45 mg; 0.32 mmol), 7-bromo-2-(4-methoxy-phenyl)-6,7-dihydro-5H-quinazolin-8-one (Example 14.c) (72 mg; 0.216 mmol) and ammonium acetate (50 mg; 0.65 mmol) are suspended in MeOH (2 ml) and stirred over night at room temperature. The reaction mixture is diluted with CH$_2$Cl$_2$ and purified via chromatography (SiO$_2$; TBME>TBME/MeOH/ NH$_{3conc}$ 96:4:0.6) and triturated with TBME to yield the title compound as yellow crystals (24 mg; 30%). 1H-NMR (400 MHz; DMSO-d6): 12.08 (bs, 1H); 8.46 (s, 1H); 8.44 (d, 2H); 7.25 (s, 1H); 7.08 (d, 2H); 3.86 (s, 3H); 3.01 (m, 2H); 2.90 (m, 2H); 2.88 (s, 2H); 0.79 (m, 2H); 0.71 (m, 2H). MS (m/z) ES+: 373 (MH+). Retention time: 2.46 minutes (LC-MS method 2).

EXAMPLE 36

2-(1-Amino-cyclobutylmethyl)-8-(4-methoxy-phenyl)-4,5-dihydro-1H-pyrrolo[2,3-f]isoquinoline-3-carboxylic acid lactam

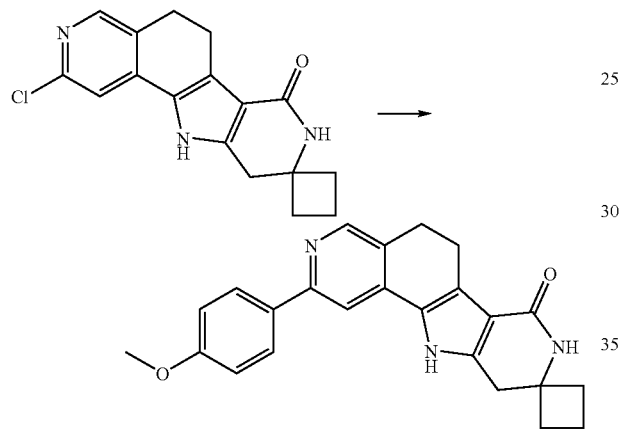

The reaction is performed in analogy to Example 1. Purification via chromatography (SiO$_2$; TBME>TBME/MeOH/ NH$_{3conc}$ 96:4:0.6) and trituration with acetone yields the title compound as colorless crystals (48 mg; 49%). 1H-NMR (400 MHz; DMSO-d6): 1.93 (s, 1H); 8.35 (s, 1H); 8.00 (d, 2H); 7.91 (s, 1H); 7.47 (s, 1H); 7.10 (d, 2H); 3.84 (s, 3H); 3.03 (s, 2H); 2.92 (m, 2H); 2.86 (m, 2H); 2.15 (m, 2H); 2.08 (m, 2H); 1.78 (m, 2H). MS (m/z) ES+: 3.86 (MH+). Retention time: 1.84 minutes (LC-MS method 2).

The starting materials are prepared as follows:

EXAMPLE 36.A 2-(1-Amino-cyclobutylmethyl)-8-chloro-4,5-dihydro-1H-pyrrolo[2,3-f]isoquinoline-3-carboxylic acid lactam

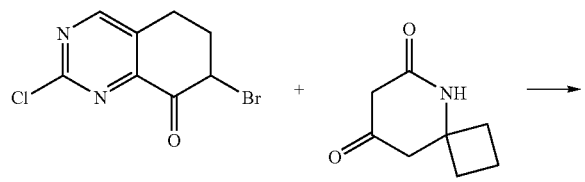

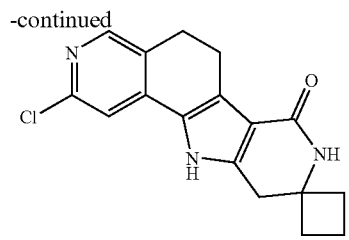

6-Bromo-3-chloro-7,8-dihydro-6H-isoquinolin-5-one (Example 1.c)(200 mg; 0.77 mmol), 5-aza-spiro[3.5]nonane-6,8-dione (142 mg; 0.93 mmol) (prepared from 1-amino-cyclobutaneacetic acid (MicroChemistry Building Blocks) in analogy to Example 30.c) and ammonium acetate (476 mg; 6.17 mmol) dissolved in MeOH (8 ml) and stirred at room temperature for 20 h. The reaction mixture is evaporated and purified via chromatography (SiO$_2$; TBME>TBME/MeOH/ NH$_{3conc}$ 98:2:0.4) to yield the title compound as off-white crystals (82 mg; 34%). 1H-NMR (400 MHz; DMSO-d6): 11.92 (bs, 1H); 8.12 (s, 1H); 7.51 d, 1H); 7.42 (s, 1H); 3.01 (s, 2H); 2.88 (m, 2H); 2.83 (s, 2H); 2.14 (m, 2H); 2.03 (m, 2H); 1.77 (m, 2H). MS (m/z) ES+: 314 (MH+).

EXAMPLE 37

2-(1-Amino-cyclobutylmethyl)-8-(4-methoxy-phenyl)-1-methyl-4,5-dihydro-1H-pyrrolo[2,3-f]isoquinoline-3-carboxylic acid lactam

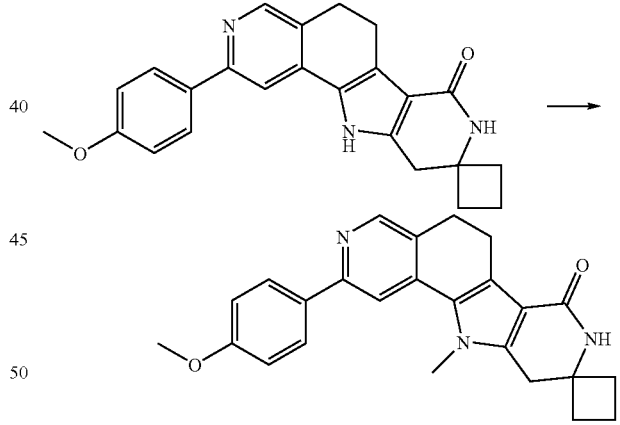

2-(1-Amino-cyclobutylmethyl)-8-(4-methoxy-phenyl)-4, 5-dihydro-1H-pyrrolo[2,3-f]isoquinoline-3-carboxylic acid lactam (Example 36)(40 mg; 0.1 mmol) in DMF (3 ml) is cooled to 5° C. and treated with KN(TMS)$_2$ (0.1 mmol; 0.125 ml of a 0.8 molar solution in toluene) under stirring. After 5 minutes at 5° C., MeI (29 mg; 0.2 mmol) in DMF (0.25 ml) is added and stirring continued for 5 minutes. The reaction mixture is evaporated, taken up in CH$_2$Cl$_2$/acetone and purified via chromatography (SiO$_2$; acetone/hexane 3:7>7:3) to yield the title compound as light-yellow crystals (24 mg; 59%). 1H-NMR (400 MHz; DMSO-d6): 8.42 (s, 1H); 8.05 (d, 2H); 7.84 (s, 1H); 7.52 (s, 1H); 7.07 (d, 2H); 3.97 (s, 3H); 3.84 (s, 3H); 3.10 (2H); 2.90 (m, 2H); 2.79 (m, 2H); 2.15 (m, 2H);

2.07 (m, 2H); 1.85 (m, 1H); 1.77 (m, 1H). MS (m/z) ES+: 400 (MH+). Retention time: 1.97 minutes (LC-MS method 2).

EXAMPLE 38

2-(3-Amino-azetidin-3-ylmethyl)-8-(4-methoxy-phenyl)-1-methyl-4,5-dihydro-1H-pyrrolo[2,3-f]isoquinoline-3-carboxylic acid lactam hydrochloride

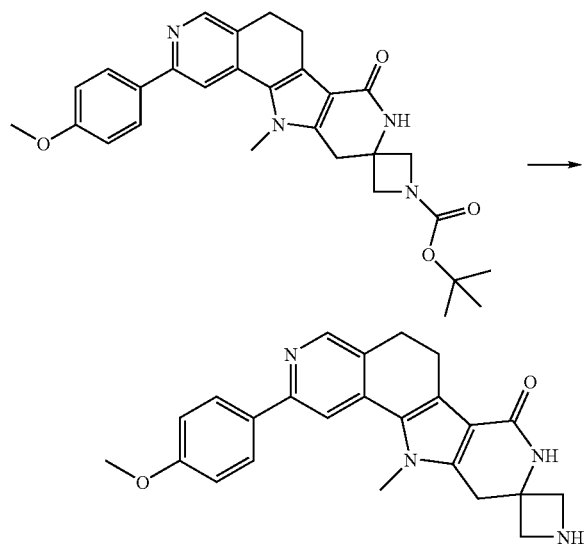

The reaction is performed in analogy to Example 24 yielding the title compound as yellow crystals (23 mg; 100%). 1H-NMR (400 MHz; DMSO-d6): 9.82 (bs, 1H); 9.20 (bs, 1H); 8.55 (s, 1H); 8.24 (s, 1H); 8.08 (d, 2H); 8.02 (s, 1H); 7.23 (d, 2H); 4.12 (m, 2H); 4.03 (s, 3H); 3.99 (m, 2H); 3.90 (s, 3H); 3.61 (s, 2H); 2.99 (bs, 4H). MS (m/z) ES+: 401 (MH+). Retention time: 1.27 minutes (LC-MS method 2).

The starting materials are prepared as follows:

38.a: 2-(3-Amino-1-tert-butoxycarbonyl-azetidin-3-ylmethyl)-8-(4-methoxy-phenyl)-1-methyl-4,5-dihydro-1H-pyrrolo[2,3-f]isoquinoline-3-carboxylic acid lactam

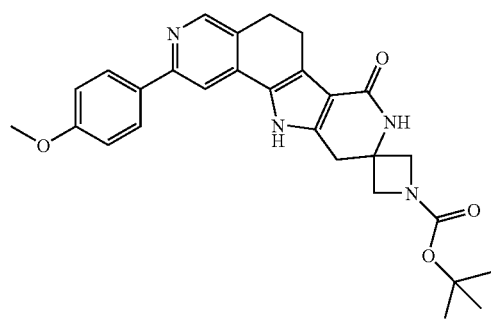

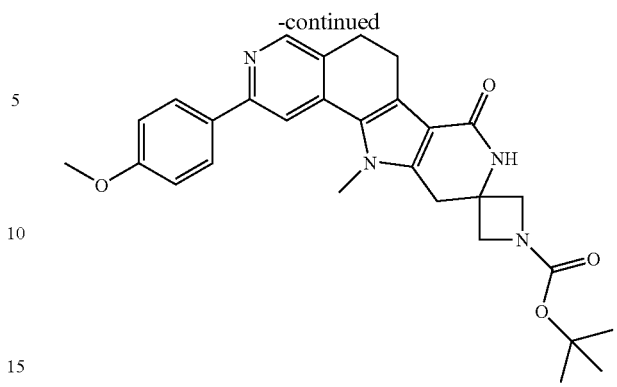

The reaction is performed in analogy to Example 37. Purification via chromatography (SiO$_2$; acetone/hexane 3:7>6:4) yields the title compound as light-yellow crystals (27 mg; 60%). 1H-NMR (400 MHz; DMSO-d6): 8.43 (s, 1H); 8.05 (d, 2H); 7.84 (bs, 2H); 7.07 (d, 2H); 3.96 (s, 3H); 3.89 (bs, 4H); 3.84 (s, 3H); 3.27 (bs, 2H); 2.90 (m, 2H); 2.80 (m, 2H); 1.41 (s, 9H). MS (m/z) ES+: 501 (MH+).

EXAMPLE 39

2-(3-Amino-1-methyl-azetidin-3-ylmethyl)-8-(4-methoxy-phenyl)-4,5-dihydro-1H-pyrrolo[2,3-f]isoquinoline-3-carboxylic acid lactam

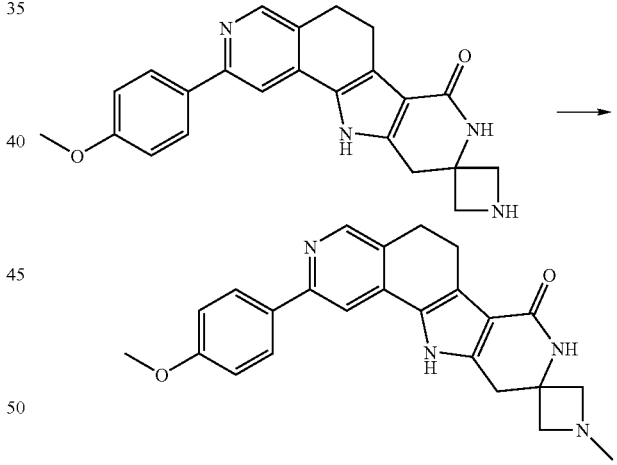

2-(3-Amino-azetidin-3-ylmethyl)-8-(4-methoxy-phenyl)-4,5-dihydro-1H-pyrrolo[2,3-f]isoquinoline-3-carboxylic acid lactam (Example 23) (31 mg; 0.08 mmol) is suspended in MeOH (8 ml) and combined under stirring at room temperature with paraformaldehyde (50 mg) and NaCNBH$_3$ (50 mg; 0.79 mmol). After 5 minutes the reaction mixture becomes an almost clear solution; 2N HCl (3 ml) is added to the reaction mixture, stirred for 1 minute and poured on a saturated solution of K$_2$CO$_3$. The reaction mixture is extracted with TBME three times. The combined organic phases are dried over Na$_2$SO$_4$, filtered and evaporated to dryness. Purification via chromatography (SiO$_2$; TBME/MeOH/NH$_{3conc}$ 95:5:1>85:15:2) yields the title compound as colorless crystals (21 mg;

64%). 1H-NMR (400 MHz; DMSO-d6): 12.06 (s, 1H); 8.35 MS (m/z) ES+: 401 (MH+). Retention time: 1.05 minutes (LC-MS method 2).

EXAMPLE 40

2-(1-Amino-cyclopropylmethyl)-8-(4-methoxy-phenyl)-4,5-dihydro-1H-pyrrolo[2,3-f]isoquinoline-3-carboxylic acid lactam

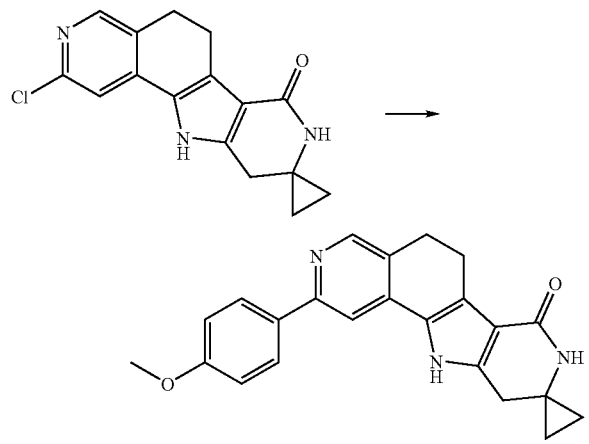

The coupling with 4-methoxyphenylboronic acid is performed in analogy to Example 1. Purification via chromatography (SiO₂; TBME/MeOH 97:3>95:5) yields the title compound as yellowish crystals (37 mg; 66%). 1H-NMR (400 MHz; DMSO-d6): 11.90 (s, 1H); 8.36 (s, 1H); 8.00 (d, 2H); 7.92 (s, 1H); 7.07 (d, 2H); 3.84 (s, 3H); 2.93 (m, 2H); 2.90 (m, 2H); 2.87 (s, 2H); 0.78 (m, 2H); 0.72 (m, 2H). MS (m/z) ES+: 372 (MH+). Retention time: 1.75 minutes (LC-MS method 2).

EXAMPLE 41

2-(3-Amino-azetidin-3-ylmethyl)-8-(4-methoxy-phenyl)-4,5-dihydro-furo[2,3-f]isoquinoline-3-carboxylic acid lactam hydrochloride

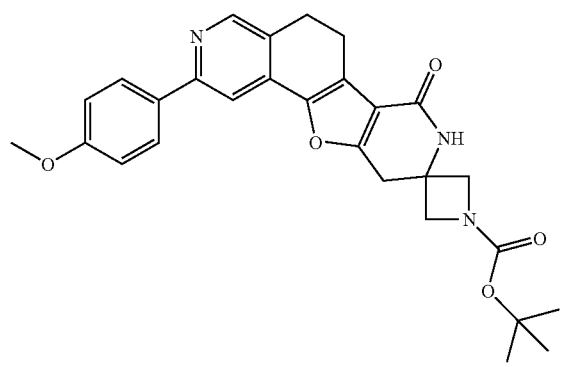

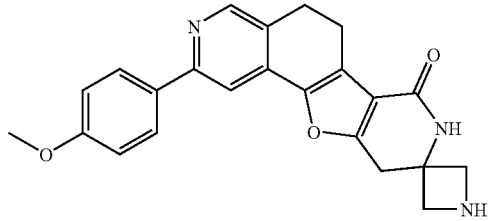

The reaction is performed in analogy to Example 25 and delivers the title compound as yellow crystals (82 mg; 97%). 1H-NMR (400 MHz; DMSO-d6): 9.98 (m, 1H); 9.04 (m, 1H); 8.54 (s, 2H); 8.09 (d, 2H); 8.05 (s, 1H); 7.14 (d, 2H); 4.12 (m, 2H); 4.00 (m, 2H); 3.86 (s, 3H); 3.73 (s, 2H); 3.08 (m, 2H); 3.02 (m, 2H). MS (m/z) ES+: 388 (MH+). Retention time: 1.35 minutes (LC-MS method 2).

The starting materials are prepared as follows:

EXAMPLE 41.A 2-(3-Amino-1-tert-butoxycarbonyl-azetidin-3-ylmethyl)-8-(4-methoxy-phenyl)-4,5-dihydro-furo[2,3-f]isoquinoline-3-carboxylic acid lactam

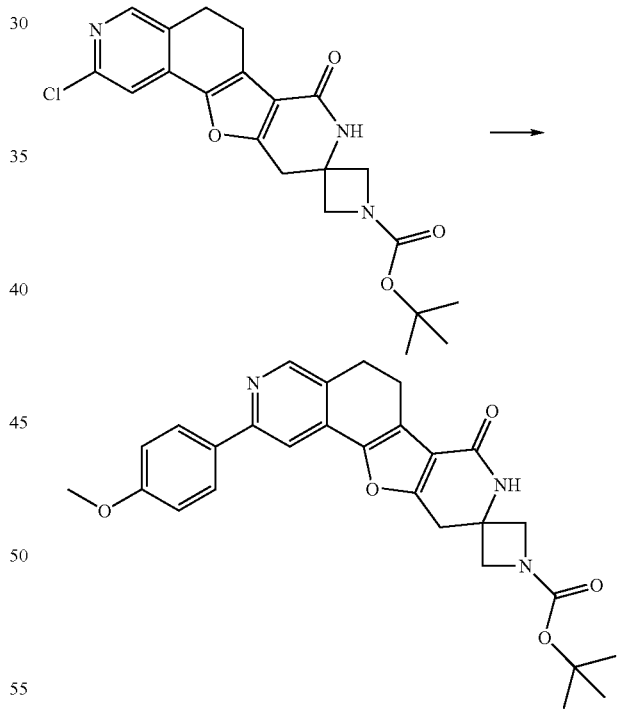

2-(3-Amino-1-tert-butoxycarbonyl-azetidin-3-ylmethyl)-8-chloro-4,5-dihydro-furo[2,3-f]isoquinoline-3-carboxylic acid lactam (Example 25.a) and 4-methoxyphenylboronic acid are coupled in analogy to Example 1. The crude product is washed with 2N NaOH to remove excess 4-methoxyphenylboronic acid. Purification via chromatography (SiO₂; TBME>TBME/MeOH/NH₃conc 98:2:0.2) yields the title compound as colorless crystals (92 mg; 78%). 1H-NMR (400 MHz; DMSO-d6): 8.48 (s, 1H); 8.31 (s, 1H); 8.06 (d, 2H); 7.75 (s, 1H); 7.06 (d, 2H); 3.94 (bs, 4H); 3.84 (s, 3H); 3.44 (s, 2H); 2.97 (m, 4H); 1.41 (s, 9H). MS (m/z) ES+: 488 (MH+). Retention time: 1.35 minutes (LC-MS method 2).

EXAMPLE 42

2-(3-Amino-1-methyl-azetidin-3-ylmethyl)-8-(4-methoxy-phenyl)-4,5-dihydro-furo[2,3-f]isoquinoline-3-carboxylic acid lactam

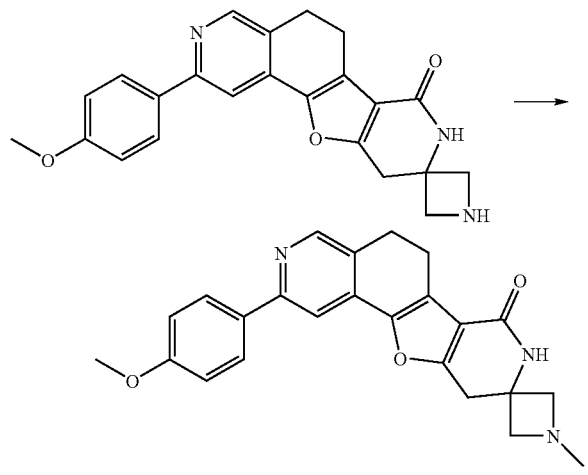

2-(3-Amino-azetidin-3-ylmethyl)-8-(4-methoxy-phenyl)-4,5-dihydro-furo[2,3-f]isoquinoline-3-carboxylic acid lactam (Example 41) is reacted in analogy to Example 39. Purification via chromatography (SiO$_2$; TBME/MeOH/NH$_{3conc}$ 95:5:1>90:10:1) yields the title compound as colorless crystals (28 mg; 59%). 1H-NMR (400 MHz; DMSO-d6): 8.46 (s, 1H); 8.08 (d, 2H); 8.06 (s, 1H); 7.75 (s, 1H); 7.06 (d, 2H); 3.83 (s, 3H); 3.43 (bd, 2H); 3.39 (s, 2H); 3.04 (m, 2H); 2.95 (m, 4H); 2.27 (s, 3H). MS (m/z) ES+: 402 (MH+). Retention time: 1.25 minutes (LC-MS method 2).

EXAMPLE 43

2-(1-Amino-cyclobutylmethyl)-8-(3-methoxy-phenyl)-4,5-dihydro-1H-1,7,9-triaza-cyclopenta[a]naphthalene-3-carboxylic acid lactam

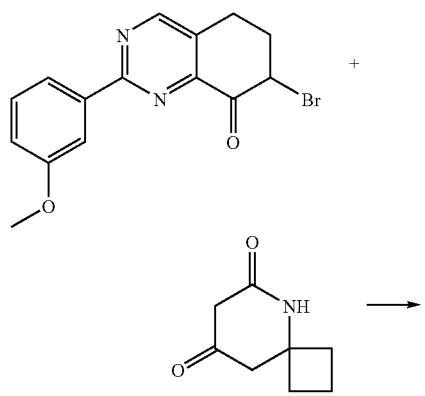

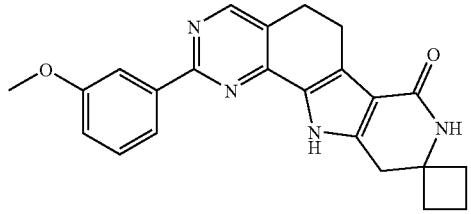

7-Bromo-2-(3-methoxy-phenyl)-6,7-dihydro-5H-quinazolin-8-one (prepared form 3-methoxy-benzamidin (Tyger Scientific Product) in analogy to Example 14.c) is reacted with 5-aza-spiro[3.5]nonane-6,8-dione in analogy to Example 34. The product is filtered and washed with MeOH followed by TBME to deliver the title compound as light yellow crystals (80 mg; 69%). 1H-NMR (400 MHz; DMSO-d6): 12.13 (bs, 1H); 8.51 (s, 1H); 8.11 (m, 2H); 7.57 (s, 1H); 7.45 (t, 1H); 7.10 (dd, 1H); 3.88 (s, 3H); 3.07 (s, 2H); 2.98 (m, 2H); 2.94 (m, 2H); 2.16 (m, 2H); 2.07 (m, 2H); 1.76 (m, 2H). MS (m/z) ES+: 387 (MH+). Retention time: 2.71 minutes (LC-MS method 2).

EXAMPLE 44

2-(3-Amino-oxetan-3-ylmethyl)-8-(3-methoxy-phenyl)-4,5-dihydro-1H-pyrrolo[2,3-f]isoquinoline-3-carboxylic acid lactam

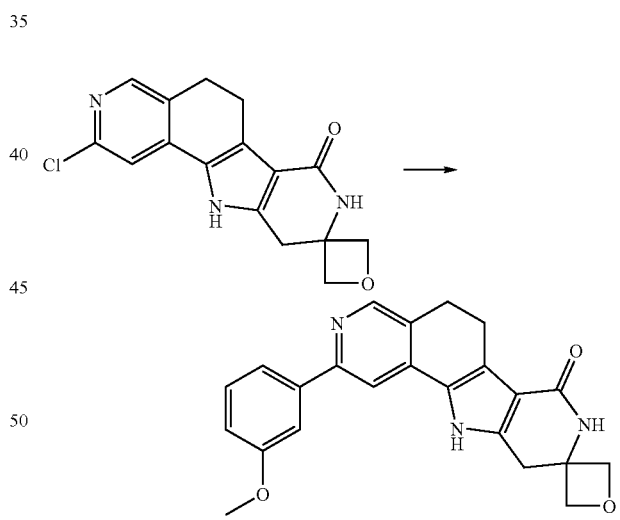

2-(3-Amino-oxetan-3-ylmethyl)-8-chloro-4,5-dihydro-1H-pyrrolo[2,3-f]isoquinoline-3-carboxylic acid lactam (Example 20.e) and 3-methoxyphenylboronic acid are coupled in analogy to Example 1. Purification via chromatography (SiO$_2$; CH$_2$Cl$_2$/MeOH 95:5) yields the title compound as light-brown crystals (33 mg; 61%). 1H-NMR (400 MHz; DMSO-d6): 12.07 (s, 1H); 8.40 (s, 1H); 8.00 (s, 1H); 7.98 (s, 1H); 7.44 (dd, 1H); 7.42 (s, 1H); 7.04 (dd, 1H); 4.60 (d, 2H); 4.49 (d, 2H); 3.86 (s, 3H); 2.91 (m, 4H); 2.31 (bs, 2H). MS (m/z) ES+: 388 (MH+). Retention time: 1.64 minutes (LC-MS method 2).

EXAMPLE 45

2-(3-Amino-oxetan-3-ylmethyl)-8-(3-methyl-phenyl)-4,5-dihydro-1H-pyrrolo[2,3-f]isoquinoline-3-carboxylic acid lactam

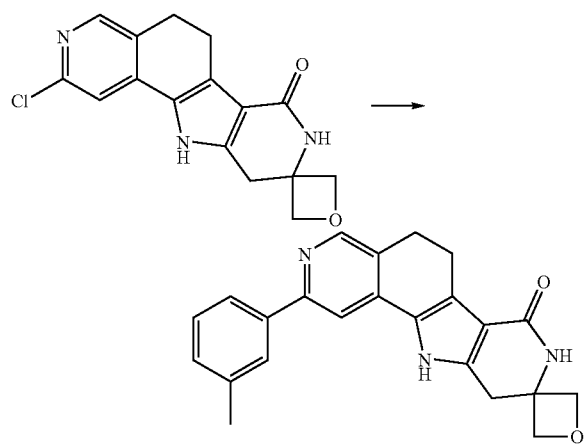

2-(3-Amino-oxetan-3-ylmethyl)-8-chloro-4,5-dihydro-1H-pyrrolo[2,3-f]isoquinoline-3-carboxylic acid lactam (Example 20.e) and 3-methylphenylboronic acid are coupled in analogy to Example 1. Purification via chromatography (SiO$_2$; CH$_2$Cl$_2$/MeOH 95:5) yields the title compound as light-brown crystals (27 mg; 57%). 1H-NMR (400 MHz; DMSO-d6): 12.09 (s, 1H); 8.40 (s, 1H); 7.98 (bs, 2H); 7.89 (s, 1H); 7.85 (d, 1H); 7.41 (t, 1H); 7.28 (d, 1H); 4.61 (d, 2H); 4.50 (d, 2H); 3.31 (s, 2H); 2.91 (m, 4H); 2.43 (s, 3H). MS (m/z) ES+: 372 (MH+). Retention time: 1.68 minutes (LC-MS method 2).

EXAMPLE 46

2-(3-Amino-oxetan-3-ylmethyl)-8-(3-chloro-phenyl)-4,5-dihydro-1H-pyrrolo[2,3-f]isoquinoline-3-carboxylic acid lactam

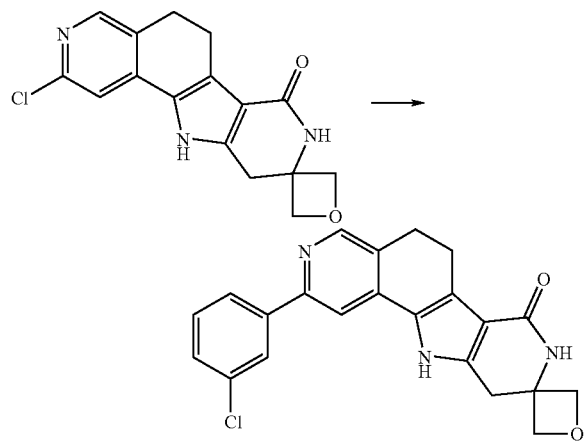

2-(3-Amino-oxetan-3-ylmethyl)-8-chloro-4,5-dihydro-1H-pyrrolo[2,3-f]isoquinoline-3-carboxylic acid lactam (Example 20.e) and 3-chloro-phenylboronic acid are coupled in analogy to Example 1. Purification via chromatography (SiO$_2$; CH$_2$Cl$_2$/MeOH 97:3>95:5) and trituration of the product with TBME yields the title compound as light-brown crystals (34 mg; 69%). 1H-NMR (400 MHz; DMSO-d6): 12.1 (s, 1H); 8.41 (s, 1H); 8.05 (m, 4H); 7.55 (m, 2H); 4.61 (d, 2H); 4.50 (d, 2H); 3.18 (s, 2H); 2.95 (m, 4H). MS (m/z) ES+: 392 (MH+). Retention time: 9.64 minutes (LC-MS method 4)

EXAMPLE 47

2-(3-Amino-oxetan-3-ylmethyl)-8-(3-trifluoromethyl-phenyl)-4,5-dihydro-1H-pyrrolo[2,3-f]isoquinoline-3-carboxylic acid lactam

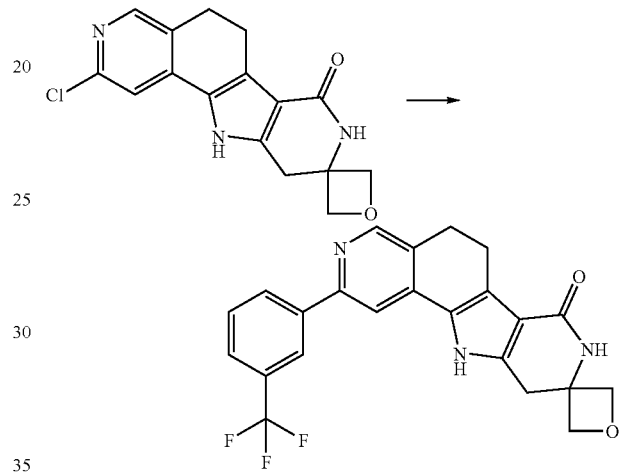

2-(3-Amino-oxetan-3-ylmethyl)-8-chloro-4,5-dihydro-1H-pyrrolo[2,3-f]isoquinoline-3-carboxylic acid lactam (Example 20.e) and 3-trifluoromethyl-phenylboronic acid are coupled in analogy to Example 1. Purification via chromatography (SiO$_2$; TBME/MeOH 95:5) and trituration of the product with acetone yields the title compound as light-brown crystals (26 mg; 48%). 1H-NMR (400 MHz; DMSO-d6): 12.09 (s, 1H); 8.45 (s, 1H); 8.36 (bs, 2H); 8.10 (s, 1H); 8.00 (bs, 1H); 7.82 (m, 1H); 7.79 (m, 1H); 4.60 (d, 2H); 4.48 (d, 2H); 3.35 (s, 2H); 2.92 (m, 4H). MS (m/z) ES+: 426 (MH+). Retention time: 2.48 minutes (LC-MS method 2)

EXAMPLE 48

2-(1-Amino-cyclobutylmethyl)-8-[4-(2-morpholin-4-yl-ethoxy)-phenyl]-4,5-dihydro-1H-1,7,9-triaza-cyclopenta[a]naphthalene-3-carboxylic acid lactam

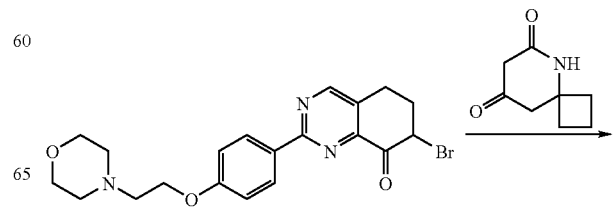

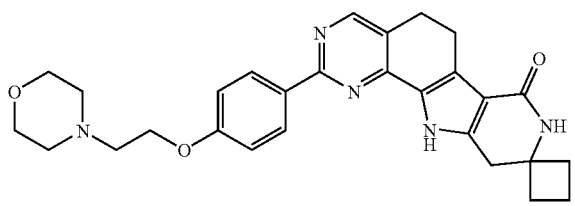

7-Bromo-2-[4-(2-morpholin-4-yl-ethoxy)-phenyl]-6,7-dihydro-5H-quinazolin-8-one (100 mg; 0.232 mmol) and 5-aza-spiro[3.5]nonane-6,8-dione (46 mg mg; 0.3 mmol) (prepared from 1-amino-cyclobutaneacetic acid (MicroChemistry Building Blocks) in analogy to Example 30.c) and ammonium acetate (54 mg; 0.67 mmol) are dissolved in MeOH (2.5 ml) and stirred at room temperature over night. The precipitate is filtered off, washed successively with water, MeOH and TBME to deliver the title compound as light-yellow crystals (54 mg; 48%). 1H-NMR (400 MHz; DMSO-d6): 12.11 (s, 1H); 8.44 (s, 1H); 8.42 (d, 2H); 7.55 (s, 1H); 7.09 (d, 2H); 4.19 (bt, 2H); 3.60 (bt, 4H); 3.05 (s, 2H); 2.97 (m, 2H); 2.90 (m, 2H); 2.74 (bt, 2H); 2.51 (bs, 4H); 2.18 M, 2H); 2.05 (m, 2H); 1.75 (m, 2H). MS (m/z) ES+: 486 (MH+). Retention time: 1.59 minutes (LC-MS method 2)

The starting materials are prepared as follows:

48.a: 4-(2-Morpholin-4-yl-ethoxy)-benzamidine

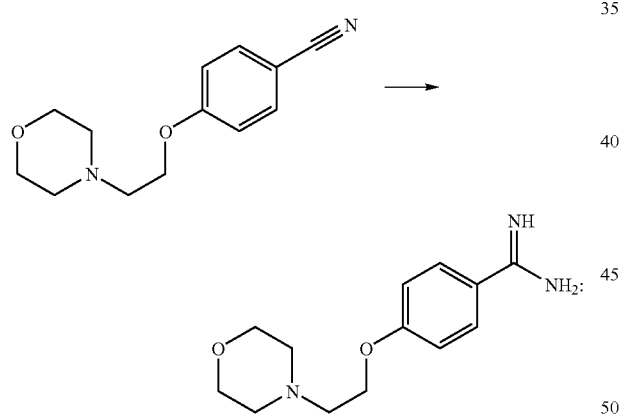

4-(2-Morpholin-4-yl-ethoxy)-benzonitrile (Maybridge CC 42116)(2.7 g; 11.64 mmol) in THF (10 ml) is combined with LiN(TMS)$_2$ (30 mmol; 30 ml of a 1M solution in THF) and stirred for 30 minutes at 55° C., kept at room temperature for 30 minutes and cooled to 5° C., while 3N HCl (28 ml) is added slowly. After 10 minutes the reaction mixture is washed with TBME and the aqueous phase is adjusted to pH ~11 with solid NaOH, saturated with solid K$_2$CO$_3$ and extracted with TBME/MeOH (~10:1) several times. The combined organic phases are dried over Na$_2$SO$_4$, filtered and evaporated to yield the title compound as yellow crystals (2.7 g; 93%). 1H-NMR (400 MHz; DMSO-d6): 7.72 (d, 2H); 6.96 (d, 2H); 6.31 (bs, 3H); 4.13 (t, 2H); 3.59 (m, 4H); 2.71 t, 2H); 2.49 (m, 4H). MS (m/z) ES+: 250 (MH+).

48.b: 8-Ethoxy-2-[4-(2-morpholin-4-yl-ethoxy)-phenyl]-5,6-dihydro-quinazoline

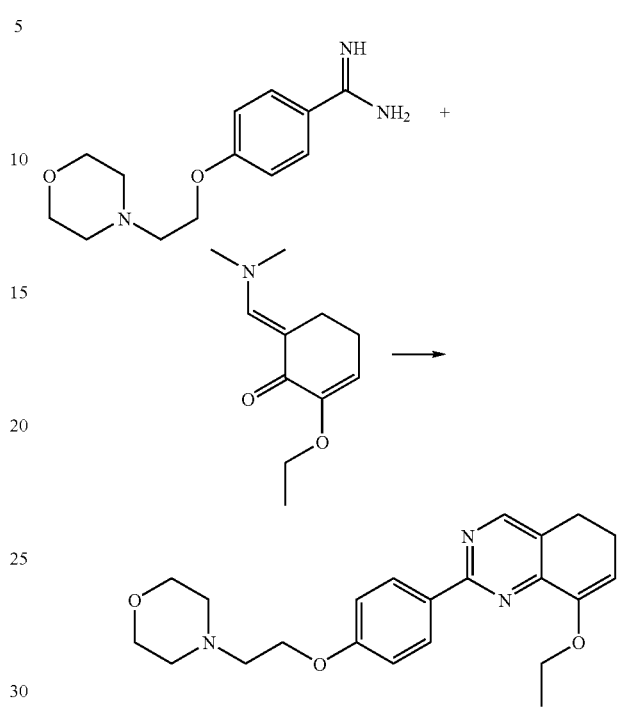

The reaction is performed in analogy to Example 14.a. Purification via chromatography (SiO$_2$; acetone/hexane (1:9>4:6) and trituration with TBME delivers the title compound as light yellow crystals (1.25 g; 64%). 1H-NMR (400 MHz; DMSO-d6): 8.60 (s, 1H); 8.31 (d, 2H); 7.09 (d, 2H); 5.65 (t, 1H); 4.18 (t, 2H); 3.94 (q, 2H); 3.60 (m, 4H); 2.78 t, 2H); 2.74 (m, 2H); 2.50 (m, 4H); 2.40 (m, 2H); 1.39 (t, 3H). MS (m/z) ES+: 382 (MH+).

EXAMPLE 48.C

2-[4-(2-Morpholin-4-yl-ethoxy)-phenyl]-6,7-dihydro-5H-quinazolin-8-one acetate

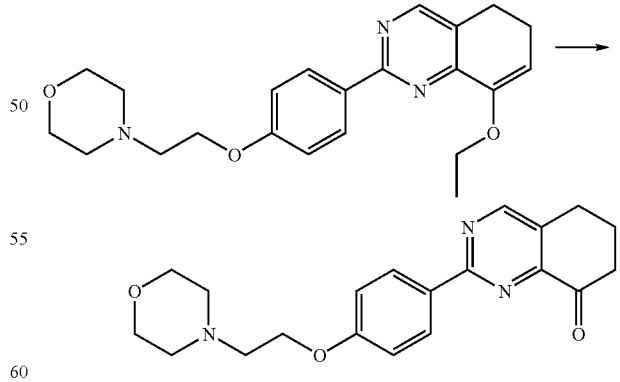

The reaction is performed in analogy to Example 14.b. The title compound is isolated as its acetate salt. (1.6 g; 100%). 1H-NMR (400 MHz; DMSO-d6): 9.06 (s, 1H); 8.34 (d, 2H); 7.12 (d, 2H); 4.19 (t, 2H); 3.60 (t, 4H); 2.99 (t, 2H); 2.76 (m, 4H); 2.50 m, 4H); 2.15 (m, 2H); 1.90 (s, 3H). MS (m/z) ES+: 354 (MH+).

48.d: 7-Bromo-2-[4-(2-morpholin-4-yl-ethoxy)-phenyl]-6,7-dihydro-5H-quinazolin-8-one

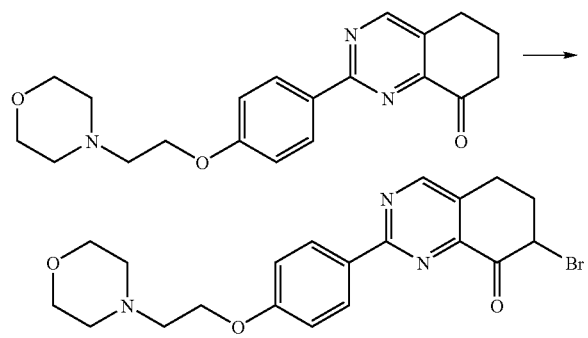

The reaction is performed in analogy to Example 14.c, yielding the title compound as light-yellow crystals (1.17 g; 83%). 1H-NMR (400 MHz; DMSO-d6): 9.12 (s, 1H); 8.36 (d, 2H); 7.14 (d, 2H); 5.23 (m, 1H); 4.22 (m, 2H); 3.62 (m, 4H); 3.10 (m, 2H); 2.74 (m, 2H); 2.49 (m, 4H); 2.46 (m, 2H). MS (m/z) ES+: 434 (MH+, 100); 432 (MH+; 99).

EXAMPLE 49

(+)-2-(2-Amino-cyclopropyl)-8-(4-methoxy-phenyl)-4,5-dihydro-1H-1,7,9-triaza-cyclopenta[a]naphthalene-3-carboxylic acid lactam

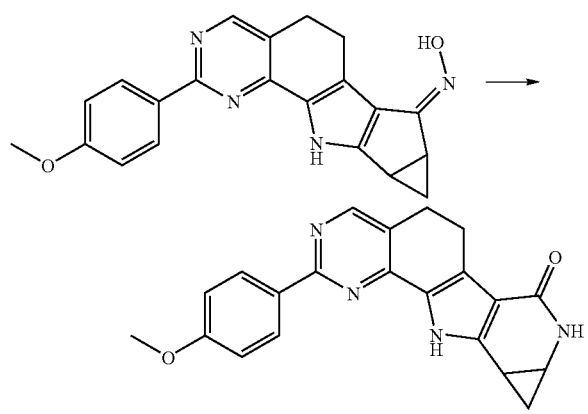

2-(4-Methoxy-phenyl)-5,8,9,10-tetrahydro-6H-1,3,10-triaza-cyclopropa[a]pentaleno[2,1-a]naphthalen-7-one oxime (24 mg; 0.067 mmol) is dissolved in polyphosphoric acid (2 ml) and heated to 125° C. for 2 h. The reaction mixture is diluted with water, adjusted to pH ~11 with a saturated solution of Na$_2$CO$_3$ in water and extracted with EtOAc three times. The combined organic phases are dried over Na$_2$SO$_4$, filtered and evaporated to dryness and purified via chromatography (SiO$_2$; acetone/hexane 3:7>100:0) to yield a product which is triturated with TBME/MeOH (9:1) and delivered the title compound as light-brown crystals (5 mg; 21%). 1H-NMR (400 MHz; DMSO-d6): 12.32 (s, 1H); 8.47 (s, 1H); 8.45 (d, 2H); 7.80 (s, 1H); 7.09 (d, 2H); 3.86 (s, 3H); 3.24 (m, 1H); 2.99 (m, 2H); 2.91 (m, 2H); 2.40 (m, 1H); 1.31 (m, 1H); 0.032 (m, 1H). MS (m/z) ES+: 359 (MH+). Retention time: 2.00 minutes (LC-MS method 2)

The starting materials are prepared as follows:

EXAMPLE 49A (+)-2-(4-Methoxy-phenyl)-5,8,9,10-tetrahydro-6H-1,3,10-triaza-cyclopropa[a]pentaleno[2,1-a]naphthalen-7-one

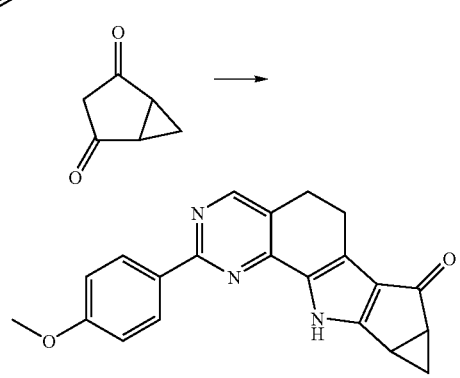

7-Bromo-2-(4-methoxy-phenyl)-6,7-dihydro-5H-quinazolin-8-one (Example 14.c) (50 mg; 0.15 mmol)

Bicyclo[3.1.0]hexan-2,4-dione (50 mg; 0.45 mmol) (Synthesis 1970, 7, 368) ammonium formate (500 mg; 7.9 mol) formic acid (750 mg; 16.3 mmol) formamide (1 g; 22 mmol) are mixed at room temperature and stirred for 1 minute, then heated for 5 minutes in an oil bath, which is preheated to 100° C. The reaction mixture dissolves gradually. The reaction mixture is cooled and poured on water, extracted with EtOAc three times. The combined organic phases are dried over Na$_2$SO$_4$, filtered, evaporated to dryness and purified via chromatography (SiO$_2$, acetone/hexane 2:8) to yield a product which after recrystallization from acetone/CH$_2$Cl$_2$ delivered the title compound as slightly pink crystals (14 mg; 27%). 1H-NMR (400 MHz; DMSO-d6): 12.52 (bs, 1H); 8.48 (s, 1H); 8.45 (d, 2H); 7.09 (d, 2H); 3.86 (s, 3H); 2.90 (m, 2H); 2.79 (m, 2H); 2.74 (m, 1H); 2.42 (m, 1H); 1.64 (m, 1H); 1.51 m, 1H). MS (m/z) ES+: 344 (MH+).

EXAMPLE 49B (+)-2-(4-Methoxy-phenyl)-5,8,9,10-tetrahydro-6H-1,3,10-triaza-cyclopropa[a]pentaleno[2,1-a]naphthalen-7-one oxime

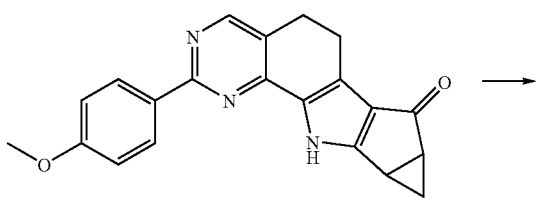

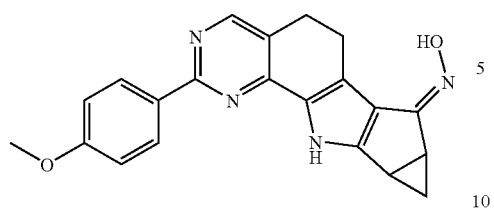

2-(4-Methoxy-phenyl)-5,8,9,10-tetrahydro-6H-1,3,10-triaza-cyclopropa[a]pentaleno[2,1-a]naphthalen-7-one (25 mg; 0.074 mmol), hydroxylamine hydrochloride (30 mg; 0.43 mmol) and pyridine (30 mg; 0.38 mmol) are refluxed in ethanol (2 ml) for 1 h. The reaction mixture is poured on water and extracted with EtOAc three times. The combined organic phases are dried over $Na_2SO_4$, filtered and evaporated to dryness to deliver the target compound as light brown amorphous powder (26 mg; 99%). 1H-NMR (400 MHz; DMSO-d6): E/Z isomers ~4:1. 12.15 (s, 1H); 10.29 (s, 1H); 8.45 (d, 2H); 8.40 (s, 1H); 7.07 (d, 2H); 0.85 (s, 3H); 2.99 (m, 2H); 2.93 (m, 2H); 2.61 (m, 1H); 2.55 (m, 1H); 1.38 (m, 1H); 0.094 (m, 1H). MS (m/z) ES+: 358 (MH+).

EXAMPLE 50

(+)-2-(2-Amino-cyclobutyl)-8-(4-methoxy-phenyl)-4,5-dihydro-1H-pyrrolo[2,3-f]isoquinoline-3-carboxylic acid lactam

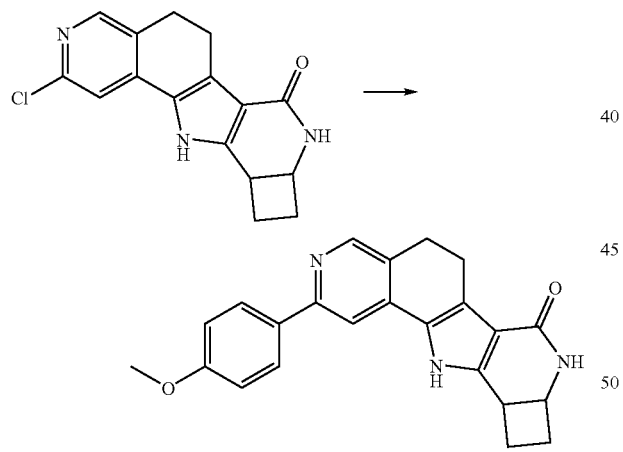

2-(2-Amino-cyclobutyl)-8-chloro-4,5-dihydro-1H-pyrrolo[2,3-f]isoquinoline-3-carboxylic acid lactam and 4-methoxyphenylboronic acid are coupled in analogy to Example 1. The crude product is filtered, washed with 1-propanol, purified via chromatography ($SiO_2$; TBME/MeOH/$NH_{3conc}$ 98:2:0.4>95:5:1) and yields the title compound as yellowish crystals (21mg; 58%) 1H-NMR (400 MHz; DMSO-d6): 11.87 (s, 1H); 8.36 (s, 1H); 8.00 (d, 2H); 7.93 (s, 1H); 7.31 (bd, 1H); 7.09 (d, 2H); 4.30 (m, 1H); 3.84 (s, 3H); 2.95 (m, 2H); 2.89 (m, 2H); 2.32 (m, 1H); 2.23 (m, 2H); 1.90 (m, 2H). MS (m/z) ES+: 372 (MH+). Retention time: 1.64 minutes (LC-MS method 2).

Starting materials are prepared as follows:

EXAMPLE 50A

3-Acetyl-bicyclo[3.2.0]heptane-2,4-dione

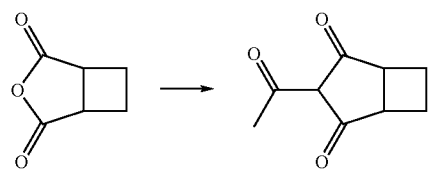

Cis-cyclobutane dicarboxylic acid anhydride (SYNTHON, Germany, ST00576) (2.6 g; 20.6 mmol) is dissolved in 1,2-dichloroethane (24 ml) and cooled to 5° C., while $AlCl_3$ (5.57 g; 41.3 mmol) is added in small portions under stirring within 5 minutes. Stirring is continued for 10 minutes, then isopropenyl acetate (2.24 ml; 20.7 mmol) is added rapidly. The reaction mixture is warmed slowly to 90° C. and kept at this temperature for 20 minutes. The reaction mixture is cooled to room temperature and poured on 10% aqueous NaHCO3 solution (100 ml), diluted with methanol (50 ml), filtered and evaporated to dryness. The solid is taken up in ethanol, filtered and evaporated to deliver the sodium salt of the title compound as white crystals (3.2 g; 83%).

MS (m/z) ES+: 167 (MH+). Retention time: 0.86 minutes (LC-MS method 2).

EXAMPLE 50B

Bicyclo[3.2.0]heptane-2,4-dione

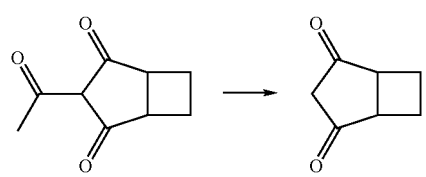

The sodium salt of 3-acetyl-bicyclo[3.2.0]heptane-2,4-dione (Example 50a; 3.2 g; 17.2 mmol) is dissolved in 2N HCl (90 ml) and refluxed for 7 hours, evaporated to dryness, taken up in $CH_2Cl_2$ and purified via chromatography (SiO2; eluents: $CH_2Cl_2$ followed by TBME then TBME/EtOH 95:5) to deliver the title compound as yellow crystals (1.1 g; 51%).

1H-NMR (400 MHz; DMSO-d6): Keto-enol tautomer. 11.95 (bs, 1H); 5.25 (s, 1H); 2.98 (bs, 2H); 2.39 (m, 2H); 1.75 (m, 2H). MS (m/z) ES+: 125 (MH+).

EXAMPLE 50C (+)-2-Chloro-5,8,9,10-tetrahydro-6H-1,10-diazacyclobuta[a]pentaleno[2,1-a]naphthalen-7-one

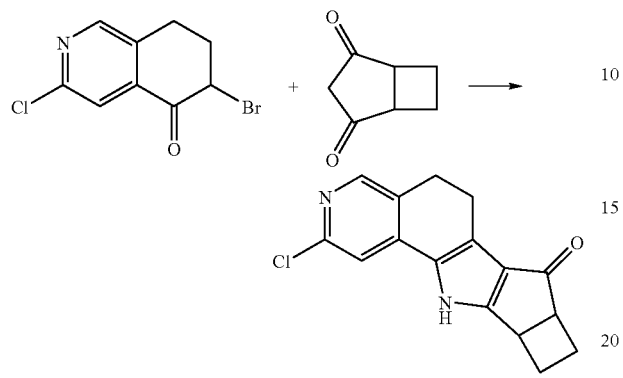

6-Bromo-3-chloro-7,8-dihydro-6H-isoquinolin-5-one (Example 1.c) (433 mg; 1.67 mmol) and bicyclo[3.2.0]heptane-2,4-dione (270 mg; 2.17 mmol) and NaOAc (137 mg; 1.67 mmol) are suspended in methanol (5 ml) and stirred over night at room temperature. The reaction mixture is evaporated to dryness, dissolved in HOAc (8 ml), NH$_4$OAc (322 mg; 4.17 mmol) is added and the mixture heated to 130° C. for 1 hour. A second portion of NH$_4$OAc (322 mg; 4.17 mmol) is added and the mixture heated to 130° C. for 1 hour. The reaction mixture is evaporated, dissolved in acetone, diluted with CH$_2$Cl$_2$, filtered and purified via chromatography (SiO2, acetone/hexanes 2:8>3:7) to yield the title compound as yellow crystals (66 mg; 14%).

1H-NMR (400 MHz; DMSO-d6): 12.29 (s, 1H); 8.20 (s, 1H); 7.49 (s, 1H); 3.72 (m, 1H); 3.42 (m, 1H); 2.90 (m, 2H); 2.84 (m, 2H); 2.58 (m, 1H); 2.48 (m, 1H); 1.81 (m, 2H). MS (m/z) ES+: 285 (MH+).

EXAMPLE 50D (+)-2-Chloro-5,8,9,10-tetrahydro-6H-1,10-diazacyclobuta[a]pentaleno[2,1a]naphthalen-7-one oxime

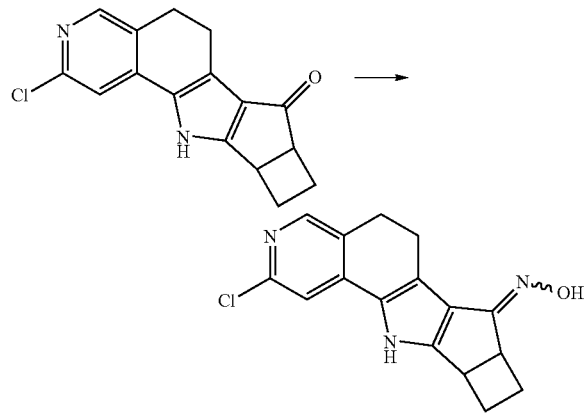

The oxime is prepared in analogy to Example 49b and delivered the title compound as yellow crystals (36 mg; 53%).

MS (m/z) ES+: 300 (MH+). Retention time: 1.93 (90%), 1.97 (10%) minutes (LC-MS method 2).

EXAMPLE 50E (+)-2-(2-Amino-cyclobutyl)-8-chloro-4,5-dihydro-1H-pyrrolo[2,3-f]isoquinoline-3-carboxylic acid lactam

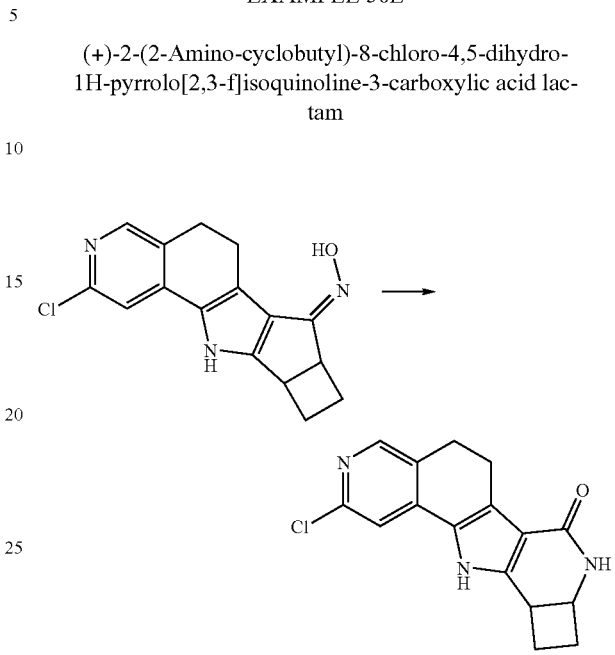

Racemic 2-chloro-5,8,9,10-tetrahydro-6H-1,10-diazacyclobuta[a]pentaleno[2,1-a]naphthalen-7-one oxime (Example 50c)(81 mg; 0.23 mmol) is suspended in polyphosphoric acid (4.5 g) and heated to 125° C. for 15 minutes. The clear reaction mixture is poured on a cold saturated aqueous solution of Na$_2$CO$_3$ and extracted with EtOAc three times. The combined organic phases are dried over Na$_2$SO$_4$, filtered and evaporated to dryness and delivered the title compound as yellow crystals (32 mg; 46%).

1H-NMR (400 MHz; DMSO-d6): 11.93 (s, 1H); 8.13 (s, 1H); 7.42 (s, 1H); 7.35 (s, 1H); 4.15 (m, 1H); 3.79 (m, 1H); 2.96 (m, 2H); 2.86 (m, 2H); 2.3 (m, 1H); 2.20 (m, 2H); 1.80 (m, 1H). MS (m/z) ES+: 300 (MH+).

EXAMPLE 51

(+)-2-(2-Amino-cyclobutyl)-8-(3-fluoro-phenyl)-4,5-dihydro-1H-pyrrolo[2,3-f]isoquinoline-3-carboxylic acid lactam

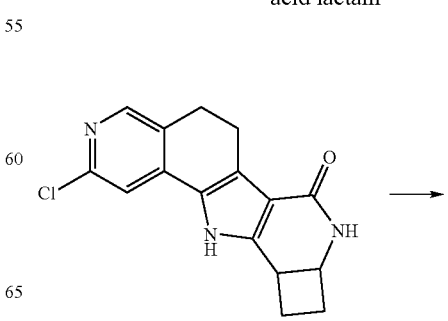

-continued

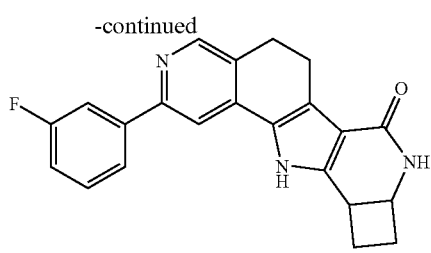

The reaction is performed in analogy to Example 50 and delivered after purification (SiO2; TBME/MeOH/NH$_{3conc}$ 98:2:0.4>96:4:0.8) the title compound as yellow crystals (227 mg; 74%).

MS (m/z) ES+: 360 (MH+). Retention time: 1.94 minutes (LC-MS method 2).

EXAMPLE 52

(+)-2-(2-Amino-cyclopropyl)-8-(4-methoxy-phenyl)-4,5-dihydro-1H-1,7-diaza-cyclopenta[a]naphthalene-3-carboxylic acid lactam

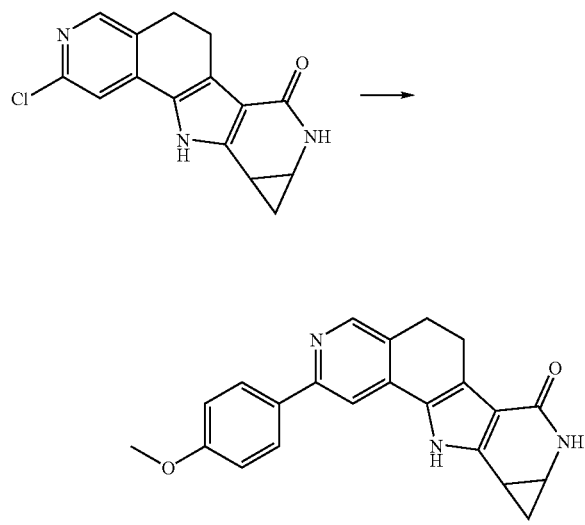

The reaction is performed in analogy to Example 50 and delivered after purification (SiO2; TBME/MeOH/NH$_{3conc}$ 97:3:0.6>95:5:1) the title compound as yellow crystals (17 mg; 35%).

1H-NMR (400 MHz; DMSO-d6): 12.15 (s, 1H); 8.35 (s, 1H); 8.03 (d, 2H); 7.92 (s, 1H); 7.73 (d, 1H); 7.08 (d, 2H); 3.85 (s, 3H); 3.23 (m, 1H); 2.91 (m, 2H); 2.84 (m, 2H); 2.36 (m, 1H); 1.27 (m, 1H); 0.21 (m, 1H). MS (m/z) ES+: 358 (MH+). Retention time: 1.50 minutes (LC-MS method 2).

Starting materials are prepared as follows:

EXAMPLE 52A (+)-2-Chloro-5,8,9,10-tetrahydro-6H-1,10-diazacyclopropa[a]pentaleno[2,1-a]naphthalen-7-one

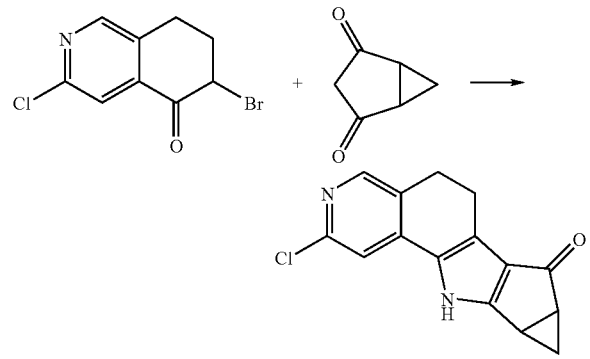

The reaction is performed in analogy to Example 50c and delivered the title compound as off-white crystals (370 mg; 36%), which are used without further purification in Example 52b.

EXAMPLE 52B (+)-2-Chloro-5,8,9,10-tetrahydro-6H-1,10-diazacyclopropa[a]pentaleno[2,1-a]naphthalen-7-one oxim

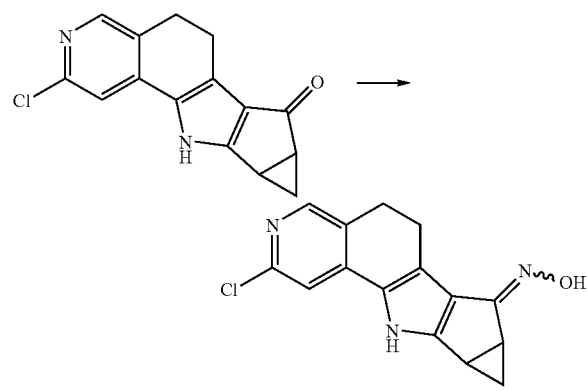

The reaction is performed in analogy to Example 50d and delivered the title compound as off-white crystals (275 mg; 70%). MS (m/z) ES+: 286 (MH+). Retention time: 1.61 minutes (LC-MS method 2).

EXAMPLE 52C (+)-2-(2-Amino-cyclopropyl)-8-(3-fluoro-phenyl)-4,5-dihydro-1H-pyrrolo[2,3-f]isoquinoline-3-carboxylic acid lactam

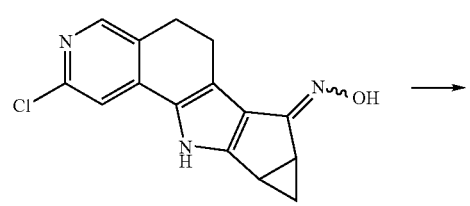

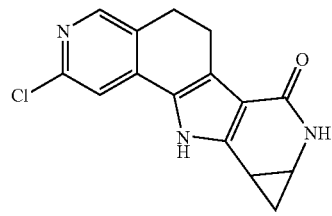

The reaction is performed in analogy to Example 50e and delivers the title compound as brownish crystals (135 mg; 35%). MS (m/z) ES+: 286 (MH+). Retention time: 1.61 minutes (LC-MS method 2).

EXAMPLE 54

2-(1-Aminomethyl-cyclopropyl)-8-(6-methoxy-pyridin-3-yl)-4,5-dihydro-1H-pyrrolo[2,3-f]isoquinoline-3-carboxylic acid lactam

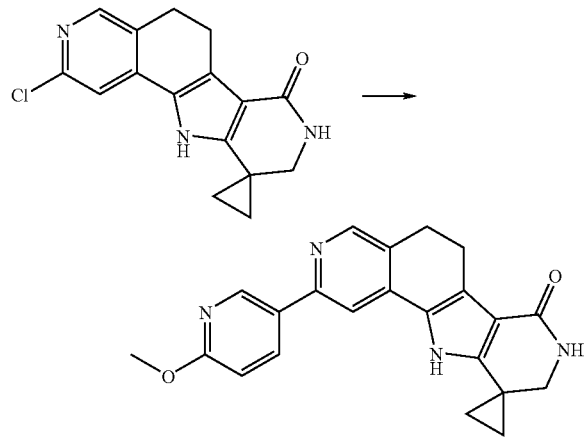

2-(1-Aminomethyl-cyclopropyl)-8-chloro-4,5-dihydro-1H-pyrrolo[2,3-f]isoquinoline-3-carboxylic acid lactam (Example 1d) and 2-methoxypyridine-5-boronic acid are coupled in analogy to Example 1 and yield the title compound as off-white crystals (26 mg; 42%).

MS (m/z) ES+: 373 (MH+). Retention time: 1.62 minutes (LC-MS method 2).

EXAMPLE 55

2-(1-Aminomethyl-cyclopropyl)-8-(5-methoxy-pyridin-3-yl)-4,5-dihydro-1H-pyrrolo[2,3-f]isoquinoline-3-carboxylic acid lactam

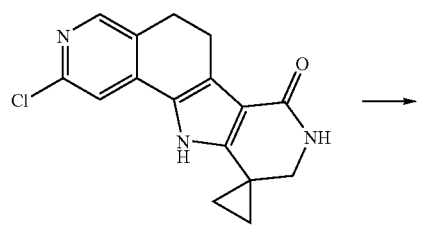

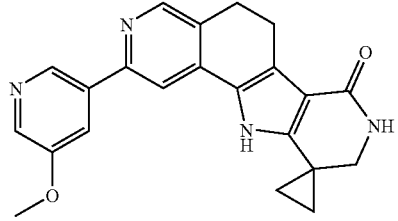

2-(1-Aminomethyl-cyclopropyl)-8-chloro-4,5-dihydro-1H-pyrrolo[2,3-f]isoquinoline-3-carboxylic acid lactam (Example 1d) and 3-methoxypyridine-5-boronic acid pinacolester (Aldrich, 676624) are coupled in analogy to Example 1 and yield the title compound as yellow crystals (21 mg; 34%). MS (m/z) ES+: 373 (MH+). Retention time: 1.64 minutes (LC-MS method 2).

EXAMPLE 56

2-(1-Aminomethyl-cyclopropyl)-8-(3-fluoro-phenyl)-4,5-dihydro-1H-pyrrolo[2,3-f]isoquinoline-3-carboxylic acid lactam

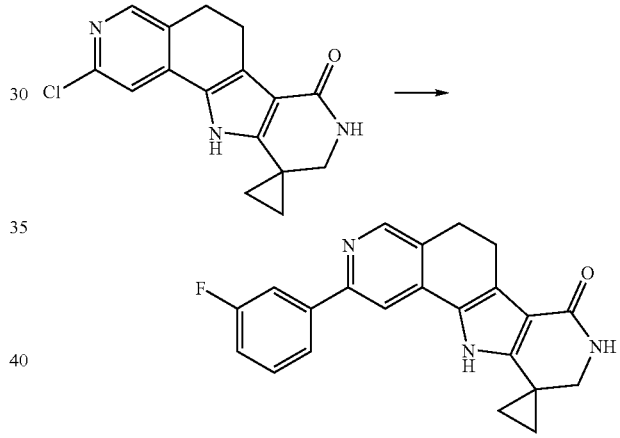

2-(1-Aminomethyl-cyclopropyl)-8-chloro-4,5-dihydro-1H-pyrrolo[2,3-f]isoquinoline-3-carboxylic acid lactam (Example 1d) and 3-fluorophenylboronic acid (Sigma-Aldrich, order number 441643) are coupled in analogy to Example 1 and yield the title compound as yellow crystals (25 mg; 46%). MS (m/z) ES+: 360 (MH+). Retention time: 1.88 minutes (LC-MS method 2).

EXAMPLE 57

2-(1-Aminomethyl-cyclopropyl)-8-(4-methoxy-phenyl)-4,5-dihydro-1H-pyrrolo[2,3-f]isoquinoline-3-carboxylic acid lactam

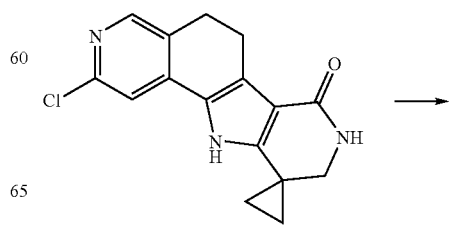

-continued

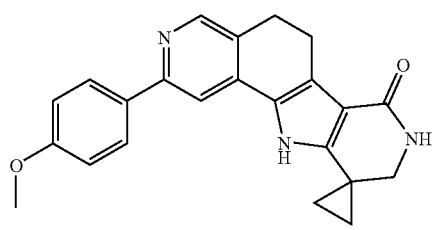

2-(1-Aminomethyl-cyclopropyl)-8-chloro-4,5-dihydro-1H-pyrrolo[2,3-f]isoquinoline-3-carboxylic acid lactam (Example 1d) and 4-methoxyphenylboronic acid (ABCR Product List, AB169111) are coupled in analogy to Example 1 and yield the title compound as yellow crystals (31 mg; 46%). MS (m/z) ES+: 372 (MH+). Retention time: 1.61 minutes (LC-MS method 2).

EXAMPLE 58

2-(1-Aminomethyl-cyclopropyl)-8-(3-fluoro-phenyl)-4,5-dihydro-1H-1,7,9-triaza-cyclopenta[a]naphthalene-3-carboxylic acid lactam

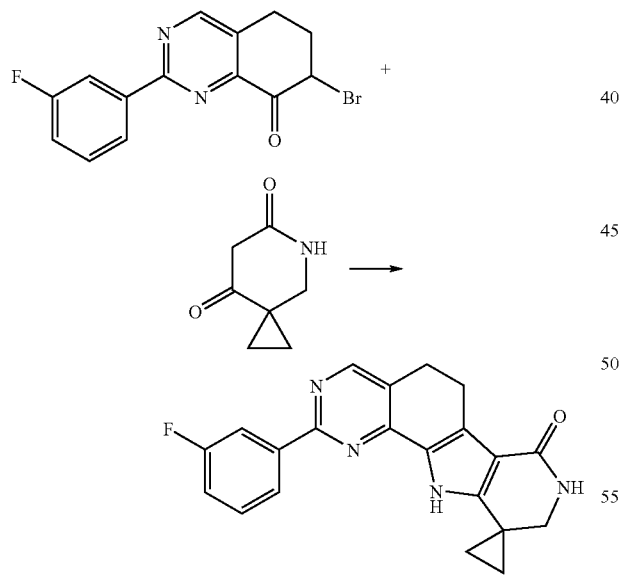

7-Bromo-2-(3-fluoro-phenyl)-6,7-dihydro-5H-quinazolin-8-one (prepared from 3-fluorobenzamidine in analogy to Example 14c) and 5-aza-spiro[2.5]octane-6,8-dione (WO 2005014572, WO 2005013986) are reacted in analogy to Example 17 and yield the title compound as colorless crystals (58 mg; 67%). MS (m/z) ES+: 361 (MH+). Retention time: 2.49 minutes (LC-MS method 2).

EXAMPLE 59

2-(3-Amino-azetidin-3-ylmethyl)-8-(4-ethoxyphenyl)-1-methyl-4,5-dihydro-1H-1,7,9-triaza-cyclopenta[a]naphthalene-3-carboxylic acid lactam hydrochloride

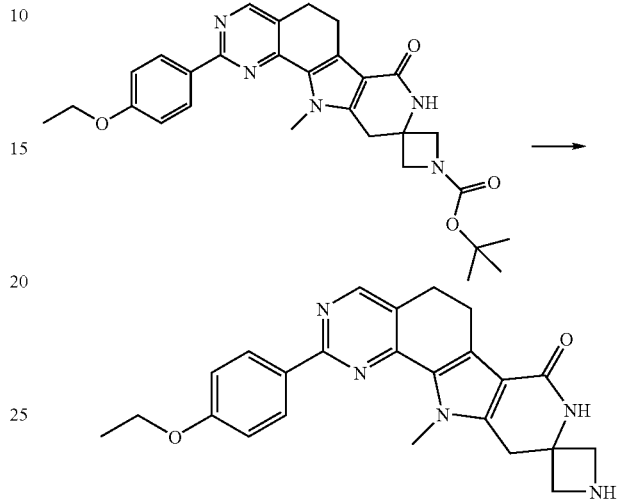

2-(3-Amino-1-tert-butoxycarbonyl-azetidin-3-ylmethyl)-8-(4-ethoxyphenyl)-1-methyl-4,5-dihydro-1H-1,7,9-triaza-cyclopenta[a]naphthalene-3-carboxylic acid lactam (prepared from 4-ethoxybenzamidin in analogy to Example 26) is treated with $HCl_{conc}$ in analogy to Example 27 and provides the title compound as yellow crystals (55 mg; 95%). MS (m/z) ES+: 416 (MH+). Retention time: 1.98 minutes (LC-MS method 2).

EXAMPLE 60

2-(1-Amino-cyclopropylmethyl)-8-(4-cyano-phenyl)-4,5-dihydro-1H-pyrrolo[2,3-f]isoquinoline-3-carboxylic acid lactam

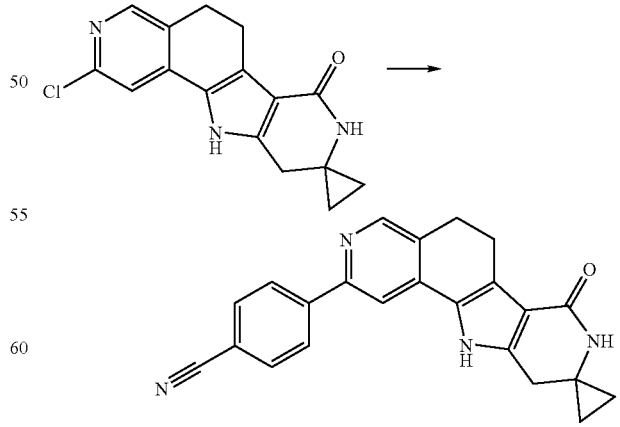

2-(1-Amino-cyclopropylmethyl)-8-chloro-4,5-dihydro-1H-pyrrolo[2,3-f]isoquinoline-3-carboxylic acid lactam (Example 31a) and 4-cyanophenylboronic acid (ALDRICH, 521418) are coupled in analogy to Example 1 and provide the

EXAMPLE 61

2-(1-Amino-cyclopropylmethyl)-8-(3-cyano-phenyl)-4,5-dihydro-1H-pyrrolo[2,3-f]isoquinoline-3-carboxylic acid lactam

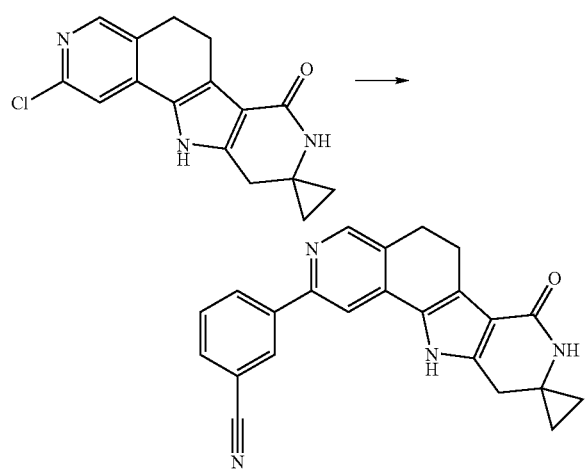

The reaction is performed with 3-cyanophenylboronic acid (Aldrich 513016) in analogy to Example 60 and delivers the title compound as off-white crystals (25 mg; 47%). MS (m/z) ES+: 367 (MH+). Retention time: 2.00 minutes (LC-MS method 2).

EXAMPLE 62

2-(1-Amino-cyclopropylmethyl)-8-benzofuran-2-yl-4,5-dihydro-1H-pyrrolo[2,3-f]isoquinoline-3-carboxylic acid lactam

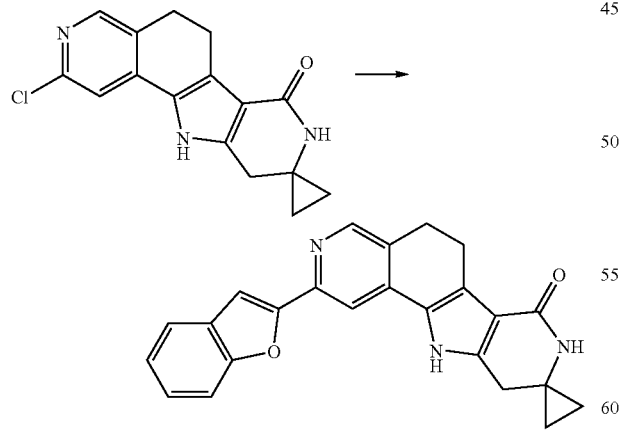

2-(1-Amino-cyclopropylmethyl)-8-chloro-4,5-dihydro-1H-pyrrolo[2,3-f]isoquinoline-3-carboxylic acid lactam (Example 31a) and benzofurane-2-boronic acid (Aldrich, 499943) are coupled in analogy to Example 1 and provide the title compound as yellowish crystals (35 mg; 45%).

MS (m/z) ES+: 381 (MH+). Retention time: 2.22 minutes (LC-MS method 2).

EXAMPLE 63

2-(1-Amino-cyclopropylmethyl)-8-(6-cyano-pyridin-3-yl)-4,5-dihydro-1H-pyrrolo[2,3-f]isoquinoline-3-carboxylic acid lactam

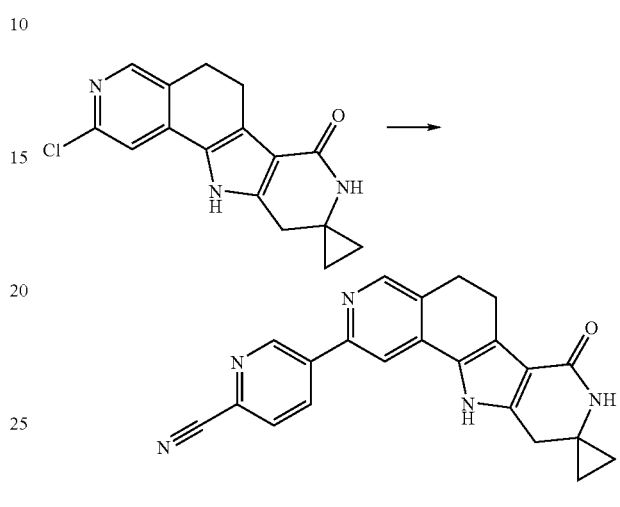

2-(1-Amino-cyclopropylmethyl)-8-chloro-4,5-dihydro-1H-pyrrolo[2,3-f]isoquinoline-3-carboxylic acid lactam (Example 31a) and 2-cyanopyridine-5-boronic acid (SYNCHEM OHG Product List, un119) are coupled in analogy to Example 1 and provide the compound as white crystals (13 mg; 29%). MS (m/z) ES+: 368 (MH+). Retention time: 1.98 minutes (LC-MS method 2).

EXAMPLE 64

2-(1-Amino-cyclopropylmethyl)-8-[4-(2-morpholin-4-yl-ethoxy)-phenyl]-4,5-dihydro-1H-pyrrolo[2,3-f]isoquinoline-3-carboxylic acid lactam

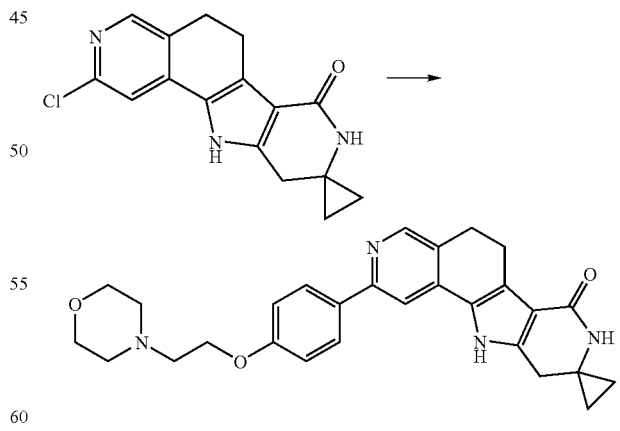

2-(1-Amino-cyclopropylmethyl)-8-chloro-4,5-dihydro-1H-pyrrolo[2,3-f]isoquinoline-3-carboxylic acid lactam (Example 31a) and 4-{2-[4-(4,4,5,5-tetramethyl-[1,3,2]dioxaborolan-2-yl)-phenoxy]-ethyl}-morpholine (Focus Synthesis Products FS000534) are coupled in analogy to Example 1 and provide the title compound as white crystals (45 mg; 59%). MS (m/z) ES+: 470 (MH+). Retention time: 1.15 minutes (LC-MS method 2).

EXAMPLE 65

2-(1-Amino-cyclopropylmethyl)-8-(4-piperidin-1-ylmethyl-phenyl)-4,5-dihydro-1H-pyrrolo[2,3-f]isoquinoline-3-carboxylic acid lactam

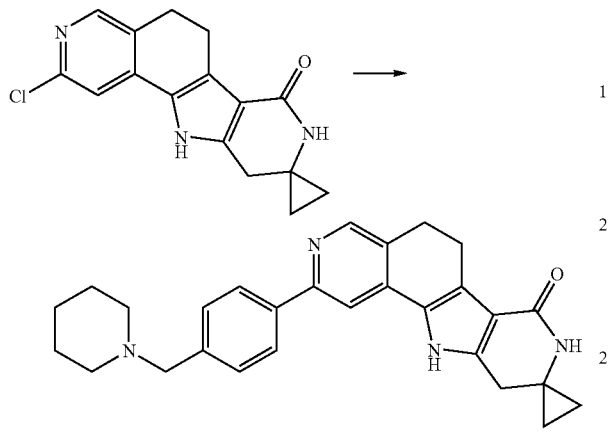

2-(1-Amino-cyclopropylmethyl)-8-chloro-4,5-dihydro-1H-pyrrolo[2,3-f]isoquinoline-3-carboxylic acid lactam (Example 31a) and 1-[4-(4,4,5,5-tetramethyl-[1,3,2]dioxaborolan-2-yl)-benzyl]-piperidine_(Intermediate K) are coupled in analogy to Example 1 and provide the title compound as yellowish crystals (33 mg; 59%). MS (m/z) ES+: 438 (MH+). Retention time: 1.24 minutes (LC-MS method 2).

EXAMPLE 66

2-(1-Amino-cyclopropylmethyl)-8-(2,3-dihydro-benzo[1,4]dioxin-6-yl)-4,5-dihydro-1H-pyrrolo[2,3-f]isoquinoline-3-carboxylic acid lactam

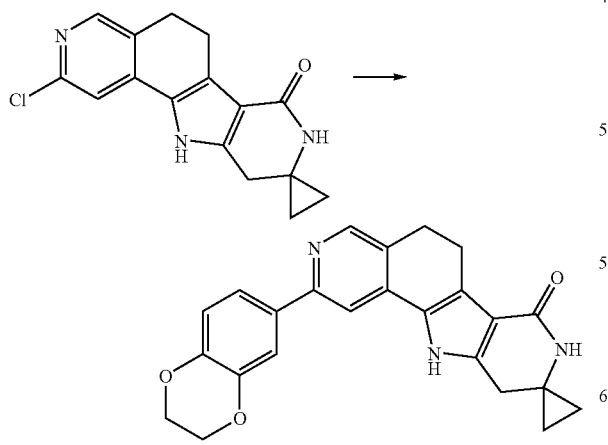

2-(1-Amino-cyclopropylmethyl)-8-chloro-4,5-dihydro-1H-pyrrolo[2,3-f]isoquinoline-3-carboxylic acid lactam (Example 31a) and 2,3-dihydro-benzo[1,4]dioxine-6-boronic acid (Aldrich 635995) are coupled in analogy to Example 1 and provide the title compound as colorless crystals (28 mg; 71%). MS (m/z) ES+: 400 (MH+). Retention time: 1.62 minutes (LC-MS method 2).

EXAMPLE 67

2-(1-Amino-cyclopropylmethyl)-8-(6-fluoro-pyridin-3-yl)-4,5-dihydro-1H-pyrrolo[2,3-f]isoquinoline-3-carboxylic acid lactam

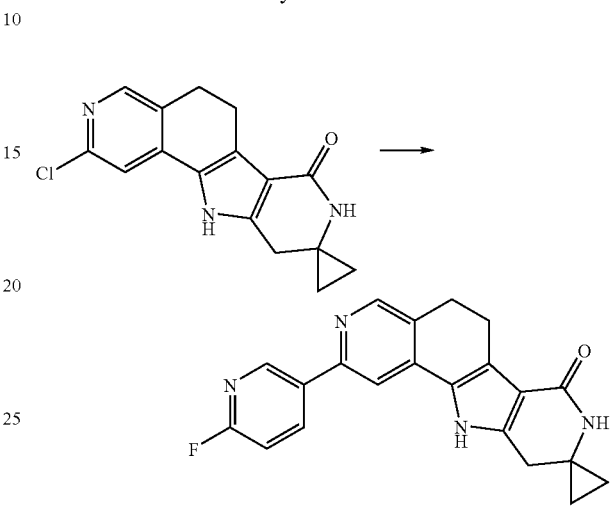

2-(1-Amino-cyclopropylmethyl)-8-chloro-4,5-dihydro-1H-pyrrolo[2,3-f]isoquinoline-3-carboxylic acid lactam (Example 31a) and 2-fluoropyridine-5-boronic acid (ABCR, AB181129) are coupled in analogy to Example 1 and provide the title compound as colorless crystals (36 mg; 74%). MS (m/z) ES+: 361 (MH+). Retention time: 1.77 minutes (LC-MS method 2).

EXAMPLE 68

2-(1-Amino-cyclopropylmethyl)-8-6-dimethylamino-pyridin-3-yl-4,5-dihydro-1H-pyrrolo[2,3-f]isoquinoline-3-carboxylic acid lactam

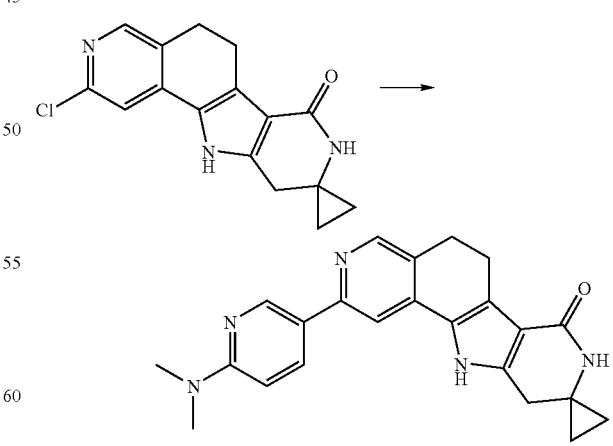

2-(1-Amino-cyclopropylmethyl)-8-chloro-4,5-dihydro-1H-pyrrolo[2,3-f]isoquinoline-3-carboxylic acid lactam (Example 31a) and 2-dimethylaminopyridine-5-boronic acid (Frontier Scientific, D9115) are coupled in analogy to Example 1 and provide the title compound as colorless crystals (39 mg; 76%). MS (m/z) ES+: 386 (MH+). Retention time: 1.49 minutes (LC-MS method 2).

EXAMPLE 69

2-(1-Amino-cyclopropylmethyl)-8-(6-methyl-pyridin-3-yl)-4,5-dihydro-1H-pyrrolo[2,3-f]isoquinoline-3-carboxylic acid lactam

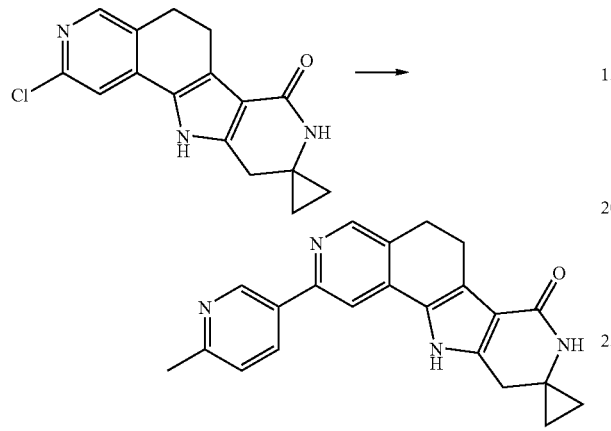

2-(1-Amino-cyclopropylmethyl)-8-chloro-4,5-dihydro-1H-pyrrolo[2,3-f]isoquinoline-3-carboxylic acid lactam (Example 31a) and 6-methylpyridine-3-boronic acid (SYNCHEM OHG, un119) are coupled in analogy to Example 1 and provide the title compound as colorless crystals (36 mg; 76%). MS (m/z) ES+: 386 (MH+). Retention time: 1.41 minutes (LC-MS method 2).

EXAMPLE 70

2-(1-Amino-cyclopropylmethyl)-8-(4-ethoxy-3-fluoro-phenyl)-4,5-dihydro-1H-pyrrolo[2,3-f]isoquinoline-3-carboxylic acid lactam

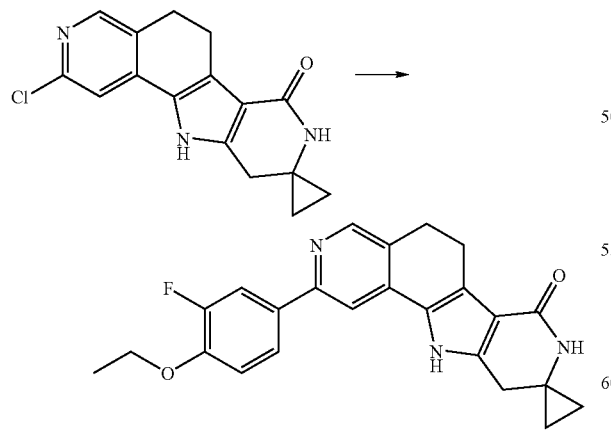

2-(1-Amino-cyclopropylmethyl)-8-chloro-4,5-dihydro-1H-pyrrolo[2,3-f]isoquinoline-3-carboxylic acid lactam (Example 31a) and 4-ethoxy-3-fluorophenyl-boronic acid (ABCR, AB150605) are coupled in analogy to Example 1 and provide the title compound as colorless crystals (32 mg; 59%). MS (m/z) ES+: 404 (MH+). Retention time: 1.93 minutes (LC-MS method 2).

EXAMPLE 71

2-(1-Amino-cyclopropylmethyl)-8-(4-ethoxy-phenyl)-4,5-dihydro-1H-pyrrolo[2,3-f]isoquinoline-3-carboxylic acid lactam

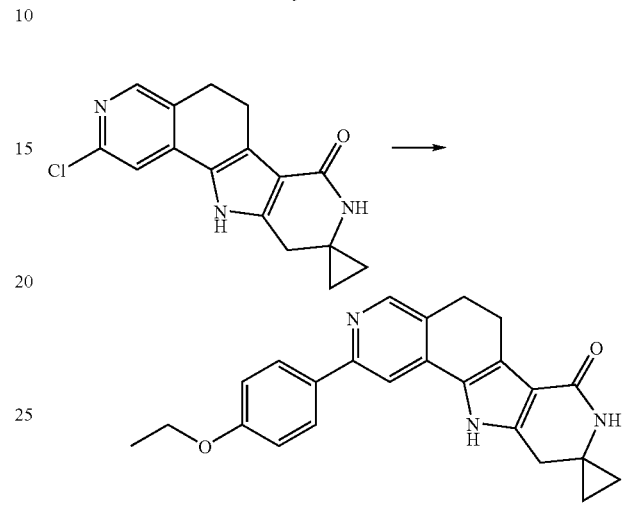

2-(1-Amino-cyclopropylmethyl)-8-chloro-4,5-dihydro-1H-pyrrolo[2,3-f]isoquinoline-3-carboxylic acid lactam (Example 31a) and 4-ethoxyphenyl-boronic acid (ABCR, AB175405) are coupled in analogy to Example 1 and provide the title compound as colorless crystals (29 mg; 58%).

MS (m/z) ES+: 386 (MH+). Retention time: 1.79 minutes (LC-MS method 2).

EXAMPLE 72

2-(1-Amino-cyclopropylmethyl)-8-(3-formyl-4-methoxy-phenyl)-4,5-dihydro-1H-pyrrolo[2,3-f]isoquinoline-3-carboxylic acid lactam

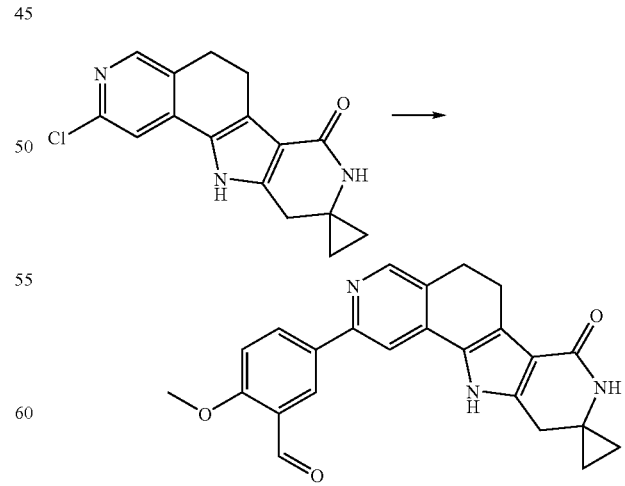

2-(1-Amino-cyclopropylmethyl)-8-chloro-4,5-dihydro-1H-pyrrolo[2,3-f]isoquinoline-3-carboxylic acid lactam (Example 31a) and 3-formyl-4-methoxyphenyl-boronic acid (ABCR, AB150374) are coupled in analogy to Example 1 and provide the title compound as colorless crystals (160 mg; 79%). MS (m/z) ES+: 400 (MH+). Retention time: 1.74 minutes (LC-MS method 2).

EXAMPLE 73

2-(1-Amino-cyclopropylmethyl)-8-(4-methoxy-3-morpholin-4-ylmethyl-phenyl)-4,5-dihydro-1H-pyrrolo[2,3-f]isoquinoline-3-carboxylic acid lactam

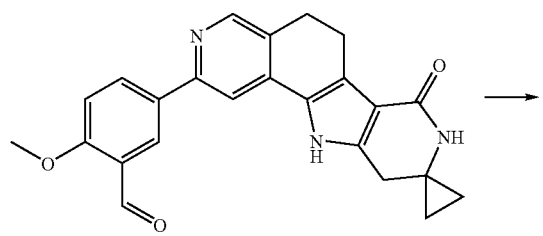

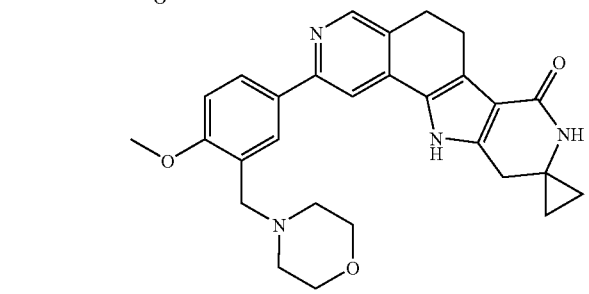

2-(1-Amino-cyclopropylmethyl)-8-(3-formyl-4-methoxy-phenyl)-4,5-dihydro-1H-pyrrolo[2,3-f]isoquinoline-3-carboxylic acid lactam (Example 72) (40 mg; 0.10 mmol) and morpholin (44 mg; 0.5 mmol) are dissolved in 1,2-dichloroethane/HOAc (4 ml/0.25 ml) and treated with NaBH(OAc)3 (42 mg; 0.2 mmol) at room temperature over night. The reaction mixture is evaporated to dryness and purified via chromatography ($SiO_2$, TBME/MeOH 93:7 then TBME/MeOH/$NH3_{conc}$ 85:15:3) to deliver the title compound as yellowish crystals (34 mg; 72%).

MS (m/z) ES+: 471 (MH+). Retention time: 1.25 minutes (LC-MS method 2).

EXAMPLE 74

2-(1-Amino-cyclopropylmethyl)-8-[4-methoxy-3-(4-methyl-piperazin-1-ylmethyl)-phenyl]-4,5-dihydro-1H-pyrrolo[2,3-f]isoquinoline-3-carboxylic acid lactam

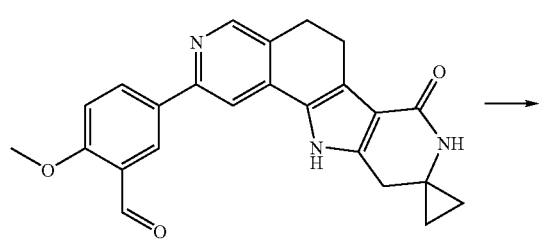

-continued

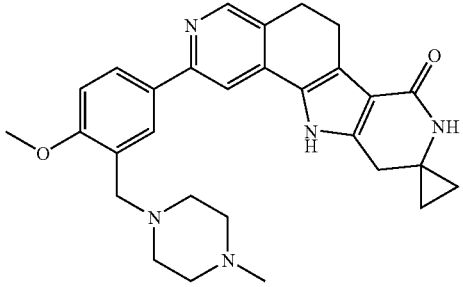

The reaction is performed in analogy to Example 73 and provided the title compound as off-white crystals (26 mg; 54%). MS (m/z) ES+: 484 (MH+). Retention time: 1.26 minutes (LC-MS method 2).

EXAMPLE 75

2-(1-Amino-cyclopropylmethyl)-8-(3-ethynyl-4-methoxy-phenyl)-4,5-dihydro-1H-pyrrolo[2,3-f]isoquinoline-3-carboxylic acid lactam

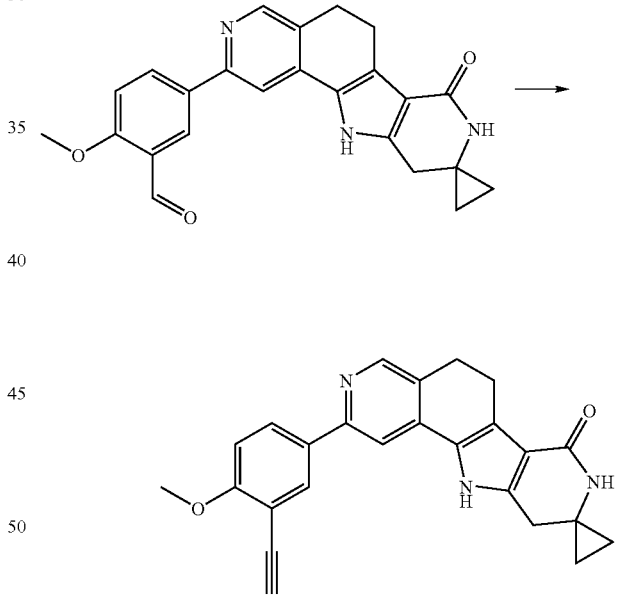

2-(1-Amino-cyclopropylmethyl)-8-(3-formyl-4-methoxy-phenyl)-4,5-dihydro-1H-pyrrolo[2,3-f]isoquinoline-3-carboxylic acid lactam (Example 72) (100 mg; 0.1 mmol) and (1-diazo-2-oxo-propyl)-phosphonic acid dimethyl ester (Paragos, 40364, Bestmann-Ohira reagent)(38 mg; 0.2 mmol), $K_2CO_3$ (35 mg; 0.25 mmol) are dissolved in MeOH/$CH_2Cl_2$ (3 ml/1 ml) and stirred over night at room temperature. The reaction mixture is evaporated to dryness and purified via chromatography ($SiO_2$, TBME/MeOH 95:5) to yield the title compound as yellowish crystals (29 mg; 74%). MS (m/z) ES+: 396 (MH+). Retention time: 1.83 minutes (LC-MS method 2).

EXAMPLE 76

2-(1-Amino-cyclopropylmethyl)-8-pyridin-3-yl-4,5-dihydro-1H-pyrrolo[2,3-f]isoquinoline-3-carboxylic acid lactam

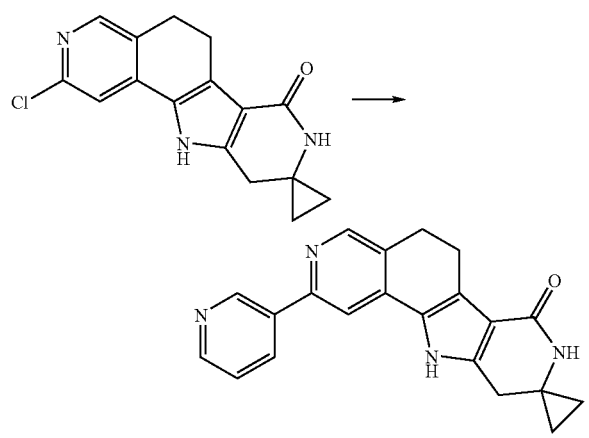

2-(1-Amino-cyclopropylmethyl)-8-chloro-4,5-dihydro-1H-pyrrolo[2,3-f]isoquinoline-3-carboxylic acid lactam (Example 31a) and pyridine-3-boronic acid (ABCR, AB152416) are coupled in analogy to Example 1 and provide the title compound as colorless crystals (34 mg; 60%).

MS (m/z) ES+: 343 (MH+). Retention time: 1.45 minutes (LC-MS method 2).

EXAMPLE 77

2-(1-Amino-cyclopropylmethyl)-8-[4-(3-hydroxy-3-methyl-butyl)-phenyl]-4,5-dihydro-1H-pyrrolo[2,3-f]isoquinoline-3-carboxylic acid lactam

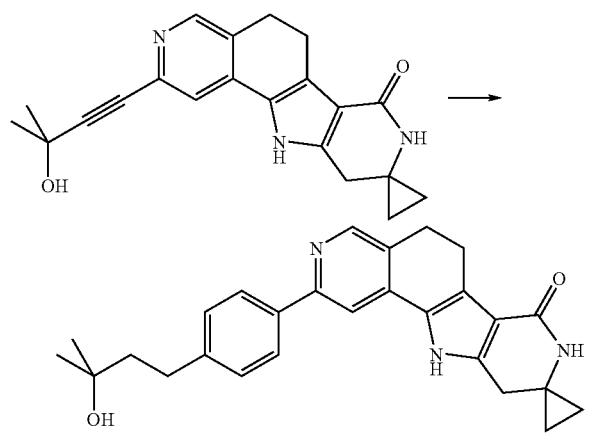

2-(1-Amino-cyclopropylmethyl)-8-[4-(3-hydroxy-3-methyl-but-1-ynyl)-phenyl]-4,5-dihydro-1H-pyrrolo[2,3-f]isoquinoline-3-carboxylic acid lactam (Example 81)(59 mg; 0.14 mmol) and ammonium formate (38 mg; 1.39 mmol) are dissolved in methanol (25 ml) and refluxed over Pd/C (10%; 55 mg) for 30 minutes. The reaction mixture is filtered, evaporated to dryness and purified via chromatography (SiO$_2$, TBME/MeOH/NH$_3$ $_{conc}$ 95:5:1) to yield the title compound as yellowish crystals (24 mg; 41%). MS (m/z) ES+: 428 (MH+). Retention time: 1.76 minutes (LC-MS method 2).

EXAMPLE 78

2-(1-Amino-cyclopropylmethyl)-8-[4-(3-amino-3-methyl-butyl)-phenyl]-4,5-dihydro-1H-pyrrolo[2,3-f]isoquinoline-3-carboxylic acid lactam

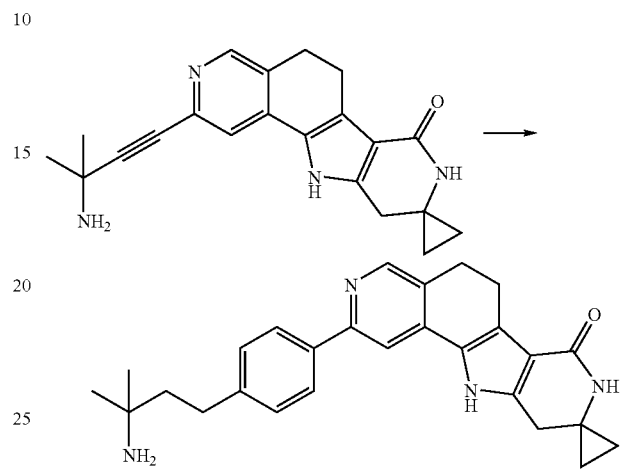

2-(1-Amino-cyclopropylmethyl)-8-[4-(3-amino-3-methyl-but-1-ynyl)-phenyl]-4,5-dihydro-1H-pyrrolo[2,3-f]isoquinoline-3-carboxylic acid lactam (Example 82) is treated in analogy to Example 77 and delivers the title compound as light-brown crystals (21 mg; 50%). MS (m/z) ES+: 427 (MH+). Retention time: 1.28 minutes (LC-MS method 2).

EXAMPLE 79

2-(1-Amino-cyclopropylmethyl)-8-[3-methoxy-4-(2-methoxy-ethoxy)-phenyl]-4,5-dihydro-1H-pyrrolo[2,3-f]isoquinoline-3-carboxylic acid lactam

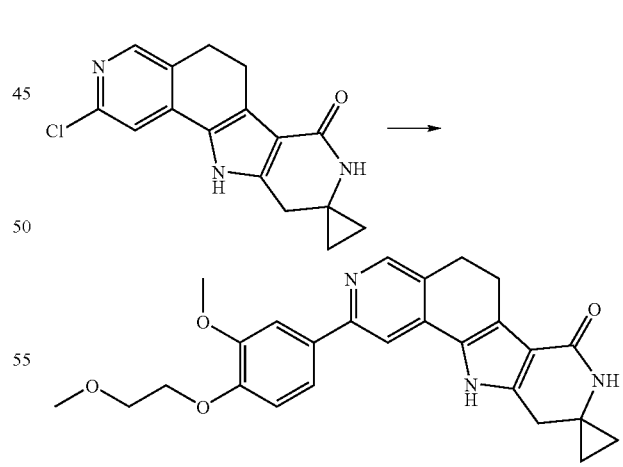

3-Methoxy-4-(2-methoxy-ethoxy)-phenyl boronic acid pinacolester and 2-(1-amino-cyclopropylmethyl)-8-chloro-4,5-dihydro-1H-pyrrolo[2,3-f]isoquinoline-3-carboxylic acid lactam (Example 31a) are coupled in analogy to Example 1 and provide the title compound as white crystals (37 mg; 53%). MS (m/z) ES+: 446 (MH+). Retention time: 1.96 minutes (LC-MS method 3).

The starting material is prepared as follows:

EXAMPLE 79A

3-Methoxy-4-(2-methoxy-ethoxy)-phenyl boronic acid pinacolester

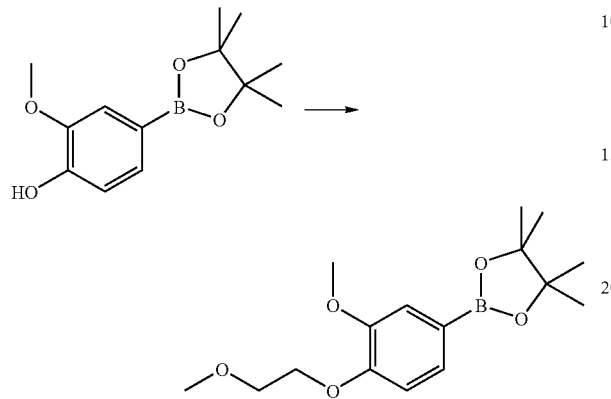

4-Hydroxy-3-methoxyphenylboronic acid pinacol ester (Aldrich, 518786) (1 g; 4 mmol), 2-bromomethyl)-methyl-ether (0.83 g; 6 mmol) and $Cs_2CO_3$ (2.6 g; 8 mmol) in DMF (10 ml) are heated to 130° C. for 45 minutes. The reaction mixture is diluted with TBME/heptane (5 ml/5 ml), filtered and evaporated to deliver the title compound as yellow oil used without further purification in Example 79.

1H-NMR (400 MHz; DMSO-d6): 7.23 (d, 1H); 7.13 (s, 1H); 6.97 (d, 1H); 4.09 (m, 2H); 3.76 (s, 3H); 3.66 (m, 2H); 3.30 (s, 3H); 1.28 (s, 12H).

EXAMPLE 80

2-(1-Amino-cyclopropylmethyl)-8-(5-cyano-pyridin-3-yl)-4,5-dihydro-1H-pyrrolo[2,3-f]isoquinoline-3-carboxylic acid lactam

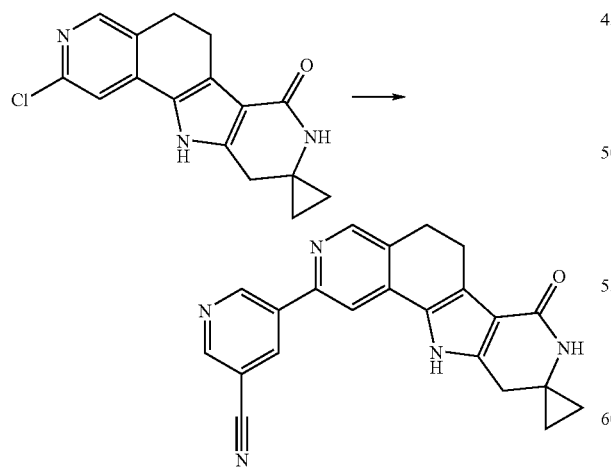

2-(1-Amino-cyclopropylmethyl)-8-chloro-4,5-dihydro-1H-pyrrolo[2,3-f]isoquinoline-3-carboxylic acid lactam (Example 31a) and (5-cyanopyridin-3-yl)boronic acid (Anichem P20027) are coupled in analogy to Example 1 and provide the title compound as colorless crystals (43 mg; 73%). MS (m/z) ES+: 368 (MH+). Retention time: 2.20 minutes (LC-MS method 3).

EXAMPLE 81

2-(1-Amino-cyclopropylmethyl)-8-[4-(3-hydroxy-3-methyl-but-1-ynyl)-phenyl]-4,5-dihydro-1H-pyrrolo[2,3-f]isoquinoline-3-carboxylic acid lactam

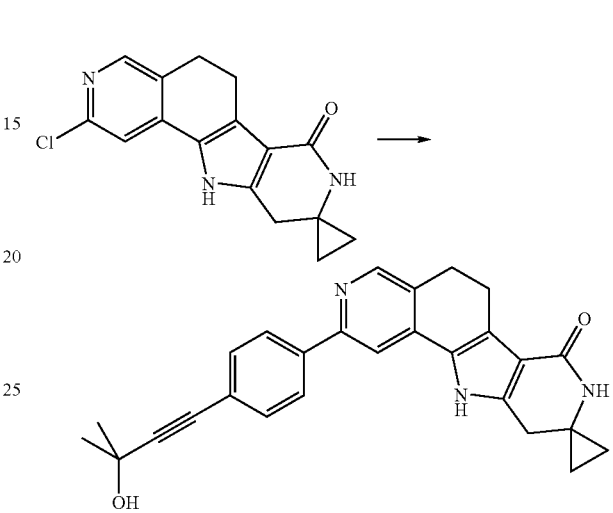

2-(1-Amino-cyclopropylmethyl)-8-chloro-4,5-dihydro-1H-pyrrolo[2,3-f]isoquinoline-3-carboxylic acid lactam (Example 31a) and 2-methyl-4-[4-(4,4,5,5-tetramethyl-[1,3,2]dioxaborolan-2-yl)-phenyl]-but-3-yn-2-ol (Intermediate L) are coupled in analogy to Example 1 and provide the title compound as colorless crystals (20 mg; 48%). MS (m/z) ES+: 424 (MH+). Retention time: 1.88 minutes (LC-MS method 2).

EXAMPLE 82

2-(1-Amino-cyclopropylmethyl)-8-[4-(3-amino-3-methyl-but-1-ynyl)-phenyl]-4,5-dihydro-1H-pyrrolo[2,3-f]isoquinoline-3-carboxylic acid lactam

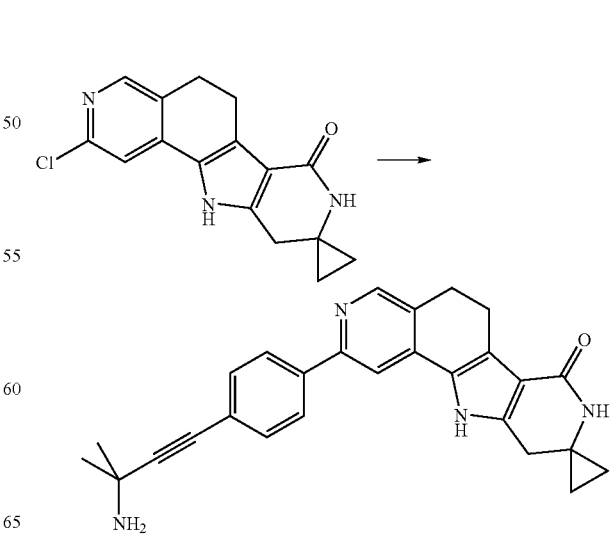

2-(1-Amino-cyclopropylmethyl)-8-chloro-4,5-dihydro-1H-pyrrolo[2,3-f]isoquinoline-3-carboxylic acid lactam (Example 31a) and 1,1-dimethyl-3-[4-(4,4,5,5-tetramethyl-[1,3,2]dioxaborolan-2-yl)-phenyl]-prop-2-ynylamine (Intermediate A) are coupled in analogy to Example 1 and provide the title compound as colorless crystals (20 mg; 56%). MS (m/z) ES+: 423 (MH+). Retention time: 1.40 minutes (LC-MS method 2).

EXAMPLE 83

2-(1-Amino-cyclopropylmethyl)-8-(3,4,5,6-tetrahydro-2H-[1,2']bipyridinyl-5'-yl)-4,5-dihydro-1H-pyrrolo[2,3-f]isoquinoline-3-carboxylic acid lactam

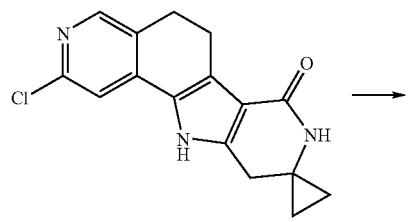

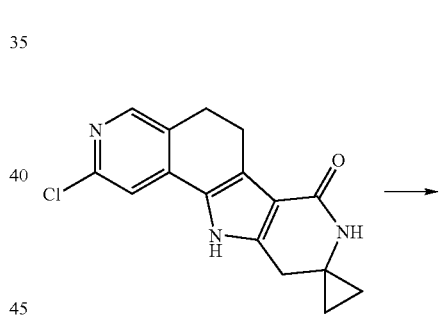

2-(1-Amino-cyclopropylmethyl)-8-chloro-4,5-dihydro-1H-pyrrolo[2,3-f]isoquinoline-3-carboxylic acid lactam (Example 31a) and 2-(piperidin-1-yl)pyridine-5-boronic acid pinacol ester (Frontier Scientific Catalog, P1758) are coupled in analogy to Example 1 and provide the title compound as colorless crystals (32 mg; 45%). MS (m/z) ES+: 426 (MH+). Retention time: 2.29 minutes (LC-MS method 3).

EXAMPLE 84

2-(1-Amino-cyclopropylmethyl)-8-(5-methyl-pyridin-3-yl)-4,5-dihydro-1H-pyrrolo[2,3-f]isoquinoline-3-carboxylic acid lactam

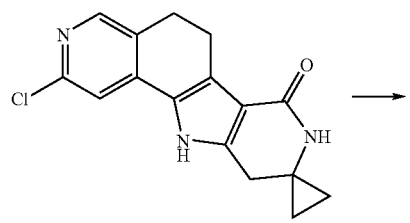

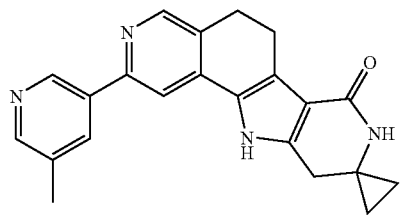

2-(1-Amino-cyclopropylmethyl)-8-chloro-4,5-dihydro-1H-pyrrolo[2,3-f]isoquinoline-3-carboxylic acid lactam (Example 31a) and 5-methylpyridine-3-boronic acid (ABCR Product List, AB175595) are coupled in analogy to Example 1 and provide the title compound as colorless crystals (30 mg; 62%). MS (m/z) ES+: 357 (MH+). Retention time: 1.90 minutes (LC-MS method 3).

EXAMPLE 85

2-(1-Amino-cyclopropylmethyl)-8-(3-fluoro-4-morpholin-4-ylmethyl-phenyl)-4,5-dihydro-1H-pyrrolo[2,3-f]isoquinoline-3-carboxylic acid lactam

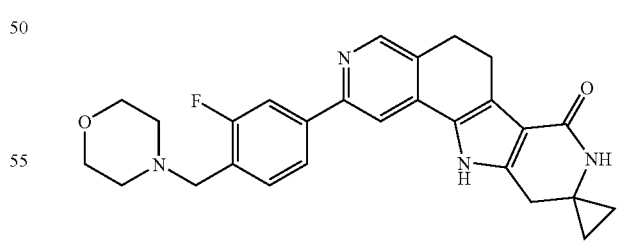

2-(1-Amino-cyclopropylmethyl)-8-chloro-4,5-dihydro-1H-pyrrolo[2,3-f]isoquinoline-3-carboxylic acid lactam (Example 31a) and 3-fluoro-4-(N-morpholinomethyl)phenylboronic acid pinacolester (Boron Molecular, BM632) are coupled in analogy to Example 1 and provide the title compound as colorless crystals (50 mg; 70%). MS (m/z) ES+: 459 (MH+). Retention time: 1.75 minutes (LC-MS method 3).

EXAMPLE 86

2-(1-Amino-cyclopropylmethyl)-8-(6-fluoro-5-methyl-pyridin-3-yl)-4,5-dihydro-1H-pyrrolo[2,3-f]isoquinoline-3-carboxylic acid lactam

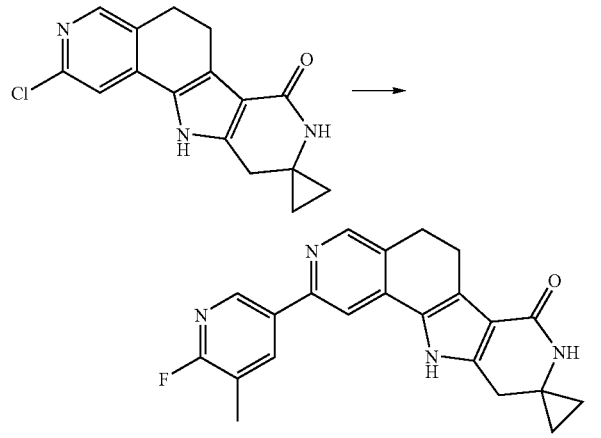

2-(1-Amino-cyclopropylmethyl)-8-chloro-4,5-dihydro-1H-pyrrolo[2,3-f]isoquinoline-3-carboxylic acid lactam (Example 31a) and 2-fluoro-3-methylpyridine-5-boronic acid (Boron Molecular, BM616) are coupled in analogy to Example 1 and provide the title compound as colorless crystals (36 mg; 67%). MS (m/z) ES+: 375 (MH+). Retention time: 2.32 minutes (LC-MS method 3).

EXAMPLE 87

2-(1-Amino-cyclopropylmethyl)-8-(5-methoxy-pyridin-3-yl)-4,5-dihydro-1H-pyrrolo[2,3-f]isoquinoline-3-carboxylic acid lactam

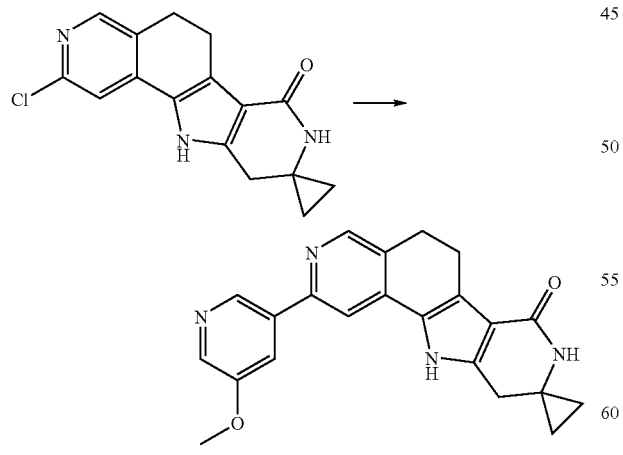

2-(1-Amino-cyclopropylmethyl)-8-chloro-4,5-dihydro-1H-pyrrolo[2,3-f]isoquinoline-3-carboxylic acid lactam (Example 31a) and 5-methoxy-3-pyridineboronic acid pinacol ester (Aldrich, 676624) are coupled in analogy to Example 1 and provide the title compound as colorless crystals (34 mg; 55%). MS (m/z) ES+: 373 (MH+). Retention time: 1.92 minutes (LC-MS method 3).

EXAMPLE 88

2-(1-Amino-cyclopropylmethyl)-8-(6-methoxy-pyridin-3-yl)-4,5-dihydro-1H-pyrrolo[2,3-f]isoquinoline-3-carboxylic acid lactam

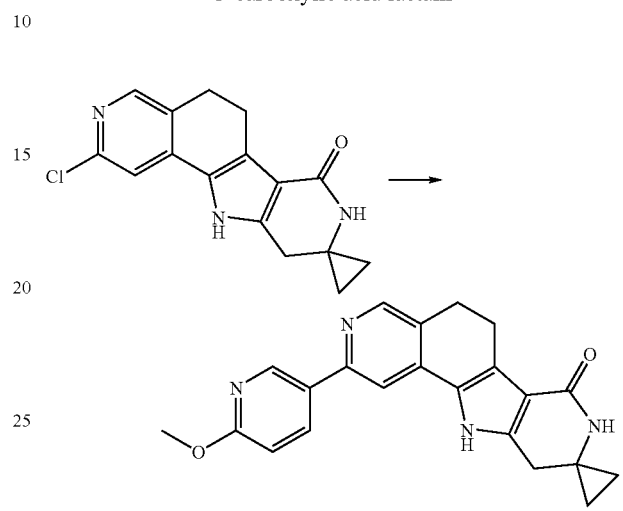

2-(1-Amino-cyclopropylmethyl)-8-chloro-4,5-dihydro-1H-pyrrolo[2,3-f]isoquinoline-3-carboxylic acid lactam (Example 31a) and 2-methoxy-5-pyridineboronic acid (Aldrich, 637610) are coupled in analogy to Example 1 and provide the title compound as colorless crystals (45 mg; 73%). MS (m/z) ES+: 373 (MH+). Retention time: 1.92 minutes (LC-MS method 3).

EXAMPLE 89

2-(1-Amino-cyclopropylmethyl)-8-(5-fluoro-pyridin-3-yl)-4,5-dihydro-1H-pyrrolo[2,3-f]isoquinoline-3-carboxylic acid lactam

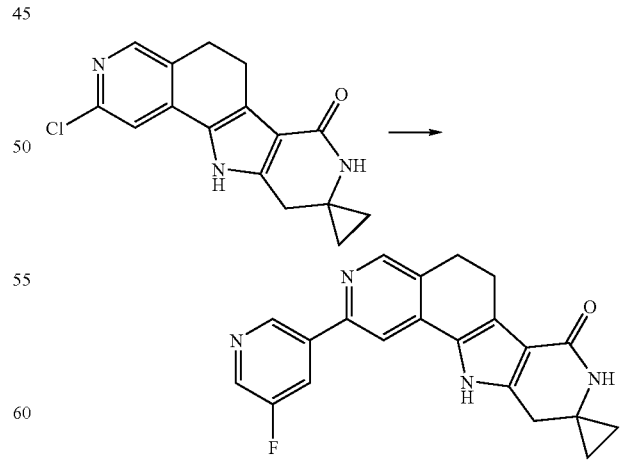

2-(1-Amino-cyclopropylmethyl)-8-chloro-4,5-dihydro-1H-pyrrolo[2,3-f]isoquinoline-3-carboxylic acid lactam (Example 31a) and 3-fluoropyridine-5-boronic acid pinacol ester (Frontier Scientific, F2018) are coupled in analogy to Example 1 and provide the title compound as colorless crystals (33 mg; 59%). MS (m/z) ES+: 361 (MH+). Retention time: 2.18 minutes (LC-MS method 3).

EXAMPLE 90

2-(1-Amino-cyclopropylmethyl)-8-(6-ethoxy-pyridin-3-yl)-4,5-dihydro-1H-pyrrolo[2,3-f]isoquinoline-3-carboxylic acid lactam

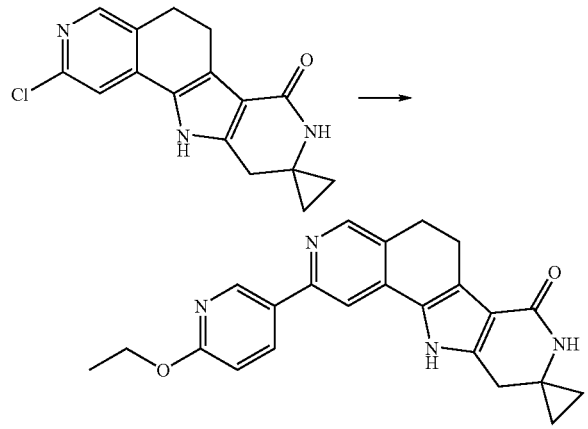

2-(1-Amino-cyclopropylmethyl)-8-chloro-4,5-dihydro-1H-pyrrolo[2,3-f]isoquinoline-3-carboxylic acid lactam (Example 31a) and 6-ethoxypyridine-3-boronic acid (ABCR, AB173053) are coupled in analogy to Example 1 and provide the title compound as colorless crystals (33 mg; 74%). MS (m/z) ES+: 387 (MH+). Retention time: 2.23 minutes (LC-MS method 3).

EXAMPLE 91

2-(1-Amino-cyclopropylmethyl)-8-(6-trifluoromethyl-pyridin-3-yl)-4,5-dihydro-1H-pyrrolo[2,3-f]isoquinoline-3-carboxylic acid lactam

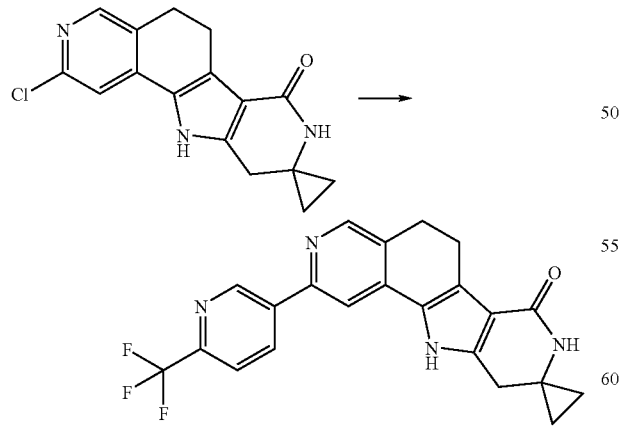

2-(1-Amino-cyclopropylmethyl)-8-chloro-4,5-dihydro-1H-pyrrolo[2,3-f]isoquinoline-3-carboxylic acid lactam (Example 31a) and 2-trifluoromethyl-pyridine-5-boronic acid (Focus Synthesis Product List, FS000599) are coupled in analogy to Example 1 and provide the title compound as colorless crystals (37 mg; 58%). MS (m/z) ES+: 411 (MH+). Retention time: 2.70 minutes (LC-MS method 3).

EXAMPLE 92

2-(1-Amino-cyclopropylmethyl)-8-(2-trifluoromethyl-phenyl)-4,5-dihydro-1H-pyrrolo[2,3-f]isoquinoline-3-carboxylic acid lactam

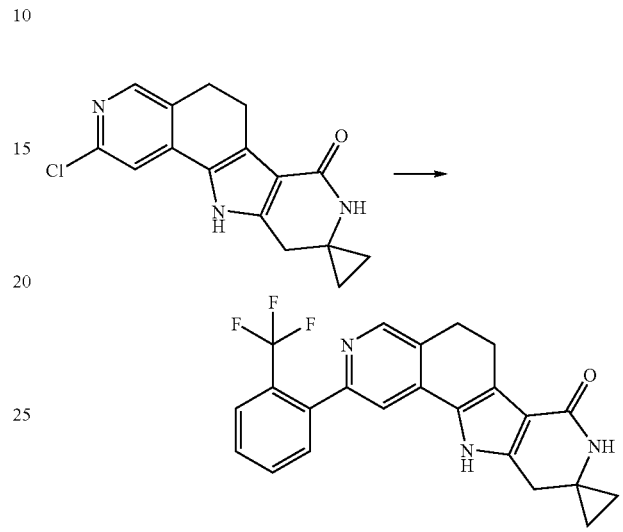

2-(1-Amino-cyclopropylmethyl)-8-chloro-4,5-dihydro-1H-pyrrolo[2,3-f]isoquinoline-3-carboxylic acid lactam (Example 31a) and 2-(trifluoromethyl)phenylboronic acid (Frontier Scientific Catalog, T6300) are coupled in analogy to Example 1 and provide the title compound as colorless crystals (20 mg; 33%). MS (m/z) ES+: 410 (MH+). Retention time: 2.30 minutes (LC-MS method 3).

EXAMPLE 93

2-(1-Amino-cyclopropylmethyl)-8-pyridin-3-yl-4,5-dihydro-1H-pyrrolo[2,3-f]isoquinoline-3-carboxylic acid lactam

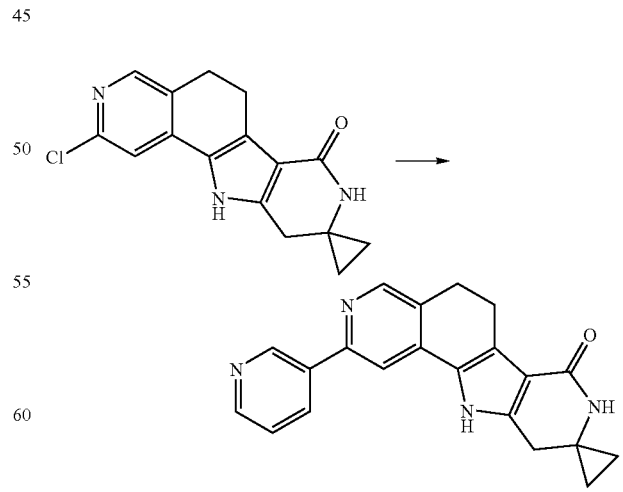

2-(1-Amino-cyclopropylmethyl)-8-chloro-4,5-dihydro-1H-pyrrolo[2,3-f]isoquinoline-3-carboxylic acid lactam (Example 31a) and pyridine-3-boronic acid (ABCR, AB152416)

are coupled in analogy to Example 1 and provide the title compound as colorless crystals (34 mg; 60%).

MS (m/z) ES+: 343 (MH+). Retention time: 1.45 minutes (LC-MS method 2).

EXAMPLE 94

2-(1-Amino-cyclopropylmethyl)-8-[5-(tetrahydro-pyran-4-yloxy)-pyridin-3-yl]-4,5-dihydro-1H-pyrrolo[2,3-f]isoquinoline-3-carboxylic acid lactam

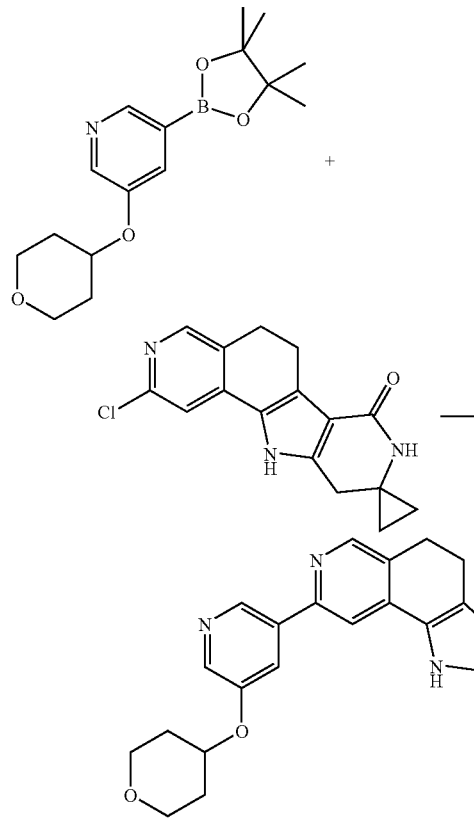

2-(1-Amino-cyclopropylmethyl)-8-chloro-4,5-dihydro-1H-pyrrolo[2,3-f]isoquinoline-3-carboxylic acid lactam (Example 31a) and 3-(tetrahydro-pyran-4-yloxy)-5-(4,4,5,5-tetramethyl-[1,3,2]dioxaborolan-2-yl)-pyridine are coupled in analogy to Example 1 and provide the title compound as colorless crystals (30 mg; 62%). MS (m/z) ES+: 443 (MH+). Retention time: 2.14 minutes (LC-MS method 3).

The starting material is prepared as follows:

EXAMPLE 94A 3-(Tetrahydro-pyran-4-yloxy)-5-(4,4,5,5-tetramethyl-[1,3,2]dioxaborolan-2-yl)-pyridine

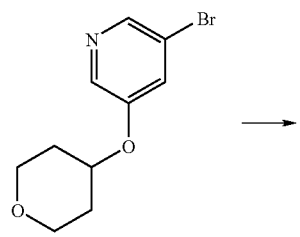

-continued

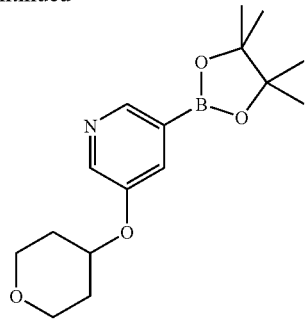

3-Bromo-5-(tetrahydro-pyran-4-yloxy)-pyridine (US 2002058652) is reacted in analogy to Example 1f to yield the title compound as a light-brown resin (292 mg; 95%) used directly in Example 94.

1H-NMR (400 MHz; DMSO-d6): 8.40 (d, 1H); 8.36 (s, 1H); 7.50 (d, 1H); 4.72 (m, 1H); 3.85 (m, 2H); 3.50 (m, 2H); 1.96 (m, 2H); 1.59 (m, 2H); 1.31 (s, 12H). MS (m/z) ES+: 306 (MH+).

EXAMPLE 95

2-(1-Amino-cyclopropylmethyl)-8-[6-(2,4-difluoro-phenoxy)-pyridin-3-yl]-4,5-dihydro-1H-pyrrolo[2,3-f]isoquinoline-3-carboxylic acid lactam

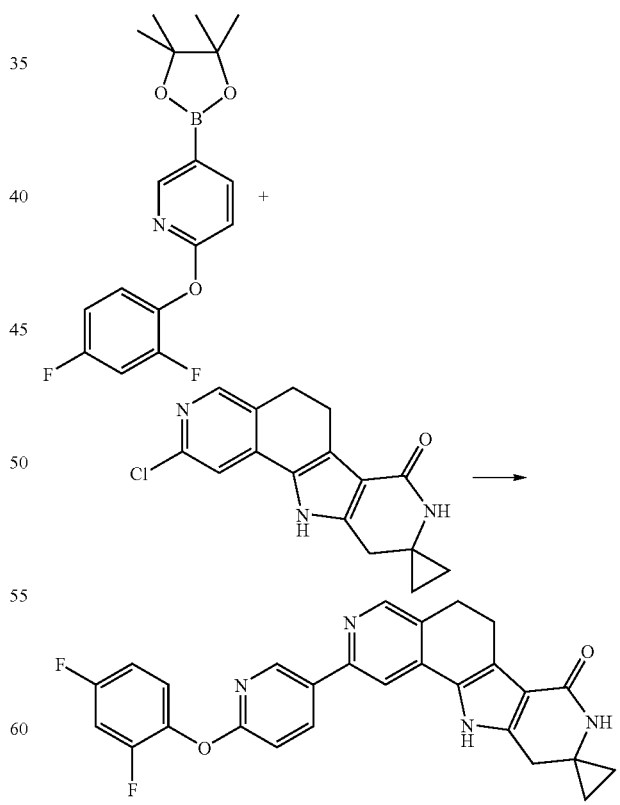

2-(1-Amino-cyclopropylmethyl)-8-chloro-4,5-dihydro-1H-pyrrolo[2,3-f]isoquinoline-3-carboxylic acid lactam (Example 31a) and 2-(2,4-difluoro-phenoxy)-5-(4,4,5,5-tetramethyl-[1,3,2]dioxaborolan-2-yl)-pyridine are coupled in analogy to Example 1 and provide the title compound as colorless crystals (35 mg; 47%). MS (m/z) ES+: 471 (MH+). Retention time: 2.91 minutes (LC-MS method 3).

The starting material is prepared as follows:

EXAMPLE 95A

5-Bromo-2-(2,4-difluoro-phenoxy)-pyridine

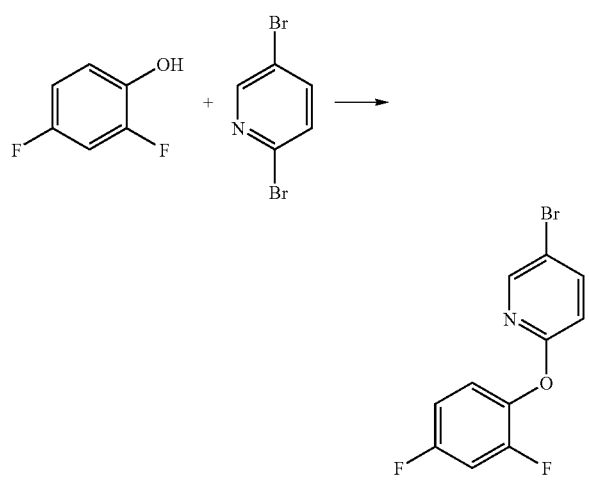

2,5-Dibromopyridine (3.0 g; 12.66 mmol), 2,4-difluorophenol (4.11 g; 31.65 mmol) and $K_2CO_3$ (5.25 g; 38 mmol) in DMF (40 ml) are stirred at 150° C. for 3 hours. The reaction mixture is poured on water and extracted with TBME three times. The combined organic phases are dried over $Na_2SO_4$, filtered, evaporated to dryness and purified via chromatography ($SiO_2$, heptane/TBME 97:3) to yield the title compound as white crystals (3.3 g; 85%). MS (m/z) ES+: 286, 288 (MH+). Retention time: 3.05 minutes (LC-MS method 2).

EXAMPLE 95B 2-(2,4-difluoro-phenoxy)-5-(4,4,5,5-tetramethyl-[1,3,2]dioxaborolan-2-yl)-pyridine

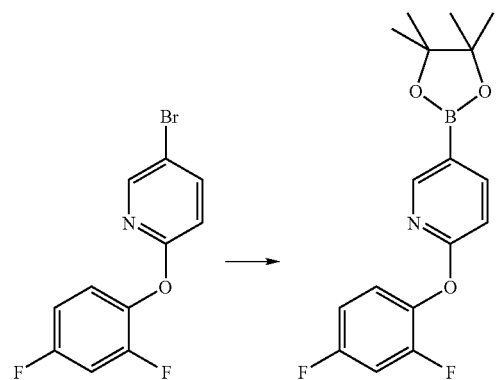

5-Bromo-2-(2,4-difluoro-phenoxy)-pyridine is reacted in analogy to Example 1f and renders the title compound as off-white crystals (1.7 g; 98%). MS (m/z) ES+: 334 (MH+). Retention time: 2.01 minutes (LC-MS method 2).

EXAMPLE 96

2-(1-Amino-cyclopropylmethyl)-8-[6-(tetrahydro-pyran-4-yloxy)-pyridin-3-yl]-4,5-dihydro-1H-pyrrolo[2,3-f]isoquinoline-3-carboxylic acid lactam

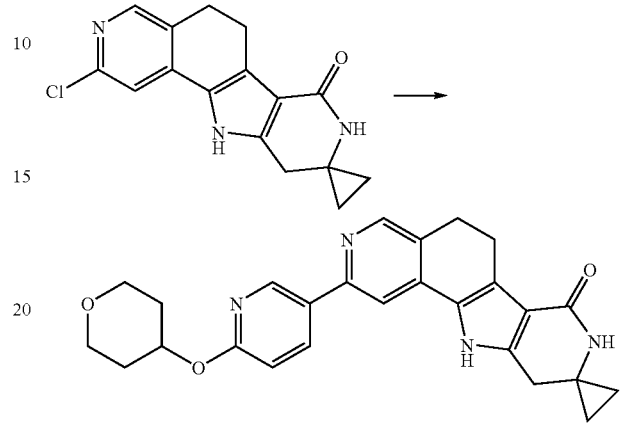

2-(1-Amino-cyclopropylmethyl)-8-chloro-4,5-dihydro-1H-pyrrolo[2,3-f]isoquinoline-3-carboxylic acid lactam (Example 31a) and 2-(tetrahydropyran-4-yloxy)-5-(4,4,5,5-tetramethyl-1,3,2-dioxaborolan-2-yl)pyridine (Maybridge Building Blocks, CC 58339) are coupled in analogy to Example 1 and provide the title compound as colorless crystals (50 mg; 47%). MS (m/z) ES+: 443 (MH+). Retention time: 2.19 minutes (LC-MS method 3).

EXAMPLE 97

2-(1-Amino-cyclobutylmethyl)-8-[4-(4-methyl-piperazin-1-ylmethyl)-phenyl]-4,5-dihydro-1H-pyrrolo[2,3-f]isoquinoline-3-carboxylic acid

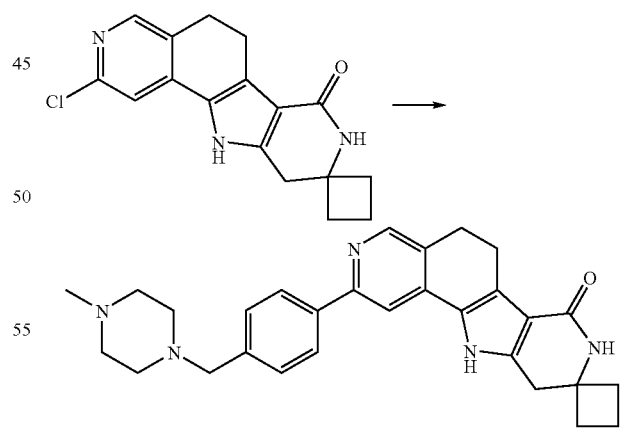

2-(1-Amino-cyclobutylmethyl)-8-chloro-4,5-dihydro-1H-pyrrolo[2,3-f]isoquinoline-3-carboxylic acid lactam (Example 36.a) and 1-methyl-4-[4-(4,4,5,5-tetramethyl-[1,3,2]dioxaborolan-2-yl)-benzyl]-piper-azine (Intermediate J) are coupled in analogy to Example 1 and provide the title compound as colorless crystals (49 mg; 69%). MS (m/z) ES+: 468 (MH+). Retention time: 1.29 minutes (LC-MS method 2).

EXAMPLE 98

2-(1-Amino-cyclobutylmethyl)-8-(6-dimethylamino-pyridin-3-yl-4,5-dihydro-1H-pyrrolo[2,3-f]isoquinoline-3-carboxylic acid lactam

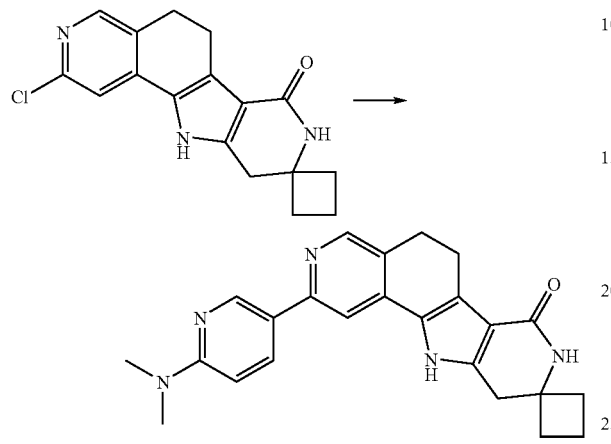

2-(1-Amino-cyclobutylmethyl)-8-chloro-4,5-dihydro-1H-pyrrolo[2,3-f]isoquinoline-3-carboxylic acid lactam (Example 36.a) and 2-(dimethylamino)pyridine-5-boronic acid (Frontier Scientific, D9115) are coupled in analogy to Example 1 and provide the title compound as colorless crystals (30 mg; 50%). MS (m/z) ES+: 400 (MH+). Retention time: 1.67 minutes (LC-MS method 2).

EXAMPLE 99

2-(1-Amino-cyclobutylmethyl)-8-(5-methoxy-pyridin-3-yl)-4,5-dihydro-1H-pyrrolo[2,3-f]isoquinoline-3-carboxylic acid lactam

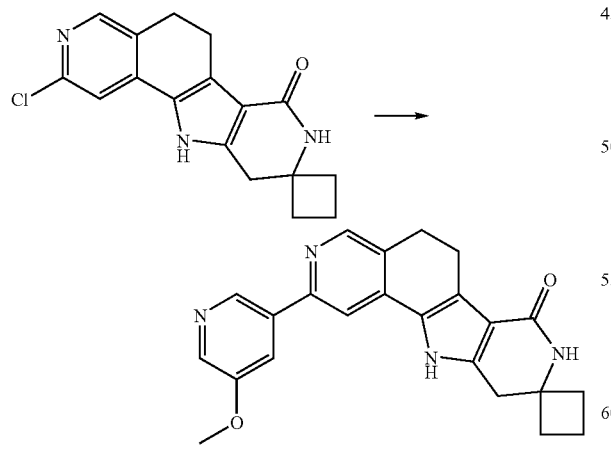

2-(1-Amino-cyclobutylmethyl)-8-chloro-4,5-dihydro-1H-pyrrolo[2,3-f]isoquinoline-3-carboxylic acid lactam (Example 36.a) and 5-methoxy-3-pyridineboronic acid pinacol ester (Aldrich, 676624) are coupled in analogy to Example 1 and provide the title compound as colorless crystals (29 mg; 52%). MS (m/z) ES+: 387 (MH+). Retention time: 1.81 minutes (LC-MS method 2).

EXAMPLE 100

2-(1-Amino-cyclobutylmethyl)-8-(6-fluoro-pyridin-3-yl)-4,5-dihydro-1H-pyrrolo[2,3-f]isoquinoline-3-carboxylic acid lactam

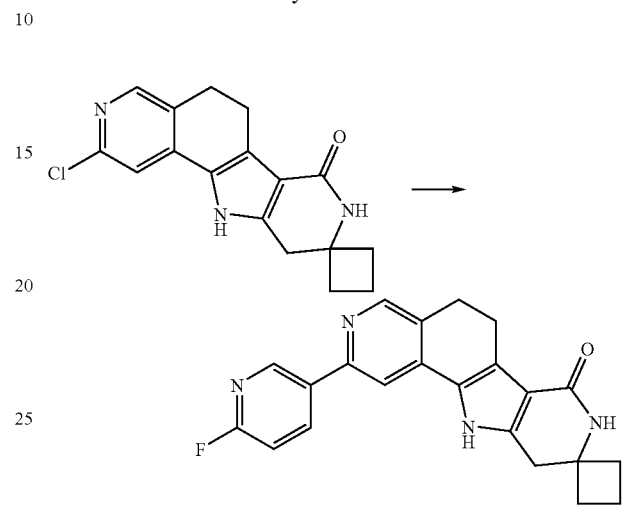

2-(1-Amino-cyclobutylmethyl)-8-chloro-4,5-dihydro-1H-pyrrolo[2,3-f]isoquinoline-3-carboxylic acid lactam (Example 36.a) and 2-fluoropyridine-5-boronic acid (ABCR, AB181129) are coupled in analogy to Example 1 and provide the title compound as colorless crystals (28 mg; 53%). MS (m/z) ES+: 375 (MH+). Retention time: 1.94 minutes (LC-MS method 2).

EXAMPLE 101

2-(1-Amino-cyclobutylmethyl)-8-(6-amino-pyridin-3-yl)-4,5-dihydro-1H-pyrrolo[2,3-f]isoquinoline-3-carboxylic acid lactam

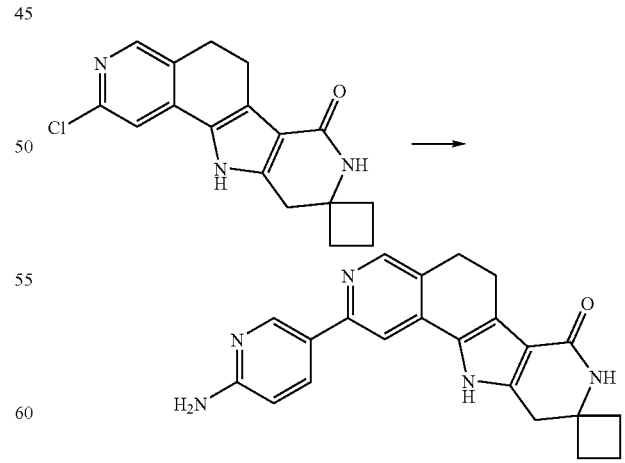

2-(1-Amino-cyclobutylmethyl)-8-chloro-4,5-dihydro-1H-pyrrolo[2,3-f]isoquinoline-3-carboxylic acid lactam (Example 36.a) and 2-aminopyridine-5-boronic acid, pinacol ester (ABCR Product List AB173868) are coupled in analogy to Example 1 and provide the title compound as colorless crystals (41 mg; 48%). MS (m/z) ES+: 372 (MH+). Retention time: 1.37 minutes (LC-MS method 2).

EXAMPLE 102

2-(1-Amino-cyclobutylmethyl)-8-(5-methyl-pyridin-3-yl)-4,5-dihydro-1H-pyrrolo[2,3-f]isoquinoline-3-carboxylic acid lactam

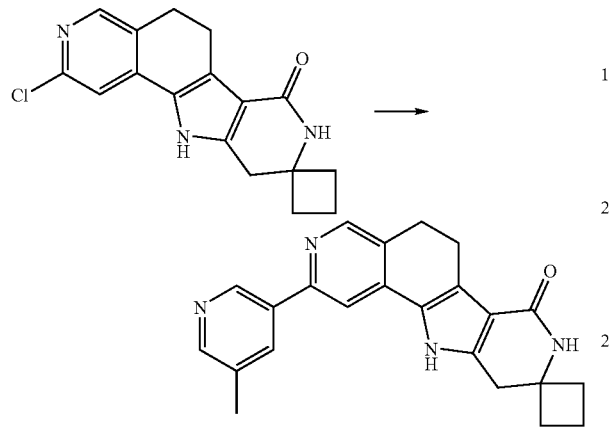

2-(1-Amino-cyclobutylmethyl)-8-chloro-4,5-dihydro-1H-pyrrolo[2,3-f]isoquinoline-3-carboxylic acid lactam (Example 36.a) and 5-methylpyridine-3-boronic acid (ABCR Product List, AB175595) are coupled in analogy to Example 1 and provide the title compound as colorless crystals (73 mg; 79%). MS (m/z) ES+: 371 (MH+). Retention time: 1.76 minutes (LC-MS method 2).

EXAMPLE 103

2-(1-Amino-cyclobutylmethyl)-8-(6-methyl-pyridin-3-yl)-4,5-dihydro-1H-pyrrolo[2,3-f]isoquinoline-3-carboxylic acid lactam

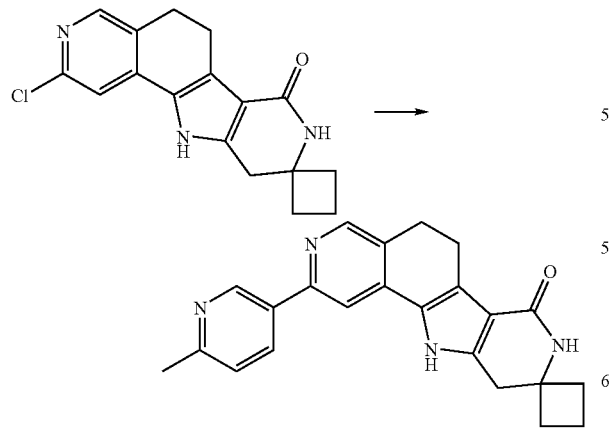

2-(1-Amino-cyclobutylmethyl)-8-chloro-4,5-dihydro-1H-pyrrolo[2,3-f]isoquinoline-3-carboxylic acid lactam (Example 36.a) and 6-methylpyridine-3-boronic acid (SYN-CHEM OHG, un119) are coupled in analogy to Example 1 and provide the title compound as colorless crystals (45 mg; 51%). MS (m/z) ES+: 371 (MH+). Retention time: 1.65 minutes (LC-MS method 2).

EXAMPLE 104

2-(1-Amino-cyclobutylmethyl)-8-pyridin-3-yl-4,5-dihydro-1H-pyrrolo[2,3-f]isoquinoline-3-carboxylic acid lactam

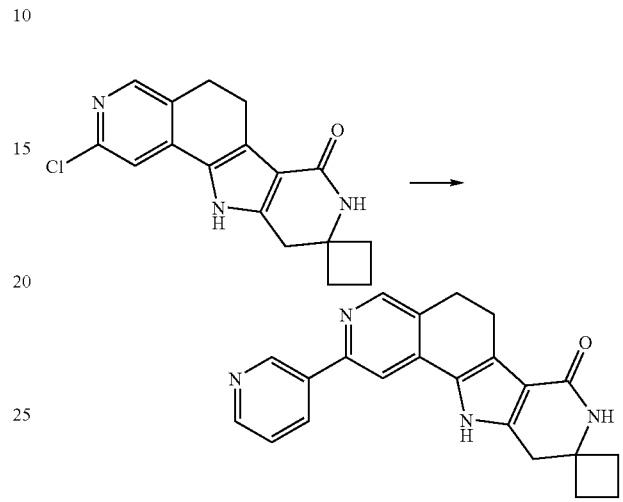

2-(1-Amino-cyclobutylmethyl)-8-chloro-4,5-dihydro-1H-pyrrolo[2,3-f]isoquinoline-3-carboxylic acid lactam (Example 36.a) and pyridine-3-boronic acid (ABCR, AB152416) are coupled in analogy to Example 1 and provide the title compound as colorless crystals (65 mg; 75%).

MS (m/z) ES+: 357 (MH+). Retention time: 1.63 minutes (LC-MS method 2).

EXAMPLE 105

2-(1-Amino-cyclobutylmethyl)-8-(5-cyano-pyridin-3-yl)-4,5-dihydro-1H-pyrrolo[2,3-f]isoquinoline-3-carboxylic acid lactam

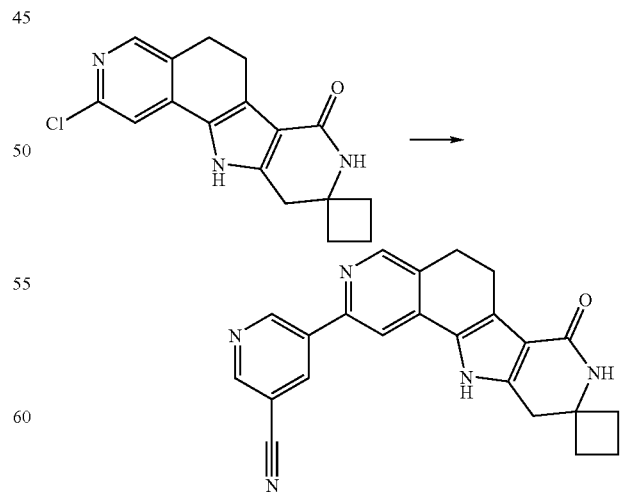

2-(1-Amino-cyclobutylmethyl)-8-chloro-4,5-dihydro-1H-pyrrolo[2,3-f]isoquinoline-3-carboxylic acid lactam (Example 36.a) and (5-cyanopyridin-3-yl)boronic acid (Anichem P20027) are coupled in analogy to Example 1 and provide the title compound as colorless crystals (77 mg; 48%). MS (m/z) ES+: 382 (MH+). Retention time: 2.35 minutes (LC-MS method 3).

EXAMPLE 106

2-(1-Amino-cyclobutylmethyl)-8-(6-cyano-pyridin-3-yl)-4,5-dihydro-1H-pyrrolo[2,3-f]isoquinoline-3-carboxylic acid lactam

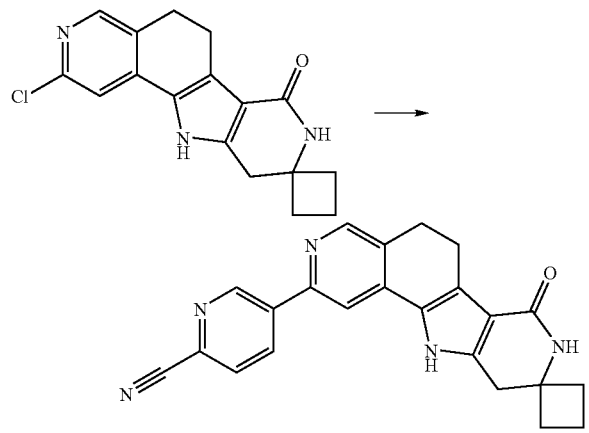

2-(1-Amino-cyclobutylmethyl)-8-chloro-4,5-dihydro-1H-pyrrolo[2,3-f]isoquinoline-3-carboxylic acid lactam (Example 36.a) and 2-cyanopyridine-5-boronic acid (SYNCHEM OHG Product List, un119) are coupled in analogy to Example 1 and provide the title compound as colorless crystals (46 mg; 48%). MS (m/z) ES+: 382 (MH+). Retention time: 2.12 minutes (LC-MS method 2).

EXAMPLE 107

2-(1-Amino-cyclobutylmethyl)-8-[3-methoxy-4-(2-methoxy-ethoxy)-phenyl]-4,5-dihydro-1H-pyrrolo[2,3-f]isoquinoline-3-carboxylic acid lactam

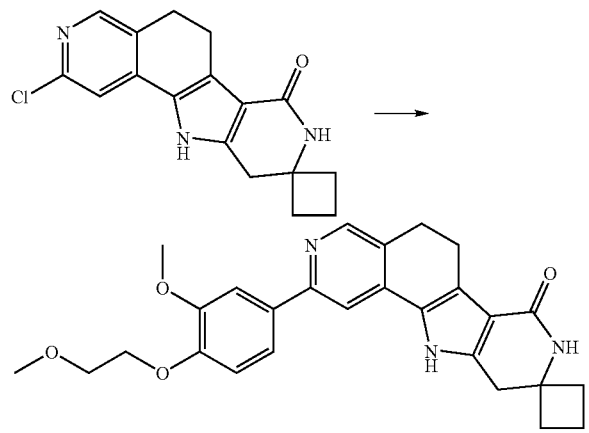

2-(1-Amino-cyclobutylmethyl)-8-chloro-4,5-dihydro-1H-pyrrolo[2,3-f]isoquinoline-3-carboxylic acid lactam (Example 36.a) and 2-[3-methoxy-4-(2-methoxy-ethoxy)-phenyl]-4,4,5,5-tetramethyl-[1,3,2]dioxaborolane (Example 79a) are coupled in analogy to Example 1 and provide the title compound as colorless crystals (37 mg; 62%). MS (m/z) ES+: 460 (MH+). Retention time: 2.12 minutes (LC-MS method 3).

EXAMPLE 108

2-(1-Amino-cyclobutylmethyl)-8-[6-(tetrahydro-pyran-4-yloxy)-pyridin-3-yl]-4,5-dihydro-1H-pyrrolo[2,3-f]isoquinoline-3-carboxylic acid lactam

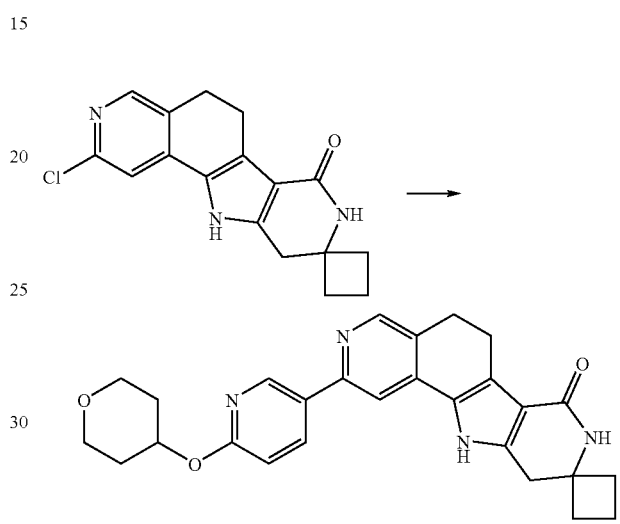

2-(1-Amino-cyclobutylmethyl)-8-chloro-4,5-dihydro-1H-pyrrolo[2,3-f]isoquinoline-3-carboxylic acid lactam (Example 36.a) and 2-(tetrahydropyran-4-yloxy)-5-(4,4,5,5-tetramethyl-1,3,2-dioxaborolan-2-yl)pyridine (Maybridge Building Blocks, CC 58339) are coupled in analogy to Example 1 and provide the title compound as colorless crystals (51 mg; 73%). MS (m/z) ES+: 457 (MH+). Retention time: 2.36 minutes (LC-MS method 3).

EXAMPLE 109

2-(1-Amino-cyclobutylmethyl)-8-[5-(tetrahydro-pyran-4-yloxy)-pyridin-3-yl]-4,5-dihydro-1H-pyrrolo[2,3-f]isoquinoline-3-carboxylic acid lactam

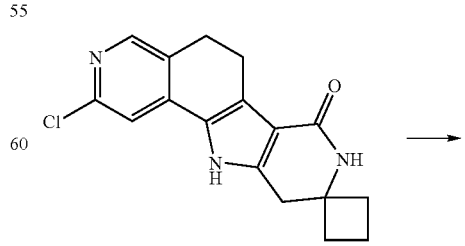

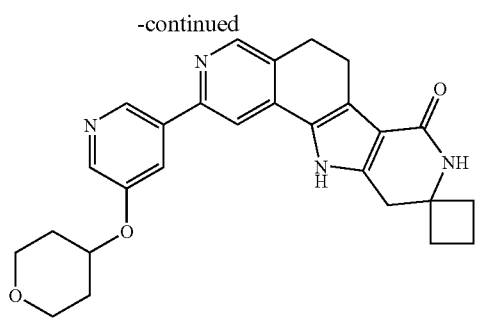

2-(1-Amino-cyclobutylmethyl)-8-chloro-4,5-dihydro-1H-pyrrolo[2,3-f]isoquinoline-3-carboxylic acid lactam (Example 36.a) and 3-(tetrahydropyran-4-yloxy)-5-(4,4,5,5-tetramethyl-1,3,2-dioxaborolan-2-yl)pyridine (Example 94a) are coupled in analogy to Example 1 and provide the title compound as colorless crystals (35 mg; 74%). MS (m/z) ES+: 457 (MH+). Retention time: 2.30 minutes (LC-MS method 3).

EXAMPLE 110

2-(1-Amino-cyclobutylmethyl)-8-(3-fluoro-4-morpholin-4-ylmethyl-phenyl)-4,5-dihydro-1H-pyrrolo[2,3-f]isoquinoline-3-carboxylic acid lactam

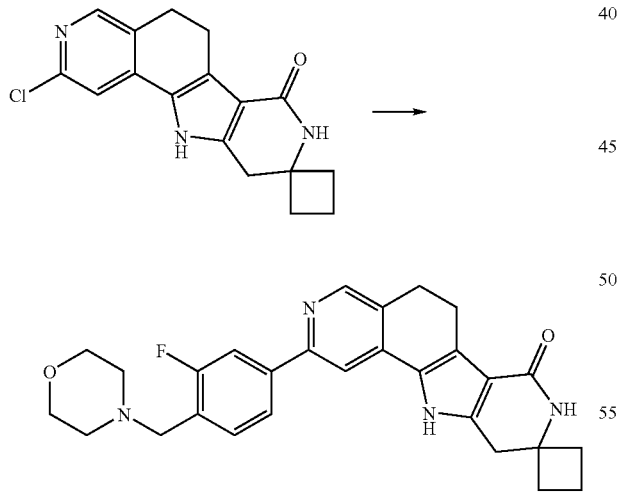

2-(1-Amino-cyclobutylmethyl)-8-chloro-4,5-dihydro-1H-pyrrolo[2,3-f]isoquinoline-3-carboxylic acid lactam (Example 36.a) and 3-fluoro-4-(N-morpholinomethyl)phenylboronic acid pinacolester (Boron Molecular, BM632) are coupled in analogy to Example 1 and provide the title compound as colorless crystals (48 mg; 65%). MS (m/z) ES+: 473 (MH+). Retention time: 1.90 minutes (LC-MS method 3).

EXAMPLE 111

2-(1-Aminomethyl-cyclopropyl)-8-(6-methyl-pyridin-3-yl)-4,5-dihydro-1H-pyrrolo[2,3-f]isoquinoline-3-carboxylic acid lactam

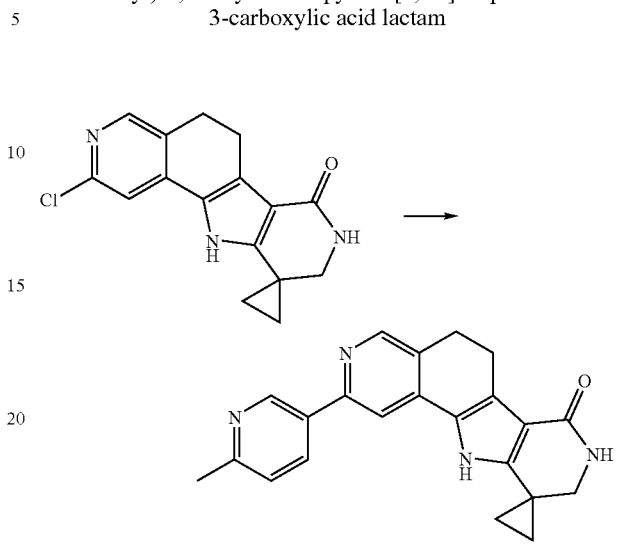

2-(1-Aminomethyl-cyclopropyl)-8-chloro-4,5-dihydro-1H-pyrrolo[2,3-f]isoquinoline-3-carboxylic acid lactam (Example 1d) and 6-methylpyridine-3-boronic acid (SYN-CHEM OHG, un119) are coupled in analogy to Example 1 and provide the title compound as colorless crystals (46 mg; 59%). MS (m/z) ES+: 357 (MH+). Retention time: 1.49 minutes (LC-MS method 2).

EXAMPLE 112

2-(1-Aminomethyl-cyclopropyl)-8-(5-fluoro-pyridin-3-yl)-4,5-dihydro-1H-pyrrolo[2,3-f]isoquinoline-3-carboxylic acid lactam

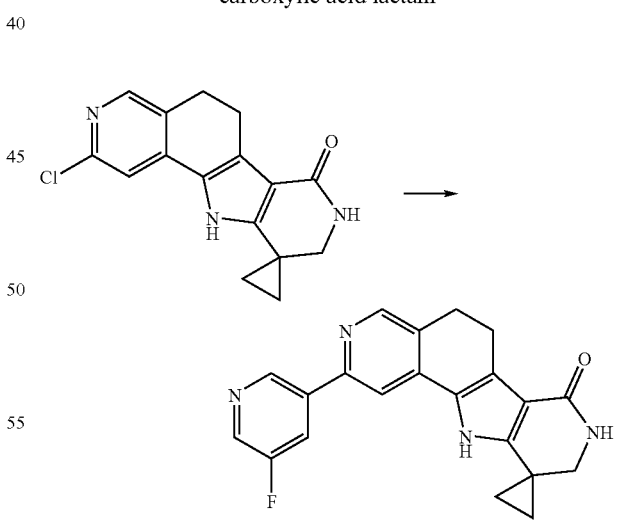

2-(1-Aminomethyl-cyclopropyl)-8-chloro-4,5-dihydro-1H-pyrrolo[2,3-f]isoquinoline-3-carboxylic acid lactam (Example 1d) and 3-fluoropyridine-5-boronic acid pinacol ester (Frontier Scientific, F2018) are coupled in analogy to Example 1 and provide the title compound as colorless crystals (24 mg; 57%). MS (m/z) ES+: 361 (MH+). Retention time: 1.88 minutes (LC-MS method 3).

EXAMPLE 113

2-(1-Aminomethyl-cyclopropyl)-8-(5-cyano-pyridin-3-yl)-4,5-dihydro-1H-pyrrolo[2,3-f]isoquinoline-3-carboxylic acid lactam

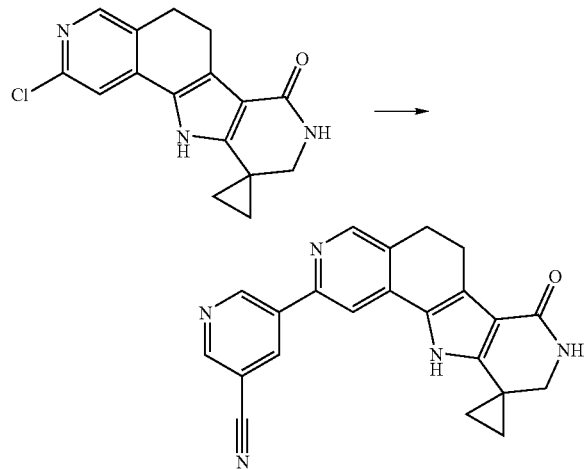

2-(1-Aminomethyl-cyclopropyl)-8-chloro-4,5-dihydro-1H-pyrrolo[2,3-f]isoquinoline-3-carboxylic acid lactam (Example 1d) and (5-cyanopyridin-3-yl)boronic acid (Anichem P20027) are coupled in analogy to Example 1 and provide the title compound as colorless crystals (33 mg; 57%). MS (m/z) ES+: 368(MH+). Retention time: 1.90 minutes (LC-MS method 2).

EXAMPLE 114

2-(1-Aminomethyl-cyclopropyl)-8-(2,3-dihydro-benzo[1,4]dioxin-6-yl)-4,5-dihydro-1H-pyrrolo[2,3-f]isoquinoline-3-carboxylic acid

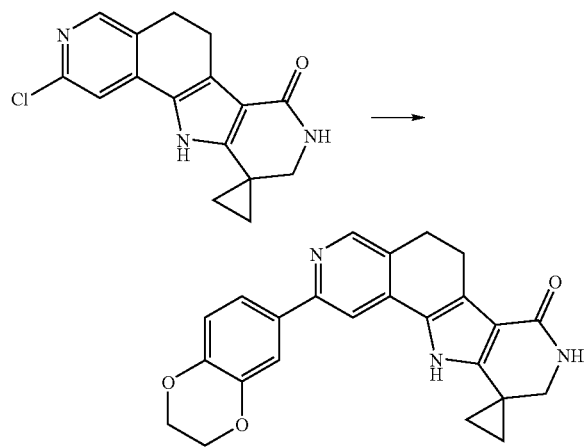

2-(1-Aminomethyl-cyclopropyl)-8-chloro-4,5-dihydro-1H-pyrrolo[2,3-f]isoquinoline-3-carboxylic acid lactam (Example 1d) and 1,4-benzodioxane-6-boronic acid (Aldrich, 635995) are coupled in analogy to Example 1 and provide the title compound as colorless crystals (16 mg; 35%). MS (m/z) ES+: 400 (MH+). Retention time: 1.65 minutes (LC-MS method 2).

EXAMPLE 115

2-(1-Aminomethyl-cyclopropyl)-8-(3-cyano-4-fluoro-phenyl)-4,5-dihydro-1H-pyrrolo[2,3-f]isoquinoline-3-carboxylic acid

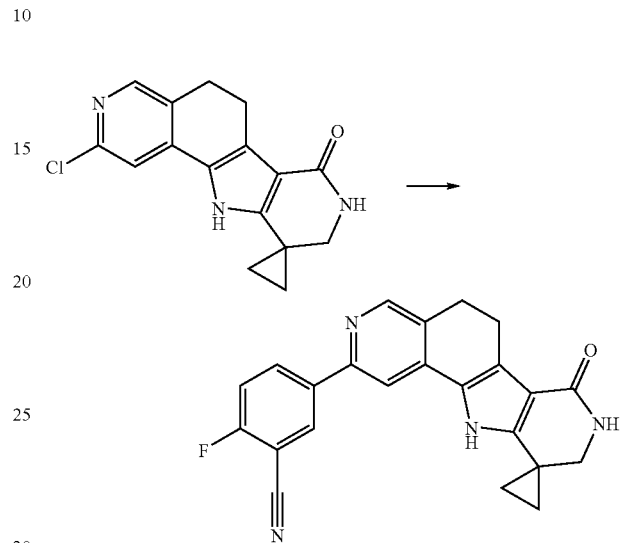

2-(1-Aminomethyl-cyclopropyl)-8-chloro-4,5-dihydro-1H-pyrrolo[2,3-f]isoquinoline-3-carboxylic acid lactam (Example 1d) and 3-cyano-4-fluorophenylboronic acid (ABCR, AB173953) are coupled in analogy to Example 1 and provide the title compound as colorless crystals (44 mg; 81%). MS (m/z) ES+: 385 (MH+). Retention time: 2.21 minutes (LC-MS method 2).

EXAMPLE 116

2-(1-Aminomethyl-cyclopropyl)-8-(6-fluoro-pyridin-3-yl)-4,5-dihydro-1H-pyrrolo[2,3-f]isoquinoline-3-carboxylic acid

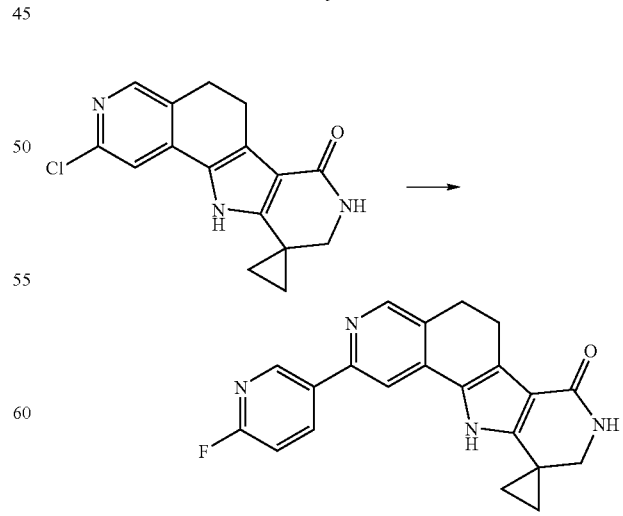

2-(1-Aminomethyl-cyclopropyl)-8-chloro-4,5-dihydro-1H-pyrrolo[2,3-f]isoquinoline-3-carboxylic acid lactam (Example 1d) and 2-fluoropyridine-5-boronic acid (ABCR, AB181129) are coupled in analogy to Example 1 and provide the title compound as colorless crystals (39 mg; 81%). MS (m/z) ES+: 361 (MH+). Retention time: 1.76 minutes (LC-MS method 2).

EXAMPLE 117

2-(1-Aminomethyl-cyclopropyl)-8-(6-dimethylamino-pyridin-3-yl)-4,5-dihydro-1H-pyrrolo[2,3-f]isoquinoline-3-carboxylic acid

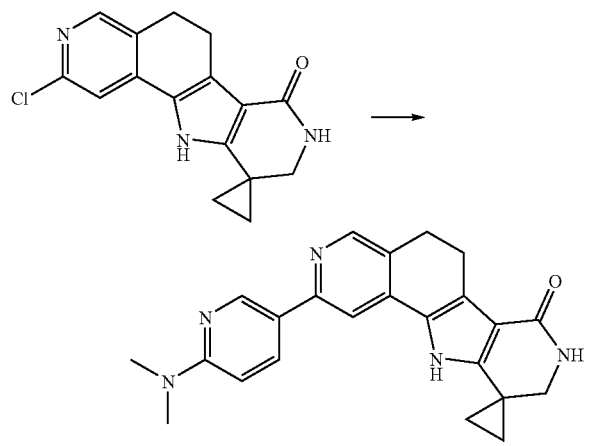

2-(1-Aminomethyl-cyclopropyl)-8-chloro-4,5-dihydro-1H-pyrrolo[2,3-f]isoquinoline-3-carboxylic acid lactam (Example 1d) and 2-dimethylaminopyridine-5-boronic acid (Frontier Scientific, D9115) are coupled in analogy to Example 1 and provide the title compound as colorless crystals (30 mg; 94%). MS (m/z) ES+: 386 (MH+). Retention time: 1.56 minutes (LC-MS method 2).

EXAMPLE 118

8-[4-(3-Amino-3-methyl-butyl)-phenyl]-2-(1-aminomethyl-cyclopropyl)-4,5-dihydro-1H-pyrrolo[2,3-f]isoquinoline-3-carboxylic acid lactam

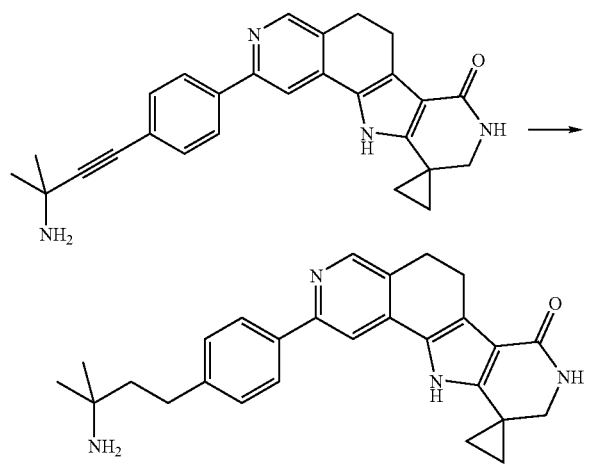

8-[4-(3-Amino-3-methyl-but-1-ynyl)-phenyl]-2-(1-aminomethyl-cyclopropyl)-4,5-dihydro-1H-pyrrolo[2,3-f]isoquinoline-3-carboxylic acid lactam (Example 121) is treated in analogy to Example 78 and delivered the title compound as colorless crystals (17 mg; 50%). MS (m/z) ES+: 427 (MH+). Retention time: 1.32 minutes (LC-MS method 2).

EXAMPLE 119

2-(1-Aminomethyl-cyclopropyl)-8-[4-(3-hydroxy-3-methyl-butyl)-phenyl]-4,5-dihydro-1H-pyrrolo[2,3-f]isoquinoline-3-carboxylic acid lactam

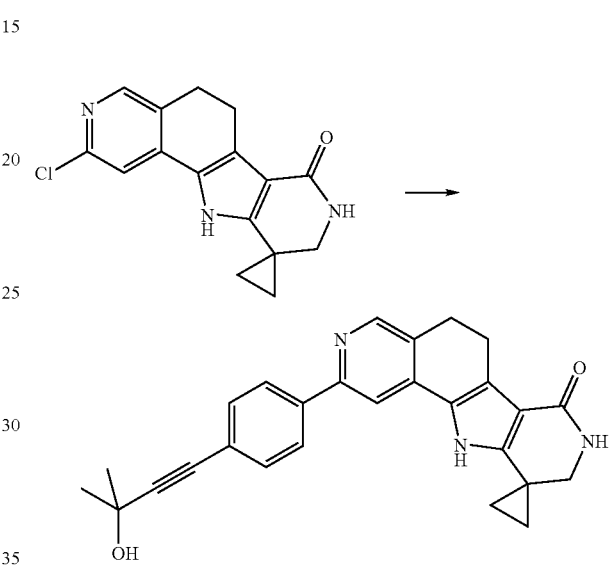

2-(1-Aminomethyl-cyclopropyl)-8-chloro-4,5-dihydro-1H-pyrrolo[2,3-f]isoquinoline-3-carboxylic acid lactam (Example 1d) and 2-methyl-4-[4-(4,4,5,5-tetramethyl-[1,3,2]dioxaborolan-2-yl)-phenyl]-but-3-yn-2-ol (Intermediate L) are coupled in analogy to Example 1 and provide the title compound as colorless crystals (5 mg; 58%). MS (m/z) ES+: 424 (MH+). Retention time: 1.89 minutes (LC-MS method 2).

EXAMPLE 120

2-(1-Aminomethyl-cyclopropyl)-8-(3-ethynyl-4-methoxy-phenyl)-4,5-dihydro-1H-pyrrolo[2,3-f]isoquinoline-3-carboxylic acid lactam

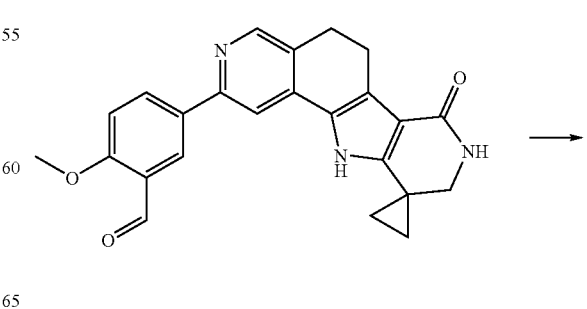

-continued

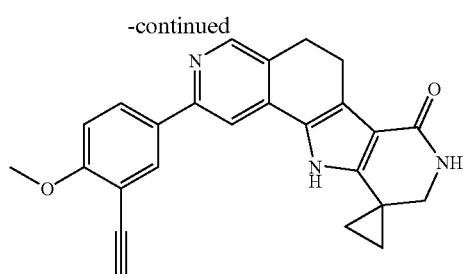

2-(1-Aminomethyl-cyclopropyl)-8-(3-formyl-4-methoxy-phenyl)-4,5-dihydro-1H-pyrrolo[2,3-f]isoquinoline-3-carboxylic acid lactam (Example 122) is treated in analogy to Example 75 and yield the title compound as colorless crystals (24 mg; 74%). MS (m/z) ES+: 396 (MH+). Retention time: 1.85 minutes (LC-MS method 2).

EXAMPLE 121

8-[4-(3-Amino-3-methyl-but-1-ynyl)-phenyl]-2-(1-aminomethyl-cyclopropyl)-4,5-dihydro-1H-pyrrolo[2,3-f]isoquinoline-3-carboxylic acid lactam

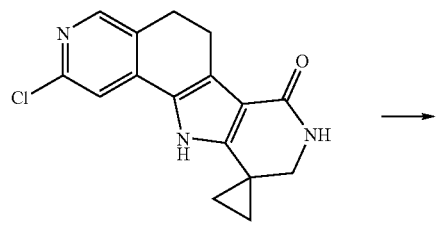

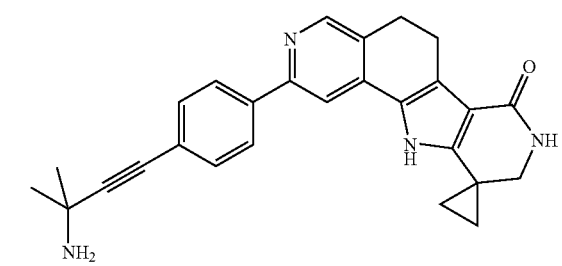

2-(1-Aminomethyl-cyclopropyl)-8-chloro-4,5-dihydro-1H-pyrrolo[2,3-f]isoquinoline-3-carboxylic acid lactam (Example 1d) and 1,1-Dimethyl-3-[4-(4,4,5,5-tetramethyl-[1,3,2]dioxaborolan-2-yl)-phenyl]-prop-2-ynylamine (Intermediate A) are coupled in analogy to Example 1 and provide the title compound as colorless crystals (21 mg; 58%). MS (m/z) ES+: 423 (MH+). Retention time: 1.44 minutes (LC-MS method 2).

EXAMPLE 122

2-(1-Aminomethyl-cyclopropyl)-8-(3-formyl-4-methoxy-phenyl)-4,5-dihydro-1H-pyrrolo[2,3-f]isoquinoline-3-carboxylic acid lactam

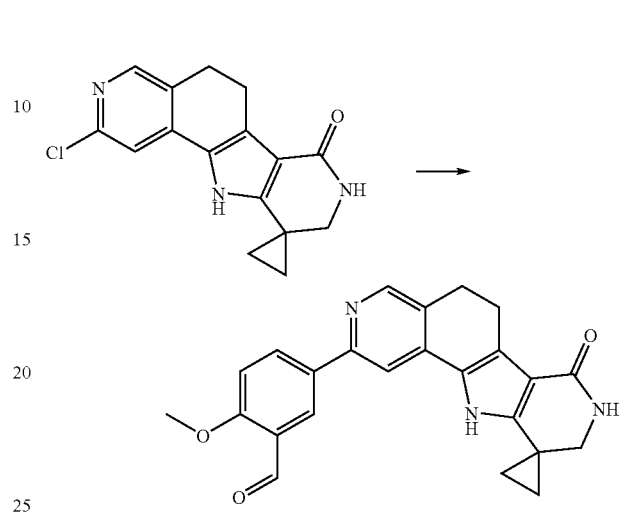

2-(1-Aminomethyl-cyclopropyl)-8-chloro-4,5-dihydro-1H-pyrrolo[2,3-f]isoquinoline-3-carboxylic acid lactam (Example 1d) and 3-formyl-4-methoxyphenyl-boronic acid (ABCR, AB150374) are coupled in analogy to Example 1 and provide the title compound as colorless crystals (45 mg; 70%). MS (m/z) ES+: 400 (MH+). Retention time: 1.78 minutes (LC-MS method 2).

EXAMPLE 123

2-(1-Aminomethyl-cyclopropyl)-8-pyrimidin-5-yl-4,5-dihydro-1H-pyrrolo[2,3f]isoquinoline-3-carboxylic acid lactam

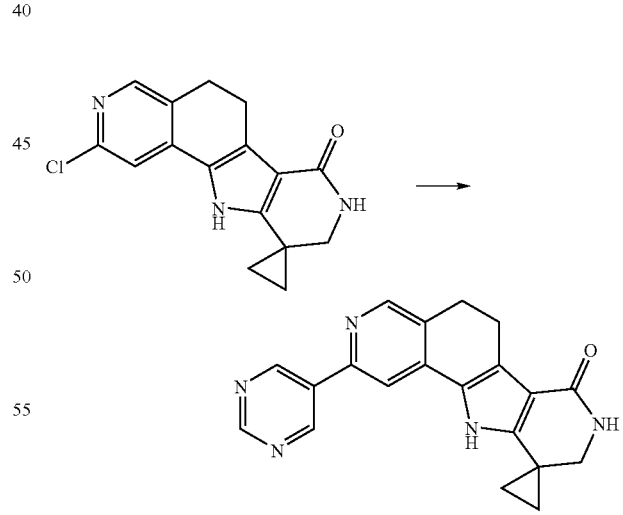

2-(1-Aminomethyl-cyclopropyl)-8-chloro-4,5-dihydro-1H-pyrrolo[2,3-f]isoquinoline-3-carboxylic acid lactam (Example 1d) and 5-pyrimidinylboronic acid (Maybridge Building Blocks, CC 07412) are coupled in analogy to Example 1 and provide the title compound as colorless crystals (35 mg; 77%). MS (m/z) ES+: 344 (MH+). Retention time: 1.54 minutes (LC-MS method 2).

EXAMPLE 124

2-(1-Aminomethyl-cyclopropyl)-8-pyridin-4-yl-4,5-dihydro-1H-pyrrolo[2,3-f]isoquinoline-3-carboxylic acid lactam

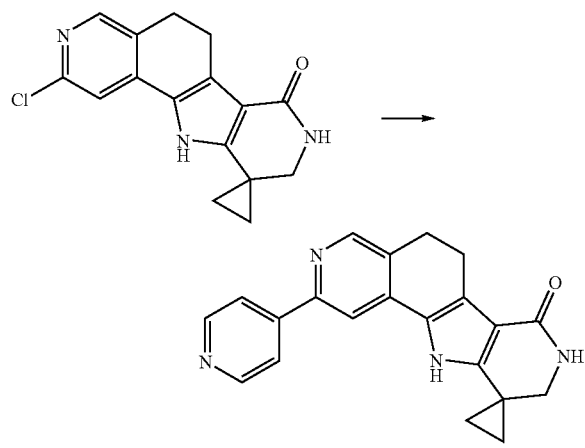

2-(1-Aminomethyl-cyclopropyl)-8-chloro-4,5-dihydro-1H-pyrrolo[2,3-f]isoquinoline-3-carboxylic acid lactam (Example 1d) and pyridin-4-ylboronic acid (Maybridge Building Blocks, CC 04212) are coupled in analogy to Example 1 and provide the title compound as colorless crystals (31 mg; 67%). MS (m/z) ES+: 343 (MH+). Retention time: 1.47 minutes (LC-MS method 2).

EXAMPLE 125

2-(1-Aminomethyl-cyclopropyl)-8-pyridin-3-yl-4,5-dihydro-1H-pyrrolo[2,3-f]isoquinoline-3-carboxylic acid lactam

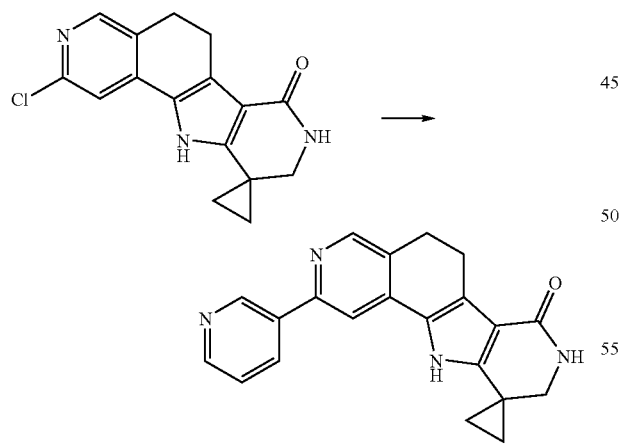

2-(1-Aminomethyl-cyclopropyl)-8-chloro-4,5-dihydro-1H-pyrrolo[2,3-f]isoquinoline-3-carboxylic acid lactam (Example 1d) and pyridine-3-boronic acid (ABCR, AB152416) are coupled in analogy to Example 1 and provide the title compound as colorless crystals (44 mg; 67%).

MS (m/z) ES+: 343 (MH+). Retention time: 1.25 minutes (LC-MS method 2).

EXAMPLE 126

2-(1-Aminomethyl-cyclopropyl)-8-[4-(3-hydroxy-3-methyl-butyl)-phenyl]-4,5-dihydro-1H-pyrrolo[2,3-f]isoquinoline-3-carboxylic acid lactam

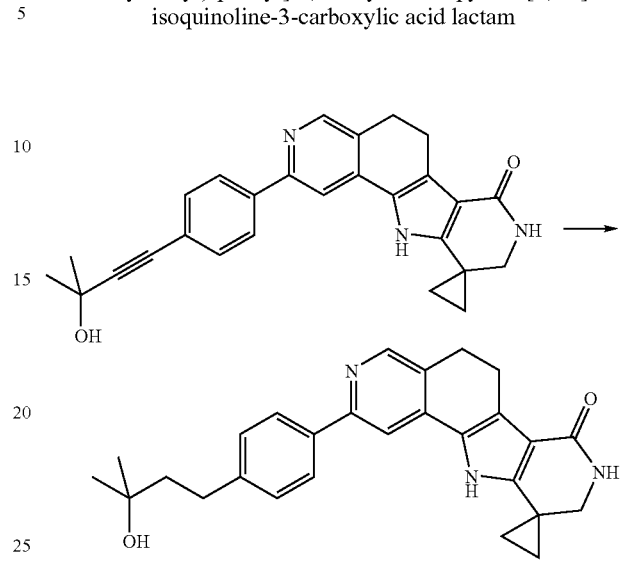

2-(1-Aminomethyl-cyclopropyl)-8-[4-(3-hydroxy-3-methyl-butyl)-phenyl]-4,5-dihydro-1H-pyrrolo[2,3-f]isoquinoline-3-carboxylic acid lactam Example 119: 2-(1-Aminomethyl-cyclopropyl)-8-[4-(3-hydroxy-3-methyl-butyl)-phenyl]-4,5-dihydro-1H-pyrrolo[2,3-f]isoquinoline-3-carboxylic acid lactam (Example 119) is treated in analogy to Example 78 and delivered the title compound as colorless crystals (19 mg; 50%). MS (m/z) ES+: 428 (MH+). Retention time: 1.96 minutes (LC-MS method 2).

EXAMPLE 127

2-(1-Aminomethyl-cyclopropyl)-8-(6-cyano-pyridin-3-yl)-4,5-dihydro-1H-pyrrolo[2,3-f]isoquinoline-3-carboxylic acid lactam

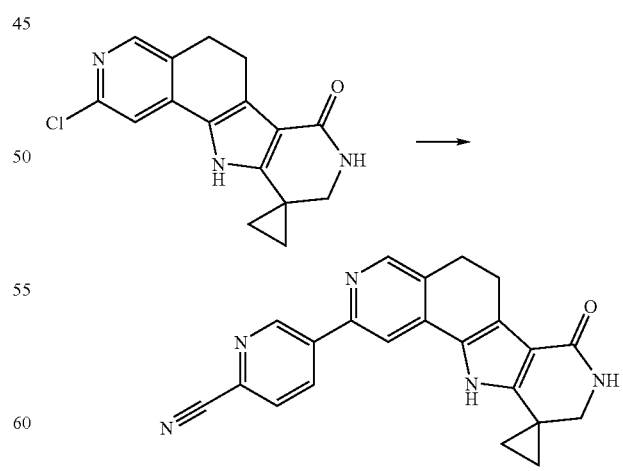

2-(1-Aminomethyl-cyclopropyl)-8-chloro-4,5-dihydro-1H-pyrrolo[2,3-f]isoquinoline-3-carboxylic acid lactam (Example 1d) and 2-cyanopyridine-5-boronic acid (SYNCHEM OHG Product List, un119) are coupled in analogy to Example

EXAMPLE 128

2-(1-Aminomethyl-cyclopropyl)-8-pyridin-3-yl-4,5-dihydro-1H-1,7,9-triaza-cyclopenta[a]naphthalene-3-carboxylic acid lactam

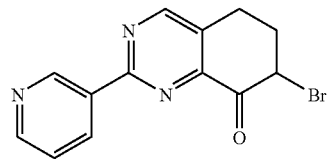

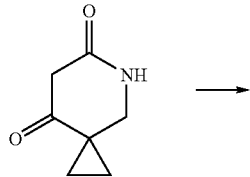

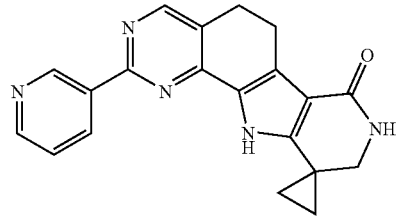

7-Bromo-2-pyridin-3-yl-6,7-dihydro-5H-quinazolin-8-one (prepared in analogy to Example 14c from pyridine-3-carboxamidine hydrochloride (Maybridge Building Blocks MO 07766) is reacted with 5-aza-spiro[2.5]octane-6,8-dione (WO 2005014572, WO 2005013986) in analogy to Example 17 to yield the title compound as colorless crystals (30 mg; 45%). MS (m/z) ES+: 344 (MH+). Retention time: 1.67 minutes (LC-MS method 2).

EXAMPLE 129

8-[4-(3-hydroxy-3-methyl-butyl)-phenyl]-2-(1-aminomethyl-cyclopropyl)-4,5-dihydro-1H-pyrrolo[2,3-f]isoquinoline-3-carboxylic acid lactam

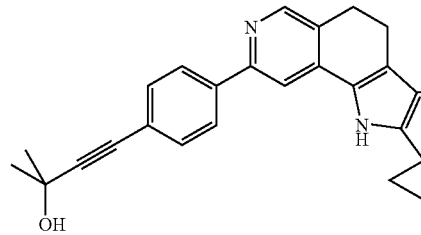

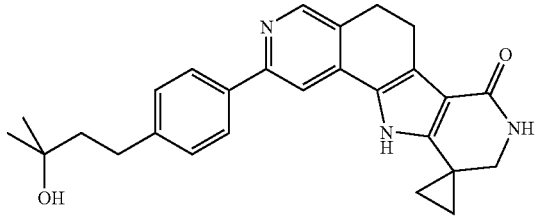

8-[4-(3-hydroxy-3-methyl-but-1-ynyl)-phenyl]-2-(1-aminomethyl-cyclopropyl)-4,5-dihydro-1H-pyrrolo[2,3-f]isoquinoline-3-carboxylic acid lactam (Example 119) is treated in analogy to Example 77 and delivered the title compound as colorless crystals (19 mg; 50%). MS (m/z) ES+: 427 (MH+). Retention time: 1.78 minutes (LC-MS method 2).

EXAMPLE 130

2-(1-Aminomethyl-cyclopropyl)-8-(4-methyl-3,4-dihydro-2H-benzo[1,4]oxazin-7-yl)-4,5-dihydro-1H-pyrrolo[2,3-f]isoquinoline-3-carboxylic acid lactam

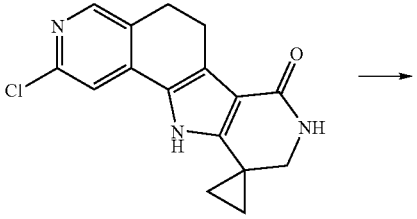

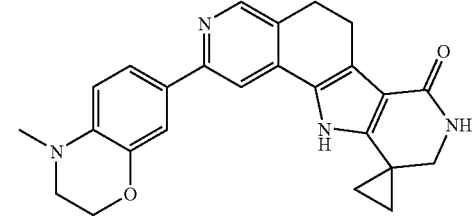

2-(1-Aminomethyl-cyclopropyl)-8-chloro-4,5-dihydro-1H-pyrrolo[2,3-f]isoquinoline-3-carboxylic acid lactam (Example 1d) and 4-methyl-7-(4,4,5,5-tetramethyl-1,3,2-dioxaborolan-2-yl)-3,4-dihydro-2H-1,4-benzoxazine (Maybridge Building Blocks CC 13539) are coupled in analogy to Example 1 and provide the title compound as colorless crystals (43 mg; 71%). MS (m/z) ES+: 413 (MH+). Retention time: 1.77 minutes (LC-MS method 2).

EXAMPLE 131

2-(3-Amino-azetidin-3-ylmethyl)-8-(4-methoxy-phenyl)-1-methyl-4,5-dihydro-1H-1,7,9-triaza-cyclopenta[a]naphthalene-3-carboxylic acid lactam hydrochloride

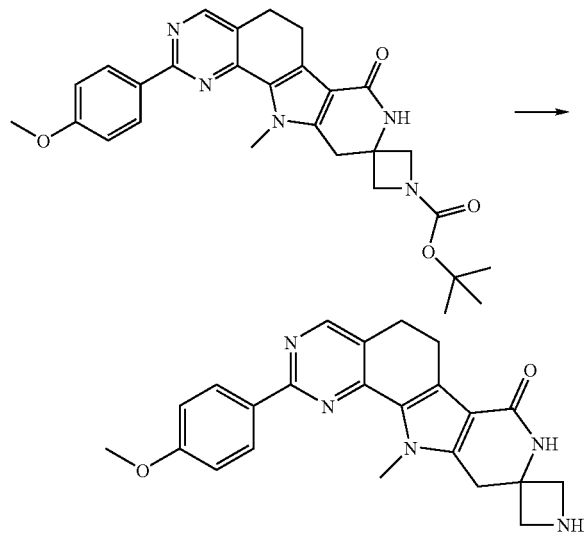

2-(3-Amino-1-tert-butoxycarbonyl-azetidin-3-ylmethyl)-8-(4-methoxy-phenyl)-1-methyl-4,5-dihydro-1H-1,7,9-triaza-cyclopenta[a]naphthalene-3-carboxylic acid lactam is treated in analogy to Example 18 and delivers the title compound as yellow crystals (74 mg; 98%).

1H-NMR (400 MHz; DMSO-d6): 9.51 (bs, 1H); 9.05 (bs, 1H); 8.55 (s, 1H); 8.35 (d, 2H); 8.12 (s, 1H); 7.13 (d, 2H); 4.20 (s, 3H); 4.10 (m, 2H); 4.03 (m, 2H); 3.87 (s, 3H); 3.51 (s, 2H); 2.99 (m, 2H); 2.90 (m, 2H). MS (m/z) ES+: 402 (MH+). Retention time: 1.79 minutes (LC-MS method 2).

The starting material is prepared as follows:

EXAMPLE 131A 2-(3-Amino-1-tert-butoxycarbonyl-azetidin-3-ylmethyl)-8-(4-methoxy-phenyl)-1-methyl-4,5-dihydro-1H-1,7,9-triaza-cyclopenta[a]naphthalene-3-carboxylic acid lactam

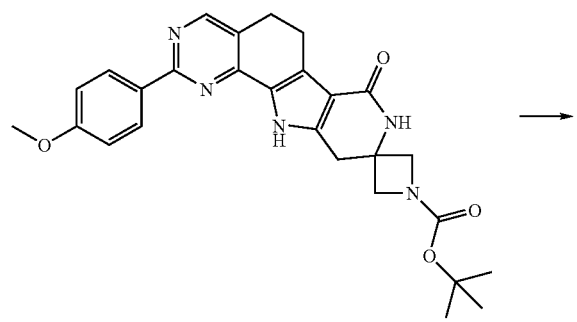

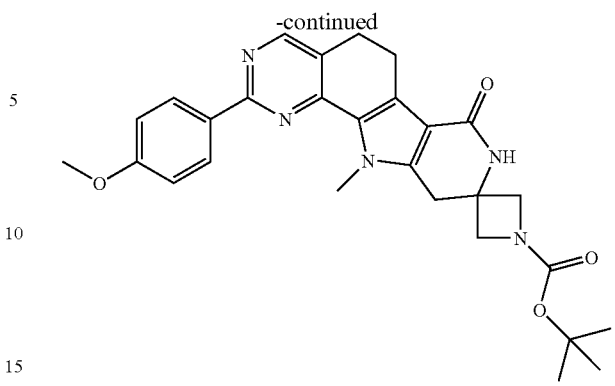

2-(3-Amino-1-tert-butoxycarbonyl-azetidin-3-ylmethyl)-8-(4-methoxy-phenyl)-4,5-dihydro-1H-1,7,9-triaza-cyclopenta[a]naphthalene-3-carboxylic acid lactam (Example 180 (118 mg; 0.24 mmol) is dissolved in DMF (5 ml) and cooled to 5° C. KHMDS solution (0.83 M; 0.29 ml; 0.24 mmol) is added, the reaction mixture stirred for 5 minutes at 5° C. and combined with MeI (100 mg; 0.73 mmol). The reaction mixture is warmed to room temperature, evaporated to dryness and purified via chromatography (SiO₂, acetone/hexanes 3:7>4:6) to yield the title compound as colorless crystals (91 mg; 75%).

1H-NMR (400 MHz; DMSO-d6): 8.52 (s) 1H); 8.33 (d, 2H); 7.92 (s, 1H); 7.10 (d, 2H); 4.19 (s, 3H); 3.91 (bs, 4H); 3.85 (s, 3H); 3.28 (bs, 2H); 2.98 (m, 2H); 2.87 (m, 2H); 1.42 (s, 9H). MS (m/z) ES+: 502 (MH+).

EXAMPLE 132

2-(3-Amino-azetidin-3-ylmethyl)-8-(3-cyano-phenyl)-1-methyl-4,5-dihydro-1H-pyrrolo[2,3-f]isoquinoline-3-carboxylic acid lactam hydrochloride

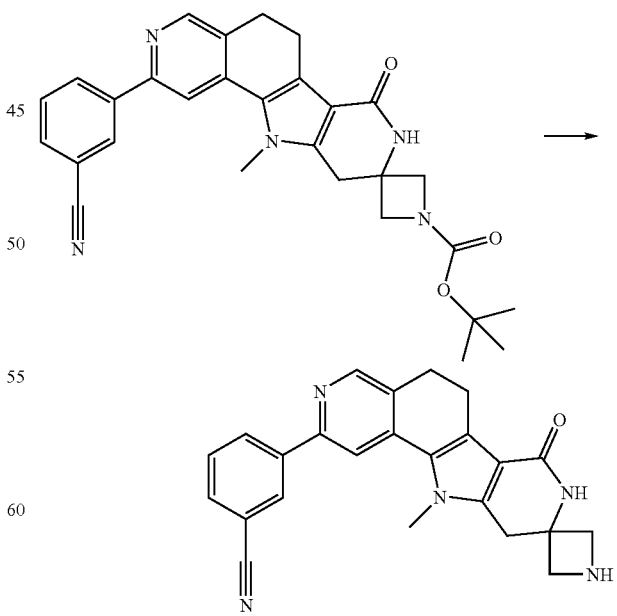

2-(3-Amino-1-tert.-butyloxycarbonyl-azetidin-3-ylmethyl)-8-(3-cyano-phenyl)-1-methyl-4,5-dihydro-1H-pyrrolo[2,3-f]isoquinoline-3-carboxylic acid lactam is treated in analogy to Example 18 and provides the title compound as yellow crystals (36 mg; 95%).

1H-NMR (400 MHz; DMSO-d6): 9.85 (bs, 1H); 9.20 (bs, 1H); 8.62 (s, 1H); 8.58 (s, 1H); 8.41 (d, 1H); 8.17 (s, 1H); 8.07 (s, 1H); 8.05 (s, 1H); 7.81 (, 1H); 4.11 (m, 2H); 4.01 (s, 3H); 3.97 (m, 2H); 3.59 (s, 2H); 2.95 (s, 4H). MS (m/z) ES+: 396 (MH+). Retention time: 1.57 minutes (LC-MS method 2).

The starting material is prepared as follows:

EXAMPLE 132A 2-(3-Amino-1-tert-butoxycarbonyl-azetidin-3-ylmethyl)-8-chloro-1-methyl-4,5-dihydro-1H-pyrrolo[2,3-f]isoquinoline-3-carboxylic acid lactam

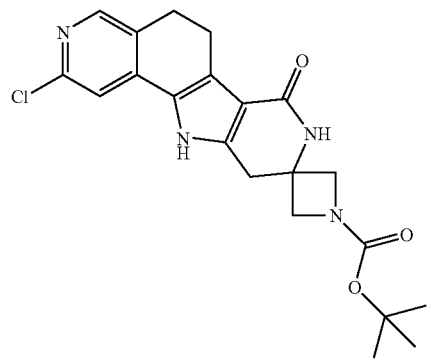

2-(3-Amino-1-tert-butoxycarbonyl-azetidin-3-ylmethyl)-8-chloro-4,5-dihydro-1H-pyrrolo[2,3-f]isoquinoline-3-carboxylic acid lactam (Example 23a) is treated in analogy to Example 131a and provides the title compound as colorless crystals (323 mg; 91%).

1H-NMR (400 MHz; DMSO-d6): 8.20 (s, 1H); 7.88 (s, 1H); 7.47 (s, 1H); 3.87 (bs, 4H); 3.85 (s, 3H); 3.25 (s, 2H); 2.87 (m, 2H); 2.77 (m, 2H); 1.40 (s, 9H). MS (m/z) ES+: 429 (MH+).

EXAMPLE 132B 2-(3-Amino-1-tert.-butyloxycarbonyl-azetidin-3-ylmethyl)-8-(3-cyano-phenyl)-1-methyl 4,5-dihydro-1H-pyrrolo[2,3-f]isoquinoline-3-carboxylic acid lactam

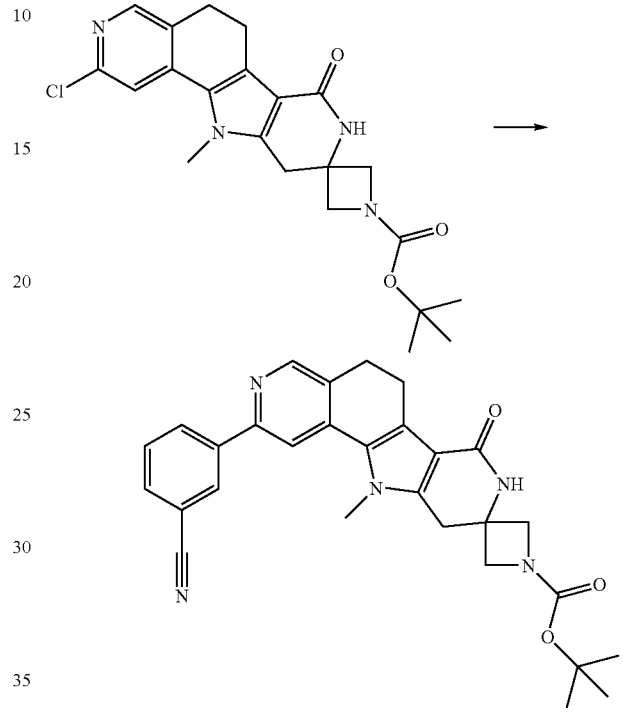

2-(3-Amino-1-tert-butoxycarbonyl-azetidin-3-ylmethyl)-8-chloro-1-methyl-4,5-dihydro-1H-pyrrolo[2,3-f]isoquinoline-3-carboxylic acid lactam and 3-cyanophenylboronic acid (Aldrich 513016) are treated in analogy to Example 1 and provide the title compound as colorless crystals (52 mg; 90%).

1H-NMR (400 MHz; DMSO-d6): 8.54 (s, 1H); 8.51 (s, 1H); 8.44 (d, 1H); 7.97 (s, 1H); 7.89 (d, 1H); 7.85 (s, 1H); 7.71 (t, 1H); 3.97 (s, 3H); 3.88 (bs 4H); 3.27 (bs, 2H); 2.88 (m, 2H); 2.83 (m, 2H); 1.39 (s, 9H). MS (m/z) ES+: 496 (MH+).

EXAMPLE 133

2-(3-Amino-azetidin-3-ylmethyl)-8-(3-fluoro-phenyl)-1-methyl-4,5-dihydro-1H-pyrrolo[2,3-f]isoquinoline-3-carboxylic acid lactam hydrochloride

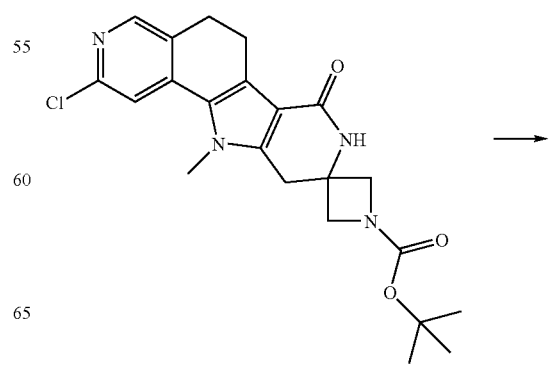

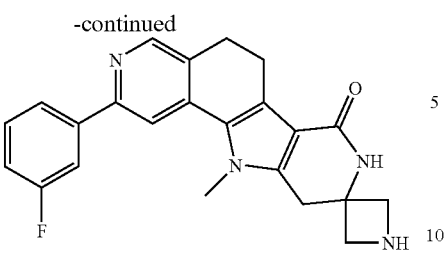

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with 3-fluorophenylboronic acid (Sigma-Aldrich, order number 441643) according to Example 1. The BOC-protective group is removed according to Example 18 delivering the title compound as yellow crystals (32 mg; 90%). MS (m/z) ES+: 389 (MH+). Retention time: 1.54 minutes (LC-MS method 2).

EXAMPLE 134

2-(3-Amino-azetidin-3-ylmethyl)-8-(6-fluoro-pyridin-3-yl)-1-methyl-4,5-dihydro-1H-pyrrolo[2,3-f]isoquinoline-3-carboxylic acid lactam hydrochloride

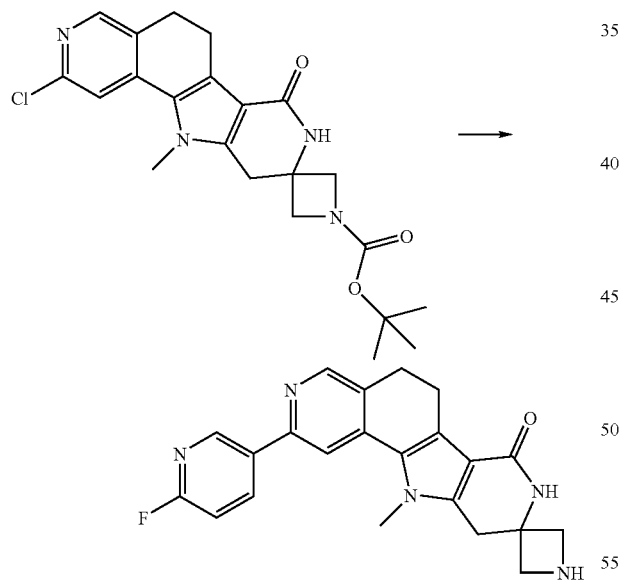

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with 2-fluoropyridine-5-boronic acid (ABCR, AB181129) according to Example 1. The BOC-protective group is removed according to Example 18 delivering the title compound as yellow crystals (39 mg; 90%). MS (m/z) ES+: 390 (MH+). Retention time: 1.38 minutes (LC-MS method 2).

EXAMPLE 135

2-(3-Amino-azetidin-3-ylmethyl)-8-[5-(2-fluoro-phenyl)-pyridin-3-yl]-1-methyl-4,5-dihydro-1H-pyrrolo[2,3-f]isoquinoline-3-carboxylic acid lactam hydrochloride

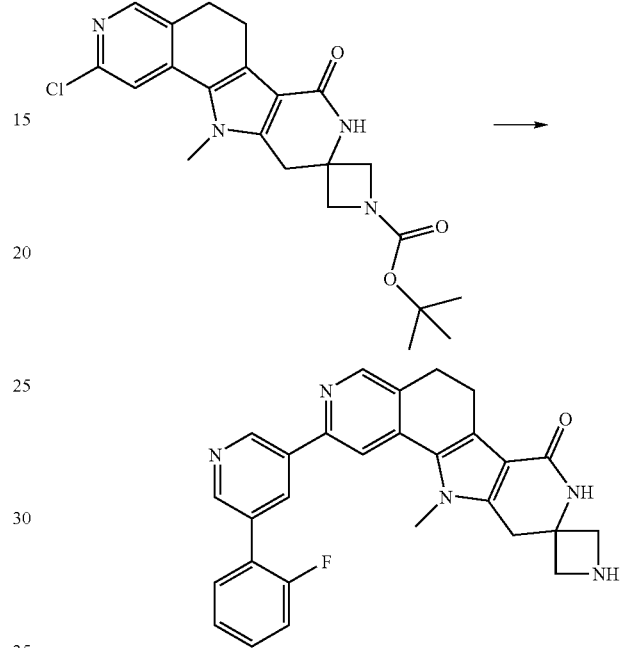

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with 3-(2-fluoro-phenyl)-5-(4,4,5,5-tetramethyl-[1,3,2]dioxaboro-lan-2-yl)-pyridine (Example 135b) according to Example 1. The BOC-protective group is removed according to Example 18 delivering the title compound as yellow crystals (26 mg; 90%). MS (m/z) ES+: 466 (MH+). Retention time: 1.85 minutes (LC-MS method 2).

The starting material is prepared as follows:

EXAMPLE 135A

3-Bromo-5-(2-fluoro-phenyl)-pyridine

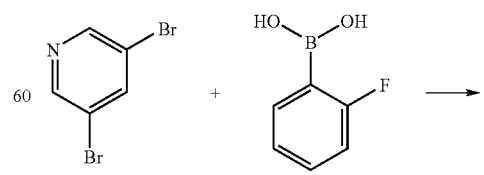

-continued

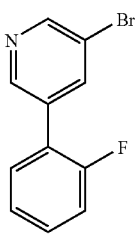

3,5-Dibromopyridine (ABCR Product List AB115322) (250 mg; 2.1 mmol), 2-fluorophenylboronic acid (Sigma-Aldrich, order number 445223)(147 mg; (2.1 mmol), Pd(PPh$_3$)$_2$Cl$_2$ (148 mg; 0.4 mmol) are combined in DMF (8 ml) and 2N Na$_2$CO$_3$ (1.3 ml) and heated to 160° C. in an oil bath for 20 minutes. The reaction mixture is evaporated to dryness, taken up in TBME/CH$_2$Cl$_2$ (30 ml/10 ml), diluted with hexanes (50 ml), filtered and evaporated to dryness. The solid white residue is dissolved in TBME (10 ml), diluted with hexanes, filtered, and purified via chromatography (SiO2, TBME/hexanes 5:95) to yield the title compound as white crystals (125 mg; 47%). MS (m/z) ES+: 252, 254 (MH+). Retention time: 2.79 minutes (LC-MS method 3).

EXAMPLE 135B 3-(2-fluoro-phenyl)-5-(4,4,5,5-tetramethyl-[1,3,2] dioxaboro-lan-2-yl)-pyridine

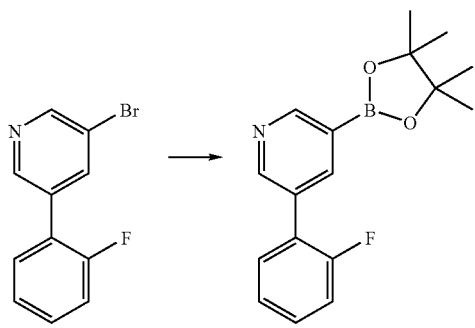

3-Bromo-5-(2-fluoro-phenyl)-pyridine (221 mg; 0.88 mmol), bis(pinacolato)diboron (Frontier Scientific Catalog D6878) (269 mg; 1.05 mmol), Pd(PPh$_3$)$_2$Cl$_2$ (20 mg; 0.025 mmol) and KOAc (260 mg; 2.64 mmol) are heated to 160° C. in DMF (6 ml) under argon for 20 minutes. The dark reaction mixture is evaporated to dryness, taken up in TBME, filtered and evaporated. The residue is dissolved in diethyl ether, diluted with hexanes, diethyl ether evaporated, filtered and evaporated to yield the title compound as brownish semi-crystalline material used in Example 135 without further purification 1H-NMR (400 MHz; DMSO-d6): 8.87 (s, 1H); 8.79 (s, 1H); 8.12 (s, 1H); 7.64 (m, 1H); 7.50 (m, 1H); 7.38 (m, 2H); 1.34 (s, 12H).

EXAMPLE 136

2-(3-Amino-azetidin-3-ylmethyl)-8-[5-(4-fluoro-phenyl)-pyridin-3-yl]-1-methyl-4,5-dihydro-1H-pyrrolo[2,3-f]isoquinoline-3-carboxylic acid lactam hydrochloride The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with 3-(4-fluoro-phenyl)-5-(4,4,5,5-tetramethyl-[1,3,2]dioxaboro-lan-2-yl)-pyridine (Example 136b) according to Example 1. The BOC-protective group is removed according to Example 18 delivering the title compound as yellow crystals (25 mg; 90%). MS (m/z) ES+: 466 (MH+). Retention time: 1.87 minutes (LC-MS method 2).

The starting material is prepared as follows:

EXAMPLE 136A 3-(4-fluoro-phenyl)-5-(4,4,5,5-tetramethyl-[1,3,2] dioxaboro-lan-2-yl)-pyridine

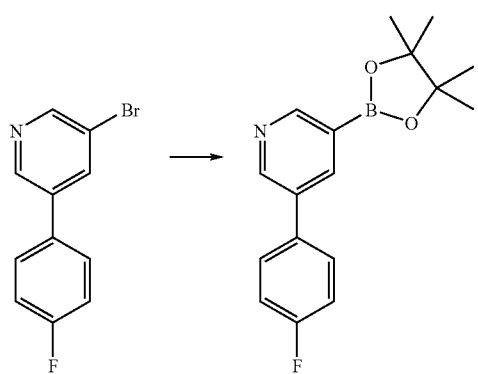

3-Bromo-5-(4-fluorophenyl)pyridine (Small Molecules Product List 12-1489) is treated with bis(pinacolato)diboron (Frontier Scientific Catalog D6878) in analogy to Example 135b and delivers the title compound as brownish resin (130 mg) used in Example 136 without further purification.

1H-NMR (400 MHz; DMSO-d6): 8.99 (s, 1H); 8.77 (s, 1H); 8.17 (t, 1H); 7.82 (dd, 2H); 7.35 (t, 2H); 1.35 (s, 12H).

EXAMPLE 137

2-(3-Amino-azetidin-3-ylmethyl)-8-(3-methoxy-phenyl)-1-methyl-4,5-dihydro-1H-1,7,9-triaza-cyclopenta[a]naphthalene-3-carboxylic acid lactam hydrochloride

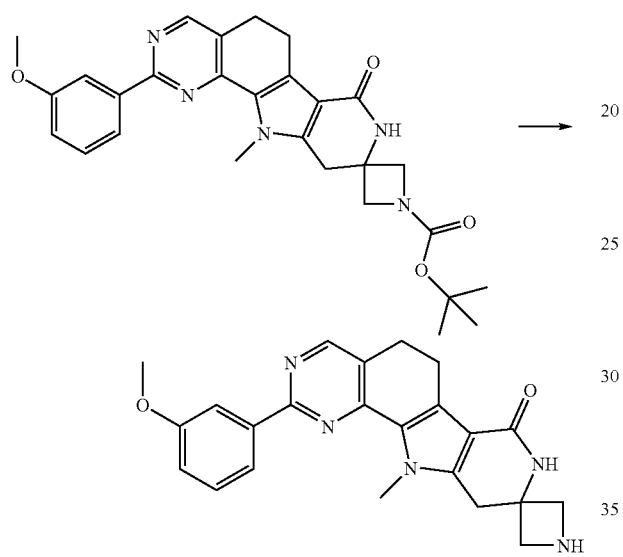

The title compound is obtained in analogy to Example 18 as yellow crystal (61 mg; 95%).

MS (m/z) ES+: 402 (MH+). Retention time: 1.81 minutes (LC-MS method 2).

The starting material is prepared as follows:

EXAMPLE 137A 2-(3-Amino-1-tert.butyloxycarbonyl-azetidin-3-ylmethyl)-8-(3-methoxy-phenyl)-1-methyl-4,5-dihydro-1H-1,7,9-triaza-cyclopenta[a]naphthalene-3-carboxylic acid lactam

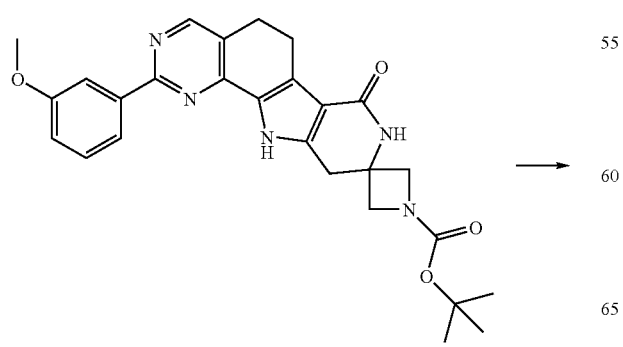

-continued

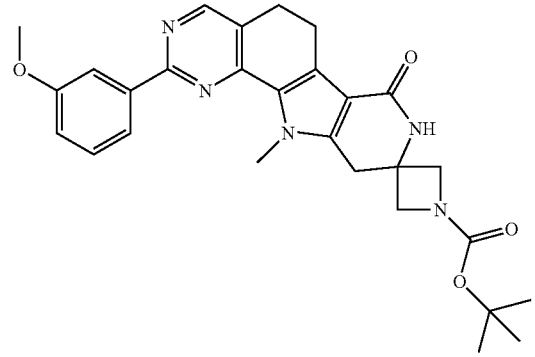

2-(3-Amino-1-tert.butyloxycarbonyl-azetidin-3-ylmethyl)-8-(3-methoxy-phenyl)-4,5-dihydro-1H-1,7,9-triaza-cyclopenta[a]naphthalene-3-carboxylic acid lactam is treated in analogy to Example 131a and delivers the title compound as off-white crystals (78 mg; 80%)

1H-NMR (400 MHz; DMSO-d6): 8.57 (s, 1H); 7.98 (d, 1H); 7.92 (s, 2H); 7.46 (t, 1H); 7.12 (dd, 1H); 4.20 (s, 3H); 3.91 (bs, 4H); 3.86 (s, 3H); 3.29 (s, 2H); 2.99 (m, 2H); 2.90 (m, 2H); 1.41 (s, 9H).

MS (m/z) ES+: 502 (MH+).

EXAMPLE 137B 2-(3-Amino-1-tert.butyloxycarbonyl-azetidin-3-ylmethyl)-8-(3-methoxy-phenyl)-4,5-dihydro-1H-1,7,9-triaza-cyclopenta[a]naphthalene-3-carboxylic acid lactam

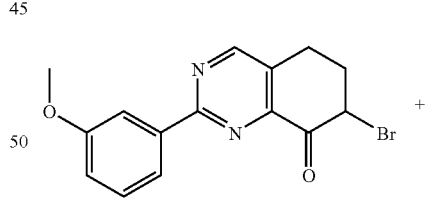

+

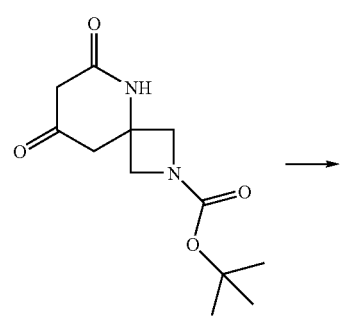

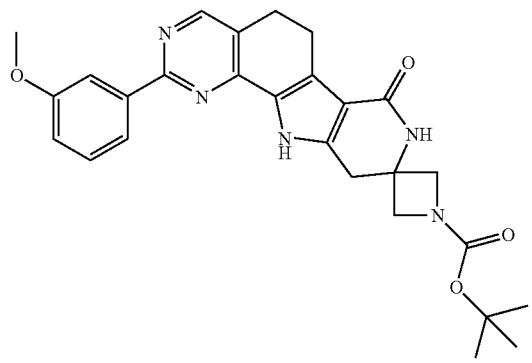

7-Bromo-2-(3-methoxy-phenyl)-6,7-dihydro-5H-quinazolin-8-one (prepared in analogy to Example 14c from 3-methoxy-benzamidine HCl (Tyger Scientific Product List M33012) and 6,8-dioxo-2,5-diaza-spiro[3.5]nonane-2-carboxylic acid tert-butyl ester (Example 18c) are reacted in analogy to Example 18f and provide the title compound as colorless crystals (96 mg; 66%).

1H-NMR (400 MHz; DMSO-d6): 12.25 (s, 1H); 8.53 (s, 1H); 8.11 (d, 1H); 8.07 (s, 1H); 7.90 (s, 1H); 7.45 (t, 1H); 7.12 (dd, 1H); 3.88 (s, 7H); 3.22 (s, 2H); 3.00 (m, 2H); 2.94 (m, 2H); 1.41 (s, 9H).

MS (m/z) ES+: 488 (MH+).

EXAMPLE 138

2-(3-Amino-azetidin-3-ylmethyl)-8-(3-fluoro-4-methoxy-phenyl)-1-methyl-4,5-dihydro-1H-1,7,9-triaza-cyclopenta[a]naphthalene-3-carboxylic acid lactam hydrochloride

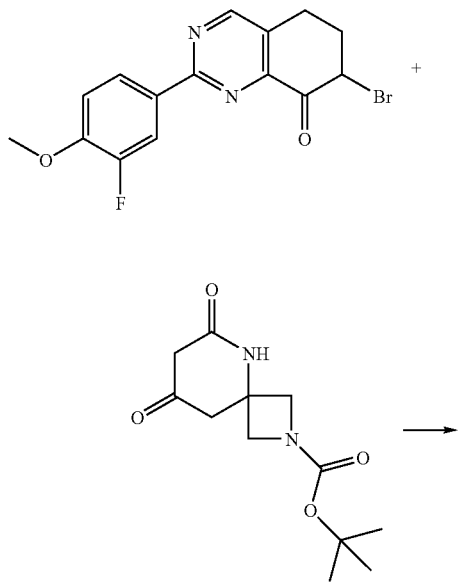

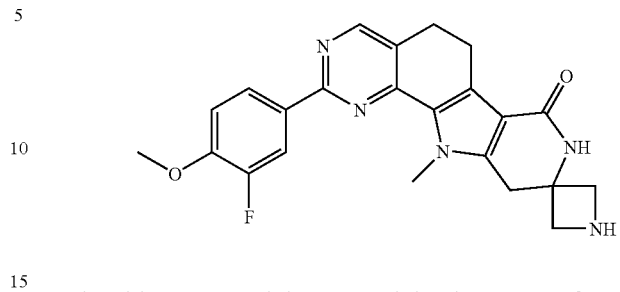

The title compound is prepared in three steps from 7-bromo-2-(3-fluoro-4-methoxy-phenyl)-6,7-dihydro-5H-quinazolin-8-one (prepared from 3-fluoro-4-methoxybenzamidine, EP 339252, in analogy to Example 14c) following the procedures described in Examples 137, 137a and 137b to yield the title compound as yellow crystals (61 mg). MS (m/z) ES+: 420 (MH+). Retention time: 1.88 minutes (LC-MS method 2).

EXAMPLE 139

2-(3-Amino-azetidin-3-ylmethyl)-8-(4-bromo-phenyl)-1-methyl-4,5-dihydro-1H-1,7,9-triaza-cyclopenta[a]naphthalene-3-carboxylic acid lactam hydrochloride

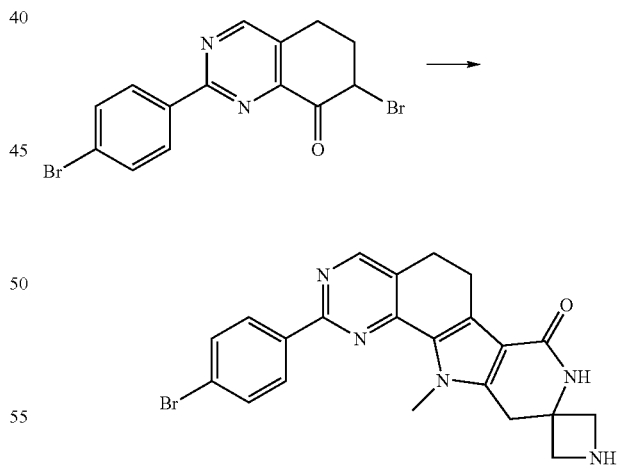

The title compound is prepared in three steps from 7-bromo-2-(4-bromo-phenyl)-6,7-dihydro-5H-quinazolin-8-one (prepared from 4-bromobenzamidine, Combi-Blocks Catalog HC-6369, in analogy to Example 14c) following the procedures described in Examples 137, 137a and 137b to yield the title compound as yellow crystals (23 mg). MS (m/z) ES+: 451 (MH+). Retention time: 2.15 minutes (LC-MS method 2).

EXAMPLE 140

2-(3-Amino-azetidin-3-ylmethyl)-8-(5-methoxy-pyridin-3-yl)-1-methyl-4,5-dihydro-1H-pyrrolo[2,3-f]isoquinoline-3-carboxylic acid lactam hydrochloride

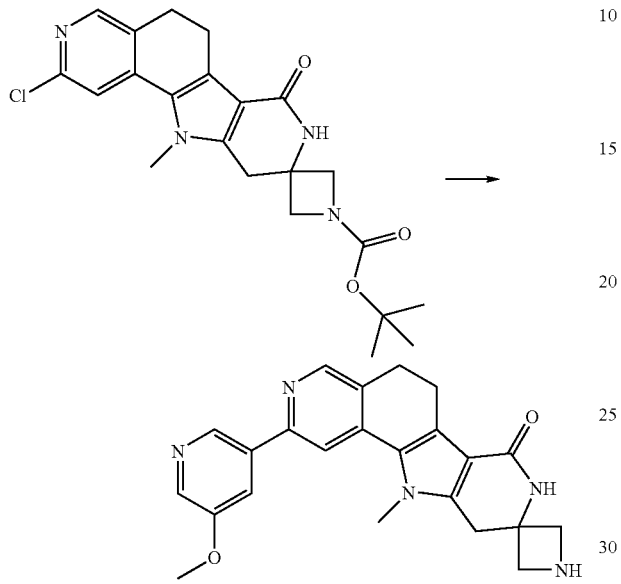

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with 5-methoxy-3-pyridineboronic acid pinacol ester (Aldrich, 676624) according to Example 1. The BOC-protective group is removed according to Example 18 delivering the title compound as yellow crystals (37 mg). MS (m/z) ES+: 402 (MH+). Retention time: 1.34 minutes (LC-MS method 2).

EXAMPLE 141

2-(3-Amino-azetidin-3-ylmethyl)-8-(6-methoxy-pyridin-3-yl)-1-methyl-4,5-dihydro-1H-pyrrolo[2,3-f]isoquinoline-3-carboxylic acid lactam hydrochloride

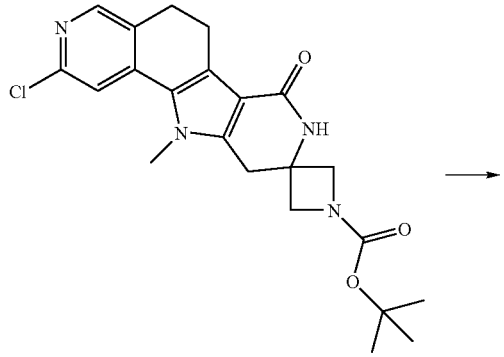

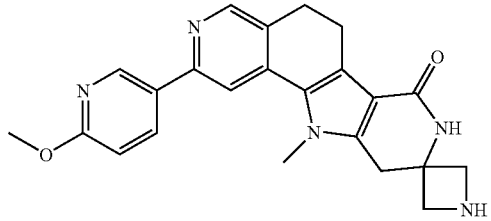

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with 2-methoxy-5-pyridineboronic acid (Aldrich, 637610) according to Example 1. The BOC-protective group is removed according to Example 18 delivering the title compound as yellow crystals (37 mg). MS (m/z) ES+: 402 (MH+). Retention time: 1.37 minutes (LC-MS method 2).

EXAMPLE 142

2-(3-Amino-1-methyl-azetidin-3-ylmethyl)-8-(6-methoxy-pyridin-3-yl)-1-methyl-4,5-dihydro-1H-pyrrolo[2,3-f]isoquinoline-3-carboxylic acid lactam

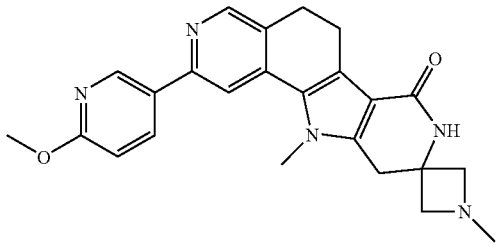

The reaction is performed in analogy to Example 39 and delivers the title compound as colorless crystals. MS (m/z) ES+: 416 (MH+). Retention time: 1.36 minutes (LC-MS method 2).

EXAMPLE 143

2-(3-Amino-azetidin-3-ylmethyl)-8-(3,5-dimethoxy-phenyl)-1-methyl-4,5-dihydro-1H-pyrrolo[2,3-f]isoquinoline-3-carboxylic acid lactam hydrochloride

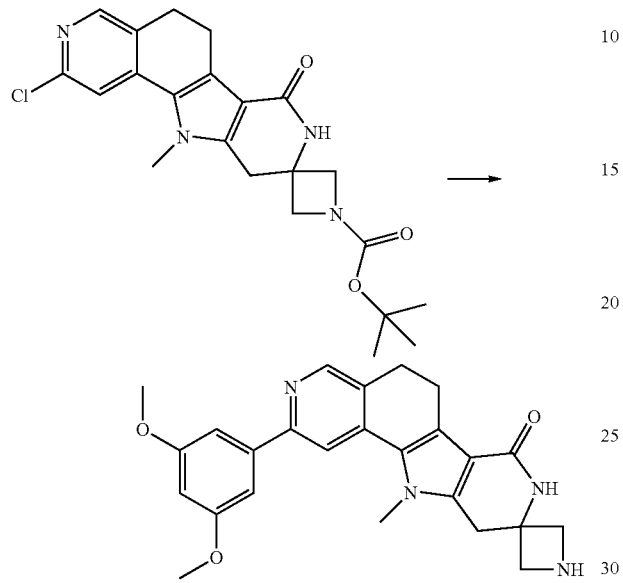

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with 3,5-dimethoxyphenylboronic acid (Combi-Blocks Catalog BB-2622) according to Example 1. The BOC-protective group is removed according to Example 18 delivering the title compound as yellow crystals.

MS (m/z) ES+: 386 (MH+). Retention time: 1.39 minutes (LC-MS method 2).

EXAMPLE 144

2-3-Amino-azetidin-3-ylmethyl)-8-(3,4-dimethoxy-phenyl)-1-methyl-4,5-dihydro-1H-pyrrolo[2,3-f]isoquinoline-3-carboxylic acid lactam hydrochloride

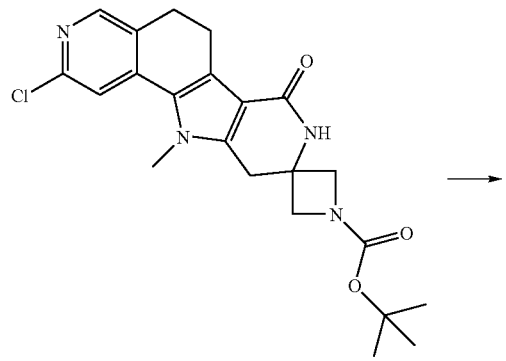

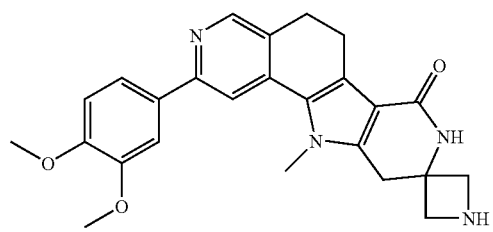

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with 3,4-dimethoxyphenylboronic acid (Aldrich, 480118) according to Example 1. The BOC-protective group is removed according to Example 18 delivering the title compound as yellow crystals. MS (m/z) ES+: 431 (MH+). Retention time: 1.12 minutes (LC-MS method 2).

EXAMPLE 145

2-(3-Amino-azetidin-3-ylmethyl)-1-methyl-8-(4-methyl-3,4-dihydro-2H-benzo[1,4]oxazin-7-yl)-4,5-dihydro-1H-pyrrolo[2,3-f]isoquinoline-3-carboxylic acid lactam hydrochloride

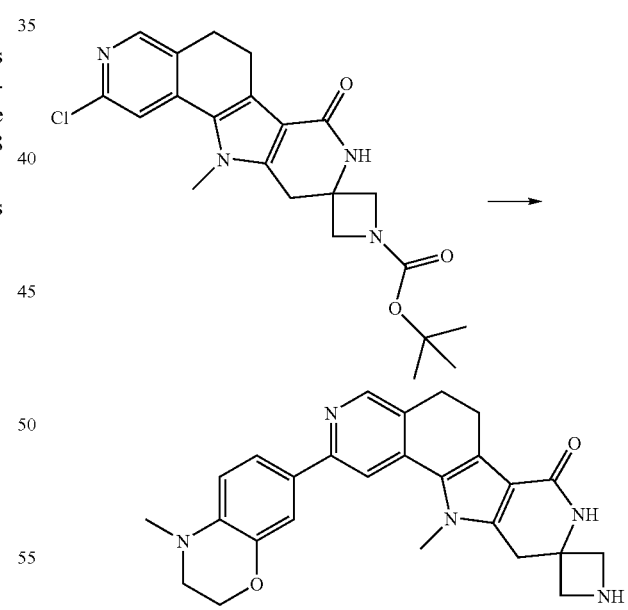

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with 4-methyl-7-(4,4,5,5-tetramethyl-1,3,2-dioxaborolan-2-yl)-3,4-dihydro-2H-1,4-benzoxazine (Maybridge Building Blocks CC 13539) according to Example 1. The BOC-protective group is removed according to Example 18 delivering the title compound as yellow crystals. MS (m/z) ES+: 442 (MH+). Retention time: 1.20 minutes (LC-MS method 2).

EXAMPLE 146

2-(3-Amino-azetidin-3-ylmethyl)-8-(3-morpholin-4-yl-phenyl)-1-methyl-4,5-dihydro-1H-pyrrolo[2,3-f]isoquinoline-3-carboxylic acid lactam hydrochloride

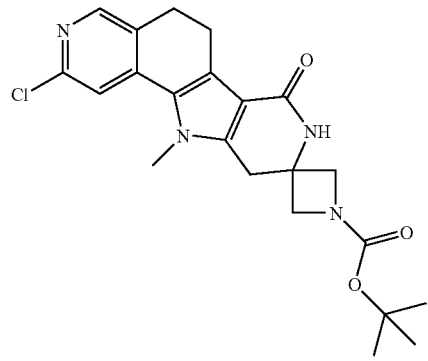

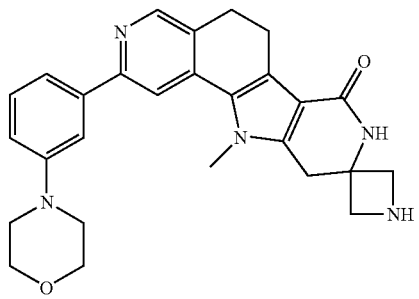

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with 3-morpholinophenylboronic acid pinacol ester (Frontier Scientific Catalog M1882) according to Example 1. The BOC-protective group is removed according to Example 18 delivering the title compound as yellow crystals. MS (m/z) ES+: 456 (MH+). Retention time: 1.22 minutes (LC-MS method 2).

EXAMPLE 147

2-(3-Amino-azetidin-3-ylmethyl)-8-(6-dimethylamino-pyridin-3-yl)-1-methyl-4,5-dihydro-1H-pyrrolo[2,3-f]isoquinoline-3-carboxylic acid lactam hydrochloride

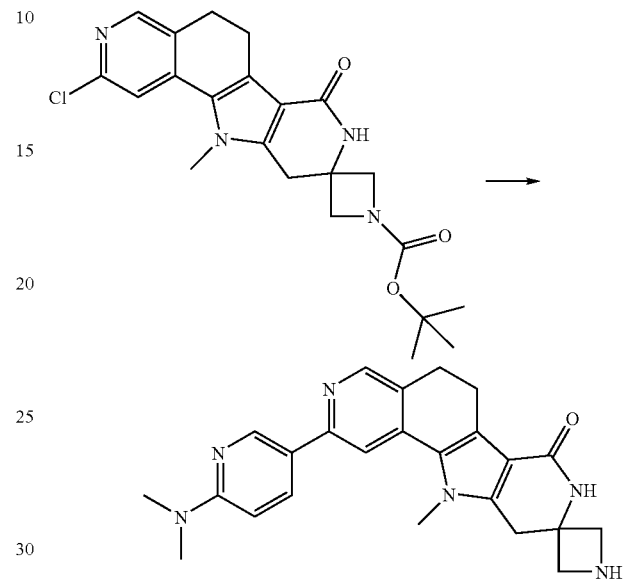

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with 2-dimethylaminopyridine-5-boronic acid (Frontier Scientific, D9115) according to Example 1. The BOC-protective group is removed according to Example 18 delivering the title compound as yellow crystals. MS (m/z) ES+: 415 (MH+). Retention time: 1.07 minutes (LC-MS method 2).

EXAMPLE 148

2-(3-Amino-azetidin-3-ylmethyl)-8-(2,3-dihydro-benzo[1,4]dioxin-6-yl)-1-methyl-4,5-dihydro-1H-pyrrolo[2,3-f]isoquinoline-3-carboxylic acid lactam hydrochloride

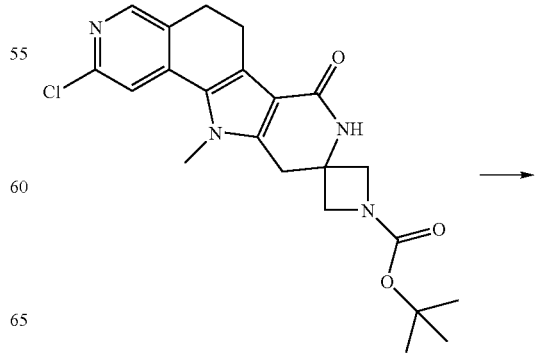

-continued

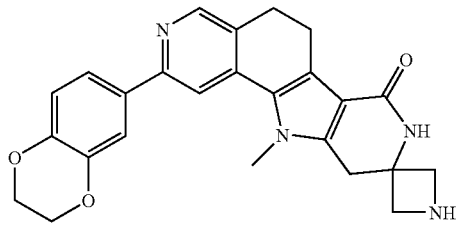

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with 1,4-benzodioxane-6-boronic acid (Aldrich, 635995) according to Example 1. The BOC-protective group is removed according to Example 18 delivering the title compound as yellow crystals. MS (m/z) ES+: 429 (MH+). Retention time: 1.18 minutes (LC-MS method 2).

EXAMPLE 149

2-(3-Amino-azetidin-3-ylmethyl)-8-(6-piperidinyl-pyridin-3-yl)-1-methyl-4,5-dihydro-1H-pyrrolo[2,3-f]isoquinoline-3-carboxylic acid lactam hydrochloride

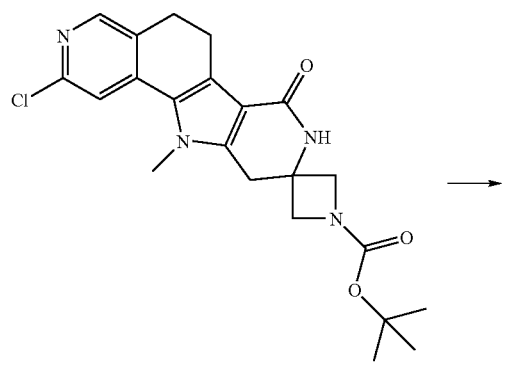

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with 2-(piperidin-1-yl)pyridine-5-boronic acid pinacol ester (Frontier Scientific Catalog, P1758) according to Example 1. The BOC-protective group is removed according to Example 18 delivering the title compound as yellow crystals. MS (m/z) ES+: 455 (MH+). Retention time: 1.41 minutes (LC-MS method 2).

EXAMPLE 150

2-(3-Amino-1-methyl-azetidin-3-ylmethyl)-8-(6-methyl-pyridin-3-yl)-1-methyl-4,5-dihydro-1H-pyrrolo[2,3-f]isoquinoline-3-carboxylic acid lactam

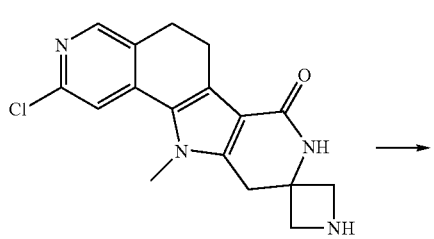

The reaction is performed in analogy to Example 39 and delivers the title compound as colorless crystals. MS (m/z) ES+: 400 (MH+). Retention time: 1.50 minutes (LC-MS method 2).

EXAMPLE 151

2-(3-Amino-azetidin-3-ylmethyl)-8-(6-methyl-pyridin-3-yl)-1-methyl-4,5-dihydro-1H-pyrrolo[2,3-f]isoquinoline-3-carboxylic acid lactam hydrochloride

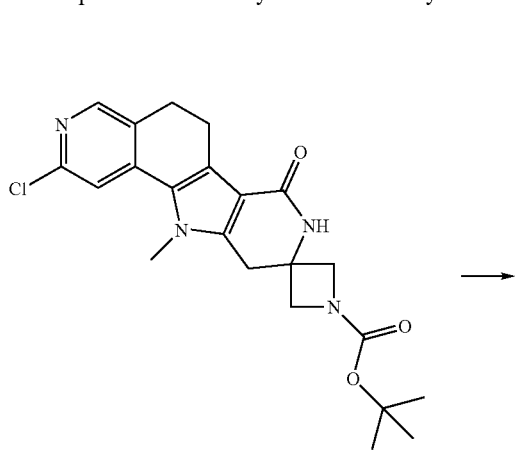

-continued

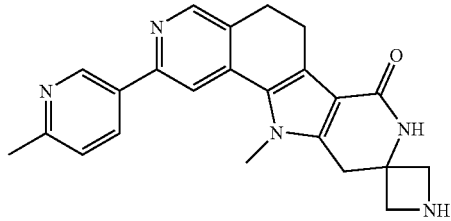

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with 6-methylpyridine-3-boronic acid (SYNCHEM OHG, un119) according to Example 1. The BOC-protective group is removed according to Example 18 delivering the title compound as yellow crystals. MS (m/z) ES+: 386 (MH+). Retention time: 1.21 minutes (LC-MS method 2).

EXAMPLE 152

2-(3-Amino-azetidin-3-ylmethyl)-8-(pyridin-4-yl)-1-methyl-4,5-dihydro-1H-pyrrolo[2,3-f]isoquinoline-3-carboxylic acid lactam hydrochloride

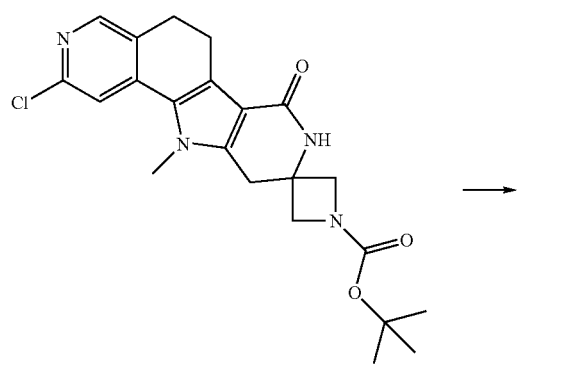

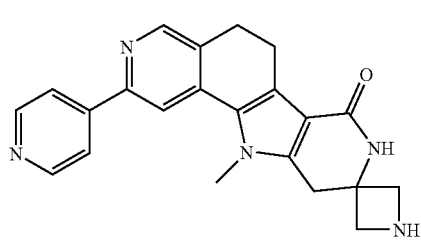

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with pyridin-4-ylboronic acid (Maybridge Building Blocks, CC 04212) according to Example 1. The BOC-protective group is removed according to Example 18 delivering the title compound as yellow crystals. MS (m/z) ES+: 372 (MH+). Retention time: 1.52 minutes (LC-MS method 2).

EXAMPLE 153

2-(3-Amino-azetidin-3-ylmethyl)-8-(pyridin-3-yl)-1-methyl-4,5-dihydro-1H-pyrrolo[2,3-f]isoquinoline-3-carboxylic acid lactam hydrochloride

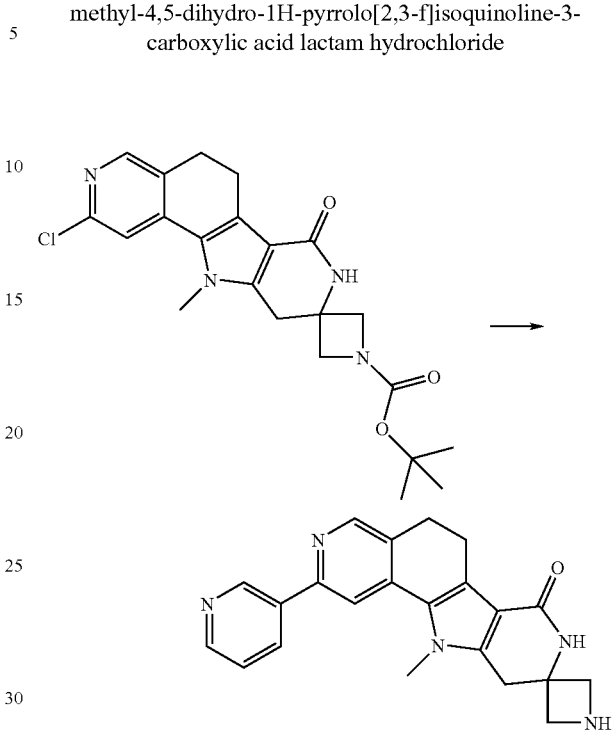

The title compound is prepared in two steps from 2-(3-amino-1-tert-butoxycarbonyl-azetidin-3-ylmethyl)-8-chloro-1-methyl-4,5-dihydro-1H-pyrrolo[2,3-f]isoquinoline-3-carboxylic acid lactam (Example 132a) which is coupled with pyridine-3-boronic acid (ABCR, AB152416) according to Example 1. The BOC-protective group is removed according to Example 18 delivering the title compound as yellow crystals. MS (m/z) ES+: 372 (MH+). Retention time: 1.16 minutes (LC-MS method 2).

EXAMPLE 154

2-(3-Aminomethyl-azetidin-3-yl)-8-[6-(2,4-difluoro-phenoxy)-pyridin-3-yl]-4,5-dihydro-1H-pyrrolo[2,3-f]isoquinoline-3-carboxylic acid lactam

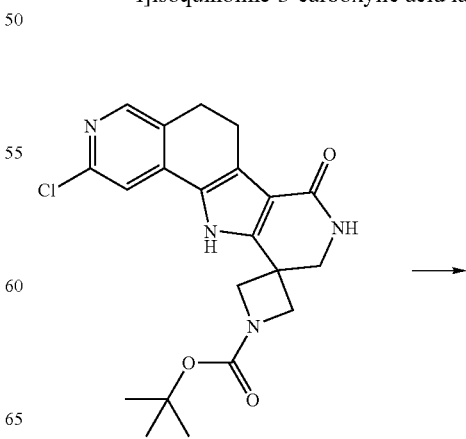

-continued

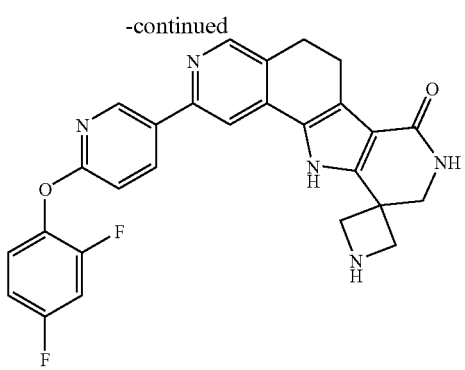

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156a) and 2-(2,4-difluoro-phenoxy)-5-(4,4,5,5-tetramethyl-[1,3,2]dioxaborolan-2-yl)-pyridine (Example 95b) are coupled in analogy to Example 1. The BOC-protective group is removed in analogy to Example 156 to yield the title compound as yellow crystals (MS (m/z) ES+: 486 (MH+). Retention time: 1.89 minutes (LC-MS method 2).

XAMPLE 155

2-(3-Aminomethyl-1-methyl-azetidin-3-yl)-8-(3-fluoro-phenyl)-4,5-dihydro-1H-pyrrolo[2,3-f]isoquinoline-3-carboxylic acid lactam

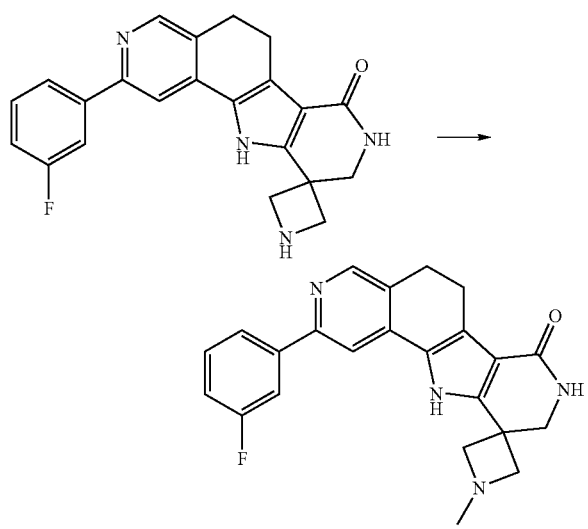

2-(3-Aminomethyl-azetidin-3-yl)-8-(3-fluoro-phenyl)-4,5-dihydro-1H-pyrrolo[2,3-f]isoquinoline-3-carboxylic acid lactam (Example 156) is azetidine N-methylated in analogy to Example 222b and delivers the title compound as colorless crystals 1H-NMR (400 MHz; DMSO-d6): 11.80 (bs, 1H); 8.38 (s, 1H); 8.20 (s, 1H); 7.93 (bd, 1H); 7.82 (bd, 1H); 7.55 (m, 1H); 7.25 (m, 1H); 7.14 (bs, 1H); 3.54 (bs, 2H); 3.35 (bd, 4H); 2.89 (m, 4H); 2.37 (s, 3H). MS (m/z) ES+: 389 (MH+). Retention time: 1.50 minutes (LC-MS method 2).

EXAMPLE 156

2-(3-Aminomethyl-azetidin-3-yl)-8-(3-fluoro-phenyl)-4,5-dihydro-1H-pyrrolo[2,3-f]isoquinoline-3-carboxylic acid lactam

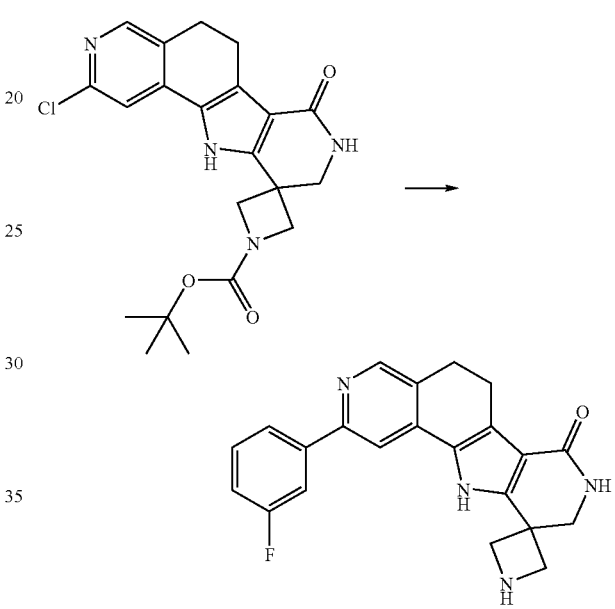

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (850 mg; 2.052 mmol), 3-fluorophenyl-boronic acid (574 mg; 4.14 mmol; Sigma-Aldrich, order number 441643), Pd(PPh$_3$)$_2$Cl$_2$ (430 mg; 0.616 mmol), Pd(dppf)Cl$_2$.CH$_2$Cl$_2$(17 mg; 0.002 mmol), PPh$_3$ (1.07 g; 4.1 mmol) and 2N Na$_2$CO$_3$ (6.2 ml) in 1-propanol (30 ml) are microwaved at 150° C. for 20 minutes. The reaction mixture is diluted with methanol (20 ml), filtered, evaporated to dryness and purified via chromatography (SiO$_2$; TBME/MeOH/NH3$_{conc}$ 96:4:0.8) to yield colorless crystals, which are washed with diethyl ether/ethanol (8:2), dried and taken up in HCl$_{conc}$ (10 ml). The reaction mixture is stirred for 3-4 minutes at room temperature and then evaporated to dryness. The resulting crystals are washed with ethanol, dried, combined with 2N NaOH (10 ml) and the suspension stirred for 2-3 minutes at room temperature. The off-white crystals are filtered, washed with water and dried to deliver the title compound (992 mg; 65%).

1H-NMR (400 MHz; DMSO-d6): 12.03 (bs, 1H); 8.41 (s, 1H); 8.22 (s, 1H); 7.93 (d, 1H); 7.83 (dd, 1H); 7.56 (m, 1H); 7.27 (m, 1H); 7.16 (s, 1H); 3.79 (bd, 2H); 3.60 (s, 2H); 3.46 (bd, 2H); 2.90 (m, 4H). MS (m/z) ES+: 375 (MH+). Retention time: 1.36 minutes (LC-MS method 2).

The starting material is prepared as follows:

EXAMPLE 156A

3-Carbamoyl-azetidine-1,3-dicarboxylic acid 1-tert-butyl ester 3-ethyl ester

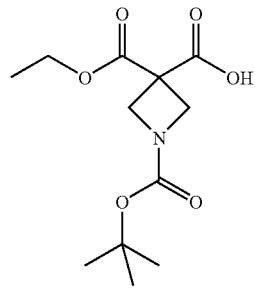

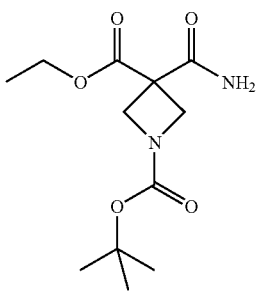

Azetidine-1,3,3-tricarboxylic acid 1-tert-butyl ester 3-ethyl ester (Example 11b; 21.5 g; 78.9 mmol) and NEt$_3$ (17.6 ml; 126 mmol) are dissolved in THF (200 ml) and cooled to 0° C. Isobutyl chloroformate (15.5 ml; 118 mmol) is added dropwise. The thick suspension is stirred for another 10 minutes at 0° C., diluted with THF (200 ml) and NH$_3$-gas introduced for 5 minutes, stirred for 15 minutes at 0° C. followed by a second NH$_3$-gas treatment for 5 minutes. The reaction mixture is warmed to room temperature and stirred for 30 minutes, poured on water and extracted with TBME three times. The combined organic phases are dried over Na$_2$SO$_4$, filtered, evaporated and purified via chromatography (SiO2; TBME ) to yield the title compound as colorless crystals (17.3 g; 80%).

1H-NMR (400 MHz; DMSO-d6): 7.60 (s, 1H); 7.42 (s, 1H); 4.19 (q, 2H); 4.09 (m, 4H); 1.40 (s, 9H); 1.22 (t, 3H). MS (m/z) ES+: 273 (MH+, 30); 173 (100).

EXAMPLE 156B

3-Cyano-azetidine-1,3-dicarboxylic acid 1-tert-butyl ester 3-ethyl ester

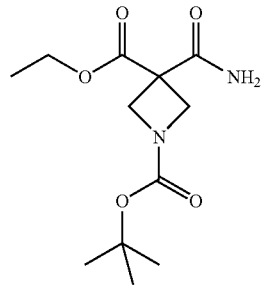

-continued

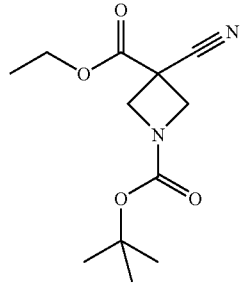

3-Carbamoyl-azetidine-1,3-dicarboxylic acid 1-tert-butyl ester 3-ethyl ester (25.4 g; 93.5 mmol) is dissolved in THF (260 ml) and pyridine (19.2 g; 243 mmol) and cooled to 0° C. under stirring. Trifluoroacetic acid anhydride (26.4 ml; 187 mmol) is added dropwise over 10 minutes, the mixture warmed to room temperature and stirred for 30 minutes, poured on water and extracted with TBME three times. The combined organic phases are dried over Na$_2$SO$_4$, filtered, evaporated and purified via chromatography (SiO2; heptane/TBME 6:4) to yield the title compound as light brown oil (22.4 g; 94%).

1H-NMR (400 MHz; DMSO-d6): 4.24 (m, 6H); 1.41 (s, 9H); 1.27 (t, 3H). MS (m/z) ES+: 255 (MH+).

EXAMPLE 156C

3-Aminomethyl-azetidine-1,3-dicarboxylic acid 1-tert-butyl ester 3-methyl ester

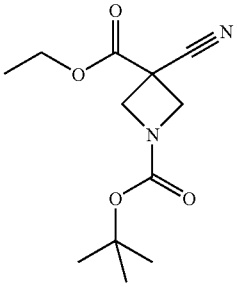

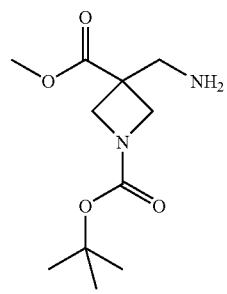

3-Cyano-azetidine-1,3-dicarboxylic acid 1-tert-butyl ester 3-ethyl ester (7.75 g; 30.5 mmol) in methanol (1000 ml) is combined with wet RaNi (~28 g) and hydrogenated at room temperature under 1 atm of hydrogen for 2 hours. The reaction mixture is filtered and evaporated to dryness to yield the title compound as light brown resin, which crystallizes slowly (6.8 g; 91%).

1H-NMR (400 MHz; DMSO-d6): 3.91 (bs, 2H); 3.75 (bs, 2H); 3.68 (s, 3H); 2.92 (s, 2H); 1.61 (bs, 2H); 1.38 (s, 9H). MS (m/z) ES+: 245 (MH+, 30); 189 (60); 145 (100).

EXAMPLE 156D

3-[(2-Ethoxycarbonyl-acetylamino)-methyl]-azetidine-1,3-dicarboxylic acid 1-tert-butyl ester 3-methyl ester

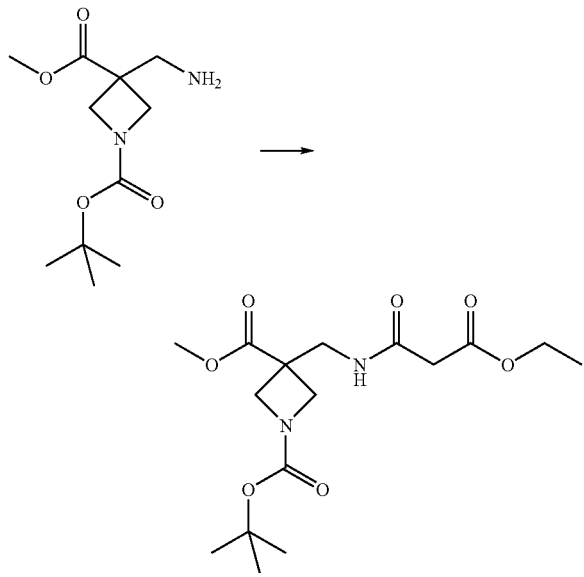

3-Aminomethyl-azetidine-1,3-dicarboxylic acid 1-tert-butyl ester 3-methyl ester (3.11 g; 12.7 mmol) and triethylamine (1.95 ml; 14.01 mmol) in CH$_2$Cl$_2$ (55 ml) are cooled to 0° C. under stirring. Chlorocarbonyl-acetic acid ethyl ester (1.9 g; 12.74 mmol) in CH$_2$Cl$_2$ (15 ml) is added dropwise within 15 minutes. The reaction mixture is warmed to room temperature and stirred for 30 minutes, poured on 10% aqueous NaHCO3 and extracted with CH$_2$Cl$_2$ three times. The combined organic phases are dried over Na$_2$SO$_4$, filtered, evaporated and purified via chromatography (SiO2; TBME/MeOH 97:3) to yield the title compound as colorless resin (3.8 g; 77%), which crystallizes slowly.

1H-NMR (400 MHz; DMSO-d6): 8.33 (bt, 1H); 4.09 (q, 2H); 3.95 (bs, 2H); 3.79 (bs, 2H); 3.69 (s, 3H); 3.56 (d, 2H); 3.24 (s, 2H); 1.39 (s, 9H); 1.19 (t, 3H). MS (m/z) ES+: 359 (MH+; 45); 303 (100); 259 (60).

EXAMPLE 156E 7,9-Dioxo-2,6-diaza-spiro[3.5]nonane-2,8-dicarboxylic acid 2-tert-butyl ester 8-methyl ester

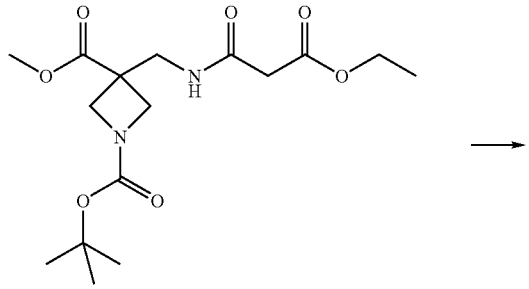

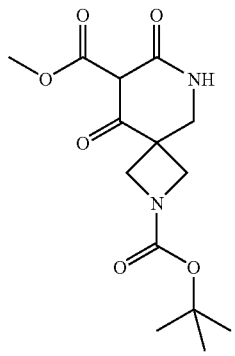

Sodium metal (870 mg; 38 mmol) is dissolved in methanol (55 ml) and combined with a solution of 3-[(2-ethoxycarbonyl-acetylamino)-methyl]-azetidine-1,3-dicarboxylic acid 1-tert-butyl ester 3-methyl ester in toluene (165 ml). The reaction mixture is heated to 90° C. for 1 hour, cooled to 7-9° C. and the precipitated white crystals (Na-salt of title compound) filtered off. The crystals are dissolved in water, acidified by the addition of 2N HCl and extracted with CH$_2$Cl$_2$ three times. The combined organic phases are dried over Na$_2$SO$_4$, filtered, evaporated and yield the title compound as white crystals (5.6 g; 48%). A second crop of the title compound is obtained by evaporating the above toluene/methanol filtrate to almost dryness, taking up the resin in 2N HCl and extracting with CH$_2$Cl$_2$ three times. The combined organic phases are dried over Na$_2$SO$_4$, filtered, evaporated and yielded the second crop of title compound as brownish solid (3.22 g; 27%).

1H-NMR (400 MHz; DMSO-d6): 9.18 (bs 1H); 3.92 (bs, 2H); 3.75 (s, 3H); 3.60 (bs, 4H); 1.39 (s, 9H).

MS (m/z) ES+: 313 (MH+, 30); 257 (100).

EXAMPLE 156F 7,9-Dioxo-2,6-diaza-spiro[3,5]nonane-2-carboxylic acid tert-butyl ester

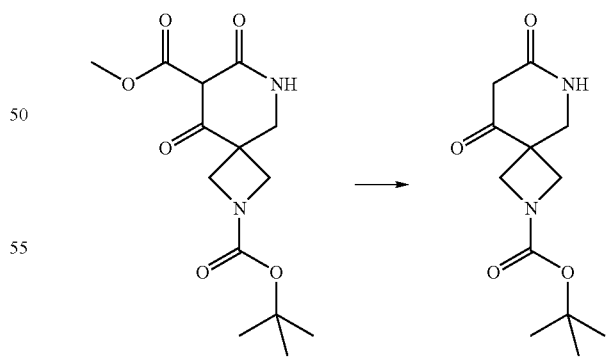

7,9-Dioxo-2,6-diaza-spiro[3.5]nonane-2,8-dicarboxylic acid 2-tert-butyl ester 8-methyl ester (Example 156g)(8.3 g; 26.6 mmol) is dissolved in acetonitrile/water (170 ml; 9/1) and refluxed for 1 hour. The reaction mixture is evaporated to dryness and delivers the title compound as white crystals (6.35 g; 94%).

1H-NMR (400 MHz; DMSO-d6): 8.12 (bs, 1H); 3.90 (bd, 2H); 3.63 (bd, 2H); 3.59 (d, 2H); 3.36 (s, 2H); 1.40 (s, 9H). MS (m/z) ES+: 255 (MH+, 40); 199 (100).

EXAMPLE 156G 2-(3-Aminomethyl-1-tert-butoxycarbonyl-azetidin-3-yl)-8-chloro-4,5-dihydro-1H-pyrrolo[2,3-f]isoquinoline-3-carboxylic acid lactam

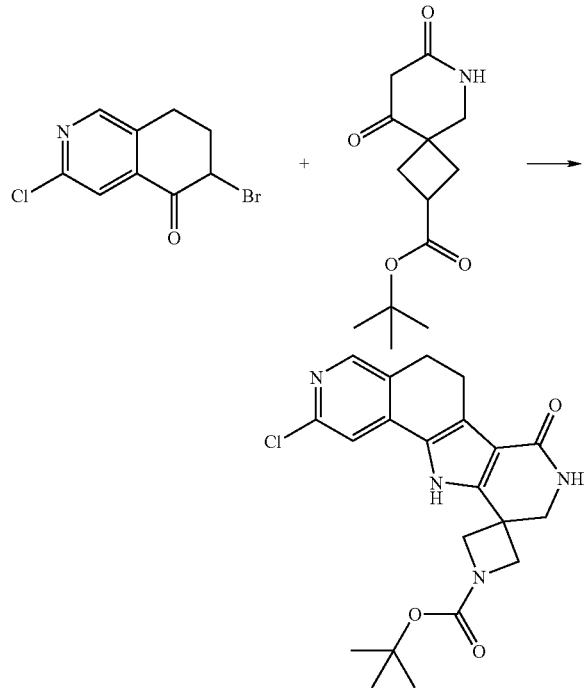

6-Bromo-3-chloro-7,8-dihydro-6H-isoquinolin-5-one (Example 1c)(1.57 g; 6.00 mmol) and 7,9-dioxo-2,6-diaza-spiro[3.5]nonane-2-carboxylic acid tert-butyl ester (Example 156)(1.83 g; 7.20 mmol) and NaOAc (492 mg; 6.00 mol) are suspended in MeOH (20 ml) and stirred over night at room temperature. The reaction mixture is evaporated to dryness and taken up in HOAc (35 ml), NH4OAc (9.2 g; 120 mmol) added and the mixture refluxed for 30 minutes.

1H-NMR (400 MHz; DMSO-d6): 12.11 (s, 1H); 8.14 (s, 1H); 7.59 (s, 1H); 7.25 (s, 1H); 4.08 (d, 2H); 3.88 (bs, 2H); 3.56 (2H); 2.89 (m, 2H); 2.83 (m, 2H); 1.42 (s, 9H).
MS (m/z) ES+: 415 (MH+).

EXAMPLE 157

2-(3-Aminomethyl-1-methyl-azetidin-3-yl)-8-[4-(2-morpholin-4-yl-ethoxy)-phenyl]-4,5-dihydro-1H-pyrrolo[2,3-f]isoquinoline-3-carboxylic acid lactam

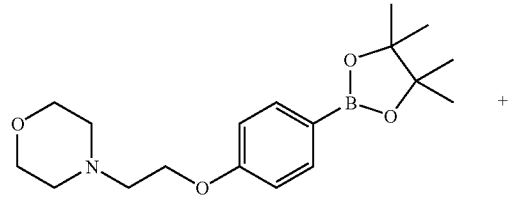

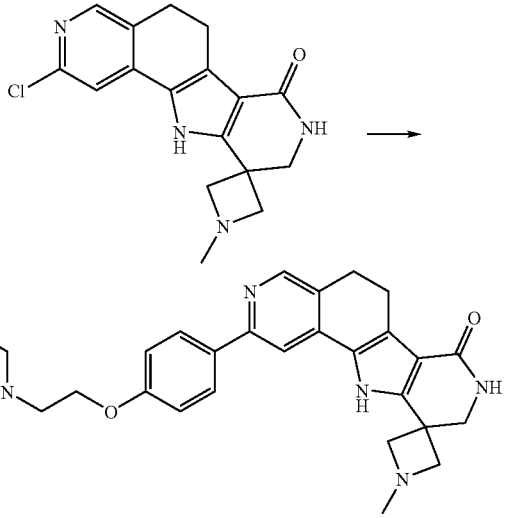

2-(3-Aminomethyl-1-methyl-azetidin-3-yl)-8-chloro-4,5-dihydro-1H-pyrrolo[2,3-f]isoquinoline-3-carboxylic acid lactam (Example 157b) and 4-{2-[4-(4,4,5,5-tetramethyl-[1,3,2]dioxaborolan-2-yl)-phenoxy]-ethyl}-morpholine (Focus Synthesis Products FS000534) are reacted in analogy to Example 1 and deliver the title compound as colorless crystals.

(MS (m/z) ES+: 500 (MH+). Retention time: 0.83 minutes (LC-MS method 2).

The starting material is prepared as follows:

EXAMPLE 157A 2-(3-Aminomethyl-azetidin-3-yl)-8-chloro-4,5-dihydro-1H-pyrrolo[2,3-f]isoquinoline-3-carboxylic acid lactam

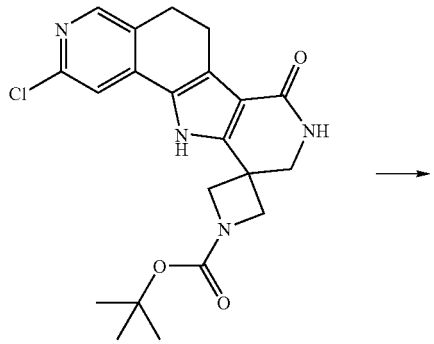

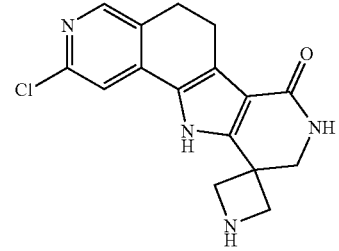

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156a) (170 mg; 0.41 mmol) is dissolved in HCl$_{conc}$ (2 ml), kept at room temperature for 2 minutes and then evaporated to dryness. The yellowish solid is dissolved in 0.5 N NaOH (4 ml). The title product precipitates as off-white solid (95 mg; 74%).

1H-NMR (400 MHz; DMSO-d6): 8.09 (s, 1H); 7.63 (s, 1H); 7.15 (bs, 1H); 3.77 (bd, 2H); 3.57 (bs, 2H); 3.35 (bd, 2H); 2.85 9 m, 2H); 2.80 (m, 2H).

(MS (m/z) ES+: 315 (MH+). Retention time: 1.14 minutes (LC-MS method 2).

EXAMPLE 157B 2-(3-Aminomethyl-1-methyl-azetidin-3-yl)-8-chloro-4,5-dihydro-1H-pyrrolo[2,3-f]isoquinoline-3-carboxylic acid lactam

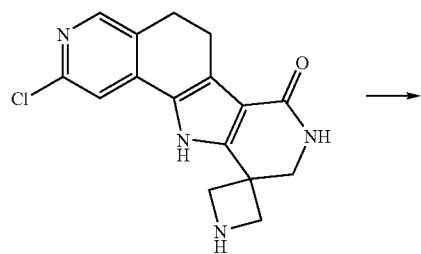

Azetidine N-methylation of 2-(3-aminomethyl-azetidin-3-yl)-8-chloro-4,5-dihydro-1H-pyrrolo[2,3-f]isoquinoline-3-carboxylic acid lactam (Example 157a) is performed in analogy to Example 222b to yield the title product as colorless crystals.

1H-NMR (400 MHz; DMSO-d6): 11.91 (bs, 1H); 8.07 (s, 1H); 7.64 (s, 1H); 7.11 (bs, 1H); 4.10 (bs, 2H); 3.65 (bs, 2H); 3.26 (bd, 2H); 2.84 (m, 2H); 2.79 (m, 2H); 2.33 (s, 3H).

MS (m/z) ES+: 329 (MH+). Retention time: 1.16 minutes (LC-MS method 2).

EXAMPLE 158

2-(1-Amino-cyclopropylmethyl)-8-(2-fluoro-6-methyl-pyridin-3-yl)-4,5-dihydro-1H-pyrrolo[2,3-f]isoquinoline-3-carboxylic acid lactam

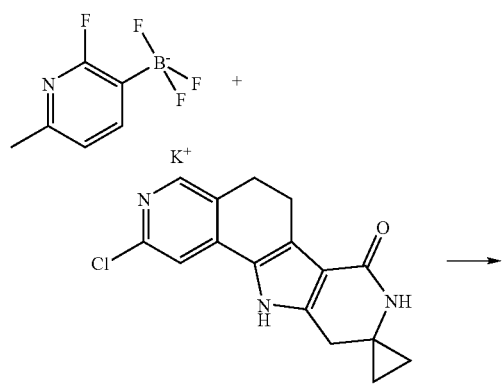

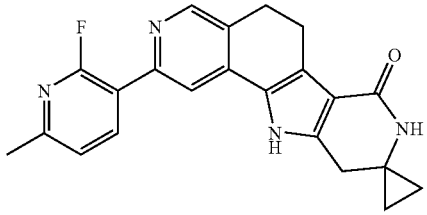

2-Fluoro-6-methylpyridine-3-trifluoroborate potassium salt (Frontier Scientific F10077) and 2-(1-amino-cyclopropylmethyl)-8-chloro-4,5-dihydro-1H-pyrrolo[2,3-f]isoquinoline-3-carboxylic acid lactam (Example 31.a) are coupled in analogy to Example 1 and yield the title compound as colorless crystals.

MS (m/z) ES+: 375 (MH+). Retention time: 1.86 minutes (LC-MS method 2).

EXAMPLE 159

2-(3-Aminomethyl-1-methyl-azetidin-3-yl)-8-(6-fluoro-pyridin-3-yl)-4,5-dihydro-1H-pyrrolo[2,3-f]isoquinoline-3-carboxylic acid lactam

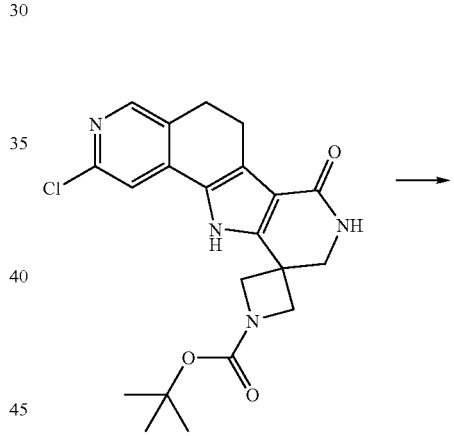

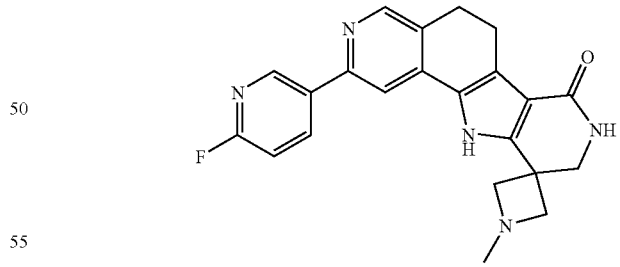

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 2-fluoropyridine-5-boronic acid (ABCR, AB181129) are coupled in analogy to Example 1. The BOC-protective group is removed in analogy to Example 156. N-methylation is performed in analogy to Example 222b and delivers the title compound as colorless crystals. MS (m/z) ES+: 390 (MH+). Retention time: 1.27 minutes (LC-MS method 2).

EXAMPLE 160

2-(3-Aminomethyl-azetidin-3-yl)-8-(6-fluoro-pyridin-3-yl)-4,5-dihydro-1H-pyrrolo[2,3-f]isoquinoline-3-carboxylic acid lactam hydrochloride

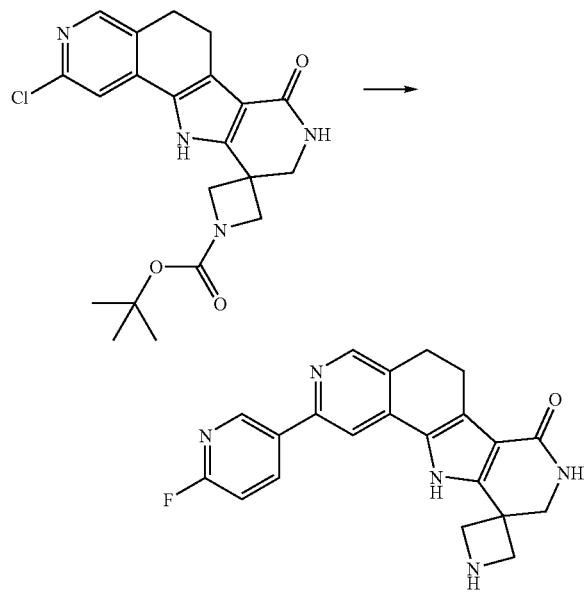

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 2-fluoropyridine-5-boronic acid (ABCR, AB181129) are coupled in analogy to Example 1. The BOC-protective group is removed in analogy to Example 156, delivering the title compound as yellow crystals. MS (m/z) ES+:376 (MH+). Retention time: 1.24 minutes (LC-MS method 2).

EXAMPLE 161

2-(3-Aminomethyl-1-methyl-azetidin-3-yl)-8-(6-fluoro-pyridin-3-yl)-1-methyl-4,5-dihydro-1H-pyrrolo[2,3-f]isoquinoline-3-carboxylic acid lactam

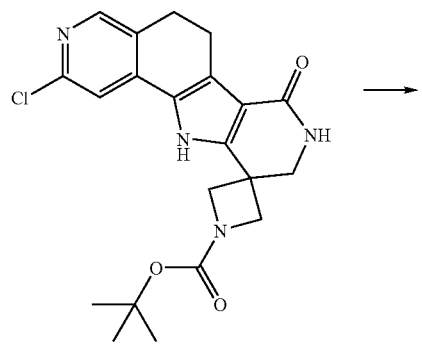

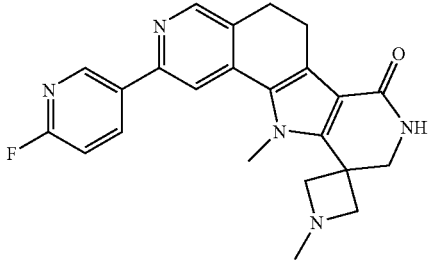

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 2-fluoropyridine-5-boronic acid (ABCR, AB181129) are coupled in analogy to Example 1. Pyrrole-N-methylation is performed in analogy to Example 137a. The BOC-protective group is removed in analogy to Example 156. Azetidine-N-methylation is carried out in analogy to Example 222b delivering the title compound as colorless crystals. MS (m/z) ES+:404 (MH+). Retention time: 1.33 minutes (LC-MS method 2).

EXAMPLE 162

2-(3-Aminomethyl-azetidin-3-yl)-8-(6-fluoro-pyridin-3-yl)-1-methyl-4,5-dihydro-1H-pyrrolo[2,3-f]isoquinoline-3-carboxylic acid lactam hydrochloride

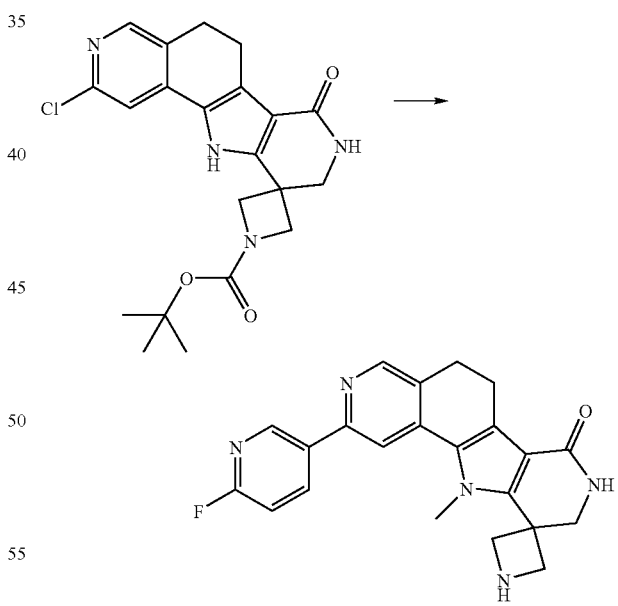

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 2-fluoropyridine-5-boronic acid (ABCR, AB181129) are coupled in analogy to Example 1. Pyrrole-N-methylation is performed in analogy to Example 137a. The BOC-protective group is removed in analogy to Example 156, delivering the title compound as yellow crystals. MS (m/z) ES+:390 (MH+). Retention time: 1.30 minutes (LC-MS method 2).

EXAMPLE 163

2-(3-Aminomethyl-azetidin-3-yl)-8-(4-methoxy-phenyl)-1-methyl-4,5-dihydro-1H-pyrrolo[2,3-f]isoquinoline-3-carboxylic acid lactam hydrochloride

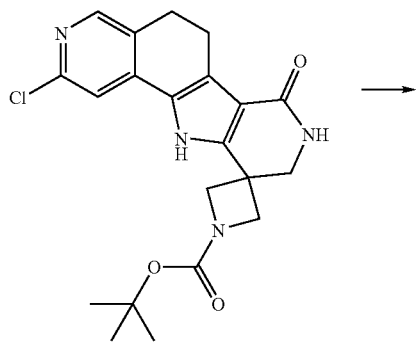

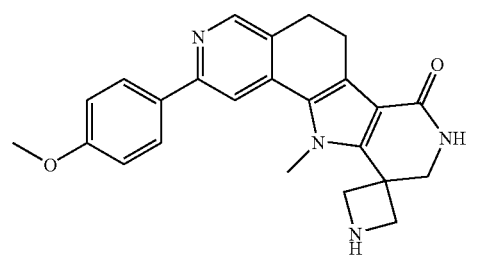

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 4-methoxyphenyl-boronic acid (ABCR Product List, AB169111) are coupled in analogy to Example 1. Pyrrole-N-methylation is performed in analogy to Example 137a. The BOC-protective group is removed in analogy to Example 156, delivering the title compound as yellow crystals. MS (m/z) ES+:401 (MH+). Retention time: 1.12 minutes (LC-MS method 2).

EXAMPLE 164

2-(3-Aminomethyl-1-methyl-azetidin-3-yl)-8-(4-methoxy-phenyl)-1-methyl-4,5-dihydro-1H-pyrrolo[2,3-f]isoquinoline-3-carboxylic acid lactam

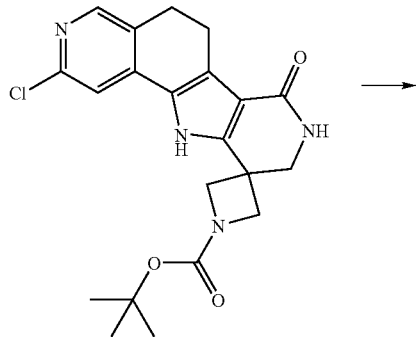

-continued

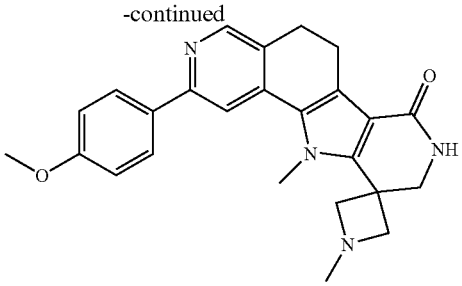

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 4-methoxyphenyl-boronic acid (ABCR Product List, AB169111) are coupled in analogy to Example 1. Pyrrole-N-methylation is performed in analogy to Example 137a. The BOC-protective group is removed in analogy to Example 156. Azetidine-N-methylation is carried out in analogy to Example 222b delivering the title compound as colorless crystals. MS (m/z) ES+:415 (MH+). Retention time: 1.15 minutes (LC-MS method 2).

EXAMPLE 165

2-(3-Aminomethyl-azetidin-3-yl)-8-(4-methoxy-phenyl)-4,5-dihydro-1H-pyrrolo[2,3-f]isoquinoline-3-carboxylic acid lactam hydrochloride

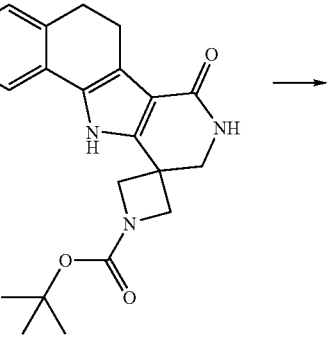

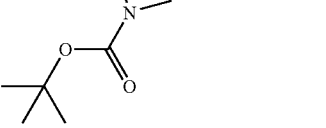

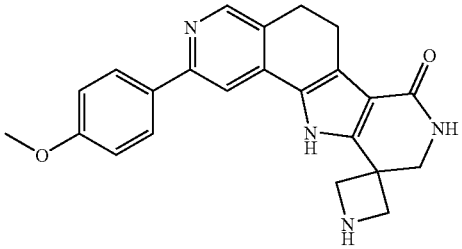

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 4-methoxyphenyl-boronic acid (ABCR Product List, AB169111) are coupled in analogy to Example 1. The BOC-protective group is removed in analogy to Example 156, delivering the title compound as yellow crystals. MS (m/z) ES+:387 (MH+). Retention time: 1.03 minutes (LC-MS method 2).

EXAMPLE 166

2-(3-Aminomethyl-azetidin-3-yl)-8-(6-trifluoromethyl-pyridin-3-yl)-4,5-dihydro-1H-pyrrolo[2,3-f]isoquinoline-3-carboxylic acid lactam hydrochloride

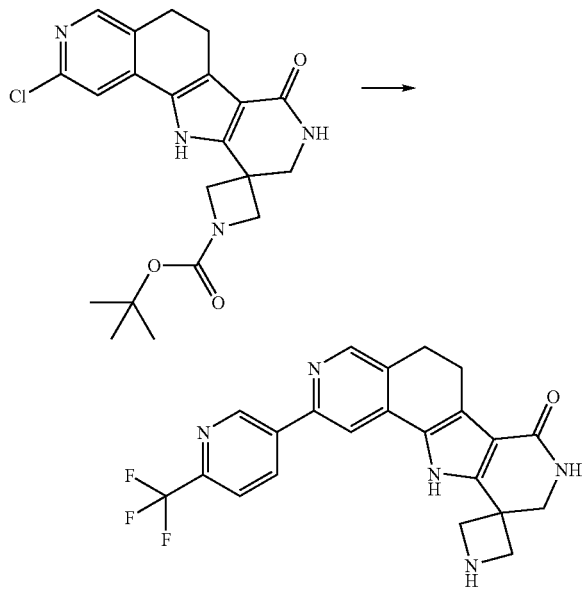

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 2-trifluoromethyl-pyridine-5-boronic acid (Focus Synthesis Product List, FS000599) are coupled in analogy to Example 1 The BOC-protective group is removed in analogy to Example 156, delivering the title compound as yellow crystals. MS (m/z) ES+:426 (MH+). Retention time: 1.94 minutes (LC-MS method 3).

EXAMPLE 167

2-(3-Aminomethyl-1-methyl-azetidin-3-yl)-8-(6-trifluoromethyl-pyridin-3-yl)-1-methyl-4,5-dihydro-1H-pyrrolo[2,3-f]isoquinoline-3-carboxylic acid lactam

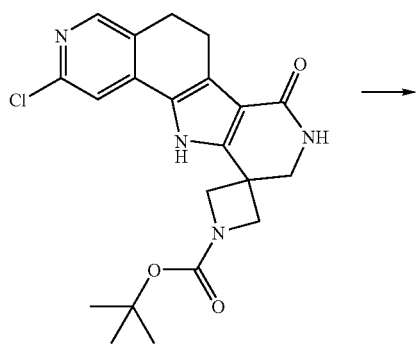

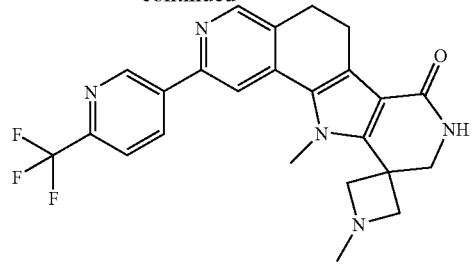

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 2-trifluoromethyl-pyridine-5-boronic acid (Focus Synthesis Product List, FS000599) are coupled in analogy to Example 1. Pyrrole-N-methylation is performed in analogy to Example 137a. The BOC-protective group is removed in analogy to Example 156. Azetidine-N-methylation is carried out in analogy to Example 222b delivering the title compound as colorless crystals. MS (m/z) ES+:454 (MH+). Retention time: 2.04 minutes (LC-MS method 3).

EXAMPLE 168

2-(3-Aminomethyl-1-methyl-azetidin-3-yl)-8-(6-trifluoromethyl-pyridin-3-yl)-4,5-dihydro-1H-pyrrolo[2,3-f]isoquinoline-3-carboxylic acid lactam

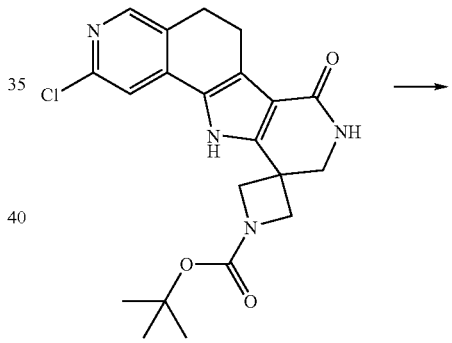

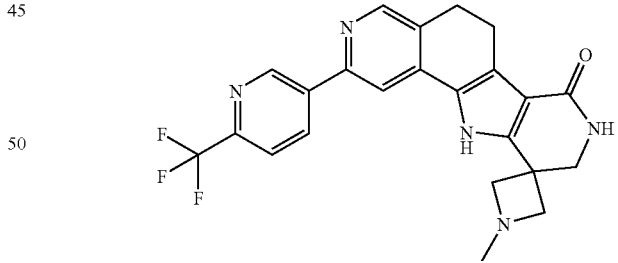

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 2-trifluoromethyl-pyridine-5-boronic acid (Focus Synthesis Product List, FS000599) are coupled in analogy to Example 1 The BOC-protective group is removed in analogy to Example 156. Azetidine-N-methylation is carried out in analogy to Example 222b delivering the title compound as colorless crystals.

MS (m/z) ES+:440 (MH+). Retention time: 1.98 minutes (LC-MS method 3).

EXAMPLE 169

2-(3-Aminomethyl-azetidin-3-yl)-8-(6-trifluoromethyl-pyridin-3-yl)-1-methyl-4,5-dihydro-1H-pyrrolo[2,3-f]isoquinoline-3-carboxylic acid lactam hydrochloride

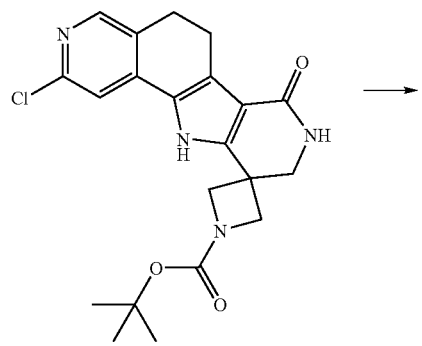

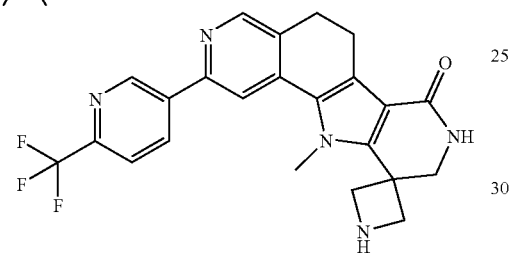

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 2-trifluoromethyl-pyridine-5-boronic acid (Focus Synthesis Product List, FS000599) are coupled in analogy to Example 1. Pyrrole-N-methylation is performed in analogy to Example 137a. The BOC-protective group is removed in analogy to Example 156, delivering the title compound as yellow crystals. MS (m/z) ES+: 440 (MH+). Retention time: 1.98 minutes (LC-MS method 3).

EXAMPLE 170

2-(3-Aminomethyl-azetidin-3-yl)-8-(2-fluoro-phenyl)-4,5-dihydro-1H-pyrrolo[2,3-f]isoquinoline-3-carboxylic acid lactam hydrochloride

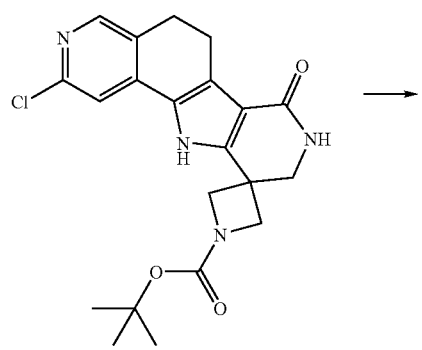

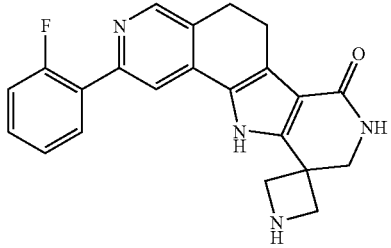

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 2-fluorophenylboronic acid (Maybridge Building Blocks AC 35934) are coupled in analogy to Example 1. The BOC-protective group is removed in analogy to Example 156, delivering the title compound as yellow crystals. MS (m/z) ES+: 375 (MH+). Retention time: 1.34 minutes (LC-MS method 2).

EXAMPLE 171

2-(3-Aminomethyl-1-methyl-azetidin-3-yl)-8-(2-fluoro-phenyl)-1-methyl-4,5-dihydro-1H-pyrrolo[2,3-f]isoquinoline-3-carboxylic acid lactam

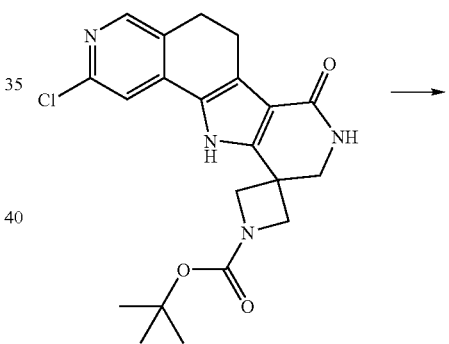

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 2-fluorophenylboronic acid (Maybridge Building Blocks AC 35934) are coupled in analogy to Example 1. Pyrrole-N-methylation is performed in analogy to Example 137a. The BOC-protective group is removed in analogy to Example 156. Azetidine-N-methylation is carried out in analogy to Example 222b delivering the title compound as colorless crystals. MS (m/z) ES+: 403 (MH+). Retention time: 1.35 minutes (LC-MS method 2).

EXAMPLE 172

2-(3-Aminomethyl-1-methyl-azetidin-3-yl)-8-(2-fluoro-phenyl)-4,5-dihydro-1H-pyrrolo[2,3-f]isoquinoline-3-carboxylic acid lactam

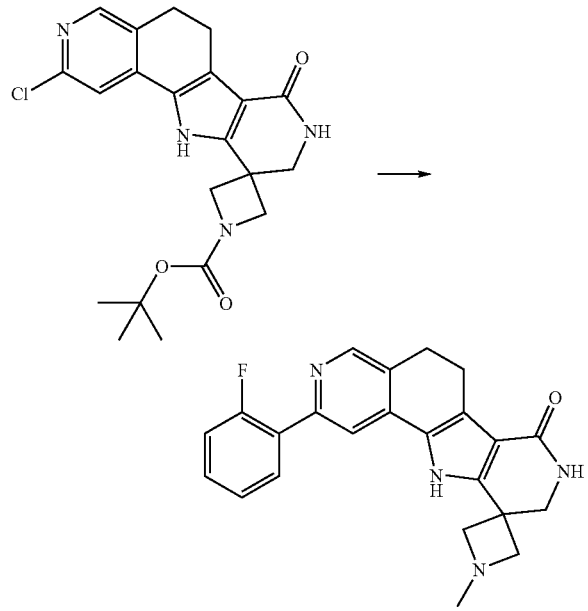

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 2-fluorophenylboronic acid (Maybridge Building Blocks AC 35934) are coupled in analogy to Example 1. The BOC-protective group is removed in analogy to Example 156. Azetidine-N-methylation is carried out in analogy to Example 222b delivering the title compound as colorless crystals.

1H-NMR (400 MHz; DMSO-d6): 11.91 (bs, 1H); 8.45 (s, 1H); 8.00 (s, 1H); 7.85 (dt, 1H); 7.49 (m, 1H); 7.37 (m, 2H); 7.18 (bs, 1H); 3.58 (s, 2H); 3.31 (m, 4H); 2.92 (m, 4H); 2.39 (s, 3H).

MS (m/z) ES+:389 (MH+). Retention time: 1.18 minutes (LC-MS method 2).

EXAMPLE 173

2-(3-Aminomethyl-azetidin-3-yl)-8-(2-fluoro-phenyl)-1-methyl-4,5-dihydro-1H-pyrrolo[2,3-f]isoquinoline-3-carboxylic acid lactam hydrochloride

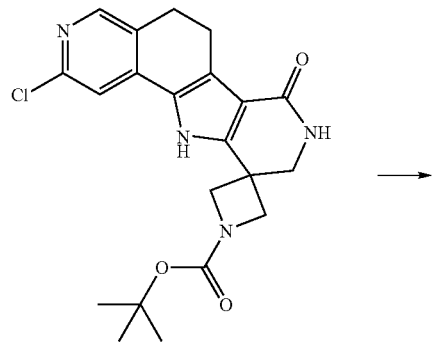

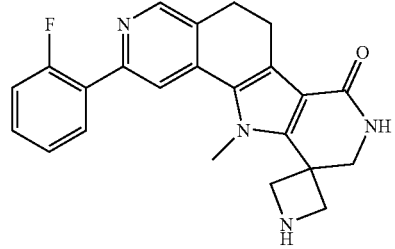

2-(3-Aminomethyl-1-tert-butoxycarbonyl-azetidin-3-yl)-8-chloro-4,5-dihydro-1H-pyrrolo[2,3-f]isoquinoline-3-carboxylic acid lactam (Example 156b) and 2-fluorophenylboronic acid (Maybridge Building Blocks AC 35934) are coupled in analogy to Example 1. Pyrrole-N-methylation is performed in analogy to Example 137a. The BOC-protective group is removed in analogy to Example 156, delivering the title compound as yellow crystals. MS (m/z) ES+:389 (MH+). Retention time: 1.31 minutes (LC-MS method 2).

EXAMPLE 174

2-(1-Acetyl-3-aminomethyl-azetidin-3-yl)-8-(2-fluoro-phenyl)-4,5-dihydro-1H-pyrrolo[2,3-f]isoquinoline-3-carboxylic acid lactam

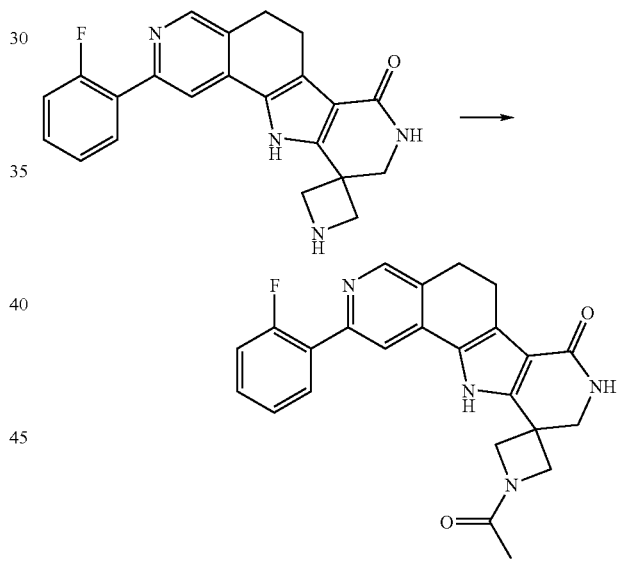

2-(3-Aminomethyl-azetidin-3-yl)-8-(2-fluoro-phenyl)-4,5-dihydro-1H-pyrrolo[2,3-f]isoquinoline-3-carboxylic acid lactam hydrochloride (Example 170) (60 mg; 0.136 mmol) and triethylamine (0.066 ml; 0.476 mmol) are dissolved in THF (1 ml), cooled to 0° C. and combined with acetyl chloride (0.012 mg; 0.15 mmol). The reaction mixture is stirred for 5 minutes and poured on 2N NaHCO₃/TBME (10 ml/20 ml). The white precipitate is filtered, washed with water, taken up in MeOH, filtered, evaporated to dryness and delivers the title compound as white crystals.

1H-NMR (400 MHz; DMSO-d6): 8.18 (s, 1H); 7.85 (dt, 1H); 7.72 (s, 1H); 7.35 (m, 1H); 7.20 (m, 2H); 4.19 (bs, 2H); 3.94 (bs, 2H); 3.46 (s, 2H); 2.91 (m, 2H); 2.77 (m, 2H); 1.81 (s, 3H).

MS (m/z) ES+:417 (MH+). Retention time: 1.45 minutes (LC-MS method 2).

EXAMPLE 175

2-(3-aminomethyl-1-ethyl-azetidin-3-yl)-8-(2-fluoro-phenyl)-4,5-dihydro-1H-pyrrolo[2,3-f]isoquinoline-3-carboxylic acid lactam

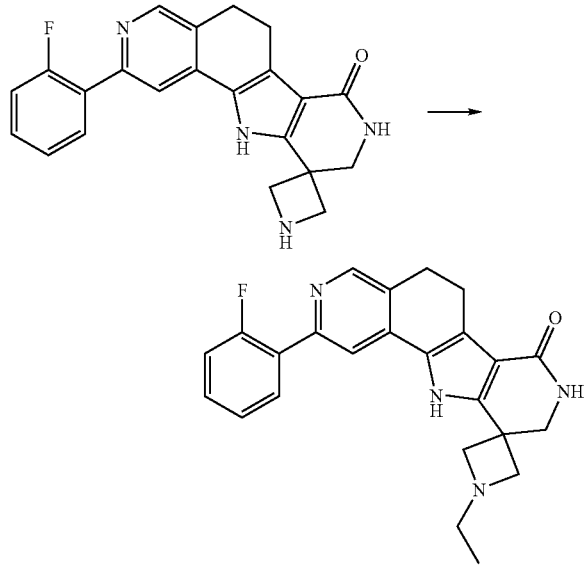

2-(3-Aminomethyl-azetidin-3-yl)-8-(2-fluoro-phenyl)-4,5-dihydro-1H-pyrrolo[2,3-f]isoquinoline-3-carboxylic acid lactam hydrochloride (Example 170) (60 mg; 0.136 mmol), triethylamine (0.066 ml; 0.476 mmol) and ethyl bromide (0.08 ml; 1.07 mmol) are dissolved in methanol and refluxed for 30 minutes. A second portion of ethyl bromide (0.08 ml; 1.07 mmol) is added and refluxing continued for another 30 minutes. The reaction mixture is diluted with $CH_2Cl_2$, filtered and purified via chromatography (SiO2, $CH_2Cl_2$/MeOH/NH$_{3\ conc}$ 90:10:1) to yield the title compound as yellowish crystals (35 mg; 65%).

1H-NMR (400 MHz; DMSO-d6): 12.18 (bs, 1H); 8.49 (s, 1H); 7.99 (s, 1H); 7.89 (dt, 1H); 7.49 (m, 1H); 7.37 (m, 3H); 3.93 (m, 2H); 3.82 (m, 4H); 3.71 (s, 2H); 2.97 (m, 2H); 2.89 (m, 2H); 1.07 (t, 3H).

MS (m/z) ES+:403 (MH+). Retention time: 1.25 minutes (LC-MS method 2).

EXAMPLE 176

2-[3-Aminomethyl-1-(2-fluoro-ethyl)-azetidin-3-yl]-8-(2-fluoro-phenyl)-4,5-dihydro-1H-pyrrolo[2,3-f]isoquinoline-3-carboxylic acid lactam

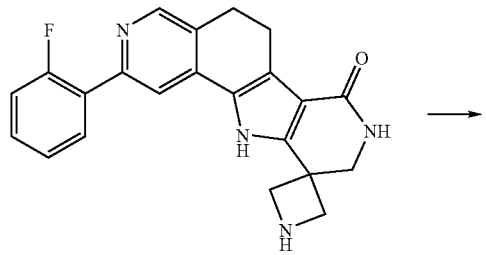

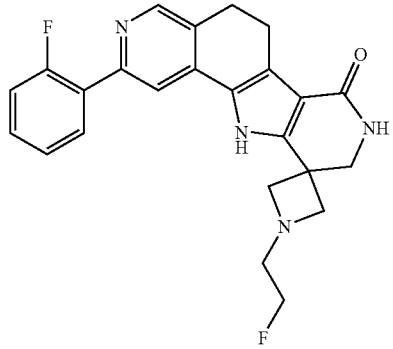

2-(3-Aminomethyl-azetidin-3-yl)-8-(2-fluoro-phenyl)-4,5-dihydro-1H-pyrrolo[2,3-f]isoquinoline-3-carboxylic acid lactam hydrochloride (Example 170) (60 mg; 0.136 mmol), triethylamine (0.066 ml; 0.476 mmol) and 1-fluoro-2-iodo-ethane (100 mg; 0.6 mmol) are refluxed in MeOH (1 ml) for 1 hour. The reaction mixture is diluted with $CH_2Cl_2$, filtered and purified via chromatography (SiO2, $CH_2Cl_2$/MeOH/NH$_{3\ conc}$ 93:7:0.7) to yield the title compound as yellowish crystals (21 mg; 38%).

1H-NMR (400 MHz; DMSO-d6): 11.49 (bs, 1H); 8.41 (s, 1H); 7.91 (s, 1H); 7.86 (dt, 1H); 7.40 (m, 1H); 7.25 (m, 2H); 6.66 (bs, 1H); 4.55 (m, 1H); 4.43 (m, 1H); 3.66 (s, 2H); 3.60 (m, 2H); 3.50 (m, 2H); 2.99 (m, 4H); 2.93 (m, 2H). MS (m/z) ES+:421 (MH+). Retention time: 1.31 minutes (LC-MS method 2).

EXAMPLE 177

2-(3-Aminomethyl-1-methyl-azetidin-3-yl)-8-(3-fluoro-phenyl)-4,5-dihydro-furo[2,3-f]isoquinoline-3-carboxylic acid lactam

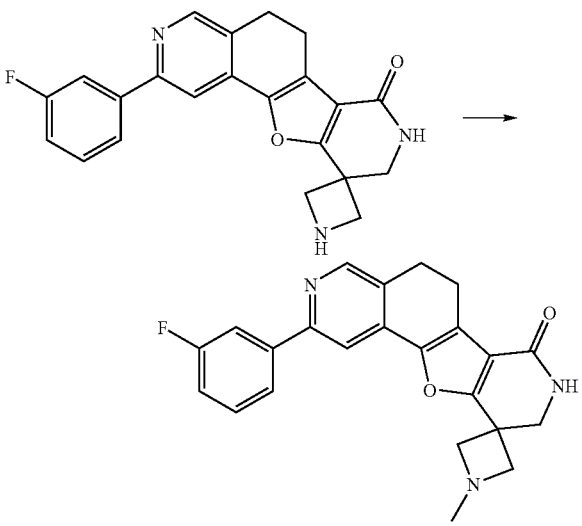

2-(3-Aminomethyl-azetidin-3-yl)-8-(3-fluoro-phenyl)-4,5-dihydro-furo[2,3-f]isoquinoline-3-carboxylic acid lactam hydrochloride (Example 178) is treated in analogy to Example 222b and delivers the title compound as yellowish crystals.

1H-NMR (400 MHz; DMSO-d6): 8.56 (s, 1H); 8.00 (m, 2H); 7.94 (dd, 1H); 7.71 (s, 1H); 7.59 (m, 1H); 7.31 (dt, 1H); 4.00-3.65 (m, 4H); 3.77 (s, 2H); 3.02 (m, 2H); 2.97 (m, 2H); 2.45 (s, 3H).

MS (m/z) ES+:390 (MH+). Retention time: 1.90 minutes (LC-MS method 3).

EXAMPLE 178

2-(3-Aminomethyl-azetidin-3-yl)-8-(3-fluoro-phenyl)-4,5-dihydro-furo[2,3-f]isoquinoline-3-carboxylic acid lactam hydrochloride

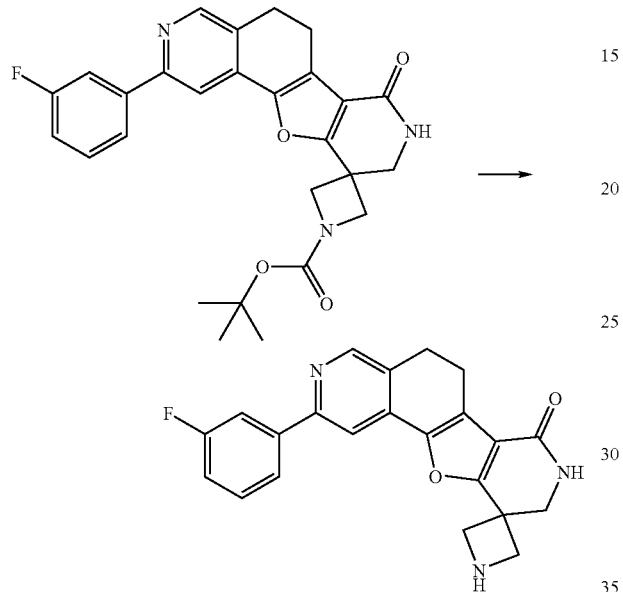

2-(3-Aminomethyl-1-tert-butoxycarbonyl-azetidin-3-yl)-8-(3-fluoro-phenyl)-4,5-dihydro-furo[2,3-f]isoquinoline-3-carboxylic acid lactam (Example 178a) is treated in analogy to Example 156 and yields the title compound as yellow crystals (56 mg; 59%)

1H-NMR (400 MHz; DMSO-d6): 9.70 (bs, 1H); 9.32 (bs, 1H); 8.60 (s, 1H); 8.10 (s, 1H); 7.95 (d, 1H); 7.90 (d, 1H); 7.60 (m, 1H); 7.35 (dt, 1H); 4.45 (m, 2H); 4.06 (m, 2H); 3.86 (s, 2H); 3.05 (m, 2H); 2.98 (m, 2H). MS (m/z) ES+:376 (MH+). Retention time: 1.59 minutes (LC-MS method 2).

EXAMPLE 178A 2-(3-Aminomethyl-1-tert-butoxycarbonyl-azetidin-3-yl)-8-(3-fluoro-phenyl)-4,5-dihydro-furo[2,3-f]isoquinoline-3-carboxylic acid lactam

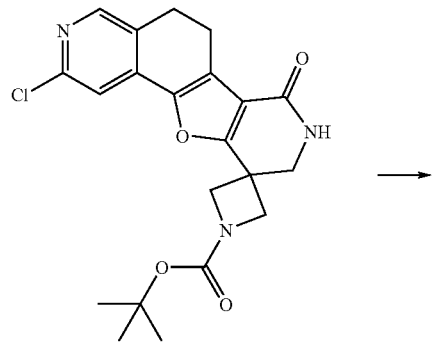

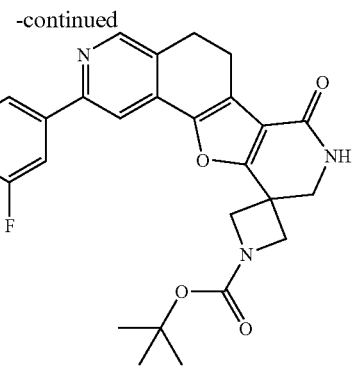

2-(3-Aminomethyl-1-tert-butoxycarbonyl-azetidin-3-yl)-8-chloro-4,5-dihydro-furo[2,3-f]isoquinoline-3-carboxylic acid lactam (Example 178b) and 3-fluorophenylboronic acid (Sigma-Aldrich, order number 441643) are reacted in analogy to Example 1 and provide the title compound as colorless crystals (118 mg; 98%).

MS (m/z) ES+:476 (MH+) Retention time: 2.96 minutes (LC-MS method 2).

EXAMPLE 178B 2-(3-Aminomethyl-1-tert-butoxycarbonyl-azetidin-3-yl)-8-chloro-4,5-dihydro-furo[2,3-f]isoquinoline-3-carboxylic acid lactam

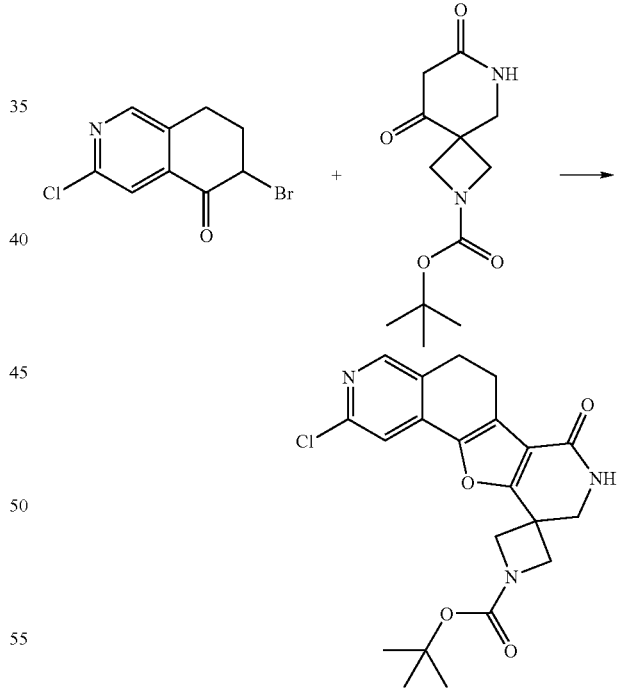

6-Bromo-3-chloro-7,8-dihydro-6H-isoquinolin-5-one (Example 1c)(140 mg; 0.54 mmol) and 7,9-dioxo-2,6-diazaspiro[3.5]nonane-2-carboxylic acid tert-butyl ester (Example 156)(150 mg; 0.59 mmol) and Cs$_2$CO$_3$ (175 mg; 0.537 mmol) are dissolved in methanol/water (2 ml/0.2 ml) stirred for 10 minutes at room temperature and 35 minutes at 50° C. The reaction mixture is evaporated to dryness, taken up in H$_2$SO$_{4conc}$ (2 ml) and stirred for 5 minutes at room temperature. The reaction mixture is poured on a saturated solution of Na₂CO₃, combined with (BOC)₂O (600 mg; 2.7 mmol) and extracted with TBME three times. The combined organic phases are dried over Na₂SO₄, filtered and evaporated to dryness to deliver a crystalline residue, which is washed with diethyl ether/ethanol and yields the title compound as colorless crystals (104 mg; 47%).

1H-NMR (400 MHz; DMSO-d6): 8.26 (s, 1H); 7.70 (s, 1H); 7.52 (s, 1H); 4.15 (bd, 2H); 3.95 (bd, 2H); 3.69 (d, 2H); 2.94 (dd, 4H); 1.45 (s, 9H). MS (m/z) ES+:416 (MH+).

EXAMPLE 179

2-(1'-Amino-bicyclopropyl-1-yl)-8-(6-fluoro-pyridin-3-yl)-4,5-dihydro-1H-pyrrolo[2,3-f]isoquinoline-3-carboxylic acid lactam

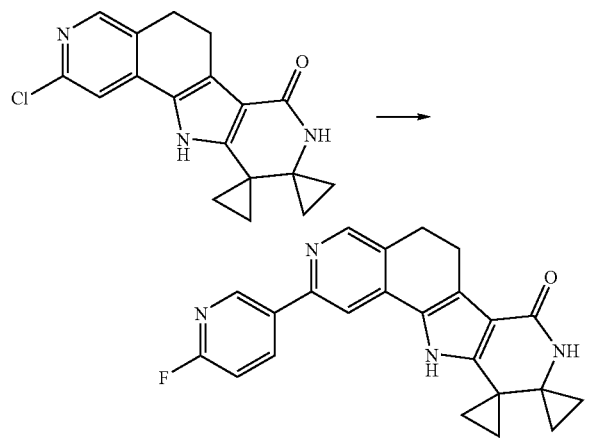

2-(1'-Amino-bicyclopropyl-1-yl)-8-chloro-4,5-dihydro-1H-pyrrolo[2,3-f]isoquinoline-3-carboxylic acid lactam (Example 179d) and 2-fluoropyridine-5-boronic acid (ABCR Product List, AB175600) are coupled in analogy to Example 1 and provide the title compound as colorless crystals (29 mg; 58%).

1H-NMR (400 MHz; DMSO-d6): 11.19 (s, 1H); 8.82 (d, 1H); 8.54 (dt, 1H); 8.41 (s, 1H); 7.99 (s, 1H); 7.36 (dd, 1H); 7.26 (s, 1H); 2.95 (m, 2H); 2.89 (m, 2H); 1.11 (m, 2H); 0.84 (m, 2H); 0.66 (m, 2H); 0.52 (m, 2H). MS (m/z) ES+: 387 (MH+). Retention time: 1.97 minutes (LC-MS method 2).

The starting material is prepared as follows:

EXAMPLE 179A

1'-(2-Ethoxycarbonyl-acetylamino)-bicyclopropyl-1-carboxylic acid ethyl ester

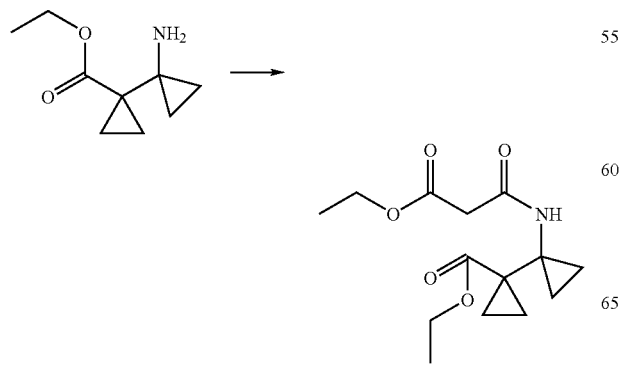

Chlorocarbonyl-acetic acid ethyl ester (1.24 ml; 11.2 mmol) in CH₂Cl₂ (5 ml) is added dropwise under stirring within 15 minutes at room temperature to a solution of 1'-amino-bicyclopropyl-1-carboxylic acid ethyl ester (1.38 g; 8.16 mmol) (Synlett. 2003, 2, 265) and triethylamine (1.02 ml; 10.4 mmol) in CH₂Cl₂ (100 ml). Stirring is continued for 5 minutes, then the reaction mixture is poured on water, acidified with 2N HCl and extracted with CH₂Cl₂ three times. The combined organic phases are dried over Na₂SO₄, filtered and evaporated to dryness. The combined organic phases are dried over Na₂SO₄, filtered, evaporated and purified via chromatography (SiO2; acetone/heptane 9:92>2/8) to yield the title compound as off-white crystals (1.9 g; 79%).

1H-NMR (400 MHz; DMSO-d6): 8.25 (s, 1H); 4.08 (q, 2H); 4.06 (q, 2H); 3.16 (s, 2H); 1.19 (t, 3H); 1.15 (t, 3H); 1.00 (m, 2H); 0.96 (m, 2H); 0.70 (m, 2H); 0.65 (m, 2H). MS (m/z) ES+: 284 (MH+).

EXAMPLE 179B 8,10-Dioxo-7-aza-dispiro[2.0.2.4]decane-9-carboxylic acid methyl ester

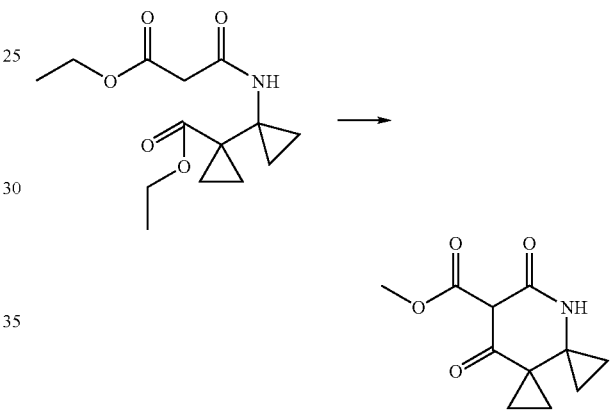

1'-(2-Ethoxycarbonyl-acetylamino)-bicyclopropyl-1-carboxylic acid ethyl ester (1 g; 3.53 mmol) in toluene (15 ml) is added rapidly to a solution of sodium (81 mg; 3.53 mmol) in methanol (3 ml) under stirring. The reaction mixture is warmed to 85° C. for 40 minutes, cooled to room temperature and the precipitate (sodium salt of title compound) filtered, washed with toluene, then heptane, dissolved in water (0.6 ml) and acidified with 2N HCl (1.75 ml). The resulting resin is decanted from water and crystallized by triturating with TBME (1 ml) to deliver the title compound as colorless crystals (633 mg; 80%).

1H-NMR (400 MHz; DMSO-d6): 8.73 (s, 1H); 4.85 (s, 1H); 3.73 (s, 3H); 0.78 (m, 2H); 0.70 (m, 2H); 0.58 (m, 2H); 0.52 (m, 2H). MS (m/z) ES+: 224 (MH+).

EXAMPLE 179C

7-Aza-dispiro[2.0.2.4]decane-8,10-dione

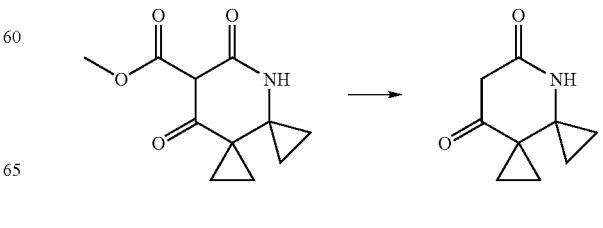

8,10-Dioxo-7-aza-dispiro[2.0.2.4]decane-9-carboxylic acid methyl ester (628 mg; 2.2 mmol) in acetonitrile/water (9 ml/0.9 ml) is refluxed for 50 minutes, cooled to room temperature, filtered and the filtrate evaporated to deliver the title compound as colorless solid (386 mg; 98%).

1H-NMR (400 MHz; DMSO-d6): 8.43 (s, 1H); 3.51 (s, 2H); 1.01 (m, 2H); 0.80 (m, 2H); 0.76 (m, 2H); 0.60 (m, 2H). MS (m/z) ES+: 166 (MH+).

EXAMPLE 179D 2-(1'-Amino-bicyclopropyl-1-yl)-8-chloro-4,5-dihydro-1H-pyrrolo[2,3-f]isoquinoline-3-carboxylic acid lactam

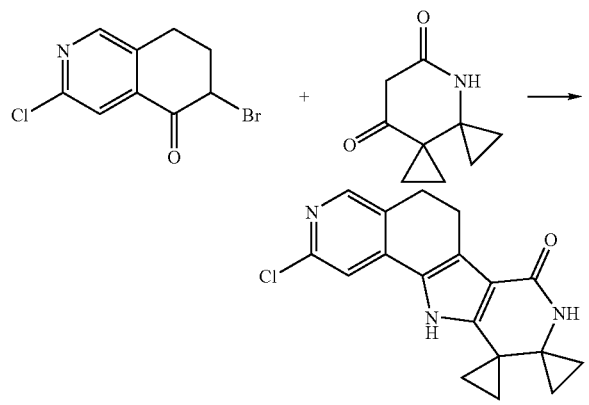

6-Bromo-3-chloro-7,8-dihydro-6H-isoquinolin-5-one (Example 1c)(71 mg; 0.27 mmol), 7-aza-dispiro[2.0.2.4]decane-8,10-dione (Example 180c)(50 mg; 0.30 mmol) and NaOAc (23 mg; 0.17 mmol) are dissolved in methanol (1 ml). The yellow solution is heated to 50° C. for 3 hours and evaporated to dryness. The residue is suspended in HOAc (2 ml), combined with NH$_4$OAc (212 mg; 2.7 mmol) and heated under argon for 2 hours at 120° C. The reaction mixture is poured on water and extracted with EtOAc three times. The combined organic phases are dried over Na$_2$SO$_4$, filtered, evaporated and purified via chromatography (SiO2; TBME/MeOH/NH3$_{conc}$ 95:5:1) to yield the title compound as yellowish crystals (54 mg; 60%) 1H-NMR (400 MHz; DMSO-d6): 11.23 (s, 1H); 8.08 (s, 1H); 7.43 (s, 1H); 7.26 (s, 1H); 2.91 (m, 2H); 2.82 (m, 2H); 1.10 (bs, 2H); 0.81 (bs, 2H); 0.65 (m, 2H); 0.51 (m, 2H). MS (m/z) ES+: 326 (MH+).

EXAMPLE 180

2-[3-(1-Amino-cyclopropyl)-azetidin-3-yl]-8-(3-fluoro-phenyl)-4,5-dihydro-1H-pyrrolo[2,3-f]isoquinoline-3-carboxylic acid lactam hydrochloride

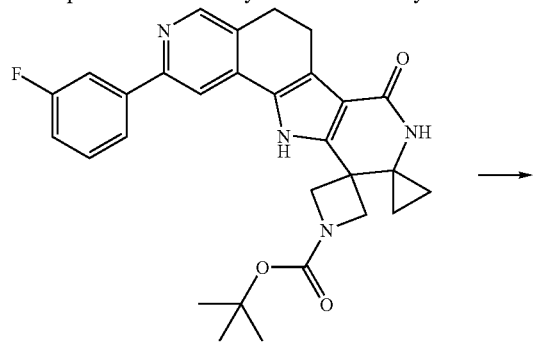

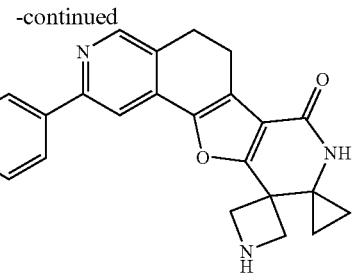

2-[3-(1-Amino-cyclopropyl)-1-tert-butoxycarbonyl-azetidin-3-yl]-8-(3-fluoro-phenyl)-4,5-dihydro-1H-pyrrolo[2,3-f]isoquinoline-3-carboxylic acid lactam (Example 180f) (11.5 mg; 0.023 mmol) is dissolved in HCl$_{conc}$ (1 ml), stirred at room temperature for 2 minutes and evaporated to dryness. The yellow crystals are washed with TBME and dried under vacuum to yield the title compound (11 mg; 100%).

1H-NMR (400 MHz; DMSO-d6): 13.74 (bs, 1H); 9.41 (bs, 1H); 9.26 (bs, 1H); 8.84 (s, 1H); 8.57 (s, 1H); 8.00 (d, 2H); 7.73 (m, 1H); 7.59 (s, 1H); 7.51 (m, 1H); 4.53 (m, 2H); 3.99 (m, 2H); 3.06 (bs, 4H); 1.22 (m, 2H); 0.89 (m, 2H). MS (m/z) ES+: 401 (MH+). Retention time: 1.44 minutes (LC-MS method 2).

The starting material is prepared as follows:

EXAMPLE 180A 3-(1-Amino-cyclopropyl)-azetidine-1,3-dicarboxylic acid 1-tert-butyl ester 3-isopropyl and ethyl ester ester

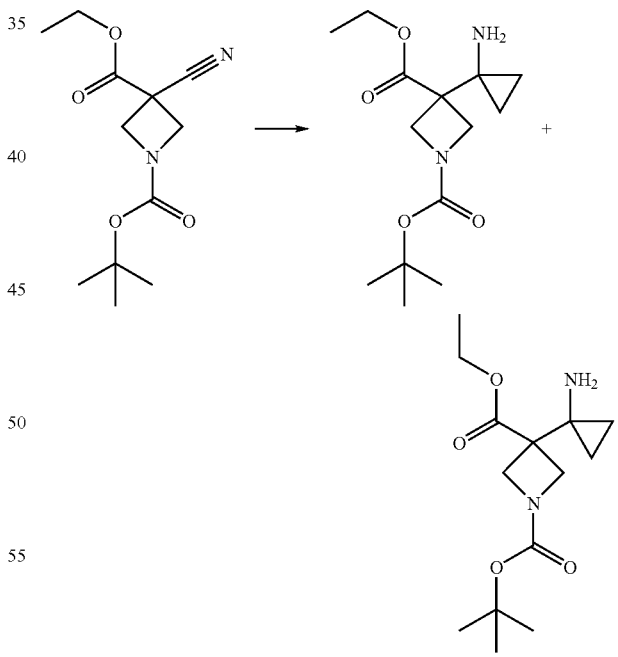

3-Cyano-azetidine-1,3-dicarboxylic acid 1-tert-butyl ester 3-ethyl ester (Example 156) (0.93 g; 3.7 mmol), titanium(IV) isopropoxide (1.2 ml; 4.02 mmol) in diethyl ether (20 ml) are cooled to 15° C. EtMgBr (3M in ether; 2.4 ml; 7.32 mmol) is added dropwise, and the resulting suspension stirred for 1 hour at room temperature. BF$_3$.OEt$_2$ (0.95 ml; 7.32 mmol) is added under cooling and stirring is continued for 45 minutes.

Water (2 ml) is added dropwise to the reaction mixture, the diluted with more water, 2N HCl (2.8 ml) and washed with TBME twice. The aqueous phase is adjusted to pH 11 with a saturated solution of Na$_2$CO$_3$ and extracted with TBME/EtOH (9:1) three times. The combined organic phases are dried over K$_2$CO$_3$, filtered and purified via chromatography (SiO2, TBME/MeOH/NH$_{3conc}$ 97:3:0.6) to deliver the title compounds as a ~1:1 mixture.

MS (m/z) ES+: 299 (MH+) and 285 (MH+).

EXAMPLE 180B

3-[1-(2-Ethoxycarbonyl-acetylamino)-cyclopropyl]-azetidine-1,3-dicarboxylic acid 1-tert-butyl ester 3-isopropyl ester and ethyl ester

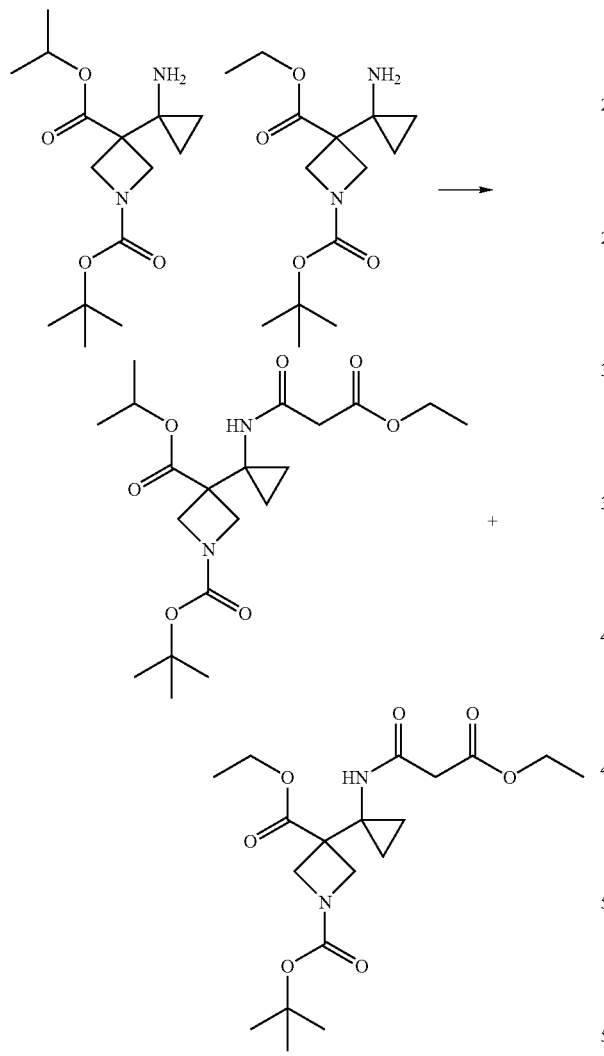

The mixture of 3-(1-amino-cyclopropyl)-azetidine-1,3-dicarboxylic acid 1-tert-butyl ester 3-isopropyl and ethyl ester ester (Example 180a) (520 mg; 1.8 mmol) and triethylamine (0.28 ml; 2.4 mmol) in CH$_2$Cl$_2$ (20 ml) are cooled to 18° C. and combined dropwise under stirring with chlorocarbonyl-acetic acid ethyl ester (0.25 ml; 2.01 mmol) in CH$_2$Cl$_2$ (1 ml). Stirring is continued for 5 minutes, the reaction mixture poured on water/2N HCl (120 ml/3 ml) and extracted with TBME three times. The combined organic phases are dried over Na$_2$SO$_4$, filtered and purified via chromatography (SiO2, acetone/hexanes 5:95>15:85) to deliver the title compounds as a ~1:1 mixture (540 mg; 74%).

MS (m/z) ES+: 413 (MH+) and 399 (MH+).

EXAMPLE 180C 8,10-Dioxo-6,11-diaza-dispiro[2.0.3.4]undecane-6,9-dicarboxylic acid 6-tert-butyl ester 9-methyl ester

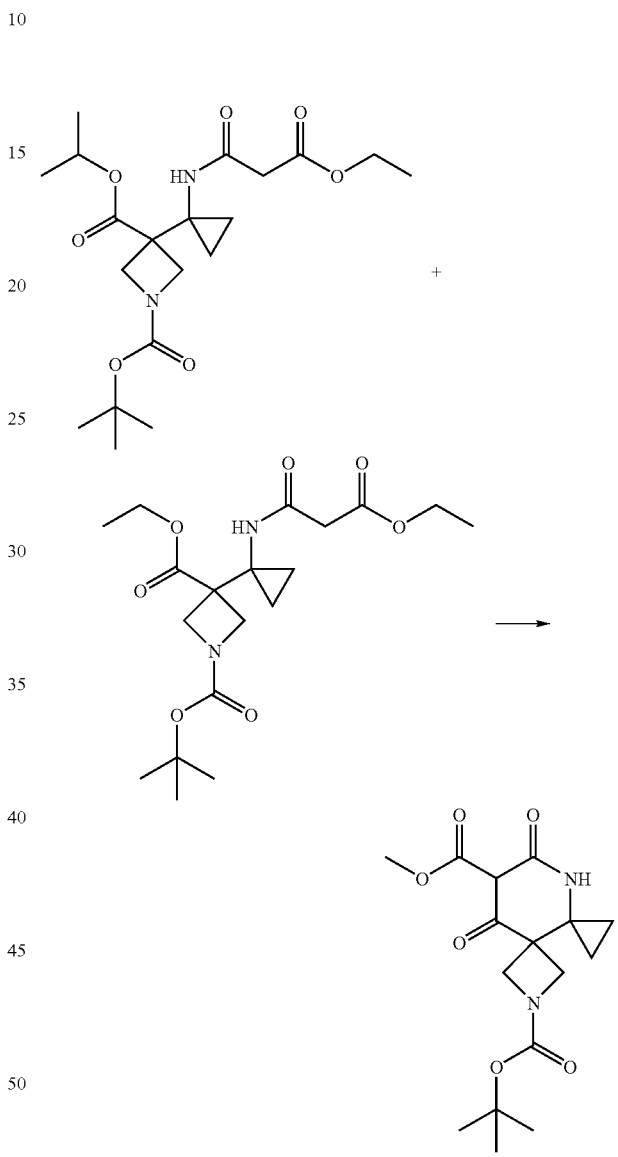

The mixture of 3-[1-(2-ethoxycarbonyl-acetylamino)-cyclopropyl]-azetidine-1,3-dicarboxylic acid 1-tert-butyl ester 3-isopropyl ester and ethyl ester (Example 180b) (350 mg; 0.35 mmol) is dissolved in toluene (5 ml) and added dropwise under stirring to a solution of sodium (20 mg; 0.85 mol) in MeOH (1 ml). The mixture is heated to 85° C. for 45 minutes, cooled, and the resulting suspension (Na-salt of title compound) filtered, washed with toluene and isopentane. The white solid is taken up in water/2N HCl (20 ml/0.5 ml) and extracted with CH$_2$Cl$_2$ three times. The combined organic phases are dried over Na$_2$SO$_4$, filtered and evaporated to dryness to deliver the title compound as almost colorless foam (166 mg; 58%).

1H-NMR (400 MHz; DMSO-d6): 9.06 (bs, 1H); 3.90 (bs, 2H); 3.74 (s, 3H); 3.38 (bd, 2H); 3.08 (s, 1H); 1.37 (s, 9H); 0.98 (bd, 4H). MS (m/z) ES+: 339 (MH+).

EXAMPLE 180D 8,10-Dioxo-6,11-diaza-dispiro[2.0.3.4]undecane-6-carboxylic acid tert-butyl ester

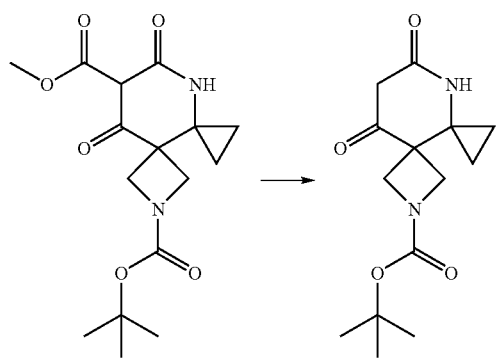

8,10-Dioxo-6,11-diaza-dispiro[2.0.3.4]undecane-6,9-dicarboxylic acid 6-tert-butyl ester 9-methyl ester (160 mg; 0.47 mmol) in acetonitrile/water (3 ml/0.3 ml) is refluxed for 1 hour and evaporated to dryness to deliver the title compound as off-white crystals (125 mg; 94%).

1H-NMR (400 MHz; DMSO-d6): 8.37 (s, 1H); 3.88 (bd, 2H); 3.46 (bs, 2H); 3.39 (bd, 2H); 1.38 (s, 9H); 0.90 (bs 4H). MS (m/z) ES+: 281 (MH+).

EXAMPLE 180E

2-[3-(1-Amino-cyclopropyl)-1-tert-butoxycarbonyl-azetidin-3-yl]-8-chloro-4,5-dihydro-1H-pyrrolo[2,3-f]isoquinoline-3-carboxylic acid lactam

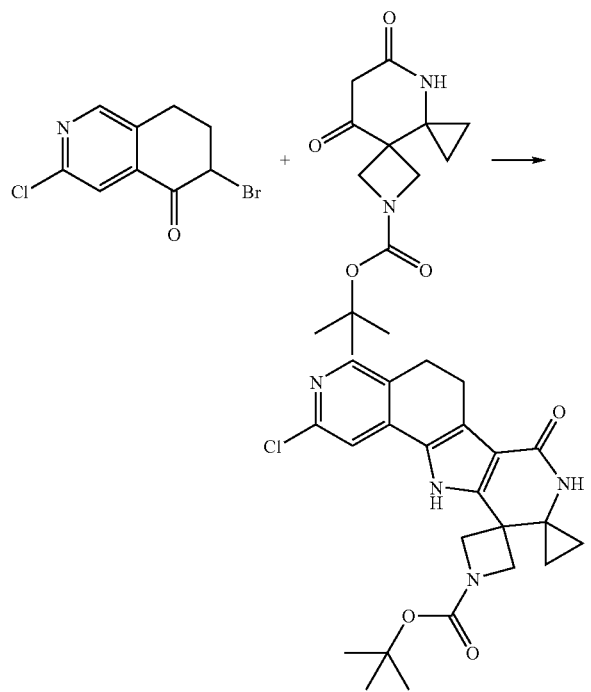

2-[3-(1-Amino-cyclopropyl)-1-tert-butoxycarbonyl-azetidin-3-yl]-8-chloro-4,5-dihydro-1H-pyrrolo[2,3-f]isoquinoline-3-carboxylic acid lactam (Example 180d) (91 mg; 0.325 mmol) and 6-bromo-3-chloro-7,8-dihydro-6H-isoquinolin-5-one (Example 1c)(70 mg; 0.27 mmol) and NaOAc (22 mg; 0.27 mmol) are dissolved in MeOH (2 ml) and evaporated to dryness. This mixture is taken up in HOAc (3 ml), combined with NH$_4$OAc (209 mg; 2.7 mmol) and heated 90° C. for 16 hours, poured on water and extracted with EtOAc three times. The combined organic phases are dried over Na$_2$SO$_4$, filtered and purified via chromatography (SiO2, TBME/MeOH/NH$_{3conc}$ 96:4:0.8) to deliver the title compound as yellow crystals (23 mg; 19%).

1H-NMR (400 MHz; DMSO-d6): 12.08 (s, 1H); 8.14 (s, 1H); 7.64 (s, 1H); 7.36 (s, 1H); 4.04 (bd, 2H); 3.71 (bs 2H); 2.91 (m, 2H); 2.85 (m, 2H); 1.41 (s, 9H); 0.94 (bs, 2H); 0.80 (bs, 2H).

MS (m/z) ES+: 441 (MH+).

EXAMPLE 180F

2-[3-(1-Amino-cyclopropyl)-1-tert-butoxycarbonyl-azetidin-3-yl]-8-(3-fluoro-phenyl)-4,5-dihydro-1H-pyrrolo[2,3-f]isoquinoline-3-carboxylic acid lactam

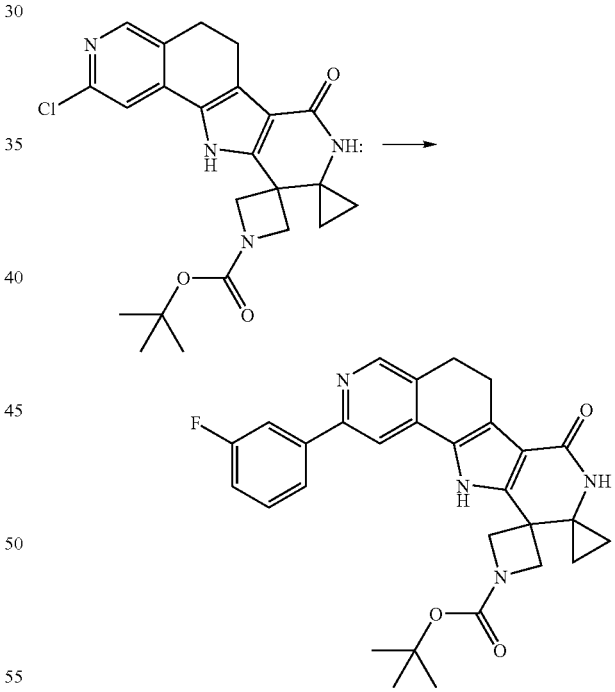

2-[3-(1-Amino-cyclopropyl)-1-tert-butoxycarbonyl-azetidin-3-yl]-8-chloro-4,5-dihydro-1H-pyrrolo[2,3-f]isoquinoline-3-carboxylic acid lactam and 3-fluorophenyl boronic acid are reacted in analogy to Example 1 and provide the title compound as slightly yellow crystals (14 mg; 43%).

1H-NMR (400 MHz; DMSO-d6): 12.14 (s, 1H); 8.43 (s, 1H); 8.17 (s, 1H); 7.91 (bd, 1H); 7.84 (bd, 1H); 7.56 (bt, 1H); 7.34 (bs, 1H); 7.27 (bt, 1H); 4.09 (d, 2H); 3.75 (bs, 2H); 2.91 (m, 4H); 1.42 (s, 9H); 0.94 (bs, 2H); 0.82 (bs, 2H). MS (m/z) ES+: 501 (MH+).

EXAMPLE 181

2-[3-Aminomethyl-1-(2-methoxy-ethyl)-azetidin-3-yl]-8-(3-chloro-phenyl)-4,5-dihydro-1H-pyrrolo[2,3-f]isoquinoline-3-carboxylic acid lactam

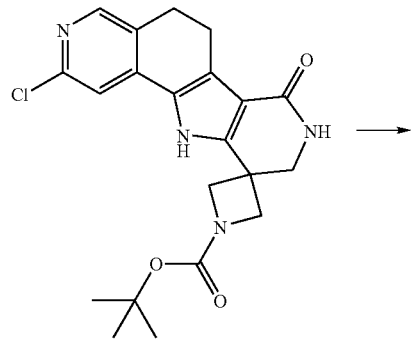

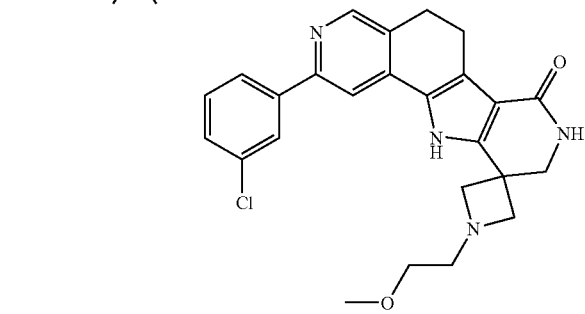

2-(3-Aminomethyl-1-tert-butoxycarbonyl-azetidin-3-yl)-8-chloro-4,5-dihydro-1H-pyrrolo[2,f]isoquinoline-3-carboxylic acid lactam (Example 156b) and 3-chlorophenylboronic acid (Aldrich, 417521) are coupled in analogy to Example 1 The BOC-protective group is removed in analogy to Example 156. Azetidine-N-alkylation with 1-bromo-2-methoxy-ethane is carried out in analogy to Example 176 delivering the title compound as colorless crystals.

MS (m/z) ES+:449 (MH+). Retention time: 1.71 minutes (LC-MS method 2).

EXAMPLE 182

2-(3-Aminomethyl-1-methyl-azetidin-3-yl)-8-(4-methoxyphenyl)-4,5-dihydro-1H-pyrrolo[2,3-f]isoquinoline-3-carboxylic acid lactam hydrochloride

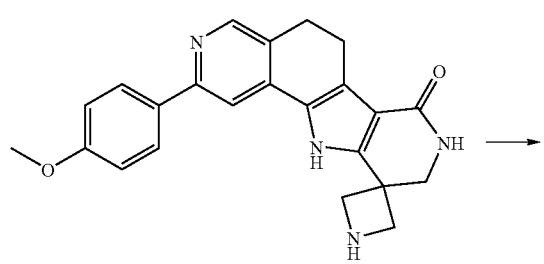

-continued

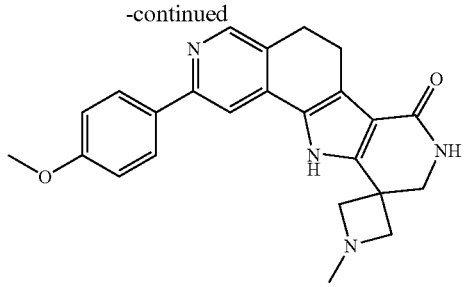

2-(3-Aminomethyl-azetidin-3-yl)-8-(4-methoxy-phenyl)-4,5-dihydro-1H-pyrrolo[2,3-f]isoquinoline-3-carboxylic acid lactam (Example 165) is methylated in analogy to Example 222b and delivers the title compound as white crystals. MS (m/z) ES+:401 (MH+). Retention time: 1.13 minutes (LC-MS method 2).

EXAMPLE 183

2-(3-Aminomethyl-1-methyl-azetidin-3-yl)-8-(6-isopropoxy-pyridin-3-yl)-1-methyl-4,5-dihydro-1H-pyrrolo[2,3-f]isoquinoline-3-carboxylic acid lactam

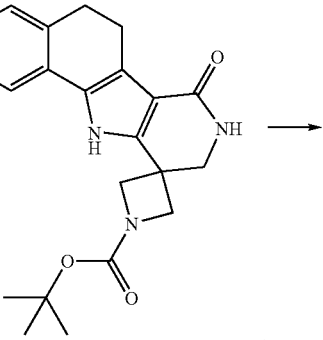

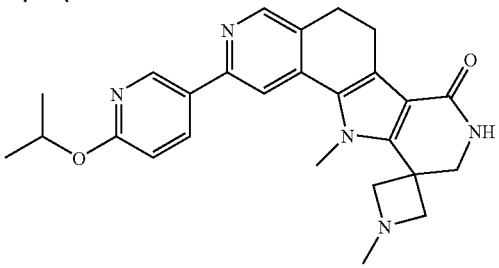

2-(3-Aminomethyl-1-tert-butoxycarbonyl-azetidin-3-yl)-8-chloro-4,5-dihydro-1H-pyrrolo[2,f]isoquinoline-3-carboxylic acid lactam (Example 156b) and 2-isopropoxy-5-(4,4,5,5-tetramethyl-1,3,2-dioxaborolan-2-yl)pyridine (ABCR, AB173057) are coupled in analogy to Example 1. Pyrrole-N-methylation is performed in analogy to Example 137a. The BOC-protective group is removed in analogy to Example 156. Azetidine-N-methylation is carried out in analogy to Example 222b delivering the title compound as colorless crystals.

MS (m/z) ES+:444 (MH+). Retention time: 1.26 minutes (LC-MS method 2).

EXAMPLE 184

2-(3-Aminomethyl-azetidin-3-yl)-8-(6-isopropoxy-pyridin-3-yl)-1-methyl-4,5-dihydro-1H-pyrrolo[2,3-f]isoquinoline-3-carboxylic acid lactam hydrochloride

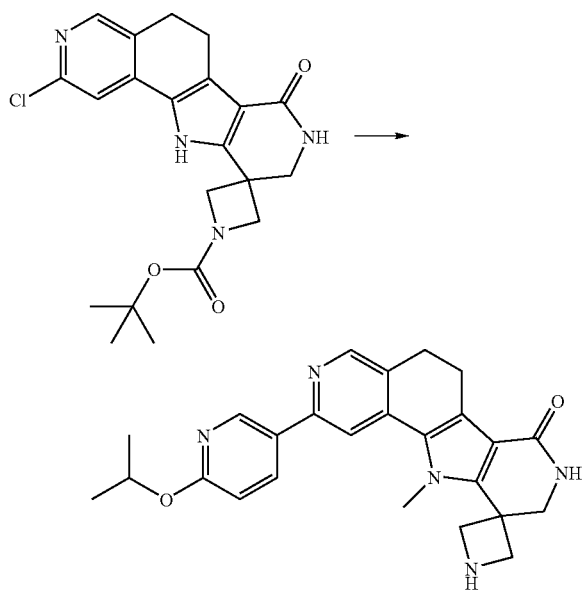

2-(3-Aminomethyl-1-tert-butoxycarbonyl-azetidin-3-yl)-8-chloro-4,5-dihydro-1H-pyrrolo[2,f]isoquinoline-3-carboxylic acid lactam (Example 156b) and 2-isopropoxy-5-(4,4,5,5-tetramethyl-1,3,2-dioxaborolan-2-yl)pyridine (ABCR, AB173057) are coupled in analogy to Example 1. Pyrrole-N-methylation is performed in analogy to Example 137a. The BOC-protective group is removed in analogy to Example 156. MS (m/z) ES+:430 (MH+). Retention time: 1.24 minutes (LC-MS method 2).

EXAMPLE 185

2-(3-Aminomethyl-1-methyl-azetidin-3-yl)-8-(6-isopropoxy-pyridin-3-yl)-4,5-dihydro-1H-pyrrolo[2,3-f]isoquinoline-3-carboxylic acid lactam hydrochloride

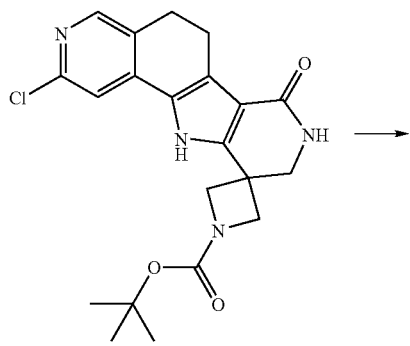

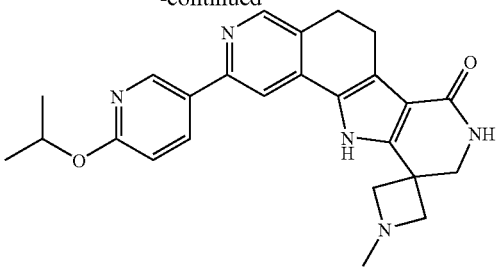

2-(3-Aminomethyl-1-tert-butoxycarbonyl-azetidin-3-yl)-8-chloro-4,5-dihydro-1H-pyrrolo[2,f]isoquinoline-3-carboxylic acid lactam (Example 156b) and 2-isopropoxy-5-(4,4,5,5-tetramethyl-1,3,2-dioxaborolan-2-yl)pyridine (ABCR, AB173057) are coupled in analogy to Example 1. The BOC-protective group is removed in analogy to Example 156. Azetidine-N-methylation is carried out in analogy to Example 222b delivering the title compound as colorless crystals. MS (m/z) ES+:430 (MH+). Retention time: 1.15 minutes (LC-MS method 2).

EXAMPLE 186

2-(3-Aminomethyl-azetidin-3-yl)-8-(6-isopropoxy-pyridin-3-yl)-4,5-dihydro-1H-pyrrolo[2,3-f]isoquinoline-3-carboxylic acid lactam hydrochloride

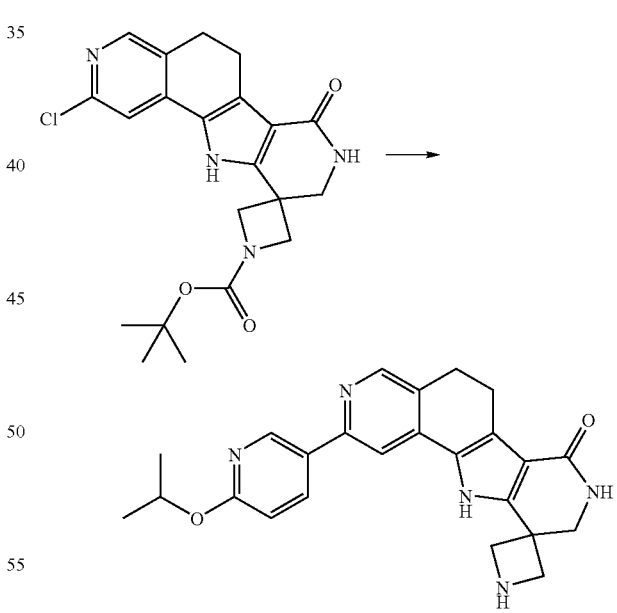

2-(3-Aminomethyl-1-tert-butoxycarbonyl-azetidin-3-yl)-8-chloro-4,5-dihydro-1H-pyrrolo[2,f]isoquinoline-3-carboxylic acid lactam (Example 156b) and 2-isopropoxy-5-(4,4,5,5-tetramethyl-1,3,2-dioxaborolan-2-yl)pyridine (ABCR, AB173057) are coupled in analogy to Example 1. The BOC-protective group is removed in analogy to Example 156, delivering the title compound as colorless crystals. MS (m/z) ES+:416 (MH+). Retention time: 1.55 minutes (LC-MS method 2).

EXAMPLE 187

2-[3-Aminomethyl-azetidin-3-yl]-8-(3-chloro-phenyl)-4,5-dihydro-1H-pyrrolo[2,3-f]isoquinoline-3-carboxylic acid lactam hydrochloride

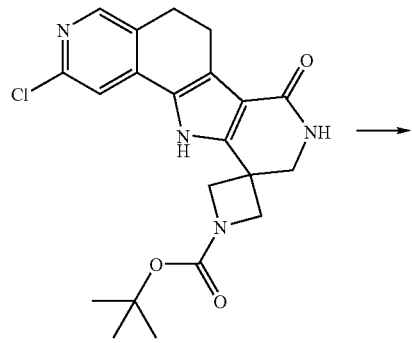

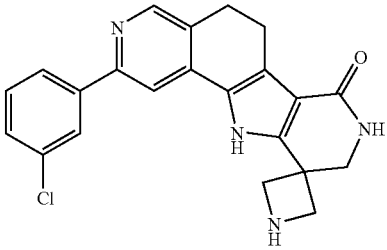

2-(3-Aminomethyl-1-tert-butoxycarbonyl-azetidin-3-yl)-8-chloro-4,5-dihydro-1H-pyrrolo[2,f]isoquinoline-3-carboxylic acid lactam (Example 156b) and 3-chlorophenylboronic acid (Aldrich, 417521) are coupled in analogy to Example 1. The BOC-protective group is removed in analogy to Example 156 delivering the title compound as colorless crystals. MS (m/z) ES+: 391 (MH+). Retention time: 1.52 minutes (LC-MS method 2).

EXAMPLE 188

2-[3-Aminomethyl-1-methyl-azetidin-3-yl]-8-(3-chloro-phenyl)-4,5-dihydro-1H-pyrrolo[2,3-f]isoquinoline-3-carboxylic acid lactam

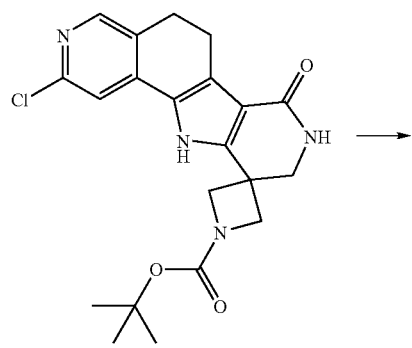

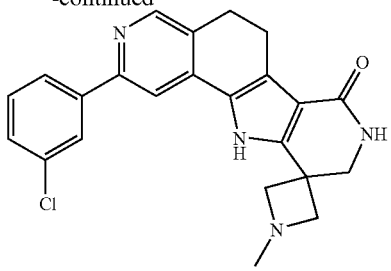

2-(3-Aminomethyl-1-tert-butoxycarbonyl-azetidin-3-yl)-8-chloro-4,5-dihydro-1H-pyrrolo[2,f]isoquinoline-3-carboxylic acid lactam (Example 156b) and 3-chlorophenylboronic acid (Aldrich, 417521) are coupled in analogy to Example 1. The BOC-protective group is removed in analogy to Example 156. Azetidine-N-methylation is carried out in analogy to Example 222b delivering the title compound as colorless crystals. MS (m/z) ES+: 406 (MH+). Retention time: 1.56 minutes (LC-MS method 2).

EXAMPLE 189

2-[3-Aminomethyl-azetidin-3-yl]-8-(3-chloro-phenyl)-1-methyl-4,5-dihydro-1H-pyrrolo[2,3-f]isoquinoline-3-carboxylic acid lactam hydrochloride

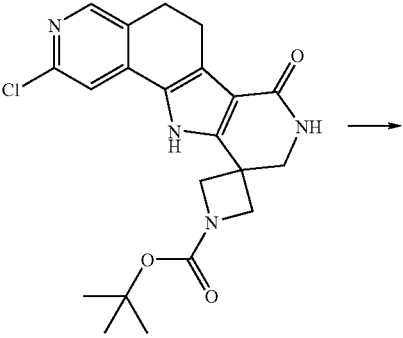

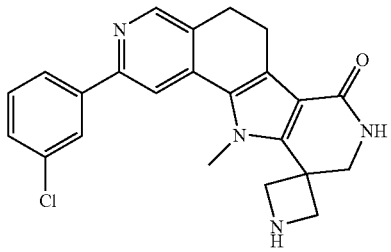

2-(3-Aminomethyl-1-tert-butoxycarbonyl-azetidin-3-yl)-8-chloro-4,5-dihydro-1H-pyrrolo[2,f]isoquinoline-3-carboxylic acid lactam (Example 156b) and 3-chlorophenylboronic acid (Aldrich, 417521) are coupled in analogy to Example 1. Pyrrole-N-methylation is performed in analogy to Example 137a. The BOC-protective group is removed in analogy to Example 156, delivering the title compound as colorless crystals. MS (m/z) ES+: 406 (MH+). Retention time: 1.32 minutes (LC-MS method 1).

EXAMPLE 190

2-[3-Aminomethyl-1-methyl-azetidin-3-yl]-8-(3-chloro-phenyl)-1-methyl-4,5-dihydro-1H-pyrrolo[2,3-f]isoquinoline-3-carboxylic acid lactam

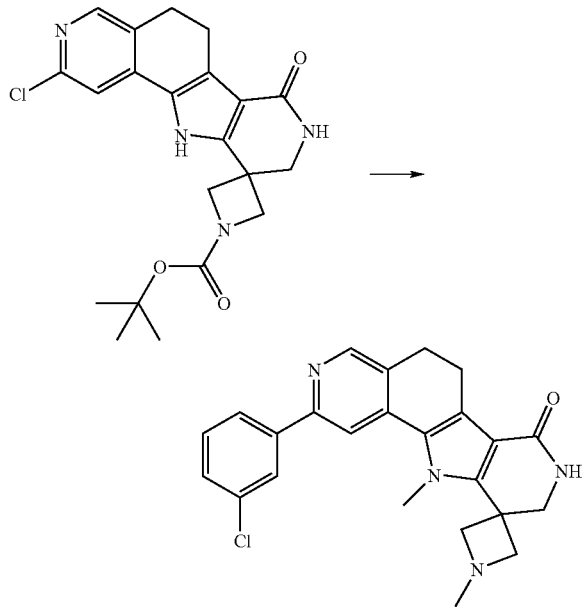

2-(3-Aminomethyl-1-tert-butoxycarbonyl-azetidin-3-yl)-8-chloro-4,5-dihydro-1H-pyrrolo[2,f]isoquinoline-3-carboxylic acid lactam (Example 156b) and 3-chlorophenylboronic acid (Aldrich, 417521) are coupled in analogy to Example 1. Pyrrole-N-methylation is performed in analogy to Example 137a. The BOC-protective group is removed in analogy to Example 156. Azetidine-N-methylation is carried out in analogy to Example 222b delivering the title compound as colorless crystals. MS (m/z) ES+: 420 (MH+).
Retention time: 1.37 minutes (LC-MS method 1).

EXAMPLE 191

2-(3-Aminomethyl-azetidin-3-yl)-8-(3-fluoro-phenyl)-4,5-dihydro-1H-1,7,9-triaza-cyclopenta[a]naphthalene-3-carboxylic acid lactam hydrochloride

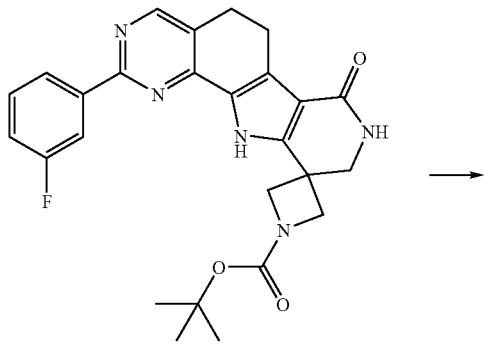

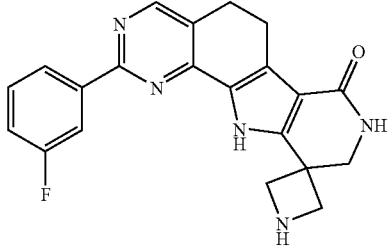

2-(3-Aminomethyl-1-tert-butoxycarbonyl-azetidin-3-yl)-8-(3-fluoro-phenyl)-4,5-dihydro-1H-1,7,9-triaza-cyclopenta[a]naphthalene-3-carboxylic acid lactam (Example 191a) is treated in analogy to Example 156 and yields the title compound as yellow crystals.

1H-NMR (400 MHz; DMSO-d6): 12.51 (bs, 1H); 9.73 (bs, 1H); 9.01 (bs, 1H); 8.57 (s, 1H); 8.36 (bd, 1H); 8.28 (bd, 1H); 7.58 (m, 1H); 7.46 (bs, 1H); 7.36 (m, 1H); 4.55 (bs, 2H); 3.95 (bs, 2H); 3.77 (s, 2H); 2.98 (m, 4H). MS (m/z) ES+: 376 (MH+). Retention time: 1.38 minutes (LC-MS method 1).

The starting material is prepared as follows:

EXAMPLE 191A 2-(3-Aminomethyl-1-tert-butoxycarbonyl-azetidin-3-yl)-8-(3-fluoro-phenyl)-4,5-dihydro-1H-1,7,9-triaza-cyclopenta[a]naphthalene-3-carboxylic acid lactam

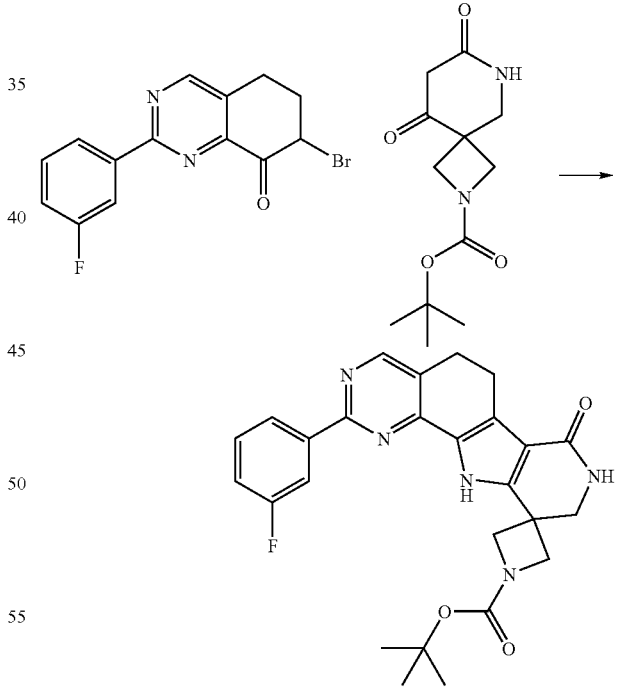

7-Bromo-2-(3-fluoro-phenyl)-6,7-dihydro-5H-quinazolin-8-one (Example 19) (286 mg; 0.894 mmol), 7,9-dioxo-2,6-diaza-spiro[3.5]nonane-2-carboxylic acid tert-butyl ester (Example 156) (250 mg; 0.984 mmol) and NH$_4$OAc (172 mg; 2.235 mmol) are suspended in methanol (7 ml) and stirred over night at room temperature. The reaction mixture is evaporated to dryness and purified via chromatography (SiO$_2$; CH$_2$Cl$_2$/MeOH/NH$_{3conc}$ 95:5:0.5) to deliver a white solid which is washed with methanol/diethyl ether to yield the title compound as colorless crystals (272 mg; 64%).

1H-NMR (400 MHz; DMSO-d6): 12.32 (s, 1H); 8.54 (s, 1H); 8.35 (bd, 1H); 8.27 (bd, 1H); 7.57 (m, 1H); 7.34 (dt, 1H); 7.31 (bs, 1H); 4.26 (bd, 2H); 3.85 (bd, 2H); 3.58 (s, 2H); 2.99 (m, 2H); 2.94 (m, 2H); 1.44 (s, 9H). MS (m/z) ES+: 476 (MH+).

EXAMPLE 192

2-(3-Aminomethyl-1-methyl-azetidin-3-yl)-8-(3-fluoro-phenyl)-4,5-dihydro-1H-1,79-triaza-cyclopenta[a]naphthalene-3-carboxylic acid lactam

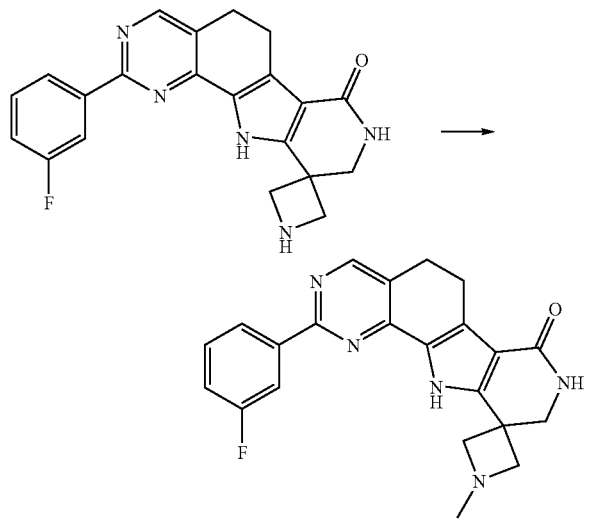

2-(3-Aminomethyl-azetidin-3-yl)-8-(3-fluoro-phenyl)-4,5-dihydro-1H-1,79-triaza-cyclopenta[a]-naphthalene-3-carboxylic acid lactam (Example 191) is treated in analogy to Example 155 to yield the title compound as colorless crystals. MS (m/z) ES+: 390 (MH+). Retention time: 1.72 minutes (LC-MS method 2).

EXAMPLE 193

2-(1'-Amino-bicyclopropyl-1-yl)-8-(6-methyl-pyridin-3-yl)-4,5-dihydro-1H-pyrrolo[2,3-f]isoquinoline-3-carboxylic acid lactam

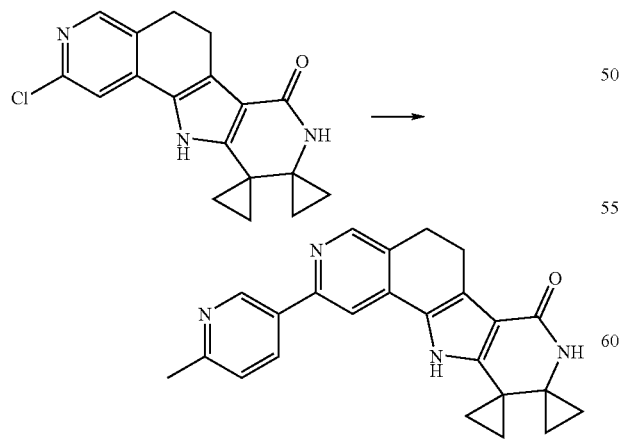

2-(1'-Amino-bicyclopropyl-1-yl)-8-chloro-4,5-dihydro-1H-pyrrolo[2,3-f]isoquinoline-3-carboxylic acid lactam (Example 179d) and 6-methylpyridine-3-boronic acid (SYNCHEM OHG, un119) are coupled in analogy to Example 1 and provide the title compound as colorless crystals. MS (m/z) ES+: 383 (MH+). Retention time: 1.65 minutes (LC-MS method 2).

EXAMPLE 194

2-(1'-Amino-bicyclopropyl-1-yl)-8-(5-fluoro-6-methoxy-pyridin-3-yl)-4,5-dihydro-1H-pyrrolo[2,3-f]isoquinoline-3-carboxylic acid lactam

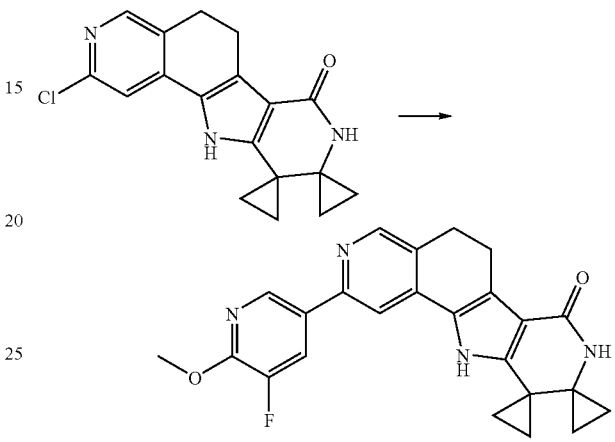

2-(1'-Amino-bicyclopropyl-1-yl)-8-chloro-4,5-dihydro-1H-pyrrolo[2,3-f]isoquinoline-3-carboxylic acid lactam (Example 179d) and 3-fluoro-2-methoxypyridine-5-boronic acid (Asymchem Product List 110641) are coupled in analogy to Example 1 and provide the title compound as colorless crystals. MS (m/z) ES+: 417 (MH+). Retention time: 2.14 minutes (LC-MS method 2).

EXAMPLE 195

2-(1'-Amino-bicyclopropyl-1-yl)-8-(3-fluoro-phenyl)-4,5-dihydro-1H-pyrrolo[2,3-f]isoquinoline-3-carboxylic acid lactam

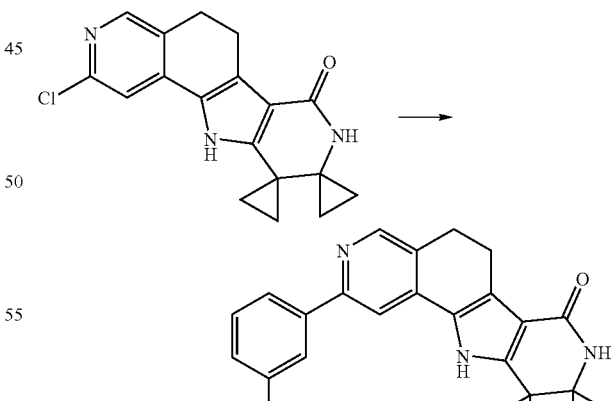

2-(1'-Amino-bicyclopropyl-1-yl)-8-chloro-4,5-dihydro-1H-pyrrolo[2,3-f]isoquinoline-3-carboxylic acid lactam (Example 179d) and 3-fluorophenylboronic acid (Sigma-Aldrich, order number 441643) are coupled in analogy to Example 1 and provide the title compound as colorless crystals.

MS (m/z) ES+: 386 (MH+). Retention time: 2.01 minutes (LC-MS method 2).

EXAMPLE 196

2-(1'-Amino-bicyclopropyl-1-yl)-8-(3-fluoro-4-morpholin-4-ylmethyl-phenyl)-4,5-dihydro-1H-pyrrolo[2,3-f]isoquinoline-3-carboxylic acid lactam

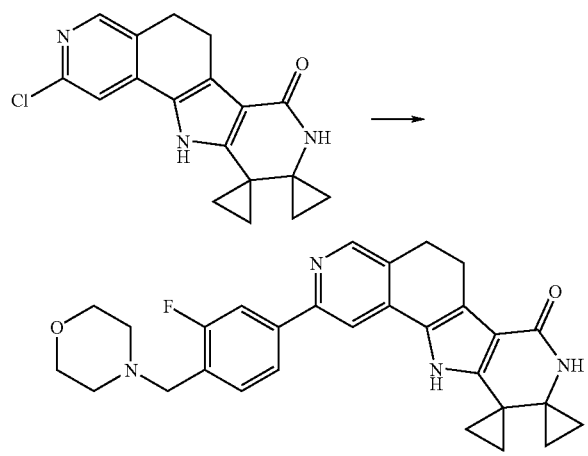

2-(1'-Amino-bicyclopropyl-1-yl)-8-chloro-4,5-dihydro-1H-pyrrolo[2,3-f]isoquinoline-3-carboxylic acid lactam (Example 179d) and 3-fluoro-4-(N-morpholinomethyl)phenylboronic acid pinacolester (Boron Molecular, BM632) are coupled in analogy to Example 1 and provide the title compound as colorless crystals. MS (m/z) ES+: 485 (MH+). Retention time: 1.23 minutes (LC-MS method 1).

EXAMPLE 197

2-(1'-Amino-bicyclopropyl-1-yl)-8-(6-dimethylamino-pyridin-3-yl)-4,5-dihydro-1H-pyrrolo[2,3-f]isoquinoline-3-carboxylic acid lactam

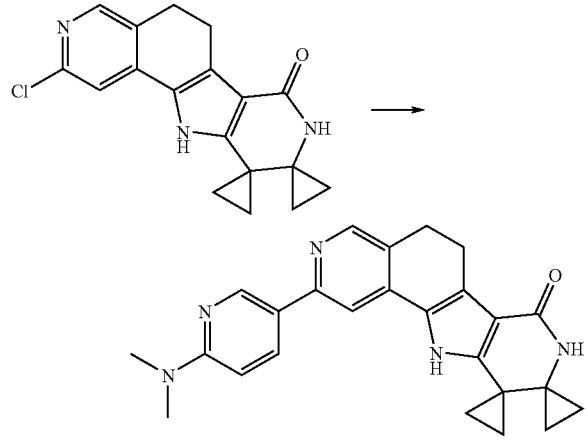

2-(1'-Amino-bicyclopropyl-1-yl)-8-chloro-4,5-dihydro-1H-pyrrolo[2,3-f]isoquinoline-3-carboxylic acid lactam (Example 179d) and 2-dimethylaminopyridine-5-boronic acid (Frontier Scientific, D9115) are coupled in analogy to Example 1 and provide the title compound as colorless crystals. MS (m/z) ES+: 412 (MH+). Retention time: 1.45 minutes (LC-MS method 1).

EXAMPLE 198

2-(1'-Amino-bicyclopropyl-1-yl)-8-[6-(tetrahydropyran-4-yloxy)-pyridin-3-yl]-4,5-dihydro-1H-pyrrolo[2,3-f]isoquinoline-3-carboxylic acid lactam

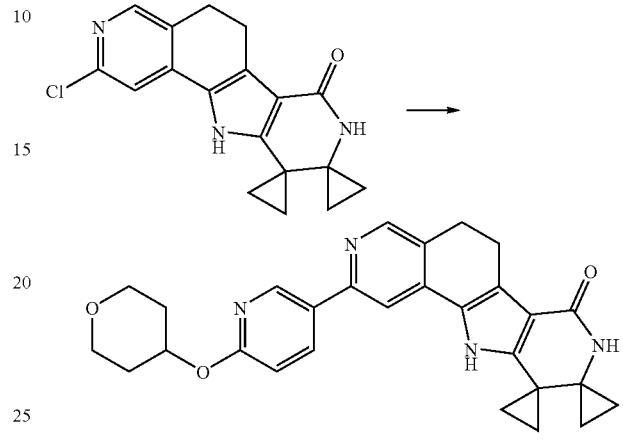

2-(1'-Amino-bicyclopropyl-1-yl)-8-chloro-4,5-dihydro-1H-pyrrolo[2,3-f]isoquinoline-3-carboxylic acid lactam (Example 179d) and 2-(tetrahydropyran-4-yloxy)-5-(4,4,5,5-tetramethyl-1,3,2-dioxaborolan-2-yl)pyridine (Maybridge Building Blocks, CC 58339) are coupled in analogy to Example 1 and provide the title compound as colorless crystals. MS (m/z) ES+: 469 (MH+). Retention time: 1.64 minutes (LC-MS method 1).

EXAMPLE 199

2-(1'-Amino-bicyclopropyl-1-yl)-8-[6-methoxy-pyridin-3-yl]-4,5-dihydro-1H-pyrrolo[2,3-f]isoquinoline-3-carboxylic acid lactam

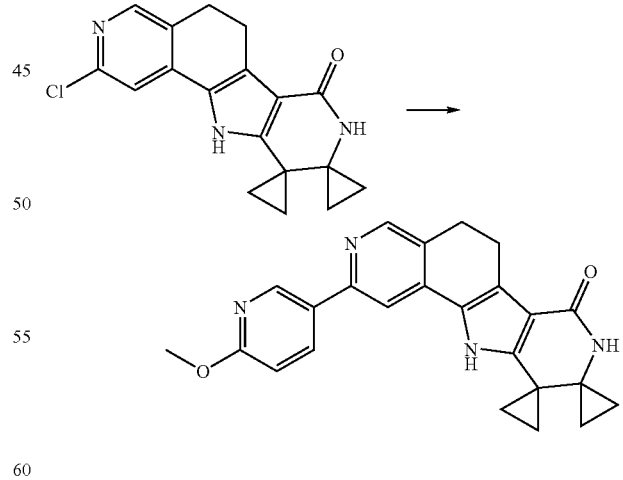

2-(1'-Amino-bicyclopropyl-1-yl)-8-chloro-4,5-dihydro-1H-pyrrolo[2,3-f]isoquinoline-3-carboxylic acid lactam (Example 179d) and 2-methoxy-5-pyridineboronic acid (Aldrich, 637610) are coupled in analogy to Example 1 and provide the title compound as colorless crystals. MS (m/z) ES+: 399 (MH+). Retention time: 1.46 minutes (LC-MS method 1).

EXAMPLE 200

2-(1'-Amino-bicyclopropyl-1-yl)-8-[6-isopropoxy-pyridin-3-yl]-4,5-dihydro-1H-pyrrolo[2,3-f]isoquinoline-3-carboxylic acid lactam

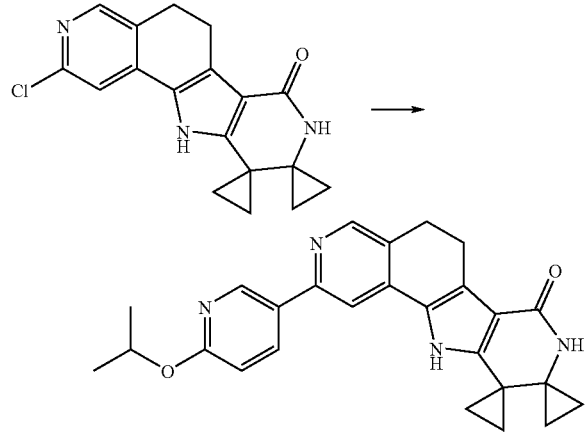

2-(1'-Amino-bicyclopropyl-1-yl)-8-chloro-4,5-dihydro-1H-pyrrolo[2,3-f]isoquinoline-3-carboxylic acid lactam (Example 179d) and 2-Isopropoxy-5-(4,4,5,5-tetramethyl-1,3,2-dioxaborolan-2-yl)pyridine (ABCR, AB173057) are coupled in analogy to Example 1 and provide the title compound as colorless crystals. MS (m/z) ES+: 427 (MH+). Retention time: 2.17 minutes (LC-MS method 2).

EXAMPLE 201

2-(1-Amino-cyclopropylmethyl)-8-(5-fluoro-6-methoxy-pyridin-3-yl)-4,5-dihydro-1H-pyrrolo[2,3-f]isoquinoline-3-carboxylic acid lactam

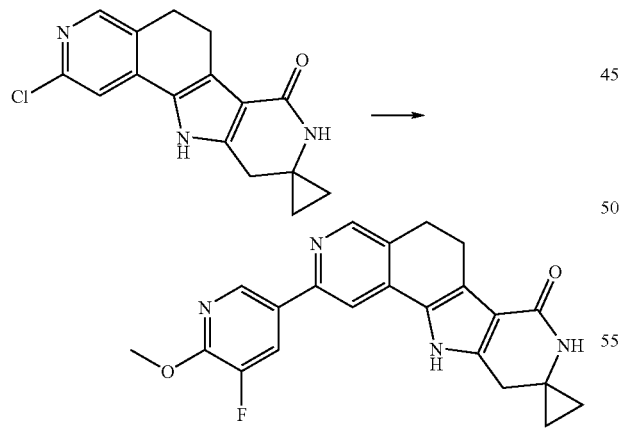

2-(1-Amino-cyclopropylmethyl)-8-chloro-4,5-dihydro-1H-pyrrolo[2,3-f]isoquinoline-3-carboxylic acid lactam (Example 31a) and 3-fluoro-2-methoxypyridine-5-boronic acid (Asymchem Product List 110641) are coupled in analogy to Example 1 and provide the title compound as colorless crystals. MS (m/z) ES+: 391 (MH+). Retention time: 1.56 minutes (LC-MS method 1).

EXAMPLE 202

2-(1-Amino-cyclopropylmethyl)-8-(2-fluoro-pyridin-4-yl)-4,5-dihydro-1H-pyrrolo[2,3-f]isoquinoline-3-carboxylic acid lactam

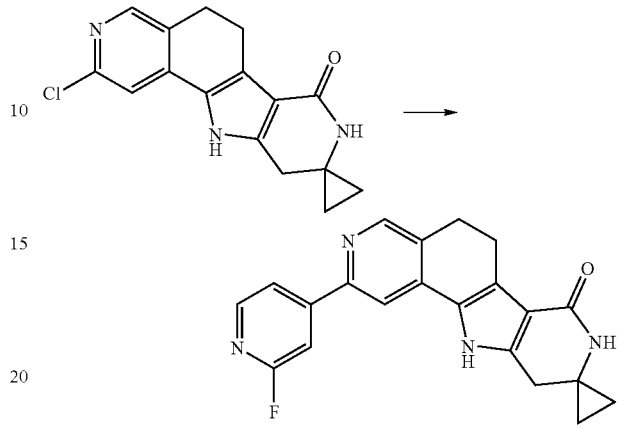

2-(1-Amino-cyclopropylmethyl)-8-chloro-4,5-dihydro-1H-pyrrolo[2,3-f]isoquinoline-3-carboxylic acid lactam (Example 31a) and 2-fluoropyridine-4-boronic acid (SYNCHEM OHG Product List un100) are coupled in analogy to Example 1 and provide the title compound as colorless crystals.

MS (m/z) ES+: 361 (MH+). Retention time: 1.56 minutes (LC-MS method 2).

EXAMPLE 203

2-(3-Aminomethyl-azetidin-3-yl)-8-(3-fluoro-phenyl)-1-methyl-4,5-dihydro-1H-1,7,9-triaza-cyclopenta[a]naphthalene-3-carboxylic acid lactam hydrochloride

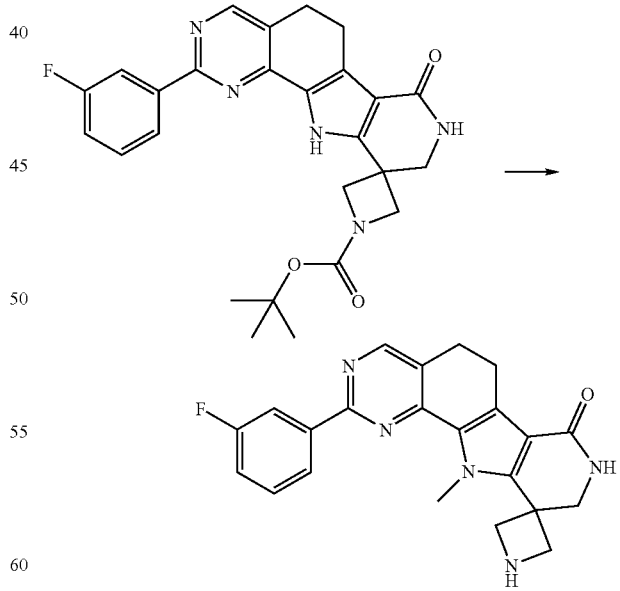

Pyrrole-N-methylation of 2-(3-aminomethyl-1-tert-butoxycarbonyl-azetidin-3-yl)-8-(3-fluoro-phenyl)-4,5-dihydro-1H-1,7,9-triaza-cyclopenta[a]naphthalene-3-carboxylic acid lactam (Example 191a) is performed in analogy to Example 137a. The BOC-protective group is removed in analogy to Example 156, delivering the title compound as yellow crystals. MS (m/z) ES+: 390 (MH+). Retention time: 1.78 minutes (LC-MS method 2).

EXAMPLE 204

2-(3-Aminomethyl-1-methyl-azetidin-3-yl)-8-(3-fluoro-phenyl)-1-methyl-4,5-dihydro-1H-1,7,9-triaza-cyclopenta[a]naphthalene-3-carboxylic acid lactam

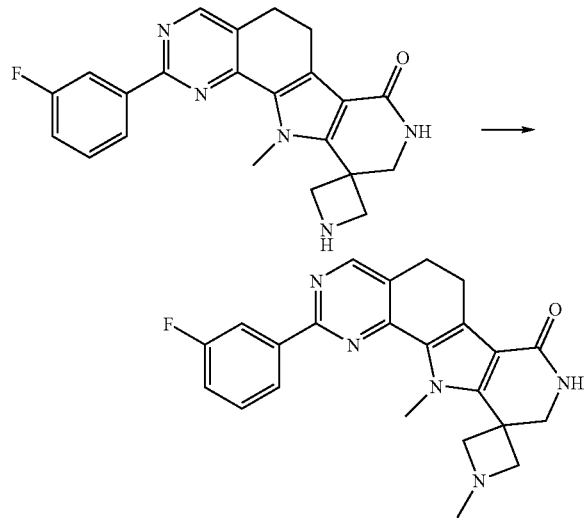

Azetidine-N-methylation of Example 203 is carried out in analogy to Example 222b delivering the title compound as colorless crystals. MS (m/z) ES+: 404 (MH+). Retention time: 1.84 minutes (LC-MS method 1).

EXAMPLE 205

2-(3-Aminomethyl-azetidin-3-yl)-8-(2,6-difluoro-pyridin-3-yl)-4,5-dihydro-1H-pyrrolo[2,3-f]isoquinoline-3-carboxylic acid lactam hydrochloride

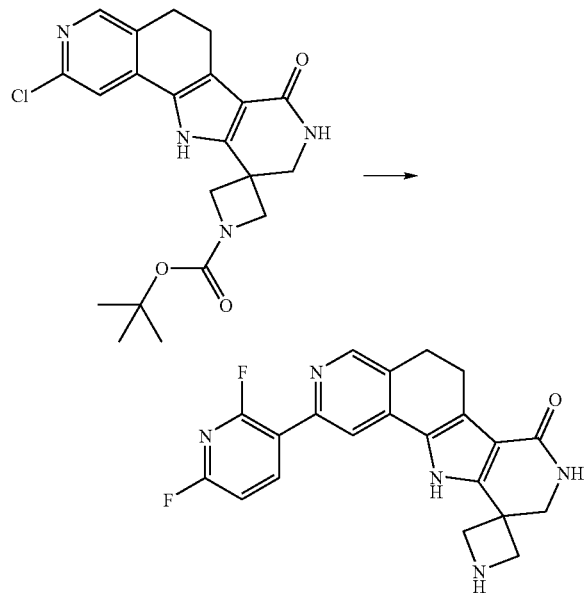

2-(3-Aminomethyl-1-tert-butoxycarbonyl-azetidin-3-yl)-8-chloro-4,5-dihydro-1H-pyrrolo[2,f]isoquinoline-3-carboxylic acid lactam (Example 156b) and 2,6-difluoropyridyl-3-boronic acid (SynChem OHG UN085) are coupled in analogy to Example 1. The BOC-protective group is removed in analogy to Example 156, delivering the title compound as yellow crystals. MS (m/z) ES+: 394 (MH+). Retention time: 3.14 minutes (LC-MS method 1).

EXAMPLE 206

2-(3-Aminomethyl-azetidin-3-yl)-8-(4-methoxy-phenyl)-4,5-dihydro-1H-1,7,9-triaza-cyclopenta[a]naphthalene-3-carboxylic acid lactam hydrochloride

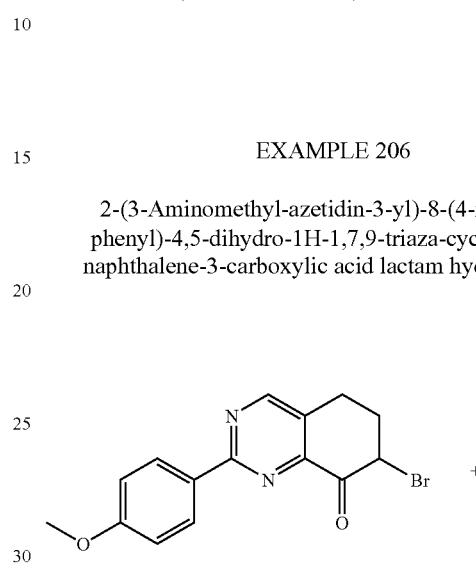

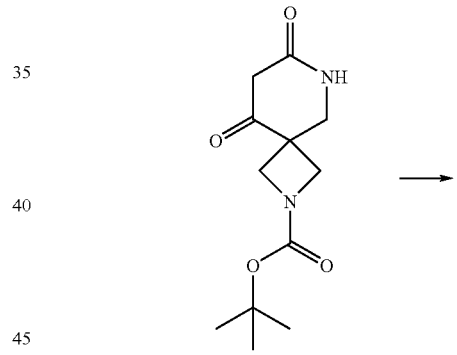

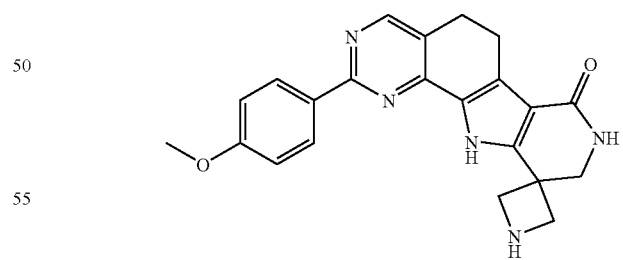

7-Bromo-2-(4-methoxy-phenyl)-6,7-dihydro-5H-quinazolin-8-one (Example 14c) and 7,9-dioxo-2,6-diaza-spiro[3.5]nonane-2-carboxylic acid tert-butyl ester (Example 156) are condensed in analogy to Example 191a. The BOC-protective group is removed in analogy to Example 156, delivering the title compound as yellow crystals. MS (m/z) ES+: 388 (MH+). Retention time: 1.58 minutes (LC-MS method 2).

EXAMPLE 207

2-(3-Aminomethyl-1-methyl-azetidin-3-yl)-8-(4-methoxy-phenyl)-4,5-dihydro-1H-1,7,9-triaza-cyclopenta[a]naphthalene-3-carboxylic acid lactam

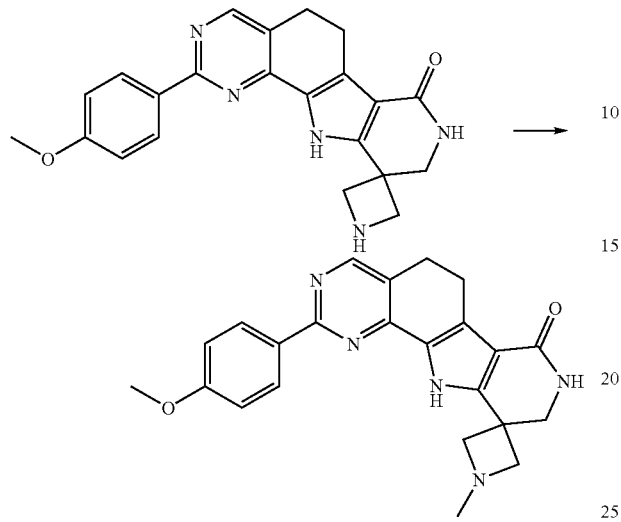

Azetidine-N-methylation of 2-(3-aminomethyl-azetidin-3-yl)-8-(4-methoxy-phenyl)-4,5-dihydro-1H-1,7,9-triaza-cyclopenta[a]naphthalene-3-carboxylic acid lactam is carried out in analogy to Example 222b delivering the title compound as colorless crystals. MS (m/z) ES+: 402 (MH+). Retention time: 1.61 minutes (LC-MS method 2).

EXAMPLE 208

2-[3-(1-Amino-cyclopropyl)-1-methyl-azetidin-3-yl]-8-(3-fluoro-phenyl)-4,5-dihydro-1H-pyrrolo[2,3-f]isoquinoline-3-carboxylic acid lactam

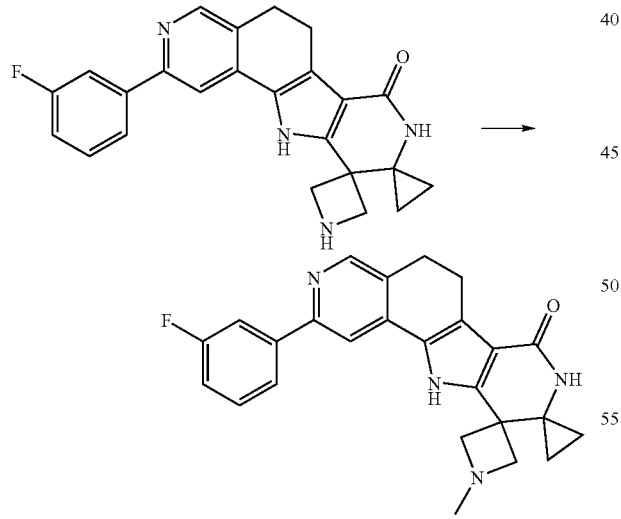

Azetidine-N-methylation of 2-[3-(1-amino-cyclopropyl)-azetidin-3-yl]-8-(3-fluoro-phenyl)-4,5-dihydro-1H-pyrrolo[2,3-f]isoquinoline-3-carboxylic acid lactam (Example 180) in analogy to Example 222b yields the title compound as colorless crystals.

MS (m/z) ES+: 415 (MH+). Retention time: 1.41 minutes (LC-MS method 1).

EXAMPLE 209

2-[3-(1-Amino-cyclopropyl)-azetidin-3-yl]-8-(3-fluoro-phenyl)-1-methyl-4,5-dihydro-1H-pyrrolo[2,3-f]isoquinoline-3-carboxylic acid lactam hydrochloride

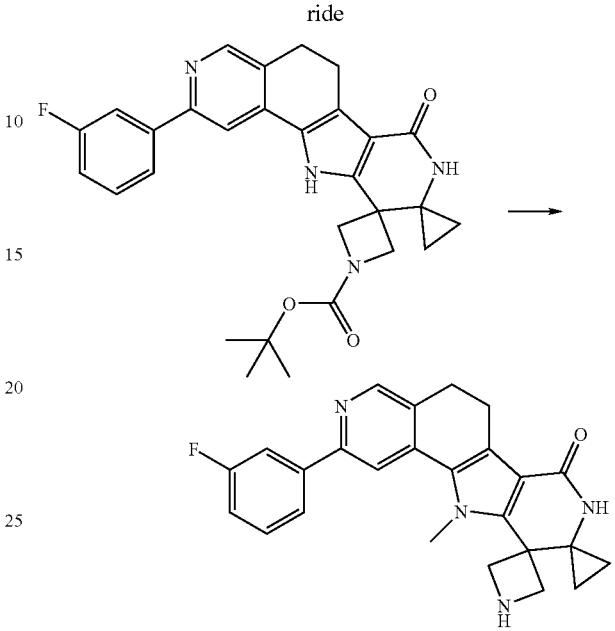

Pyrrole-N-methylation of 2-[3-(1-amino-cyclopropyl)-1-tert-butoxycarbonyl-azetidin-3-yl]-8-(3-fluoro-phenyl)-4,5-dihydro-1H-pyrrolo[2,3-f]isoquinoline-3-carboxylic acid lactam (Example 180f) is performed in analogy to Example 137a. The BOC-protective group is removed in analogy to Example 156, yielding the title compound as yellow crystals.

MS (m/z) ES+: 415 (MH+). Retention time: 1.55 minutes (LC-MS method 1).

EXAMPLE 210

2-[3-(1-Amino-cyclopropyl)-1-methyl-azetidin-3-yl]-8-(3-fluoro-phenyl)-1-methyl-4,5-dihydro-1H-pyrrolo[2,3-f]isoquinoline-3-carboxylic acid lactam

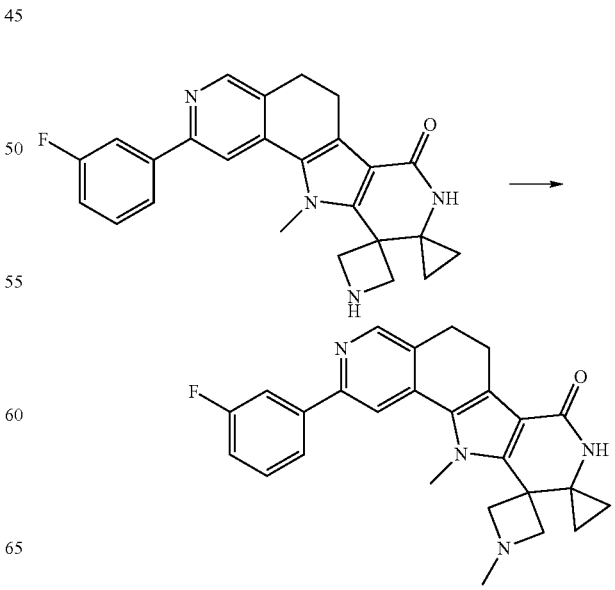

Azetidine N-methylation of 2-[3-(1-amino-cyclopropyl)-azetidin-3-yl]-8-(3-fluoro-phenyl)-1-methyl-4,5-dihydro-1H-pyrrolo[2,3-f]isoquinoline-3-carboxylic acid lactam is performed in analogy to Example 222b to yield the title compound as colorless crystals.

MS (m/z) ES+: 429 (MH+). Retention time: 1.59 minutes (LC-MS method 1).

EXAMPLE 211

2-[3-(1-Amino-cyclopropyl)-azetidin-3-yl]-8-(6-trifluoromethyl-pyridin-3-yl)-4,5-dihydro-1H-pyrrolo[2,3-f]isoquinoline-3-carboxylic acid lactam hydrochloride

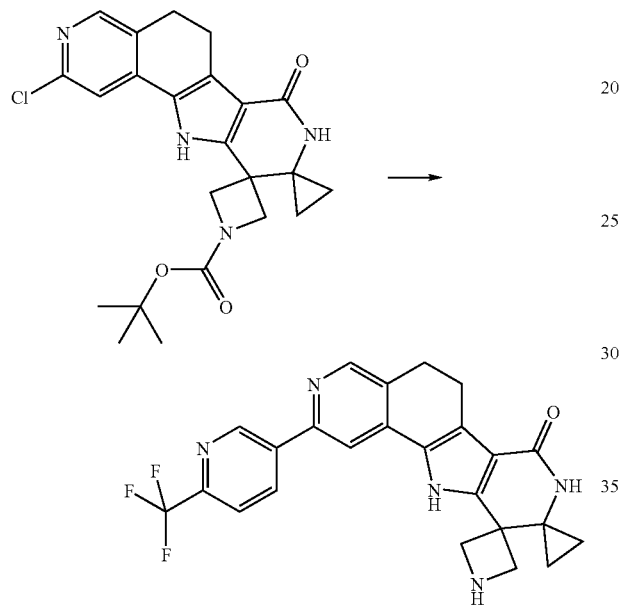

2-[3-(1-Amino-cyclopropyl)-1-tert-butoxycarbonyl-azetidin-3-yl]-8-chloro-4,5-dihydro-1H-pyrrolo[2,3-f]isoquinoline-3-carboxylic acid lactam (Example 180e) and 2-trifluoromethyl-pyridine-5-boronic acid (Focus Synthesis Product List, FS000599) are coupled in analogy to Example 1. The BOC-protective group is removed in analogy to Example 156, delivering the title compound as yellow crystals.

MS (m/z) ES+: 452 (MH+). Retention time: 1.78 minutes (LC-MS method 2).

EXAMPLE 212

2-[3-(1-Amino-cyclopropyl)-azetidin-3-yl]-8-(3-fluoro-phenyl)-4,5-dihydro-1H-1,7,9-triaza-cyclopenta[a]naphthalene-3-carboxylic acid lactam hydrochloride

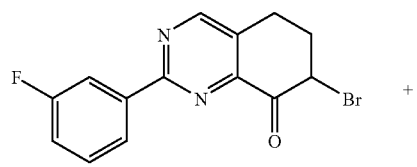 +

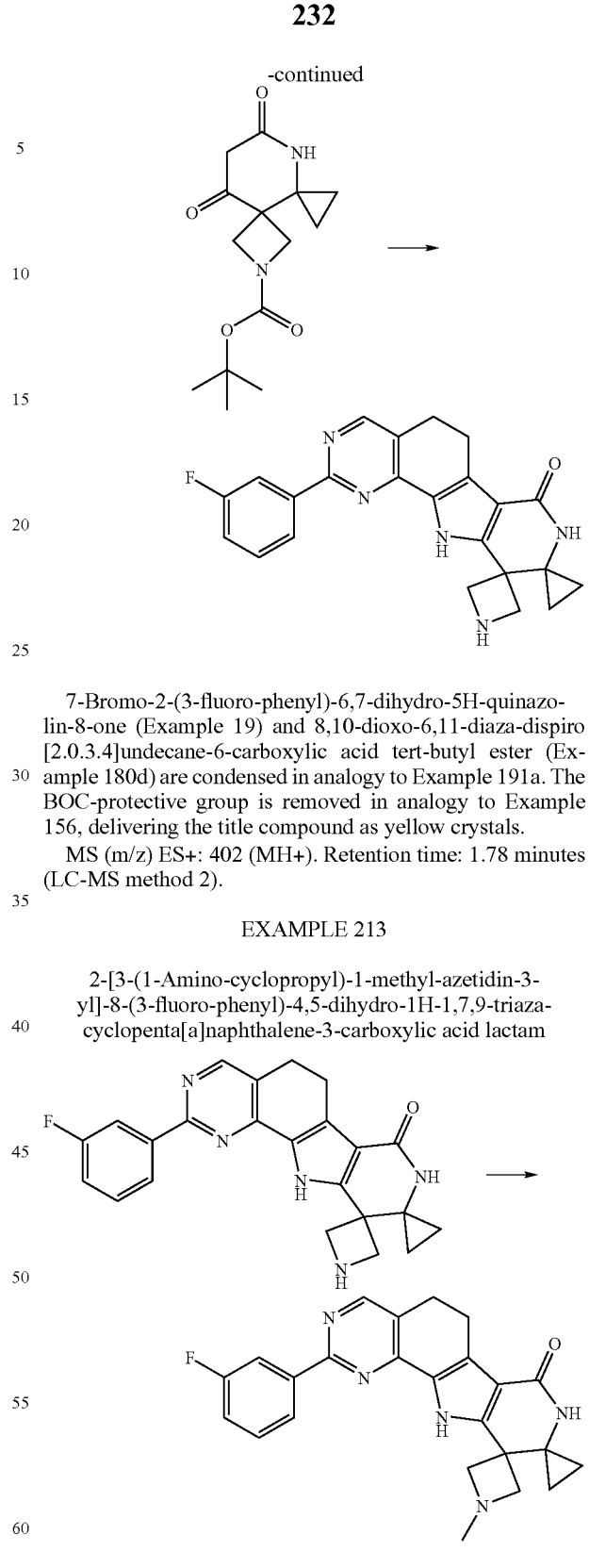

7-Bromo-2-(3-fluoro-phenyl)-6,7-dihydro-5H-quinazolin-8-one (Example 19) and 8,10-dioxo-6,11-diaza-dispiro[2.0.3.4]undecane-6-carboxylic acid tert-butyl ester (Example 180d) are condensed in analogy to Example 191a. The BOC-protective group is removed in analogy to Example 156, delivering the title compound as yellow crystals.

MS (m/z) ES+: 402 (MH+). Retention time: 1.78 minutes (LC-MS method 2).

EXAMPLE 213

2-[3-(1-Amino-cyclopropyl)-1-methyl-azetidin-3-yl]-8-(3-fluoro-phenyl)-4,5-dihydro-1H-1,7,9-triaza-cyclopenta[a]naphthalene-3-carboxylic acid lactam Azetidine N-methylation of Example 212 is performed in analogy to Example 222b to yield the title compound as colorless crystals.

MS (m/z) ES+: 416 (MH+). Retention time: 1.81 minutes (LC-MS method 2).

EXAMPLE 214

2-[3-(1-Amino-cyclopropyl)-azetidin-3-yl]-8-(4-methoxy-phenyl)-4,5-dihydro-1H-1,7,9-triaza-cyclopenta[a]naphthalene-3-carboxylic acid lactam hydrochloride

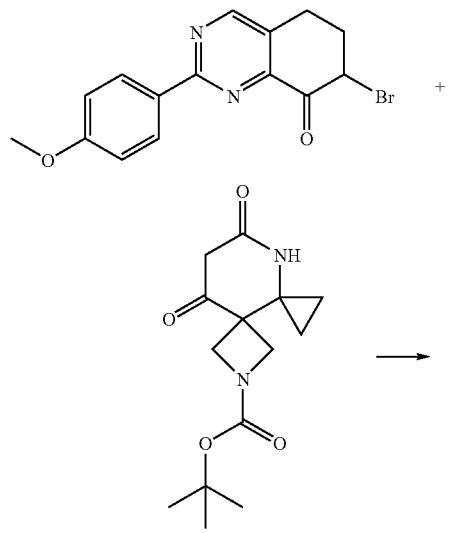

7-Bromo-2-(4-methoxy-phenyl)-6,7-dihydro-5H-quinazolin-8-one (Example 14c) and 8,10-dioxo-6,11-diaza-dispiro[2.0.3.4]undecane-6-carboxylic acid tert-butyl ester (Example 180d) are condensed in analogy to Example 191a. The BOC-protective group is removed in analogy to Example 156, delivering the title compound as yellow crystals.

MS (m/z) ES+: 414 (MH+). Retention time: 1.68 minutes (LC-MS method 2).

EXAMPLE 215

2-[3-(1-Amino-cyclopropyl)-1-methyl-azetidin-3-yl]-8-(4-methoxy-phenyl)-4,5-dihydro-1H-1,7,9-triaza-cyclopenta[a]naphthalene-3-carboxylic acid lactam

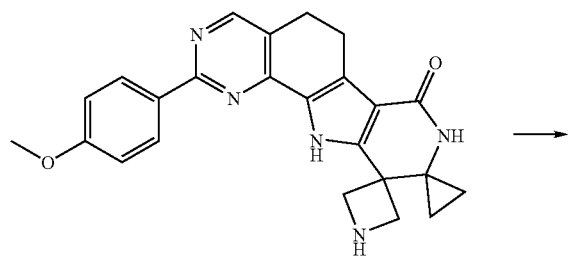

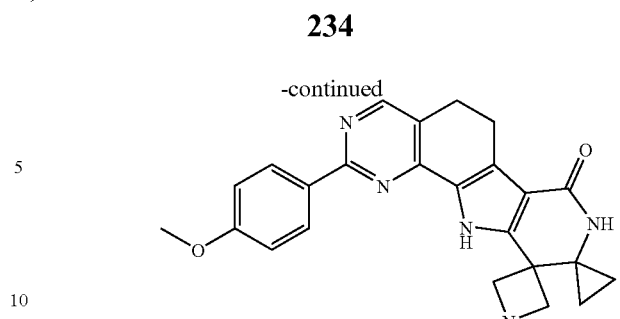

Azetidine N-methylation of Example 214 is performed in analogy to Example 222b to yield the title compound as colorless crystals.

1H-NMR (400 MHz; DMSO-d6): 11.95 (bs, 1H); 8.49 (d, 2H); 8.44 (s, 1H); 7.28 (s, 1H); 7.06 (d, 2H); 3.84 (s, 3H); 3.50 (d, 2H); 3.15 (d, 2H); 2.97 (m, 2H); 2.90 (m, 2H); 2.32 (s, 3H); 1.05 (m, 2H); 0.78 (m, 2H). MS (m/z) ES+: 428 (MH+). Retention time: 1.71 minutes (LC-MS method 2).

EXAMPLE 216

2-(1-Amino-cyclopropylmethyl)-8-(4-piperazin-1-yl-phenyl)-4,5-dihydro-1H-pyrrolo[2,3-f]isoquinoline-3-carboxylic acid lactam hydrochloride

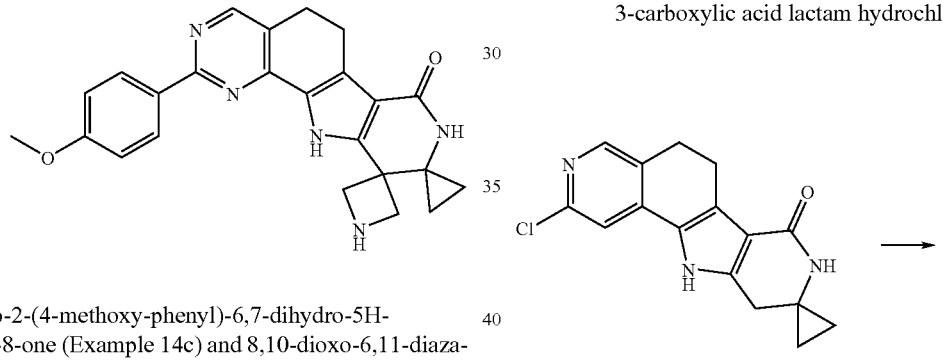

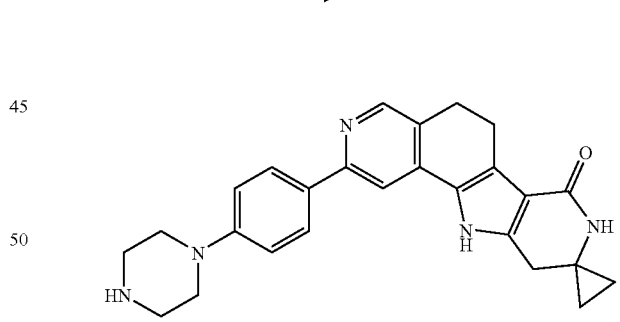

2-(1-Amino-cyclopropylmethyl)-8-chloro-4,5-dihydro-1H-pyrrolo[2,3-f]isoquinoline-3-carboxylic acid lactam (Example 31a) and 4-(4-tert-butoxycarbonylpiperazinyl)phenylboronic acid (ABCR AB175376) are coupled in analogy to Example 1. The BOC-protective group is removed in analogy to Example 156, delivering the title compound as yellow crystals.

1H-NMR (400 MHz; DMSO-d6): 12.89 (s, 1H); 9.25 (s, 1H); 8.37 (s, 1H); 8.31 (s, 1H); 7.98 (d, 2H); 7.37 (s, 1H); 7.21 (d, 2H); 3.62 (m, 4H); 3.23 (bs, 4H); 3.03 (s, 4H); 2.92 (s, 2H); 0.79 (m, 2H); 0.73 (s, 2H). MS (m/z) ES+: 426 (MH+). Retention time: 1.11 minutes (LC-MS method 2).

EXAMPLE 217

2-(1-Amino-cyclopropylmethyl)-8-(4-methyl-piperazin-1-yl-phenyl)-4,5-dihydro-1H-pyrrolo[2,3-f]isoquinoline-3-carboxylic acid lactam

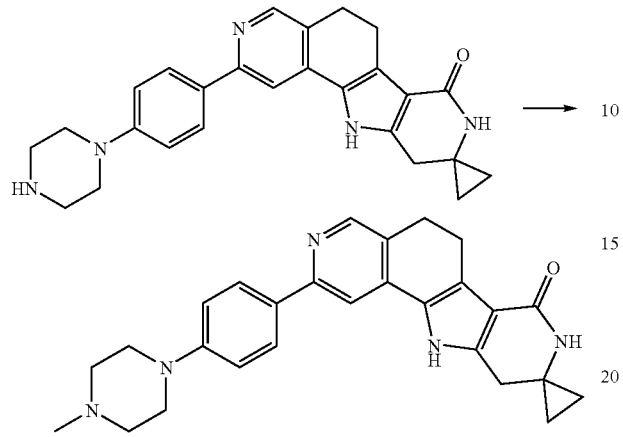

Piperazine N-methylation of Example 216 is performed in analogy to Example 222b to yield the title compound as colorless crystals.

MS (m/z) ES+: 440 (MH+). Retention time: 1.11 minutes (LC-MS method 2).

EXAMPLE 218

2-(3-Aminomethyl-azetidin-3-yl)-8-(4-methoxy-phenyl)-1-methyl-4,5-dihydro-1H-1,7,9-triaza-cyclopenta[a]naphthalene-3-carboxylic acid lactam hydrochloride

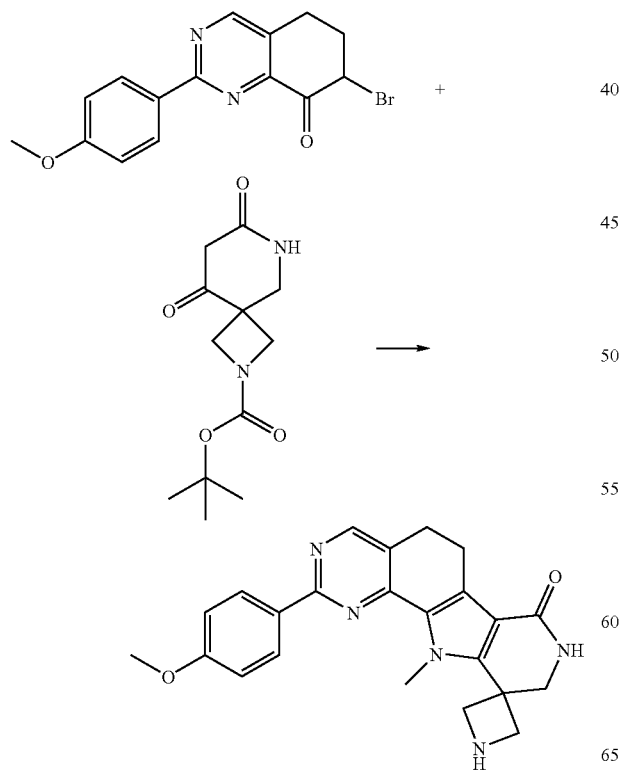

7-Bromo-2-(4-methoxy-phenyl)-6,7-dihydro-5H-quinazolin-8-one (Example 14c) and 7,9-dioxo-2,6-diaza-spiro[3.5]nonane-2-carboxylic acid tert-butyl ester (Example 156) are condensed in analogy to Example 191a. Pyrrole N-methylation is performed in analogy to Example 156. The BOC-protective group is removed in analogy to Example 156, delivering the title compound as yellow crystals MS (m/z) ES+: 402 (MH+). Retention time: 1.70 minutes (LC-MS method 2).

EXAMPLE 219

2-(3-Aminomethyl-1-methyl-azetidin-3-yl)-8-(4-methoxy-phenyl)-1-methyl-4,5-dihydro-1H-1,7,9-triaza-cyclopenta[a]naphthalene-3-carboxylic acid lactam

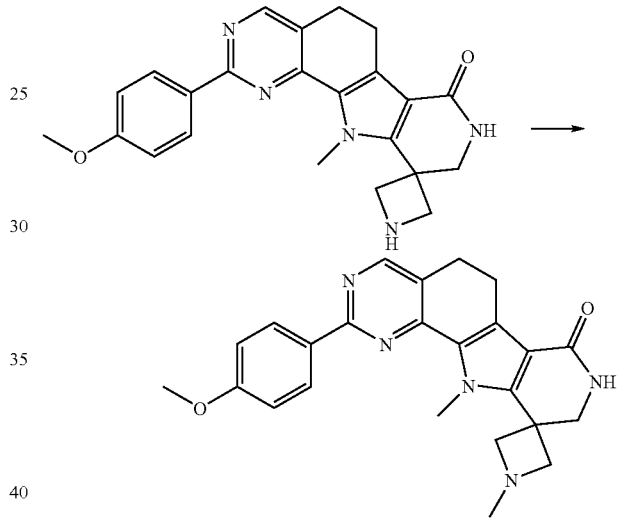

Azetidine-N-methylation of Example 218 is carried out in analogy to Example 222b delivering the title compound as colorless crystals.

MS (m/z) ES+: 416 (MH+). Retention time: 1.73 minutes (LC-MS method 2).

EXAMPLE 220

2-(1'-Amino-bicyclopropyl-1-yl)-8-(4-piperazin-1-yl-phenyl)-4,5-dihydro-1H-pyrrolo[2,3-f]isoquinoline-3-carboxylic acid lactam hydrochloride

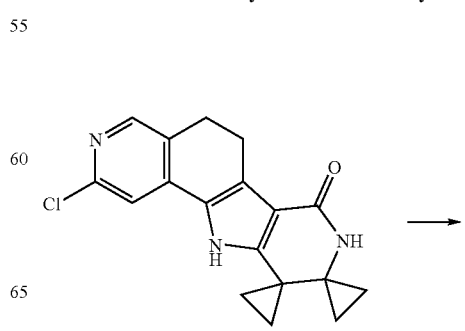

-continued

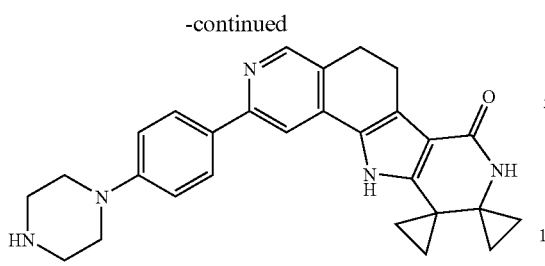

2-(1'-Amino-bicyclopropyl-1-yl)-8-chloro-4,5-dihydro-1H-pyrrolo[2,3-f]isoquinoline-3-carboxylic acid lactam (Example 179d) and 4-(4-tert-butoxycarbonylpiperazinyl)phenylboronic acid (ABCR AB175376) are coupled in analogy to Example 1. The BOC-protective group is removed in analogy to Example 156, delivering the title compound as yellow crystals MS (m/z) ES+: 452 (MH+). Retention time: 1.23 minutes (LC-MS method 2).

EXAMPLE 221

2-(1'-Amino-bicyclopropyl-1-yl)-8-[4-(4-methyl-piperazin-1-yl)-phenyl]-4,5-dihydro-1H-pyrrolo[2,3-f]isoquinoline-3-carboxylic acid lactam

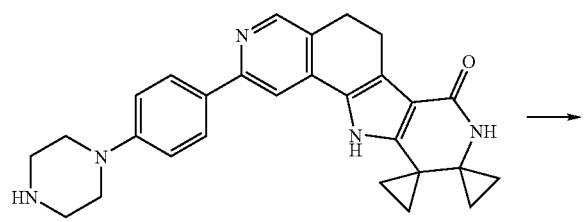

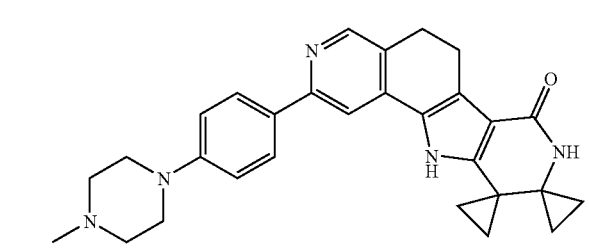

Piperazine-N-methylation of Example 220 is performed in analogy to Example 222n delivering the title compound as colorless crystals.

MS (m/z) ES+: 466 (MH+). Retention time: 1.25 minutes (LC-MS method 2).

EXAMPLE 222

2-[3-(1-Amino-cyclopropyl)-1-methyl-azetidin-3-yl]-8-(6-trifluoromethyl-pyridin-3-yl)-4,5-dihydro-1H-pyrrolo[2,3-f]isoquinoline-3-carboxylic acid lactam

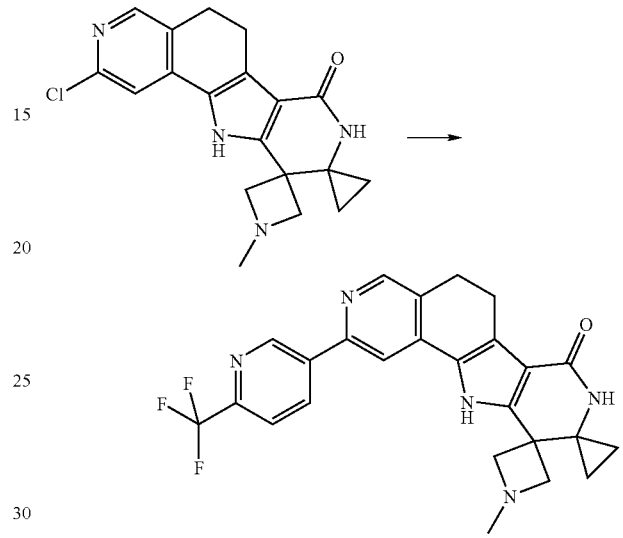

2-Trifluoromethyl-pyridine-5-boronic acid (Focus Synthesis Product List, FS000599) and Example 222b are coupled in analogy to Example 1 and deliver the title compound as colorless crystals.

1H-NMR (400 MHz; DMSO-d6): 11.87 (s, 1H); 9.42 (s, 1H); 8.65 (d, 1H); 8.48 (s, 1H); 8.45 (s, 1H); 8.08 (d, 1H); 7.23 (s, 1H); 3.42 (d, 2H); 3.10 (d, 2H); 2.95 (m, 4H); 2.33 (s, 3H); 0.98 (m, 2H); 0.78 (m, 2H). MS (m/z) ES+: 466 (MH+). Retention time: 1.83 minutes (LC-MS method 2).

The starting material is prepared as follows:

EXAMPLE 222A

2-[3-(1-Amino-cyclopropyl)-azetidin-3-yl]-8-chloro-4,5-dihydro-1H-pyrrolo[2,3-f]isoquinoline-3-carboxylic acid lactam

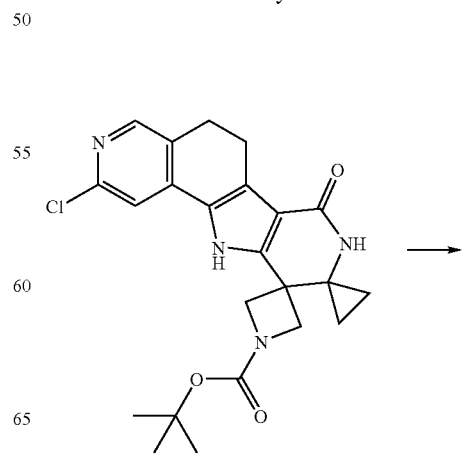

-continued

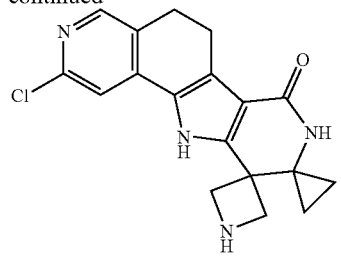

2-[3-(1-Amino-cyclopropyl)-1-tert-butoxycarbonyl-azetidin-3-yl]-8-chloro-4,5-dihydro-1H-pyrrolo[2,3-f]isoquinoline-3-carboxylic acid lactam (Example 180e)(270 mg; 0.61 mmol) is dissolved in HCl$_{conc}$ (4 ml) and kept at room temperature for 2 minutes. The reaction mixture is evaporated to dryness, the resulting HCl-salt dissolved in 2N NaOH (4 ml) and the title compound precipitated as greenish crystals (200 mg; 97%) by neutralizing with 2N HCl.

1H-NMR (400 MHz; DMSO-d6): 8.09 (s, 1H)'; 7.71 (s, 1H); 7.20 (s, 1H); 3.60 (bd, 2H); 3.40 (m, 2H); 2.89 (m, 2H); 2.82 (m, 2H); 1.02 (m, 2H); 0.74 (m, 2H). MS (m/z) ES+: 341 (MH+). Retention time: 1.25 minutes (LC-MS method 2).

EXAMPLE 222B

2-[3-(1-Amino-cyclopropyl)-1-methyl-azetidin-3-yl]-8-chloro-4,5-dihydro-1H-pyrrolo[2,3-f]isoquinoline-3-carboxylic acid lactam

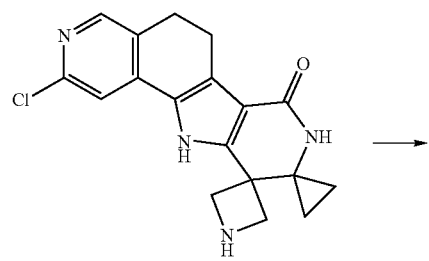

2-[3-(1-Amino-cyclopropyl)-azetidin-3-yl]-8-chloro-4,5-dihydro-1H-pyrrolo[2,3-f]isoquinoline-3-carboxylic acid lactam (Example 222a)(175 mg; 0.58 mmol) is suspended in MeOH (40 ml) and combined with paraformaldehyde (180 mg) and NaCNBH$_3$ (560 mg; 9 mmol) in MeOH (20 ml). Dissolution and reduction are initiated upon addition of 2N HCl (2 ml). After stirring at room temperature for 10 minutes, solid K$_2$CO$_3$ (500 mg) is added, the reaction mixture filtered, evaporated to dryness and purified via chromatography (SiO$_2$, TBME/MeOH/NH$_3$ $_{conc}$ 90:10:1) to deliver the title compound as yellowish crystals (113 mg; 54%)

1H-NMR (400 MHz; DMSO-d6): 11.88 (bs, 1H); 8.02 (s, 1H); 7.65 (bs, 1H); 7.07 (bs, 1H); 3.30 (d, 2H); 3.10 (d, 2H); 2.86 (m, 2H); 2.78 (m, 2H); 2.27 (s, 3H); 0.97 (m, 2H); 0.71 (m, 2H).

MS (m/z) ES+: 355 (MH+). Retention time: 1.27 minutes (LC-MS method 2).

EXAMPLE 223

2-[3-(1-Amino-cyclopropyl)-1-methyl-azetidin-3-yl]-8-(6-fluoro-pyridin-3-yl)-4,5-dihydro-1H-pyrrolo[2,3-f]isoquinoline-3-carboxylic acid lactam

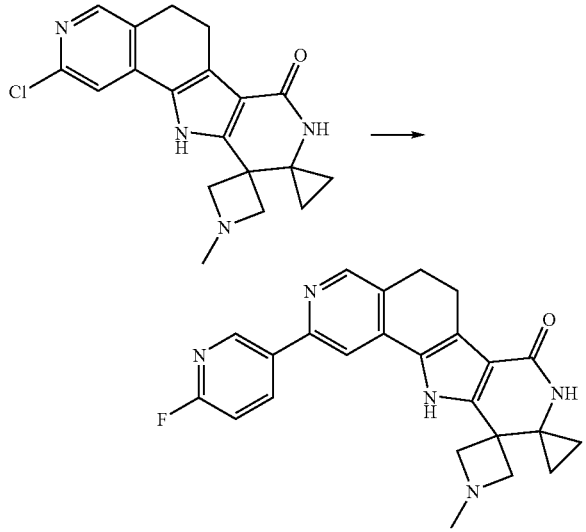

2-Fluoropyridine-5-boronic acid (ABCR, AB181129) and Example 222b are coupled in analogy to Example 1 to deliver the title compound as colorless crystals.

MS (m/z) ES+:416 (MH+). Retention time: 1.41 minutes (LC-MS method 2).

EXAMPLE 224

2-[3-(1-Amino-cyclopropyl)-1-methyl-azetidin-3-yl]-8-(3-chlorophenyl)-4,5-dihydro-1H-pyrrolo[2,3-f]isoquinoline-3-carboxylic acid lactam

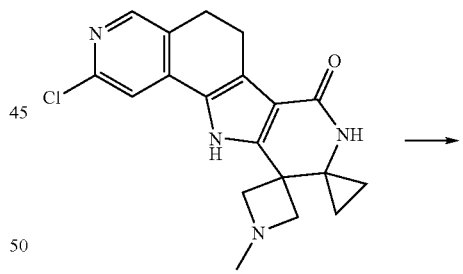

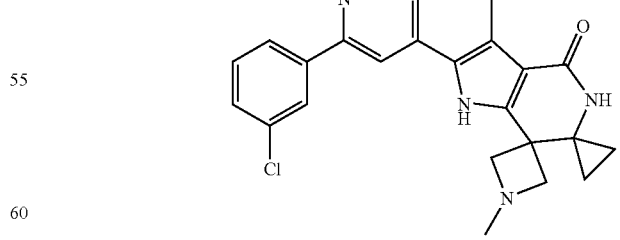

3-Chlorophenylboronic acid (Aldrich, 417521) and Example 222b are coupled in analogy to Example 1 to deliver the title compound as colorless crystals.

MS (m/z) ES+:431 (MH+). Retention time:1.69 minutes (LC-MS method 2).

EXAMPLE 225

2-[3-(1-Amino-cyclopropyl)-1-methyl-azetidin-3-yl]-8-(4-methoxyphenyl)-4,5-dihydro-1H-pyrrolo[2,3-f]isoquinoline-3-carboxylic acid lactam

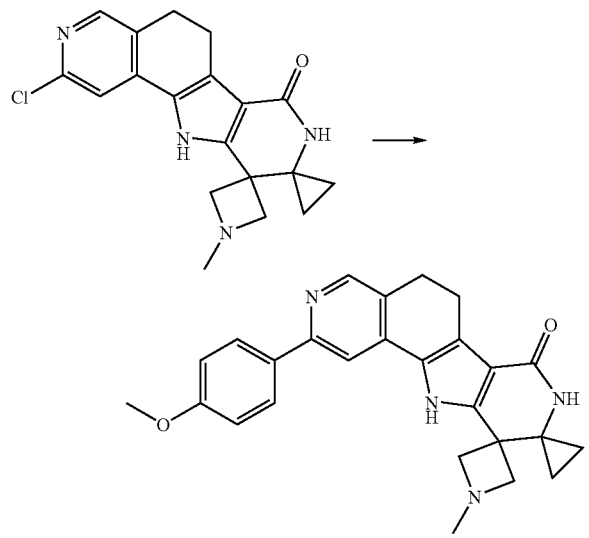

4-Methoxyphenylboronic acid (ABCR Product List, AB169111) and Example 222b are coupled in analogy to Example 1 to deliver the title compound as colorless crystals.

MS (m/z) ES+:427 (MH+). Retention time: 1.21 minutes (LC-MS method 2).

EXAMPLE 226

2-[3-(1-Amino-cyclopropyl)-1-methyl-azetidin-3-yl]-8-(3-benzylcarbamoyl-phenyl)-4,5-dihydro-1H-pyrrolo[2,3-f]isoquinoline-3-carboxylic acid lactam

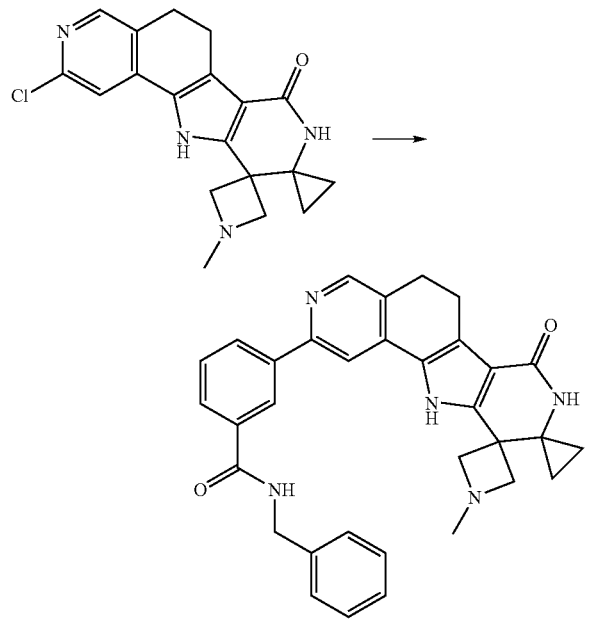

3-(N-Benzylaminocarbonyl)phenylboronic acid (Combi-Blocks BB-3055) and Example 222b are coupled in analogy to Example 1 to deliver the title compound as colorless crystals.

MS (m/z) ES+:530 (MH+). Retention time: 1.66 minutes (LC-MS method 2).

EXAMPLE 227

2-[3-(1-Amino-cyclopropyl)-1-methyl-azetidin-3-yl]-8-[4-(2-morpholin-4-yl-ethoxy)-phenyl]-4,5-dihydro-1H-1,7,9-triaza-cyclopenta[a]naphthalene-3-carboxylic acid lactam

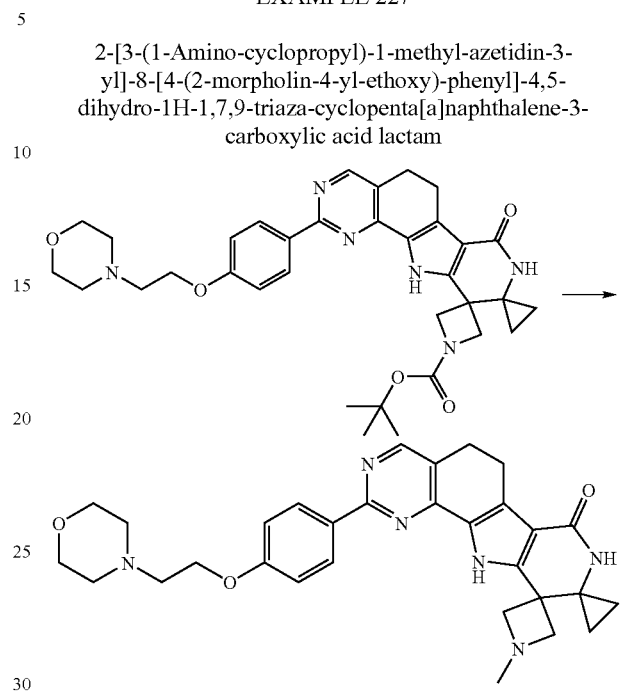

The BOC-protective group of Example 228a is removed in analogy to Example 156. Azetidine-N-methylation is carried out in analogy to Example 222b delivering the title compound as colorless crystals.

MS (m/z) ES+:527 (MH+). Retention time: 1.19 minutes (LC-MS method 2).

The starting material is prepared as follows:

EXAMPLE 227A

2-[3-(1-Amino-cyclopropyl)-1-tert-butoxycarbonyl-azetidin-3-yl]-8-[4-(2-morpholin-4-yl-ethoxy)-phenyl]-4,5-dihydro-1H-1,7,9-triaza-cyclopenta[a]naphthalene-3-carboxylic acid lactam

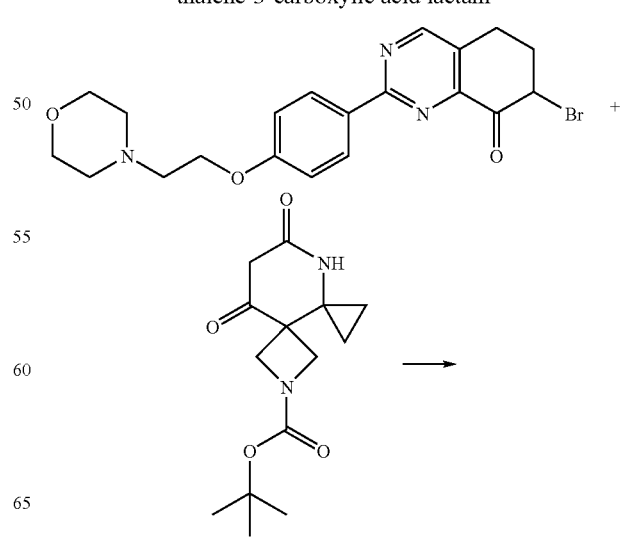

-continued

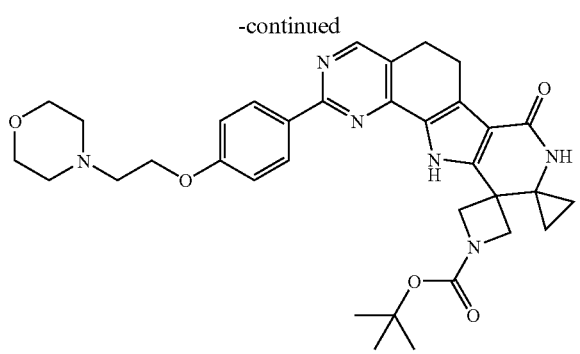

7-Bromo-2-[4-(2-morpholin-4-yl-ethoxy)-phenyl]-6,7-dihydro-5H-quinazolin-8-one (Example 48d) and 8,10-dioxo-6,11-diaza-dispiro[2.0.3.4]undecane-6-carboxylic acid tert-butyl ester (Example 180d) are condensed in analogy to Example 191a delivering the title compound as yellow crystals.

MS (m/z) ES+: 613 (MH+). Retention time: 2.03 minutes (LC-MS method 2).

EXAMPLE 228

2-(1-Amino-cyclopropylmethyl)-8-[4-(2-morpholin-4-yl-ethoxy)-phenyl]-4,5-dihydro-1H-1,7,9-triaza-cyclopenta[a]naphthalene-3-carboxylic acid lactam

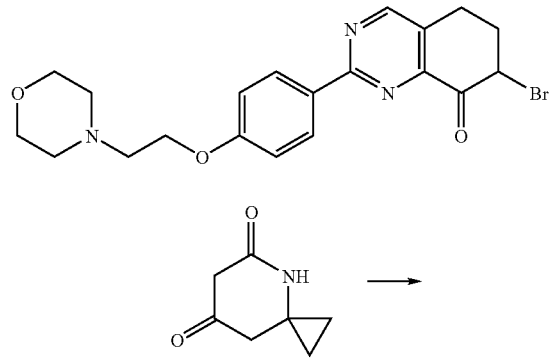

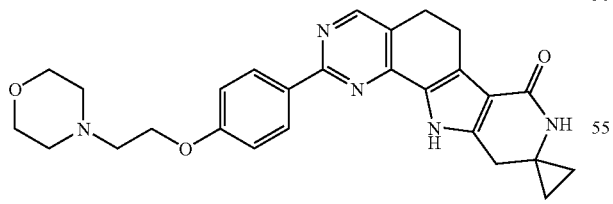

7-Bromo-2-[4-(2-morpholin-4-yl-ethoxy)-phenyl]-6,7-dihydro-5H-quinazolin-8-one (Example 48d) and 4-aza-spiro[2.5]octane-5,7-dione (Example 30c) condensed in analogy to Example 191a delivering the title compound as yellow crystals.

MS (m/z) ES+:472 (MH+). Retention time: 1.51 minutes (LC-MS method 2).

EXAMPLE 229

2-(3-Aminomethyl-1-methyl-azetidin-3-yl)-8-[4-(2-morpholin-4-yl-ethoxy)-phenyl]-4,5-dihydro-1H-1,7,9-triaza-cyclopenta[a]naphthalene-3-carboxylic acid lactam

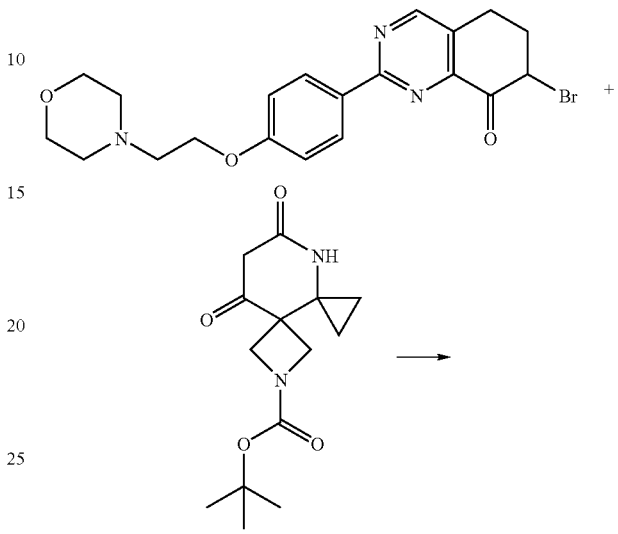

7-Bromo-2-[4-(2-morpholin-4-yl-ethoxy)-phenyl]-6,7-dihydro-5H-quinazolin-8-one (Example 48d) and 7,9-dioxo-2,6-diaza-spiro[3.5]nonane-2-carboxylic acid tert-butyl ester (Example 156) are condensed in analogy to Example 191a. The BOC-protective group is removed in analogy to Example 156. Azetidine-N-methylation is carried out in analogy to Example 156 delivering the title compound as colorless crystals.

MS (m/z) ES+:501 (MH+). Retention time: 2.54 minutes (LC-MS method 2).

EXAMPLE 230

2-(1'-Amino-bicyclopropyl-1-yl)-8-[4-(2-morpholin-4-yl-ethoxy)-phenyl]-4,5-dihydro-1H-pyrrolo[2,3-f]isoquinoline-3-carboxylic acid lactam

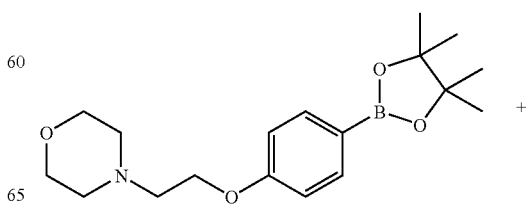

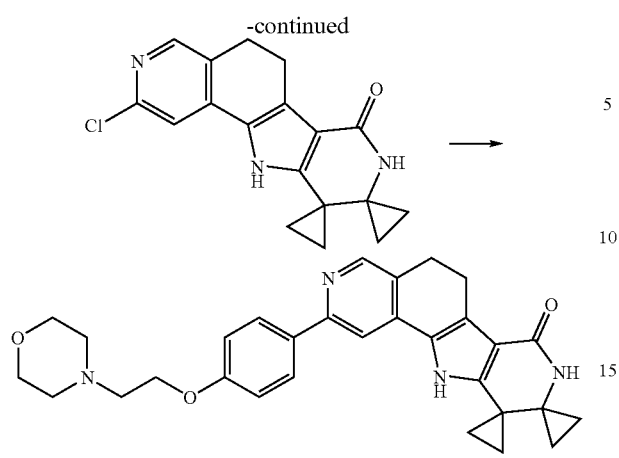

7-Aza-dispiro[2.0.2.4]decane-8,10-dione (Example 179c) and 4-{2-[4-(4,4,5,5-tetramethyl-[1,3,2]dioxaborolan-2-yl)-phenoxy]-ethyl}-morpholine (Focus Synthesis Products FS000534) are reacted in analogy to Example 1 and deliver the title compound as colorless crystals.

MS (m/z) ES+: 497 (MH+). Retention time: 1.31 minutes (LC-MS method 2).

EXAMPLE 231

2-(1-Amino-cyclobutylmethyl)-8-[4-(2-morpholin-4-yl-ethoxy)-phenyl]-4,5-dihydro-1H-pyrrolo[2,3-f]isoquinoline-3-carboxylic acid lactam

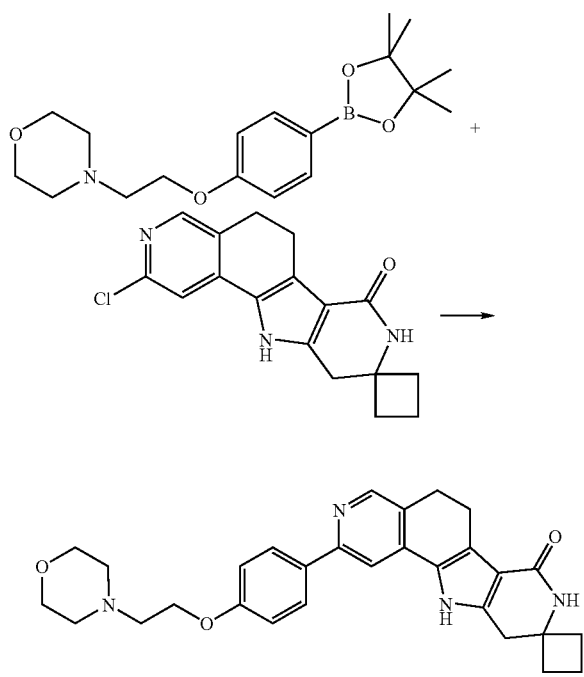

2-(1-Amino-cyclobutylmethyl)-8-chloro-4,5-dihydro-1H-pyrrolo[2,3-f]isoquinoline-3-carboxylic acid lactam (Example 36a) 4-{2-[4-(4,4,5,5-tetramethyl-[1,3,2]dioxaborolan-2-yl)-phenoxy]-ethyl}-morpholine (Focus Synthesis Products FS000534) are reacted in analogy to Example 1 and deliver the title compound as colorless crystals.

MS (m/z) ES+:485 (MH+). Retention time:1.26 minutes (LC-MS method 2).

EXAMPLE 232

2-(1-Amino-cyclopropylmethyl)-8-[3-(2-methoxy-ethoxy)-phenyl]-4,5-dihydro-1H-pyrrolo[2,3-f]isoquinoline-3-carboxylic acid lactam

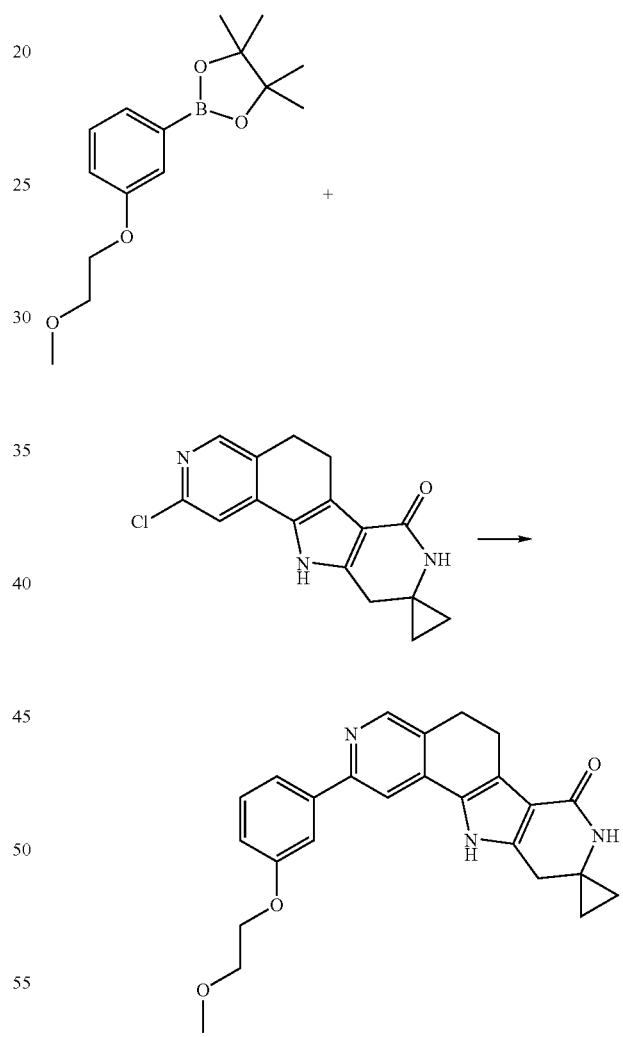

2-[3-(2-Methoxyethoxy)phenyl]-4,4,5,5-tetramethyl-1,3,2-dioxaborolane (US 2007287708) and 2-(1-amino-cyclopropylmethyl)-8-chloro-4,5-dihydro-1H-pyrrolo[2,3-f]isoquinoline-3-carboxylic acid lactam (Example 31a) are reacted in analogy to Example 1 and deliver the title compound as colorless crystals.

MS (m/z) ES+:416 (MH+). Retention time:1.82 minutes (LC-MS method 2).

EXAMPLE 233

2-(1-Amino-cyclobutylmethyl)-8-(6-methoxy-pyridin-3-yl)-4,5-dihydro-1H-pyrrolo[2,3-f]isoquinoline-3-carboxylic acid lactam

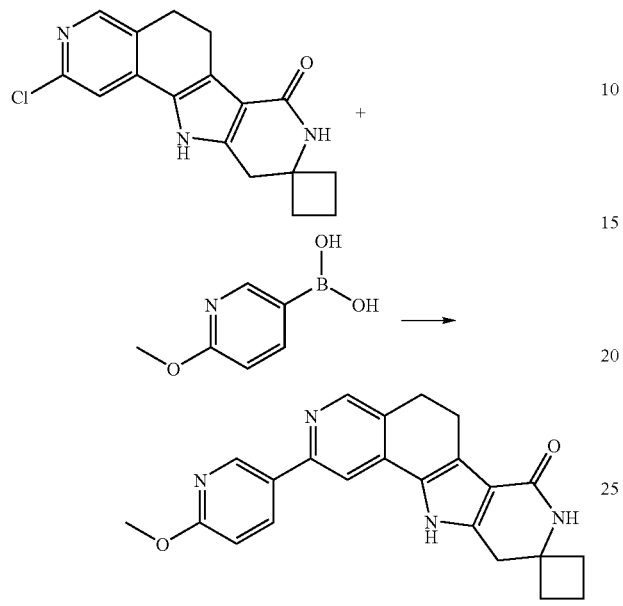

2-(1-Amino-cyclobutylmethyl)-8-chloro-4,5-dihydro-1H-pyrrolo[2,3-f]isoquinoline-3-carboxylic acid lactam (Example 36a) and 2-methoxy-5-pyridineboronic acid (Aldrich, 637610) are reacted in analogy to Example 1 and deliver the title compound as colorless crystals.

MS (m/z) ES+: 387 (MH+). Retention time: 1.88 minutes (LC-MS method 2).

EXAMPLE 234

2-(1-Amino-cyclobutylmethyl)-8-(6-isopropoxy-pyridin-3-yl)-4,5-dihydro-1H-pyrrolo[2,3-f]isoquinoline-3-carboxylic acid lactam

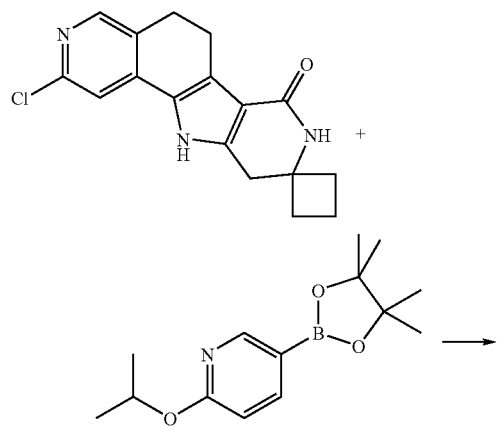

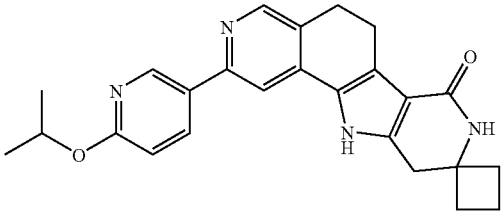

2-(1-Amino-cyclobutylmethyl)-8-chloro-4,5-dihydro-1H-pyrrolo[2,3-f]isoquinoline-3-carboxylic acid lactam (Example 36a) and 2-Isopropoxy-5-(4,4,5,5-tetramethyl-1,3,2-dioxaborolan-2-yl)pyridine (ABCR, AB173057) are reacted in analogy to Example 1 and deliver the title compound as colorless crystals.

MS (m/z) ES+: 415 (MH+). Retention time: 2.32 minutes (LC-MS method 2).

EXAMPLE 235

2-(1-Amino-cyclopropylmethyl)-8-(6-isopropoxy-pyridin-3-yl)-4,5-dihydro-1H-pyrrolo[2,3-f]isoquinoline-3-carboxylic acid lactam

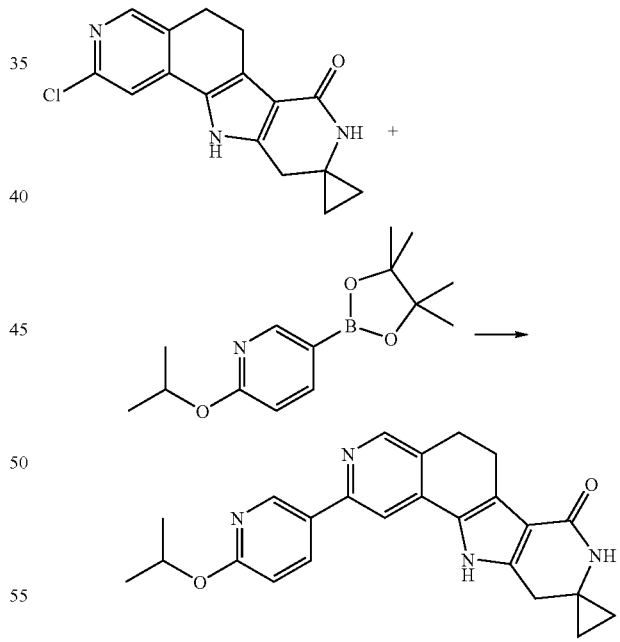

2-Isopropoxy-5-(4,4,5,5-tetramethyl-1,3,2-dioxaborolan-2-yl)pyridine (ABCR, AB173057) and 2-(1-amino-cyclopropylmethyl)-8-chloro-4,5-dihydro-1H-pyrrolo[2,3-f]isoquinoline-3-carboxylic acid lactam (Example 31a) are reacted in analogy to Example 1 and deliver the title compound as colorless crystals.

MS (m/z) ES+: 401 (MH+). Retention time: 2.15 minutes (LC-MS method 2).

EXAMPLE 236

2-(1-Amino-cyclopropylmethyl)-8-(6-morpholin-4-yl-pyridin-3-yl)-4,5-dihydro-1H-pyrrolo[2,3-f]iso-quinoline-3-carboxylic acid lactam

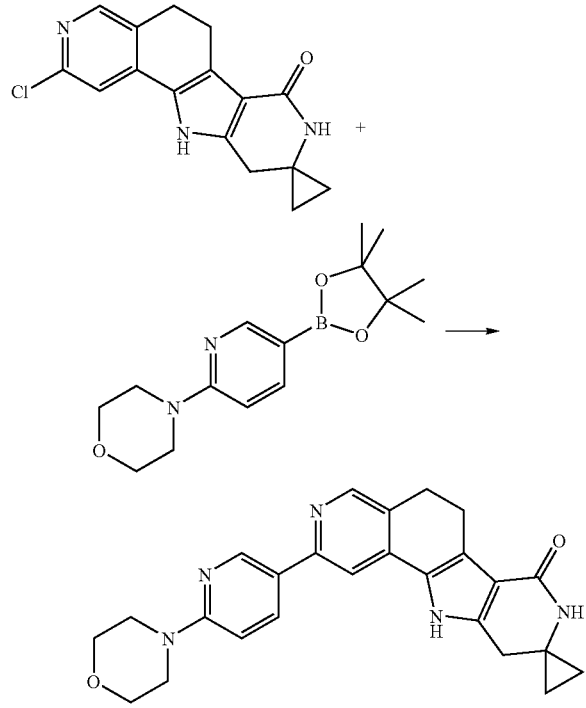

6-Morpholinopyridine-3-boronic acid pinacolester (ABCR AB172701) and 2-(1-amino-cyclopropylmethyl)-8-chloro-4,5-dihydro-1H-pyrrolo[2,3-f]isoquinoline-3-carboxylic acid lactam (Example 31a) are reacted in analogy to Example 1 and deliver the title compound as colorless crystals.

MS (m/z) ES+: 428 (MH+). Retention time:1.63 minutes (LC-MS method 2).

EXAMPLE 237

2-(1-Amino-cyclopropylmethyl)-8-(3-morpholin-4-yl-phenyl)-4,5-dihydro-1H-pyrrolo[2,3-f]isoquino-line-3-carboxylic acid lactam

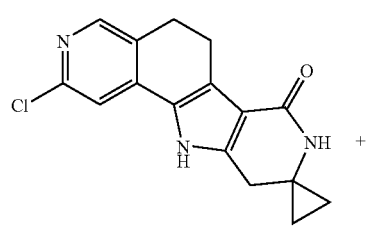

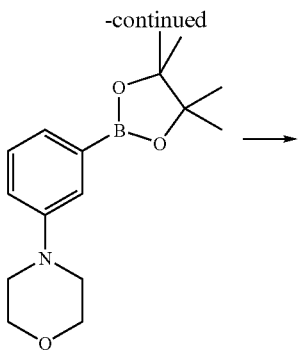
-continued

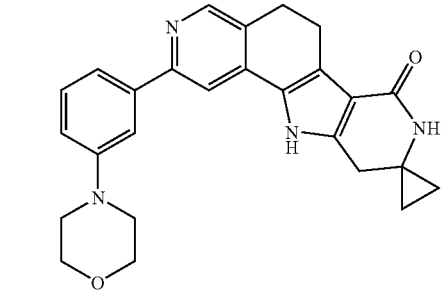

3-Morpholinophenylboronic acid pinacol ester (Frontier Scientific Catalog M1882) and 2-(1-amino-cyclopropylmethyl)-8-chloro-4,5-dihydro-1H-pyrrolo[2,3-f]isoquinoline-3-carboxylic acid lactam (Example 31a) are reacted in analogy to Example 1 and deliver the title compound as colorless crystals.

MS (m/z) ES+: 427 (MH+). Retention time: 1.75 minutes (LC-MS method 2).

EXAMPLE 238

2-(1-Amino-cyclopropylmethyl)-8-(3-fluoro-4-methoxy-phenyl)-4,5-dihydro-1H-pyrrolo[2,3-f]isoquino-line-3-carboxylic acid lactam

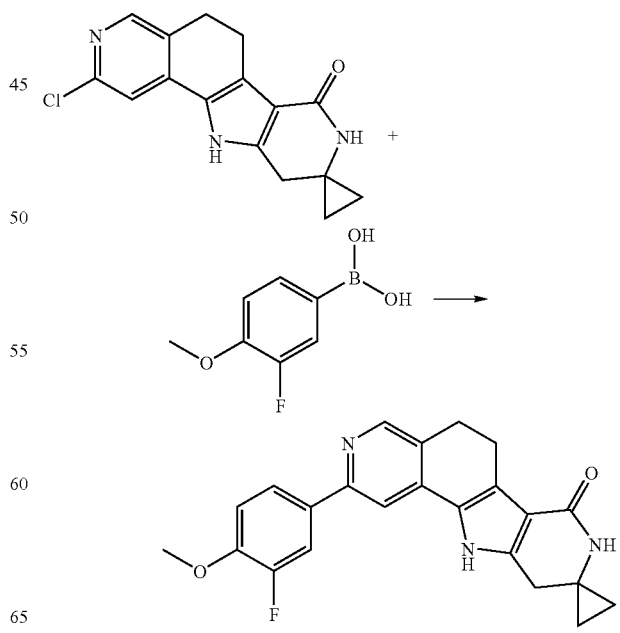

3-Fluoro-4-methoxyphenylboronic acid (Aldrich 564036) and 2-(1-amino-cyclopropylmethyl)-8-chloro-4,5-dihydro-1H-pyrrolo[2,3-f]isoquinoline-3-carboxylic acid lactam (Example 31a) are reacted in analogy to Example 1 and deliver the title compound as colorless crystals.

MS (m/z) ES+: 390 (MH+). Retention time:1.89 minutes (LC-MS method 2).

EXAMPLE 239

2-(1-Amino-cyclopropylmethyl)-8-(2-fluoro-phenyl)-4,5-dihydro-1H-pyrrolo[2,3-f]isoquinoline-3-carboxylic acid lactam

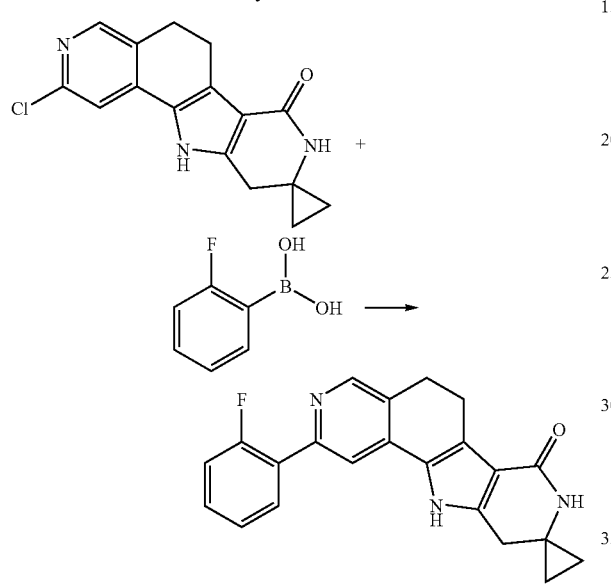

2-Fluorophenylboronic acid (Maybridge Building Blocks AC 35934) and 2-(1-amino-cyclopropylmethyl)-8-chloro-4,5-dihydro-1H-pyrrolo[2,3-f]isoquinoline-3-carboxylic acid lactam (Example 31a) are reacted in analogy to Example 1 and deliver the title compound as colorless crystals.

MS (m/z) ES+: 360 (MH+). Retention time: 1.77 minutes (LC-MS method 2).

EXAMPLE 240

2-(1-Amino-cyclopropylmethyl)-8-(6-hydroxymethyl-pyridin-3-yl)-4,5-dihydro-1H-pyrrolo[2,3-f]isoquinoline-3-carboxylic acid lactam

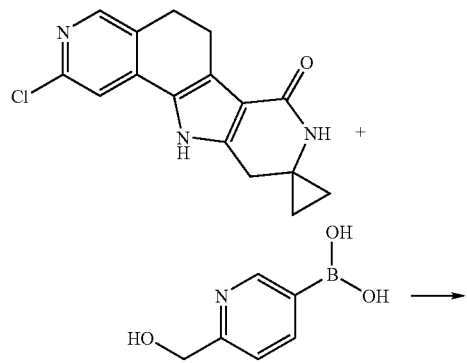

-continued

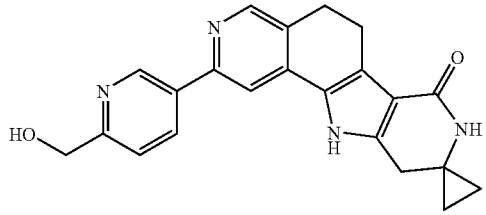

6-(Hydroxymethyl)pyridine-3-boronic acid (Combi-Blocks BB-3541) and 2-(1-amino-cyclopropylmethyl)-8-chloro-4,5-dihydro-1H-pyrrolo[2,3-f]isoquinoline-3-carboxylic acid lactam (Example 31a) are reacted in analogy to Example 1 and deliver the title compound as colorless crystals.

MS (m/z) ES+: 373 (MH+). Retention time: 1.35 minutes (LC-MS method 2).

EXAMPLE 241

2-(1-Amino-cyclopropylmethyl)-8-(2-fluoro-pyridin-3-yl)-4,5-dihydro-1H-pyrrolo[2,3-f]isoquinoline-3-carboxylic acid lactam

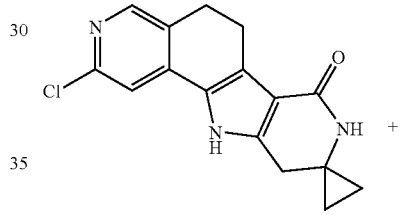

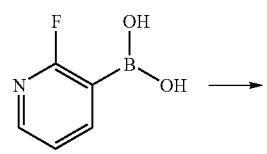

2-Fluoropyridine-3-boronic acid (ABCR, AB175551) and 2-(1-amino-cyclopropylmethyl)-8-chloro-4,5-dihydro-1H-pyrrolo[2,3-f]isoquinoline-3-carboxylic acid lactam (Example 31a) are reacted in analogy to Example 1 and deliver the title compound as colorless crystals.

MS (m/z) ES+: 361 (MH+). Retention time: 1.75 minutes (LC-MS method 2).

EXAMPLE 242

2-(1-Amino-cyclopropylmethyl)-8-(4-morpholin-4-yl-phenyl)-4,5-dihydro-1H-pyrrolo[2,3-f]isoquinoline-3-carboxylic acid lactam

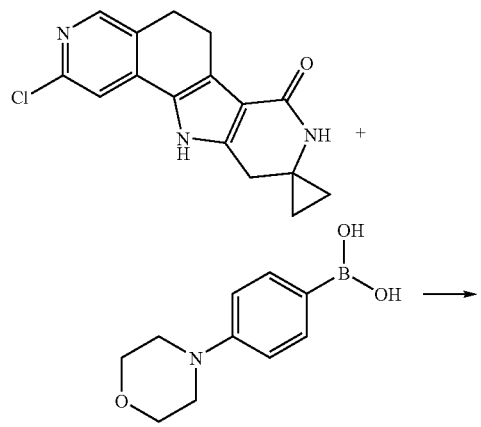

4-Morpholinophenylboronic acid (Maybridge Building Blocks CC 17412) and 2-(1-amino-cyclopropylmethyl)-8-chloro-4,5-dihydro-1H-pyrrolo[2,3-f]isoquinoline-3-carboxylic acid lactam (Example 31a) are reacted in analogy to Example 1 and deliver the title compound as colorless crystals.

MS (m/z) ES+: 427 (MH+). Retention time: 1.71 minutes (LC-MS method 2).

EXAMPLE 243

2-(1-Amino-cyclopropylmethyl)-8-[6-(3,3-difluoro-azetidin-1-yl)-pyridin-3-yl]-4,5-dihydro-1H-pyrrolo[2,3-f]isoquinoline-3-carboxylic acid lactam

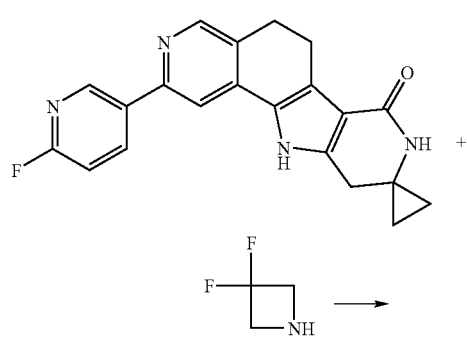

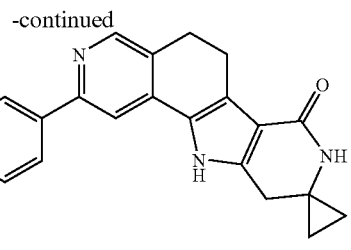

2-(1-Amino-cyclopropylmethyl)-8-(6-fluoro-pyridin-3-yl)-4,5-dihydro-1H-pyrrolo[2,3-f]isoquinoline-3-carboxylic acid lactam (Example 67) (90 mg; 0.25 mmol), 3,3-difluoro-azetidine hydrochloride (ABCR, AB174329) (330 mg; 2.5 mmol) and K$_2$CO$_3$ (330 mg; 2.5 mmol) are dissolved in DMSO (0.8 ml) and microwaved at 150° C. for 80 minutes. Purification via chromatography (SiO$_2$, acetone/heptane/HOAc 40:60:1) delivers the title compound as yellowish crystals (46 mg; 44%).

MS (m/z) ES+: 434 (MH+). Retention time: 1.77 minutes (LC-MS method 2).

EXAMPLE 244

8-(6-Acetoxymethyl-pyridin-3-yl)-2-(1-amino-cyclopropylmethyl)-4,5-dihydro-1H-pyrrolo[2,3-f]isoquinoline-3-carboxylic acid lactam

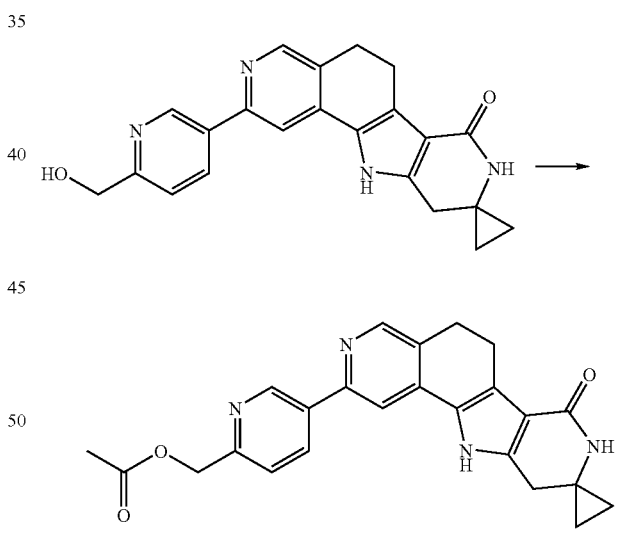

2-(1-Amino-cyclopropylmethyl)-8-(6-hydroxymethyl-pyridin-3-yl)-4,5-dihydro-1H-pyrrolo[2,3-f]isoquinoline-3-carboxylic acid lactam (Example 240) (30 mg; 0.08 mmol) in pyridine (5 ml) is cooled to 5° C. and combined dropwise under stirring with acetyl chloride (0.06 ml; 0.8 mmol) in CH$_2$Cl$_2$ (1 ml). The reaction mixture is warmed to room temperature, evaporated to dryness, taken up in TBME and washed with cold 2N Na$_2$CO$_3$, which precipitates the title compound as off-white crystals. (31 mg; 93%). MS (m/z) ES+: 415 (MH+). Retention time: 1.69 minutes (LC-MS method 2).

EXAMPLE 245

2-(1-Amino-cyclopropylmethyl)-8-(2,6-difluoro-pyridin-3-yl)-4,5-dihydro-1H-pyrrolo[2,3-f]isoquinoline-3-carboxylic acid lactam

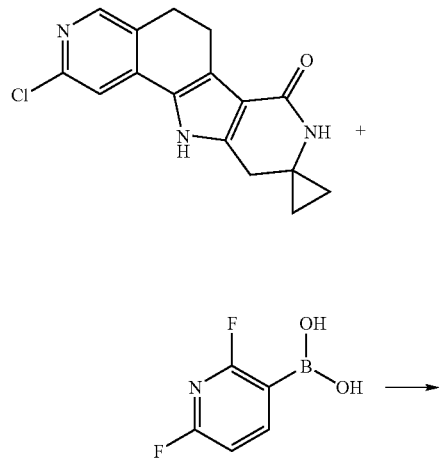

+

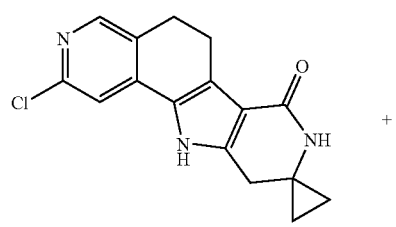

→

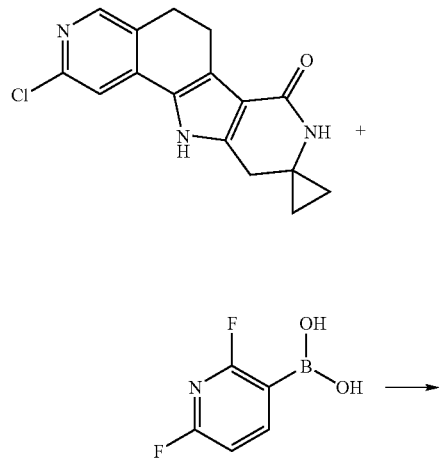

2,6-Difluoropyridine-3-boronic acid (SYNCHEM OHG Product List, un085) and 2-(1-amino-cyclopropylmethyl)-8-chloro-4,5-dihydro-1H-pyrrolo[2,3-f]isoquinoline-3-carboxylic acid lactam (Example 31a) are reacted in analogy to Example 1 and deliver the title compound as colorless crystals.

MS (m/z) ES+: 379 (MH+). Retention time: 2.03 minutes (LC-MS method 2).

EXAMPLE 246

2-(1-Amino-cyclopropylmethyl)-8-[4-(3-morpholin-4-yl-propyl)-phenyl]-4,5-dihydro-1H-pyrrolo[2,3-f]isoquinoline-3-carboxylic acid lactam

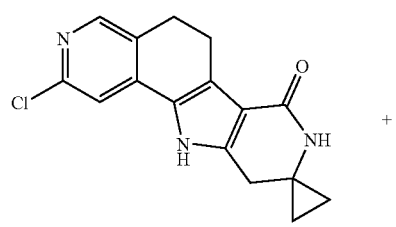

+

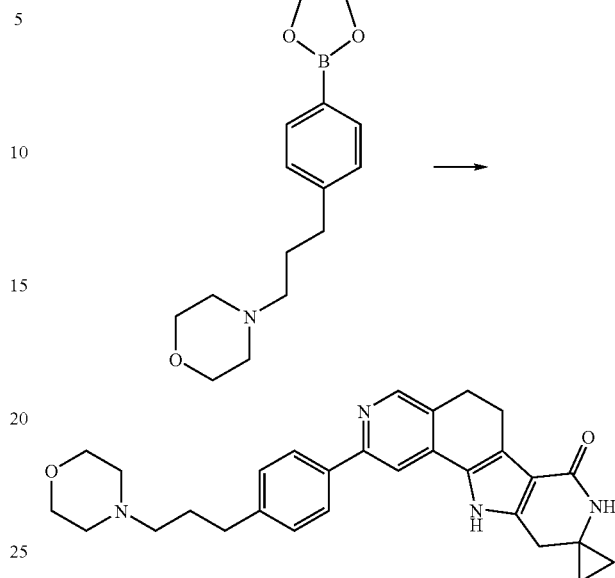

→

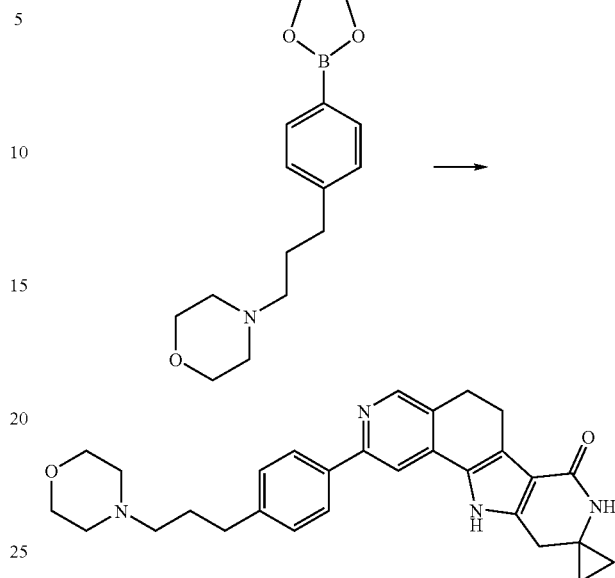

4-{3-[4-(4,4,5,5-Tetramethyl-[1,3,2]dioxaborolan-2-yl)-phenyl]-propyl}-morpholine and 2-(1-amino-cyclopropylmethyl)-8-chloro-4,5-dihydro-1H-pyrrolo[2,3-f]isoquinoline-3-carboxylic acid lactam (Example 31a) are reacted in analogy to Example 1 and deliver the title compound as colorless foam.

MS (m/z) ES+: 469 (MH+). Retention time: 1.22 minutes (LC-MS method 2).

The starting material is prepared as follows:

EXAMPLE 246A

4-{3-[4-(4,4,5,5-Tetramethyl-[1,3,2]dioxaborolan-2-yl)-phenyl]-propyl}-morpholine

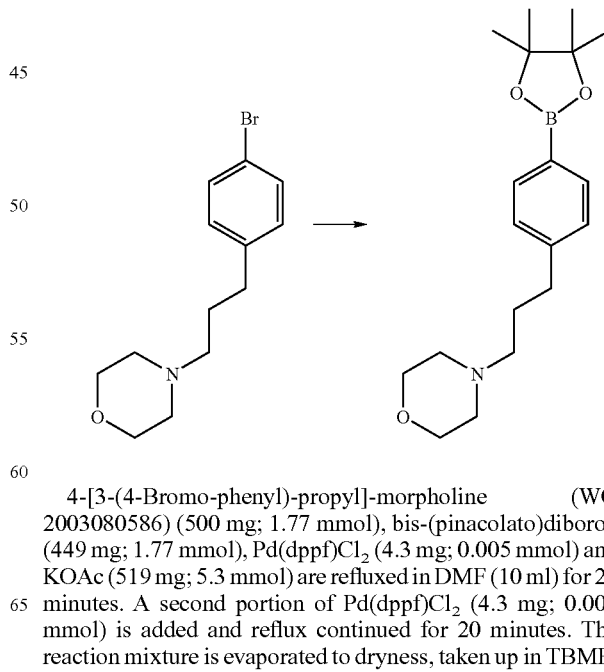

4-[3-(4-Bromo-phenyl)-propyl]-morpholine (WO 2003080586) (500 mg; 1.77 mmol), bis-(pinacolato)diboron (449 mg; 1.77 mmol), Pd(dppf)Cl₂ (4.3 mg; 0.005 mmol) and KOAc (519 mg; 5.3 mmol) are refluxed in DMF (10 ml) for 20 minutes. A second portion of Pd(dppf)Cl₂ (4.3 mg; 0.005 mmol) is added and reflux continued for 20 minutes. The reaction mixture is evaporated to dryness, taken up in TBME, filtered and evaporated. The residue is taken up in heptane, filtered and evaporated to dryness to deliver the title compound as yellowish oil (600 mg; 99%).

1H-NMR (400 MHz; DMSO-d6): 7.54 (d, 2H); 7.19 (d, 2H); 3.54 (bt, 4H); 2.59 (bt, 2H); 2.30 (bs, 4H); 2.22 (bt, 2H); 1.70 (m, 2H); 1.27 (s, 12H).

MS (m/z) ES+: 222 (MH+). Retention time:2.03 minutes (LC-MS method 2).

EXAMPLE 247

2-(1-Amino-cyclopropylmethyl)-8-[6-(3-hydroxy-azetidin-1-yl)-pyridin-3-yl]-4,5-dihydro-1H-pyrrolo[2,3-f]isoquinoline-3-carboxylic acid lactam

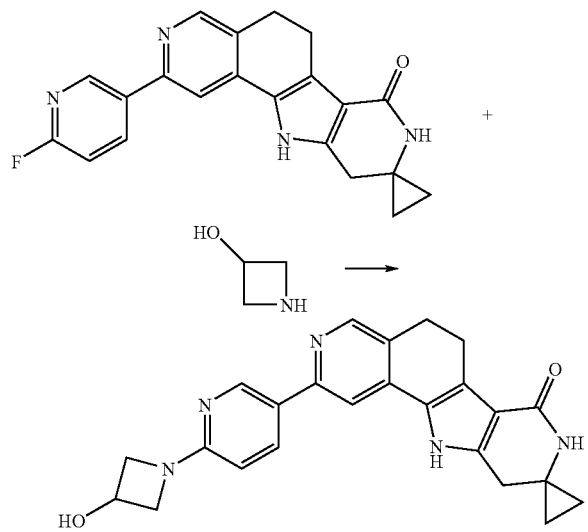

2-(1-Amino-cyclopropylmethyl)-8-(6-fluoro-pyridin-3-yl)-4,5-dihydro-1H-pyrrolo[2,3-f]isoquinoline-3-carboxylic acid lactam (Example 67)(60 mg; 0.17 mmol), 3-hydroxyazetidine hydrochloride (Atlantic Scitech Group, 880012)(183 mg; 1.67 mmol) and K2CO3 (228 mg; 1.67 mmol) in DMSO (1.8 ml) are microwaved for 10 minutes at 150° C. The reaction mixture is evaporated to dryness, taken up in $CH_2Cl_2$/MeOH (~3:1), filtered and evaporated. The residue is suspended in water, filtered and washed with Et2O/EtOH (~3:1) to deliver the title compound as yellowish crystals (48 mg; 69%)

MS (m/z) ES+: 414 (MH+). Retention time: 1.35 minutes (LC-MS method 2).

EXAMPLE 248

2-(1-Amino-cyclopropylmethyl)-8-{4-[3-(3-hydroxy-azetidin-1-yl)-propyl]-phenyl}-4,5-dihydro-1H-pyrrolo[2,3-f]isoquinoline-3-carboxylic acid lactam

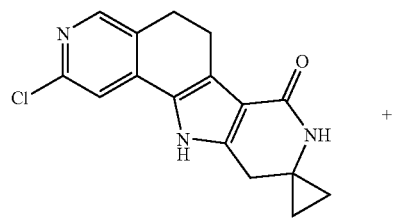

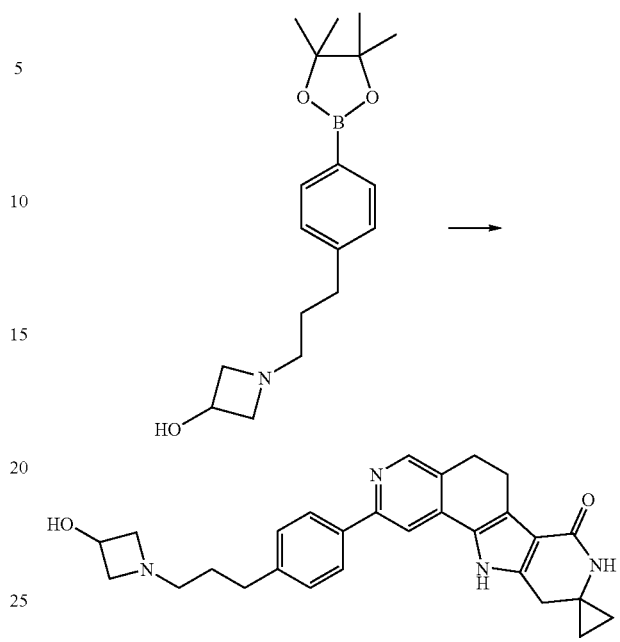

1-{3-[4-(4,4,5,5-Tetramethyl-[1,3,2]dioxaborolan-2-yl)-phenyl]-propyl}-azetidin-3-ol and 2-(1-amino-cyclopropyl-methyl)-8-chloro-4,5-dihydro-1H-pyrrolo[2,3-f]isoquinoline-3-carboxylic acid lactam (Example 31a) are reacted in analogy to Example 1 and deliver the title compound as colorless crystals.

MS (m/z) ES+: 455 (MH+). Retention time: 1.20 minutes (LC-MS method 2).

The starting material is prepared as follows:

EXAMPLE 248A

1-{3-[4-(4,4,5,5-Tetramethyl-[1,3,2]dioxaborolan-2-yl)-phenyl]-propyl}-azetidin-3-ol

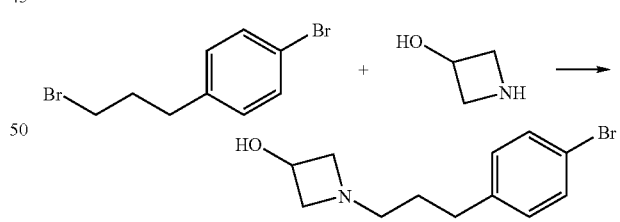

1-Bromo-4-(3-bromo-propyl)-benzene (WO 2008008234) (450 mg; 1.6 mmol) and 3-hydroxyazetidine hydrochloride (Atlantic Scitech Group, 880012) (950 mg; 8.7 mmol) and $K_2CO_3$ (1.2 g; 8.7 mmol) in DMSO (4 ml) are microwaved at 150° C. for 10 minutes. The reaction mixture is evaporated to dryness, taken up in TBME, filtered and the filtrate purified via chromatography (SiO2; acetone/heptane 3/7 then acetone/methanol (1/0 to 95/5) to yield the title compound as yellow oil. (308 mg; 70%).

MS (m/z) ES+: 270 (MH+). Retention time: 1.54 minutes (LC-MS method 2).

EXAMPLE 248B

1-{3-[4-(4,4,5,5-Tetramethyl-[1,3,2]dioxaborolan-2-yl)-phenyl]-propyl}-azetidin-3-ol

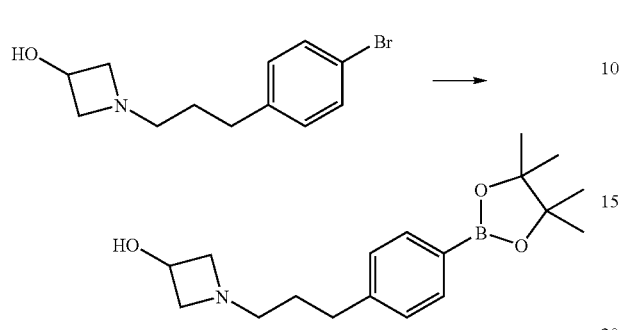

The title compound is obtained following the procedure described in Example 1f. The compound is used in the next step without further purification.

MS (m/z) ES+:317 (MH+). Retention time:1.97 minutes (LC-MS method 2).

EXAMPLE 250

2-[3-(1-Amino-cyclopropyl)-1-ethyl-azetidin-3-yl]-8-(6-isopropoxy-pyridin-3-yl)-4,5-dihydro-1H-pyrrolo[2,3-f]isoquinoline-3-carboxylic acid

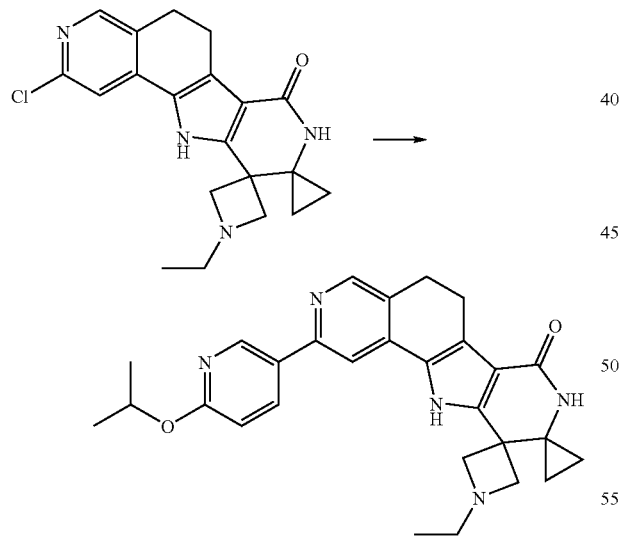

2-[3-(1-Amino-cyclopropyl)-1-ethyl-azetidin-3-yl]-8-chloro-4,5-dihydro-1H-pyrrolo[2,3-f]isoquinoline-3-carboxylic acid lactam and 2-isopropoxy-5-(4,4,5,5-tetramethyl-1,3,2-dioxaborolan-2-yl)pyridine (ABCR, AB173057) are reacted in analogy to Example 1 and deliver the title compound as colorless crystals.

MS (m/z) ES+: 470 (MH+). Retention time: 1.71 minutes (LC-MS method 2).

The starting material is prepared as follows

EXAMPLE 250A

2-[3-(1-Amino-cyclopropyl)-1-ethyl-azetidin-3-yl]-8-chloro-4,5-dihydro-1H-pyrrolo[2,3-f]isoquinoline-3-carboxylic acid lactam

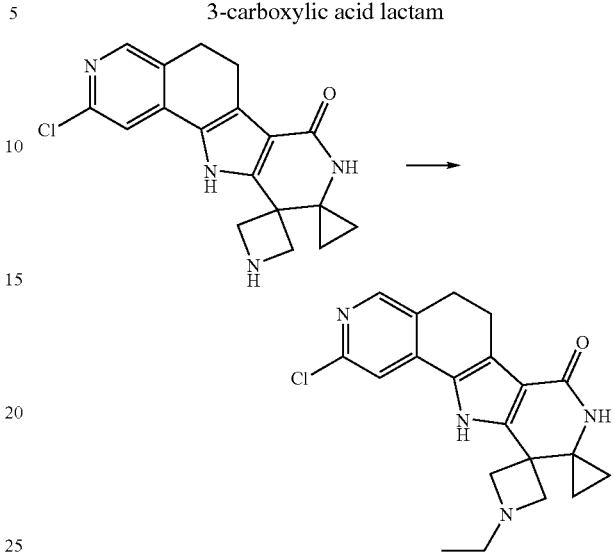

2-(3-Aminomethyl-azetidin-3-yl)-8-chloro-4,5-dihydro-1H-pyrrolo[2,3-f]isoquinoline-3-carboxylic acid lactam (Example 157a)(201 mg; 0.59 mmol) ethyl bromide (2.2 g; 20 mmol), triethylamine (0.29 ml; 2.07 mmol) in methanol (4 ml) are microwaved at 80° C. for 40 minutes. The reaction mixture is diluted with CH$_2$Cl$_2$, filtered and the filtrate purified via chromatography (CH$_2$Cl$_2$/MeOH/NH$_{3conc}$ 95:5:0.5). The resulting crystals are washed with Et$_2$O and delivered the title compound as colorless crystals) 118 mg; 54%).

MS (m/z) ES+: 369 (MH+). Retention time: 1.32 minutes (LC-MS method 2).

EXAMPLE 251

2-[3-(1-Amino-cyclopropyl)-1-ethyl-azetidin-3-yl]-8-(6-methoxy-pyridin-3-yl)-4,5-dihydro-1H-pyrrolo[2,3-f]isoquinoline-3-carboxylic acid lactam

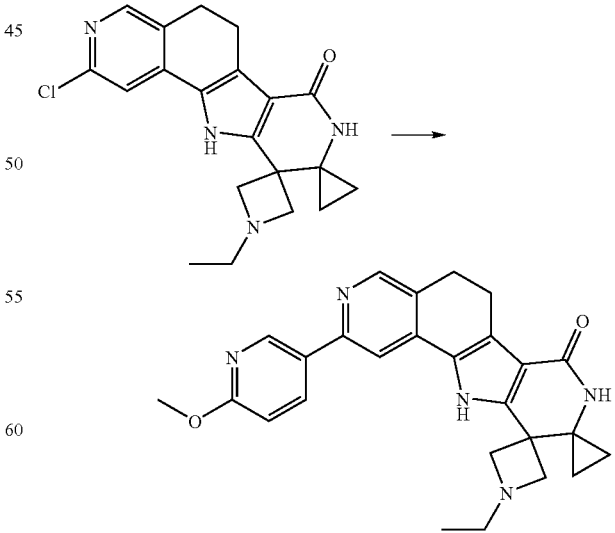

2-[3-(1-Amino-cyclopropyl)-1-ethyl-azetidin-3-yl]-8-chloro-4,5-dihydro-1H-pyrrolo[2,3-f]isoquinoline-3-car-

EXAMPLE 252

2-[3-(1-Amino-cyclopropyl)-1-ethyl-azetidin-3-yl]-8-(5-fluoro-6-methoxy-pyridin-3-yl)-4,5-dihydro-1H-pyrrolo[2,3-f]isoquinoline-3-carboxylic acid lactam

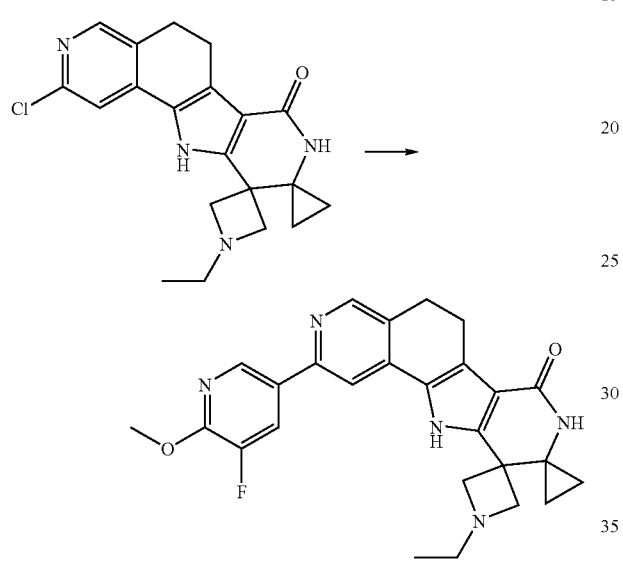

2-[3-(1-Amino-cyclopropyl)-1-ethyl-azetidin-3-yl]-8-chloro-4,5-dihydro-1H-pyrrolo[2,3-f]isoquinoline-3-carboxylic acid lactam (Example 250a) and 3-fluoro-2-methoxypyridine-5-boronic acid (Asymchem Product List 110641) are reacted in analogy to Example 1 and deliver the title compound as colorless crystals.

MS (m/z) ES+: 460 (MH+). Retention time: 1.68 minutes (LC-MS method 2).

EXAMPLE 253

2-[3-(1-Amino-cyclopropyl)-1-ethyl-azetidin-3-yl]-8-(2-fluoro-phenyl)-4,5-dihydro-1H-pyrrolo[2,3-f]isoquinoline-3-carboxylic acid lactam

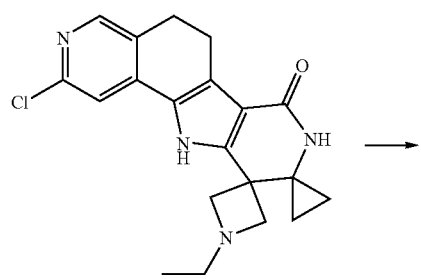

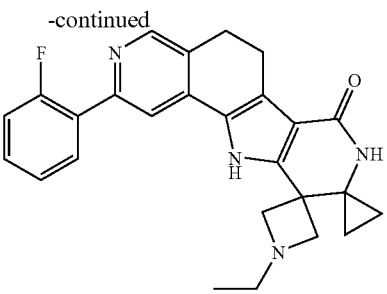

2-[3-(1-Amino-cyclopropyl)-1-ethyl-azetidin-3-yl]-8-chloro-4,5-dihydro-1H-pyrrolo[2,3-f]isoquinoline-3-carboxylic acid lactam (Example 250a) and 2-fluorophenylboronic acid (Maybridge Building Blocks AC 35934) are reacted in analogy to Example 1 and deliver the title compound as colorless crystals.

MS (m/z) ES+: 429 (MH+). Retention time: 1.31 minutes (LC-MS method 2).

EXAMPLE 254

2-[3-(1-Amino-cyclopropyl)-1-methyl-azetidin-3-yl]-8-(6-isopropoxy-pyridin-3-yl)-4,5-dihydro-1H-pyrrolo[2,3-f]isoquinoline-3-carboxylic acid lactam

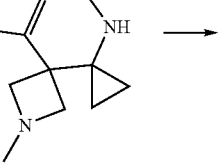

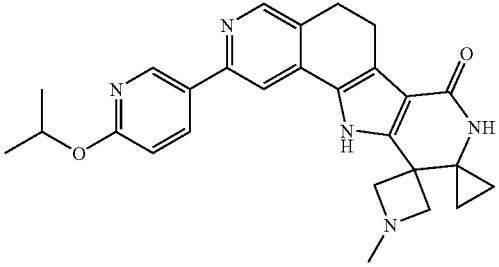

2-(3-Aminomethyl-1-methyl-azetidin-3-yl)-8-chloro-4,5-dihydro-1H-pyrrolo[2,3-f]isoquinoline-3-carboxylic acid lactam (Example 157b) and 2-isopropoxy-5-(4,4,5,5-tetramethyl-1,3,2-dioxaborolan-2-yl)pyridine (ABCR, AB173057) are reacted in analogy to Example 1 and deliver the title compound as colorless crystals.

MS (m/z) ES+: 456 (MH+). Retention time: 1.66 minutes (LC-MS method 2).

EXAMPLE 255

2-[3-(1-Amino-cyclopropyl)-1-methyl-azetidin-3-yl]-8-(6-methoxy-pyridin-3-yl)-4,5-dihydro-1H-pyrrolo[2,3-f]isoquinoline-3-carboxylic acid lactam

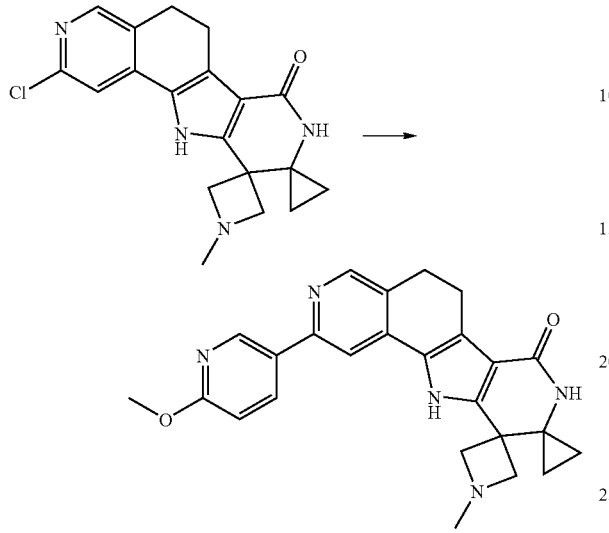

2-(3-Aminomethyl-1-methyl-azetidin-3-yl)-8-chloro-4,5-dihydro-1H-pyrrolo[2,3-f]isoquinoline-3-carboxylic acid lactam (Example 157b) and 2-methoxy-5-pyridineboronic acid (Aldrich, 637610) are reacted in analogy to Example 1 and deliver the title compound as colorless crystals.

MS (m/z) ES+: 428 (MH+). Retention time: 1.26 minutes (LC-MS method 2).

EXAMPLE 256

2-[3-(1-Amino-cyclopropyl)-1-methyl-azetidin-3-yl]-8-(2-fluoro-phenyl)-4,5-dihydro-1H-pyrrolo[2,3-f]isoquinoline-3-carboxylic acid lactam

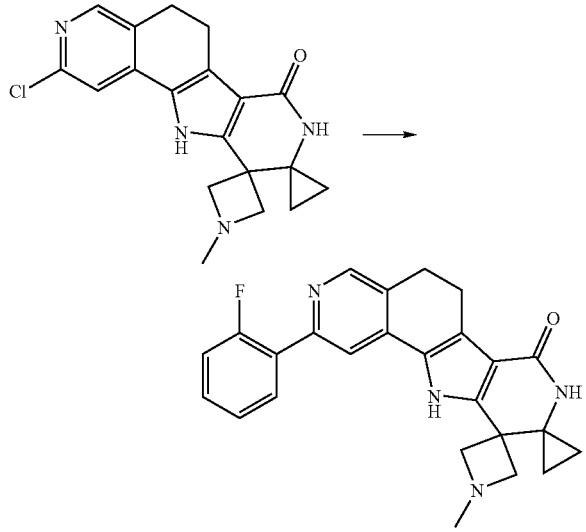

2-(3-Aminomethyl-1-methyl-azetidin-3-yl)-8-chloro-4,5-dihydro-1H-pyrrolo[2,3-f]isoquinoline-3-carboxylic acid lactam (Example 157b) and 2-fluorophenylboronic acid (Maybridge Building Blocks AC 35934) are reacted in analogy to Example 1 and deliver the title compound as colorless crystals.

MS (m/z) ES+: 415 (MH+). Retention time: 1.22 minutes (LC-MS method 2).

EXAMPLE 257

2-(1-Amino-cyclopropylmethyl)-8-(2-fluoro-phenyl)-4,5-dihydro-1H-1,7,9-triaza-cyclopenta[a]naphthalene-3-carboxylic acid lactam

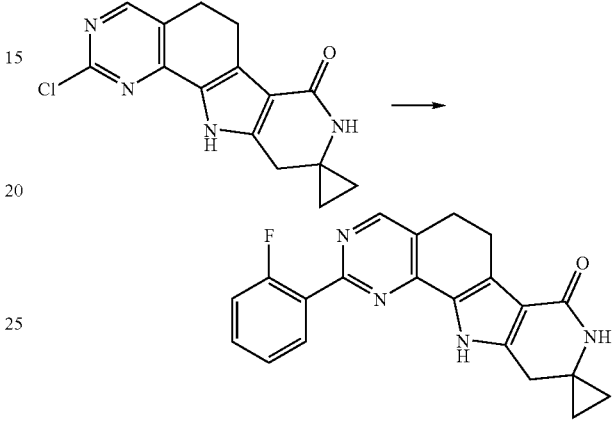

2-(1-Amino-cyclopropylmethyl)-8-chloro-4,5-dihydro-1H-1,7,9-triaza-cyclopenta[a]naphthalene-3-carboxylic acid lactam (Example 257d) and 2-fluorophenylboronic acid (Maybridge Building Blocks AC 35934) are reacted in analogy to Example 1 and deliver the title compound as colorless crystals.

1H-NMR (400 MHz; DMSO-d6):

MS (m/z) ES+: 361 (MH+). Retention time: 2.12 minutes (LC-MS method 2).

The starting material is prepared as follows:

EXAMPLE 257A

2-Chloro-6,7-dihydro-5H-quinazolin-8-one oxime

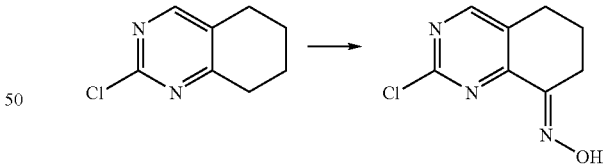

2-Chloro-5,6,7,8-tetrahydro-quinazoline (Eur. J. Med. Chem. 1982, 17, 75)(1.0 g; 5.9 mmol) is dissolved in THF (80 ml) and cooled to −78° C. KOtBu (667 mg; 5.9 mmol) in THF (10 ml) is added dropwise and stirred for 5 minutes after complete addition. t-Butyl nitrite (2 ml; 27.8 mmol) is added to the orange solution and the reaction mixture warmed to room temperature. After 10 minutes the reaction mixture is poured on water/HOAc (800/1 ml) and extracted with ethyl acetate three times. The combined organic phases are dried over $Na_2SO_4$, filtered and evaporated to dryness to deliver the title compound as yellow-orange crystals (1.1 g; 95%).

1H-NMR (400 MHz; DMSO-d6): 12.16 (s, 1H); 8.61 (s, 1H); 2.70 (m, 4H); 1.77 (m, 2H). 1H-ROESY proves OHconfiguration. MS (m/z) ES+: 198 (MH+). Retention time: 1.36 minutes (LC-MS method 2).

EXAMPLE 257B

2-Chloro-6,7-dihydro-5H-quinazolin-8-one

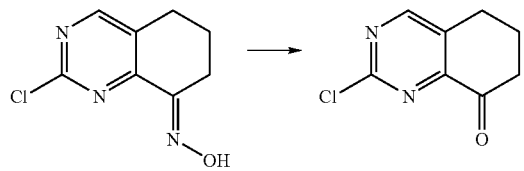

2-Chloro-6,7-dihydro-5H-quinazolin-8-one oxime (Example 257a)(620 mg; 3.1 mmol) is dissolved in $HCl_{conc}$ (12 ml), combined with water (50 ml) and acetone (12 ml) and heated to 80° C. for 20 minutes. The yellow solution is cooled and poured on $Na_2CO_3$/water (12 g/150 ml) and extracted with ethyl acetate three times. The combined organic phases are dried over $Na_2SO_4$, filtered and evaporated to dryness to deliver the title compound as yellow crystals (480 mg; 84%).

1H-NMR (400 MHz; DMSO-d6): 8.97 (s, 1H); 2.95 (m, 2H); 2.71 (m, 2H); 2.07 (m, 2H).

MS (m/z) ES+: 183 (MH+). Retention time: 1.17 minutes (LC-MS method 2).

EXAMPLE 257C

7-Bromo-2-chloro-6,7-dihydro-5H-quinazolin-8-one

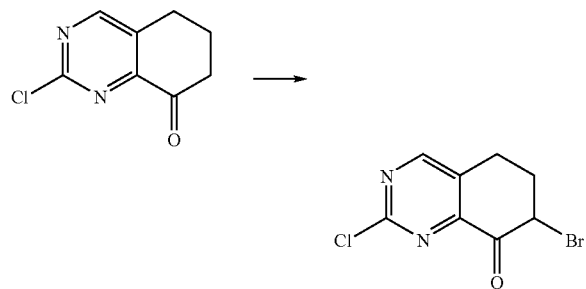

2-Chloro-6,7-dihydro-5H-quinazolin-8-one (570 mg; 3.1 mmol) is dissolved in $HCl_{conc}$ (20 ml) and combined at room temperature with $Br_2$ (500 mg; 3.1 mmol) in $HCl_{conc}$ (3.4 ml). The reaction mixture is warmed to 35° C. for 10 minutes, poured on water and extracted with ethyl acetate three times. The combined organic phases are dried over $Na_2SO_4$, filtered and evaporated to dryness to deliver the title compound as brown-yellow crystals (740 mg; 91%) which are used in the next step without further purification.

EXAMPLE 257D 2-(1-Amino-cyclopropylmethyl)-8-chloro-4,5-dihydro-1H-1,7,9-triaza-cyclopenta[a]naphthalene-3-carboxylic acid lactam

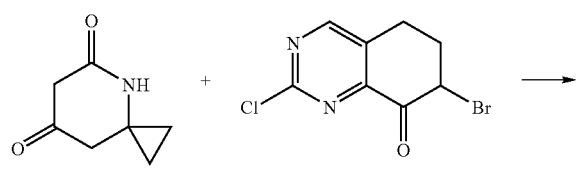

-continued

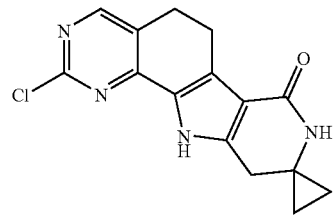

7-Bromo-2-chloro-6,7-dihydro-5H-quinazolin-8-one (Example 257c)(238 mg; 0.91 mmol), 4-aza-spiro[2.5]octane-5,7-dione (Example 30c) (191 mg; 13.7 mmol) and NaOAc (75 mg; 0.91 mmol) are dissolved in methanol (3 ml) and stirred for 10 minutes at room temperature. $NH_4OAc$ (141 mg; 1.83 mmol) is added and the reaction mixture stirred over night at room temperature. The yellowish precipitate is filtered and washed with methanol followed by TBME and dried to deliver the title compound as slightly yellow crystals (175 mg; 64%). 1H-NMR (400 MHz; DMSO-d6): 12.30 (s, 1H); 8.28 (s, 1H); 7.27 (s, 1H); 2.96 (m, 2H); 2.86 (m, 2H); 2.79 (s, 2H); 0.74 (m, 2H); 0.64 (m, 2H).

MS (m/z) ES+: 301 (MH+). Retention time: 1.72 minutes (LC-MS method 2).

EXAMPLE 258

2-[3-(1-Amino-cyclopropyl)-1-methyl-azetidin-3-yl]-8-(5-fluoro-6-methoxy-pyridin-3-yl)-4,5-dihydro-1H-pyrrolo[2,3-f]isoquinoline-3-carboxylic acid lactam

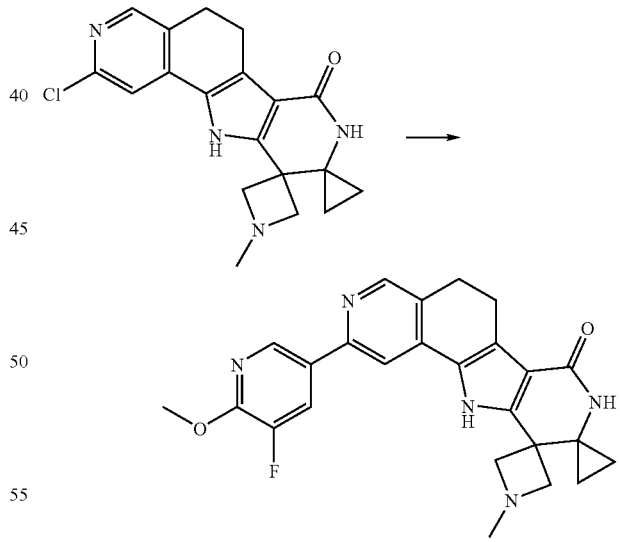

3-Fluoro-2-methoxypyridine-5-boronic acid (Asymchem Product List 110641) and 2-[3-(1-amino-cyclopropyl)-1-methyl-azetidin-3-yl]-8-chloro-4,5-dihydro-1H-pyrrolo[2,3-f]isoquinoline-3-carboxylic acid lactam (Example 222b) are reacted in analogy to Example 1 and deliver the title compound as colorless crystals.

MS (m/z) ES+: 446 (MH+). Retention time: 1.60 minutes (LC-MS method 2).

EXAMPLE 259

2-[3-(1-Amino-cyclopropyl)-1-methyl-azetidin-3-yl]-8-[4-(2-morpholin-4-yl-ethoxy)-phenyl]-4,5-dihydro-1H-pyrrolo[2,3-f]isoquinoline-3-carboxylic acid lactam

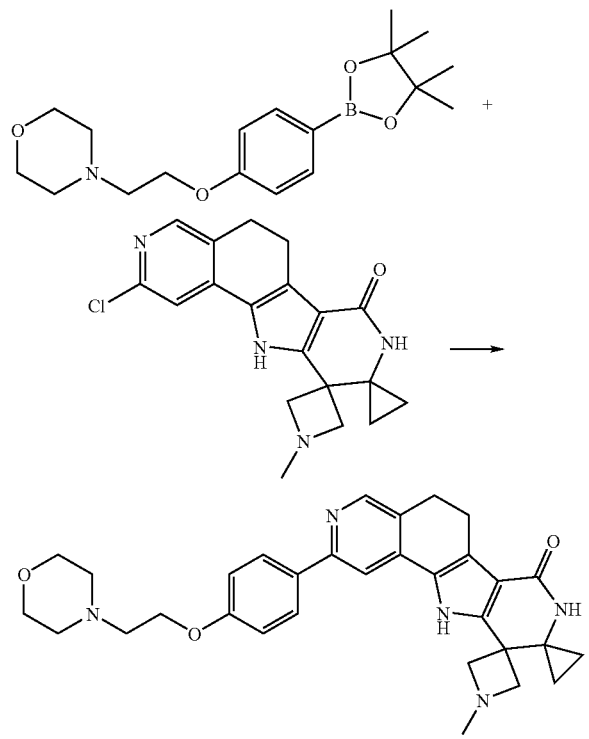

2-[3-(1-Amino-cyclopropyl)-1-methyl-azetidin-3-yl]-8-chloro-4,5-dihydro-1H-pyrrolo[2,3-f]isoquinoline-3-carboxylic acid lactam (Example 222b) and 4-{2-[4-(4,4,5,5-tetramethyl-[1,3,2]dioxaborolan-2-yl)-phenoxy]-ethyl}-morpholine (Focus Synthesis Products FS000534) are reacted in analogy to Example 1 and deliver the title compound as colorless crystals.

MS (m/z) ES+: 526 (MH+). Retention time: 0.90 minutes (LC-MS method 2).

EXAMPLE 260

2-[3-(1-Amino-cyclopropyl)-1-methyl-azetidin-3-yl]-8-[4-(3-morpholin-4-yl-propyl)-phenyl]-4,5-dihydro-1H-pyrrolo[2,3-f]isoquinoline-3-carboxylic acid lactam

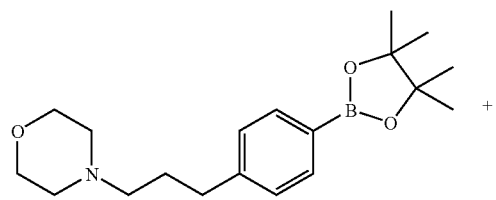

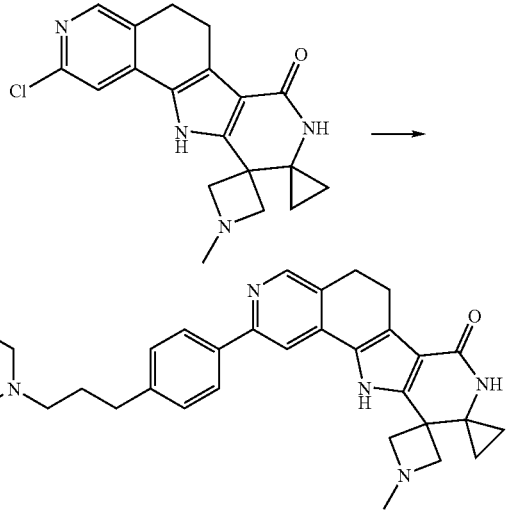

2-[3-(1-Amino-cyclopropyl)-1-methyl-azetidin-3-yl]-8-chloro-4,5-dihydro-1H-pyrrolo[2,3-f]isoquinoline-3-carboxylic acid lactam (Example 222b) and 4-{3-[4-(4,4,5,5-tetramethyl-[1,3,2]dioxaborolan-2-yl)-phenyl]-propyl}-morpholine (Example 246a) are reacted in analogy to Example 1 and deliver the title compound as colorless crystals.

MS (m/z) ES+: 524 (MH+). Retention time: 0.95 minutes (LC-MS method 2).

EXAMPLE 261

2-(3-Aminomethyl-1-cyclopropylmethyl-azetidin-3-yl)-8-(3-benzylcarbamoyl-phenyl)-4,5-dihydro-1H-pyrrolo[2,3-f]isoquinoline-3-carboxylic acid lactam

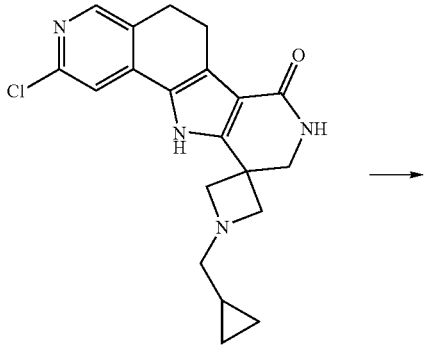

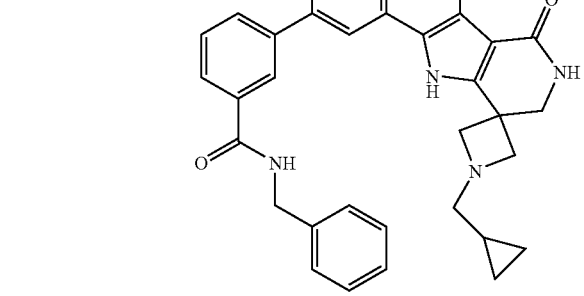

2-(3-Aminomethyl-1-cyclopropylmethyl-azetidin-3-yl)-8-chloro-4,5-dihydro-1H-pyrrolo[2,3-f]isoquinoline-3-carboxylic acid lactam and 3-(N-benzylaminocarbonyl)phenylboronic acid (Combi-Blocks BB-3055) are coupled in analogy to Example 1 to deliver the title compound as colorless crystals.

MS (m/z) ES+: 544 (MH+). Retention time: 1.73 minutes (LC-MS method 2).

The starting material is prepared as follows:

EXAMPLE 261A 2-(3-Aminomethyl-1-cyclopropylmethyl-azetidin-3-yl)-8-chloro-4,5-dihydro-1H-pyrrolo[2,3-f]isoquinoline-3-carboxylic acid lactam

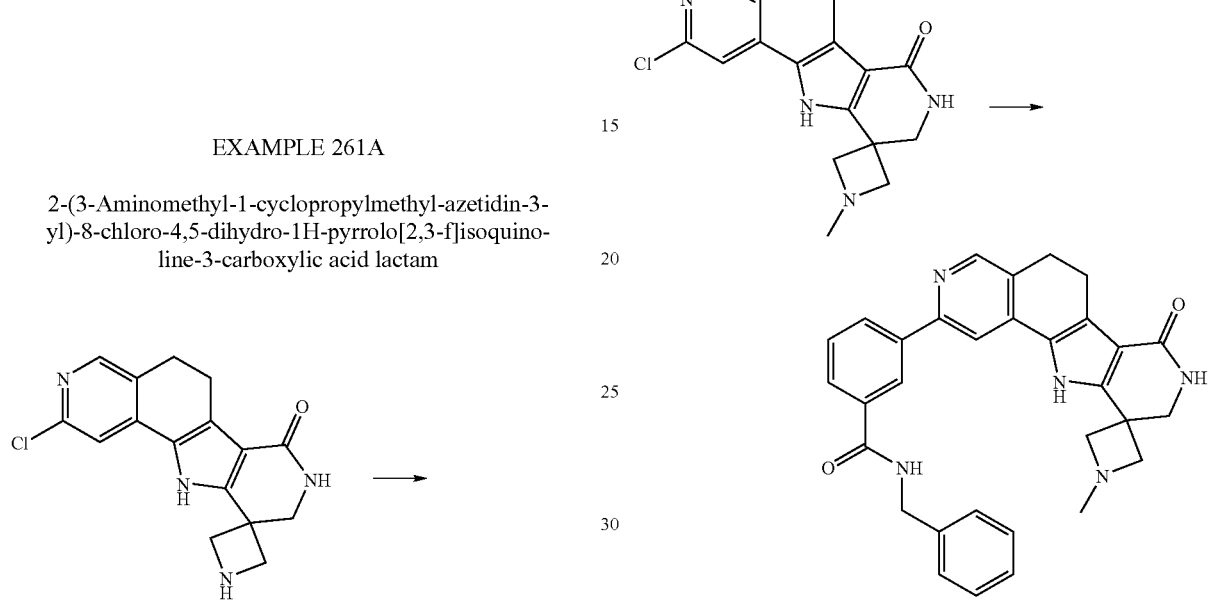

2-(3-Aminomethyl-azetidin-3-yl)-8-chloro-4,5-dihydro-1H-pyrrolo[2,3-f]isoquinoline-3-carboxylic acid lactam (Example 157a) (400 mg; 1.274 mmol), triethylamine (0.62 ml; 4.46 mmol) and bromomethylcyclopropane (Fluka 17163) (1.4 g; 10.3 mmol) in methanol (3 ml) are microwaved at 80° C. for 25 minutes, evaporated to dryness and purified via chromatography (SiO$_2$; CH$_2$Cl$_2$/MeOH/NH$_3$conc 93:7:0.7) to deliver the title compound as yellowish crystals (254 mg; 54%).

1H-NMR (400 MHz; DMSO-d6): 12.18 (s, 1H); 8.15 (s, 1H); 7.57 (s, 1H); 7.41 (s, 1H); 4.46 (m, 2H); 4.24 (m, 2H); 3.74 (s, 2H); 3.25 (m, 2H); 2.88 (m, 2H); 2.82 (m, 2H); 1.01 (m, 1H); 0.61 (bd 2H); 0.42 (bs, 2H).

MS (m/z) ES+: 369 (MH+). Retention time: 1.36 minutes (LC-MS method 2).

EXAMPLE 262

2-(3-Aminomethyl-1-methyl-azetidin-3-yl)-8-(3-benzylcarbamoyl-phenyl)-4,5-dihydro-1H-pyrrolo[2,3-f]isoquinoline-3-carboxylic acid lactam

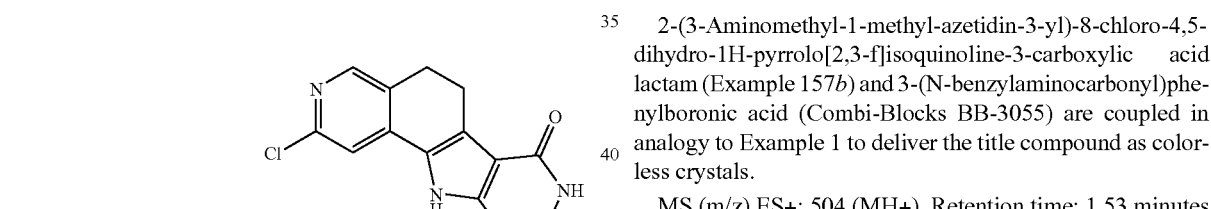

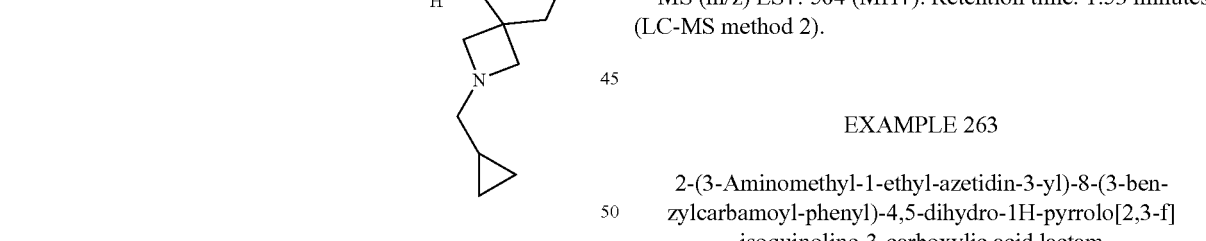

2-(3-Aminomethyl-1-methyl-azetidin-3-yl)-8-chloro-4,5-dihydro-1H-pyrrolo[2,3-f]isoquinoline-3-carboxylic acid lactam (Example 157b) and 3-(N-benzylaminocarbonyl)phenylboronic acid (Combi-Blocks BB-3055) are coupled in analogy to Example 1 to deliver the title compound as colorless crystals.

MS (m/z) ES+: 504 (MH+). Retention time: 1.53 minutes (LC-MS method 2).

EXAMPLE 263

2-(3-Aminomethyl-1-ethyl-azetidin-3-yl)-8-(3-benzylcarbamoyl-phenyl)-4,5-dihydro-1H-pyrrolo[2,3-f]isoquinoline-3-carboxylic acid lactam

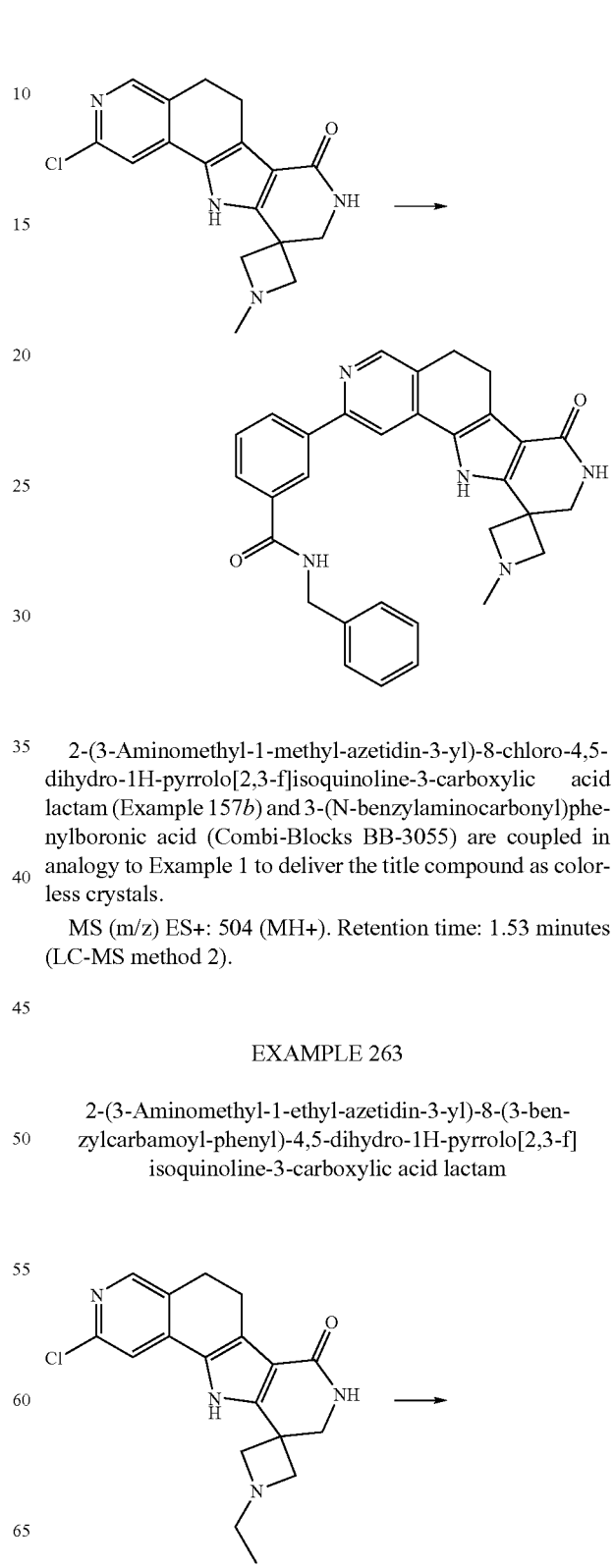

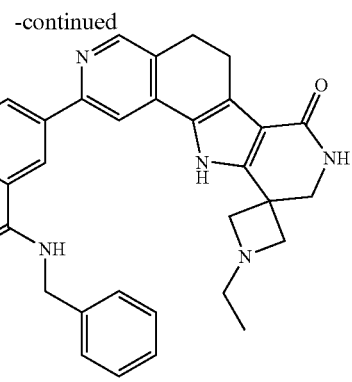

2-(3-Aminomethyl-1-ethyl-azetidin-3-yl)-8-chloro-4,5-dihydro-1H-pyrrolo[2,3-f]isoquinoline-3-carboxylic acid lactam and 3-(N-benzylaminocarbonyl)phenylboronic acid (Combi-Blocks BB-3055) are coupled in analogy to Example 1 to deliver the title compound as colorless crystals. MS (m/z) ES+: 518 (MH+). Retention time: 1.60 minutes (LC-MS method 2).

The starting material is prepared as follows:

EXAMPLE 263A 2-(3-Aminomethyl-1-ethyl-azetidin-3-yl)-8-chloro-4,5-dihydro-1H-pyrrolo[2,3-f]isoquinoline-3-carboxylic acid lactam

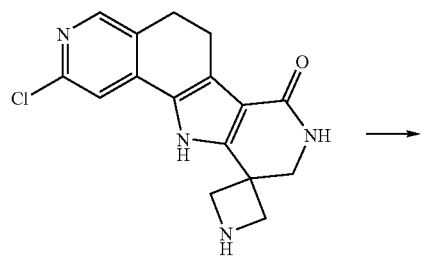

2-(3-Aminomethyl-azetidin-3-yl)-8-chloro-4,5-dihydro-1H-pyrrolo[2,3-f]isoquinoline-3-carboxylic acid lactam (Example 157a) (1.00 g; 3.18 mmol), triethylamine (1.56 ml; 11.14 mmol) and ethyl bromide (5 ml; 66 mmol) in methanol (10 ml) are heated in a sealed vessel at 80° C. for 15 minutes. The reaction mixture is diluted with CH2Cl2, filtered, the filtrate evaporated to dryness and purified via chromatography (SiO$_2$; CH$_2$Cl$_2$/MeOH/NH$_3$conc 90:10:1) to deliver the title compound as yellowish crystals (624 mg; 57%).

1H-NMR (400 MHz; DMSO-d6): 11.77 (bs, 1H); 8.09 (s, 1H); 7.64 (s, 1H); 7.15 (s, 1H); 3.55 (s, 2H); 3.28 (s, 4H); 2.85 (m, 2H); 2.75 (m, 2H); 2.49 (q, 2H); 0.93 (t, 3H).

MS (m/z) ES+: 343 (MH+). Retention time: 1.22 minutes (LC-MS method 2).

EXAMPLE 264

2-(1-Amino-cyclopropylmethyl)-8-piperidin-1-yl-4,5-dihydro-1H-1,7,9-triaza-cyclopenta[a]naphthalene-3-carboxylic acid lactam

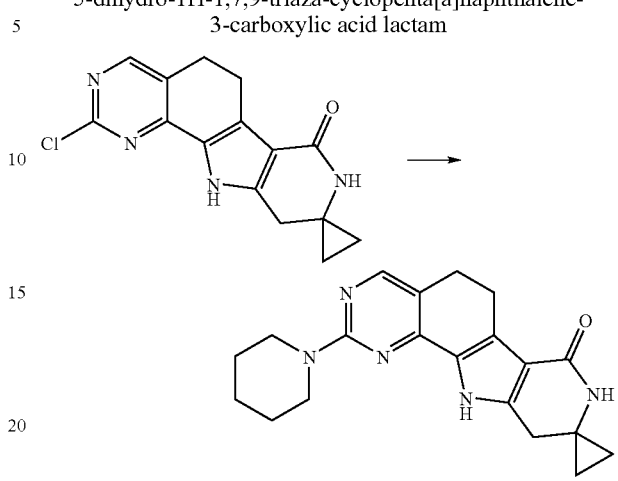

2-(1-Amino-cyclopropylmethyl)-8-chloro-4,5-dihydro-1H-1,7,9-triaza-cyclopenta[a]naphthalene-3-carboxylic acid lactam (Example 257d) (26 mg; 0.087 mmol) is dissolved in piperidine (1 ml) and refluxed for 20 minutes. The reaction mixture is evaporated to dryness and the solid residue recrystallized from methanol. The resulting crystals are washed with water followed by TBME and heptane to deliver the title compound as slightly yellow crystals (23 mg; 77%)

1H-NMR (400 MHz; DMSO-d6): 11.68 (s, 1H); 7.96 (s, 1H); 7.13 (s, 1H); 3.74 (m, 4H); 2.85 (m, 2H); 2.79 (s, 2H); 2.70 (m, 2H); 1.52 (bs, 2H); 1.50 (bs, 4H); 0.74 (m, 2H); 0.66 (m, 2H). MS (m/z) ES+: 350 (MH+). Retention time: 1.63 minutes (LC-MS method 2).

EXAMPLE 265

2-(1-Amino-cyclopropylmethyl)-8-(3,4-dihydro-1H-isoquinolin-2-yl)-4,5-dihydro-1H-1,7,9-triaza-cyclopenta[a]naphthalene-3-carboxylic acid lactam

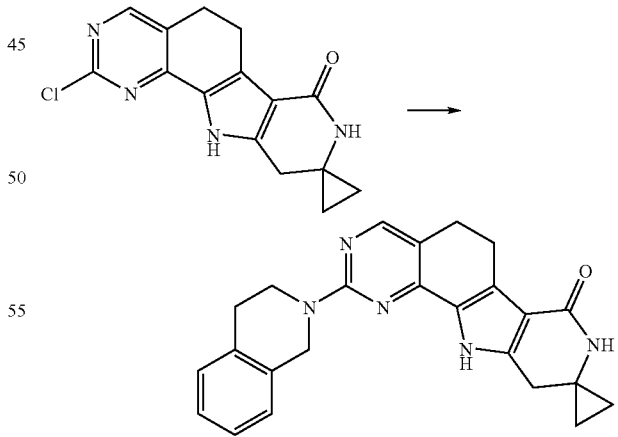

2-(1-Amino-cyclopropylmethyl)-8-chloro-4,5-dihydro-1H-1,7,9-triaza-cyclopenta[a]naphthalene-3-carboxylic acid lactam (Example 257d) (26 mg; 0.087 mmol) is dissolved in 1,2,3,4-tetrahydroisoquinoline (1 ml) and heated to 125° C. for 20 minutes. The reaction mixture is evaporated to dryness and the solid residue triturated with NH$_3$ $_{conc}$, washed with water and recrystallized from methanol to deliver the title compound as yellow crystals (30 mg; 87%).

1H-NMR (400 MHz; DMSO-d6): 11.79 (bs, 1H); 8.03 (s, 1H); 7.20 (m, 5H); 4.88 (s, 2H); 4.03 (t, 2H); 2.86 (m, 4H); 2.83 (s, 2H); 2.71 (t, 2H); 0.75 (m, 2H); 0.65 (m, 2H).

MS (m/z) ES+: 398 (MH+). Retention time: 2.09 minutes (LC-MS method 2).

EXAMPLE 266

2-(1-Amino-cyclopropylmethyl)-8-(2,4-difluoro-phenoxy)-4,5-dihydro-1H-1,7,9-triaza-cyclopenta[a]naphthalene-3-carboxylic acid lactam

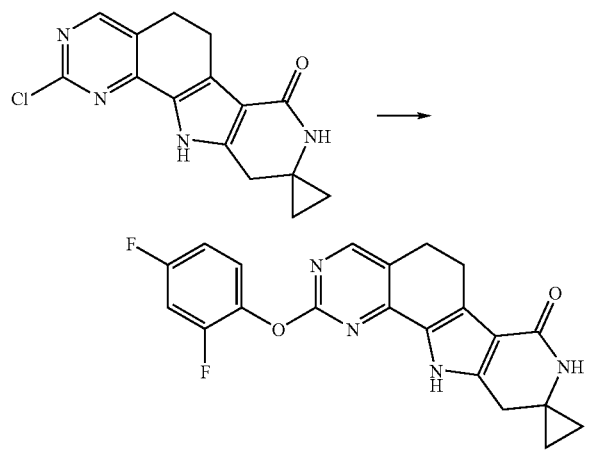

2-(1-Amino-cyclopropylmethyl)-8-chloro-4,5-dihydro-1H-1,7,9-triaza-cyclopenta[a]naphthalene-3-carboxylic acid lactam (Example 257d) (30 mg; 0.01 mmol), 2,4-difluorophenol (200 mg; 1.5 mol) and K₂CO₃ (200 mg; 1.4 mmol) are refluxed in formamide (2 ml) for 2 minutes. The reaction mixture is diluted with water and the precipitate filtered off, washed with water, ethyl acetate and methanol to deliver the title compound as yellowish crystals (25 mg; 63%)

1H-NMR (400 MHz; DMSO-d6): 12.16 (bs, 1H); 8.12 (s, 1H); 7.42 (m, 2H); 7.25 (s, 1H); 7.12 (m, 1H); 2.96 (m, 2H); 2.84 (m, 2H); 2.81 (s, 2H); 0.76 (m, 2H); 0.68 (m, 2H).

MS (m/z) ES+: 395 (MH+). Retention time: 2.33 minutes (LC-MS method 2).

EXAMPLE 267

2-(1-Amino-cyclopropylmethyl)-8-(2-fluoro-phenylamino)-4,5-dihydro-1H-1,7,9-triaza-cyclopenta[a]naphthalene-3-carboxylic acid lactam

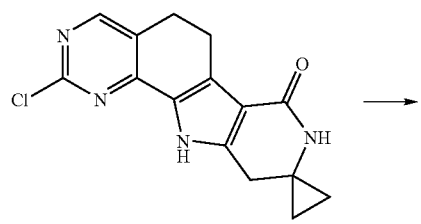

-continued

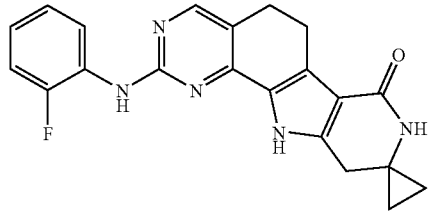

2-(1-Amino-cyclopropylmethyl)-8-chloro-4,5-dihydro-1H-1,7,9-triaza-cyclopenta[a]naphthalene-3-carboxylic acid lactam (Example 257d) (30 mg; 0.01 mmol) and 2-fluoroaniline (Fluka 46470)(200 mg; 1.8 mmol) in formamide (2 ml) are heated to 190° C. for 40 minutes. The reaction mixture is evaporated to dryness, the resulting solid washed with water, purified via chromatography (SiO2; EtOAc/heptane/HOAc 50:50:1) and crystallized from acetone to deliver the title compound as yellowish solid (10 mg; 26%).

1H-NMR (400 MHz; DMSO-d6): 11.82 (bs, 1H); 8.19 (s, 1H); 8.14 (bt, 1H); 8.11 (s, 1H); 7.21 (m, 2H); 7.16 (bt, 1H); 7.03 (m, 1H); 2.92 (t, 2H); 2.82 (s, 2H); 2.77 (t, 2H); 0.74 (m, 2H); 0.65 (m, 2H).

MS (m/z) ES+: 376 (MH+). Retention time: 2.12 minutes (LC-MS method 2).

EXAMPLE 268

2-(3-Aminomethyl-azetidin-3-yl)-8-(3-fluoro-4-methoxy-phenyl)-4,5-dihydro-1H-1,7,9-triaza-cyclopenta[a]naphthalene-3-carboxylic acid lactan hydrochloride

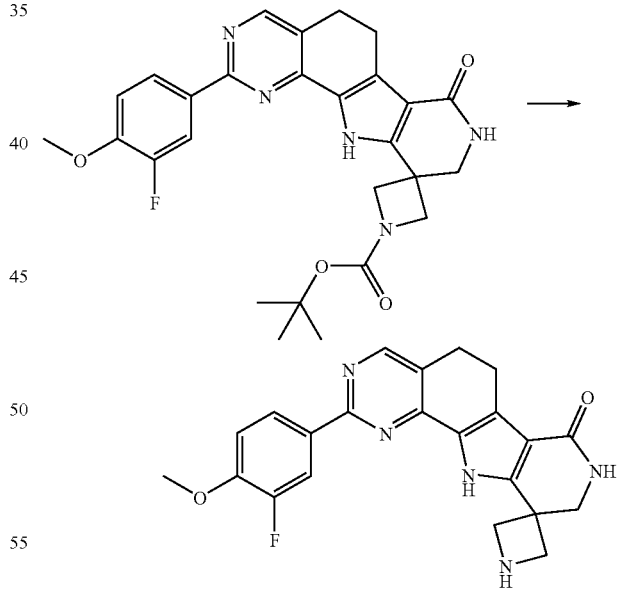

2-(3-Aminomethyl-1-tert-butoxycarbonyl-azetidin-3-yl)-8-(3-fluoro-4-methoxy-phenyl)-4,5-dihydro-1H-1,7,9-triaza-cyclopenta[a]naphthalene-3-carboxylic acid lactam (Example 268a)(92 mg; 0.18 mmol) is dissolved in HCl_conc (2 ml) and the rapidly formed precipitate stirred at room temperature for 2 minutes. The reaction mixture is evaporated to dryness, taken up in methanol, evaporated again and triturated with methanol to yield the title compound as yellow crystals (90 mg; 100%).

1H-NMR (400 MHz; DMSO-d6): 12.56 (s, 1H); 9.73 (bs, 1H); 9.04 (bs, 1H); 8.53 (s, 1H); 8.36 (m, 2H); 7.47 (bs, 1H); 7.31 (m, 1H); 4.55 (m, 2H); 3.97 (m, 2H); 3.93 (s, 3H); 3.76 (s, 2H); 2.98 (m, 2H); 2.92 (m, 2H). MS (m/z) ES+: 406 (MH+). Retention time: 1.69 minutes (LC-MS method 2).

The starting material is prepared as follows:

EXAMPLE 268A 2-(3-Aminomethyl-1-tert-butoxycarbonyl-azetidin-3-yl)-8-(3-fluoro-4-methoxy-phenyl)-4,5-dihydro-1H-1,7,9-triaza-cyclopenta[a]naphthalene-3-carboxylic acid lactam

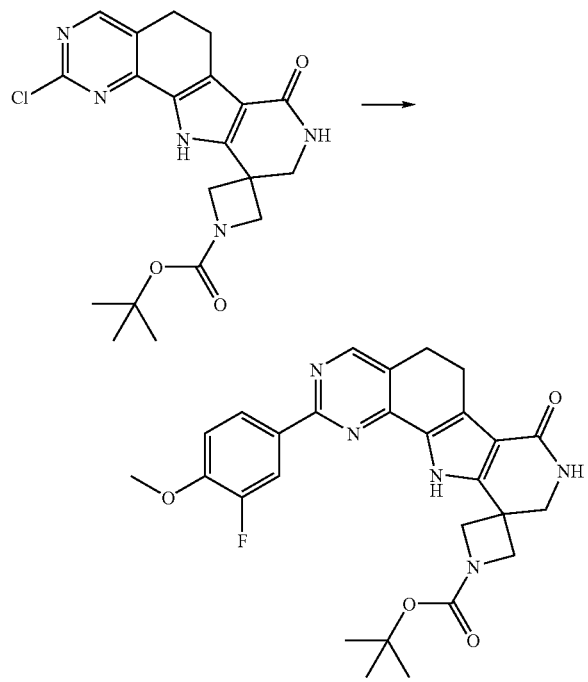

2-(3-Aminomethyl-1-tert-butoxycarbonyl-azetidin-3-yl)-8-chloro-4,5-dihydro-1H-1,7,9-triaza-cyclopenta[a]naphthalene-3-carboxylic acid lactam (Example 268b)(103 mg; 0.25 mmol), 3-fluoro-4-methoxyphenylboronic acid (Aldrich 564036) (84 mg; 0.49 mmol), bis-(triphenylphosphin)-palladium(II)-dichlorid (Pd(PPh₃)₂Cl₂; Fluka 15253)(52 mg; 0.074 mmol), triphenylphosphine (195 mg; 0.74 mmol) and 2N Na₂CO₃ (0.49 ml; 1 mmol) in 1-propanol (4 ml) are microwaved as a suspension at 135° C. for 15 minutes. The reaction mixture is filtered, the residue washed with 1-propanol and the filtrate purified via chromatography (SiO2; acetone/heptane/HOAc 40:60:1) to yield the title compound as colorless crystals (95 mg; 76%).

1H-NMR (400 MHz; DMSO-d6): 12.32 (s, 1H); 8.49 (s, 1H); 8.31 (m, 2H); 7.32 (s, 1H); 7.30 (m, 1H); 4.25 (bd, 2H); 3.92 (s, 3H); 3.83 (bs, 2H); 3.57 (s, 2H); 2.97 (m, 2H); 2.90 (m, 2H); 1.43 (s, 9H).

MS (m/z) ES+: 506 (MH+). Retention time: 2.89 minutes (LC-MS method 2).

EXAMPLE 268B 2-(3-Aminomethyl-1-tert-butoxycarbonyl-azetidin-3-yl)-8-chloro-4,5-dihydro-1H-1,7,9-triaza-cyclopenta[a]naphthalene-3-carboxylic acid lactam

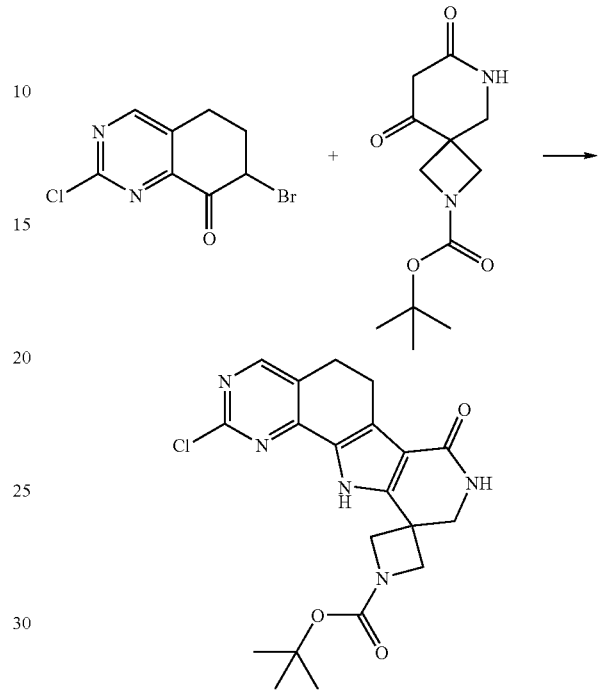

7-Bromo-2-chloro-6,7-dihydro-5H-quinazolin-8-one (Example 257c) (100 mg; 0.38 mmol), 7,9-dioxo-2,6-diaza-spiro[3.5]nonane-2-carboxylic acid tert-butyl ester (Example 156) (147 mg; 0.57 mmol) and NaOAc (32 mg; 0.38 mmol) are dissolved in methanol (3 ml) and stirred for 10 minutes at room temperature. NH4OAc (59 mg; 0.76 mmol) is added and the yellow suspension stirred for 48 hours at room temperature. The yellow solid is filtered, washed with methanol and TBME to yield the title compound as yellow crystals (105 mg; 66%).

1H-NMR (400 MHz; DMSO-d6): 12.69 (s, 1H); 8.34 (s, 1H); 7.34 (s, 1H); 4.21 (bs, 2H); 3.75 (bs, 2H); 3.55 (s, 2H); 2.94 (m, 2H); 2.87 (m, 2H); 1.41 (s, 9H).

MS (m/z) ES+: 416 (MH+). Retention time: 2.29 minutes (LC-MS method 2).

EXAMPLE 269

2-(1-Amino-cyclopropylmethyl)-8-cyclopentyloxy-4,5-dihydro-1H-1,7,9-triaza-cyclopenta[a]naphthalene-3-carboxylic acid lactam

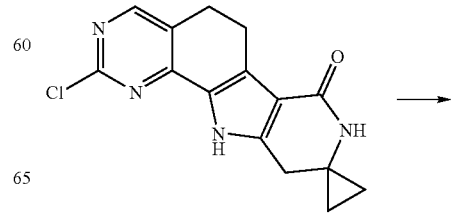

-continued

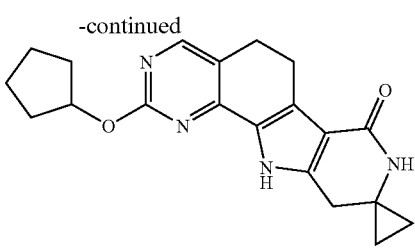

NaH (50% in mineral oil, 25 mg; 0.52 mmol) is added to DMF/cylopentanol (4 ml/0.3 ml) and stirred for 5 minutes until gas evolution has stopped. 2-(1-Amino-cyclopropylmethyl)-8-chloro-4,5-dihydro-1H-1,7,9-triaza-cyclopenta[a]naphthalene-3-carboxylic acid lactam (Example 257d) (26 mg; 0.0087 mmol) dissolved in DMF (0.5 ml) is added and the reaction mixture heated to 150° C. for 10 minutes. The reaction mixture is filtered, evaporated to dryness and purified via chromatography (SiO2; acetone/heptan/HOAc 40:60:1) to yield the title compound as colorless crystals after recrystallization from acetone (7 mg; 25%)

1H-NMR (400 MHz; DMSO-d6): 11.61 (s, 1H); 7.92 (s, 1H); 7.15 (s, 1H); 4.28 (m, 1H); 2.85 (m, 2H); 2.79 (s, 2H); 2.67 (m, 2H); 1.93 (m, 2H); 1.67 (m, 2H); 1.52 (m, 2H); 1.43 (m, 2H); 0.73 (m, 2H); 0.64 (m, 2H).

MS (m/z) ES+: 351 (MH+). Retention time: 2.24 minutes (LC-MS method 2).

EXAMPLE 270

2-(1-Amino-cyclopropylmethyl)-8-cyclopentylamino-4,5-dihydro-1H-1,7,9-triaza-cyclopenta[a]naphthalene-3-carboxylic acid lactam

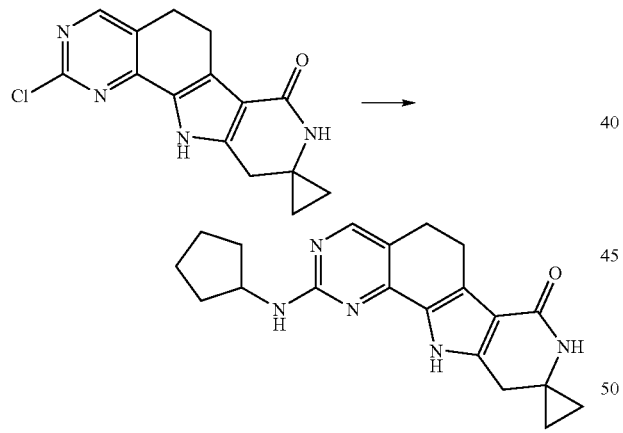

2-(1-Amino-cyclopropylmethyl)-8-chloro-4,5-dihydro-1H-1,7,9-triaza-cyclopenta[a]naphthalene-3-carboxylic acid lactam (Example 257d) (26 mg; 0.0087 mmol) and cyclopentylamine (1 ml) in N,N-dimethylacetamide (2 ml) are microwaved at 170° C. for 20 minutes. The reaction mixture is evaporated to dryness, washed with water and recrystallized from methanol to deliver the title compound as colorless crystals (17 mg; 35%).

1H-NMR (400 MHz; DMSO-d6): 12.14 (bs, 1H); 8.15 (s, 1H); 7.21 (s, 1H); 5.35 (m, 1H); 2.91 (m, 2H); 2.79 (m, 5H); 1.91 (m, 2H); 1.71 (m, 2H); 1.69 (m, 2H); 1.59 (m, 2H); 0.73 (m, 2H); 0.65 (m, 2H).

MS (m/z) ES+: 350 (MH+). Retention time: 1.61 minutes (LC-MS method 2).

EXAMPLE 271

2-(1-Amino-cyclopropylmethyl)-8-(3-ethoxycarbonyl)-phenyl-4,5-dihydro-1H-pyrrolo[2,3-f]isoquinoline-3-carboxylic acid lactam

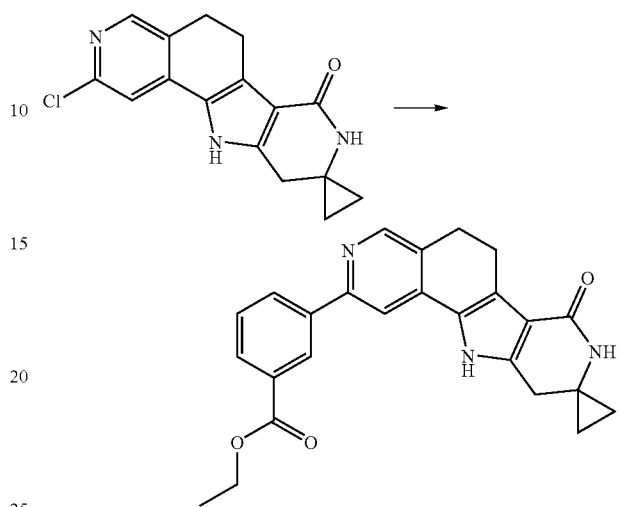

The coupling of 2-(1-Amino-cyclopropylmethyl)-8-chloro-4,5-dihydro-1H-pyrrolo[2,3-f]isoquinoline-3-carboxylic acid lactam (245.0 mg; 0.83 mmol) (Example 31a) with 3-ethoxycarbonylphenylboronic acid is performed in analogy to Example 1. Crystallization from MeOH yields the title compound as yellowish crystals (320 mg; 99%). MS (m/z) ES+: 414 (MH+). Retention time: 2.48 minutes (LC-MS method 2).

EXAMPLE 272

2-(1-Amino-cyclopropylmethyl)-8-(3-carboxy)-phenyl-4,5-dihydro-1H-pyrrolo[2,3-f]isoquinoline-3-carboxylic acid lactam

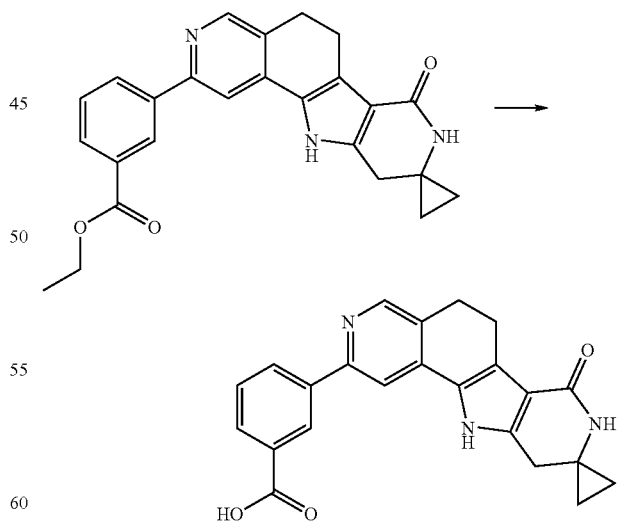

A solution of 2-(1-Amino-cyclopropylmethyl)-8-(3-ethoxycarbonyl)-phenyl-4,5-dihydro-1H-pyrrolo[2,3-f]isoquinoline-3-carboxylic acid lactam (130 mg; 0.31 mmol) in 3.0 ml methanol is treated with 1 N NaOH (0.39 ml; 0.79 mmol) and heated to reflux for 2 h. After cooling to RT the solution is acidified with 2 N HCl and the precipitate is isolated by filtration. The crude product is directly used for the next steps.

EXAMPLE 273

2-(1-Amino-cyclopropylmethyl)-8-(3-(4-methoxymethylbenzylcarbamoyl)-phenyl-4,5-dihydro-1H-pyrrolo[2,3-f]isoquinoline-3-carboxylic acid lactam

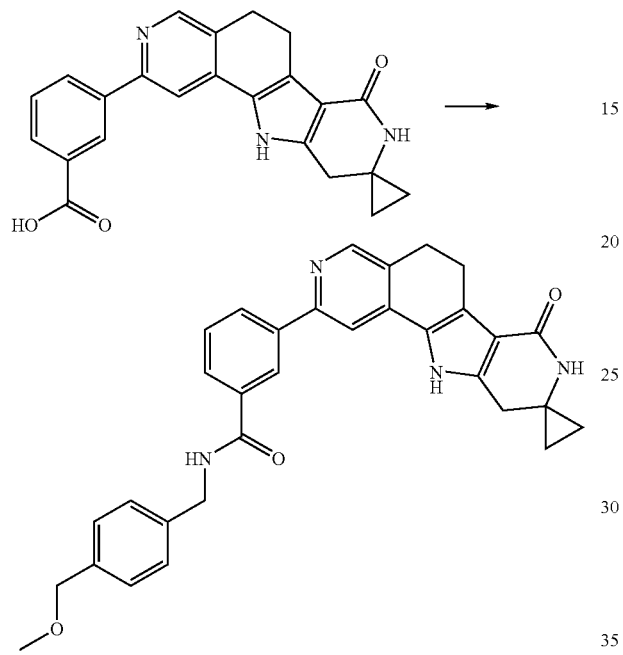

To a mixture of 2-(1-Amino-cyclopropylmethyl)-8-(3-carboxy)-phenyl-4,5-dihydro-1H-pyrrolo[2,3-f]isoquinoline-3-carboxylic acid lactam (65.5 mg; 0.17 mmol), 4-methoxymethyl-benzylamine (51.5 mg 0.34 mmol) and DIPEA (110 µl; 0.68 mmol) in 2.0 ml DMF is added TBTU (84.4 mg; 0.26 mmol). The clear solution is stirred for 90 min. at RT, poured onto water and extracted 3 times with EtOAc. The crude product is purified by crystallization from MeOH to afford colorless crystals. MS (m/z) ES+: 519 (MH+). Retention time: 2.00 minutes (LC-MS method 2).

EXAMPLE 274

2-(1-Amino-cyclopropylmethyl)-8-(3-(3-aza-4-methoxybenzylcarbamoyl)-phenyl-4,5-dihydro-1H-pyrrolo[2,3-f]isoquinoline-3-carboxylic acid lactam

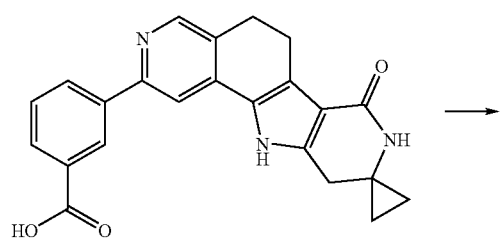

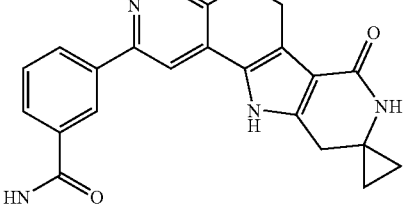

The reaction is performed in analogy to Example 273 yielding the title compound as yellow crystals. MS (m/z) ES+: 506 (MH+). Retention time: 1.82 minutes (LC-MS method 2).

EXAMPLE 275

S-2-(1-Amino-cyclopropylmethyl)-8-(3-(α-methyllbenzylcarbamoyl)-phenyl-4,5-dihydro-1H-pyrrolo[2,3-f]isoquinoline-3-carboxylic acid lactam

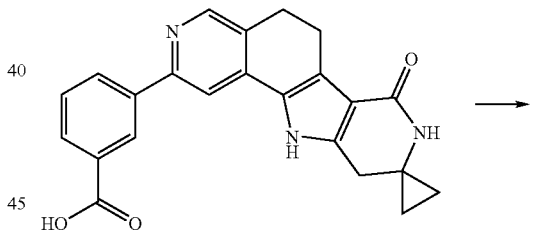

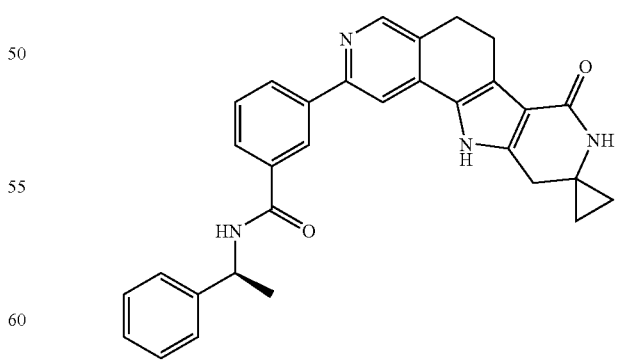

The reaction is performed in analogy to Example 273 yielding the title compound as yellow crystals. MS (m/z) ES+: 489 (MH+). Retention time: 2.14 minutes (LC-MS method 2).

EXAMPLE 276

2-(1-Amino-cyclopropylmethyl)-8-(3-benzylcarbamoyl)-phenyl-4,5-dihydro-1H-pyrrolo[2,3-f]isoquinoline-3-carboxylic acid lactam

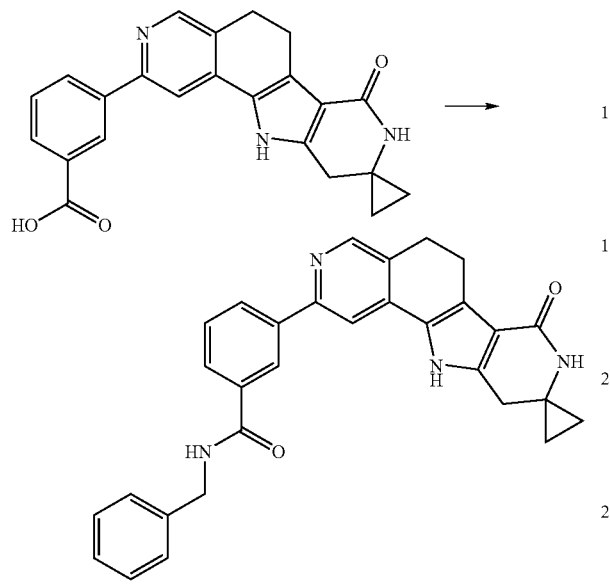

The reaction is performed in analogy to Example 273 yielding the title compound as yellow crystals. MS (m/z) ES+: 475 (MH+). Retention time: 2.02 minutes (LC-MS method 2).

EXAMPLE 277

2-(1-Amino-cyclopropylmethyl)-8-(3-benzyl benzylcarbamoyl)-(5-fluorophenyl)-4,5-dihydro-1H-pyrrolo[2,3-f]isoquinoline-3-carboxylic acid lactam

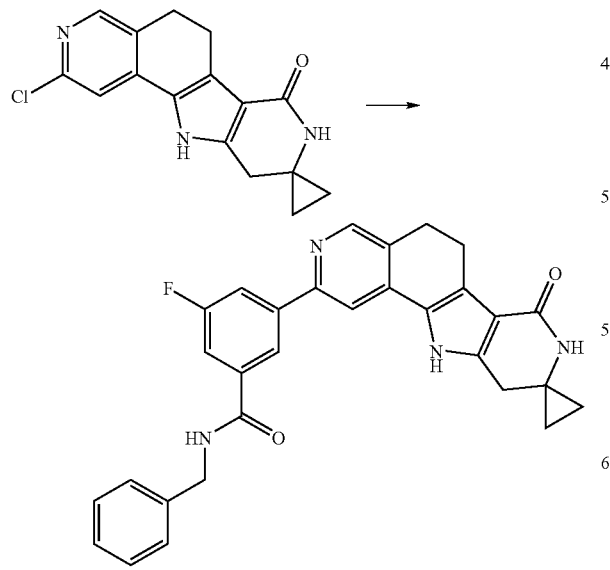

The coupling of 2-(1-Amino-cyclopropylmethyl)-8-chloro-4,5-dihydro-1H-pyrrolo[2,3-f]isoquinoline-3-carboxylic acid lactam (Example 31a) with 3-(Benzylcarbamoyl)-5-fluorophenylboronic acid is performed in analogy to Example 1. Purification via chromatography (SiO2; EtOAc>EtOAc/MeOH 9:1) delivers the title compound as light-yellow solid. MS (m/z) ES+: 493 (MH+). Retention time: 2.33 minutes (LC-MS method 2).

EXAMPLE 278

2-(1-Amino-cyclopropylmethyl)-8-(3-benzylbenzylcarbamoyl)-(6-fluorophenyl)-4,5-dihydro-1H-pyrrolo[2,3-f]isoquinoline-3-carboxylic acid lactam

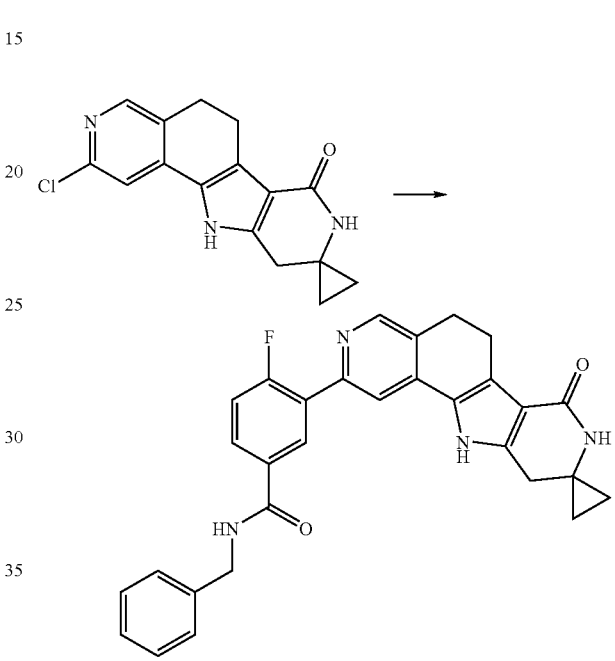

The coupling of 2-(1-Amino-cyclopropylmethyl)-8-chloro-4,5-dihydro-1H-pyrrolo[2,3-f]isoquinoline-3-carboxylic acid lactam (Example 31a) with 3-(Benzylcarbamoyl)-6-fluorophenylboronic acid is performed in analogy to Example 1. Purification via chromatography (SiO2; EtOAc>EtOAc/MeOH 9:1) delivers the title compound as light-yellow solid. MS (m/z) ES+: 493 (MH+). Retention time: 2.06 minutes (LC-MS method 2).

EXAMPLE 279

2-(1-Amino-cyclopropylmethyl)-8-(3-benzylbenzylcarbamoyl)-(4-fluorophenyl)-4,5-dihydro-1H-pyrrolo[2,3-f]isoquinoline-3-carboxylic acid lactam

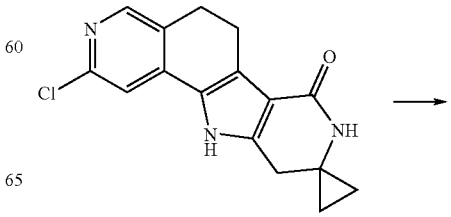

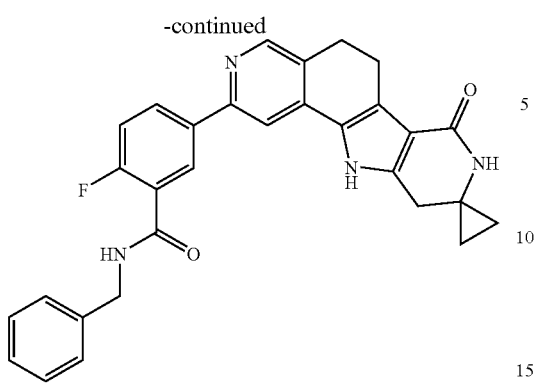

The coupling of 2-(1-Amino-cyclopropylmethyl)-8-chloro-4,5-dihydro-1H-pyrrolo[2,3-f]isoquinoline-3-carboxylic acid lactam (Example 31a) with 3-(Benzylcarbamoyl)-4-fluorolphenylboronic acid is performed in analogy to Example 1. Purification via chromatography (SiO2; EtOAc>EtOAc/MeOH 9:1) delivers the title compound as light-yellow solid. MS (m/z) ES+: 493 (MH+). Retention time: 0.85 minutes (LC-MS method 5).

EXAMPLE 280

2-(1-Amino-cyclopropylmethyl)-8-(3-benzylcarbamoyl)-(4-fluoro-3-pyridyl)-4,5-dihydro-1H-pyrrolo[2,3-f]isoquinoline-3-carboxylic acid lactam

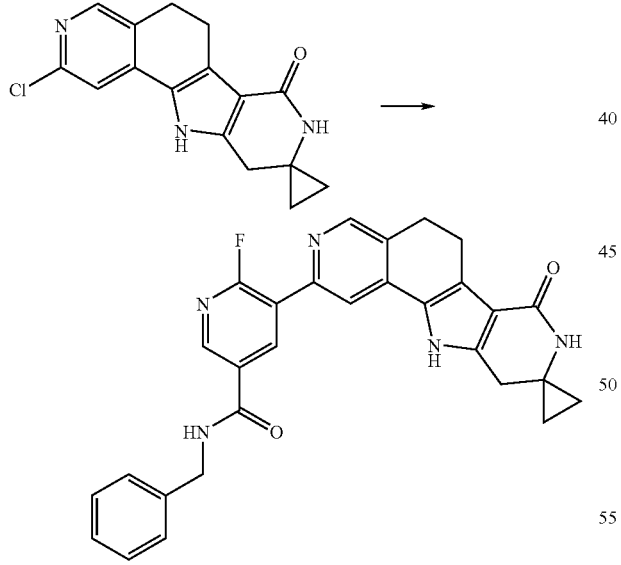

The coupling of 2-(1-Amino-cyclopropylmethyl)-8-chloro-4,5-dihydro-1H-pyrrolo[2,3-f]isoquinoline-3-carboxylic acid lactam (Example 31a) with N-Benzyl-6-fluoro-5-(4,4,5,5-tetramethyl-[1,3,2]dioxaborolan-2-yl)-nicotinamide is performed in analogy to Example 1. Purification via chromatography (SiO2; EtOAc>EtOAc/MeOH 9:1) delivers the title compound as light-yellow solid. MS (m/z) ES+: 494 (MH+). Retention time: 2.23 minutes (LC-MS method 2).

The starting materials are prepared as follows:

a) 3-Bromo-2-fluoro-nicotinic acid

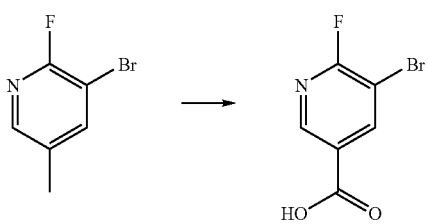

3-Bromo-2-fluoro-5-methylpyridine (1.0 g; 5.26 mmol) is added to a solution of KMnO4 (2.10 g; 13.2 mmol) in 80 ml of water and heated to reflux for 4 h. After cooling to RT the mixture is filtered through a pad of Hyflo. The filtrate is concentrated to 50 ml and acidified to pH 3-4 with 2 N HCl. The resulting suspension is extracted with EtOAc and the organic layer is washed with brine and dried over Na2SO4. Evaporation afforded the title compound as colorless crystals. MS (m/z) ES+: 221 (MH+). Retention time: 0.79 minutes (LC-MS method 5).

b) N-Benzyl-5-bromo-6-fluoro-nicotinamide

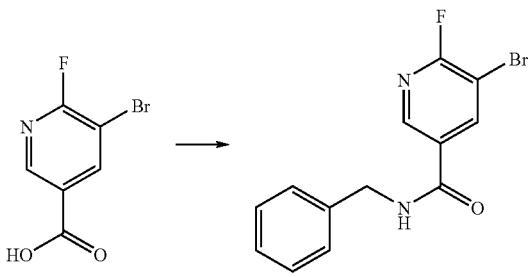

The reaction is performed in analogy to Example 273 yielding the title compound as colorless crystals. MS (m/z) ES+: 310 (MH+). Retention time: 1.11 minutes (LC-MS method 5).

c) N-Benzyl-6-fluoro-5-(4,4,5,5-tetramethyl-[1,3,2]dioxaborolan-2-yl)-nicotinamide

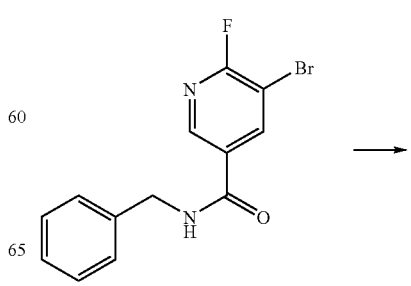

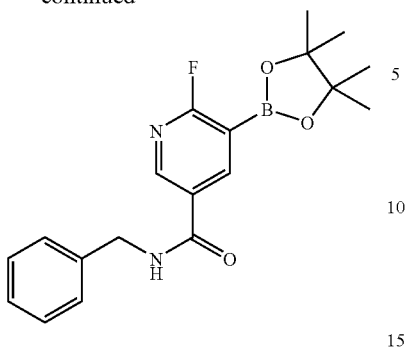

A mixture of N-Benzyl-5-bromo-6-fluoro-nicotinamide (80 mg; 0.26 mmol), bis(pinacolato)diboron (131 mg; 0.52 mmol), 1,1'-bis(diphenylphosphino)ferrocene dichloropalladium(II) (9.5 mg; 0.013 mmol) and KOAc (157 mg; 1.55 mmol) in 2.5 ml of DME is heated to 150° C. for 20 min. in a Personal Chemistry microwave apparatus. The reaction mixture is diluted with EtOAc, washed with water and brine, dried over $Na_2SO_4$ and concentrated in vacuo to give the crude product which is used in the next step without purification. MS (m/z) ES+: 275 (MH+) (boronic acid). Retention time: 2.73 minutes (LC-MS method 5).

EXAMPLE 281

4-(9-Spirocyclopropyl-7-oxo-6,7,8,9,10,11-hexahydro-5H-3,8,11-triaza-benzo[a]fluoren-2-yl)-thiophene-2-carboxylic acid benzylamide

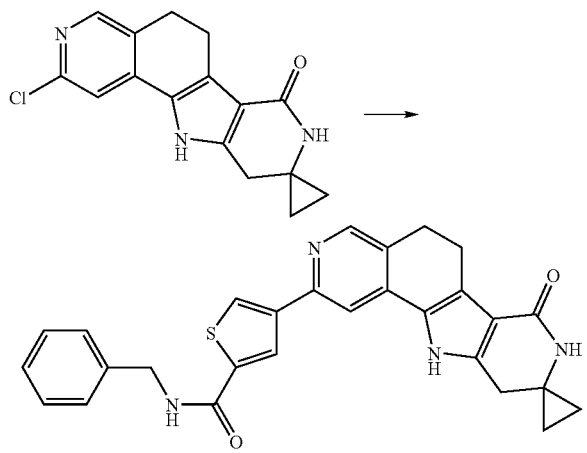

The coupling of 2-(1-Amino-cyclopropylmethyl)-8-chloro-4,5-dihydro-1H-pyrrolo[2,3-f]isoquinoline-3-carboxylic acid lactam (Example 31a) with 4-(4,4,5,5-Tetramethyl-[1,3,2]dioxaborolan-2-yl)-thiophene-2-carboxylic acid benzylamide is performed in analogy to Example 1. Purification via chromatography (SiO2; EtOAc>EtOAc/MeOH 9:1) delivers the title compound as light-yellow solid. MS (m/z) ES+: 481 (MH+). Retention time: 2.03 minutes (LC-MS method 2).

The starting materials are prepared as follows:

a) 4-Bromo-thiophene-2-carboxylic acid benzylamide

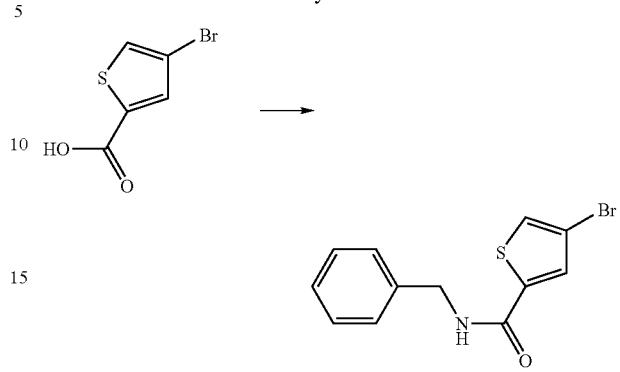

The reaction is performed in analogy to Example 273 yielding the title compound as pale yellow crystals. MS (m/z) ES+: 297 (MH+). Retention time: 1.20 minutes (LC-MS method 5).

b) 4-(4,4,5,5-Tetramethyl-[1,3,2]dioxaborolan-2-yl)-thiophene-2-carboxylic acid benzylamide

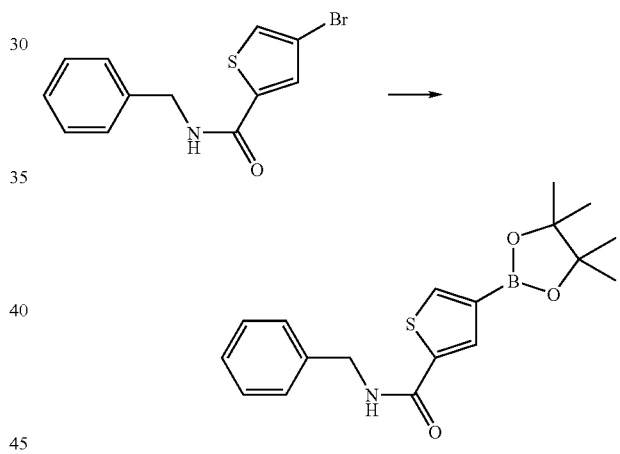

The reaction is performed in analogy to Example 280c yielding the crude title compound as dark solid. MS (m/z) ES+: 262 (MH+) (boronic acid). Retention time: 1.45 minutes (LC-MS method 5).

EXAMPLE 282

5-(9,9-Spirocyclopropyl-7-oxo-6,7,8,9,10,11-hexahydro-5H-3,8,11-triaza-benzo[a]fluoren-2-yl)-furan-2-carboxylic acid benzylamide

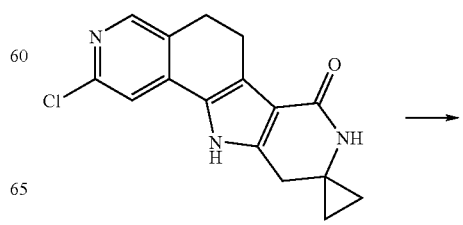

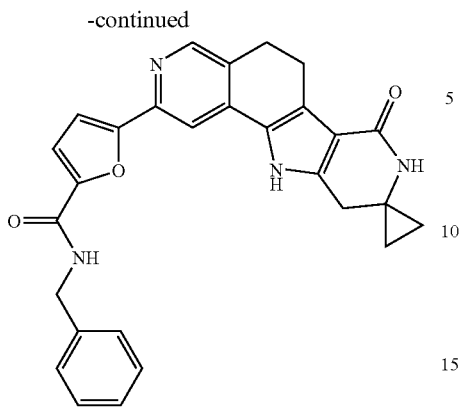

The coupling of 2-(1-Amino-cyclopropylmethyl)-8-chloro-4,5-dihydro-1H-pyrrolo[2,3-f]isoquinoline-3-carboxylic acid lactam (Example 31a) with 5-(4,4,5,5-Tetramethyl-[1,3,2]dioxaborolan-2-yl)-furan-2-carboxylic acid benzylamide is performed in analogy to Example 1. Purification via crystallization from EtOAc delivers the title compound as light-yellow solid. MS (m/z) ES+: 465 (MH+). Retention time: 2.16 minutes (LC-MS method 2).

The starting materials are prepared as follows:

a) 5-Bromo-furan-2-carboxylic acid benzylamide

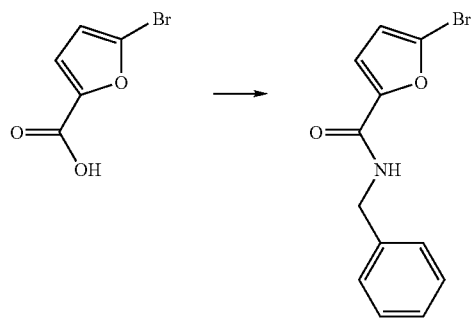

The reaction is performed in analogy to Example 273 yielding the title compound as yellow oil. MS (m/z) ES+: 281 (MH+). Retention time: 1.10 minutes (LC-MS method 5).

b) 5-(4,4,5,5-Tetramethyl-[1,3,2]dioxaborolan-2-yl)-furan-2-carboxylic acid benzylamide

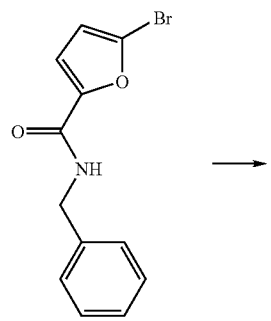

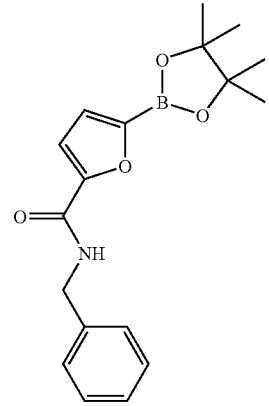

The reaction is performed in analogy to Example 280c yielding the crude title compound as dark solid. MS (m/z) ES+: 246 (MH+) (boronic acid). Retention time: 1.40 minutes (LC-MS method 5).

EXAMPLE 283

2-(1-Amino-cyclopropylmethyl)-8-(2-methoxy-5-thiazolyl)-4,5-dihydro-1H-pyrrolo[2,3-f]isoquinoline-3-carboxylic acid lactam

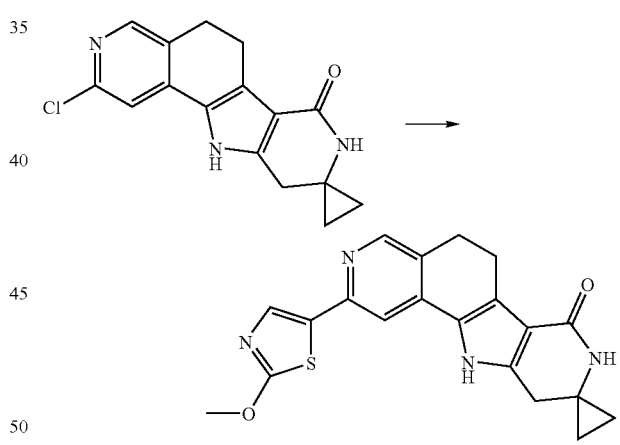

2-(1-Amino-cyclopropylmethyl)-8-chloro-4,5-dihydro-1H-pyrrolo[2,3-f]isoquinoline-3-carboxylic acid lactam (245.0 mg; 0.83 mmol) (Example 31a) (50.0 mg; 0.167 mmol), 2-methoxy-5-tributylstannylthiazole (80.9 mg; 0.20 mmol), $PdCl_2(PPh_3)_2$ (11.7 mg; 0.017 mmol) and triphenylphospine (21.9 mg; 0.084 mmol) are dissolved in 1.5 ml of DMA under Argon and heated for 20 min. at 180° C. in a Personal Chemistry Microwave apparatus. The crude mixture is diluted with EtOAc, washed with water and brine and dried over $Na_2SO_4$. After evaporation, the crude product is purified via chromatography (SiO2; EtOAc>EtOAc/MeOH 9:1) to afford the title compound as yellow crystals. MS (m/z) ES+: 379 (MH+). Retention time: 2.01 minutes (LC-MS method 2).

EXAMPLE 284

2-(1-Amino-cyclopropylmethyl)-8-(2-ethoxy-5-thiazolyl)-4,5-dihydro-1H-pyrrolo[2,3-f]isoquinoline-3-carboxylic acid lactam

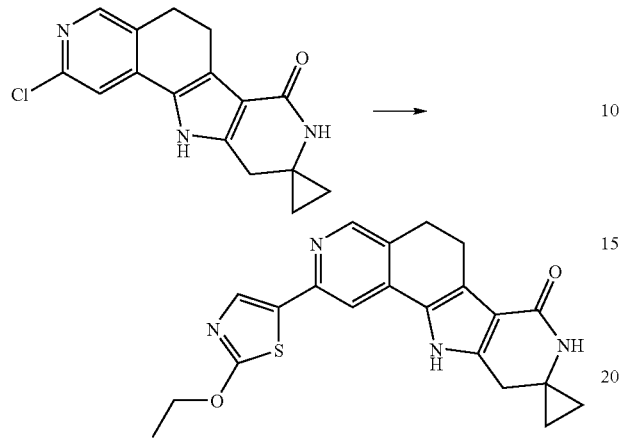

The reaction is performed in analogy to Example 283. Purification via chromatography (SiO2; EtOAc>EtOAc/ MeOH 9:1) yields the title compound as yellow crystals. MS (m/z) ES+: 393 (MH+). Retention time: 2.19 minutes (LC-MS method 2).

EXAMPLE 285

2-(3-Amino-azetidin-3-ylmethyl)-8-(3-bromo-phenyl)-4,5-dihydro-1H-1,7,9-triaza-cyclopenta[a]naphthalene-3-carboxylic acid lactam hydrochloride

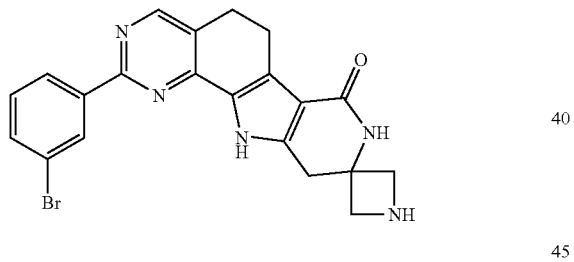

The title compound is prepared in analogy to Example 26 starting from 3-bromo-benzamidine to give yellow crystals. MS (m/z) ES+: 438 (MH+). Retention time: 1.97 minutes (LC-MS method 2).

EXAMPLE 286

2-(3-Amino-azetidin-3-ylmethyl)-8-(3-bromo-phenyl)-1-methyl-4,5-dihydro-1H-1,7,9-triaza-cyclopenta[a]naphthalene-3-carboxylic acid lactam hydrochloride

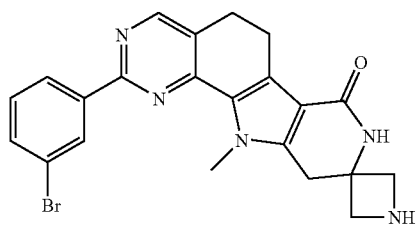

The title compound is prepared in analogy to Example 27 starting from 3-bromo-benzamidine to give yellow crystals. MS (m/z) ES+: 452 (MH+). Retention time: 2.14 minutes (LC-MS method 2).

EXAMPLE 287

2-(3-Amino-azetidin-3-ylmethyl)-8-(3-cyano-phenyl)-1-methyl-4,5-dihydro-1H-1,7,9-triaza-cyclopenta[a]naphthalene-3-carboxylic acid lactam hydrochloride

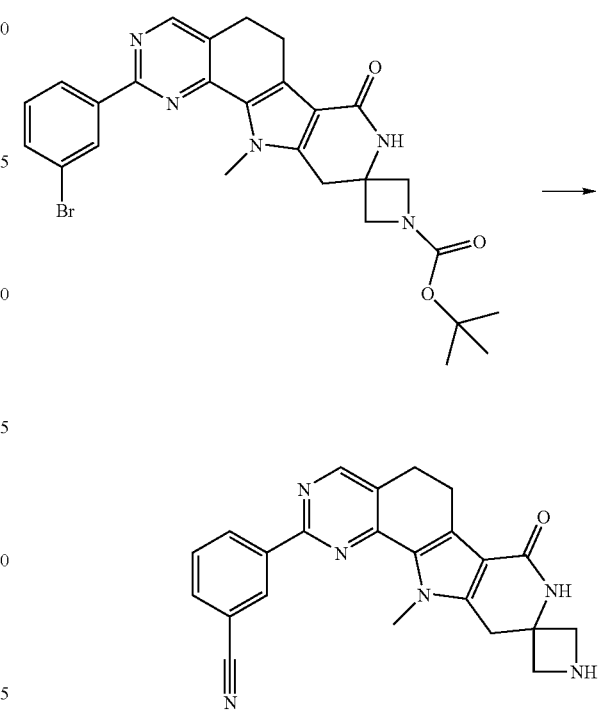

A mixture of N-Boc-2-(3-Amino-azetidin-3-ylmethyl)-8-(3-bromo-phenyl)-1-methyl-4,5-dihydro-1H-1,7,9-triaza-cyclopenta[a]naphthalene-3-carboxylic acid lactam, prepared in analogy to Example 27 (75.0 mg; 0.136 mmol), Zn(CN)2 (19.2 mg; 0.16 mmol), dppf (75.5 mg; 0.14 mmol), Pd$_2$(dba)$_3$ (12.5 mg; 0.014 mmol) and Zn dust (0.89 mg; 0.014 mmol) in 1 ml of DMA is heated to 165° C. for 20 min. in a Personal Chemistry microwave apparatus. The reaction mixture is diluted with EtOAc, washed with NaHCO$_3$ and brine and dried over MgSO$_4$. The "boc-protected" intermediate is purified by crystallization from MeOH. Finally, boc-cleavage is performed in dioxane (1.0 ml) by treating with 1.0 ml of 4 M HCl in dioxane at RT for 2 hours. MS (m/z) ES+: 397 (MH+). Retention time: 1.80 minutes (LC-MS method 2).

EXAMPLE 288

2-(1-Amino-cyclobutylmethyl)-8-(3-bromophenyl)-4,5-dihydro-1H-1,7,9-triaza-cyclopenta[a]naphthalene-3-carboxylic acid lactam

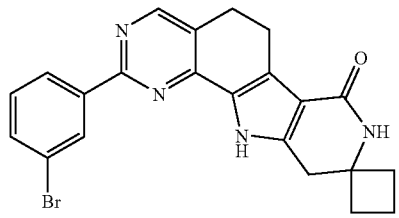

The title compound is prepared in analogy to Example 34 starting from 3-bromo-benzamidine to give yellow crystals. MS (m/z) ES+: 437 (MH+). Retention time: 3.25 minutes (LC-MS method 2).

EXAMPLE 289

2-(1-Amino-cyclobutylmethyl)-8-(3-cyanophenyl)-4,5-dihydro-1H-1,7,9-triaza-cyclopenta[a]naphthalene-3-carboxylic acid lactam

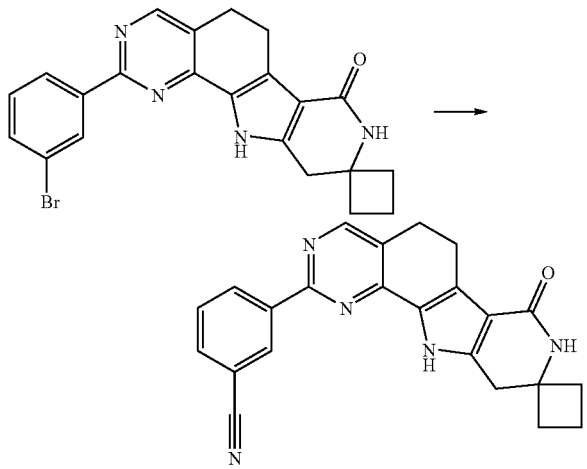

The title compound is prepared in analogy to Example 287 starting from 2-(1-Amino-cyclobutylmethyl)-8-(3-bromophenyl)-4,5-dihydro-1H-1,7,9-triaza-cyclopenta[a]naphthalene-3-carboxylic acid lactam to give a colorless solid. MS (m/z) ES+: 382 (MH+). Retention time: 1.50 minutes (LC-MS method 5).

EXAMPLE 290

N-Benzyl-5-(10-spirocyclopropyl-7-oxo-6,7,8,9,10,11-hexahydro-5H-1,3,8,11-tetraaza-benzo[a]fluoren-2-yl)-nicotinamide

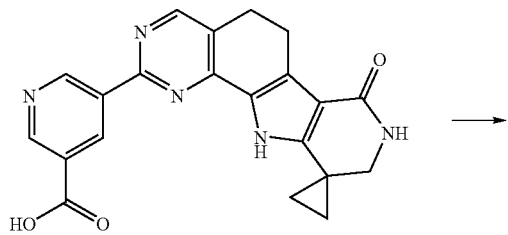

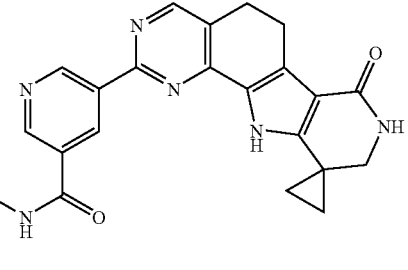

The title compound is prepared in analogy to Example 273 starting from 5-(10-Spirocyclopropyl-7-oxo-6,7,8,9,10,11-hexahydro-5H-1,3,8,11-tetraaza-benzo[a]fluoren-2-yl)-nicotinic acid ethyl ester and benzylamine. Purification via chromatography (SiO2; EtOAc>EtOAc/MeOH 8:2) delivers the title compound as light-yellow solid. MS (m/z) ES+: 477 (MH+). Retention time: 2.24 minutes (LC-MS method 2).

The starting materials are prepared as follows:

a) 5-(10-Spirocyclopropyl-7-oxo-6,7,8,9,10,11-hexahydro-5H-1,3,8,11-tetraaza-benzo[a]fluoren-2-yl)-nicotinic acid ethyl ester

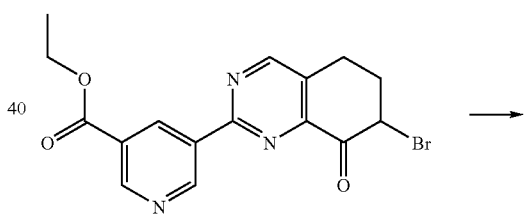

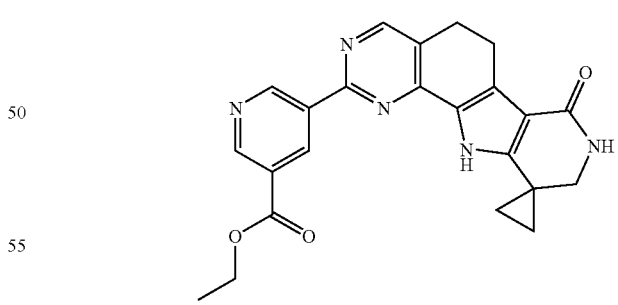

The title compound is prepared in analogy to Example 58 starting from 5-(7-Bromo-8-oxo-5,6,7,8-tetrahydro-quinazolin-2-yl)-nicotinic acid ethyl ester (prepared in analogy to Example 26 starting from 5-Carbamimidoyl-nicotinic acid ethyl ester) and 5-aza-spiro[2.5]octane-6,8-dione to give the crude product which is used in the next step without purification. MS (m/z) ES+: 416 (MH+). Retention time: 1.51 minutes (LC-MS method 5).

293 b) 5-(10-Spirocyclopropyl-7-oxo-6,7,8,9,10,11-hexahydro-5H-1,3,8,11-tetraaza-benzo[a]fluoren-2-yl)-nicotinic acid

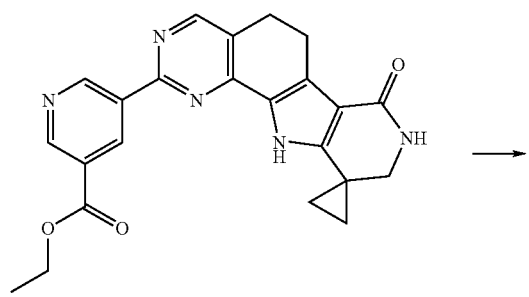

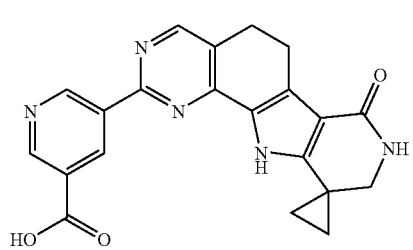

The ester hydrolysis is carried out in analogy to Example 272 to give pale crystals. MS (m/z) ES+: 388 (MH+). Retention time: 1.24 minutes (LC-MS method 5).

EXAMPLE 291

N-Benzyl-3-(10-spirocyclopropyl-7-oxo-6,7,8,9,10,11-hexahydro-5H-1,3,8,11-tetraaza-benzo[a]fluoren-2-yl)-benzamide

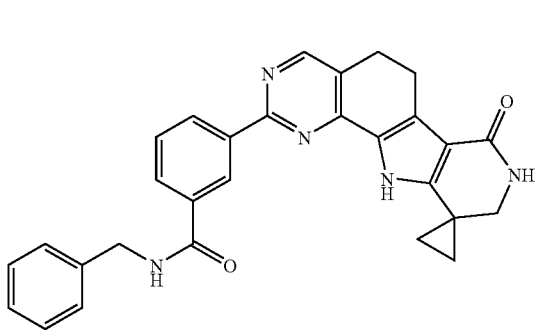

The title compound is prepared in analogy to Example 290 starting from 3-carbamimidoyl-benzoic acid methylester. Purification by chromatography (SiO2; EtOAc>EtOAc/MeOH 1:1). MS (m/z) ES+: 475 (MH+). Retention time: 2.44 minutes (LC-MS method 2).

294

EXAMPLE 292

3-(9-Spirocyclopropyl-7-oxo-6,7,8,9,10,11-hexahydro-5H-1,3,8,11-tetraaza-benzo[a]fluoren-2-yl)-N-(4-fluoro-benzyl)-benzamide

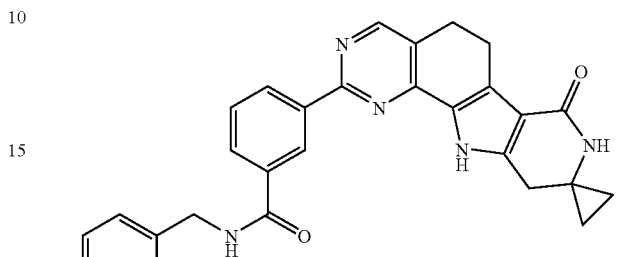

The title compound is prepared in analogy to Example 290 starting from 3-carbamimidoyl-benzoic acid methylester. Purification by crystallization from MeOH/Et₂O. MS (m/z) ES+: 494 (MH+). Retention time: 2.53 minutes (LC-MS method 2).

EXAMPLE 293

3-(9-Spirocyclobutyl-7-oxo-6,7,8,9,10,11-hexahydro-5H-1,3,8,11-tetraaza-benzo[a]fluoren-2-yl)-N-(4-fluoro-benzyl)-benzamide The title compound is prepared in analogy to Example 290 starting from 3-carbamimidoyl-benzoic acid methylester. Purification by crystallization from MeOH/Et₂O. MS (m/z) ES+: 508 (MH+). Retention time: 2.66 minutes (LC-MS method 2).

EXAMPLE 294

N-(2,6-Difluoro-benzyl)-3-(9-spirocyclopropyl-7-oxo-6,7,8,9,10,11-hexahydro-5H-1,3,8,11-tetraaza-benzo[a]fluoren-2-yl)-benzamide

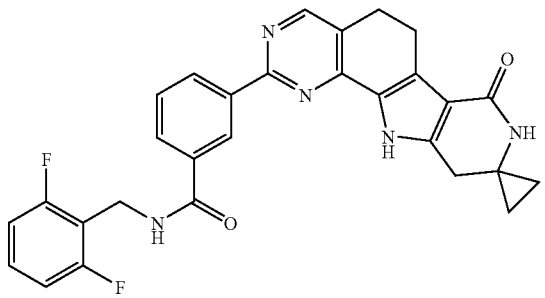

The title compound is prepared in analogy to Example 290 starting from 3-carbamimidoyl-benzoic acid methylester. Purification by crystallization from MeOH/Et$_2$O. MS (m/z) ES+: 512 (MH+). Retention time: 2.53 minutes (LC-MS method 2).

EXAMPLE 295

N-(2,6-Difluoro-benzyl)-3-(9-spirocyclobutyll-7-oxo-6,7,8,9,10,11-hexahydro-5H-1,3,8,11-tetraaza-benzo[a]fluoren-2-yl)-benzamide

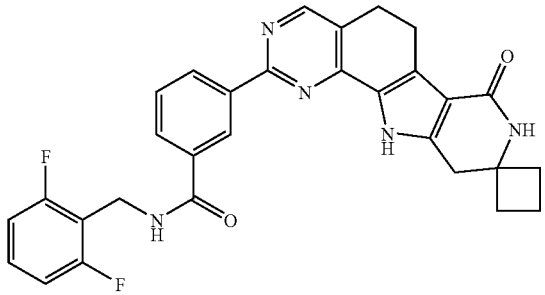

The title compound is prepared in analogy to Example 290 starting from 3-carbamimidoyl-benzoic acid methylester. Purification by crystallization from MeOH/Et$_2$O. MS (m/z) ES+: 526 (MH+). Retention time: 2.67 minutes (LC-MS method 2).

EXAMPLE 296

2-(3-Amino-azetidin-3-ylmethyl)-8-(3-benzylcarbamoyl-3-pyridyl)-1-methyl-4,5-dihydro-1H-1,7,9-triaza-cyclopenta[a]naphthalene-3-carboxylic acid lactam hydrochloride

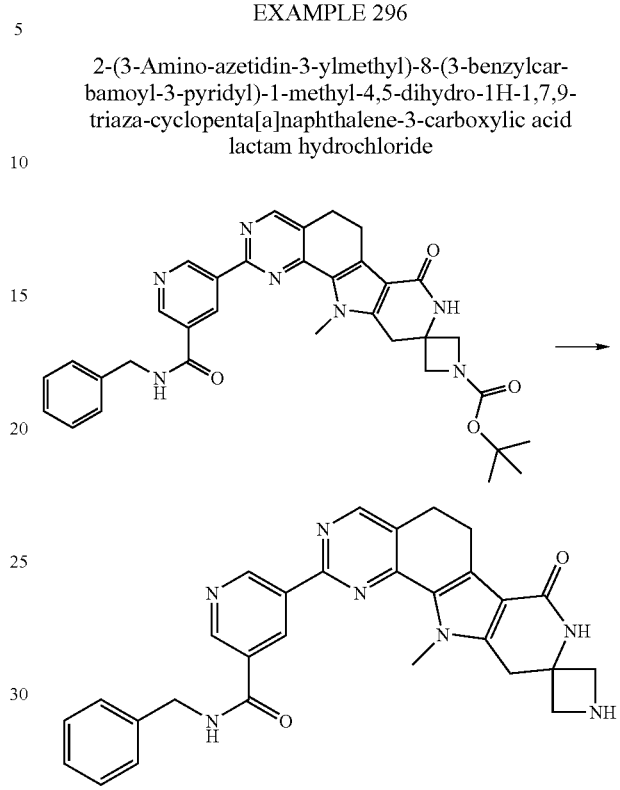

The title compound is prepared in analogy to Example 287 from 5-(7-Bromo-8-oxo-5,6,7,8-tetrahydro-quinazolin-2-yl)-nicotinic acid ethyl ester (Example 290) to afford yellow crystals. MS (m/z) ES+: 506 (MH+). Retention time: 1.77 minutes (LC-MS method 2).

EXAMPLE 297

N-Benzyl-4-(9-spirocyclobutyl-7-oxo-5,6,7,8,9,10-hexahydro-1,3,8,10-tetraaza-pentaleno[2,1-a]naphthalen-2-yl)-benzamide

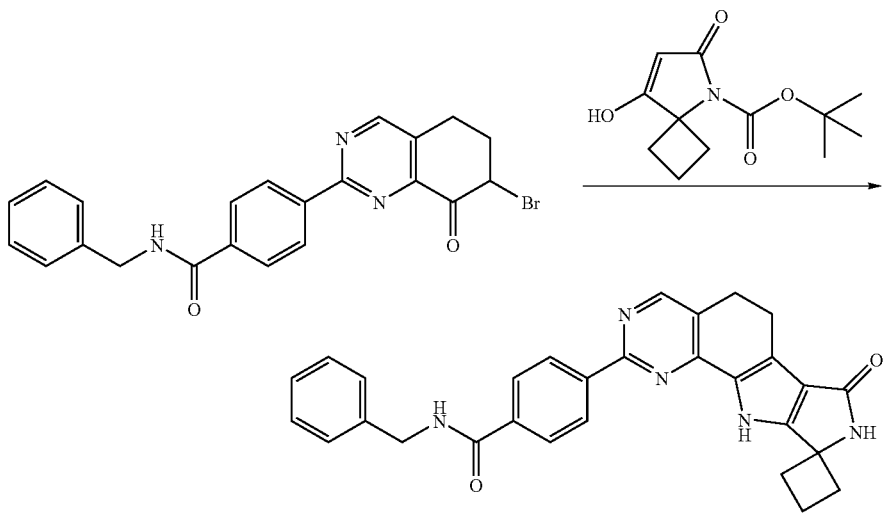

N-Benzyl-4-(7-bromo-8-oxo-5,6,7,8-tetrahydro-quinazolin-2-yl)-benzamide (30 mg; 0.069 mmol) and 8-Hydroxy-6-oxo-5-aza-spiro[3.4]oct-7-ene-5-carboxylic acid tert-butyl ester (19.7 mg: 0.082 mmol) are dissolved in 2.0 ml AcOH, ammonium acetate (18.6 mg; 0.24 mmol) is added and the mixture is heated in a Personal Chemistry microwave apparatus to 140° C. for 5 min. Following the evaporation of the solvent, the residue is dissolved in EtOAc and washed with sat. NaHCO₃ and brine and dried over Na₂SO₄. Purification via chromatography (SiO2; EtOAc>EtOAc/MeOH 4:1) delivers the title compound as light-yellow solid. MS (m/z) ES+: 476 (MH+). Retention time: 2.43 minutes (LC-MS method 2).

The starting materials are prepared as follows:

a) 4-(8-Oxo-5,6,7,8-tetrahydro-quinazolin-2-yl)-benzoic acid

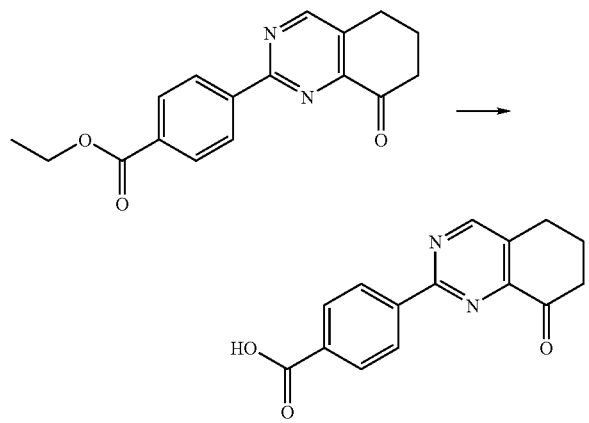

The title compound is prepared from 4-(8-Oxo-5,6,7,8-tetrahydro-quinazolin-2-yl)-benzoic acid ethyl ester (prepared in analogy to Example 26 starting from 4-Carbamimidoyl-benzoic acid ethyl ester) in analogy to Example 272 to give pale crystals. MS (m/z) ES+: 269 (MH+). Retention time: 3.13 minutes (LC-MS method 5).

b) N-Benzyl-4-(8-oxo-5,6,7,8-tetrahydro-quinazolin-2-yl)-benzamide

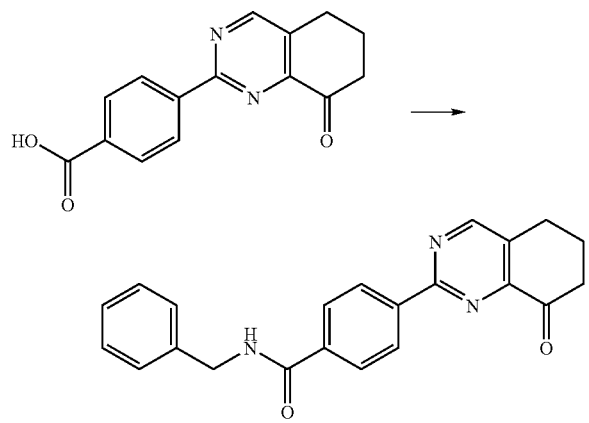

The reaction is performed in analogy to Example 273 yielding the title compound as yellow crystals. MS (m/z) ES+: 358 (MH+). Retention time: 2.55 minutes (LC-MS method 2).

c) N-Benzyl-4-(7-bromo-8-oxo-5,6,7,8-tetrahydro-quinazolin-2-yl)-benzamide

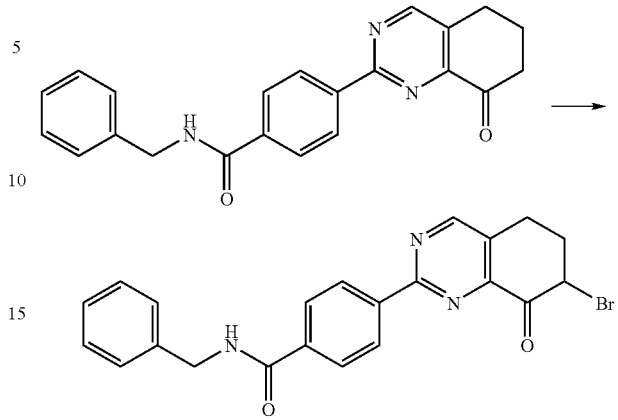

The reaction is performed in analogy to Example 14c, yielding the title compound as light-brown crystals. The product is used in the next step without further purification.

d) {1-[(2,2-Dimethyl-4,6-dioxo-[1,3]dioxan-5-ylidene)-hydroxy-methyl]-cyclobutyl}-carbamic acid tert-butyl ester

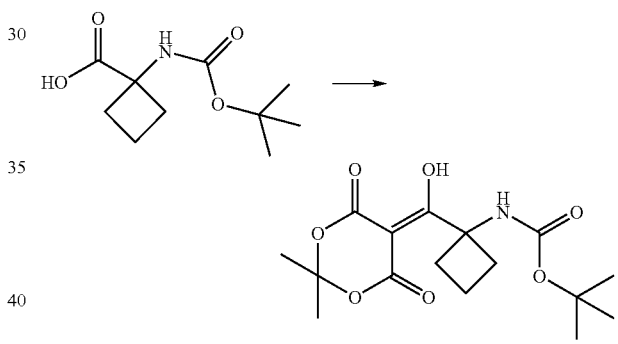

1-tert-Butoxycarbonylamino-cyclobutanecarboxylic acid (1.0 g, 4.6 mmol) and Meldrum's acid (2,2-dimethyl-[1,3]dioxane-4,6-dione, 0.74 g, 5.1 mmol) are dissolved in 20 ml dichloromethane. 4-Dimethylaminopyridin (0.88 g, 7.2 mmol) and EDCl (1.07 g, 5.6 mmol) are added and the mixture is left in a refrigerator (4° C.) overnight. The reaction mixture is diluted with additional 200 ml dichloromethane and washed twice with 0.1 N HCl and with brine. Drying of the organic phase and evaporation of the solvent delivered the crude title compound which is used in the subsequent step without further purification.

e) 8-Hydroxy-6-oxo-5-aza-spiro[3.4]oct-7-ene-5-carboxylic acid tert-butyl ester

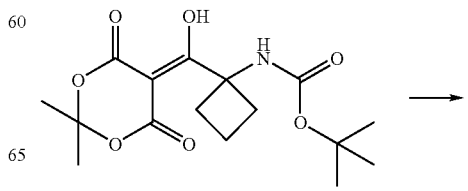

-continued

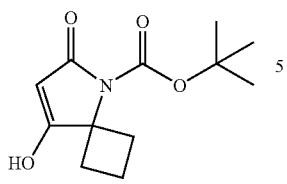

{1-[(2,2-Dimethyl-4,6-dioxo-[1,3]dioxan-5-ylidene)-hydroxy-methyl]-cyclobutyl}-carbamic acid tert-butyl ester (1.2 g, 3.5 mmol) is refluxed in ethyl acetate for 4 hours. The solvent is removed in vacuo and the resulting residue is crystallized from ether. 1H-NMR (400 MHz; DMSO-d6): 12.5 (s, 1H), 4.73 (s, 1H), 2.87 (dt, 2H), 2.35-2.25 (m, 2H), 1.85 (quint, 2H), 1.51 (s, 9H); LC-MS (m/z, ES−): 238 (M−H), Retention time: 2.24 mins (LC-MS method 3)

EXAMPLE 298

2-(3-Fluoro-4-morpholin-4-ylmethyl-phenyl)-10-spirocyclobutyl-5,6,8,9,10,11-exahydro-3,8,11-triaza-benzo[a]fluoren-7-one

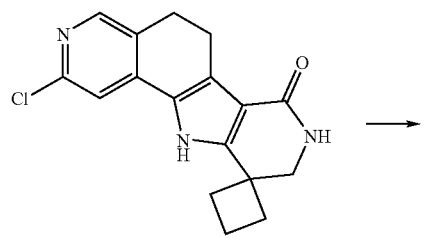

2-Chloro-10-spirocyclobutyl-5,6,8,9,10,11-hexahydro-3,8,11-triaza-benzo[a]fluoren-7-one (100 mg, 0.32 mmol) and 4-[2-Fluoro-4-(4,4,5,5-tetramethyl-[1,3,2]dioxaborolan-2-yl)-benzyl]-morpholine (154 mg, 0.48 mmol) are dissolved in 3 ml of a 4:1 mixture of 1-propanol and 2N Na2CO3 solution. Bis(triphenylphosphine)palladium dichloride (11.2 mg, 0.016 mmol) is added and the mixture is heated to 160° C. in a microwave oven (Personal Chemistry) for 20 minutes. The reaction mixture is poured onto aq. NaHCO3 solution and extracted with ethyl acetate. Drying and evaporation of the organic phase provided the crude title product which is further purified by crystallization from methanol. 1H-NMR (400 MHz; DMSO-d6): 11.73 (s, 1H), 8.39 (s, 1H), 8.13 (s, 1H), 7.91 (dd, 1H), 7.81 (d, 1H); 7.56 (t, 1H), 7.15 (s, 1H), 3.55-3.60 (brs, 6H), 3.44 (s, 2H), 2.84-2.90 (m, 4H), 2.37-2.45 (m, 8H), 2.10-2.30 (m, 2H); LC-MS (m/z, ES+): 473 (MH+), retention time: 1.56 mins (LC-MS method 2)

The starting materials are prepared as follows:

a) 1-[(2-Methoxycarbonyl-acetylamino)-methyl]-cyclobutanecarboxylic acid ethyl ester

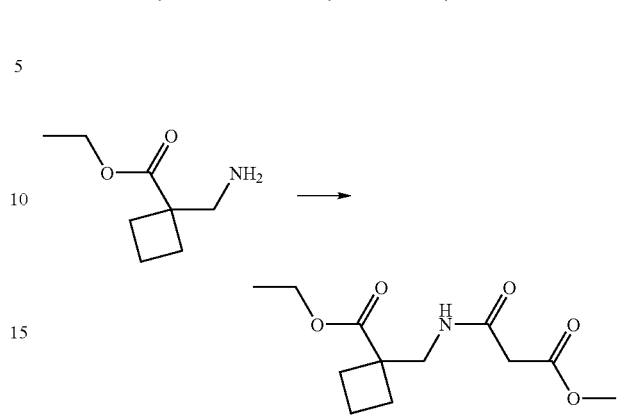

1-Aminomethyl-cyclobutanecarboxylic acid ethyl ester (WO2006/100208) (1.26 g, 8.0 mmol) and triethylamine (0.88 ml, 9.6 mmol) are dissolved in 30 ml dichloromethane (DCM). The solution is cooled to 0° C. and methylmalonyl-chloride (0.88 ml, 8.0 mmol) in 10 ml DCM is added within 15 minutes. The reaction mixture is stirred for 1 hour at 0° C. followed by 72 hours stirring at room temperature. The reaction mixture is diluted with 400 ml ethyl acetate, and washed with NaHCO3 solution, 1N HCl and brine. Evaporation of the solvent provides the title compound as viscous oil. LC-MS (m/z, ES+): 258 (MH+), retention time: 1.28 mins (LC-MS method 8)

b) 7,9-Dioxo-6-aza-spiro[3.5]nonane-8-carboxylic acid methyl ester

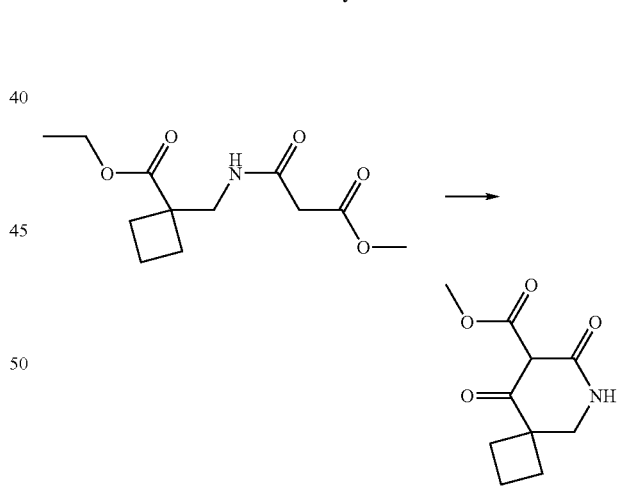

1-[(2-Methoxycarbonyl-acetylamino)-methyl]-cyclobutanecarboxylic acid ethyl ester (1.62 g, 6.3 mmol) dissolved in 15 ml toluene is added dropwise to a freshly prepared solution of sodium (0.15 g, 6.5 mmol) in methanol (20 ml). The reaction mixture is refluxed for 3 hours and then extracted 3 times with water. The aqueous phase is acidified using HClconc. and the now acidic solution is extracted with ethyl acetate. Drying and evaporation of the solvent delivered the crude product which is used in the next step without further purification.

c) 6-Aza-spiro[3.5]nonane-7,9-dione

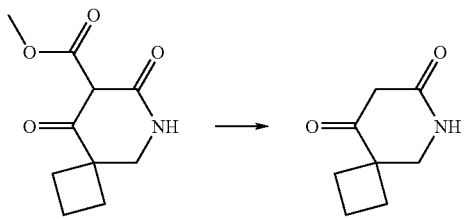

7,9-Dioxo-6-aza-spiro[3.5]nonane-8-carboxylic acid methyl ester (1.30 g, 6.2 mmol) in 30 ml acetonitrile/water (10:1) is refluxed for 1 hour. The reaction mixture is evaporated and the product purified by chromatography on silica. 1H-NMR (400 MHz; DMSO-d6): 8.02 (s, 1H), 3.40 (brs, 2H), 3.25 (s, 2H), 2.30-2.15 (m, 2H), 2.04-1.88 (m, 1H), 1.86-1.70 (m, 3H); LC-MS (m/z, ES+): 153 (MH+), retention time: 0.86 mins (LC-MS method 2)

d) 2-Chloro-10-spirocyclobutyl-5,6,8,9,10,11-hexahydro-3,8,11-triaza-benzo[a]fluoren-7-one

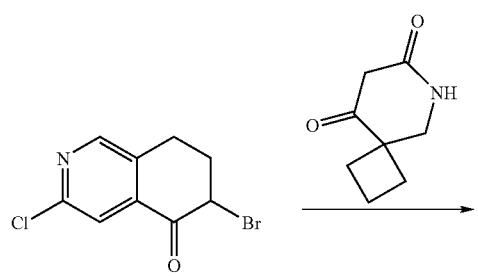

6-Bromo-3-chloro-7,8-dihydro-6H-isoquinolin-5-one (Example 1c) (0.965 g, 3.70 mmol), 6-Aza-spiro[3.5]nonane-7,9-dione (0.680 g, 4.44 mmol) and ammonium acetate (0.06 g, 11.1 mmol) are dissolved in 40 ml methanol and stirred initially at room temperature for 16 hours, then at 60 C for 2 additional hours. The reaction is quenched by addition of aq. NaHCO3 solution and the product is extracted into ethyl acetate. The crude product obtained after removal of the solvent is purified by chromatography on silica. 1H-NMR (400 MHz; DMSO-d6): 11.82 (s, 1H), 8.12 (s, 1H), 7.62 (s, 1H), 7.18 (s, 1H), 3.43 (s, 2H), 2.83-2.78 (m, 4H), 2.45-2.30 (m, 2H), 2.10-1.94 (m, 2H), 1.85-1.75 (m, 2H); LC-MS (m/z, ES+): 314 (MH+), retention time: 1.98 mins (LC-MS method 2)

EXAMPLE 299

2-(3-Fluoro-4-methoxy-phenyl)-10-spirocyclobutyl-5,6,8,9,10,11-hexahydro-3,8,11-triaza-benzo[a]fluoren-7-one

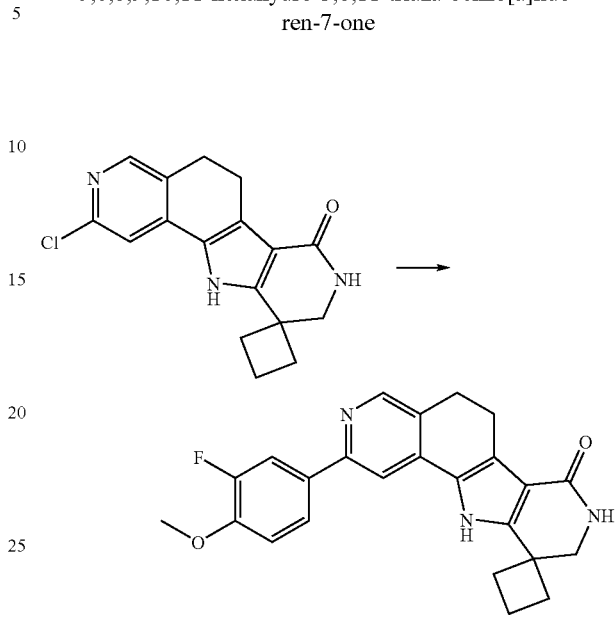

The title compound is prepared in analogy to Example 298. LC-MS (m/z, ES+): 404 (MH+), Retention time: 1.99 mins (LC-MS method 1)

EXAMPLE 300

2-(6-Fluoro-pyridin-3-yl)-10-spirocyclobutyl-5,6,8,9,10,11-hexahydro-3,8,11-triaza-benzo[a]fluoren-7-one

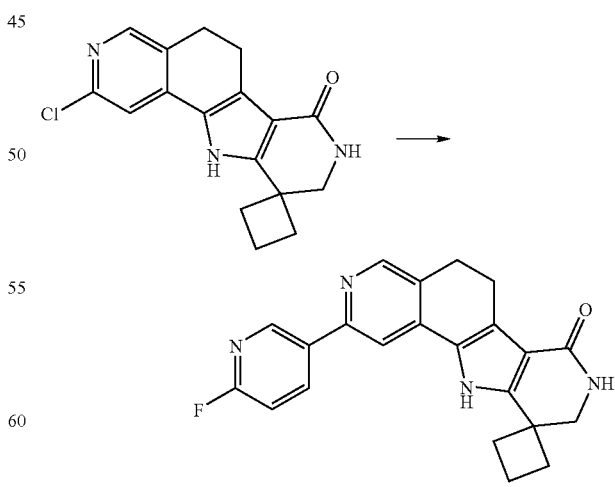

The title compound is prepared in analogy to Example 298. LC-MS (m/z, ES+): 375 (MH+), Retention time: 1.96 mins (LC-MS method 2)

EXAMPLE 301

2-(3-Fluoro-4-morpholin-4-ylmethyl-phenyl)-10-spirocyclopropyl-5,6,8,9,10,11-exahydro-3,8,11-triaza-benzo[a]fluoren-7-one

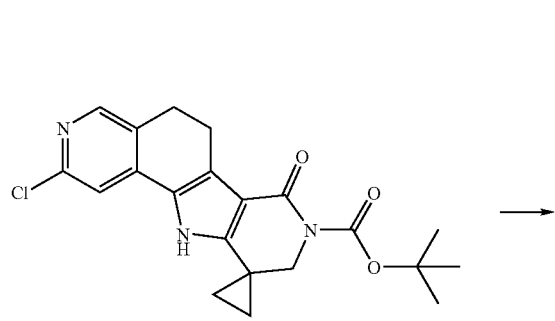

2-Chloro-7-oxo-10-spirocyclopropyl-5,6,7,9,10,11-hexahydro-3,8,11-triaza-benzo[a]fluorene-8-carboxylic acid tert-butyl ester (prepared in analogy to Example 3b) and 4-[2-Fluoro-4-(4,4,5,5-tetramethyl-[1,3,2]dioxaborolan-2-yl)-benzyl]-morpholine are coupled as described in Example 298 to yield the title compound. MS (m/z) ES+: 459 (MH+), Retention time: 1.75 mins (LC-MS method 2).

In analogous manner the following compounds are prepared:

EXAMPLE 302

2-(5-Morpholin-4-yl-pyridin-3-yl)-10-spirocyclopropyl-5,6,8,9,10,11-hexahydro-3,8,11-triaza-benzo[a]fluoren-7-one

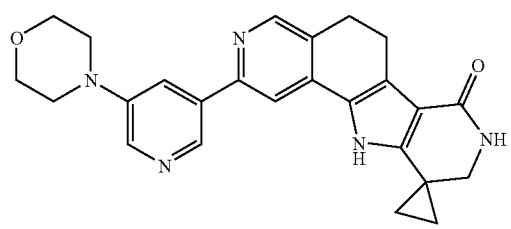

MS (m/z) ES+: 428 (MH+).

EXAMPLE 303

2-(3-Fluoro-5-isobutoxy-phenyl)-10-spirocyclopropyl-5,6,8,9,10,11-hexahydro-3,8,11-triaza-benzo[a]fluoren-7-one

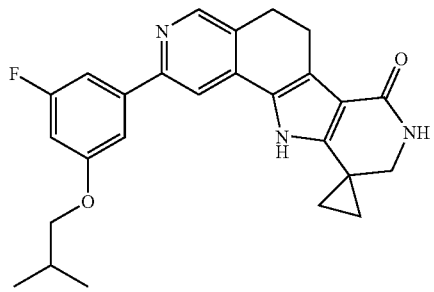

LC-MS (m/z, ES+): 432 (MH+), Retention time: 0.99 mins (LC-MS method 7)

EXAMPLE 304

2-[3-Fluoro-5-(2-methoxy-ethoxy)-phenyl]-10-spirocyclopropyl-5,6,8,9,10,11-hexahydro-3,8,11-triaza-benzo[a]fluoren-7-one

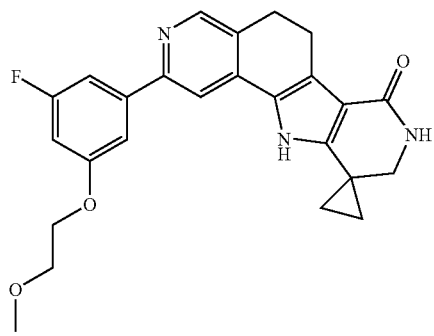

LC-MS (m/z, ES+): 434 (MH+), Retention time: 2.39 mins (LC-MS method 2)

a) 1-Bromo-3-fluoro-5-(2-methoxy-ethoxy)-benzene

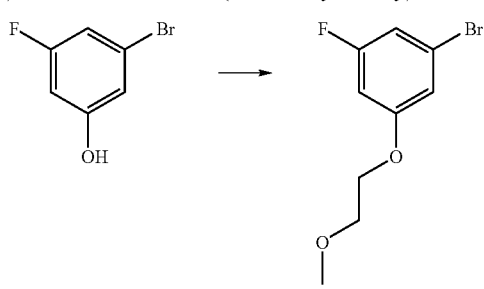

3-Bromo-5-fluoro-phenol (5.0 g, 26.2 mmol), 2-bromoethylether (4.0 g, 28.8 mmol) and K2CO3 (4.4 g, 31.4 mmol) are mixed in 50 ml DMF and stirred at 50 C overnight. Addition of aqueous NaHCO3 solution and extraction into ethyl acetate yields the title compound.

b) 2-[3-Fluoro-5-(2-methoxy-ethoxy)-phenyl]-4,4,5,5-tetramethyl-[1,3,2]dioxaborolane

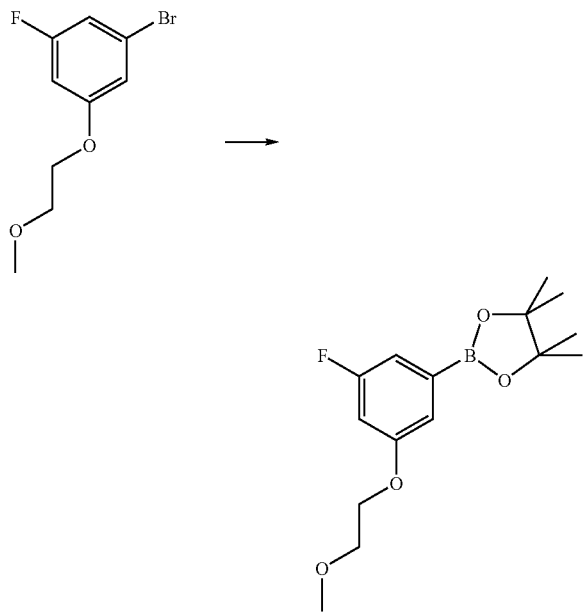

The title compound is obtained by Pd-catalyzed borylation as described in Example 306 and is used as crude product without further purification.

EXAMPLE 305

2-(2-Morpholin-4-yl-ethoxy)-5-(7-oxo-10-spirocyclopropyl-6,7,8,9,10,11-hexahydro-5H-3,8,11-triazabenzo[a]fluoren-2-yl)-benzonitrile

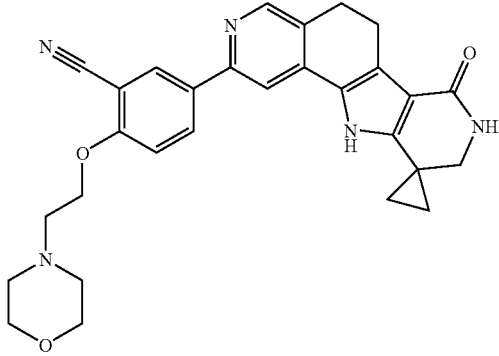

LC-MS (m/z, ES+): 496 (MH+), Retention time: 1.76 mins (LC-MS method 2)

a) 2-(2-Morpholin-4-yl-ethoxy)-5-(4,4,5,5-tetramethyl-[1,3,2]dioxaborolan-2-yl)-benzonitrile

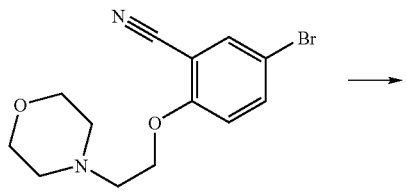

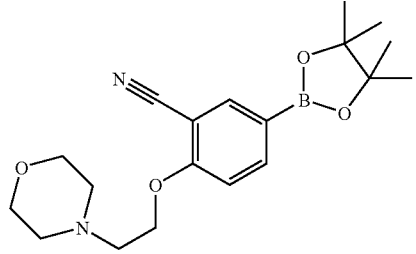

The title compound is obtained by Pd-catalyzed borylation as described in Example 306. LC-MS (m/z, ES+): 359 (MH+), Retention time: 0.84 mins (LC-MS method 7)

EXAMPLE 306

2-(4-Methyl-piperazin-1-yl)-5-(7-oxo-10-spirocyclopropyl-6,7,8,9,10,11-hexahydro-5H-3,8,11-triazabenzo[a]fluoren-2-yl)-benzonitrile

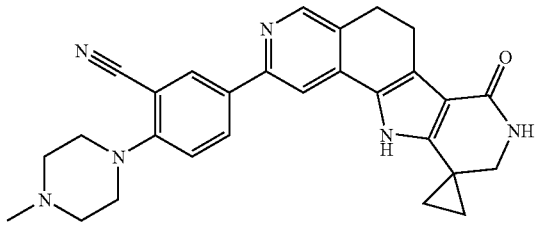

LC-MS (m/z, ES+): 465 (MH+), Retention time: 1.63 mins (LC-MS method 2)

a) 5-Bromo-2-(4-methyl-piperazin-1-yl)-benzonitrile

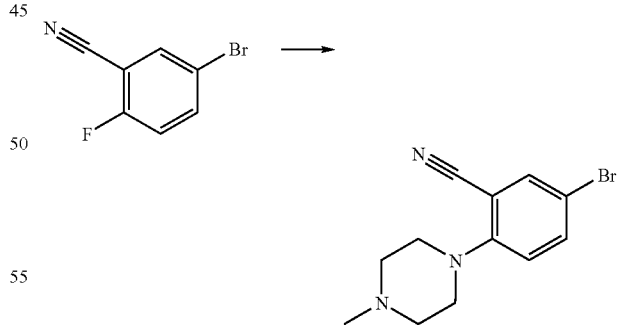

5-Bromo-2-fluorobenzonitrile (2.0 g, 10 mmol), Cesium carbonate (6.58 g, 20 mmol) and 1-methylpiperazine (1.35 ml, 12 mmol) in 100 ml DMSO are stirred at 120 C for 1 hour. The reaction is quenched by the addition of water and extracted with ethyl acetate. The organic phases are dried and the solvent evaporated. The product obtained is considered pure enough for the next synthesis steps. LC-MS (m/z, ES+): 280 (MH+), Retention time: 1.03 mins (LC-MS method 8)

b) 2-(4-Methyl-piperazin-1-yl)-5-(4,4,5,5-tetramethyl-[1,3,2]dioxaborolan-2-yl)-benzonitrile b) 2-Morpholino-5-(4,4,5,5-tetramethyl-[1,3,2]dioxaborolan-2-yl)-benzonitrile

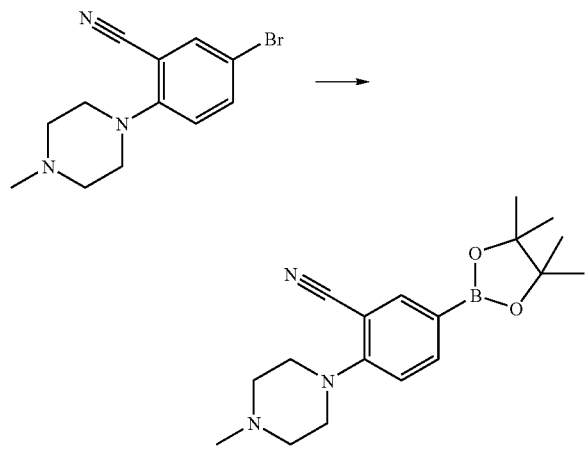

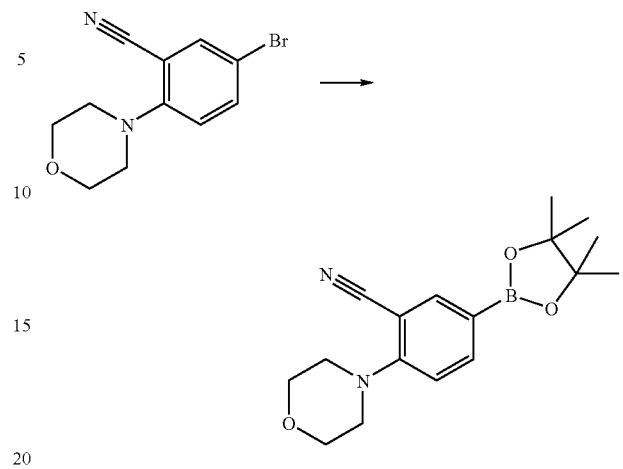

5-Bromo-2-(4-methyl-piperazin-1-yl)-benzonitrile (2.65 g, 9.5 mmol) is dissolved in 100 ml dioxane. Bis(pinacolato)diboron (4.80 g, 18.9 mmol), potassium acetate (5.62 g, 56.8 mmol) and Pd(Cl2)(dppf)2 (774 mg, 0.95 mmol) are added. The reaction mixture is stirred at 80 C for 16 hours. Addition of water and extraction into ethylacetate yields the crude title compound which is used without further purification. LC-MS (m/z, ES+): 328 (MH+), Retention time: 0.87 mins (LC-MS method 7)

The title compound is prepared as described in Example 306. LC-MS (m/z, ES+): 315 (MH+), Retention time: 1.34 mins (LC-MS method 7)

EXAMPLE 308

2-(2-Dimethylamino-ethoxy)-5-(7-oxo-10-spirocyclopropyl-6,7,8,9,10,11-hexahydro-5H-3,8,11-triaza-benzo[a]fluoren-2-yl)-benzonitrile

EXAMPLE 307

2-Morpholin-4-yl-5-(7-oxo-10-spirocyclopropyl-6,7,8,9,10,11-hexahydro-5H-3,8,11-triaza-benzo[a]fluoren-2-yl)-benzonitrile

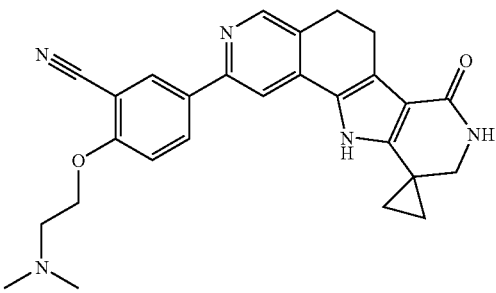

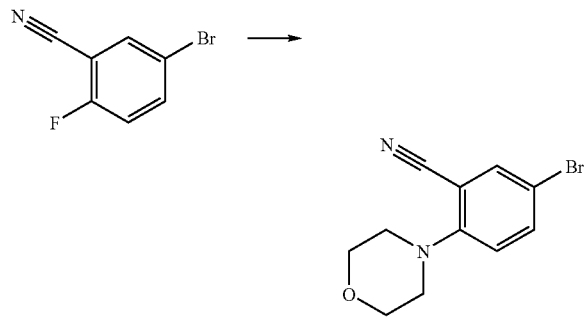

LC-MS (m/z, ES+): 454 (MH+), Retention time: 1.62 mins (LC-MS method 2)

LC-MS (m/z, ES+): 452 (MH+), Retention time: 2.33 mins (LC-MS method 2)

a) 2-(2-Dimethylamino-ethoxy)-5-(4,4,5,5-tetramethyl-[1,3,2]dioxaborolan-2-yl)-benzonitrile a) 5-Bromo-2-morpholino-benzonitrile

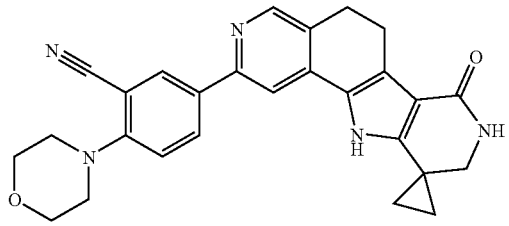

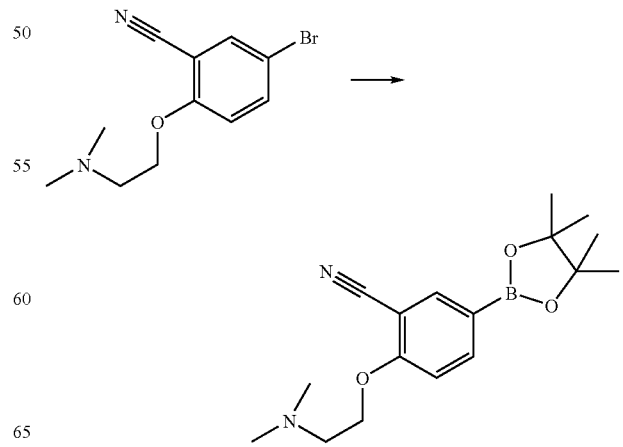

The title compound is prepared as described in Example 306. LC-MS (m/z, ES+): 280 (MH+), Retention time: 1.03 mins (LC-MS method 8)

309

The title compound is obtained by Pd-catalyzed borylation as described in Example 306 and used as crude material for the next synthesis step. LC-MS (m/z, ES+): 317 (MH+), Retention time: 0.83 mins (LC-MS method 7)

EXAMPLE 309

2-(2-Methoxy-ethoxy)-5-(7-oxo-10-spirocyclopropyl-6,7,8,9,10,11-hexahydro-5H-3,8,11-triaza-benzo[a]fluoren-2-yl)-benzonitrile

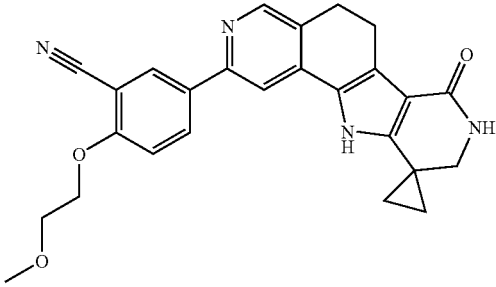

LC-MS (m/z, ES+): 441 (MH+), Retention time: 1.91 mins (LC-MS method 2)

a) 5-Bromo-2-(2-methoxy-ethoxy)-benzonitrile

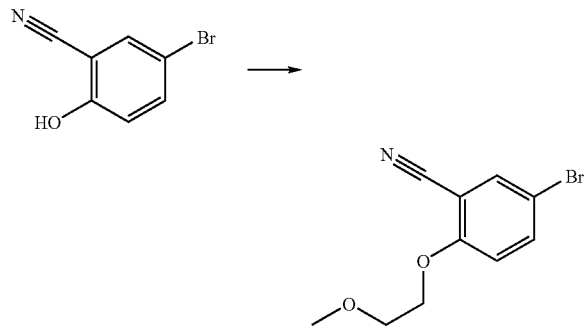

5-Bromo-2-hydroxy-benzonitrile (5.4 g, 27.0 mmol), 2-bromoethylether (2.76 ml, 29.7 mmol) and K2CO3 (4.5 g, 32.4 mmol) are mixed in 50 ml DMF. The reaction mixture is stirred at 50 C overnight. Addition of water and extraction into ethylacetate yields the title compound which is further purified by tituration with ether/hexanes. 1H-NMR (400 MHz; DMSO-d6): 7.99 (d, 1H), 7.82 (dd, 1H), 7.23 (d, 1H), 4.27 (t, 2H), 3.69 (t, 2H), 3.33 (s, 3H). LC-MS (m/z, ES+): 273 (M+NH4+), retention time: 2.77 mins (LC-MS method 3)

b) 2-(2-Methoxy-ethoxy)-5-(4,4,5,5-tetramethyl-[1,3,2]dioxaborolan-2-yl)-benzonitrile

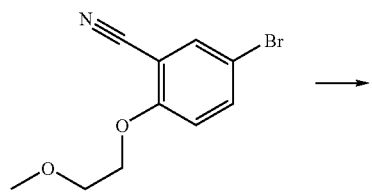

310

-continued

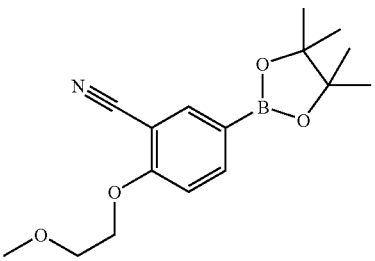

The title compound is obtained essentially as described in Example 306 and used as crude material for the next synthesis step. LC-MS (m/z, ES+): 304 (MH+), Retention time: 1.31 mins (LC-MS method 7)

EXAMPLE 310

2-[4-Fluoro-3-(2-methoxy-ethoxy)-phenyl]-10-spirocyclopropyl-5,6,8,9,10,11-hexahydro-3,8,11-triaza-benzo[a]fluoren-7-one

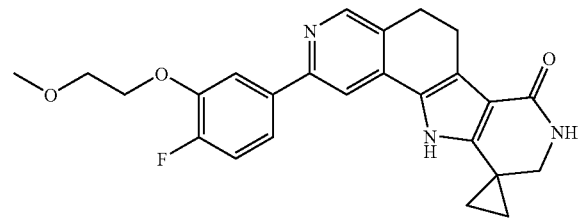

LC-MS (m/z, ES+): 434 (MH+), Retention time: 0.74 mins (LC-MS method 7)

a) 4-Bromo-1-fluoro-2-(2-methoxy-ethoxy)-benzene

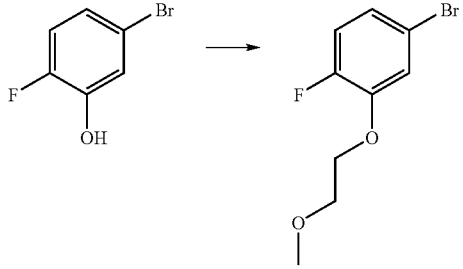

5-Bromo-2-fluoro-phenol (5.0 g, 26.2 mmol), 2-bromoethylether (2.71 ml, 28.8 mmol) and K2CO3 (4.4 g, 31.4 mmol) are mixed in 50 ml DMF and stirred at 50 C for 6 hours. Addition of aqueous NaHCO3 solution and extraction into ethyl acetate yields the title compound as viscous oil. 1H-NMR (400 MHz; DMSO-d6): 7.40 (d, 1H), 7.21 (dd, 1H), 7.08-7.14 (m, 1H), 4.21 (t, 2H), 3.66 (t, 2H), 3.30 (s, 3H). LC-MS (m/z, ES+): 248 (MH+), retention time: 3.02 mins (LC-MS method 3)

b) 2-[4-Fluoro-3-(2-methoxy-ethoxy)-phenyl]-4,4,5,5-tetramethyl-[1,3,2]dioxaborolane

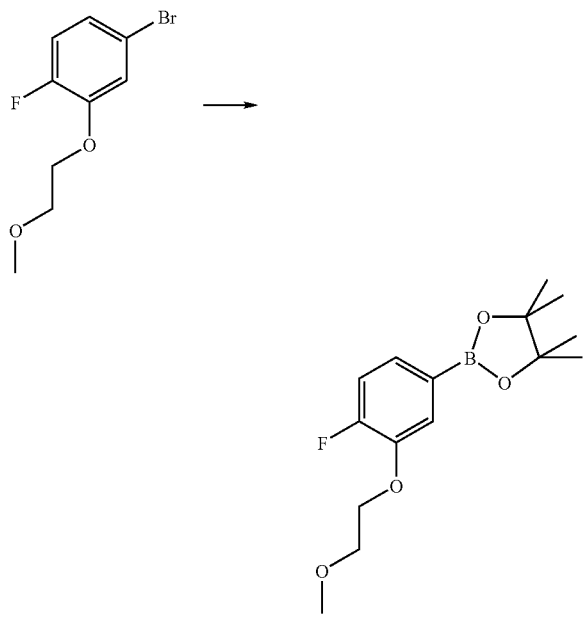

The title boronate is obtained as described in Example 306 and used as crude material for the next synthesis step. LC-MS (m/z, ES+): 314 (M+NH4+), Retention time: 3.57 mins (LC-MS method 3)

EXAMPLE 311

2-[3-(2-Dimethylamino-ethoxy)-4-fluoro-phenyl]-10-spirocyclopropyl-5,6,8,9,10,11-hexahydro-3,8,11-triaza-benzo[a]fluoren-7-one

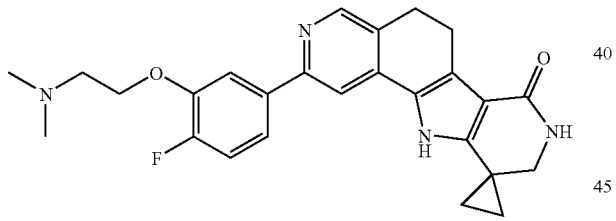

LC-MS (m/z, ES+): 447 (MH+), Retention time: 1.28 mins (LC-MS method 2)

a) [2-(5-Bromo-2-fluoro-phenoxy)-ethyl]-dimethyl-amine

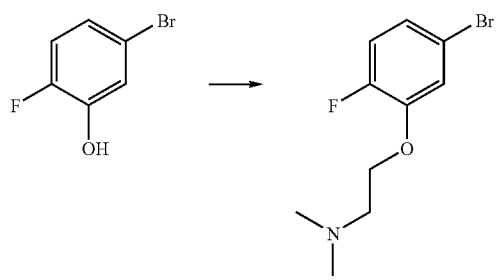

5-Bromo-2-fluoro-phenol (5.0 g, 26.2 mmol), 2-Dimethylaminoethylchlorid×HCl (5.66 g, 39.3 mmol) and K2CO3 (11.0 g, 78.5 mmol) are suspended/dissolved in 260 ml dry acetone and stirred at room temperature for 72 hours. Addition of aqueous NaHCO3 solution and extraction into ethyl acetate yields a crude product which is further purified by chromatography on silica. 1H-NMR (400 MHz; DMSO-d6): 7.41 (d, 1H), 7.20 (dd, 1H), 7.08-7.14 (m, 1H), 4.15 (t, 2H), 2.63 (t, 2H), 2.22 (s, 6H). MS (m/z, ES+): 262 (MH+).

b) {2-[2-Fluoro-5-(4,4,5,5-tetramethyl-[1,3,2]dioxaborolan-2-yl)-phenoxy]-ethyl}-dimethyl-amine

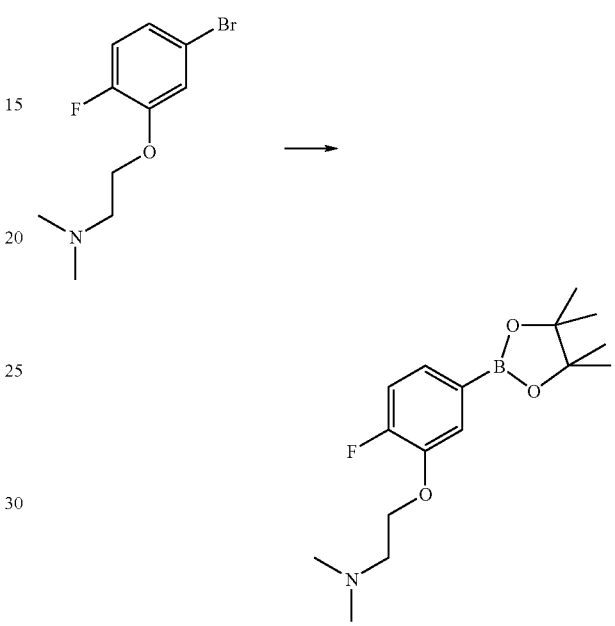

The title boronate is obtained as described in Example 306 and used without further characterization as crude material for the next synthesis step.

EXAMPLE 312

2-(3-Hydroxy-pyrrolidin-1-yl)-10-spirocyclopropyl-5-(7-oxo-6,7,8,9,10,11-hexahydro-5H-3,8,11-triaza-benzo[a]fluoren-2-yl)-benzonitrile

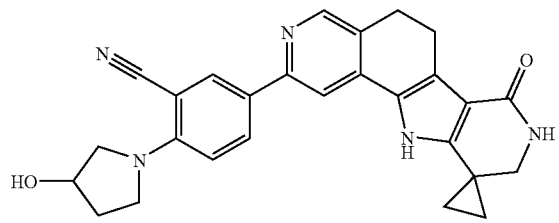

LC-MS (m/z, ES+): 452 (MH+), Retention time: 1.61 mins (LC-MS method 1)

a) 5-Bromo-2-(3-hydroxy-pyrrolidin-1-yl)-benzonitrile

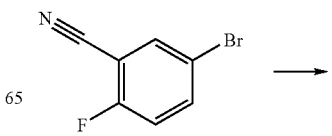

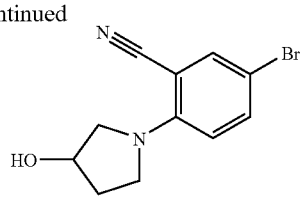

The title compound is prepared as described in Example 306. LC-MS (m/z, ES+): 268 (MH+), Retention time: 1.03 mins (LC-MS method 7)

b) 2-(3-Hydroxy-pyrrolidin-1-yl)-5-(4,4,5,5-tetramethyl-[1,3,2]dioxaborolan-2-yl)-benzonitrile

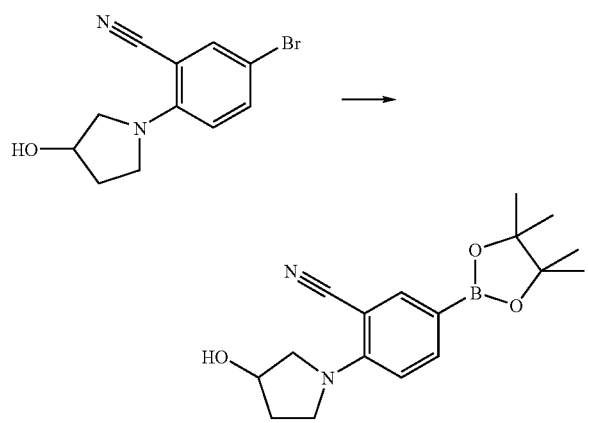

The title boronate is prepared as described in Example 306. LC-MS (m/z, ES+): 315 (MH+), Retention time: 1.17 mins (LC-MS method 7)

EXAMPLE 313

2-(4-Acetyl-piperazin-1-yl)-10-spirocyclopropyl-5-(7-oxo-6,7,8,9,10,11-hexahydro-5H-3,8,11-triazabenzo[a]fluoren-2-yl)-benzonitrile

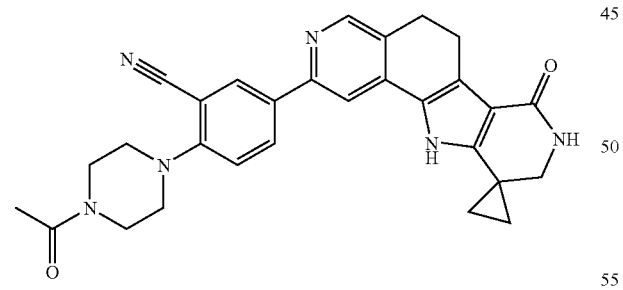

LC-MS (m/z, ES+): 493 (MH+), Retention time: 1.68 mins (LC-MS method 1)

a) 2-(4-Acetyl-piperazin-1-yl)-5-bromo-benzonitrile

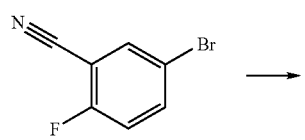

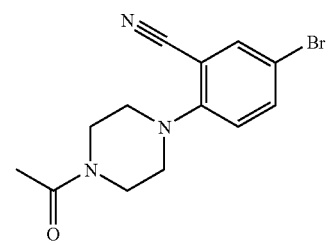

The title compound is obtained as described in Example 306. LC-MS (m/z, ES+): 308 (MH+), Retention time: 1.01 mins (LC-MS method 7)

b) 2-(4-Acetyl-piperazin-1-yl)-5-(4,4,5,5-tetramethyl-[1,3,2]dioxaborolan-2-yl)-benzonitrile

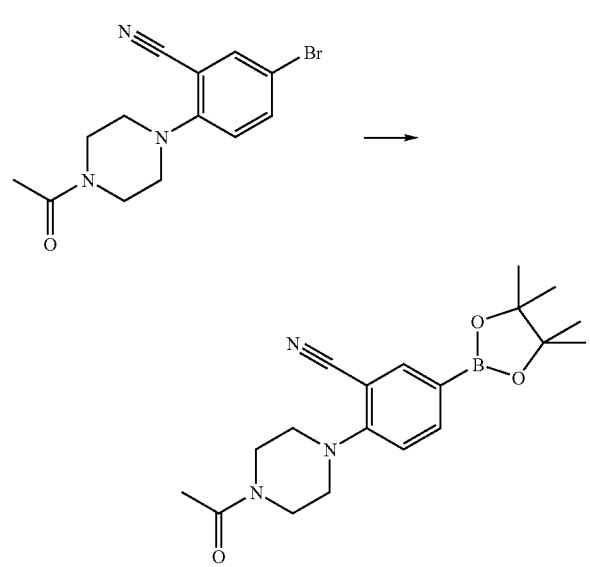

The title boronate is prepared as described in Example 306. LC-MS (m/z, ES+): 356 (MH+), Retention time: 1.18 mins (LC-MS method 7)

EXAMPLE 314

2-(4-Isopropyl-piperazin-1-yl)-10-spirocyclopropyl-5-(7-oxo-6,7,8,9,10,11-hexahydro-5H-3,8,11-triazabenzo[a]fluoren-2-yl)-benzonitrile

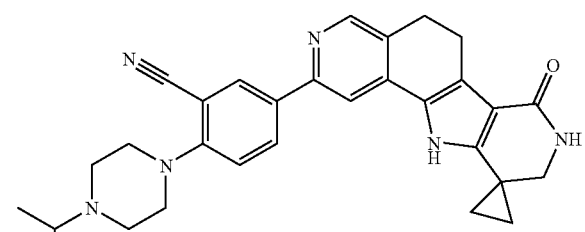

LC-MS (m/z, ES+): 493 (MH+), Retention time: 1.40 mins (LC-MS method 2)

315 a) 5-Bromo-2-(4-isopropyl-piperazin-1-yl)-benzonitrile

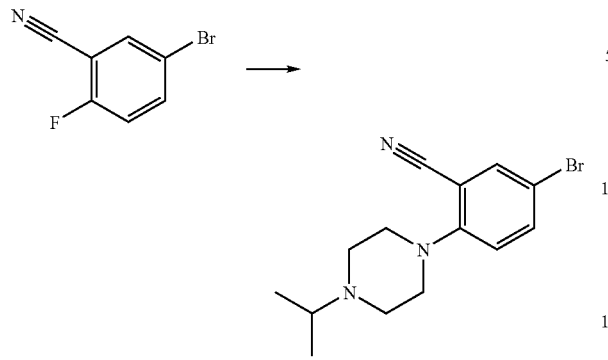

The title compound is obtained as described in Example 306. LC-MS (m/z, ES+): 308 (MH+), Retention time: 0.65 mins (LC-MS method 7)

b) 2-(4-Isopropyl-piperazin-1-yl)-5-(4,4,5,5-tetramethyl-[1,3,2]dioxaborolan-2-yl)-benzonitrile

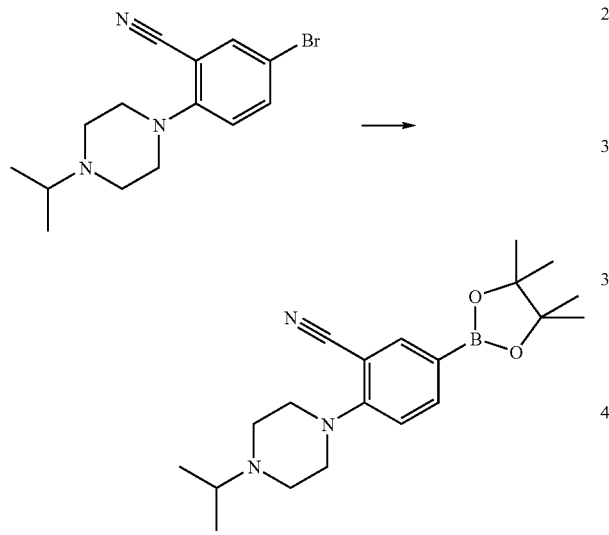

The title boronate is prepared as described in Example 306. LC-MS (m/z, ES+): 356 (MH+), Retention time: 0.93 mins (LC-MS method 7)

EXAMPLE 315

2-[4-(2-Hydroxy-ethyl)-piperazin-1-yl]-10-spirocyclopropyl-5-(7-oxo-6,7,8,9,10,11-hexahydro-5H-3,8,11-triaza-benzo[a]fluoren-2-yl)-benzonitrile

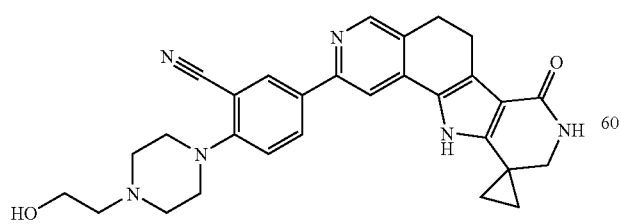

LC-MS (m/z, ES+): 495 (MH+), Retention time: 1.26 mins (LC-MS method 2)

316 a) 5-Bromo-2-(4-hydroxyethyl-piperazin-1-yl)-benzonitrile

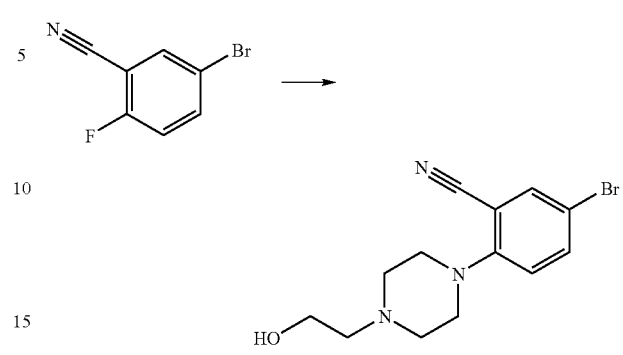

The title compound is obtained as described in Example 306. LC-MS (m/z, ES+): 310 (MH+), Retention time: 0.63 mins (LC-MS method 7)

b) 2-(4-Hydroxyethyl-piperazin-1-yl)-5-(4,4,5,5-tetramethyl-[1,3,2]dioxaborolan-2-yl)-benzonitrile

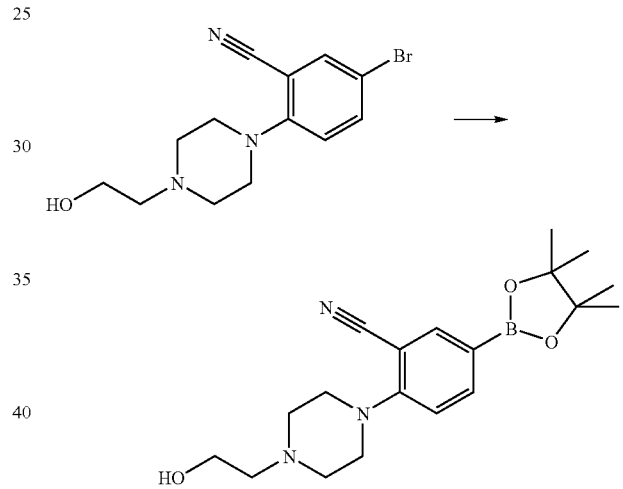

The title boronate is prepared as described in Example 306 and used as crude material. LC-MS (m/z, ES+): 358 (MH+), Retention time: 0.87 mins (LC-MS method 7)

EXAMPLE 316

2-[6-(4-Methyl-piperazin-1-yl)-pyridin-3-yl]-10-spirocyclopropyl-5,6,8,9,10,11-hexahydro-3,8,11-triaza-benzo[a]fluoren-7-one

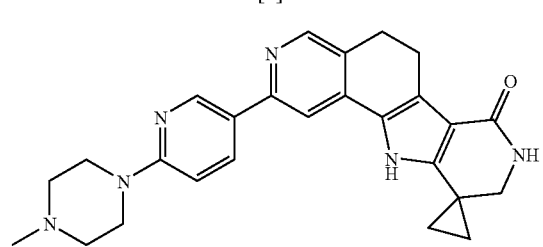

LC-MS (m/z, ES+): 441 (MH+), Retention time: 1.09 mins (LC-MS method 2)

317

EXAMPLE 317

3-Fluoro-2-(4-methyl-piperazin-1-yl)-10-spirocyclo-propyl-5-(7-oxo-6,7,8,9,10,11-hexahydro-5H-3,8,11-triaza-benzo[a]fluoren-2-yl)-benzonitrile

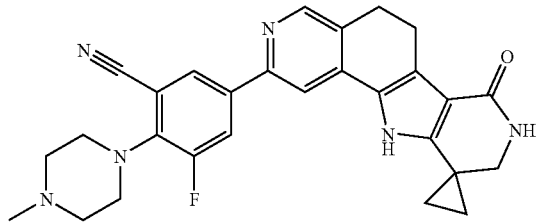

LC-MS (m/z, ES+): 483 (MH+), Retention time: 1.51 mins (LC-MS method 2)

a) 5-Bromo-3-fluoro-2-(4-methyl-piperazin-1-yl)-benzonitrile

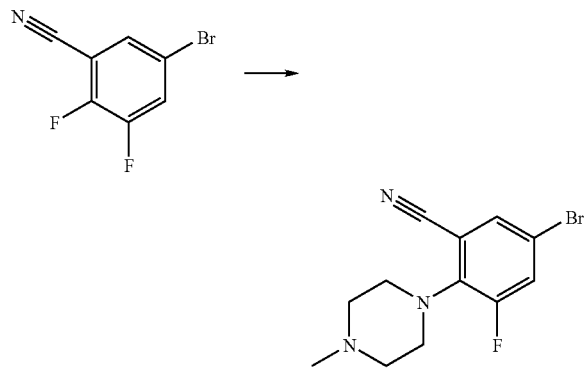

The title compound, which contained still minor amounts of starting material is obtained as described in Example 306. LC-MS (m/z, ES+): 298 (MH+), Retention time: 0.63 mins (LC-MS method 7)

b) 3-Fluoro-2-(4-methyl-piperazin-1-yl)-5-(4,4,5,5-tetramethyl-[1,3,2]dioxaborolan-2-yl)-benzonitrile

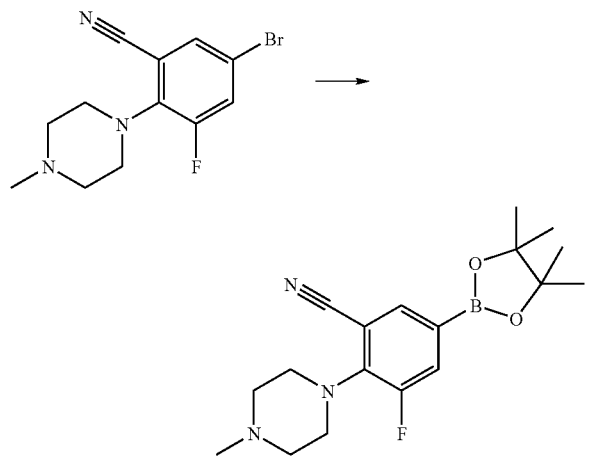

318

The title boronate is prepared as described in Example 306 and used as crude material. LC-MS (m/z, ES+): 346 (MH+), Retention time: 0.94 mins (LC-MS method 7)

EXAMPLE 318

2-(3-Dimethylamino-pyrrolidin-1-yl)-10-spirocyclo-propyl-5-(7-oxo-6,7,8,9,10,11-hexahydro-5H-3,8,11-triaza-benzo[a]fluoren-2-yl)-benzonitrile

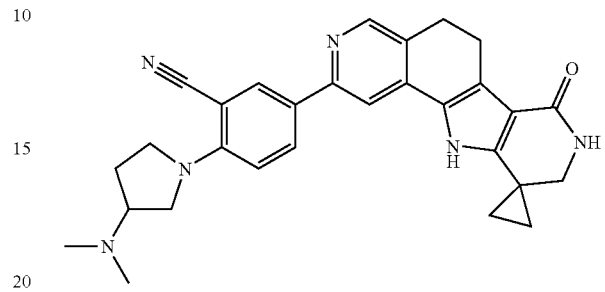

LC-MS (m/z, ES+): 479 (MH+), Retention time: 1.32 mins (LC-MS method 2)

a) 5-Bromo-2-(3-dimethylamino-pyrrolidin-1-yl)-benzonitrile

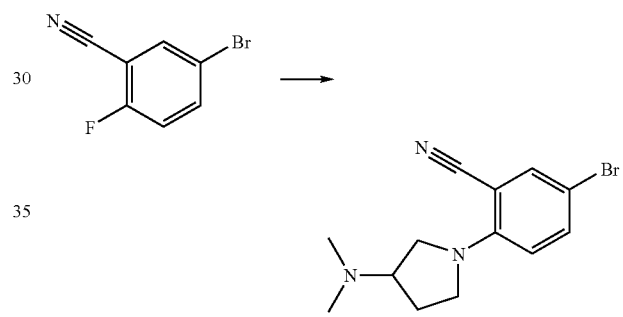

The title compound is prepared as described in Example 306. 1H-NMR (400 MHz; DMSO-d6): 7.64 (d, 1H), 7.48 (dd, 1H), 6.71 (d, 1H), 3.50-3.68 (m, 2H), 3.27-3.38 (m, 2H), 2.74 (qint, 1H), 2.18 (s, 6H), 2.09-2.20 (m, 1H), 1.77 (quint, 1H). LC-MS (m/z, ES+): 294 (MH+), Retention time: 1.56 mins (LC-MS method 2)

b) 2-(3-Dimethylamino-pyrrolidin-1-yl)-5-(4,4,5,5-tetramethyl-[1,3,2]dioxaborolan-2-yl)-benzonitrile

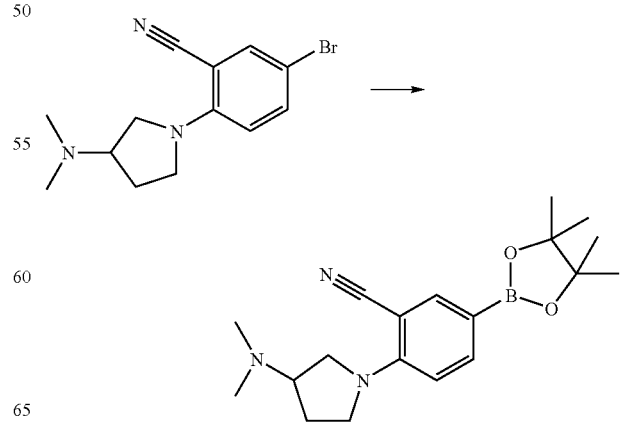

EXAMPLE 319

2-Morpholin-4-ylmethyl-10-spirocyclopropyl-5-(7-oxo-6,7,8,9,10,11-hexahydro-5H-3,8,11-triaza-benzo[a]fluoren-2-yl)-benzonitrile

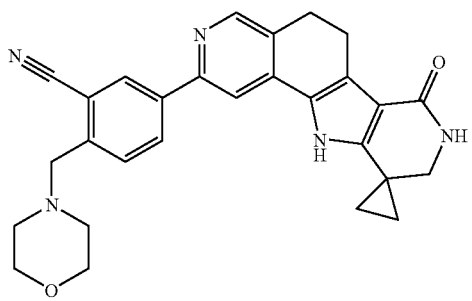

LC-MS (m/z, ES+): 466 (MH+), Retention time: 2.09 mins (LC-MS method 3)

a) 5-Bromo-2-morpholin-4-ylmethyl-benzonitrile

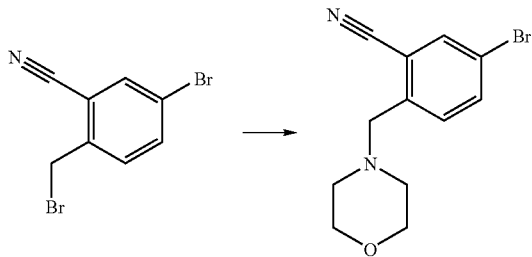

A mixture of 5-bromo-2-bromomethyl-benzonitrile (2.0 g, 7.3 mmol), morpholine (0.76 g, 8.7 mmol) and K2CO3 (1.0 g, 7.3 mmol) is stirred in 50 DMF at room temperature for 72 hours. The reaction mixture is filtered and the filtrate is dried under vacuum to yield the title compound. 1H-NMR (400 MHz; DMSO-d6): 8.11 (d, 1H), 7.90 (dd, 1H), 7.53 (d, 1H), 3.60 (s, 2H), 3.56 (t, 4H), 2.39 (t, 4H). LC-MS (m/z, ES+): 281 (MH+), Retention time: 1.79 mins (LC-MS method 2)

b) 2-Morpholin-4-ylmethyl-5-(4,4,5,5-tetramethyl-[1,3,2]dioxaborolan-2-yl)-benzonitrile

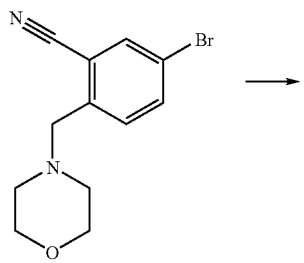

The title boronate is prepared as described in Example 306 and used as crude product without further purification and characterization.

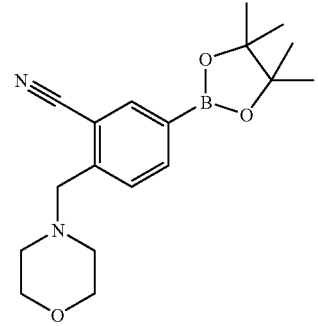

The title boronate is prepared as described in Example 306 and used as crude product without further purification. LC-MS (m/z, ES+): 329 (MH+), Retention time: 1.27 mins (LC-MS method 8)

EXAMPLE 320

10-Spirocyclopropyl-5,6,8,9,10,11-hexahydro-3,8,11-triaza-benzo[a]fluoren-7-one

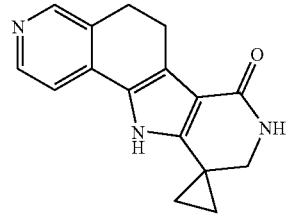

The title compound is obtained as side product in the preparation of Example 316. LC-MS (m/z, ES−): 264 (M−H), Retention time: 0.99 mins (LC-MS method 2)

EXAMPLE 321

2-(4-Methyl-piperazin-1-yl)-9-spirocyclopropyl-5-(7-oxo-6,7,8,9,10,11-hexahydro-5H-3,8,11-triaza-benzo[a]fluoren-2-yl)-benzonitrile

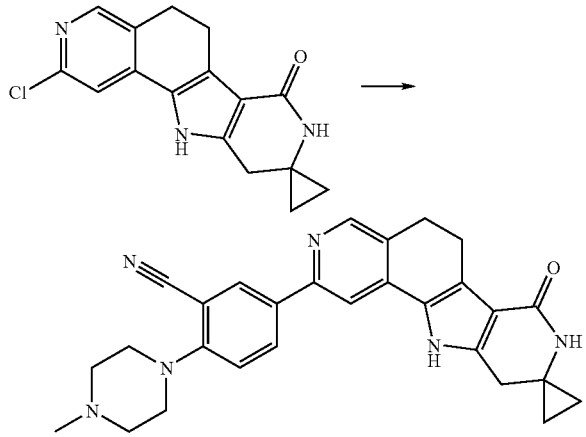

2-Chloro-7-oxo-9-spirocyclopropyl-5,6,7,9,10,11-hexahydro-3,8,11-triaza-benzo[a]fluorene (100 mg, 0.33 mmol) (Example #31a) and 2-(4-Methyl-piperazin-1-yl)-5-(4,4,5,5-tetramethyl-[1,3,2]dioxaborolan-2-yl)-benzonitrile (82 mg, 0.25 mmol) are coupled in analogy to Example 1 to yield the title compound. MS (m/z) ES+: 465 (MH+).

EXAMPLE 322

2-(3-Chloro-4-morpholin-4-yl-phenyl)-9-spirocyclobutyl-5,6,8,9,10,11-hexahydro-1,3,8,11-tetraazabenzo[a]fluoren-7-one

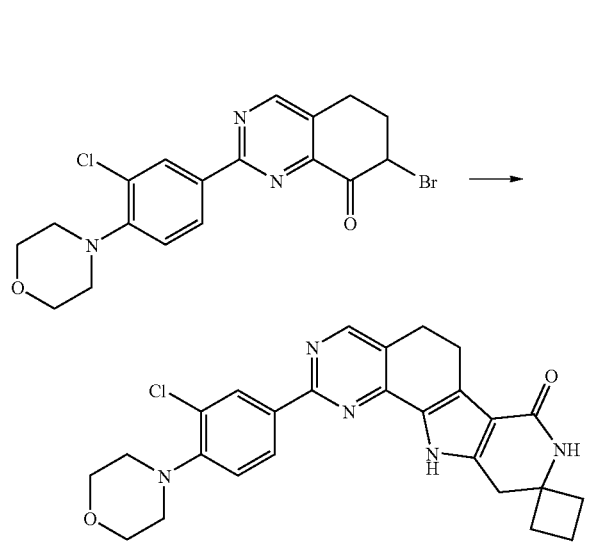

7-Bromo-2-[3-chloro-4-morpholin-4-yl)-phenyl]-6,7-dihydro-5H-quinazolin-8-one (0.10 g, 0.2 mmol) and 5-Azaspiro[3.5]nonane-6,8-dione (Example 34) (40 mg, 0.3 mmol) are dissolved in 2 ml methanol. Ammonium acetate (55 mg, 0.7 mmol) is added and the mixture is stirred at room temperature overnight. Addition of aq. NaHCO3 solution, extraction with ethyl acetate, drying and evaporation yields the crude product, which is further purified by RP-HPLC (Waters X-Terra, acetonitrile/water gradient). 1H-NMR (400 MHz; DMSO-d6): 12.1 (s, 1H), 8.49 (d, 1H), 8.43 (s, 1H), 8.33 (dd, 1H), 7.52 (s, 1H), 7.24 (d, 1H), 3.76 (brs, 4H), 3.07 (brs, 4H), 3.03 (s, 2H), 2.95 (d, 2H), 2.89 (d, 2H), 2.20-1.98 (m, 4H), 1.80-1.67 (m, 2H); LC-MS (m/z, ES+): 476 (MH+), Retention time: 2.85 mins (LC-MS method 2)

The starting materials are prepared as follows:

a) 3-Chloro-4-morpholin-4-yl-benzonitrile

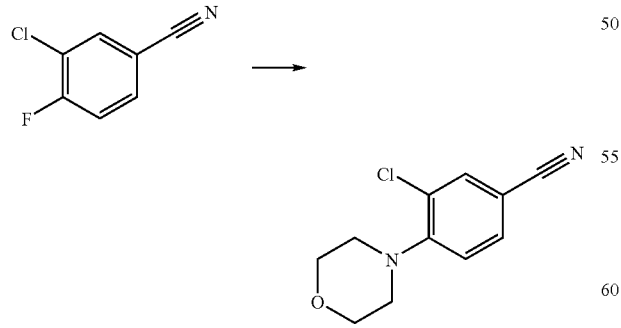

3-Chloro-4-morpholin-4-yl-benzonitrile is synthesized starting from 3-Chloro-4-fluoro-benzonitrile and morpholine as described in Example 306. LC-MS (m/z, ES+): 223 (MH+), Retention time: 1.11 mins (LC-MS method 7)

b) 2-(3-Chloro-4-morpholin-4-yl-phenyl)-8-ethoxy-5,6-dihydro-quinazoline

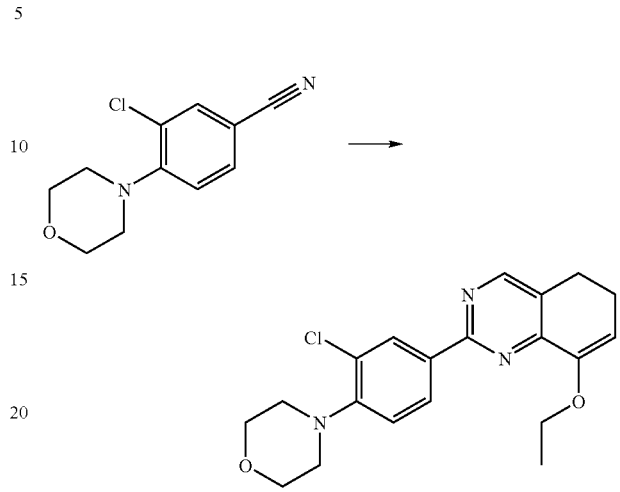

3-Chloro-4-morpholin-4-yl-benzonitrile (3.0 g, 13.5 mmol) is dissolved in 150 ml dry THF. Lithium hexamethyldisilazide (21.6 ml 1.0 M solution in hexane) is added and the mixture is stirred for one hour at room temperature. 50 ml aq. NaHCO3 solution is added and the mixture is extracted vigorously with ethyl acetate to give the crude amidine. The crude material (2.0 g) is dissolved in 8 ml methanol and 6-[1-Dimethylamino-methylidene]-2-ethoxy-cyclohex-2-enone (0.81 g, 4.2 mmol) is added. The reaction mixture is heated in a microwave oven to 140 C for 15 minutes. Addition of aq. NaHCO3 solution and extraction with ethyl acetate, followed by tituration with ethyl acetate delivered the title compound, which is used as such in the following step.

c) 2-(3-Chloro-4-morpholin-4-yl-phenyl)-6,7-dihydro-5H-quinazolin-8-one

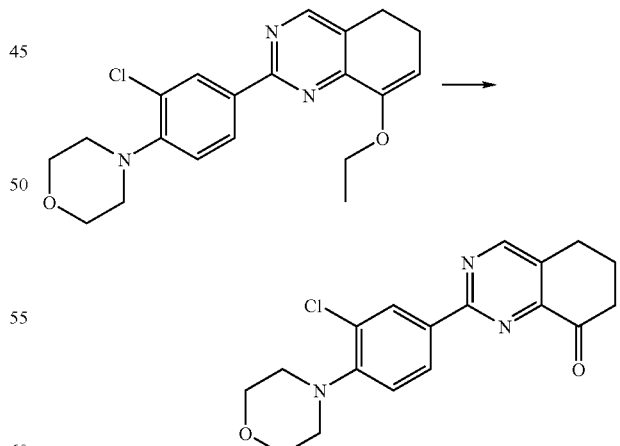

2-(3-Chloro-4-morpholin-4-yl-phenyl)-8-ethoxy-5,6-dihydro-quinazoline (0.38 g, 1.0 mmol) is refluxed in 20 ml 25% aqueous acetic acid for 1 hour. The reaction mixture is neutralized using solid NaHCO3 and the product is extracted with ethyl acetate. MS (m/z, ES+): 344 (MH+).

323 d) 7-Bromo-2-(3-chloro-4-morpholin-4-yl-phenyl)-6,7-dihydro-5H-quinazolin-8-one

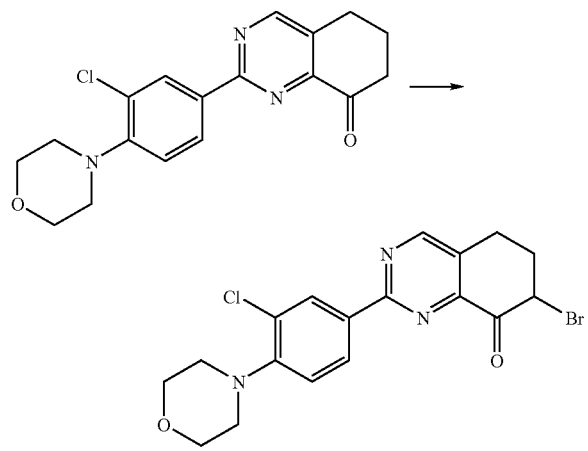

2-(3-Chloro-4-morpholin-4-yl-phenyl)-6,7-dihydro-5H-quinazolin-8-one (328 mg, 0.95 mmol) is dissolved in acetic acid (7 ml) and HBr$_{conc}$. (7 ml). Bromine in HBr$_{conc}$. (0.95 ml 1N solution) is added at room temperature. After stirring for one hour the mixture is poured onto ice, neutralized with NaHCO3 and the product is extracted with ethyl acetate. 1H-NMR (400 MHz; DMSO-d6): 9.10 (s, 1H), 8.43 (s, 1H), 8.28 (d, 1H), 7.30 (d, 1H), 5.21(dd, 1H), 3.76 (brs, 4H), 3.09 (brs, 4H), 3.00-2.40 (m, 4H); LC-MS (m/z, ES+): 422 (MH+), Retention time: 3.05 mins (LC-MS method 2)

In analogy to Example 322 the following compounds are prepared:

EXAMPLE 323

2-[3-Chloro-4-(4-methyl-piperazin-1-yl)-phenyl]-9-spirocyclobutyl-5,6,8,9,10,11-hexahydro-1,3,8,11-tetraaza-benzo[a]fluoren-7-one

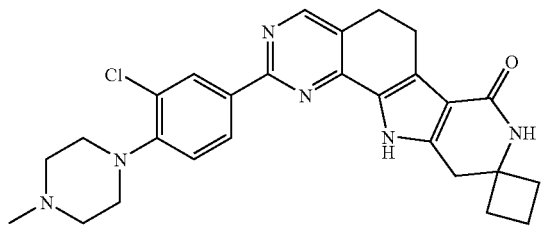

1H-NMR (400 MHz; DMSO-d6): 12.1 (s, 1H), 8.48 (d, 1H), 8.42 (s, 1H), 8.31 (dd, 1H), 7.52 (s, 1H), 7.22 (d, 1H), 3.07 (brs, 4H), 3.03 (s, 2H), 2.93 (d, 2H), 2.89 (d, 2H), 2.24 (s, 3H), 2.20-1.98 (m, 4H), 1.80-1.67 (m, 2H), 2H obscured. LC-MS (m/z, ES+): 489 (MH+), Retention time: 1.85 mins (LC-MS method 2)

EXAMPLE 324

2-(3-Fluoro-4-morpholin-4-ylmethyl-phenyl)-9-spirocyclobutyl-5,6,8,9,10,11-hexahydro-1,3,8,11-tetraaza-benzo[a]fluoren-7-one

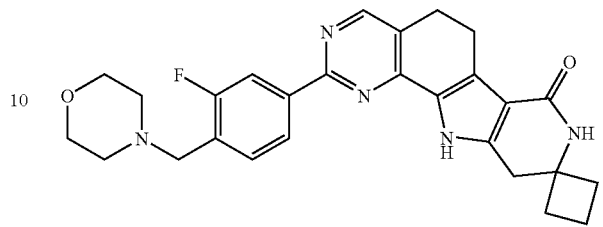

1H-NMR (400 MHz; DMSO-d6): 12.1 (s, 1H), 8.46 (s, 1H), 8.22 (s, 1H), 8.21 (d, 1H), 7.52 (s, 1H), 7.51 (t, 1H), 3.57 (brs, 4H), 3.03 (s, 2H), 2.98-2.89 (m, 4H), 2.41 (brs, 4H), 2.20-1.98 (m, 4H), 1.80-1.67 (m, 2H); LC-MS (m/z, ES+): 474 (MH+), Retention time: 1.76 mins (LC-MS method 2)

EXAMPLE 325

2-(3-Fluoro-4-morpholin-4-ylmethyl-phenyl)-9-spirocyclopropyl-5,6,8,9,10,11-hexahydro-1,3,8,11-tetraaza-benzo[a]fluoren-7-one

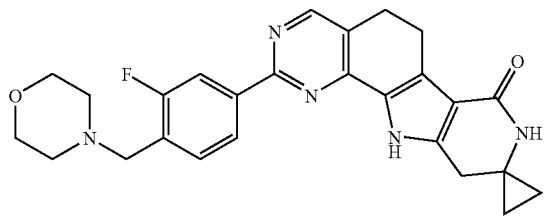

1H-NMR (400 MHz; DMSO-d6): 12.08 (s, 1H), 8.47 (s, 1H), 8.22 (s, 1H), 8.21 (d, 1H), 7.51 (t, 1H), 7.22 (s, 1H), 3.57 (brs, 6H), 2.98-2.89 (m, 4H), 2.86 (s, 2H), 2.41 (brs, 4H), 0.76 (brs, 2H), 0.70 (brs, 2H); LC-MS (m/z, ES+): 460 (MH+), Retention time: 1.62 mins (LC-MS method 2)

EXAMPLE 326

2-(3-Aminomethyl-azetidin-3-yl)-8-(3-fluoro-4-morpholin-4-ylmethyl-phenyl)-4,5-dihydro-1H-1,7,9-triaza-cyclopenta[a]naphthalene-3-carboxylic acid lactam

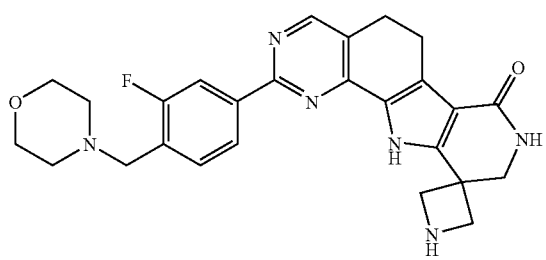

LC-MS (m/z, ES+): 475 (MH+), Retention time: 1.12 mins (LC-MS method 2)

EXAMPLE 327

2-(6-Morpholin-4-yl-pyridin-3-yl)-9-spirocyclobutyl-5,6,8,9,10,11-hexahydro-1,3,8,11-tetraaza-benzo[a]fluoren-7-one

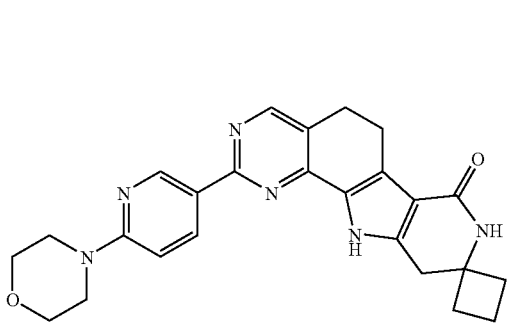

1H-NMR (400 MHz; DMSO-d6): 12.0 (brs, 1H), 9.18 (s, 1H), 8.50 (d, 1H), 8.37 (s, 1H), 7.47 (s, 1H), 6.92 (d, 1H), 3.71 (brs, 4H), 3.58 (brs, 4H), 2.98-2.89 (m, 4H), 2.20-1.95 (m, 4H), 1.79-1.66 (m, 2H); LC-MS (m/z, ES+): 443 (MH+), Retention time: 2.09 mins (LC-MS method 2)

EXAMPLE 328

2-(6-Morpholin-4-yl-pyridin-3-yl)-9-spirocyclopropyl-5,6,8,9,10,11-hexahydro-1,3,8,11-tetraaza-benzo[a]fluoren-7-one

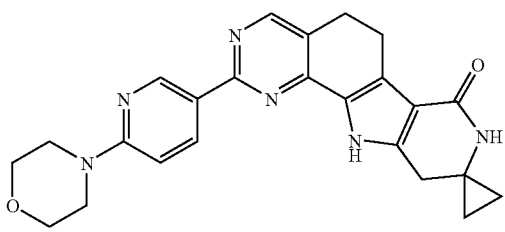

LC-MS (m/z, ES+): 429 (MH+), Retention time: 1.93 mins (LC-MS method 2)

EXAMPLE 329

2-(3-Aminomethyl-azetidin-3-yl)-8-(6-morpholin-4-yl-pyridin-3-yl)-4,5-dihydro-1H-1,7,9-triaza-cyclopenta[a]naphthalene-3-carboxylic acid lactam

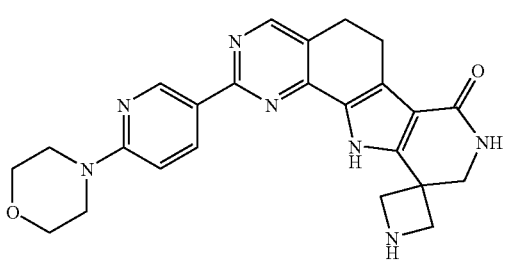

LC-MS (m/z, ES+): 444 (MH+), Retention time: 1.40 mins (LC-MS method 2)

EXAMPLE 330

N-Benzyl-3-fluoro-5-(7-oxo-10-spirocyclopropyl-6,7,8,9,10,11-hexahydro-5H-1,3,8,11-tetraaza-benzo[a]fluoren-2-yl)-benzamide

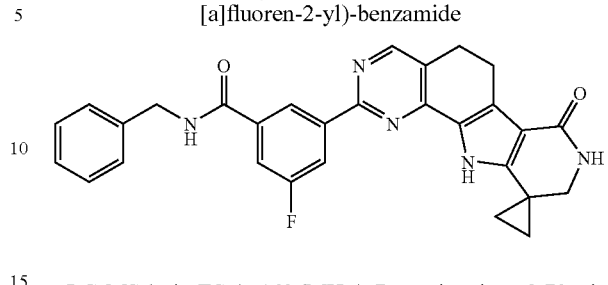

LC-MS (m/z, ES+): 460 (MH+), Retention time: 2.70 mins (LC-MS method 1)

EXAMPLE G1

Pharmaceutical Formulation

Tablets, comprising as active ingredient 100 mg of one of the active compounds of the preceding examples, e.g. examples 1 to 330 respectively, are prepared with the following composition, following standard procedures:

| Pharmaceutical Composition | |
|---|---|
| Active ingredient | 100 mg |
| Crystalline lactose | 240 mg |
| Avicel | 80 mg |
| PVPPXL | 20 mg |
| Aerosil | 2 mg |
| Magnesium stearate | 5 mg |
| | 447 mg |

Galenic procedure: The active ingredient is admixed with the carrier materials and compressed by means of a tabletting machine (Korsch EKO, Stempeldurchmesser 10 mm).

Avicel® is microcrystalline cellulose (FMC, Philadelphia, USA).

PVPPXL is polyvinylpolypyrrolidone, cross-linked (BASF, Ludwigshafen, Germany).

Aerosil® is silicium dioxide (Degussa, Germany).

EXAMPLE P1

MK2 Inhibition

Using the MAPKAPK2 kinase assay system described below, compounds of the formula I exhibit typically the following inhibition values:

| Example | IC$_{50}$ [nM] | Example | IC$_{50}$ [nM] |
|---|---|---|---|
| 1 | 47 | 2 | 21 |
| 3 | 63 | 4 | 65 |
| 10 | >10 | 12 | >10 |
| 18 | 18 | 23 | 6 |
| 24 | 13 | 26 | 15 |
| 27 | 43 | 76 | 51 |
| 83 | 73 | 84 | 39 |

| Example | IC$_{50}$ [nM] | Example | IC$_{50}$ [nM] |
|---|---|---|---|
| 87 | 42 | 88 | 38 |
| 89 | 79 | 90 | 91 |
| 93 | 51 | 94 | 53 |
| 95 | 100 | 96 | 45 |
| 108 | 49 | 109 | 42 |
| 110 | 84 | 166 | 7 |
| 169 | 93 | 168 | 14 |
| 173 | 39 | 175 | 35 |
| 273 | 19 | 274 | 16 |
| 275 | 20 | 276 | 11 |
| 305 | 12 | 306 | 9 |
| 307 | 14 | 308 | 15 |
| 309 | 20 | 310 | 97 |
| 311 | 27 | 312 | 15 |

MAPKAPK2 Kinase Assay

MAPKAPK2 is pre-activated in kinase buffer (25 mM TRIS-HCL, pH 7.5, 25 mM beta-glycerophosphate, 0.1 mM sodium orthovanadate, 25 mM MgCl$_2$, 20 µM DTT) containing 5 µM ATP, 150 µg/ml human MK2 (HPLC purified in house), 30 µg/ml active human p38α (HPLC purified in house) for 30 min at 22° C. For the measurement of compound inhibition on activated MAPKAPK2, each reaction contained test compound (10 µl; 0.5% DMSO final) or vehicle control, 250 nM Hsp27 peptide biotinyl-AY-SRALSRQLSSGVSEIR-COOH as substrate (10 µl) and pre-activated MAPKAP2 kinase mix (10 µl) containing ATP (5 µM final). To define non-specific, reactions are performed in the absence of substrate. Following incubation at 22° C. for 45 min, kinase reactions are terminated with 125 µM EDTA (10 µl). Samples (10 µl) are transferred to black low volume 384-well plates (Greiner) prior to the detection of phosphorylated substrate by time-resolved fluorescence resonance energy transfer (TR-FRET). Phosphorylated Hsp27 is measured using an antibody mix (10 µl) containing a rabbit anti-phospho-Hsp27 (Ser[82]) antibody (2.5 nM, Upstate) in conjunction with an anti-rabbit europium-labeled secondary antibody LANCE Eu-W1024 (2.5 nM; Perkin Elmer) as fluorescence donor along with streptavidin SureLight-APC (6.25 nM; Perkin Elmer) as a fluorescence acceptor. Following incubation at 22° C. for 90 min, plates are measured at 615 and 665 nm using a PHERAstar (BMG Labtech). The 615/665 nm ratio is determined following subtraction of background. Values are expressed as % inhibition using control values. Individual IC$_{50}$ values of compounds are determined by nonlinear regression after fitting of curves to the experimental data using Excel XL fit 4.0 (Microsoft). Compounds of the formula I preferably show IC50 values in the range from 5 nM, preferably 6 nM, to 50 µM, preferably 30 µM.

An alternative assay may be utilized:

This alternative assay is performed in 384 well microtiter plates. Each assay plate contains 8-point serial dilutions for 40 test compounds, as well as two 16-point serial dilutions of staurosporine as reference compound, plus 16 high- and 16 low controls. Liquid handling and incubation steps are done on a Thermo CatX workstation equipped with a Innovadyne Nanodrop Express. Between pipetting steps, tips are cleaned in wash cycles using wash buffer. Plates with terminated kinase reactions are transferred to Caliper LC3000 workstations for reading. Phosphorylated and unphosphorylated peptides are separated using the Caliper microfluidic mobiliti-shift technology and kinase activities are calculated from the amounts of formed phospho-peptide. The kinase reaction is prepared in 384 low volume plates by the following sequence:

1. 0.05 µl of a Compound described herein (start with 1.8 mM in 90% DMSO/10% H$_2$O)
2. +4.5 µl 2× HSP27-peptide (FITC-Ahx-SRALSRQLSS-GVSEIR-NH2, 1.8 µM)/ATP (10 µM)
3. +4.5 µl 2× MAPKAPK2 enzyme solution (0.013 nM HIS-MK2, Invitrogen PV4019)
4. Incubate for 60 min at 30° C.
5. +16 µl stop/run buffer All kinase reactions are performed in 50 mM HEPES, pH 7.5, 1 mM DTT, 0.02% Tween20, 0.02% BSA, 1 mM MgCl$_2$ and 0.6% DMSO.

Using the assay described above the following IC$_{50}$ values are obtained:

| Example | IC$_{50}$ [nM] | Example | IC$_{50}$ [nM] |
|---|---|---|---|
| 38 | 20 | 39 | 45 |
| 41 | 21 | 50 | 21 |
| 51 | 28 | 52 | 35 |
| 54 | 22 | 55 | 11 |
| 59 | 13 | 60 | 75 |
| 63 | 89 | 64 | 97 |
| 65 | 46 | 66 | 60 |
| 67 | 55 | 68 | 49 |
| 69 | 35 | 75 | 98 |
| 77 | 85 | 78 | 18 |
| 82 | 24 | 99 | 72 |
| 101 | 98 | 102 | 62 |
| 103 | 57 | 104 | 67 |
| 111 | 5 | 112 | 9 |
| 113 | 23 | 114 | 41 |
| 115 | 36 | 116 | 25 |
| 117 | 19 | 118 | 16 |
| 119 | 89 | 120 | 40 |
| 123 | 30 | 124 | 55 |
| 125 | 16 | 126 | 34 |
| 129 | 34 | 130 | 45 |
| 131 | 6 | 132 | 14 |
| 133 | 18 | 134 | 20 |
| 135 | 32 | 136 | 23 |
| 137 | 49 | 138 | 10 |
| 139 | 18 | 140 | 12 |
| 141 | 17 | 142 | 34 |
| 143 | 69 | 144 | 58 |
| 145 | 29 | 146 | 45 |
| 147 | 89 | 148 | 15 |
| 149 | 23 | 150 | 92 |
| 151 | 35 | 152 | 15 |
| 153 | 17 | 154 | <3 |
| 155 | <3 | 156 | <3 |
| 157 | <3 | 158 | 51 |
| 159 | <3 | 160 | <3 |
| 161 | 86 | 162 | 20 |
| 163 | 6 | 164 | 22 |
| 165 | <3 | 170 | 13 |
| 172 | <3 | 180 | <3 |
| 181 | 79 | 182 | <3 |
| 183 | 9 | 184 | 9 |
| 185 | <3 | 186 | <3 |
| 187 | <3 | 188 | <3 |
| 189 | 6 | 190 | 7 |
| 191 | 6 | 192 | 6 |
| 193 | 12 | 194 | 42 |
| 197 | 38 | 198 | 20 |
| 199 | 23 | 200 | 37 |
| 203 | 34 | 204 | 22 |
| 205 | <3 | 206 | <3 |
| 207 | <3 | 208 | <3 |
| 209 | 3 | 210 | 45 |
| 211 | <3 | 212 | 5 |
| 213 | 19 | 214 | 6 |
| 215 | 18 | 216 | 18 |
| 217 | 93 | 218 | 30 |
| 219 | 20 | 220 | 26 |
| 221 | 29 | 222 | <3 |

-continued

| Example | IC$_{50}$ [nM] | Example | IC$_{50}$ [nM] |
|---|---|---|---|
| 223 | <3 | 224 | <3 |
| 225 | <3 | 226 | <3 |
| 227 | 7 | 229 | <3 |
| 230 | 36 | 231 | 72 |
| 235 | 65 | 236 | 22 |
| 238 | 68 | 240 | 11 |
| 243 | 69 | 244 | 43 |
| 246 | 100 | 247 | 50 |
| 248 | 80 | 250 | <3 |
| 251 | 3 | 252 | 8 |
| 253 | 15 | 254 | <3 |
| 255 | <3 | 256 | <3 |
| 259 | <3 | 260 | <3 |
| 261 | 11 | 262 | <3 |
| 263 | <3 | 264 | >10 |
| 266 | >10 | 268 | 8 |
| 282 | 21 | 283 | 98 |
| 285 | 7 | 286 | 48 |
| 287 | 25 | 290 | 86 |
| 296 | 17 | 298 | 20 |
| 299 | 39 | 300 | 15 |
| 301 | 29 | 302 | 22 |
| 311 | 27 | 312 | 15 |
| 313 | 8 | 314 | 12 |
| 315 | 9 | 316 | 11 |
| 317 | 51 | 318 | 6 |
| 319 | 38 | 321 | 9 |
| 326 | 15 | 329 | 6 |

Agents of the Invention possess MAPKAPK2 (MAP Kinase Activated Protein Kinase) inhibiting activity. Thus the Agents of the Invention act to inhibit production of inflammatory cytokines, such as TNF-α, and also to potentially block the effects of these cytokines on their target cells. These and other pharmacological activities of the Agents of the Invention as may be demonstrated in standard test methods for example as described herein:

Assay for Inhibition of TNF-α Release from hPBMCs

Human peripheral blood mononuclear cells (hPBMCs) are prepared from the peripheral blood of healthy volunteers using Ficoll-Plaque Plus (Amersham) density separation according to the method described within. Cells are seeded at a 1×10$^5$ cells/well in 96-well plates in RPMI 1640 medium (Invitrogen) containing 10% (v/v) fetal calf serum (FCS). Cells are pre-incubated with serial dilutions of test compound (0.25% v/v DMSO final) for 30 min at 37° C. Cells are stimulated with the addition of IFNγ (10 ng/ml) and lipopolysaccharide(LPS) (5 µg/ml) per well and incubated for 3 h at 37° C. Following a brief centrifugation (250×g for 2 min), supernatant (10 µl) samples are taken from each well and measured against a TNFα calibration curve using a HTRF TNFα kit (CisBio) as described within. Individual IC$_{50}$ values of compounds are determined by nonlinear regression after fitting of curves to the experimental data using Excel XL fit 4.0 (Microsoft). In this assay, compounds of the formula I preferably show IC50 values for inhibition in the range from 10 nM, preferably 30 nM to 30 µM, preferably 10 µM.

Using the TNF-α release assay described above, compounds of the formula I can be shown to have the following inhibition values:

| Example | IC$_{50}$ [nM] |
|---|---|
| 1 | 320 |
| 40 | 220 |
| 99 | 311 |
| 103 | 336 |
| 127 | 264 |
| 172 | 347 |
| 185 | 134 |
| 187 | 156 |
| 195 | 333 |
| 207 | 130 |
| 301 | 256 |

Assay for Inhibition of TNF-α Production in LPS Stimulated Mice

Injection of lipopolysaccharide (LPS) induces a rapid release of soluble tumour necrosis factor (TNF-α) into the periphery. This model is be used to analyze prospective blockers of TNF release in vivo.

LPS (20 mg/kg) is injected i.v. into OF1 mice (female, 8 week old). One (1) hour later blood is withdrawn from the animals and TNF levels are analyzed in the plasma by an ELISA method using an antibody to TNF-α. Using 20 mg/kg of LPS levels of up to 15 ng of TNF-α/ml plasma are usually induced. Compounds to be evaluated are given either orally or s.c. 1 to 4 hours prior to the LPS injection. Inhibition of LPS-induced TNF-release is taken as the readout.

Exemplified Agents of the Invention typically suppress TNF release in this assay with an ED$_{50}$ from about 1 or preferably 3 mg/kg p.o. to 100 or preferably 30 mg/kg p.o.

Agents of the invention (as the compounds of the formula I or their byproducts are also referred to herein) are useful for the prevention and/or treatment of diseases, conditions and disorders that are mediated especially by TNF alpha and other pro-inflammatory cytokines including IL-1, IL-6, IL-8 and IFN-gamma, and/or by MK2, e.g. as described hereinafter.

The agents of the invention may be used for the treatment of any of one or more of the following disorders: connective tissue and joint disorders, neoplasia disorders, cardiovascular disorders, ophthalmic disorders, respiratory disorders, gastrointestinal disorders, angiogenesis-related disorders, autoimmune and immunological disorders, allergic disorders, infectious diseases and disorders, endocrine disorders, metabolic disorders, neurological and neurodegenerative disorders, pain, hepatic and biliary disorders, musculoskeletal disorders, genitourinary disorders, gynaecological and obstetric disorders, injury and trauma disorders, muscle disorders, surgical disorders, dental and oral disorders, sexual dysfunction orders, dermatological disorders, hematological disorders, and poisoning disorders.

As used herein autoimmune and inflammatory disorders are selected from arthritis (e.g. rheumatoid arthritis, psoriatic arthritis, juvenile chronic arthritis, reactive arthritis, arthritis deformans, gouty arthritis, osteoarthritis, Lyme disease), acute synovitis, autoimmune haematological disorders (e.g. hemolytic anaemia, aplastic anaemia, pure red cell anaemia and idiopathic thrombocytopenia), enterogenic spondyloarthropathies, ankylosing spondylitis, inflammatory bowel disease, ulcerative colitis, gastritis, pancreatitis, Crohn's disease, multiple sclerosis, lumbar spondylarthrosis, carpal tunnel syndrome, systemic lupus erythematosus, lupus nephritis, glomerulonephritis, polychondritis, scleroderma, Wegener granulomatosis, Stevens-Johnson syndrome, giant cell arteritis, mixed connective tissue disease (Sharp syndrome), Reiter syndrome, rheumatic fever, dermatomyositis, polymyositis, gout, tendonitis and bursitis, organ or transplant rejection (e.g for the treatment of recipients of heart, lung, combined heart and lung, liver, kidney, pancreatic, skin or corneal transplants), graft-versus-host disease, bacterial induced inflammation and viral induced inflammation, sepsis, septic shock, Behcet's disease, uveitis (anterior and posterior), Muckle-Wells syndrome, psoriasis, cutaneous lupus erythematosus, dermatitis, atopic dermatitis, contact dermatitis, acne vulgaris, eczema, xerosis, type I diabetes, Graves disease, Hashimoto thyroiditis, Sjogrens syndrome, blistering disorders (e.g. pemphigus vulgaris), and UV exposure (sunburn).

As used herein neoplasia disorders are selected from acral lentiginous melanoma, actinic keratoses, adenocarcinoma, adenomas, familial adenomatous polyposis, polyps, adenosarcoma, adenosquamous carcinoma, adrenocortical carcinoma, AIDS-related lymphoma, anal cancer, astrocytic tumours, batholin gland carcinoma, basal cell carcinoma, bile duct cancer, bladder cancer, brainstem glioma, brain tumours, breast cancer, bronchial gland carcinomas, capillary carcinoma, carcinoids, carcinoma, carcinomasarcoma, cavernous, central nervous system lymphoma, cerebral astrocytoma, cholangiocarcinoma, chondrosarcoma, choroid plexus papilloma/carcinoma, clear cell carcinoma, skin cancer, brain cancer, colon cancer, colorectal cancer, cutaneous T-cell lymphoma, cystadenoma, endodermal sinus tumour, endometrial hyperplasia, endometrial stromal sarcoma, endometrioid adenocarcinoma, ependymal-, epitheloid-, esophagal cancer, Ewing's sarcoma, fibrolamellar, focal nodular hyperplasia, gallbladder cancer, gastrinoma, germ cell tumours, gestation trophoblastic tumour, glioblastoma, hemangioblastomas, hemangiomas, hepatic adenomas, hepatic adenomatosis, hepatocellular carcinoma, Hodgkin's lymphoma, hypopharyngeal cancer, hypothalamic and visual pathway glioma, insulinoma, intraepithelial neoplasia, interepithelial cell carcinoma, Kaposi's sarcoma, kidney cancer, laryngeal cancer, leiomyosarcoma, lentigo maligna melanomas, leukemia-related disorders, lip and oral cavity cancer liver cancer, lung cancer, lymphoma, malignant mesothelial tumours, malignant thymoma, medulloblastoma, medulloepithelioma, melanoma, meningeal, Merkel cell carcinoma, mesothelial, metastatic carcinoma, mucoepidermoid carcinoma, multiple myeloma/plasma cell neoplasm, mycosis fungoides, myelodysplastic syndrome, myeloproliferative disorders, acute and chronic myelogenous leukemia, nasal cavity and paranasal sinus cancer, nasopharyngeal cancer, neuroblastoma, and neuroepithelial adenocarcinoma nodular melanoma, non-Hodgkin's lymphoma, oat cell carcinoma, oligodendroglial, oral cancer, oropharyngeal cancer, osteosarcoma, ovarian cancer, ovarian germ cell cancer, pancreatic cancer, papillary serous adenocarcinoma, pituitary tumours, plasmacytoma, pseudosarcoma, pulmonary blastoma, parathyroid cancer, penile cancer, pheochromcytoma, dermal tumours, plasma cell neoplasm, pleuropulmonay blastoma, prostate cancer, rectal cancer, renal cell carcinoma, retinoblastoma, rhabdomysarcoma, sarcoma, serous carcinoma, small cell carcinoma, small intestine cancer, soft tissue carcinomas, squamous carcinoma, squamous cell carcinoma, supratentorial primitive neurectodermal tumours, thyroid cancer, undifferentiated carcinoma, urethral cancer, uterine sarcoma, uveal melanoma, verrucous carcinoma, vaginal cancer, vipoma, vulvar cancer, Waldonstrom's macroglobulinemia, well differentiated carcinoma, and Wilm's tumour.

As used herein cardiovascular disorders, are selected from myocardial ischaemia, hypertension, hypotension, heart arrhythmias, pulmonary hypertension, hypokalaemia, cardiac ischaemia, myocardial infarction, cardiac remodelling, cardiac fibrosis, myocardial necrosis, aneurysm, arterial fibrosis, embolism, vascular plaque inflammation, vascular plaque rupture, oedema, fluid accumulation, cirrhosis of the liver, Bartter's syndrome, myocarditis, arteriosclerosis, atherosclerosis, calcification (such as vascular calcification and valvar calcification), coronary artery disease, acute coronary syndrome, heart failure, congestive heart failure, shock, arrhythmia, left ventricular hypertrophy, angina, diabetic nephropathy, hepatitis, kidney failure, eye damage, vascular diseases, migraine headaches, aplastic anaemia, cardiac damage, diabetic cardiac myopathy, renal insufficiency, renal injury, renal arteriography, peripheral vascular disease, left ventricular hypertrophy, cognitive dysfunction, stroke and headache.

As used herein bone and muscle disorders are selected from sarcopenia, muscular dystrophy, cachexia or wasting syndrome associated with morbid TNF release (e.g. consequent to infection, cancer or organ dysfunction, especially AIDS-related cachexia), and osteoporosis.

As used herein respiratory disorders are selected from asthma and bronchitis, chronic obstructive pulmonary disease (COPD), cystic fibrosis, pulmonary oedema, pulmonary embolism, pneumonia, pulmonary sarcoidosis, silicosis, pulmonary fibrosis, respiratory failure, acute respiratory distress syndrome, primary pulmonary hypertension and emphysema.

As used herein neurological and neurodegenerative disorders are selected from headaches, migraine, pain, dental pain, neuropathic and inflammatory pain, Alzheimer's disease, Parkinson's disease, dementia, memory loss, senility, amyotrophy, ALS (amyotrophic lateral sclerosis), amnesia, seizures, multiple sclerosis, muscular dystrophy, epilepsy, schizophrenia, depression, anxiety, attention deficit disorder, hyperactivity, spongiform encephalopathy, Creutzfeld-Jacob disease, Huntington's Chorea, ischemia, and cerebral ischemia.

In particular, the agents of the invention may be used for the prevention and treatment of autoimmune and inflammatory disorders such as arthritis (e.g. rheumatoid arthritis, psoriatic arthritis, juvenile chronic arthritis, reactive arthritis, arthritis deformans, gouty arthritis, osteoarthritis, Lyme disease), acute synovitis, autoimmune haematological disorders (e.g. hemolytic anaemia, aplastic anaemia, pure red cell anaemia and idiopathic thrombocytopenia), enterogenic spondyloarthropathies, ankylosing spondylitis, inflammatory bowel disease, ulcerative colitis, gastritis, pancreatitis, Crohn's disease, multiple sclerosis, lumbar spondylarthrosis, carpal tunnel syndrome, systemic lupus erythematosus, lupus nephritis, glomerulonephritis, polychondritis, scleroderma, Wegener granulomatosis, Stevens-Johnson syndrome, giant cell arteritis, mixed connective tissue disease (Sharp syndrome), Reiter syndrome, rheumatic fever, dermatomyositis, polymyositis, gout, tendonitis and bursitis, organ or transplant rejection (e.g for the treatment of recipients of heart, lung, combined heart and lung, liver, kidney, pancreatic, skin or corneal transplants), graft-versus-host disease, bacterial induced inflammation and viral induced inflammation, sepsis, septic shock, Behcet's disease, uveitis (anterior and posterior), Muckle-Wells syndrome, psoriasis, cutaneous lupus erythematosus, dermatitis, atopic dermatitis, contact dermatitis, acne vulgaris, eczema, xerosis, type I diabetes, Graves disease, Hashimoto thyroiditis, Sjogrens syndrome, blistering disorders (e.g. pemphigus vulgaris), headaches, migraine, pain, dental pain, neuropathic and inflammatory pain, UV exposure (sunburn), atherosclerosis, myocarditis, bone and muscle disorders such as sarcopenia, muscular dystrophy, cachexia or wasting syndrome associated with morbid TNF release (e.g. consequent to infection, cancer or organ dysfunction, especially AIDS-related cachexia), respiratory disorders such as asthma and bronchitis, chronic obstructive pulmonary disease (COPD), cystic fibrosis, pulmonary oedema, pulmonary embolism, pneumonia, pulmonary sarcoidosis, silicosis, pulmonary fibrosis, respiratory failure, acute respiratory distress syndrome, primary pulmonary hypertension and emphysema, neoplasia disorders, such as adenocarcinoma, multiple myeloma, bladder cancer, brain tumours, breast cancer, skin cancer, brain cancer, colon cancer, colorectal cancer, cutaneous T-cell lymphoma, glioblastoma, Hodgkin's lymphoma, Kaposi's sarcoma, kidney cancer, maligna melanomas, leukemia-related disorders, liver cancer, lung cancer, lymphoma, metastatic carcinoma, myeloproliferative disorders, acute and chronic myelogenous leukemia, non-Hodgkin's lymphoma, ovarian cancer, pancreatic cancer, pituitary tumours, prostate cancer, sarcoma.

Typically, the agents of the invention may be used for the prevention and treatment of arthritis (e.g. rheumatoid arthritis, psoriatic arthritis, juvenile chronic arthritis, reactive arthritis, arthritis deformans, gouty arthritis, osteoarthritis, Lyme disease), acute synovitis, autoimmune haematological disorders (e.g. hemolytic anaemia, aplastic anaemia, pure red cell anaemia and idiopathic thrombocytopenia), enterogenic spondyloarthropathies, ankylosing spondylitis, inflammatory bowel disease, ulcerative colitis, gastritis, pancreatitis, Crohn's disease, multiple sclerosis, lumbar spondylarthrosis, carpal tunnel syndrome, systemic lupus erythematosus, lupus nephritis, glomerulonephritis, polychondritis, scleroderma, Wegener granulomatosis, Stevens-Johnson syndrome, giant cell arteritis, mixed connective tissue disease (Sharp syndrome), Reiter syndrome, rheumatic fever, dermatomyositis, polymyositis, gout, tendonitis and bursitis, organ or transplant rejection (e.g for the treatment of recipients of heart, lung, combined heart and lung, liver, kidney, pancreatic, skin or corneal transplants), graft-versus-host disease, bacterial induced inflammation, sepsis, septic shock, Behcet's disease, uveitis (anterior and posterior), Muckle-Wells syndrome, psoriasis, cutaneous lupus erythematosus, dermatitis, atopic dermatitis, contact dermatitis, acne vulgaris, eczema, xerosis, Graves disease, Hashimoto thyroiditis, Sjogrens syndrome, blistering disorders (e.g. pemphigus vulgaris), UV exposure (sunburn), atherosclerosis, myocarditis, headaches, migraine, pain, dental pain, neuropathic and inflammatory pain, sarcopenia, muscular dystrophy, cachexia or wasting syndrome associated with morbid TNF release (e.g. consequent to infection, cancer or organ dysfunction, especially AIDS-related cachexia), asthma and bronchitis, chronic obstructive pulmonary disease (COPD), cystic fibrosis, pulmonary oedema, pulmonary embolism, pneumonia, pulmonary sarcoidosis, silicosis, pulmonary fibrosis, acute respiratory distress syndrome, adenocarcinoma, multiple myeloma, bladder cancer, brain tumours, breast cancer, skin cancer, brain cancer, colon cancer, colorectal cancer, cutaneous T-cell lymphoma, glioblastoma, Hodgkin's lymphoma, Kaposi's sarcoma, kidney cancer, maligna melanomas, leukemia-related disorders, liver cancer, lung cancer, lymphoma, metastatic carcinoma, myeloproliferative disorders, acute and chronic myelogenous leukemia, non-Hodgkin's lymphoma, ovarian cancer, pancreatic cancer, prostate cancer.

Typically, the agents of the invention may be used for the prevention and treatment of arthritis (e.g. rheumatoid arthritis, psoriatic arthritis, juvenile chronic arthritis, reactive arthritis, arthritis deformans, gouty arthritis, osteoarthritis, Lyme disease), acute synovitis, autoimmune haematological disorders (e.g. hemolytic anaemia, aplastic anaemia, pure red cell anaemia and idiopathic thrombocytopenia), enterogenic spondyloarthropathies, ankylosing spondylitis, inflammatory bowel disease, ulcerative colitis, gastritis, pancreatitis, Crohn's disease, multiple sclerosis, lumbar spondylarthrosis, systemic lupus erythematosus, lupus nephritis, glomerulonephritis, polychondritis, scleroderma, Wegener granulomatosis, Stevens-Johnson syndrome, dermatomyositis, polymyositis, gout, tendonitis and bursitis, organ or transplant rejection (e.g for the treatment of recipients of heart, lung, combined heart and lung, liver, kidney, pancreatic, skin or corneal transplants), graft-versus-host disease, bacterial induced inflammation, sepsis, septic shock, Behcet's disease, uveitis (anterior and posterior), Muckle-Wells syndrome, psoriasis, cutaneous lupus erythematosus, dermatitis, atopic dermatitis, contact dermatitis, eczema, xerosis, Graves disease, Hashimoto thyroiditis, Sjogrens syndrome, blistering disorders (e.g. pemphigus vulgaris), UV exposure (sunburn), atherosclerosis, myocarditis, headaches, migraine, pain, dental pain, neuropathic and inflammatory pain, sarcopenia, cachexia or wasting syndrome associated with morbid TNF release (e.g. consequent to infection, cancer or organ dysfunction, especially AIDS-related cachexia), asthma and bronchitis, chronic obstructive pulmonary disease (COPD), cystic fibrosis, pulmonary oedema, pulmonary sarcoidosis, pulmonary fibrosis, acute respiratory distress syndrome, adenocarcinoma, multiple myeloma, bladder cancer, brain tumours, breast cancer, skin cancer, brain cancer, colon cancer, colorectal cancer, cutaneous T-cell lymphoma, glioblastoma, Hodgkin's lymphoma, Kaposi's sarcoma, kidney cancer, maligna melanomas, leukemia-related disorders, liver cancer, lung cancer, lymphoma, metastatic carcinoma, myeloproliferative disorders, acute and chronic myelogenous leukemia, non-Hodgkin's lymphoma, ovarian cancer, pancreatic cancer, prostate cancer.

Generally, the agents of the invention may be used for the prevention and treatment of arthritis (e.g. rheumatoid arthritis, psoriatic arthritis, juvenile chronic arthritis, reactive arthritis, arthritis deformans, gouty arthritis, osteoarthritis, Lyme disease), acute synovitis, autoimmune haematological disorders (e.g. hemolytic anaemia, aplastic anaemia, pure red cell anaemia and idiopathic thrombocytopenia), enterogenic spondyloarthropathies, ankylosing spondylitis, inflammatory bowel disease, ulcerative colitis, gastritis, pancreatitis, Crohn's disease, multiple sclerosis, lumbar spondylarthrosis, systemic lupus erythematosus, lupus nephritis, glomerulonephritis, polychondritis, scieroderma, Wegener granulomatosis, Stevens-Johnson syndrome, dermatomyositis, polymyositis, gout, tendonitis and bursitis, organ or transplant rejection (e.g for the treatment of recipients of heart, lung, combined heart and lung, liver, kidney, pancreatic, skin or corneal transplants), graft-versus-host disease, sepsis, septic shock, Behcet's disease, uveitis (anterior and posterior), psoriasis, cutaneous lupus erythematosus, dermatitis, atopic dermatitis, contact dermatitis, eczema, xerosis, Graves disease, Hashimoto thyroiditis, Sjogrens syndrome, blistering disorders (e.g. pemphigus vulgaris), UV exposure (sunburn), atherosclerosis, myocarditis, headaches, dental pain, neuropathic and inflammatory pain, cachexia or wasting syndrome associated with morbid TNF release (e.g. consequent to infection, cancer or organ dysfunction, especially AIDS-related cachexia), asthma and bronchitis, chronic obstructive pulmonary disease (COPD), cystic fibrosis, pulmonary sarcoidosis, pulmonary fibrosis, acute respiratory distress syndrome, multiple myeloma, bladder cancer, brain tumours, breast cancer, skin cancer, brain cancer, colon cancer, colorectal cancer, Hodgkin's lymphoma, kidney cancer, maligna melanomas, leukemia-related disorders, liver cancer, lung cancer, lymphoma, metastatic carcinoma, myeloproliferative disorders, acute and chronic myelogenous leukemia, non-Hodgkin's lymphoma, ovarian cancer, pancreatic cancer, prostate cancer.

In particular the agents of the invention may be used for the prevention and treatment of arthritis (e.g. rheumatoid arthritis, psoriatic arthritis, juvenile chronic arthritis, reactive arthritis, arthritis deformans, gouty arthritis, osteoarthritis, Lyme disease), acute synovitis, autoimmune haematological disorders (e.g. hemolytic anaemia, aplastic anaemia, pure red cell anaemia and idiopathic thrombocytopenia), enterogenic spondyloarthropathies, ankylosing spondylitis, inflammatory bowel disease, ulcerative colitis, gastritis, pancreatitis, Crohn's disease, multiple sclerosis, lumbar spondylarthrosis, systemic lupus erythematosus, lupus nephritis, glomerulonephritis, polychondritis, scleroderma, Wegener granulomatosis, Stevens-Johnson syndrome, dermatomyositis, polymyositis, gout, tendonitis and bursitis, organ or transplant rejection (e.g for the treatment of recipients of heart, lung, combined heart and lung, liver, kidney, pancreatic, skin or corneal transplants), graft-versus-host disease, sepsis, septic shock, Behcet's disease, uveitis (anterior and posterior), psoriasis, cutaneous lupus erythematosus, dermatitis, atopic dermatitis, contact dermatitis, eczema, xerosis, Sjogrens syndrome, blistering disorders (e.g. pemphigus vulgaris), atherosclerosis, myocarditis, headaches, neuropathic and inflammatory pain, cachexia or wasting syndrome associated with morbid TNF release (e.g. consequent to infection, cancer or organ dysfunction, especially AIDS-related cachexia), asthma and bronchitis, chronic obstructive pulmonary disease (COPD), cystic fibrosis, pulmonary sarcoidosis, pulmonary fibrosis, acute respiratory distress syndrome, multiple myeloma, maligna melanomas, leukemia-related disorders, lymphoma, metastatic carcinoma, myeloproliferative disorders, acute and chronic myelogenous leukemia.

Typically the agents of the invention may be used for the prevention and treatment of arthritis (e.g. rheumatoid arthritis, psoriatic arthritis, juvenile chronic arthritis, reactive arthritis, arthritis deformans, gouty arthritis, osteoarthritis, Lyme disease), acute synovitis, enterogenic spondyloarthropathies, ankylosing spondylitis, inflammatory bowel disease, ulcerative colitis, gastritis, pancreatitis, Crohn's disease, multiple sclerosis, lumbar spondylarthrosis, systemic lupus erythematosus, lupus nephritis, glomerulonephritis, polychondritis, scleroderma, Wegener granulomatosis, dermatomyositis, polymyositis, tendonitis and bursitis, graft-versus-host disease, sepsis, septic shock, Behcet's disease, uveitis (anterior and posterior), psoriasis, cutaneous lupus erythematosus, dermatitis, atopic dermatitis, contact dermatitis, eczema, xerosis, Sjogrens syndrome, atherosclerosis, myocarditis, inflammatory pain, cachexia or wasting syndrome associated with morbid TNF release (e.g. consequent to infection, cancer or organ dysfunction, especially AIDS-related cachexia), asthma and bronchitis, chronic obstructive pulmonary disease (COPD).

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treat-ment" refers to preventing or delaying the onset or development or progression of the disease or disorder.

For all the above uses, an indicated daily dosage is in the range from about 0.02 to 2500 mg, especially 0.03 to about 300 mg, preferably 0.03 to 30, more preferably 0.1 to 10 mg of a compound of the invention. Agents of the Invention may be administered twice a day or up to twice a week.

The Agents of the Invention may be administered in free form or in pharmaceutically acceptable salt form. Such salts may be prepared in conventional manner and exhibit the same order of activity as the free compounds. The present invention also provides a pharmaceutical composition comprising an Agent of the Invention in free base form or in pharmaceutically acceptable salt form in association with a pharmaceutically acceptable diluent or carrier. Such compositions may be formulated in conventional manner. The Agents of the Invention may be administered by any conventional route, for example parenterally e.g. in form of injectable solutions, microemulsions or suspensions, enterally, e.g. orally, for example in the form of tablets, capsules or drinking solutions; sub-lingual, topically or transdermally, e.g. in form of a dermal cream or gel or for the purpose of administration to the eye in the form of an ocular cream, gel or eye-drop preparation, or it may be administered by inhalation.

The compounds of the invention may also be administered simultaneously, separately or sequentially in combination with one or more other suitable active agents selected from the following classes of agents: Anti IL-1 agents, e.g: Anakinra; anti cytokine and anti-cytokine receptor agents, e.g. anti TNFα Ab, anti TNFα receptor Ab, soluble TNFα receptor, anti IL-6 R Ab, anti IL-15 Ab, anti IL-17 Ab, anti IL-12 Ab; B-cell and T-cell modulating drugs, e.g. anti CD20 Ab; CTLA4-Ig, disease-modifying anti-rheumatic agents (DMARDs), e.g. methotrexate, leflunomide, sulfasalazine; gold salts, penicillamine, hydroxychloroquine and chloroquine, azathioprine, cyclophosphamide, glucocorticoids and non-steroidal anti-inflammatories (NSAIDs), e.g. cyclooxygenase inhibitors, selective COX-2 inhibitors, agents which modulate migration of immune cells, e.g. chemokine receptor antagonists, modulators of adhesion molecules, e.g. inhibitors of LFA-1, VLA-4.

The invention claimed is:

1. A compound of formula (IA) or (IB),

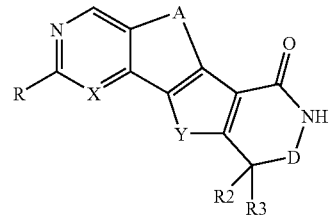

(IA)

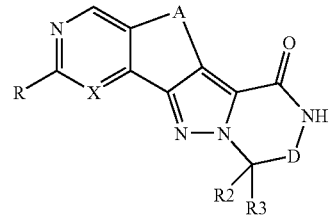

(IB)

wherein

R is hydrogen, halogen, —Y—$C_3$-$C_7$cycloalkyl, unsubstituted or substituted aryl, unsubstituted or substituted heterocyclyl, unsubstituted or substituted aryl-$C_2$-

$C_7$alkenyl, mono- or di -(unsubstituted or substituted $C_1$-$C_7$-alkyl)-amino or unsubstituted or substituted-arylamino;

A is —$CH_2$—, —$CH_2$—$CH_2$—, —$CH_2$—$CH_2$—$CH_2$— or —CH=CH—;

D is a bond between the carbon and the nitrogen atom to which it is bound or is C(R4R5);

R2 and R3 are hydrogen or together form an ethylene or trimethylene bridge in each of which one of the carbon atoms can be replaced with O, S or NR6;

R3 and R4 are hydrogen or $C_1$-$C_4$-alkyl or together form an ethylene or trimethylene bridge in each of which one of the carbon atomscan be replaced with O, S or NR6;

or one of R2 and R3 is hydrogen and one of R4 and R5 is hydrogen, while the other of R2 and R3 together with the other of R4 and R5 forms an ethy lene wherein one of the carbon atoms can be replaced with O, S or NR6, or a methylene bridge, with the proviso that at least one of the mentioned bridges must be present in a compound of formula (IA) or (IB) and is formed by R2 and R3, by R4 and R5, or by R2 or R3 and R4 or R5, so that not more than two of R2, R3, R4 and R5 are hydrogen or $C_1$-$C_4$-alkyl;

R6 is hydrogen, alkyl, $C_1$-$C_7$-alkyl, halo-$C_1$-$C_7$-alkyl, hydroxy-$C_1$-$C_7$alkyl, unsubstituted or substituted aryl-$C_1$-$C_7$-alkyl or acyl, X is N; and Y is O, S or NR7 wherein R7 is hydrogen, unsubstituted or substituted alkyl, unsubstituted or substituted cycloalkyl, unsubstituted or substituted aryl-$C_1$-$C_7$alkyl, unsubstituted or substituted saturated heterocyclyl or unsubstituted or substituted heterocyclyl-$C_1$-$C_7$-alkyl;

and/or a pharmaceutically acceptable salt thereof.

2. A compound of the formula IA or IB according to claim 1, wherein, where mentioned, unsubstituted or substituted aryl is aryl with 6 to 28, and may be mono-, bi-, tri- or tetracyclic, and is unsubstituted or substituted by one or more substituents independently selected from the group consisting of unsubstituted or substituted phenyl, unsubstituted or substituted phenyloxy, unsubstituted or substituted saturated heterocyclyl, $C_1$-$C_7$-alkyl, halo-$C_1$-C,alkyl, hydroxyl-$C_1$-$C_7$-alkyl, amino-$C_1$-$C_7$-alkyl, mono- or di- $C_1$-$C_7$-alkyl-amino-$C_1$-$C_7$-alkyl, saturated heterocyclyl-$C_1$-$C_7$-alkyl, pyrrolidinyl-$C_1$-$C_7$-alkyl imi-dazolidinyl -$C_1$-$C_7$-alkyl, imidazolidino-$C_1$-$C_7$-alkyl, pyrazolidinyl-$C_1$-$C_7$alkyl, piperidinyl-$C_1$-$C_7$-alkyl, (unsubstituted or $C_1$-$C_7$-alkyl-substituted piperazino)-$C_1$-$C_7$-alkyl, morpholinyl-$C_1$-$C_7$-alkyl, thiomorpholinyl-$C_1$-$C_7$-alkyl, S-oxo-thiomorpholinyl-$C_1$-$C_7$-alkyl, or S,S-dioxo-thiomorpholinyl-$C_1$-$C_7$-alkyl, $C_2$-$C_7$-alkenyl, $C_6$-$C_{10}$-aryl-$C_2$-$C_7$-alkenyl, $C_2$-$C_7$alkynyl, amino-$C_3$-$C_7$-alkynyl, hydroxyl-$C_3$-$C_7$alkynyl, halo, hydroxyl, $C_1$-$C_7$-alkoxy, $C_1$-$C_7$-alkoxy-$C_1$-$C_7$-alkoxy, halo-$C_1$ $C_7$-alkoxy, saturated heterocyclyl-$C_1$-$C_7$-alkoxy imidazolidinyl-$C_1$-$C_7$-alkoxy, imidazolidino-$C_1$-$C_7$-alkoxy, pyrazolidinyl-$C_1$-$C_7$-alkoxy, piperidinyl-$C_1$-$C_7$ -alkoxy, (unsubstituted or $C_1$-$C_7$alkyl -substituted piperazino)-$C_1$-$C_7$-alkoxy, morpholinyl-$C_1$-$C_7$-alkoxy, thiomorpholinyl-$C_1$-$C_7$alkoxy, S-oxo-thiomorpholinyl-$C_1$-$C_7$-alkoxy, or S,S-dioxo-thiomorpholinyl-$C_1$-$C_7$-alkoxy, mono- or di-($C_1$-$C_7$-alkyl)-amino-$C_1$-$C_7$-alkoxy, $C_1$-$C_7$alkylenedioxy, amino, mono- or di-($C_1$-$C_7$-alkyl and/or phenyl-$C_1$-$C_7$alkyl)-amino, formyl, carboxy, $C_1$-$C_7$alkoxy-carbonyl, aryl-$C_1$-$C_7$-alkoxycarbonyl, carbamoyl, mono-or di-($C_1$-$C_7$alkyl, unsaturated heterocyclyl-$C_1$-$C_7$alkyl and/or aryl-$C_1$-$C_7$-alkyl, sulfonyl (—S(O)$_2$—OH), sulfamoyl, mono- or di-($C_1$-$C_7$alkyl and/or phenyl -$C_1$-$C_7$alkyl)-sulfamoyl, nitro, acyl and cyano;

unsubstituted or substituted heterocyclyl is a mono-, di- or tricyclic ring with 3 to 24 ring atoms, of which one or more, independently of each other, are heteroatoms selected from N, O and S, and is saturated, or partially unsaturated or unsaturated (=carrying the highest possible number of conjugated double bonds in the ring), where heterocyclyl is unsubstituted or substituted by one or more substituents independently selected from those mentioned as substituents for substituted aryl, mono- or di-(unsubstituted or substituted $C_1$-$C_7$alkyl)-amino is amino substituted by one or two moieties selected from $C_1$-$C_7$-alkyl, $C_1$-$C_7$alkoxy-$C_1$-$C_7$alkyl, amino- or mono- or di-($C_1$-$C_7$alkyl and/or $C_6$-$C_{10}$-aryl-$C_1$-$C_7$alkyl), or $C_1$-$C_7$alkyl substituted by one or more of the further substituents mentioned as substituents for substituted aryl;

in unsubstituted or substituted-arylamino, unsubstituted or substituted aryl is as defined above;

A is —$CH_2$—, —$CH_2$—$CH_2$—$CH_2$— or —CH=CH—, if D is a bond between the two carbon atoms to which it is bound, then the ring including D has five ring atoms;

If R2 and R3 together form an ethylene or trimethylene bridge in each of which one of the carbon atoms can be replaced with O, S or NR6, then R2 and R3 together with the binding carbon atoms form a 3- to 4-membered ring;

if R3 and R4 together form an ethylene or trimethylene bridge in each of which one of the carbon atoms can be replaced with O, S or NR6, then R3 and R4 together with the binding carbons atoms form a 3-to 4-membered ring;

if one of R2 and R3 is hydrogen and one of R4 and R5 is hydrogen, while the other of R2 and R3 together with the other of R4 and R5 forms an ethylene wherein one of the carbon atoms can be replaced with O, S or NR6, or a methylene bridge, R2 or R3 and R4 or R5 together with the two carbon atoms to which they are bound form a three- to four-membered ring;

the proviso that at least one ring is formed by R2 and R3, by R4 and R5, or by R2 or R3 and R4 or R5, so that not more than two of R2; R3, R5 and R5 are hydrogen or $C_1$-$C_4$-alkyl, means that at least one annealed or spiro, ring must be formed by these substituents and the carbon atoms to which they are bound;

alkyl may be branched, unbranched or cyclic, and is $C_1$-$C_{20}$-alkyl in substituted alkyl, it may be substituted by one or more substituents as mentioned as substituents mentioned for aryl;

unsubstituted or substituted aryl-$C_1$-$C_7$alkyl is $C_1$-$C_7$alkyl that is substituted by unsubstituted or substituted aryl as defined above;

cycloalkyl represents a cyclic hydrocarbon containing from 3 to 12 ring atoms where cycloalkyl may optionally be substituted by one or more substituents independently selected from those mentioned as substituents for substituted aryl, in the (R,S)— or in the (R)— or (S)— form; in the case of R7, cycloalkyl is cyclohexyl or cyclopentyl, each unsubstituted or substituted with hydroxyl;

acyl is the radical of an organic acid, or is $C_1$-$C_7$-alkanoyl, $C_1$-$C_7$-alkanesutfonyl, benzoyl, naphthoyl, $C_7$-$C_7$-alkoxycarbonyl,or $C_6$-$C_{10}$-aryl-$C_1$-C-$_7$alkoxycarbonyl;

unsubstituted or substituted saturated heterocyclyl is unsubstituted or substituted saturated heterocyclyl as defined above and is unsubstituted or substituted by one or more of the substituents independently selected from the substituents mentioned for substituted aryl above;

in unsubstituted or substituted heterocyclyl-$C_1$-$C_7$alkyl, unsubstituted or substituted heterocyclyl is as defined above and is unsubstituted or substituted by one or more of the substituents independently selected from the substituents mentioned for substituted aryl above;

and/or a pharmaceutically acceptable salt thereof.

3. A compound of the formula IA or of the formula IB according to claim 1, wherein R is phenyl, pyridyl, each of which is unsubstituted or substituted by up to three moieties independently selected from the group consisting of halo-$C_1$-$C_7$-alkyl, hydroxyl-$C_1$-$C_7$-alkyl, amino-$C_1$-$C_7$-alkyl, pyrrolidinyl-$C_1$-$C_7$-alkyl, pyrrolidino-methyl, imidazolidinyl-$C_1$-$C_7$-alkyl, imidazolidino-$C_1$-$C_7$-alkyl, piperidinyl-$C_1$-$C_7$-alkyl, (unsubstituted or $C_1$-$C_7$-alkyl-substituted piperazino)-$C_1$-$C_7$-alkyl, $C_6$-$C_{10}$-aryl-$C_2$-$C_7$-alkenyl, amino-$C_3$-$C_7$-alkynyl, hydroxyl-$C_3$-$C_7$-alkynyl, halo, $C_1$-$C_7$-alkoxy, $C_1$-$C_7$-alkoxy-$C_1$-$C_7$-alkoxy, halo-$C_1$-$C_7$-alkoxy, pyrrolidinyl-$C_1$-$C_7$-alkoxy, imidazolidinyl-$C_1$-$C_7$-alkoxy, imidazolidino-$C_1$-$C_7$-alkoxy, piperidinyl-$C_1$-$C_7$-alkoxy, (unsubstituted or $C_1$-$C_7$-alkyl-substituted piperazino)-$C_1$-$C_7$-alkoxy, $C_1$-$C_7$-alkylenedioxy, amino, carbamoyl, nitro and cyano;

A is —$CH_2$—, —$CH_2$—$CH_2$—, —$CH_2$—$CH_2$—$CH_2$— or —CH=CH—,

D is a bond between the two carbon atoms to which it is bound or is C(R4R5);

R2 and R3 are hydrogen or together form an ethylene or trimethylene bridge in each of which one of the carbon atoms can be replaced with O, S or NR6;

R3 and R4 are hydrogen or $C_1$-$C_4$-alkyl or together form an ethylene or trimethylene bridge in each of which one of the carbon atoms can be replaced with O, S or NR6;

or one of R2 and R3 is hydrogen and one of R4 and R5 is hydrogen, while the other of R2 and R3 together with the other of R4 and R5 forms a forms an ethylene bridge wherein one of the carbon atoms can be replaced with O, S or NR6, or a methylene bridge, with the proviso that at least one of the mentioned bridges is formed by R2 and R3, by R4 and R5, or by R2 or R3 and R4 or R5, so that not more than two of R2, R3, R5 and R5 are hydrogen or $C_1$-$C_4$-alkyl;

R6 is hydrogen, $C_1$-$C_7$alkyl, phenyl-$C_1$-$C_7$alkyl, $C_3$-$C_8$-cycloalkyl that is unsubstituted or substituted by hydroxyl, $C_1$-$C_7$alkanoyl or $C_1$-$C_7$.alkoxycarbonyl, X is N; and Y is O, N or NR7 wherein R7 is hydrogen, $C_1$-$C_7$alkyl, hydroxyl-$C_1$-$C_7$alkyl or $C_3$-$C_8$-cycloalkyl that is unsubstituted or substituted by hydroxyl;

and/or a pharmaceutically acceptable salt thereof.

4. A compound of the formula I according to claim 1, selected from the group of compounds consisting of:

2-(1-amino-cyclobutylmethyl)-8-(4-methoxy-phenyl)-4,5-dihydro-1 H-1,7,9-triazacyclopenta[a]naph-thalene-3-carboxylic acid lactame, 2-(1-amino-cyclobutylmethyl)-8-[4-(3-amino-3-methyl-but-1-ynyl)-phenyl]-4,5-dihydro-1H-1,7,9-triaza-cyclopenta[a]naphthalene-3-carboxylic acid lactame, 2-(1-amino-cyclobutylmethyl)-8-[4-(3-amino-3-methyl-butyl)-phenyl]-4,5-dihydro-1H-1,7,9-triaza -cyclopenta[a]naphthalene-3-carboxylic acid lactame, 2-(1-aminomethyl-cyclopropyl)-8-(4-methoxy-phenyl)-4,5-dihydro-1H-1,7,9-triaza -cyclopenta[a]naph thalene-3-carboxylic acid lactame, 2-(3-amino-azetidin-3-ylmethyl)-8-(4-methoxy-phenyl)-4,5-dihydro-1H-1,7,9-triaza -cyclopenta[a]naphthalene-3-carbcoxylic acid lactame, 2-(1-amino-cyclobutylmethyl)-8-(3-fluoro-phenyl)-4,5-dihydro-1H-1,7,9-triaza -cyclopenta[a]naphthalene-3-carboxylic acid lactame, 2-(3-amino-oxetan-3-ylmethyl)-8-(4-methoxy-phenyl)-4,5-dihydro-1H-1,7,9-triaza -cyclopenta[a]naphthalene-3-carboxylic acid lactame, 2-(3-amino-oxetan-3-ylmethyl)-8-(3-fluoro-phenyl)-4,5-dihydro-1H-1,7,9-triaza -cyclopenta[a]naphthalene-3-carboxylic acid lactame, and/or a pharmaceutically acceptable salt thereof.

5. A compound selected from the group of compounds consisting of 2-(3-Aminomethyl-azetidin-3-yl)-8-(4-methoxy-phenyl)-4,5-dihydro-1H-1,7,9-triaza -cyclopenta[a]naphthalene-3-carboxylic acid lactam hydrochloride, 2-(3-Aminomethyl-1-methyl-azetidin-3-yl)-8-(4-methoxy-phenyl)-4,5-dihydro-1H-1,7,9-triaza -cyclopenta[a]naphthalene-3-carboxylic acid lactam, 2-(3-Aminomethyl-azetidin-3-yl)-8-(3-fluoro-4-morpholin-4-ylmethyl-phenyl)-4,5-dihydro-1H -1,7,9-triaza-cyclopenta[a]naphthalene-3-carboxylic acid lactam, and/or a pharmaceutically acceptable salt thereof.

6. A pharmaceutical composition comprising a compound of formula (IA) or (IB), and/or a pharmaceutically acceptable salt thereof, according to claim 1, and at least one pharmaceutically acceptable carrier.

7. A process for the manufacture of a compound of the formula IA or IB according to claim 1, comprising a) for the manufacture of a compound of the formula IB wherein A is —$CH_2$— or —$CH_2$—$CH_2$— and X is N, reacting a compound of the formula IV, (IV)

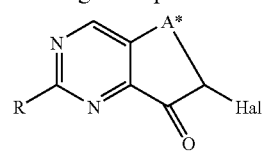

wherein R is as defined for a compound of the formula IB in any one of claims 1 to 5, Hal is halo and A* is —$CH_2$— or is —$CH_2$—$CH_2$—, with a compound of the formula V, (V)

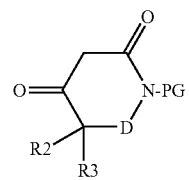

wherein PG is a protecting group, e.g. tert-butoxycarbonyl, and R2, R3 and D are as defined for a compound of the formula IB, in the presence of an amine of the formula VI,

R7-$NH_2$ (VI)

wherein R7 is as defined for a compound of the formula IB in any one of claims 1 to 5, or a salt thereof, and removing the protecting group PG, or b) for the manufacture of a compound of the formula IB, deprotecting a compound of the formula VII,

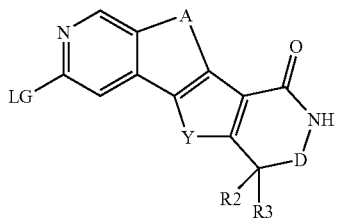

(II)

wherein R, A, Y, R2, R3 and D are as defined for a compound of the formula IB in any one of claims 1 to 5; and PG* is an amino protecting group;
wherein in any of the starting materials mentioned-in process variants a), b) or c) protecting groups may be present that can be removed at appropriate stages;
and, if desired, converting an obtainable free compound of the formula (IA) or (IB) into a and/or a pharmaceutically acceptable salt thereof, respectively, an obtainable salt into the free compound or into a different salt, and/or into a different compound of the formula IA or IB, if desired separating the enantionmers of a compound of the formula (IA) or (IB) into the enantiomers thereof.

8. A composition comprising a compound according to claim 1 in combination with one or more active agents selected from the group consisting of: Anti IL-1 agents, anti cytokine and anti-cytokine receptor agents, B-cell and T-cell modulating drugs, disease-modifying anti-rheumatic agents (DMARDs), gold salts, penicillamine, hydroxychloroquine and chloroquine, azathioprine, glucocorticoids, non-steroidal anti-inflammatories (NSAIDs), selective COX-2 inhibitors, agents which modulate migration of immune cells, chemokine receptor antagonists, modulators of adhesion molecules, for simultaneous, separate or sequential administration.

9. The compound of the formula IA or IB according to claim 1, wherein, where mentioned,
unsubstituted or substituted aryl is phenyl, indenyl, naphthyl or fluorenyl, and is unsubstituted or substituted by-up to three, substituents independently selected from the group consisting of 4-fluorophenyl, 2,4-difluorophenoxy, 1-morpholinyl, 4-alkyl-piperazin-1-yl or 1-piperidinyl, methyl, trifluoromethyl or bromomethyl, 3-hydroxy-3-methyl-butyl, 3-amino-3-methyl-butyl, pyrrolidinyl -$C_1$-$C_7$-alkyl, pyrrolidino-methyl, imidazolidinyl-$C_1$-$C_7$-alkyl, pyrazoldin-1-yl-$C_1$-$C_7$-alkyl, piperidino-methyl, 2-piperidino-ethyl, 4-methylpiperazin-1-yl-methyl, ethyl, morpholino-methyl, 2-morpholino-ethyl, thiomorpholino-methyl, 2-thiomorpholino-ethyl, S-oxo-thiomorpholino-methyl, 2-S-oxo-thiomorpholino-ethyl, S,S-di-thiomorpholino-methyl, 2-S,S-di-thiomorpholino-ethyl, (E,Z)—, (E)-, (Z)-styryl, 3-amino-3-methyl-but-1-ynyl, 3-hydroxy-3-methylbut-1-ynyl, fluoro, chloro, bromo, methoxy, isopropoxy, 2-methoxy-ethoxy, trifluoromethoxy, pyrrolidinyl-$C_1$-$C_7$-alkoxy, pyrrolidino-methoxy, pyrazilidin-1-yl-$C_1$-$C_7$-alkoxy, piperidino-methoxy, 2-piperidino -ethoxy, 4-methylpiperazin-1-yl-methoxy, 2-(4-methylpiperazin-1-yl)-ethoxy, morpholino -methoxy, 2-morpholino-ethoxy, thiomorpholino-methoxy, 2-thiomorpholino-ethoxy, S-oxo -thiomorpholino-methoxy, 2-S-oxo-thiomorpholino-ethoxy, S,S-di-thiomorpholino-methoxy, 2-S,S -di-thiomorpholino-ethoxy, dimethylamino-ethoxy, ethlyendioxy, phenyl-$C_1$-$C_7$alkoxycarbonyl, and phenyl-$C_1$-$C_7$alkyl)-carbamoyl;
unsubstituted or substituted heterocyclyl selected froth the group consisting of azetidinyl, pyrrolidinyl, imidazolidinyl, pyrazolidinyl, piperidinyl, piperazinyl, indolinyl, isoindolinyl, quinuclidinyl, morpholinyl, thiomorpholinyl, S-oxo-thiomorpholinyl and S,S-dioxothiomorpholinyl;
pyrrolyl, imidazolyl, pyrazolyl, indazolyl, purinyl, pyridinyl, pyrazinyl, pyrimidinyl, pyridazinyl, indolyll, isoindolyl, quinolyl, isoquinolyl, quinolizinyl, phthalazinyl, napthyridinyl, quinoxalinyl, quinazolinyl, cinnolinyl, pteridinyl, indolizinyl, carbazolyl, beta-carbolinyl, acridinyl, phenanthridinyl, phenazinyl, phenanthrolinyl, perimidinyl, furyl, thiophenyl (= thienyl), 2H- or 4H -pyranyl or -thiopyranyl, oxazolyl, thiazolyl, isochromanyl, chromanyl, benzofuranyl, 2H -benzo[1,4]oxazinyl, isobenzofuranyl, 2H-chromenyl, 2H-thiochromenyl, thianthrenyl, xanthenyl, phenoxathiinyl, phenoxazinyl and phenothiazinyl; where heterocyclyl is unsubstituted or substituted by one to three, substituents independently selected from $C_1$-$C_7$-alkoxy, $C_1$-$C_7$-alkyl, hydroxy- $C_1$-$C_2$-alkyl, acyl, $C_1$-$C_7$-alkoxy-$C_1$-$C_7$-alkoxy, halo, amino, mono- or di- $C_1$-$C_7$-alkyl -amino, and hydroxyl;
and/or a pharmaceutically acceptable salt thereof.

10. The compound of the formula IA or IB according to claim 1, wherein A is —$CH_2$—$CH_2$—, and/or a pharmaceutically acceptable salt thereof.

11. The compound of the formula IA or IB according to claim 1, wherein where mentioned, alkyl is methyl, ethyl, propyl, butyl, isopropyl, isobutyl, tertiary butyl or 2,2-dimethylpropyl; each of which may be substituted with hydroxyl;
unsubstituted or substituted aryl-$C_1$-$C_7$alkyl is benzyl;
cycloalkyl is cyclopropyl, cyclobutyl, cyclopentyl, or cyclohexyl, where cycloalkyl may optionally with hydroxyl, the (R,S)— or in the (R)— or (S)— form;
acyl is a carboxylic acid or a sulfonic acid, or acetyl, or tert-butoxycarbonyl, or benzyloxycarbonyl; or
and/or a pharmaceutically acceptable salt thereof.

12. A compound of the formula IA or of the formula IB according to claim 3, wherein R is phenyl, pyridine-2-yl or 2-phenylvinyl, each of which is unsubstituted or substituted by up to three moieties independently selected from the group consisting of trifluoromethyl or bromomethyl, 3-hydroxy-3-methyl-butyl, 3-amino-3-methyl-butyl, piperidino-methyl or 2-piperidino-ethyl, 4-methylpiperazin-1-yl-methyl or -ethyl, (E,Z)—, (E)-, (Z)-styryl, 3-amino-3-methyl-but-1-ynyl, 3-hydroxy-3-methylbut-1-ynyl, fluoro, chloro or bromo, methoxy, isopropoxy, 2-methoxy-ethoxy, trifluoromethoxy, pyrrolidino-methoxy, piperidino-methoxy or 2-piperidino -ethoxy, 4-methylpiperazin-1-yl-methoxy and 2-(4-methylpiperazin-1-yl)-ethoxy;
A is $CH_2$— or —$CH_7$—$CH_2$—;
D is a bond between the two carbon atoms to which it is bound or is C(R4R5);
R2 and R3 are hydrogen or together form an ethylene or trimethylene bridge in each of which one of the carbon atoms can be replaced with O, S or NR6;
R3 and R4 are hydrogen or $C_1$-$C_4$-alkyl or together form an ethylene or trimethylene bridge in each of which one of the carbon atoms can be replaced with O, S or NR6;
or one of R2 and R3 is hydrogen and one of R4 and R5 is hydrogen, while the other of R2 and R3 together with the other of R4 and R5 forms a forms an ethylene bridge wherein one of the carbon atoms can be replaced with O, S or NR6, or a methylene bridge,
with the proviso that at least one of the mentioned bridges is formed by R2 and R3, by R4 and R5, or by R2 or R3 and R4 or R5, so that not more than two of R2, R3, R5 and R5 are hydrogen or $C_1$-$C_4$-alkyl;

R6 is hydrogen, $C_1$-$C_7$alkyl, phenyl-$C_1$-$C_7$alkyl, $C_3$-$C_8$-cycloalkyl that is unsubstituted or substituted by hydroxyl, $C_1$-$C_7$alkanoyl or $C_1$-$C_7$.alkoxycarbonyl, X is N; and Y is NR7 wherein R7 is hydrogen, $C_1$-$C_7$alkyl, hydroxyl-$C_1$-$C_7$alkyl or $C_3$-$C_8$-cycloalkyl that is unsubstituted or substituted by hydroxyl;

and/or a pharmaceutically acceptable salt thereof.

* * * * *